(12) United States Patent
Bhattacharyya et al.

(10) Patent No.: US 12,051,488 B2
(45) Date of Patent: Jul. 30, 2024

(54) INTERACTIVE TRIAL DESIGN PLATFORM

(71) Applicant: Cytel Inc., Waltham, MA (US)

(72) Inventors: Jaydeep Bhattacharyya, Acton, MA (US); James Bolognese, Woodbridge, NJ (US); Alexandre Buer, Holliston, MA (US); Eric Edwards, Nolensville, TN (US); Stanley Y. Huang, Wellesley, MA (US); Yannis Jemiai, Lexington, MA (US); Cyrus Mehta, Cambridge, MA (US); Nitin Patel, Cambridge, MA (US); Anne Pelz, Arlington, MA (US); Ajay Prabhakar Sathe, Pune (IN); Joshua A. Schultz, Boston, MA (US); Pralay Senchaudhuri, Cambridge, MA (US)

(73) Assignee: Cytel Inc., Waltham, MA (US)

( * ) Notice: Subject to any disclaimer, the term of this patent is extended or adjusted under 35 U.S.C. 154(b) by 619 days.

(21) Appl. No.: 17/163,438

(22) Filed: Jan. 30, 2021

(65) Prior Publication Data

US 2021/0241866 A1  Aug. 5, 2021

Related U.S. Application Data

(63) Continuation of application No. PCT/US2021/015954, filed on Jan. 30, 2021.
(Continued)

(51) Int. Cl.
*G16H 10/20* (2018.01)
*G06F 30/27* (2020.01)
(Continued)

(52) U.S. Cl.
CPC ............ *G16H 10/20* (2018.01); *G06F 30/27* (2020.01); *G06N 5/04* (2013.01); *G06N 20/00* (2019.01);
(Continued)

(58) Field of Classification Search
None
See application file for complete search history.

(56) References Cited

U.S. PATENT DOCUMENTS

| 8,781,882 | B1 | 7/2014 | Arboletti et al. |
| 10,878,169 | B2 * | 12/2020 | Goel ............... G06F 40/106 |

(Continued)

FOREIGN PATENT DOCUMENTS

| WO | 0217211 A2 | 2/2002 |
| WO | 2010043240 A1 | 4/2010 |

(Continued)

OTHER PUBLICATIONS

Lee, Kim May, et al., "Design of experiments for a confirmatory trial of precision", In: Journal of Statistical Planning and Inference 199 (2019) 179-187, Jun. 23, 2018, [online] [retrieved on May 12, 2021 (May 12, 2021)] Retrieved from the Internet < URL: https://www.sciencedirect.com/science/article/pii/S0378375818300080 >, entire document,, 9 pages.

(Continued)

*Primary Examiner* — Toan H Vu
(74) *Attorney, Agent, or Firm* — GTC Law Group PC & Affiliates

(57) ABSTRACT

A method for trial design includes presenting on a graphical interface, a set of cards, wherein each card in the set is representative of a different trial design from a set of trial designs. The method further includes: monitoring a first set of user interactions with the set of cards; determining a user preference for one or more values of one or more parameters of the set of trial designs from the first set of user interactions; and presenting on the graphical interface a new card that is representative of a trial design consistent with the determined user preference. The method may also include monitoring a second set of user interactions with the new card and refining the determined user preference based at (Continued)

least in part on the second set of user interactions with the new card.

20 Claims, 160 Drawing Sheets

Related U.S. Application Data

(60) Provisional application No. 63/086,474, filed on Oct. 1, 2020, provisional application No. 63/085,700, filed on Sep. 30, 2020, provisional application No. 63/037,977, filed on Jun. 11, 2020, provisional application No. 63/002,197, filed on Mar. 30, 2020, provisional application No. 63/002,253, filed on Mar. 30, 2020, provisional application No. 62/968,874, filed on Jan. 31, 2020.

(51) Int. Cl.
*G06N 5/04* (2023.01)
*G06N 20/00* (2019.01)
*G06Q 10/067* (2023.01)
*G06Q 10/101* (2023.01)
*G16H 40/20* (2018.01)
*G16H 50/50* (2018.01)
*G06F 3/0484* (2022.01)
*G06F 111/06* (2020.01)

(52) U.S. Cl.
CPC ......... *G06Q 10/067* (2013.01); *G06Q 10/101* (2013.01); *G16H 40/20* (2018.01); *G16H 50/50* (2018.01); *G06F 3/0484* (2013.01); *G06F 2111/06* (2020.01)

(56) References Cited

U.S. PATENT DOCUMENTS

| | | |
|---|---|---|
| 2002/0077853 A1 | 6/2002 | Boru et al. |
| 2003/0065669 A1 | 4/2003 | Kahn et al. |
| 2003/0088320 A1 | 5/2003 | Sale |
| 2007/0026365 A1 | 2/2007 | Friedrich et al. |
| 2007/0292012 A1 | 12/2007 | Brandon et al. |
| 2008/0010044 A1 | 1/2008 | Ruetsch |
| 2008/0133270 A1 | 6/2008 | Michelson et al. |
| 2008/0215512 A1 | 9/2008 | Narzisi et al. |
| 2008/0256006 A1 | 10/2008 | Buscema et al. |
| 2008/0312951 A1 | 12/2008 | Herpichboehm et al. |
| 2008/0313025 A1 | 12/2008 | Chowdhury |
| 2009/0292554 A1 | 11/2009 | Schultz |
| 2010/0211411 A1 | 8/2010 | Hudson |
| 2010/0268544 A1 | 10/2010 | Nitahara et al. |
| 2011/0301982 A1* | 12/2011 | Green, Jr. ............... G16H 40/67 705/3 |
| 2012/0089418 A1 | 4/2012 | Kamath et al. |
| 2013/0132042 A1 | 5/2013 | Chan |
| 2013/0197878 A1 | 8/2013 | Fiege et al. |
| 2013/0304504 A1 | 11/2013 | Powell |
| 2013/0304542 A1 | 11/2013 | Powell |
| 2014/0006039 A1 | 1/2014 | Khan et al. |
| 2014/0006042 A1 | 1/2014 | Keefe et al. |
| 2014/0122126 A1 | 5/2014 | Riskin |
| 2014/0350966 A1* | 11/2014 | Khatana ................. G16H 10/60 705/3 |
| 2015/0073830 A1 | 3/2015 | Hill et al. |
| 2015/0088783 A1 | 3/2015 | Mun |
| 2015/0106110 A1 | 4/2015 | Edwards et al. |
| 2016/0129282 A1 | 5/2016 | Yin et al. |
| 2016/0198223 A1* | 7/2016 | Maluk ............... H04N 21/44218 709/206 |
| 2016/0255139 A1* | 9/2016 | Rathod ............... H04N 1/32101 709/203 |
| 2016/0314280 A1 | 10/2016 | Fusari et al. |
| 2017/0147794 A1 | 5/2017 | Harder et al. |
| 2017/0213307 A1 | 7/2017 | Platt et al. |
| 2018/0046780 A1 | 2/2018 | Graiver et al. |
| 2018/0063386 A1 | 3/2018 | Sharma et al. |
| 2018/0165808 A1 | 6/2018 | Bagci et al. |
| 2018/0239524 A1* | 8/2018 | Snibbe ................. G11B 27/34 |
| 2019/0006024 A1 | 1/2019 | Kapoor |
| 2019/0019570 A1 | 1/2019 | Fuertinger et al. |
| 2019/0103192 A1* | 4/2019 | Bent ..................... G16H 10/60 |
| 2019/0259291 A1* | 8/2019 | Pradhan ............... A61B 5/4088 |
| 2019/0261908 A1* | 8/2019 | Alailima ............... A61B 5/7405 |
| 2019/0355459 A1 | 11/2019 | Li et al. |
| 2020/0034690 A1 | 1/2020 | Ghose et al. |
| 2020/0075148 A1 | 3/2020 | Nguyen et al. |
| 2020/0090796 A1 | 3/2020 | Krishnan et al. |
| 2020/0105380 A1 | 4/2020 | Ennist et al. |
| 2020/0176098 A1 | 6/2020 | Lucas et al. |
| 2020/0258599 A1 | 8/2020 | Clark et al. |
| 2020/0258600 A1 | 8/2020 | Will et al. |
| 2020/0321083 A1* | 10/2020 | Vergetis ................. G06F 40/30 |
| 2020/0365239 A1 | 11/2020 | Sabharwal et al. |
| 2020/0411199 A1 | 12/2020 | Shrager et al. |
| 2021/0090694 A1 | 3/2021 | Colley et al. |
| 2021/0097444 A1* | 4/2021 | Bansal ..................... G06N 3/08 |
| 2021/0166330 A1* | 6/2021 | Baker ..................... G06F 9/466 |
| 2021/0235008 A1* | 7/2021 | Su ........................ H04N 23/695 |
| 2021/0240883 A1 | 8/2021 | Bhattacharya et al. |
| 2021/0240884 A1 | 8/2021 | Bhattacharya et al. |
| 2021/0240885 A1 | 8/2021 | Bhattacharya et al. |
| 2021/0240886 A1 | 8/2021 | Bhattacharya et al. |
| 2021/0241144 A1 | 8/2021 | Bhattacharya et al. |
| 2021/0241859 A1 | 8/2021 | Bhattacharya et al. |
| 2021/0241860 A1 | 8/2021 | Bhattacharya et al. |
| 2021/0241861 A1 | 8/2021 | Bhattacharya et al. |
| 2021/0241862 A1 | 8/2021 | Bhattacharya et al. |
| 2021/0241863 A1 | 8/2021 | Bhattacharya et al. |
| 2021/0241864 A1 | 8/2021 | Bhattacharya et al. |
| 2021/0241865 A1 | 8/2021 | Bhattacharya et al. |
| 2021/0319158 A1 | 10/2021 | Bhattacharyya et al. |
| 2022/0374558 A1 | 11/2022 | Patel et al. |
| 2022/0375551 A1 | 11/2022 | Patel et al. |
| 2022/0382935 A1 | 12/2022 | Patel et al. |

FOREIGN PATENT DOCUMENTS

| | | |
|---|---|---|
| WO | 2016024915 A1 | 2/2016 |
| WO | 2016170368 A1 | 10/2016 |
| WO | 2019144116 A1 | 7/2019 |
| WO | 2020188341 A1 | 9/2020 |
| WO | 2021155329 A1 | 8/2021 |
| WO | 2022271876 A1 | 12/2022 |

OTHER PUBLICATIONS

PCT/US2021/015954 , "International Application Serial No. PCT/US2021/015954, International Search Report and Written Opinion mailed Jun. 3, 2021", PCT/US2021/015954, 13 pages.
PCT/US2021/015954 , "International Application Serial No. PCT/US2021/015954, Invitation to Pay Additional Fees and, Where Applicable, Protest Fee mailed Apr. 1, 2021", Cytel Inc., 3 pages.
Chen, Qi , et al., "An optimization framework to combine operable space maximization with design of experiments.", AIChE Journal., 2018, 14 pages.
Grayling , et al., "Admissible multiarm stepped-wedge cluster randomized trial designs", John Wiley & Sons Ltd, 2017, pp. 1103-1119.
PCT/US2021/015954 , "International Application Serial No. PCT/US2021/015954, International Preliminary Report on Patentability mailed Aug. 11, 2022", Cytel Inc., 11 pages.
PCT/US2022/034599 , "International Application Serial No. PCT/US2022/034599, International Search Report and Written Opinion mailed Dec. 5, 2022", Cytel Inc., 17 pages.
PCT/US2022/034599 , "International Application Serial No. PCT/US2022/034599, Invitation to Pay Additional Fees and, Where Applicable, Protest Fee mailed Sep. 28, 2022", Cytel Inc., 3 pages.
Qi , et al., "A Delaunay Triangulation Based Density Measurement for Evolutionary Multi-objective Optimization", Springer Artificial

(56) References Cited

OTHER PUBLICATIONS

Life and Computational Intelligence, Second Australasian Conference ACALCI 2016 Proceedings,, 2016, pp. 183-192.

Sverdlov , "On Optimal Designs for Clinical Trials: An Updated Review", 2019, pp. 1-29.

Zhao , "Systematic data-driven modeling . . . experimental design and hypothesis evaluation", Available from ProQuest Dissertations and Theses Professional. (304875988). Retrieved from https://dialog.proquest.com/professional/docview/304875988?accountid=131, 2009, 142 pages.

21748352.8 , "European Application Serial No. 21748352.8, Extended European Search Report mailed Jan. 31, 2024", Cytel Inc., 7 pages.

Deb, Kalyanmoy , et al., "Evaluating the s-Domination Based Multi-Objective Evolutionary Algorithm for a Quick Computation of Pareto-Optimal Solutions", Massachusetts Institute of Technology, Evolutionary Computation 13(4), 2005, pp. 501-525.

Mozaffari, Ahmad , et al., "An introduction to synchronous self-learning Pareto strategy", 2013, arXiv.org, Cornell University, all pages, all figures, all tables, https://arxiv.org/abs/1312.4132, 2013, 17 pages.

PCT/US2022/034599 , "International Application Serial No. PCT/US2022/034599, International Preliminary Search Report on Patentability and Written Opinion mailed Dec. 14, 2023", Cytel Inc., 9 pages.

\* cited by examiner

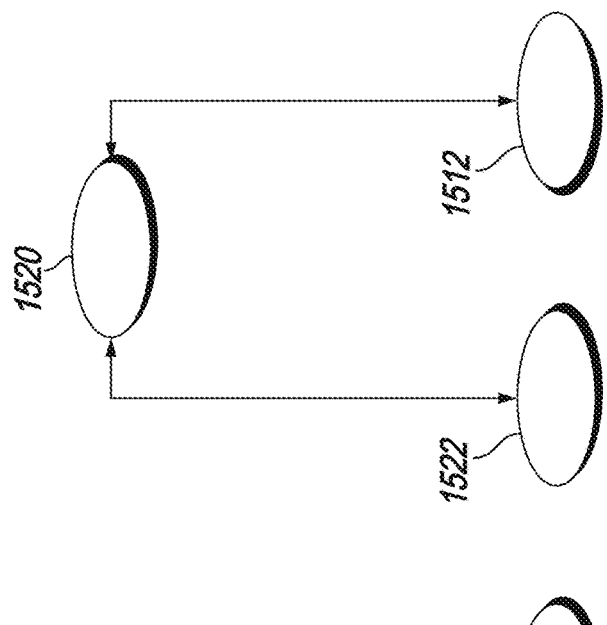
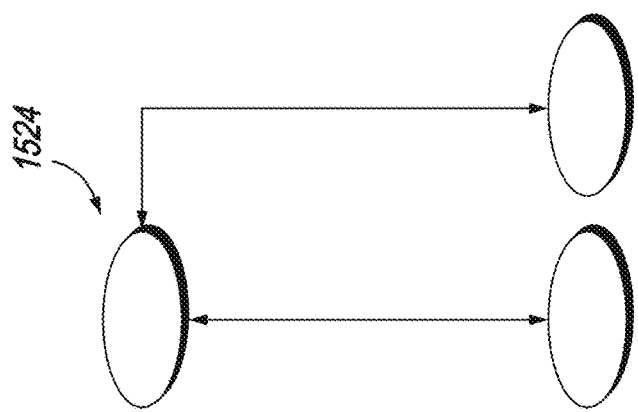
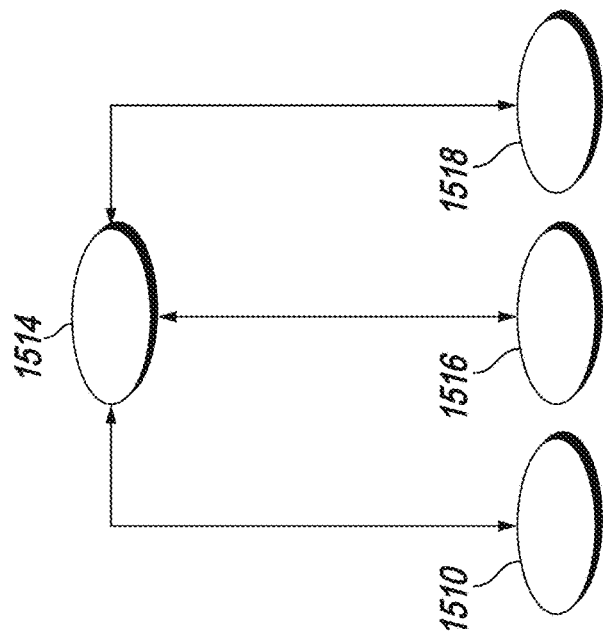
FIG. 15

1600

1610 CONFIGURE EXECUTION FLOW USING CONFIGURABLE INTERFACE

1612 EXECUTE CLINICAL TRIAL DESIGN EVALUATION USING EXECUTION FLOW

1614 RECONFIGURE EXECUTION FLOW USING CONFIGURABLE INTERFACE

1616 EXECUTE CLINICAL TRIAL EVALUATION USING RECONFIGURED EXECUTION FLOW

1710 CONFIGURE EXECUTION FLOW USING CONFIGURABLE INTERFACE

1712 DETERMINE FIRST USER TYPE INTERACTING WITH EXECUTION FLOW

1714 CONFIGURE FIRST VIEW OF EXECUTION FLOW FOR FIRST USER TYPE

1716 DETERMINE SECOND USER TYPE INTERACTING WITH EXECUTION FLOW

1718 CONFIGURE SECOND VIEW OF EXECUTION FLOW FOR SECOND USER TYPE

FIG. 17

3902 — MAXIMIZE ENPV

| $3.73B ENPV | 88.50% PROBABILITY OF SUCCESS |
|---|---|
| 24.48M DISCOUNTED COST | 18.80 STUDY DURATION (MONTHS) |
| 253 SAMPLE SIZE | 107 EVENTS | 15 ACCRUAL (PER MONTH) |

3904 — MAXIMIZE POS

| $2.11B ENPV | 89.64% PROBABILITY OF SUCCESS |
|---|---|
| 21.53M DISCOUNTED COST | 30.26 STUDY DURATION (MONTHS) |
| 280 SAMPLE SIZE | 186 EVENTS | 15 ACCRUAL (PER MONTH) |

3906 — MINIMIZE DISCOUNTED COST

| $2.11B ENPV | 89.64% PROBABILITY OF SUCCESS |
|---|---|
| 21.53M DISCOUNTED COST | 30.26 STUDY DURATION (MONTHS) |
| 280 SAMPLE SIZE | 186 EVENTS | 15 ACCRUAL (PER MONTH) |

3908 — MINIMIZE STUDY DURATION

| $3.73B ENPV | 88.50% PROBABILITY OF SUCCESS |
|---|---|
| 24.48M DISCOUNTED COST | 18.80 STUDY DURATION (MONTHS) |
| 253 SAMPLE SIZE | 107 EVENTS | 15 ACCRUAL (PER MONTH) |

3910 — FILTERS

- EXPECTED NPV
- PROB. OF SUCCESS
- DISCOUNTED COST
- STUDY DURATION

FIG. 39

| POWER | COST | DURATION | EPSET | PSET |
|---|---|---|---|---|
| 0.954 | 25091350 | 30.63245 | 1 | 1 |
| 0.924 | 20466450 | 34.96243 | 2 | 2 |
| 0.926 | 22859250 | 26.09028 | 3 | 3 |
| 0.952 | 23704850 | 30.41021 | 4 | 4 |
| 0.927 | 20466450 | 36.33291 | 5 | 5 |
| 0.922 | 22502700 | 26.09185 | -3 | 6 |
| 0.952 | 24487550 | 29.90601 | -1 | 7 |
| 0.919 | 20466450 | 32.87677 | -2 | 8 |
| 0.927 | 22814550 | 26.10527 | 9 | 9 |
| 0.951 | 23704850 | 28.5557 | -4 | 10 |
| 0.924 | 20466450 | 34.96254 | -2 | 11 |
| 0.928 | 22863350 | 26.16529 | 12 | 12 |
| 0.951 | 24597450 | 28.18466 | -1 | 13 |
| 0.927 | 20466450 | 36.33304 | -5 | 14 |
| 0.939 | 22952400 | 26.28304 | 15 | 15 |
| 0.95 | 23701800 | 29.02333 | -4 | 16 |
| 0.919 | 20466450 | 32.87677 | -2 | 17 |
| 0.949 | 24112800 | 27.59833 | -1 | 19 |
| 0.924 | 20466450 | 34.96247 | -2 | 20 |
| 0.927 | 22853650 | 26.30556 | -9 | 21 |

THE BOLD CELLS SHOWS THE SORTING ORDER

THE COLUMN 'PSET' INDICATED THE FULL SET OF PARETO DESIGNS WITH +ve ID

THE COLUMN 'EPSET' INDICATES THE ε-PARETO DESIGNS WITH +ve ID

THE NEGATIVE VALUE INDICATES THE DOMINANT PARETO DESIGN

THIS DESIGN IS A PARETO DESIGN IN THE FULL SET DOMINATED BY THE PARETO DESIGN 3 IN THE ε-PARETO SET

12 OUT OF THESE 21 PARETO DESIGNS ARE FILTERED OUT BY THE ε-FILTER

ADDITIONAL PAS CREATED CLUSTERS OF DOMINATED DESIGNS FOR EACH PARETO POINT

*FIG. 49*

| DESIGN ID | POWER | COST ($M) | DURATION (MO.) |
|---|---|---|---|
| 1 | 0.954 | 25.1 | 30.6 |
| 4 | 0.952 | 23.7 | 30.4 |
| 54 | 0.943 | 23.3 | 26.4 |
| 15 | 0.939 | 23.0 | 26.3 |
| 12 | 0.928 | 22.9 | 26.2 |
| 5 | 0.927 | 20.5 | 36.3 |
| 9 | 0.927 | 22.8 | 26.1 |
| 3 | 0.926 | 22.9 | 26.1 |
| 2 | 0.924 | 20.5 | 35.0 |

| SIMCUBE ROW # | SIM ID | %EVENTS OBSERVERED AT INTERIM | MIN PROMISING ZONE POINT | MAX PROMISING ZONE POINT | MAX EVENTS MULTIPLIER | MAX SUBJS MULTIPLIER | ADAPTIVE Wt1 | ADAPTIVE Wt2= 1-Wt1 | KEY | | | | | |
|---|---|---|---|---|---|---|---|---|---|---|---|---|---|---|
| 1 | 1 | 40 | 0.2 | 0.9 | 1 | 1 | 0.4 | 0.5 | 1 | 1 | 1 | 1 | 1 | 1 |
| 2 | 2 | 40 | 0.2 | 0.9 | 1 | 1 | 0.5 | 0.5 | 1 | 1 | 1 | 1 | 1 | 2 |
| 3 | | | | | | | | | | | | | | |
| 4 | | | | | | | | | | | | | | |
| 5 | 3 | 40 | 0.2 | 0.9 | 1 | 1.5 | 0.4 | 0.5 | 1 | 1 | 1 | 1 | 2 | 1 |
| 6 | 4 | 40 | 0.2 | 0.9 | 1 | 1.5 | 0.5 | 0.5 | 1 | 1 | 1 | 1 | 2 | 2 |
| 7 | | | | | | | | | | | | | | |
| 8 | | | | | | | | | | | | | | |
| 9 | 5 | 40 | 0.2 | 0.9 | 1 | 1.777778 | 0.4 | 0.5 | 1 | 1 | 1 | 1 | 3 | 1 |
| 10 | 6 | 40 | 0.2 | 0.9 | 1 | 1.777778 | 0.5 | 0.5 | 1 | 1 | 1 | 1 | 3 | 2 |
| 11 | | | | | | | | | | | | | | |
| 12 | | | | | | | | | | | | | | |
| 13 | 7 | 40 | 0.2 | 0.9 | 1.333333 | 1 | 0.4 | 0.5 | 1 | 1 | 1 | 2 | 1 | 1 |
| ... | ... | ... | ... | ... | ... | ... | ... | ... | ... | ... | ... | ... | ... | ... |
| 1724 | 754 | 70 | 0.5 | 0.99 | 1.733333 | 1.5 | 0.7 | 0.3 | 4 | 3 | 3 | 4 | 2 | 4 |
| 1725 | 755 | 70 | 0.5 | 0.99 | 1.733333 | 1.777778 | 0.5 | 0.3 | 4 | 3 | 3 | 4 | 3 | 2 |
| 1726 | | | | | | | | | 4 | 3 | 3 | 4 | 3 | 3 |

FIG. 171(b)

| 1RZAQ122 | SELECT DESIGN 1 | SELECT DESIGN 2 | SELECT DESIGN 3 | SELECT DESIGN N |
|---|---|---|---|---|
| DISTANCE WITHIN | 3 | | | |
| SCORE WITHIN ε | 5% | | | |
| IF | 70 | | | |
| PZMIN | 0.2 | | | |
| PZSHAPE | 0.95 | | | |
| MAXE | 1.533333 | | | |
| MAXS | 1.777778 | | | |
| WEIGHT1 | 0.5 | | | |
| WEIGHT2 | 0.5 | | | |
| ACCRUAL | 16.875 | | | |
| CTRL | 5 | | | |
| HR | 0.69 | | | |
| POWER | 0.982 | | | |
| COST | 23234700 | | | |
| DURATION | 29.17565919 | | | |
| SCORE | 0.856352279 | 0.856352279 | 0.8499182 | |

PROJECT 1

INPUT ADVISOR | TRADEOFF ADVISOR

- 🗋 PLANS
- ≡ DESIGNS
- ⚛ RESPONSE
- ⊕ ENROLLMENT
- 🗋 COSTS
- ⊞ REVENUES
- ⚔ SCORING
- ⊚ COLLECTIONS

0
MODELS

[SIMULATE]

⚔ SCORING

YOU MUST SELECT EXACTLY THREE CRITERIA TO CALCULATE A PERFORMANCE SCORE.
THE WEIGHT MUST ADD UP TO 100%

| | WEIGHT (%) | THRESHOLD VALUE (OPTIONAL) |
|---|---|---|
| ☑ MAXIMIZE POWER | 30 | |
| ☐ MINIMIZE SAMPLE SIZE | | |
| ☑ MINIMIZE STUDY DURATION | 60 | |
| ☑ MINIMIZE STUDY COST | 10 | |

PROJECT 1

INPUT ADVISOR — TRADEOFF ADVISOR

- PLANS
- DESIGNS
- RESPONSE
- ENROLLMENT
- COSTS
- REVENUES
- SCORING
- COLLECTIONS

540 MODELS

SIMULATE

◇ COLLECTIONS

NUMBER OF SIMULATION RUN: 1000

RANDOM NUMBER SEED: CLOCK

COLLECTION 1

PLAN: OS

TARGET POPULATION: MULTIPLE MYELOMA

CONTROL ARM: SoC

TREATMENT ARM: PTX171

PRIMARY ENDPOINT: OS

RESPONSE SET(S): BASE CASE X

ENROLLMENT SET(S): BASE CASE X

DESIGN SET(S):

CLOSE

INTERACTIVE TRIAL DESIGN PLATFORM

CROSS-REFERENCE TO RELATED APPLICATIONS

This application is a continuation of International Application No. PCT/US21/15954 filed Jan. 30, 2021 entitled "TRIAL DESIGN PLATFORM."

International Application No. PCT/US21/15954 filed Jan. 30, 2021 entitled "TRIAL DESIGN PLATFORM" claims the benefit of priority to U.S. Provisional Patent Application Ser. No. 62/968,874, filed Jan. 31, 2020, and entitled "CLINICAL TRIAL DESIGN PLATFORM"; U.S. Provisional Patent Application Ser. No. 63/002,197, filed Mar. 30, 2020, and entitled "CLINICAL TRIAL DESIGN PLATFORM"; U.S. Provisional Patent Application Ser. No. 63/002,253, filed Mar. 30, 2020, and entitled "CLINICAL TRIAL DESIGN PLATFORM"; U.S. Provisional Patent Application Ser. No. 63/037,977, filed Jun. 11, 2020, and entitled "CLINICAL TRIAL DESIGN PLATFORM"; U.S. Provisional Patent Application Ser. No. 63/085,700, filed Sep. 30, 2020, and entitled "CLINICAL TRIAL DESIGN PLATFORM"; and U.S. Provisional Patent Application Ser. No. 63/086,474, filed Oct. 1, 2020, and entitled "CLINICAL TRIAL DESIGN PLATFORM".

This application claims the benefit of priority to U.S. Provisional Patent Application Ser. No. 62/968,874, filed Jan. 31, 2020, and entitled "CLINICAL TRIAL DESIGN PLATFORM"; U.S. Provisional Patent Application Ser. No. 63/002,197, filed Mar. 30, 2020, and entitled "CLINICAL TRIAL DESIGN PLATFORM"; U.S. Provisional Patent Application Ser. No. 63/002,253, filed Mar. 30, 2020, and entitled "CLINICAL TRIAL DESIGN PLATFORM"; U.S. Provisional Patent Application Ser. No. 63/037,977, filed Jun. 11, 2020, and entitled "CLINICAL TRIAL DESIGN PLATFORM"; U.S. Provisional Patent Application Ser. No. 63/085,700, filed Sep. 30, 2020, and entitled "CLINICAL TRIAL DESIGN PLATFORM"; and U.S. Provisional Patent Application Ser. No. 63/086,474, filed Oct. 1, 2020, and entitled "CLINICAL TRIAL DESIGN PLATFORM".

All of the above patent documents are incorporated herein by reference in their entirety.

SUMMARY

The success and the performance of a clinical trial depends on the design of the trial. Different choices for the design of a trial may result in very different costs, completion times, and/or other performance parameters for the trial. A trial design platform, systems, and methods are described herein for evaluation and/or comparison of designs for a clinical trial. Evaluation and/or comparison may include a large number of design options. Embodiments of the current disclosure may be used to evaluate hundreds, thousands, or even millions of design options for a clinical trial and may be used to find the optimal or near-optimal design for a trial.

The success of the clinical trial often depends on the ability to recruit a satisfactory number of patients, suitable to participate in the clinical trial. The number of suitable patients available to be recruited for a clinical trial is, in turn, typically a function of the sites selected for the clinical trial. The selection of sites for a clinical trial may include considerations and tradeoffs between hundreds or even thousands of site selections. Embodiments of the current disclosure may provide for a site selection platform, systems, and methods for evaluation and/or comparison of site selection options for a clinical trial.

The success of the clinical trial often depends on the availability of resources needed to conduct the clinical trial. The selection of sites for a clinical trial, with respect to optimizing available resources, may include considerations and tradeoffs between hundreds or even thousands of site selections. Embodiments of the current disclosure may provide for a resource optimization platform, systems, and methods for evaluation and/or comparison of site selection options with respect to optimizing resource availability for a clinical trial. In embodiments, the platform, systems, and methods described herein may be used to evaluate hundreds, thousands, or even millions of site selection options for a clinical trial and may be used to find the optimal or near-optimal resource availability for a trial.

BRIEF DESCRIPTION OF THE FIGURES

FIG. 15 is a diagram of user types corresponding to the views of FIG. 14, in accordance with an embodiment of the current disclosure;

FIG. 16 is a flow chart depicting a method for configuring and managing an execution flow for a clinical trial design evaluation, in accordance with an embodiment of the current disclosure;

FIG. 17 is a flow chart depicting another method for configuring and managing an execution flow for a clinical trial design evaluation, in accordance with an embodiment of the current disclosure;

FIG. 39 shows aspects of a card interface, in accordance with an embodiment of the current disclosure;

FIG. 49 is a table showing aspects of Pareto analysis in accordance with an embodiment of the current disclosure;

FIG. 75 is a diagram of a set of recommended clinical trial designs, in accordance with an embodiment of the current disclosure;

FIG. 120 is a diagram of a platform/system for generating an interactive interface for exploration/evaluation of spaces related to patient recruitment for a clinical trial, in accordance with an embodiment of the current disclosure;

FIG. 121 is a flow chart depicting a method for generating an interactive interface for exploration/evaluation of spaces related to patient recruitment for a clinical trial, in accordance with an embodiment of the current disclosure;

FIG. 122 is a schematic diagram of an apparatus for generating an interactive interface for exploration/evaluation of spaces related to patient recruitment for a clinical trial, in accordance with an embodiment of the current disclosure;

FIG. 123 is a flow chart depicting a method for updating patient recruitment, in accordance with an embodiment of the current disclosure;

FIG. 124 is a flow chart depicting another method for updating patient recruitment, in accordance with an embodiment of the current disclosure;

FIG. 125 is a block diagram of a platform for providing global optimization of resource availability for clinical trial designs, in accordance with an embodiment of the current disclosure;

FIG. 126 is a diagram of a process for globally optimizing resource availability for clinical trial designs, in accordance with an embodiment of the current disclosure;

FIG. 127 is a schematic diagram of an apparatus for determining a site selection to globally optimize available resources for a clinical trial, in accordance with an embodiment of the current disclosure;

FIG. 128 is a schematic diagram of another apparatus for determining a site selection to globally optimize available resources for a clinical trial, in accordance with an embodiment of the current disclosure;

FIG. 129 is a flow chart depicting a method for determining a site selection to globally optimize available resources for a clinical trial, in accordance with an embodiment of the current disclosure;

FIG. 130 is a flow chart depicting another method for determining a site selection to globally optimize available resources for a clinical trial, in accordance with an embodiment of the current disclosure;

FIG. 131 is a flow chart depicting another method for determining a site selection to globally optimize available resources for a clinical trial, in accordance with an embodiment of the current disclosure;

Figure 132:
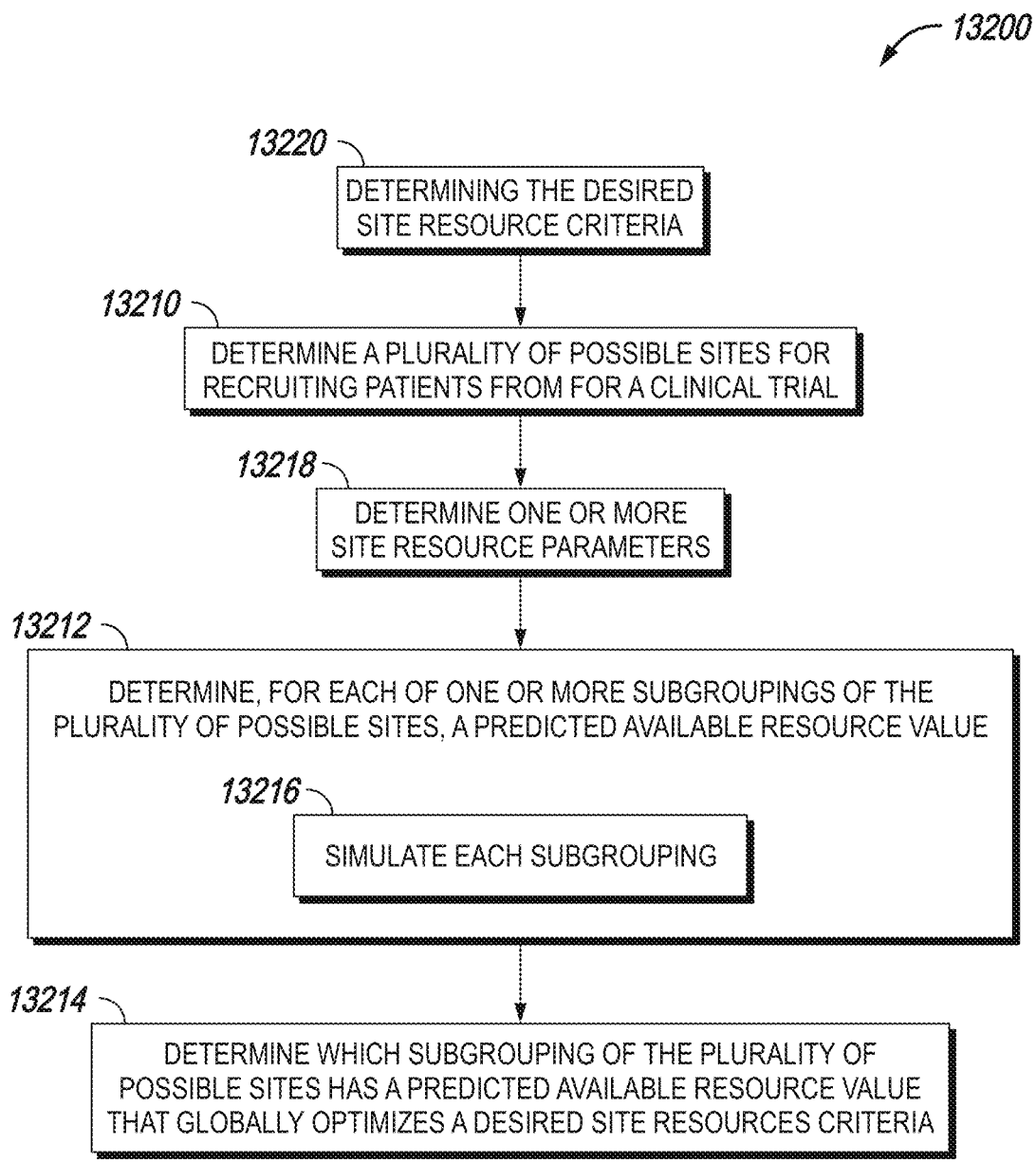
Figure 133:
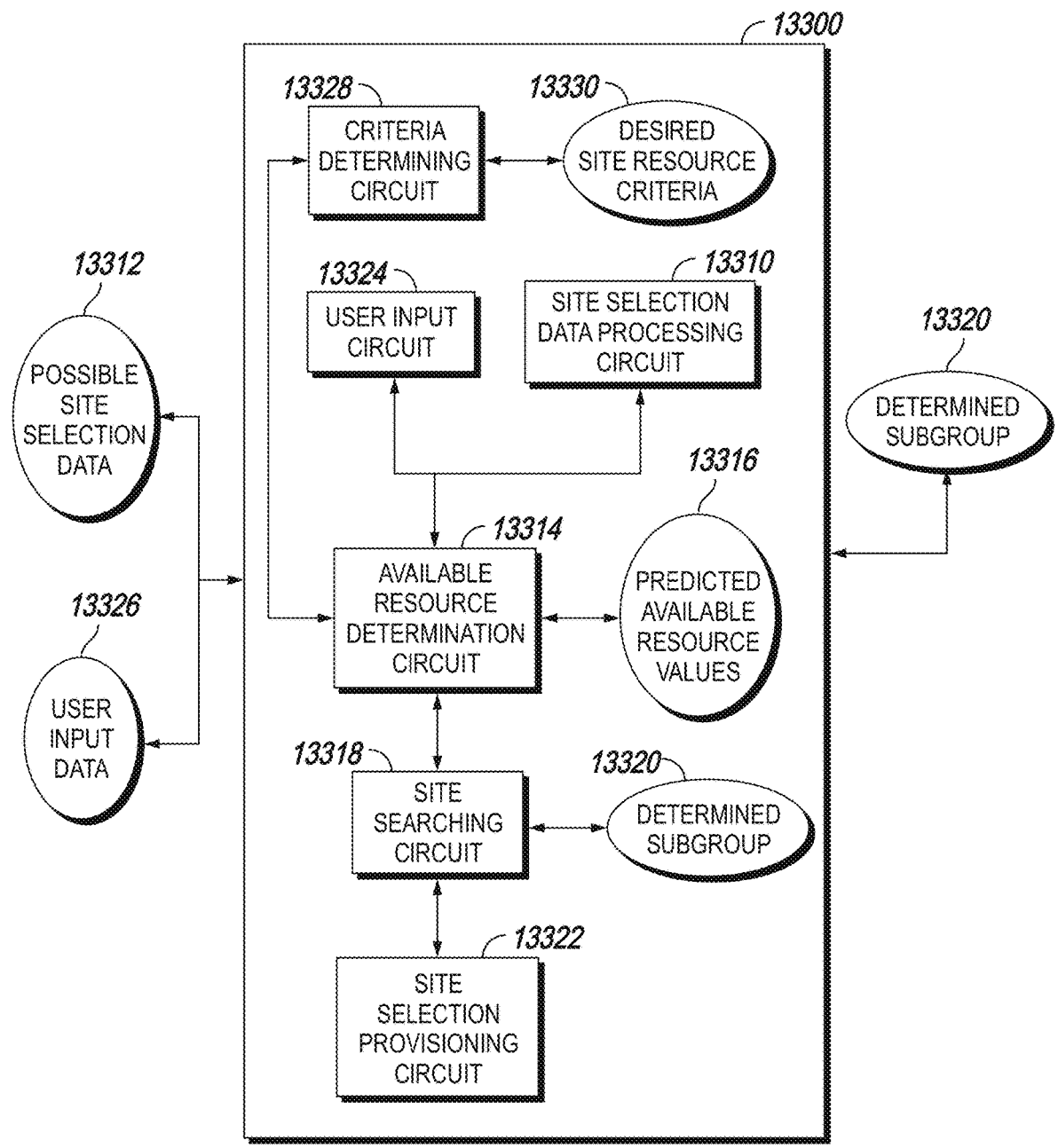
Figure 134:
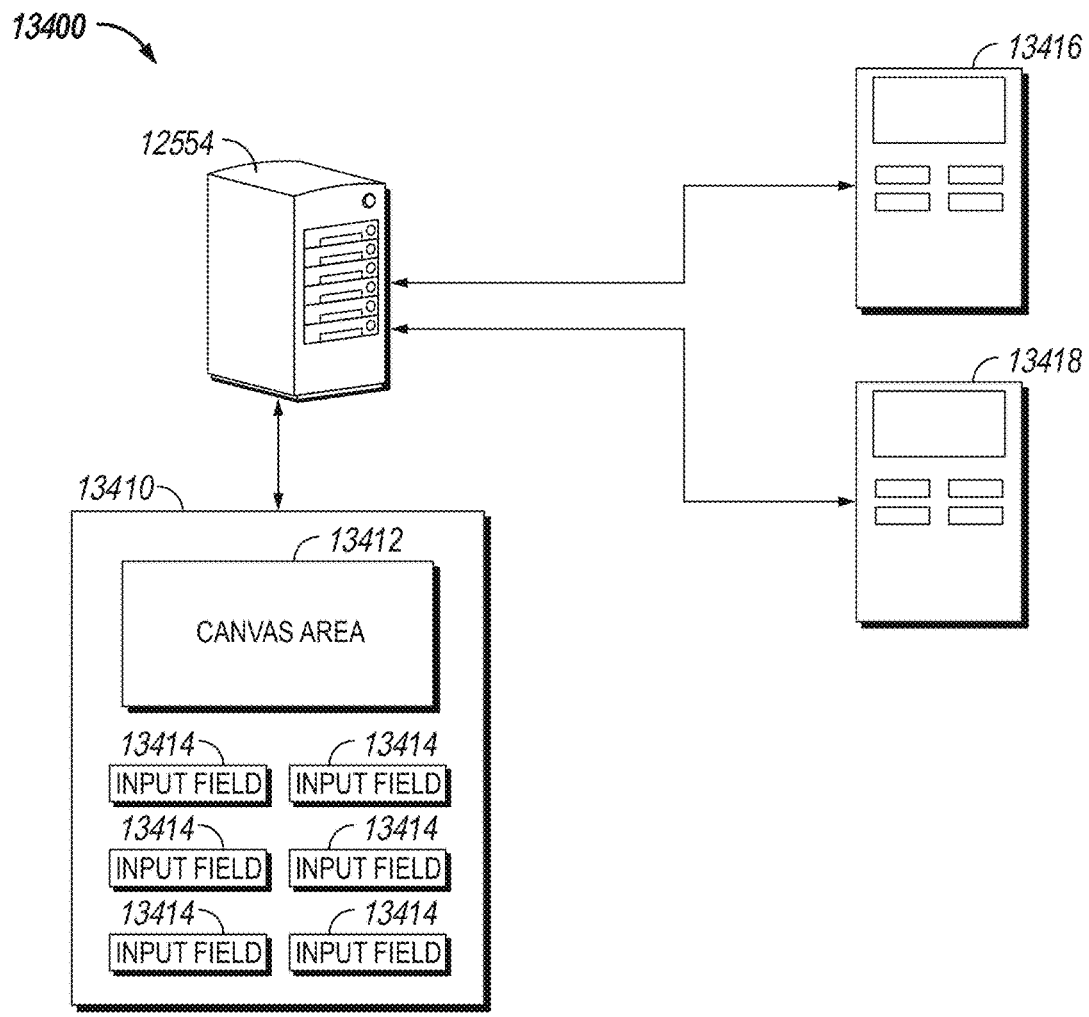
Figure 135:
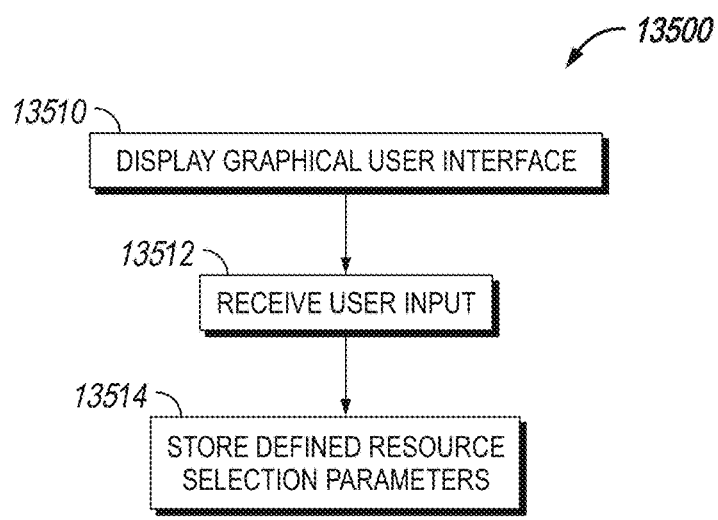
Figure 136:
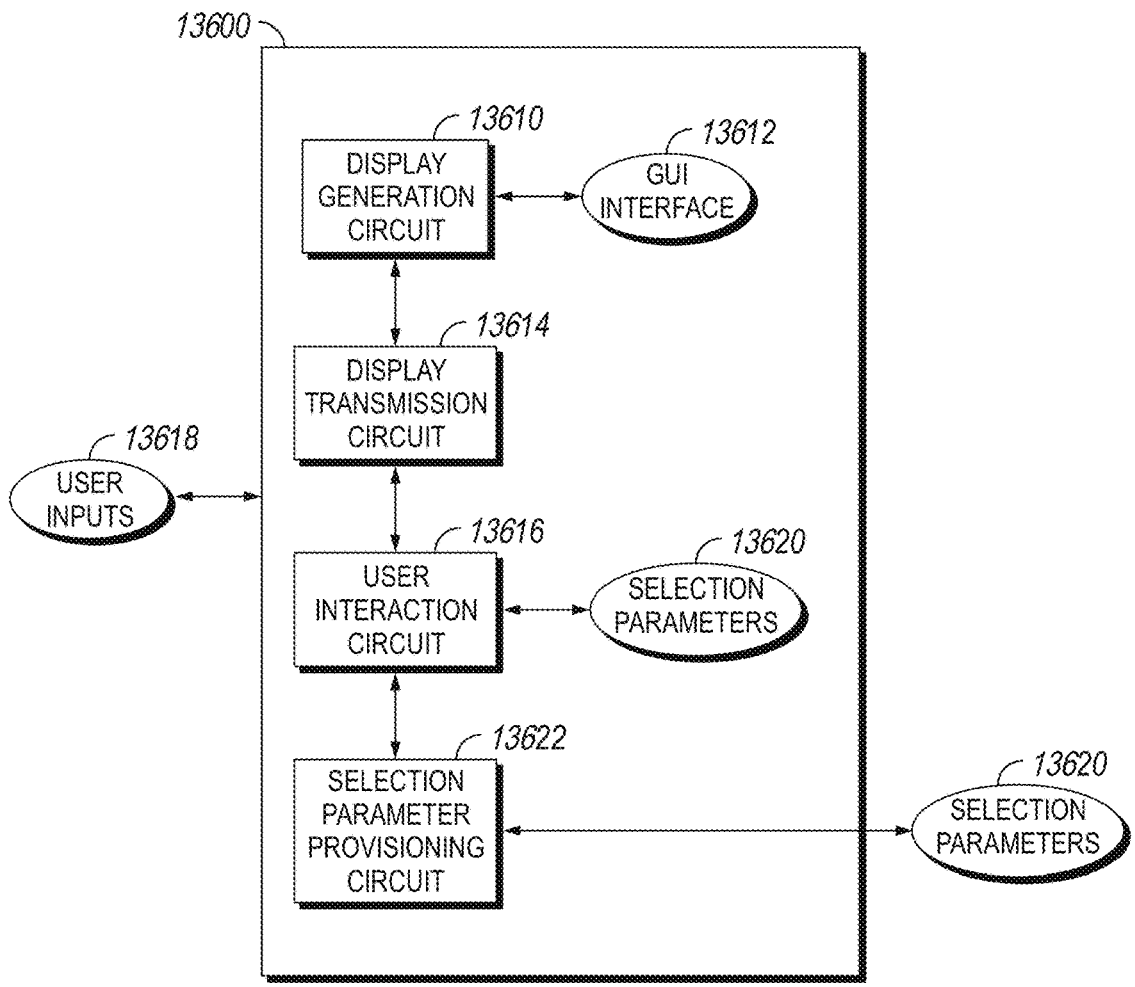
Figure 137:
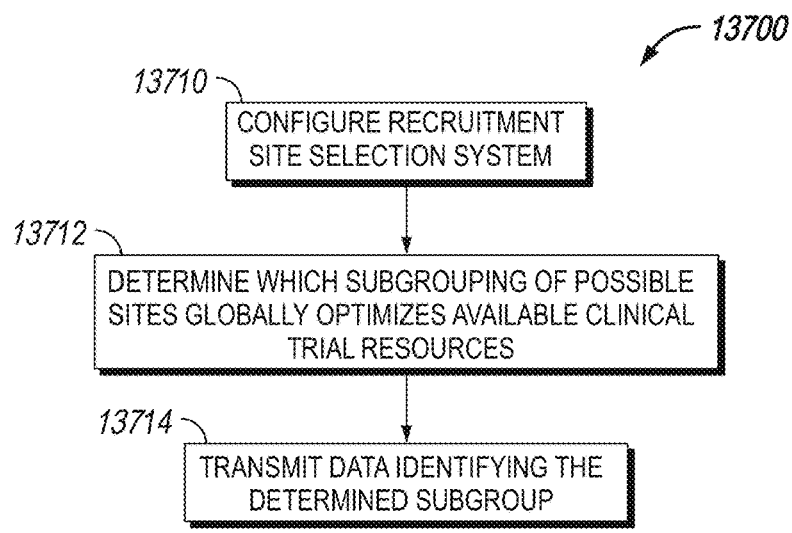
Figure 138:
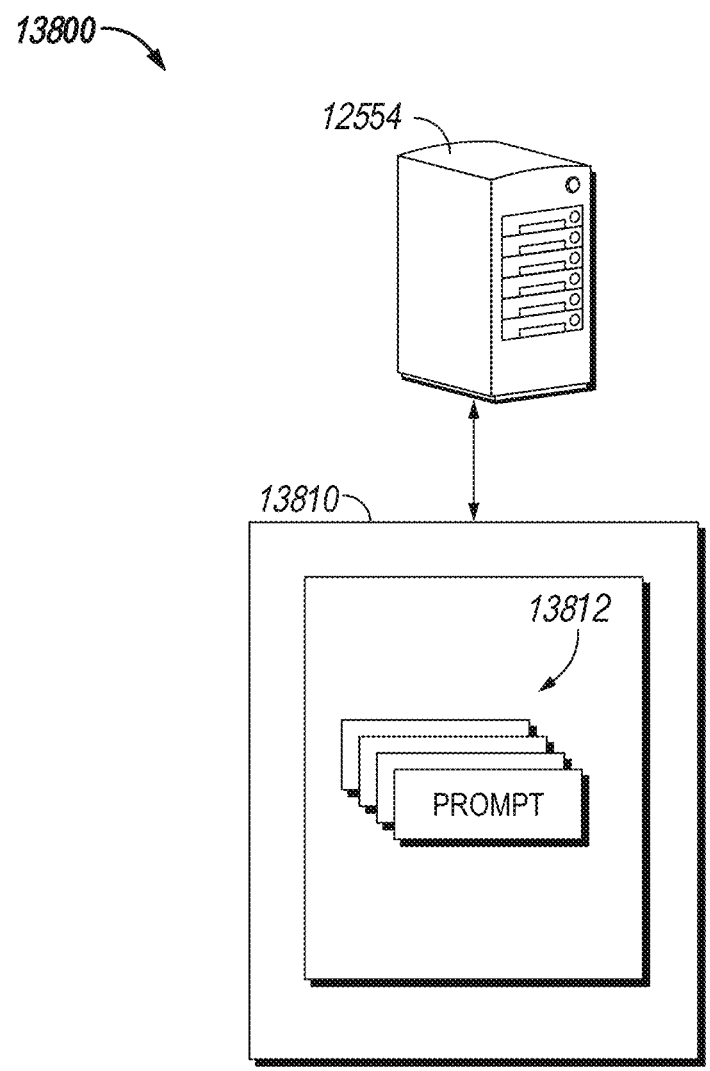
Figure 139:
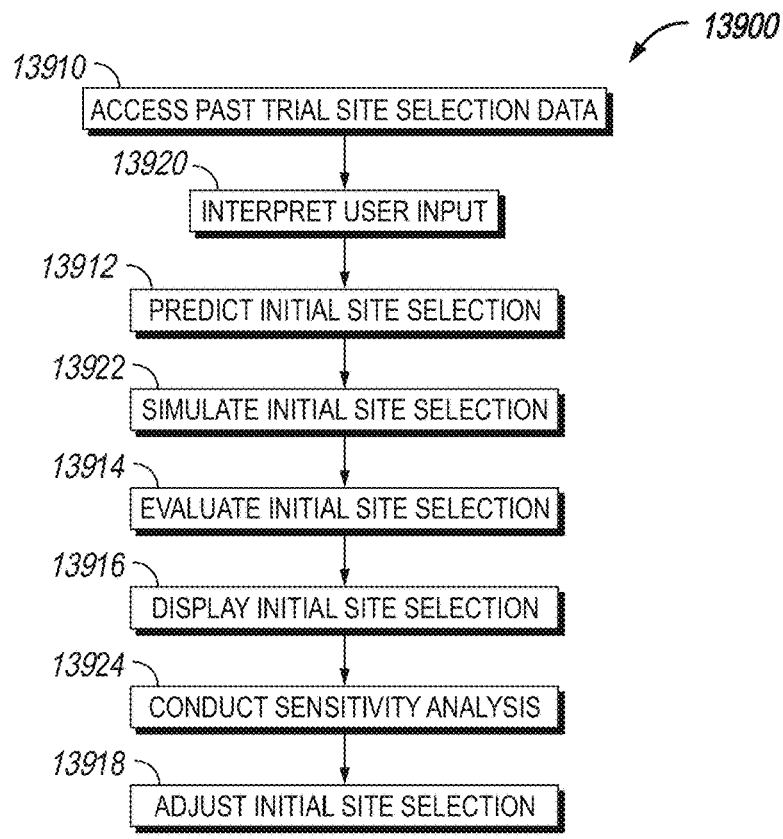
Figure 140:
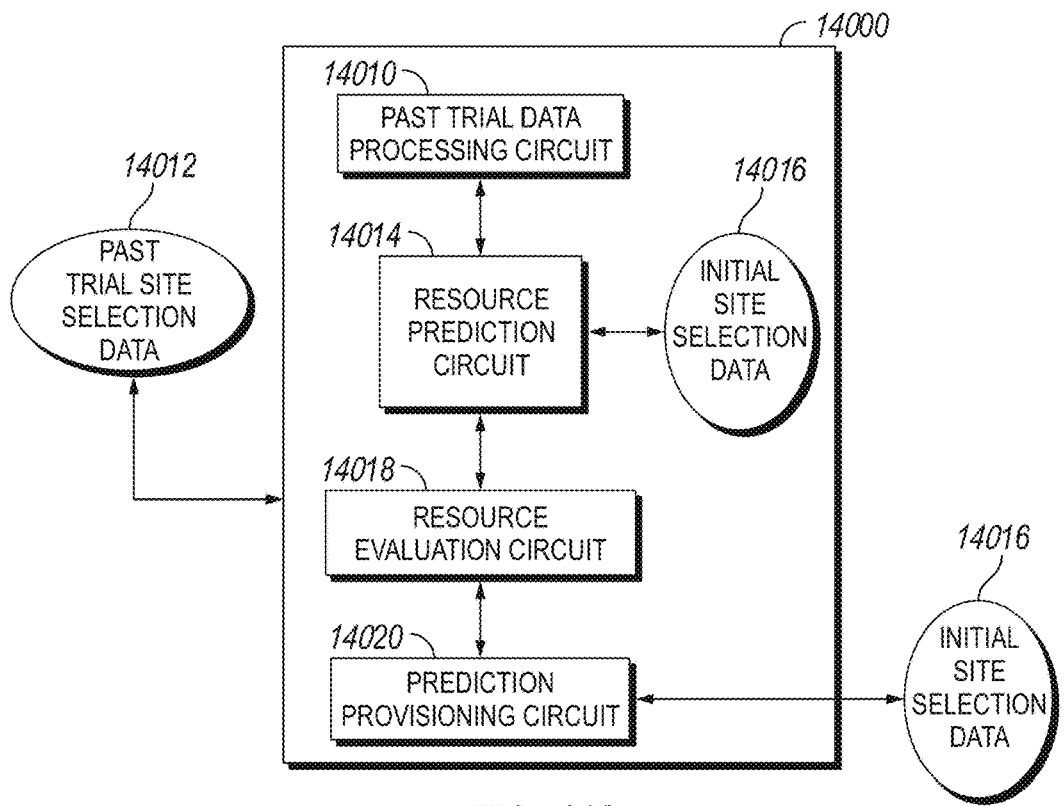
Figure 141:
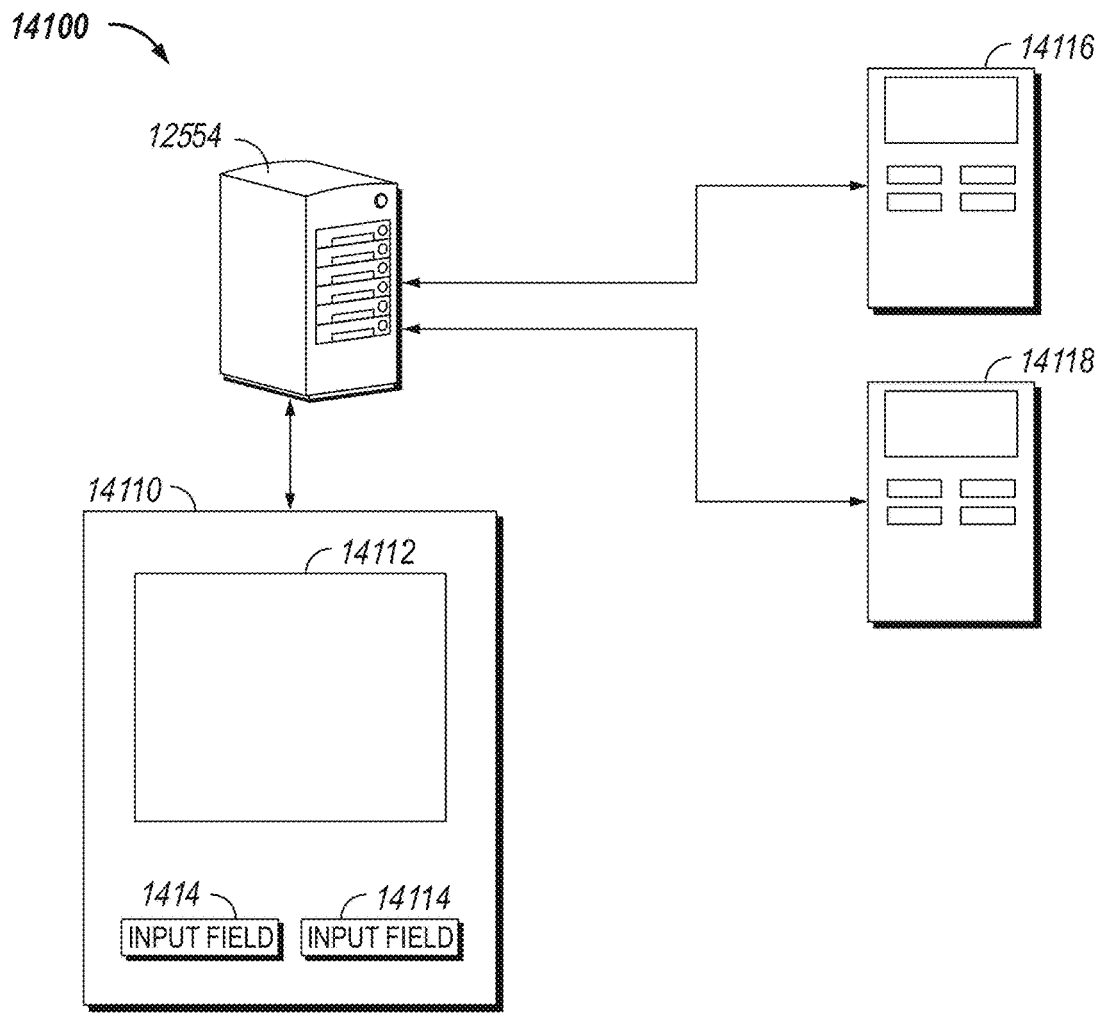
Figure 142:
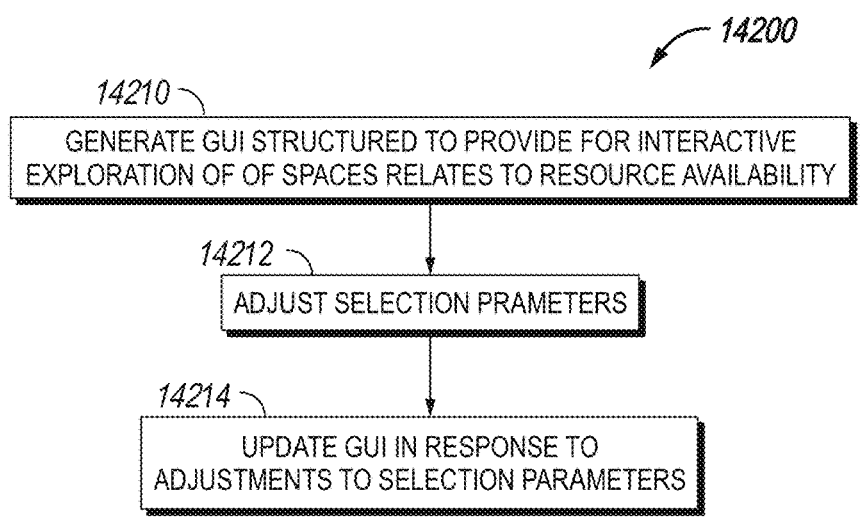
Figure 143:
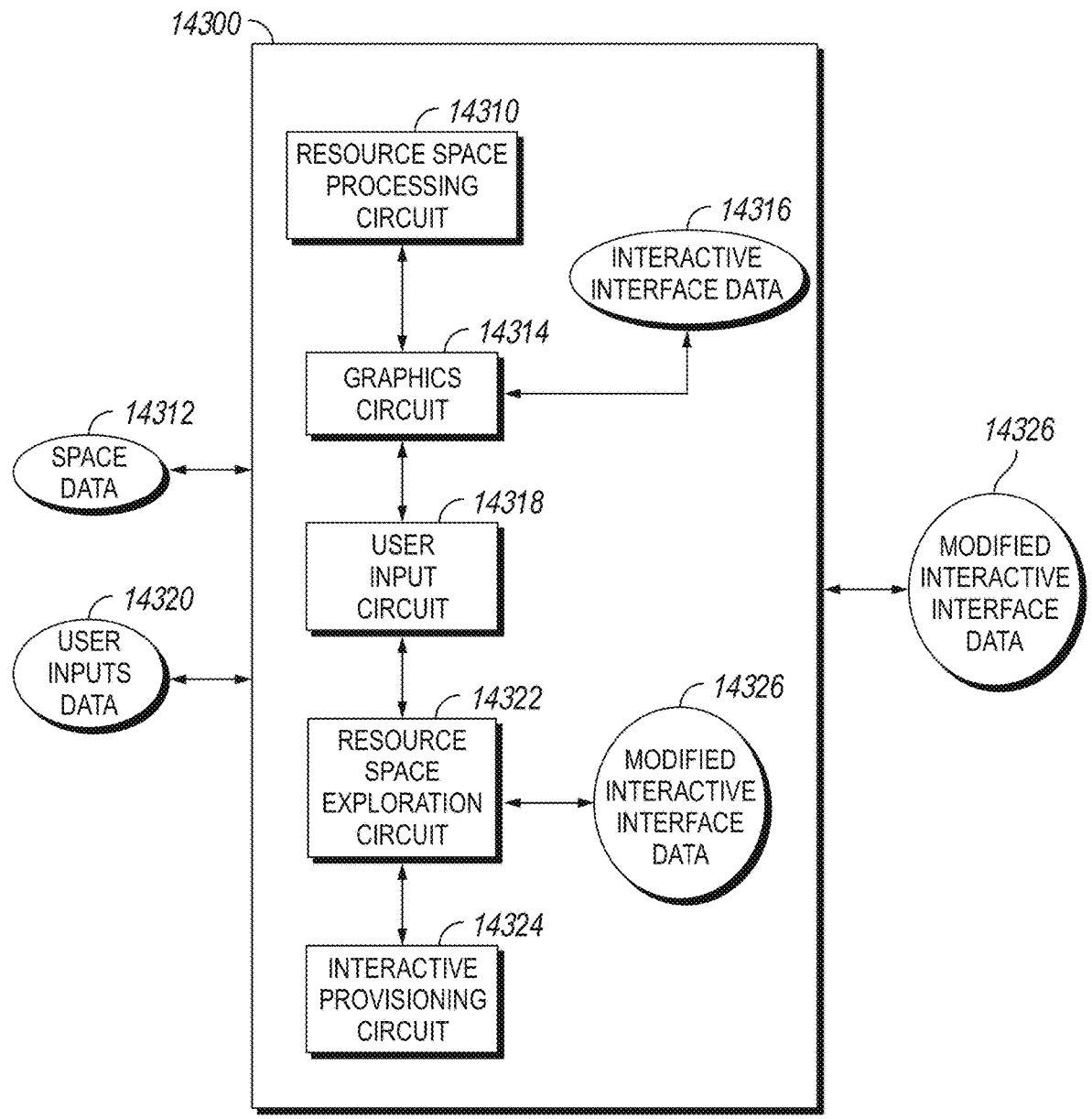
Figure 144:
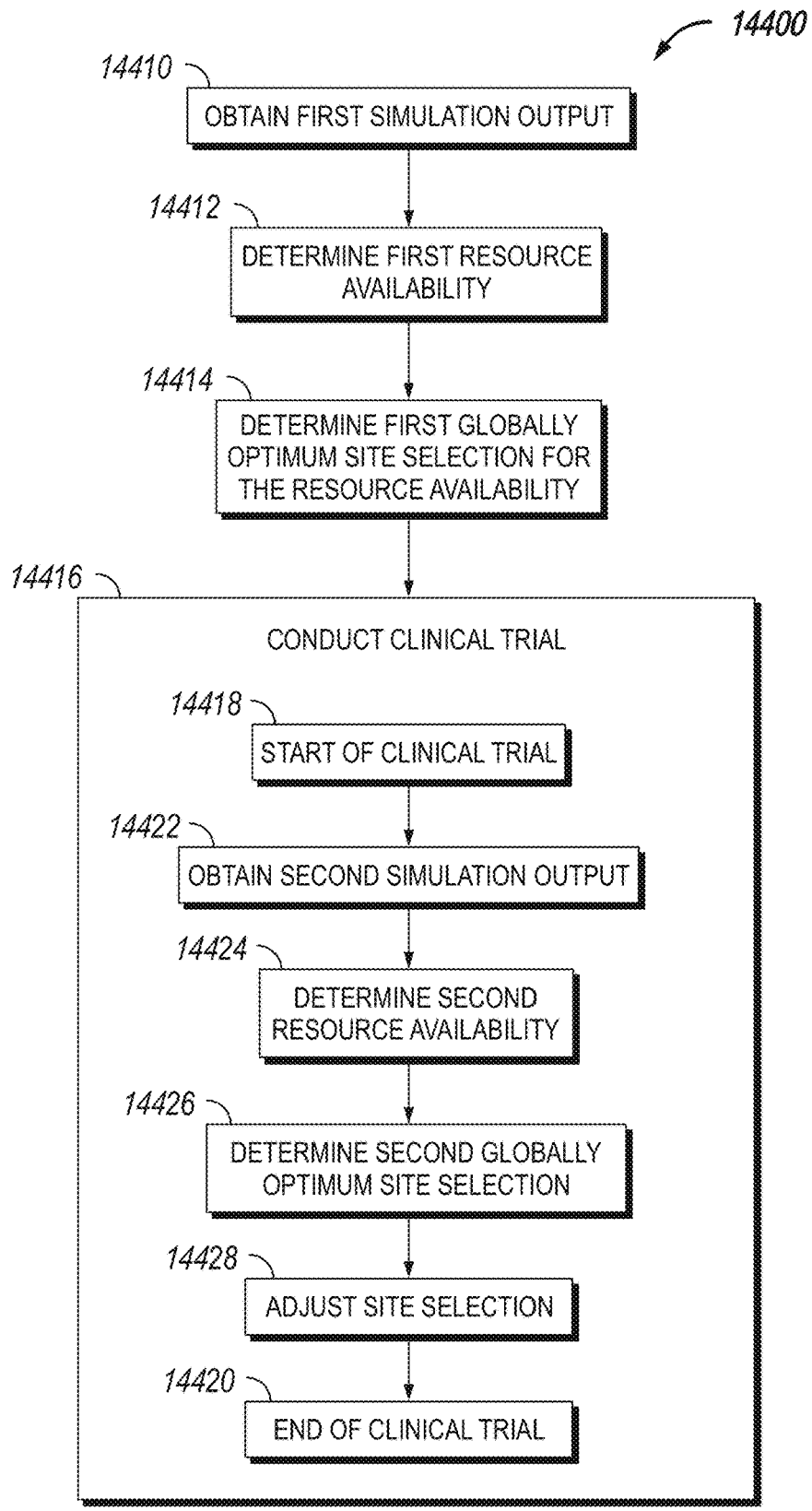
Figure 145:
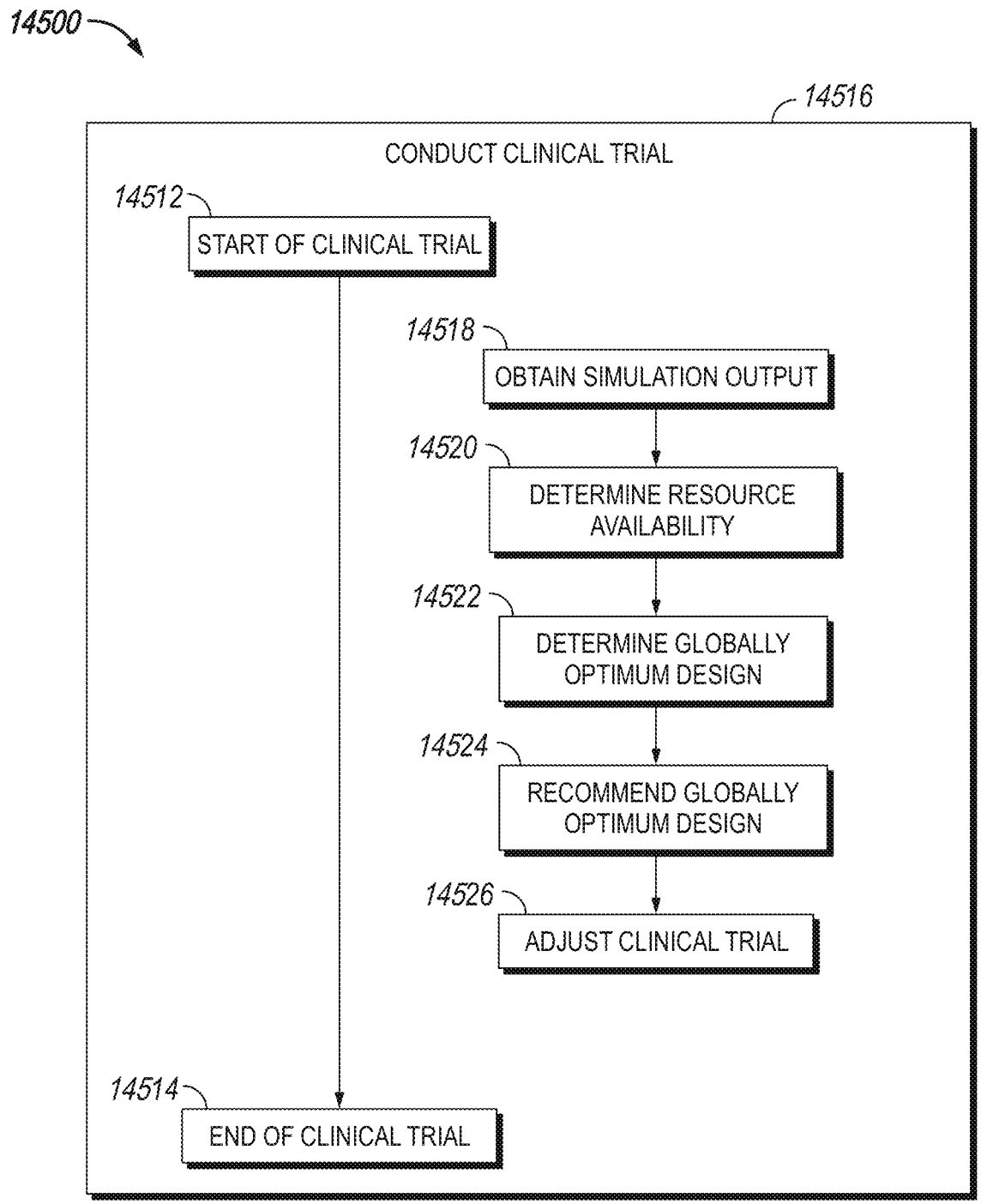
Figure 146:
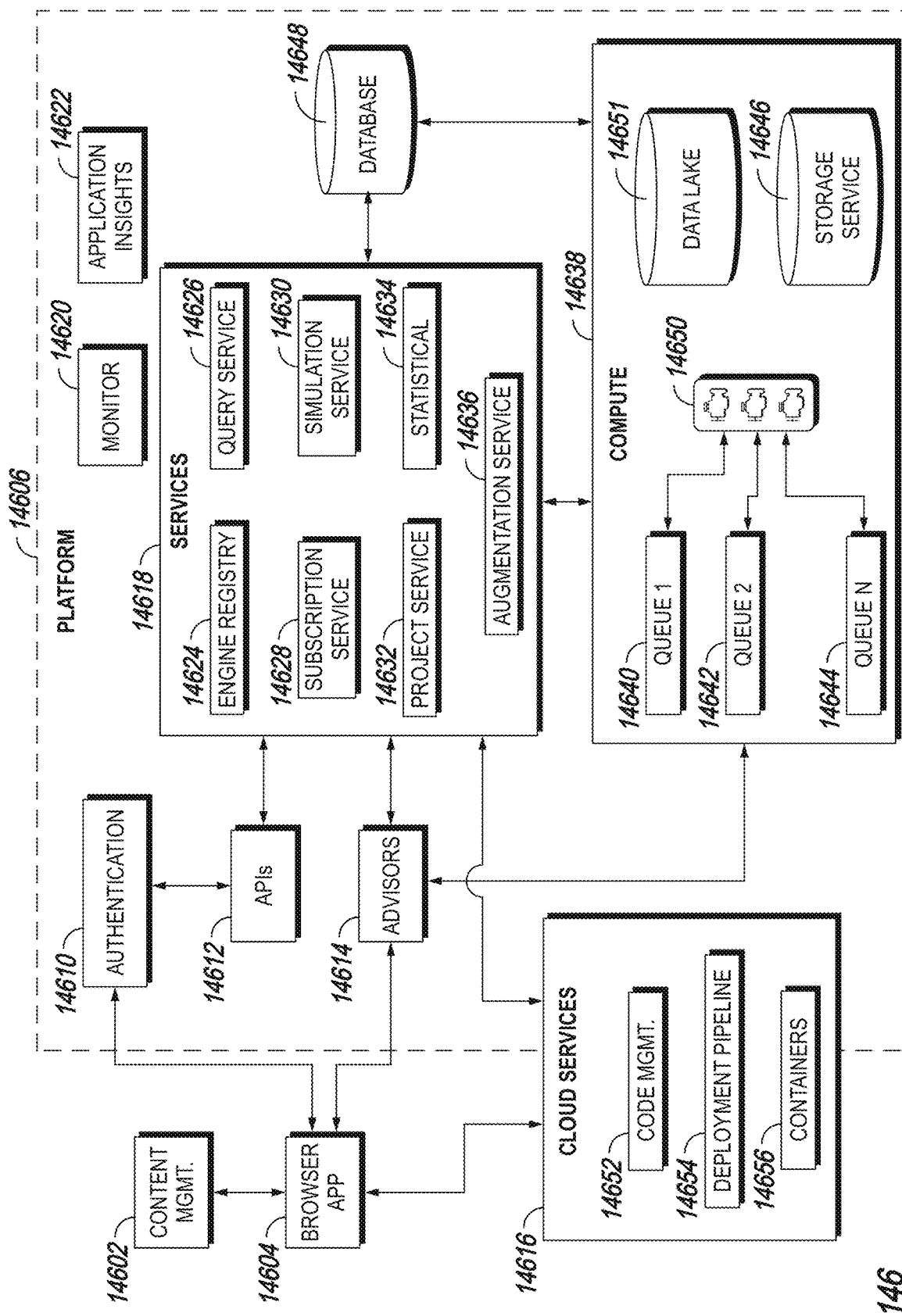
Figure 147:
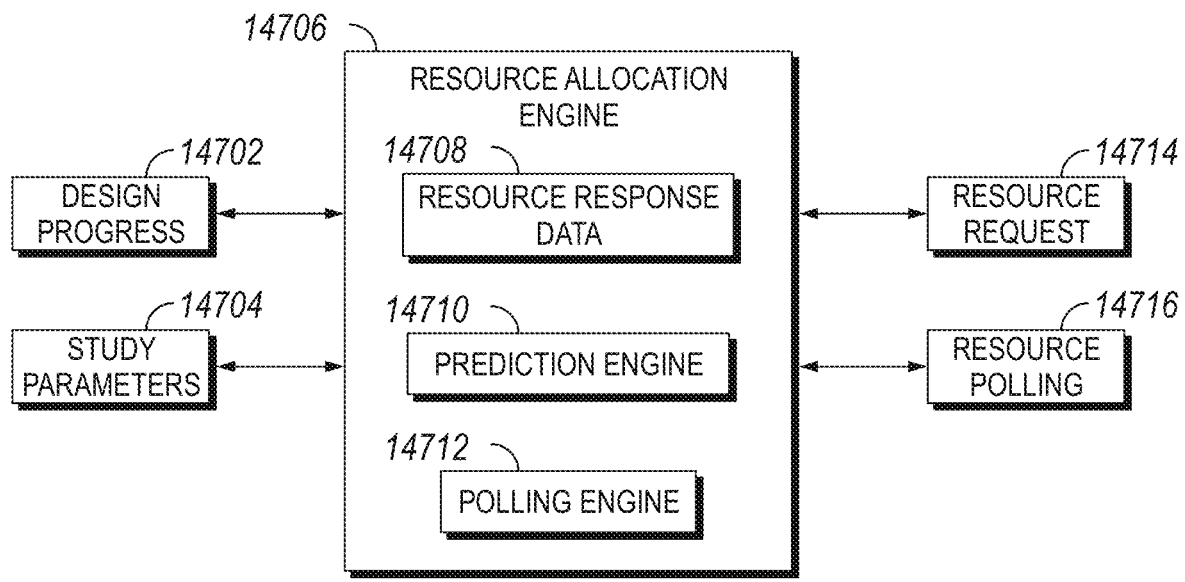
Figure 148:
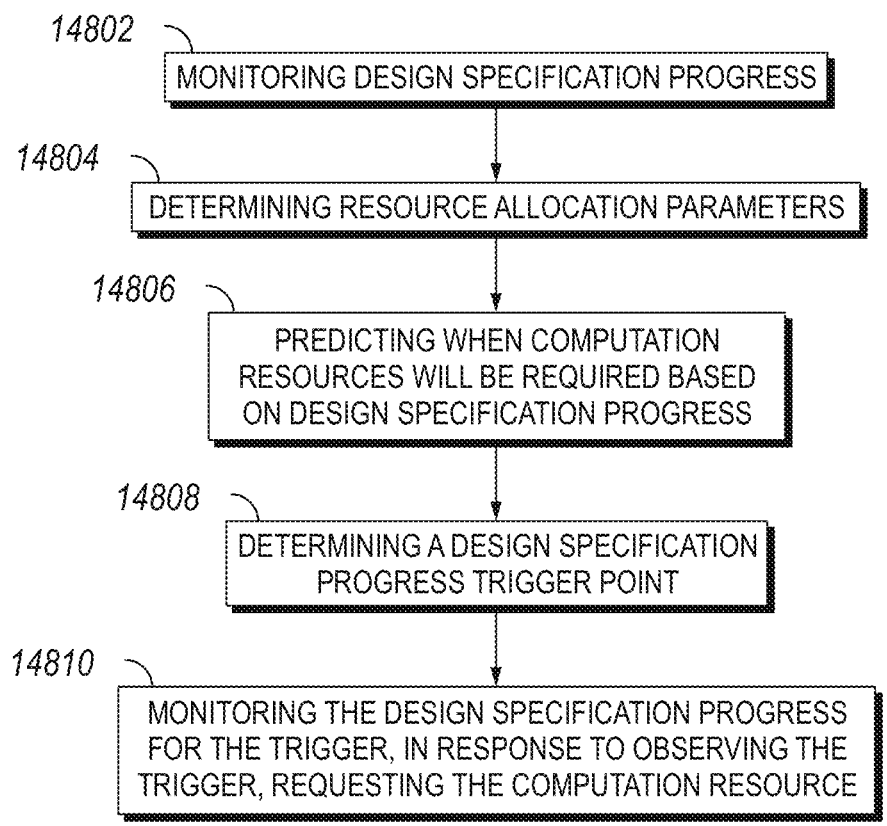
Figure 149:
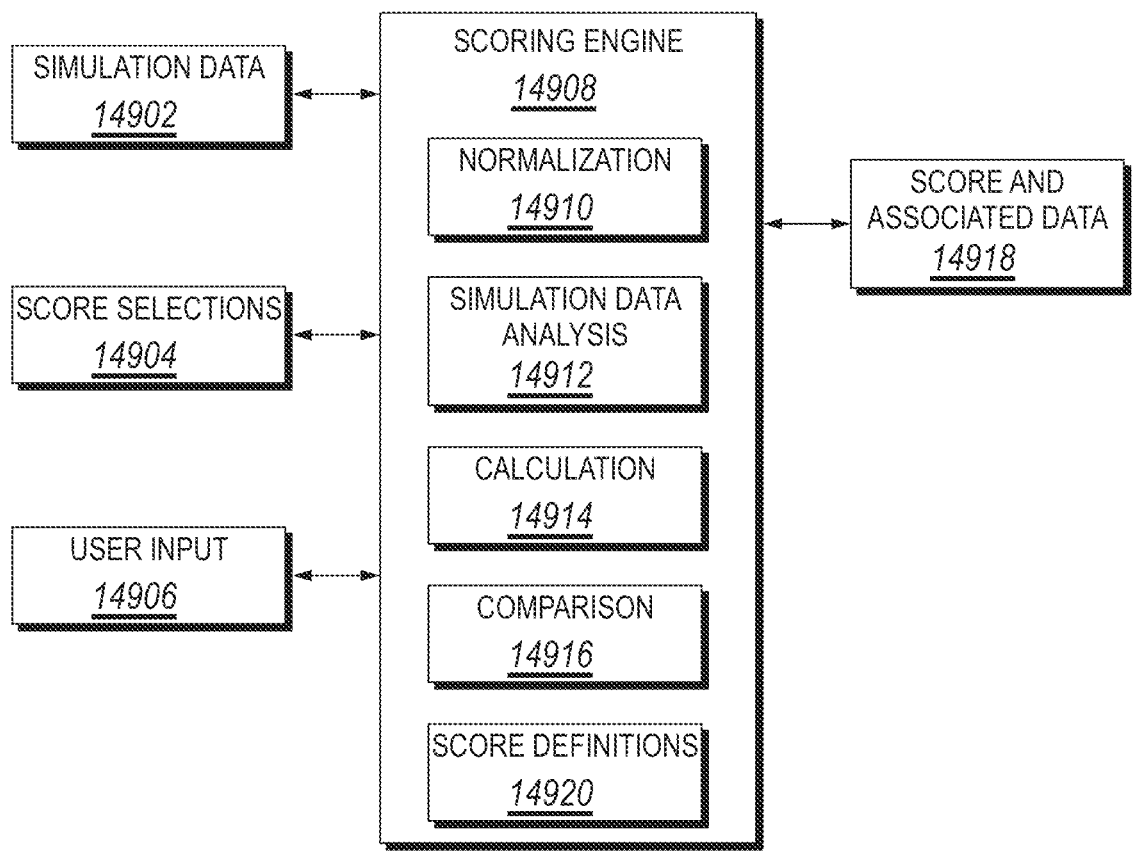
Figure 150:
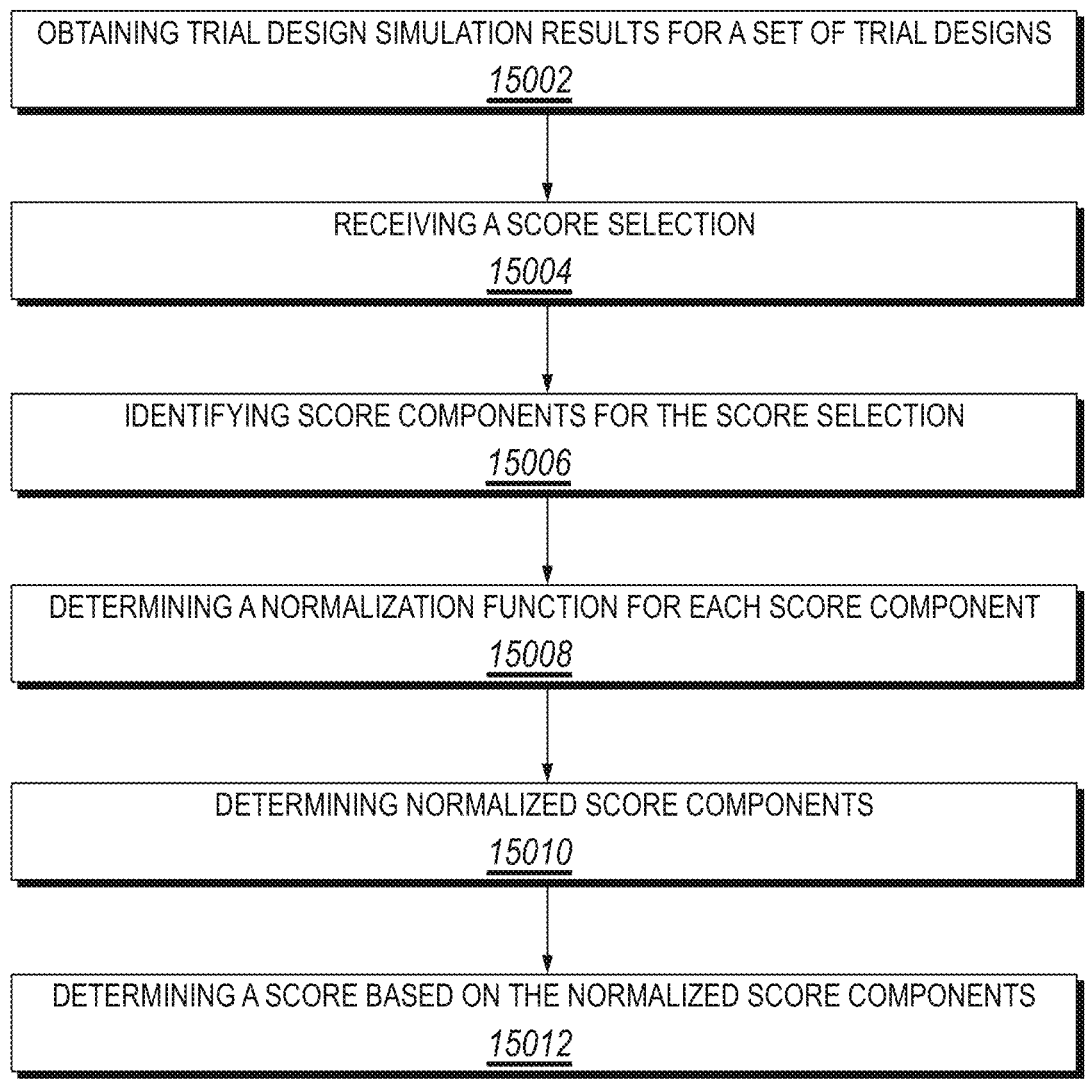
Figure 151:
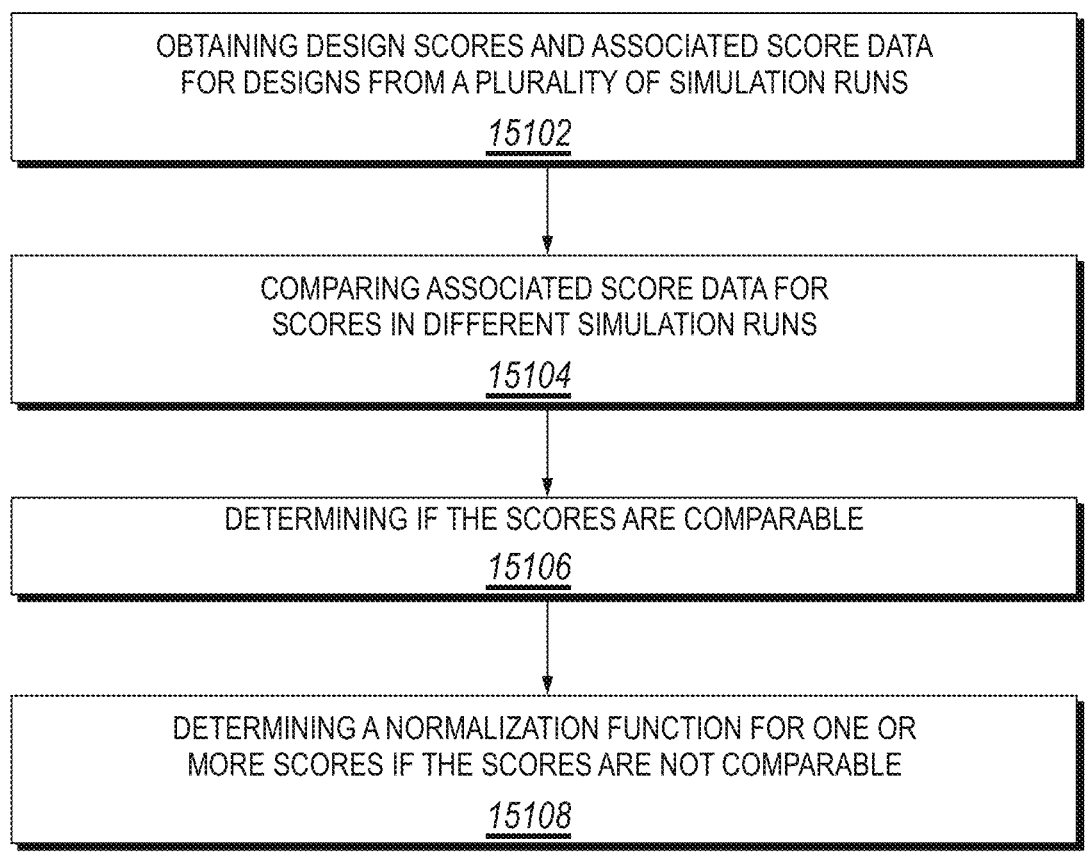
Figure 152:
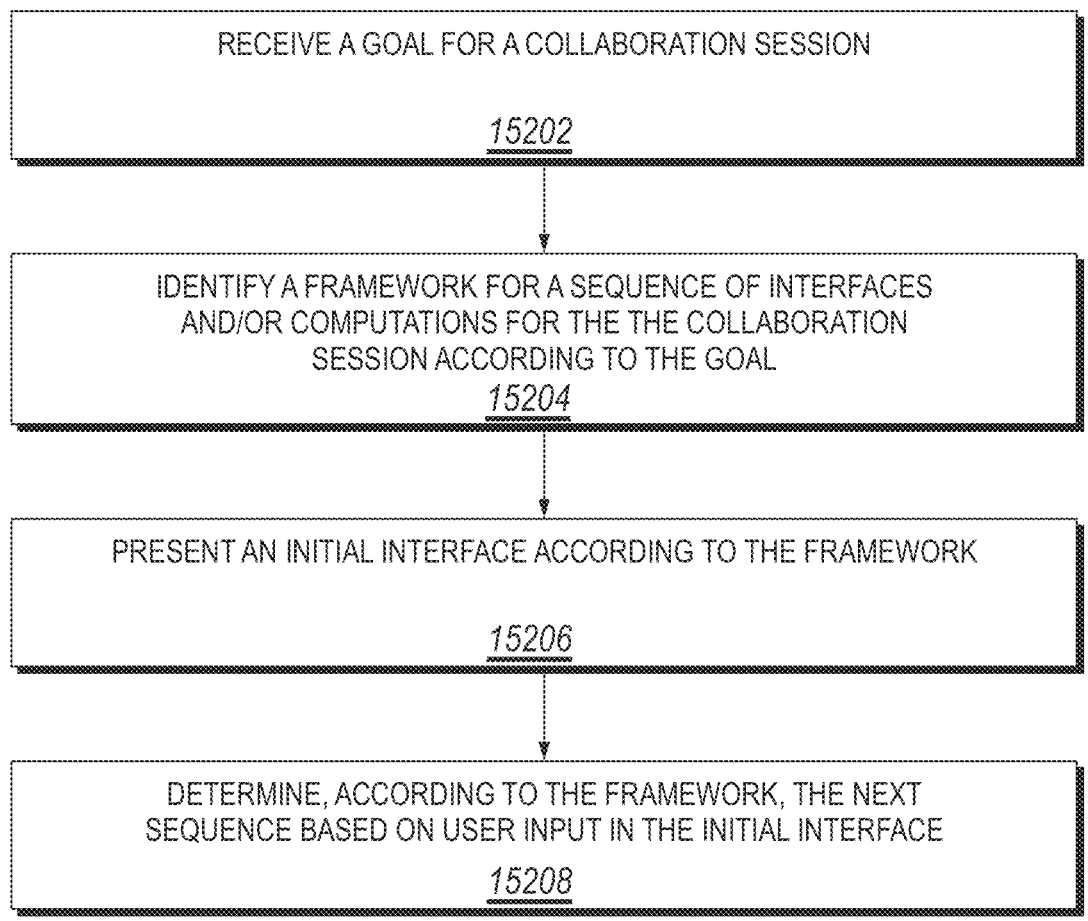
Figure 153:
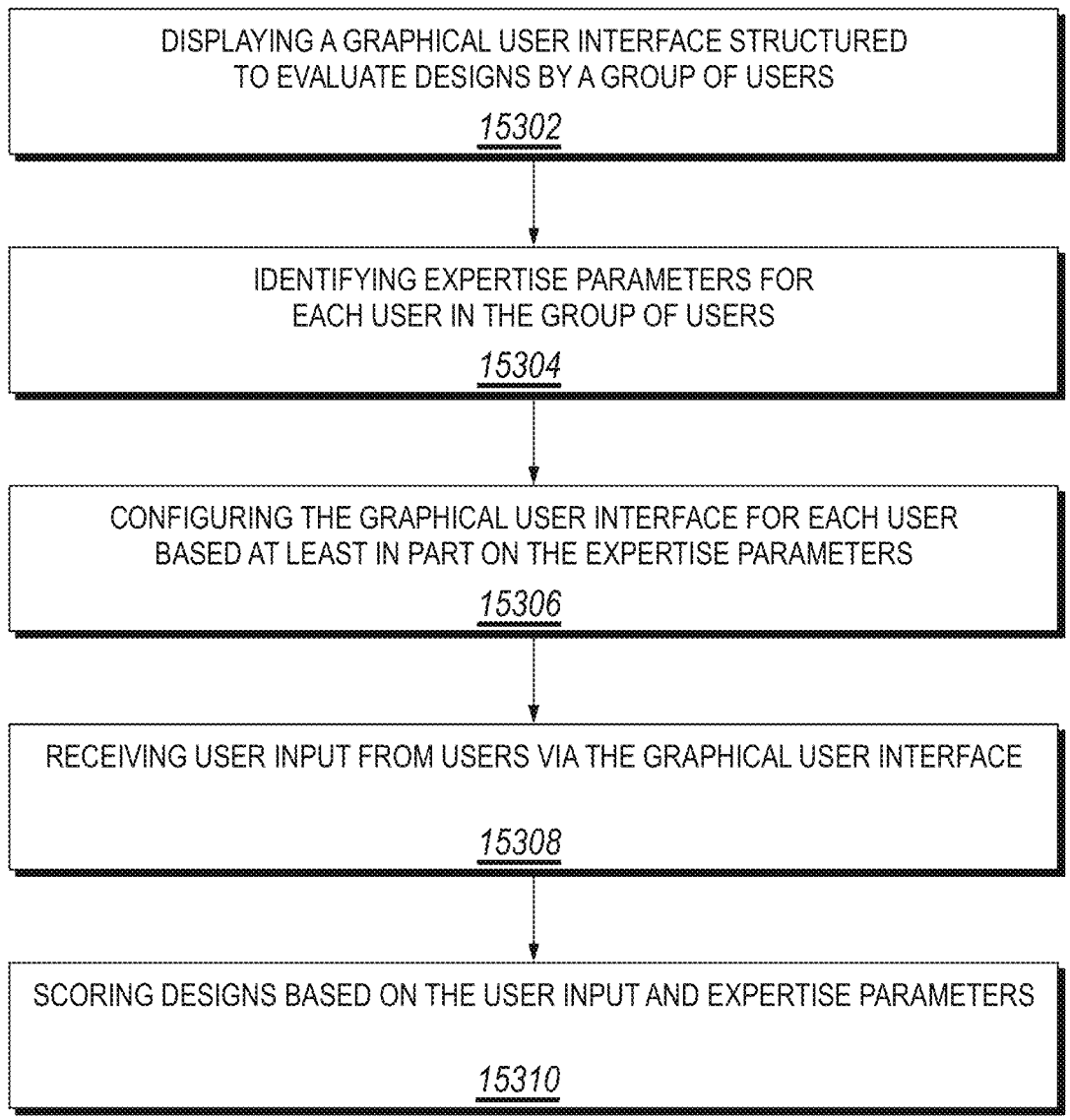
Figure 154:
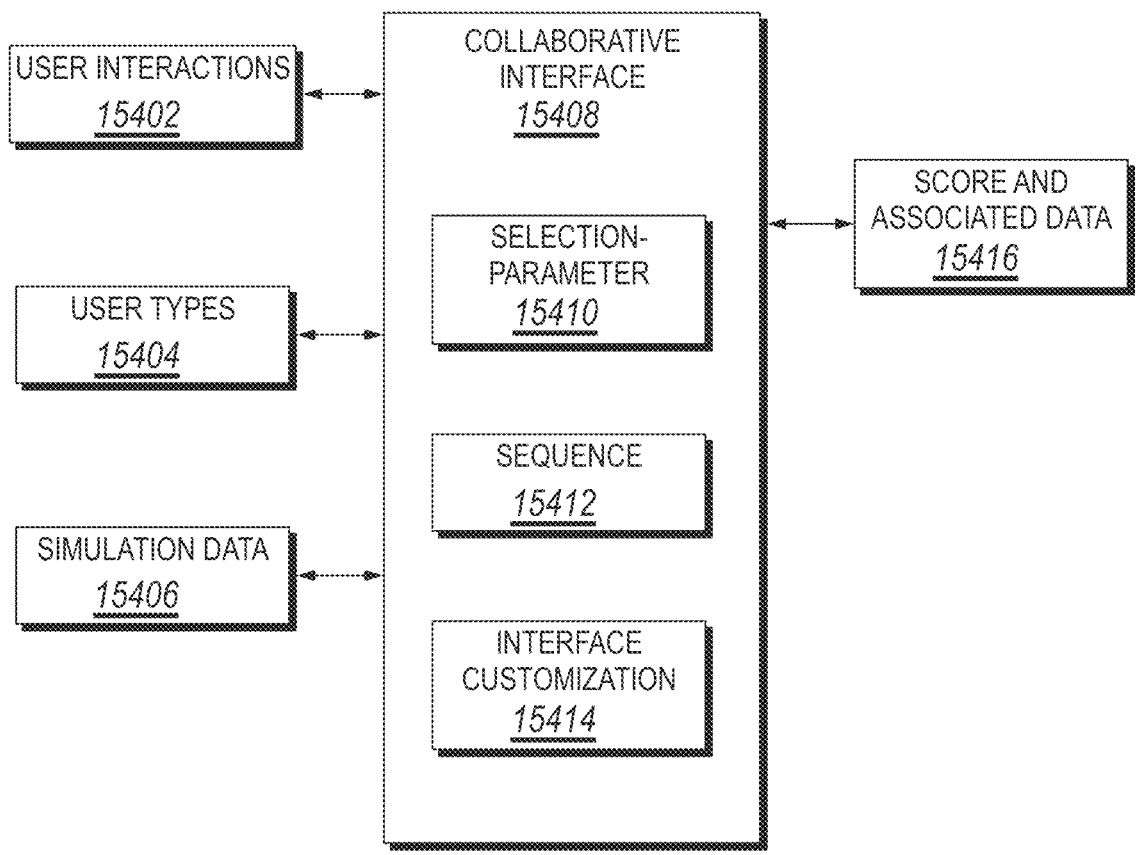
Figure 155:
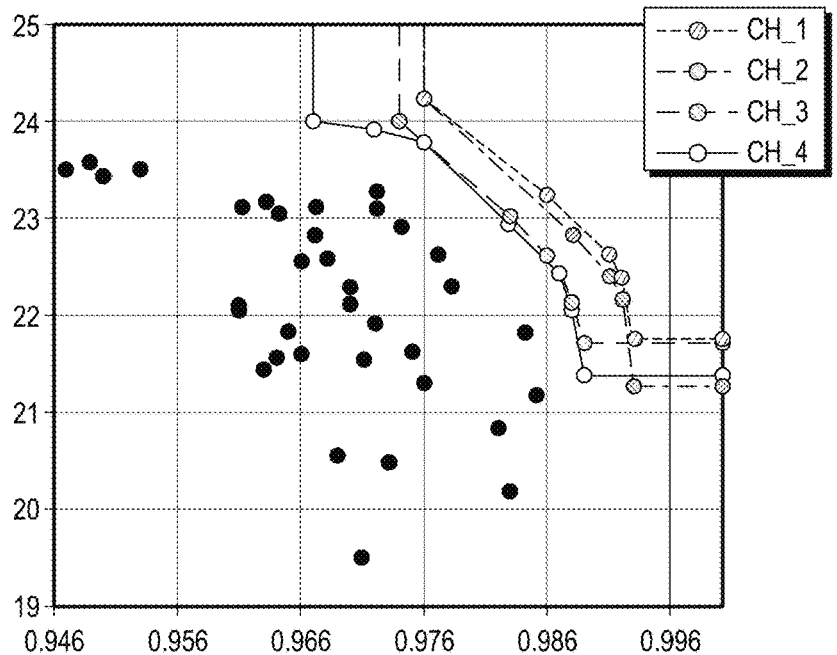
Figure 156:
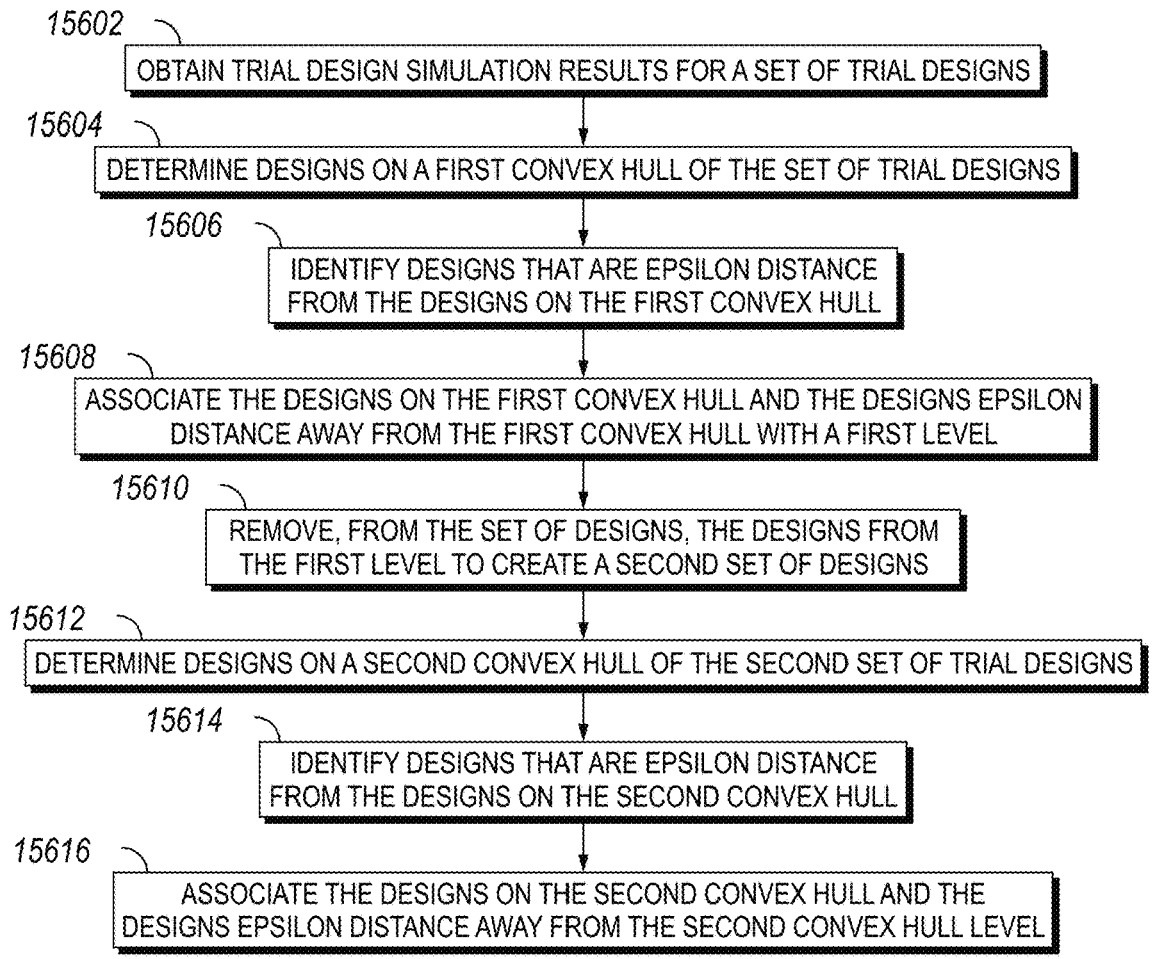
Figure 157A:
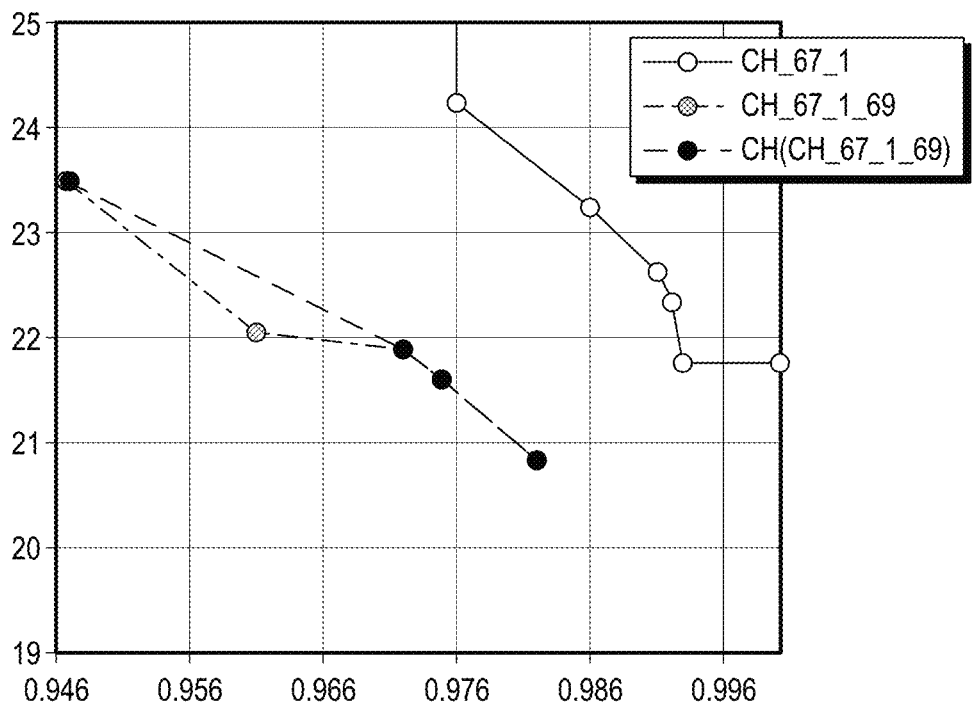
Figure 157B:
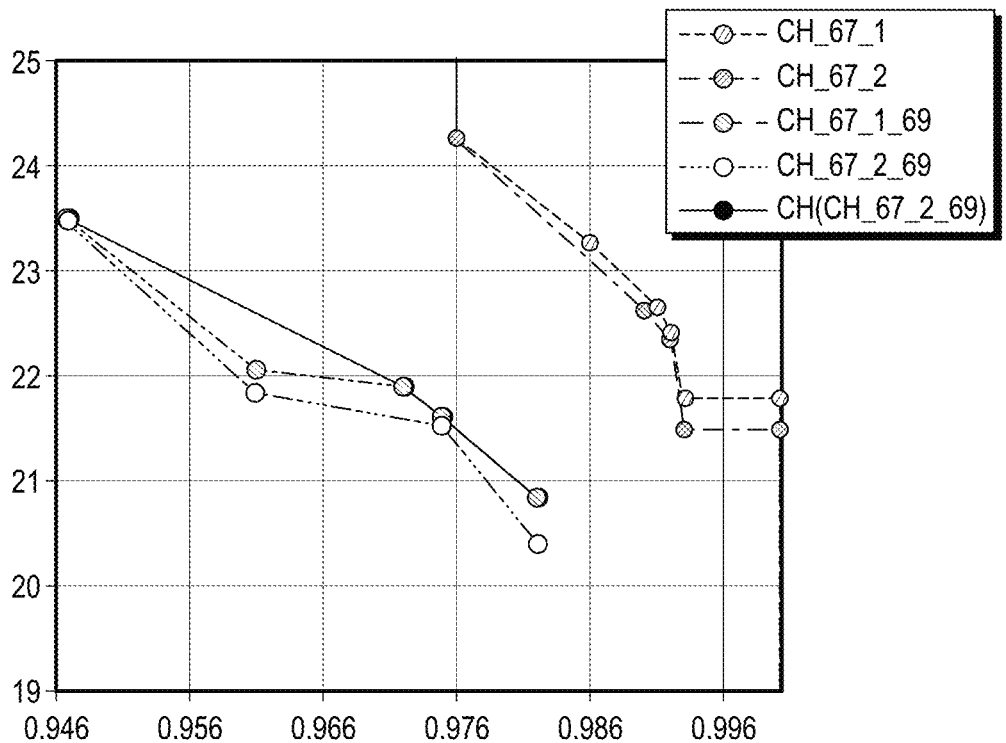
Figure 157C:
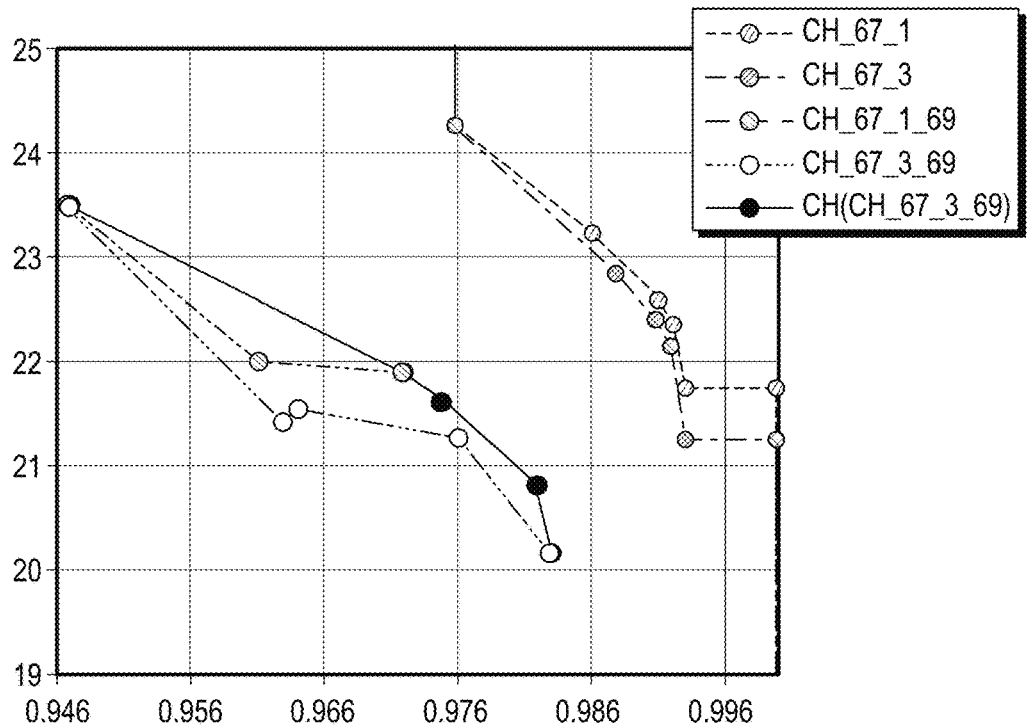
Figure 157D:
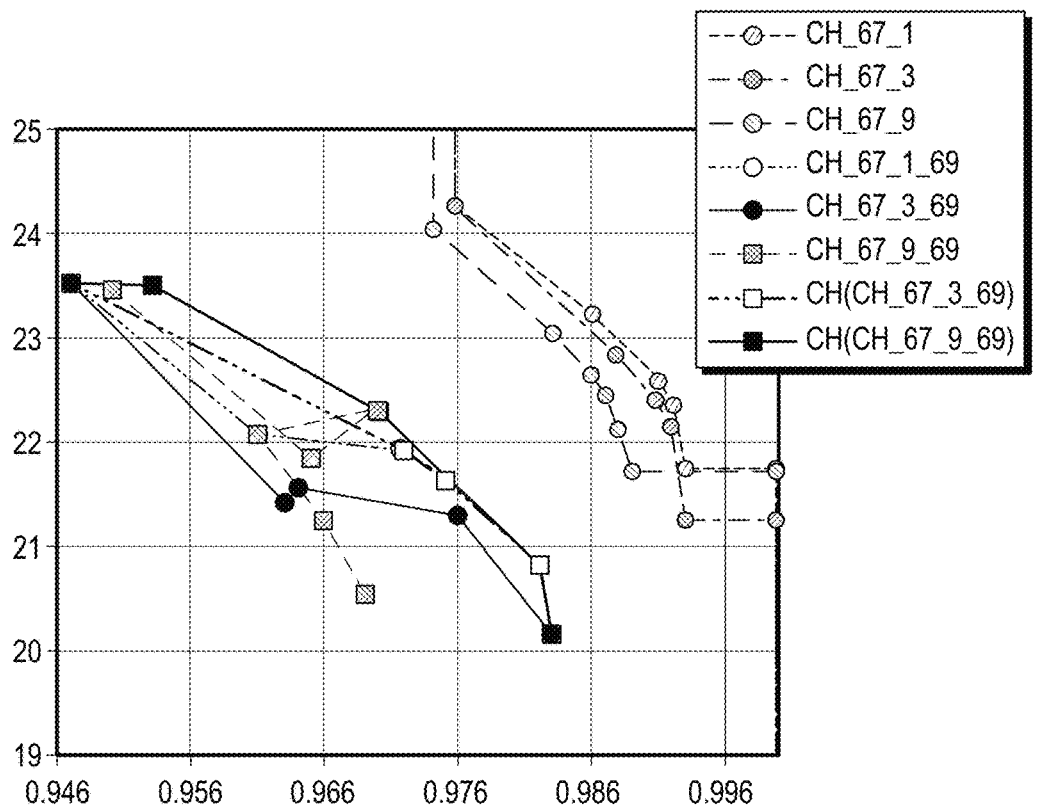
Figure 157E:
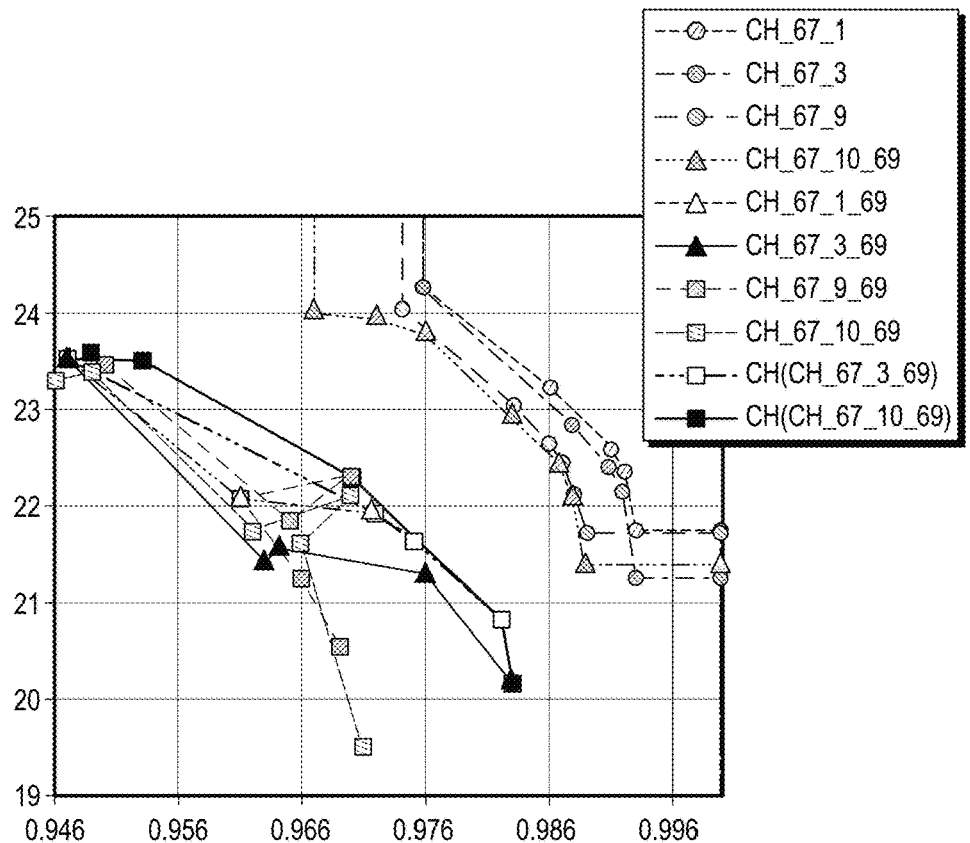
Figure 158:
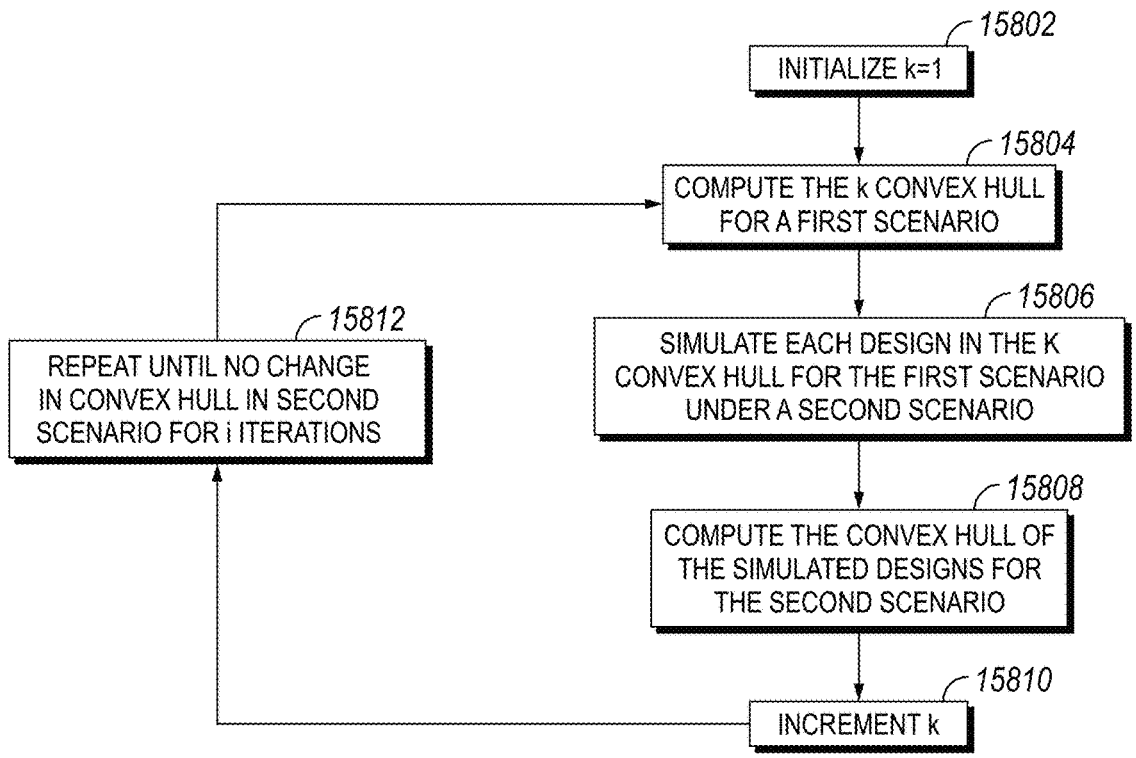
Figure 159:
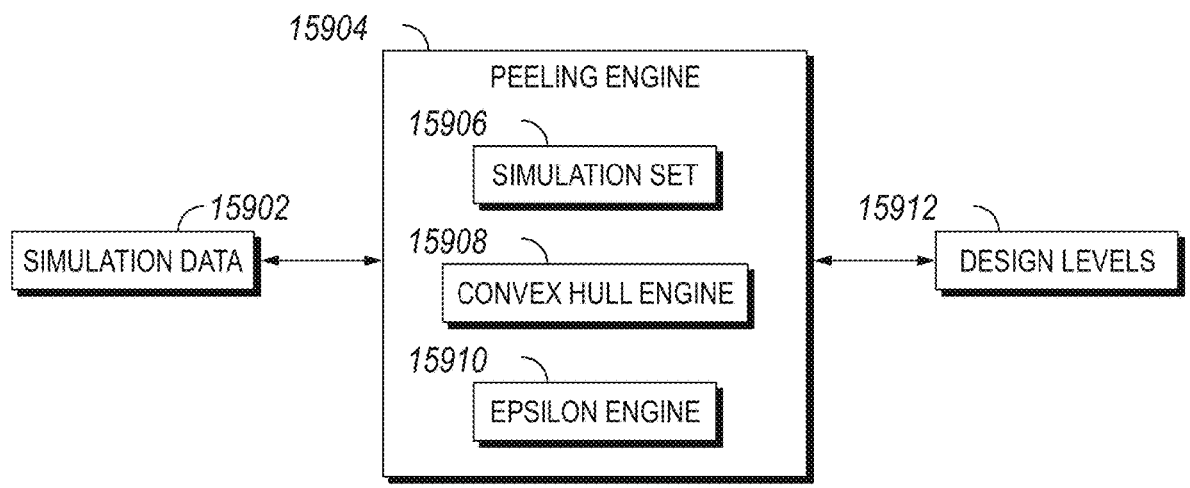
Figure 160:
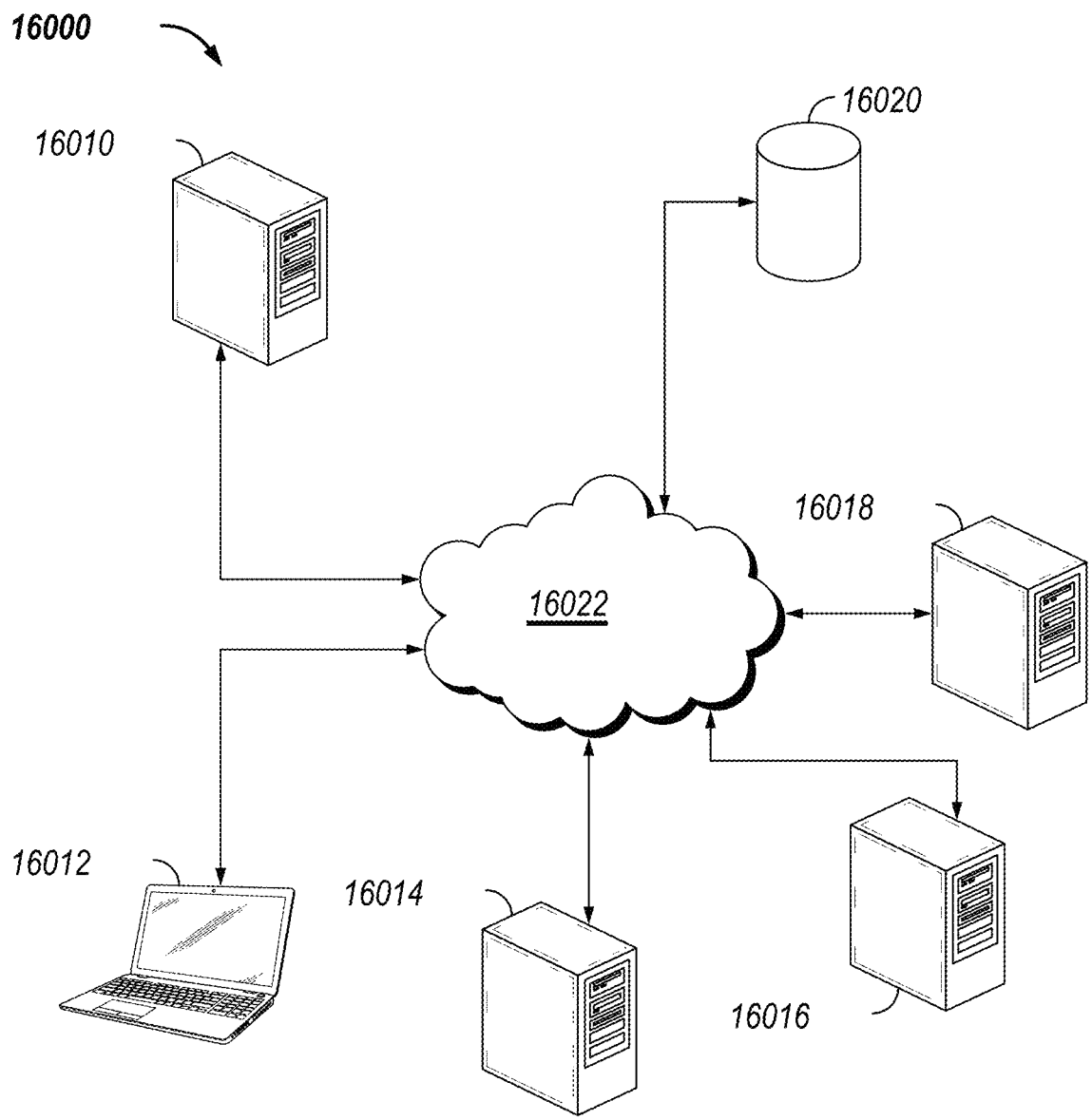
Figure 161:
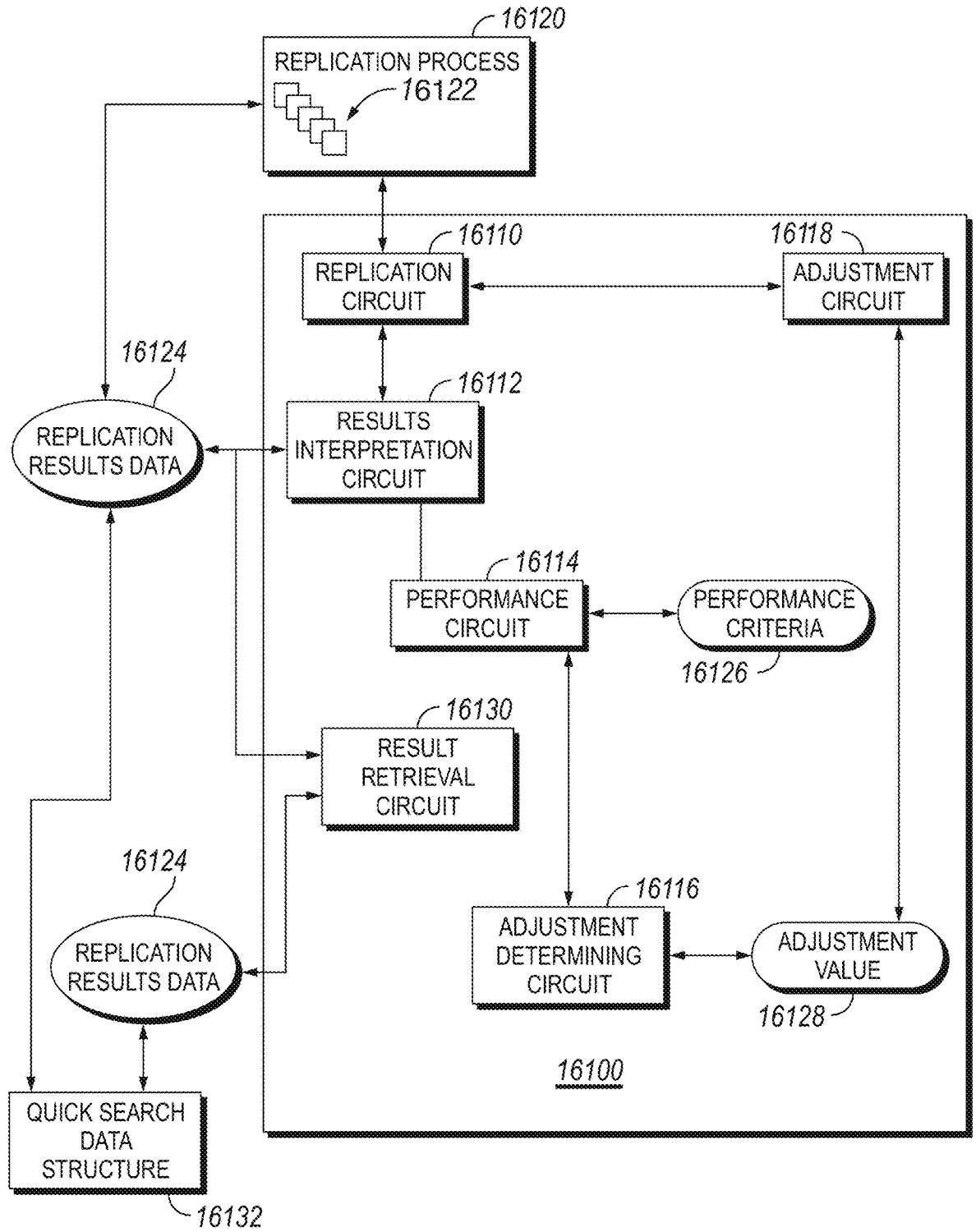
Figure 162:
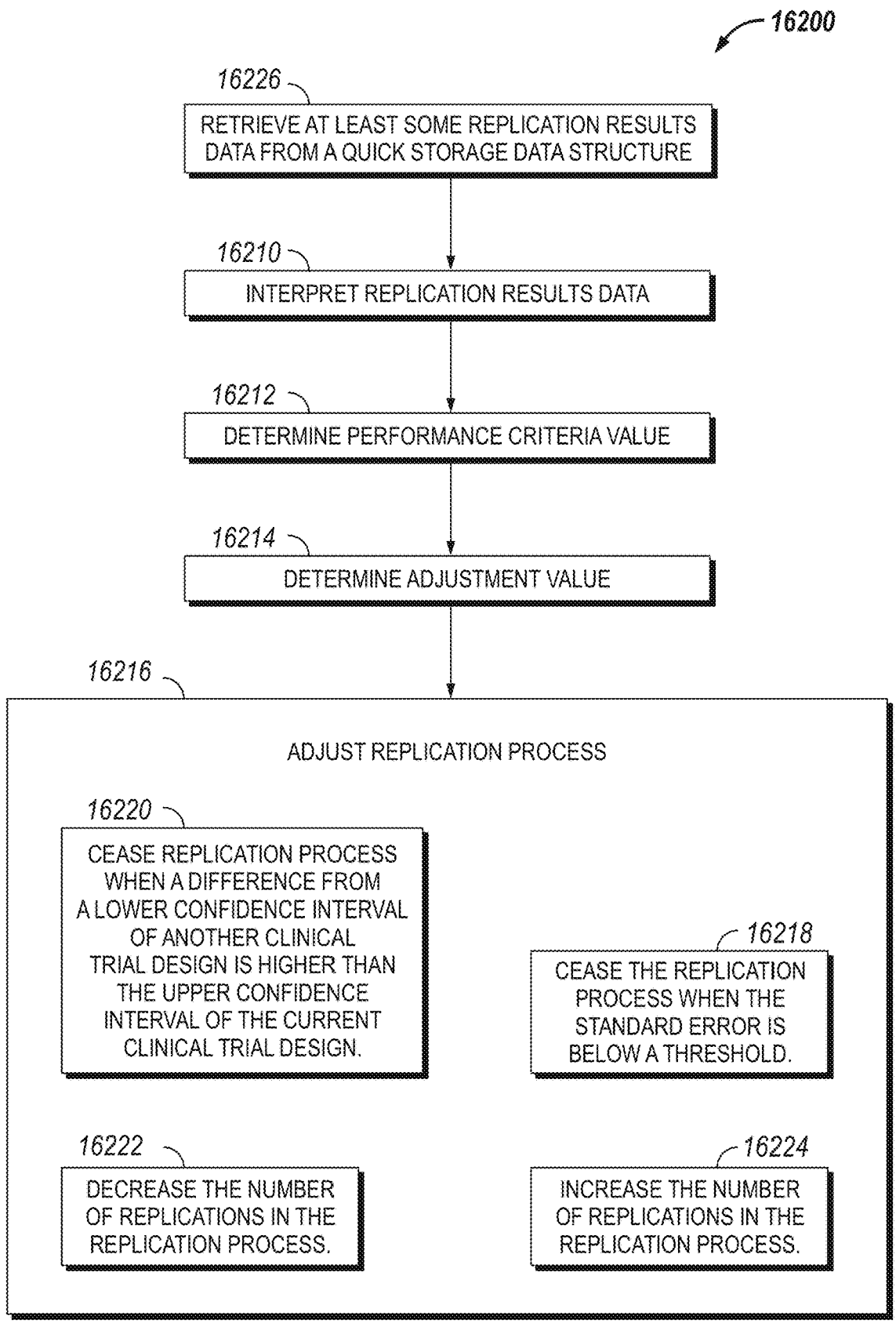
Figure 163:
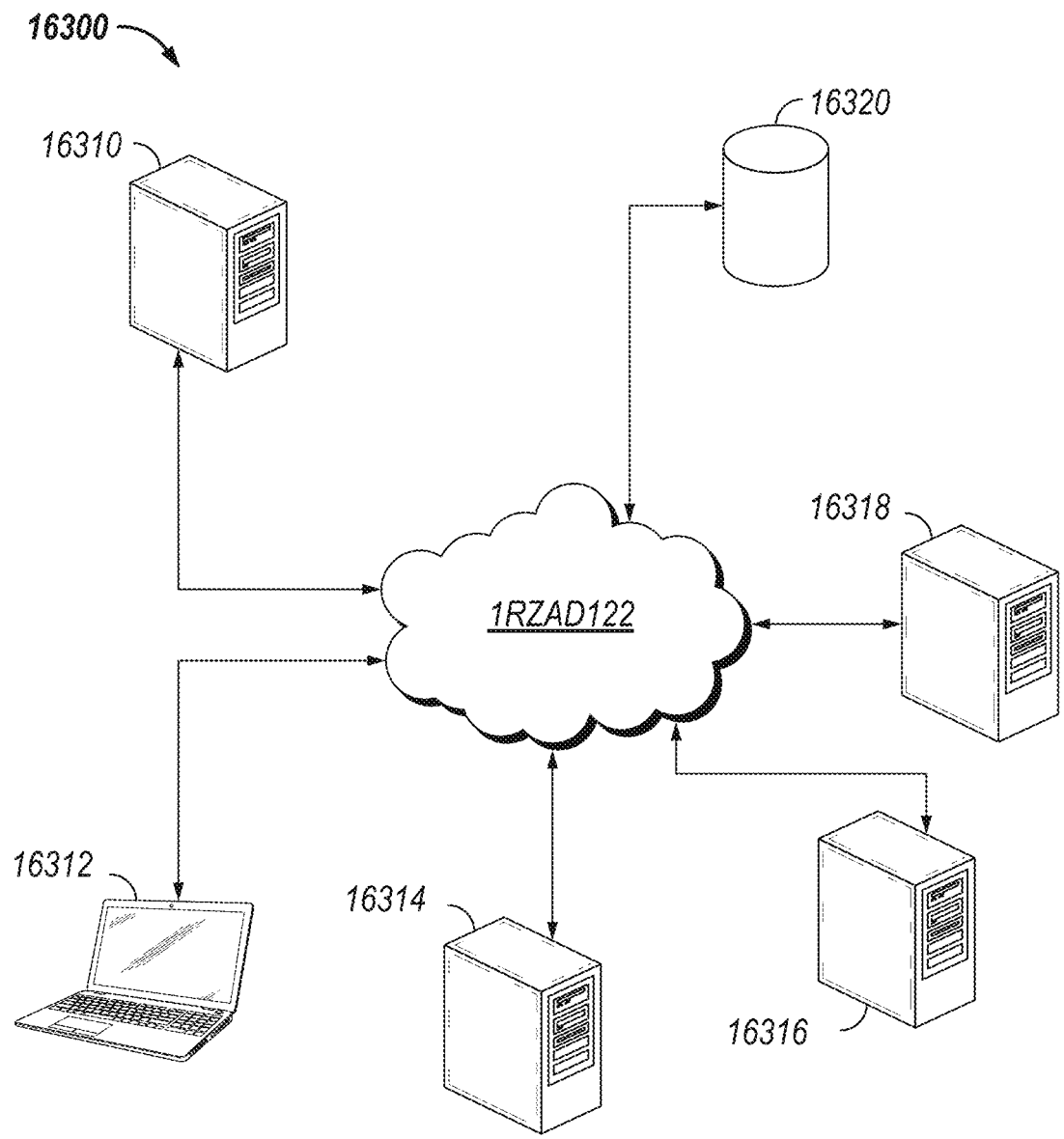
Figure 164:
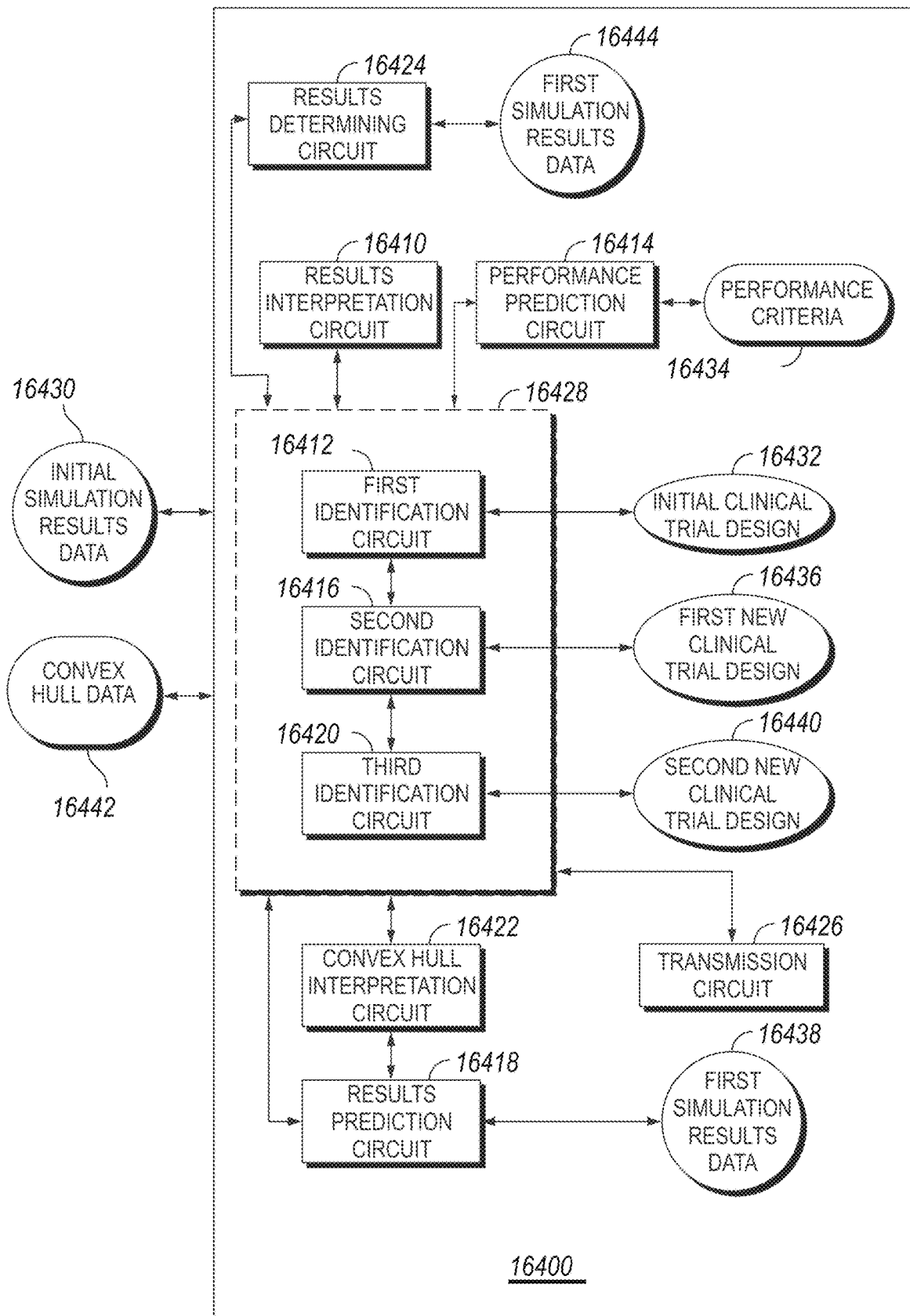
Figure 165:
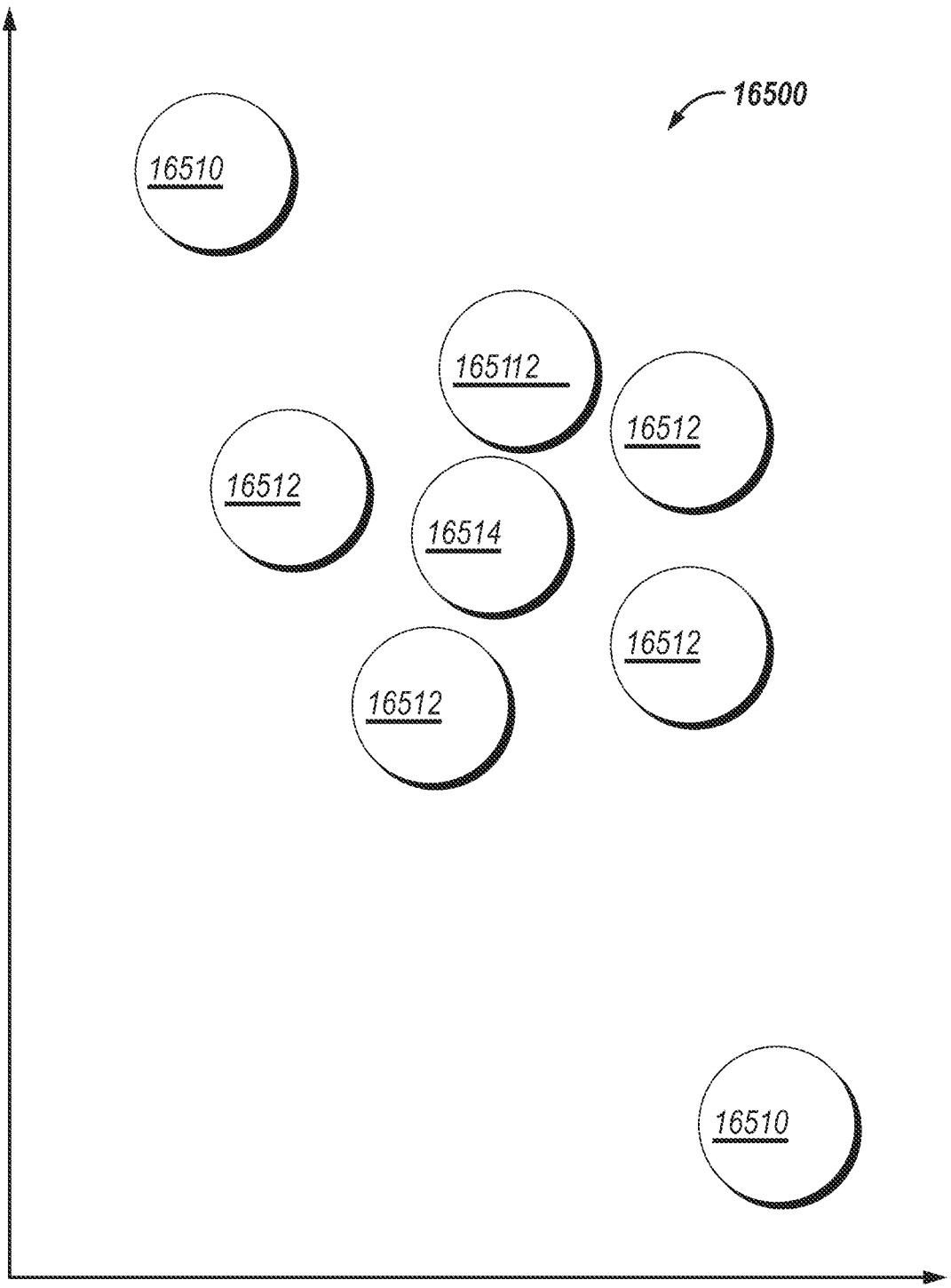
Figure 166:
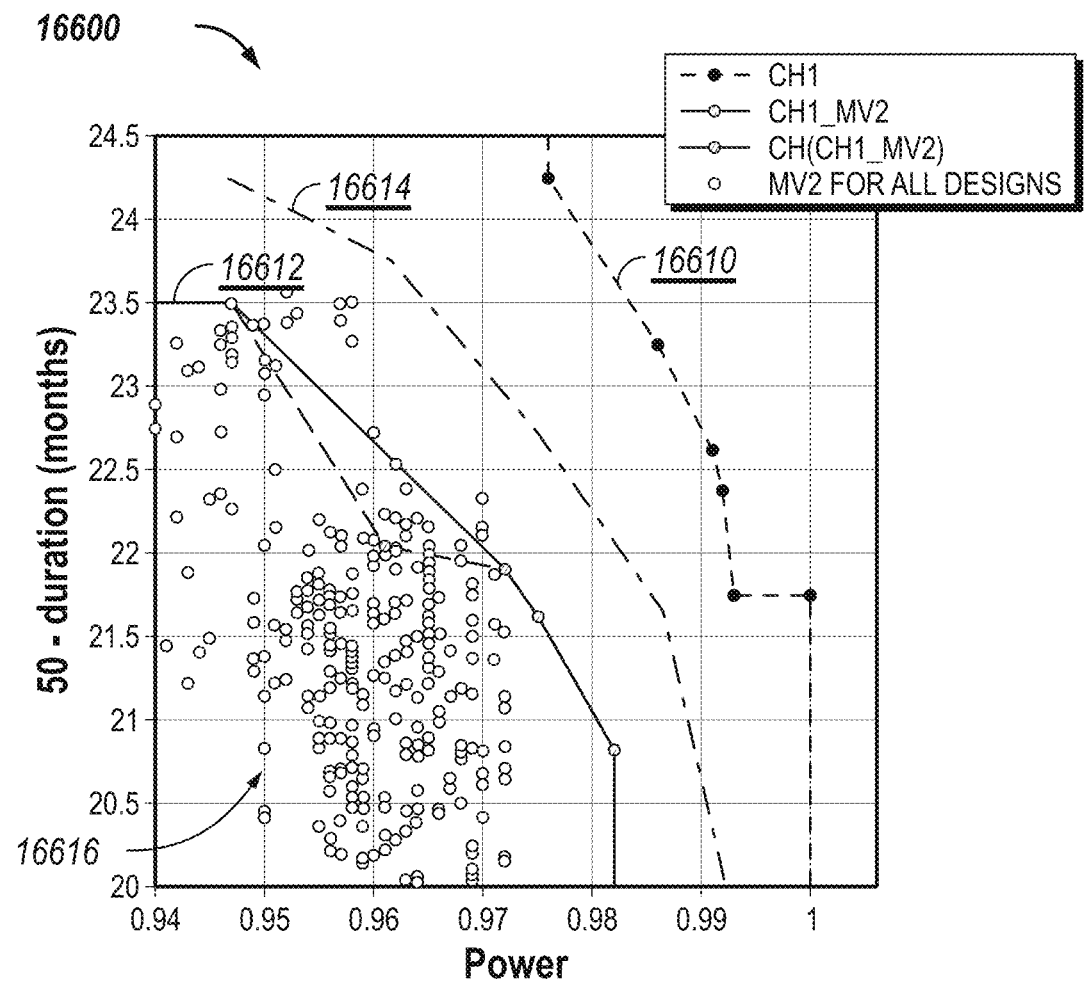
Figure 167:
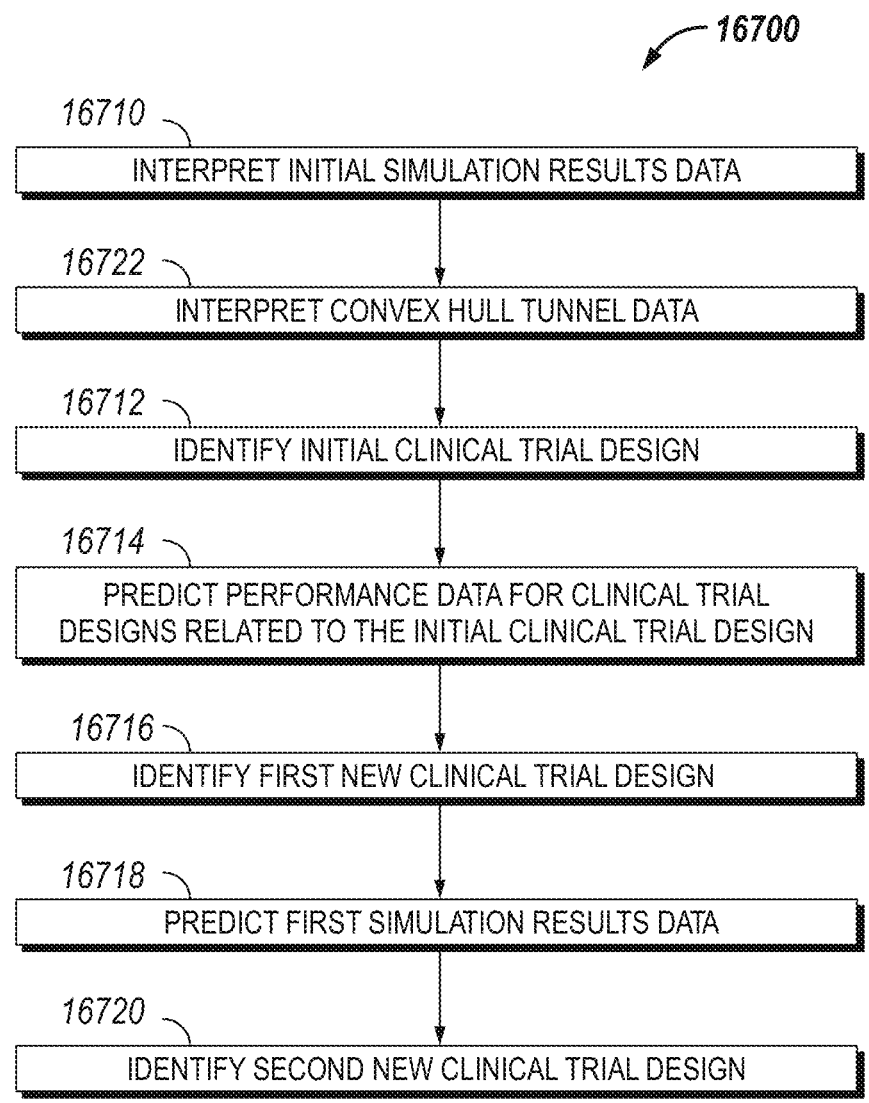
Figure 168:
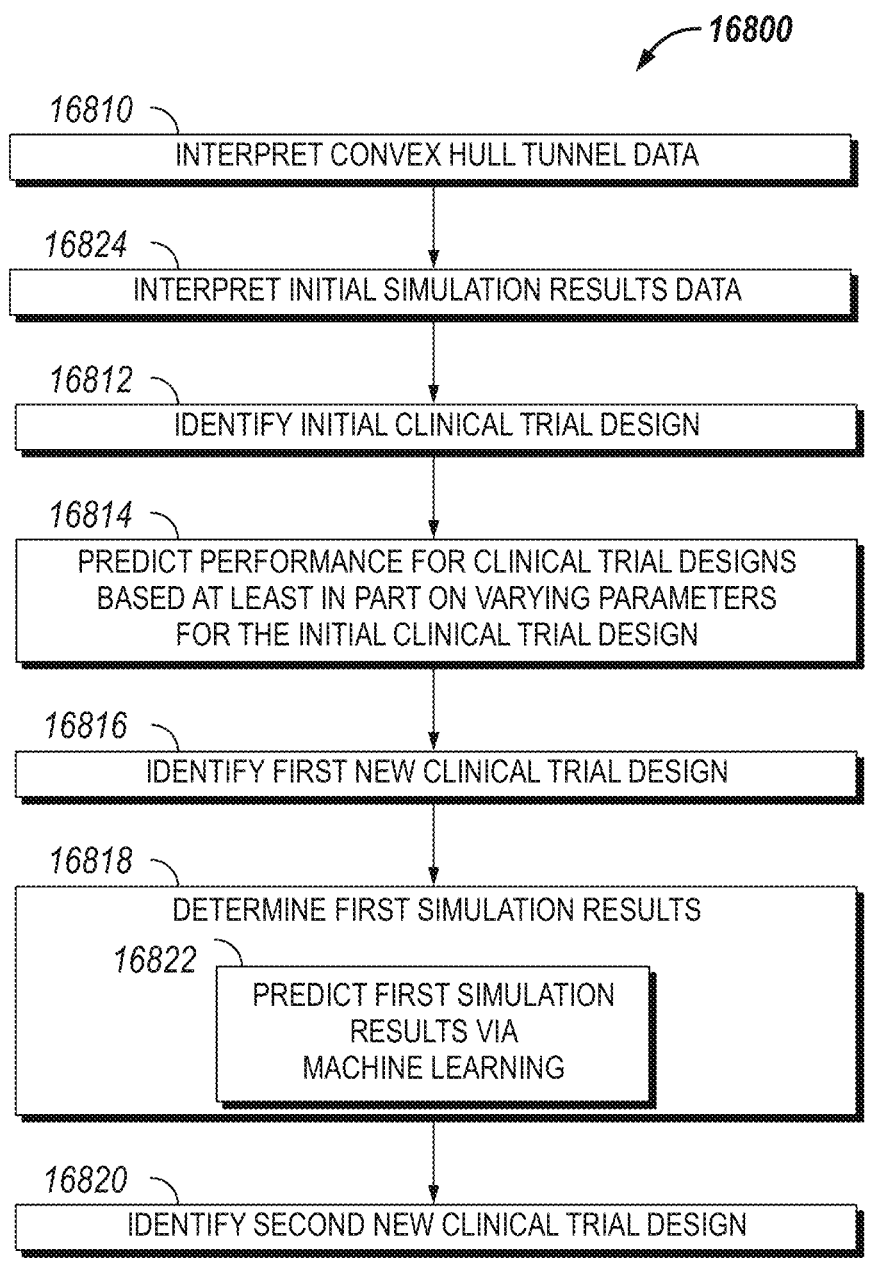
Figure 169:
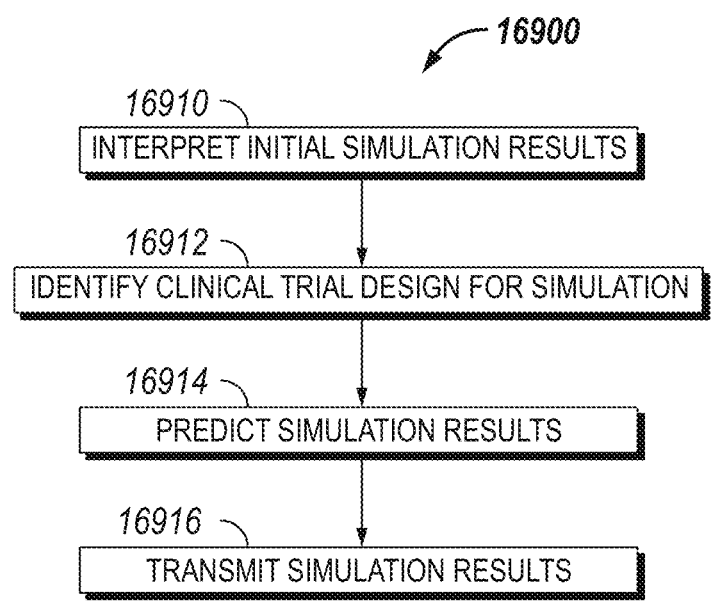
Figure 170:
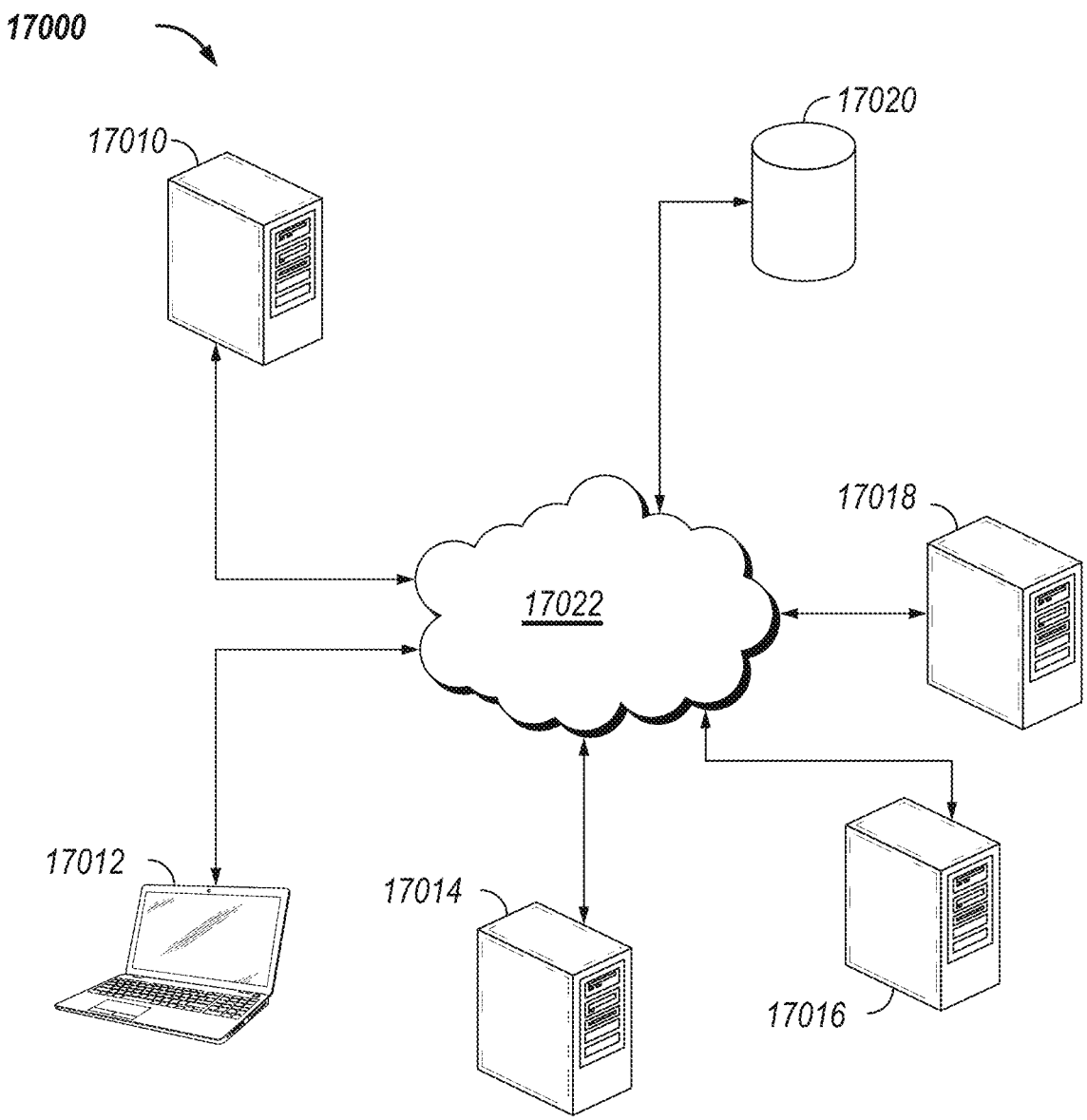
Figure 171A:
Figure 172:
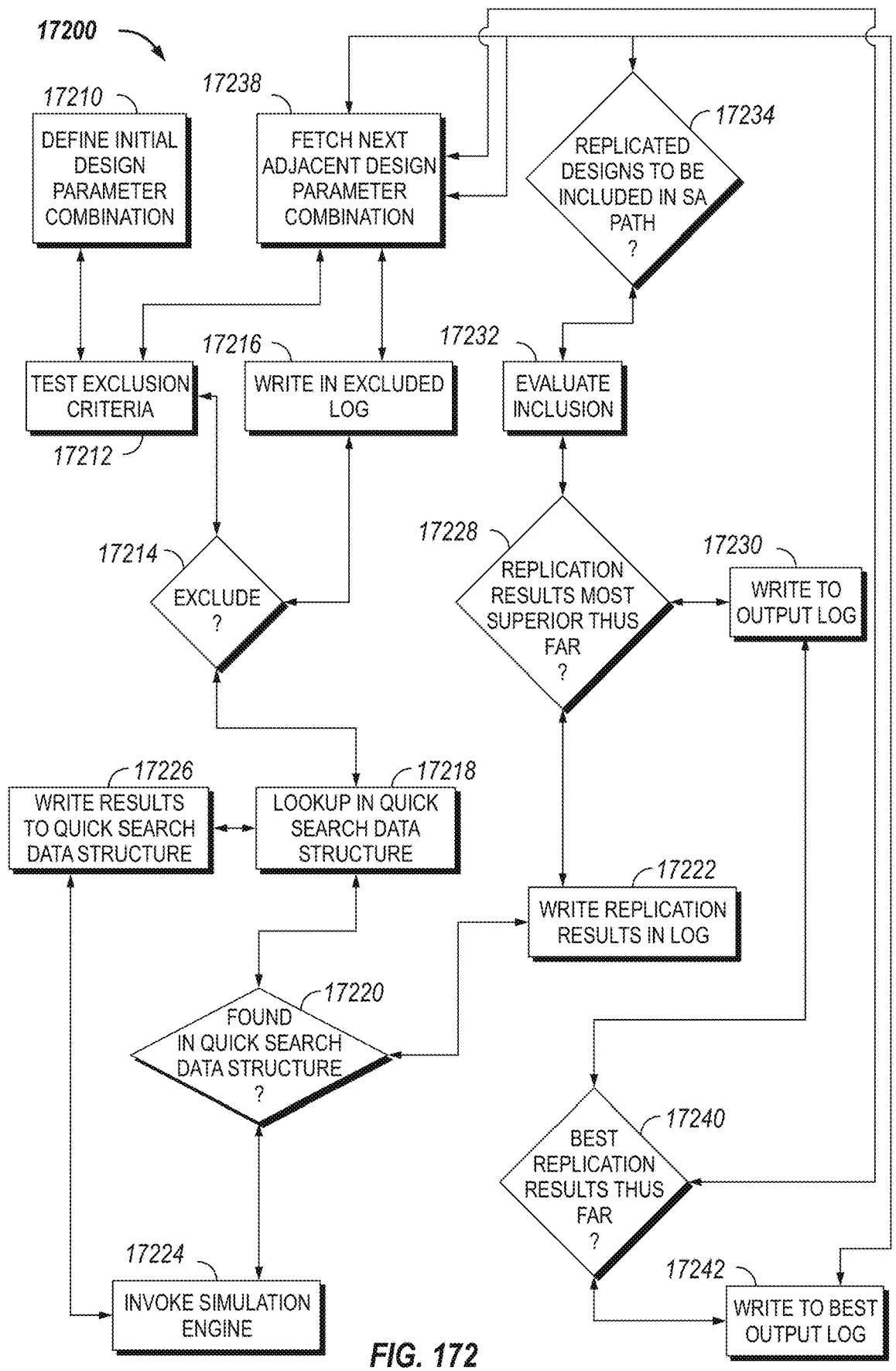
Figure 173:
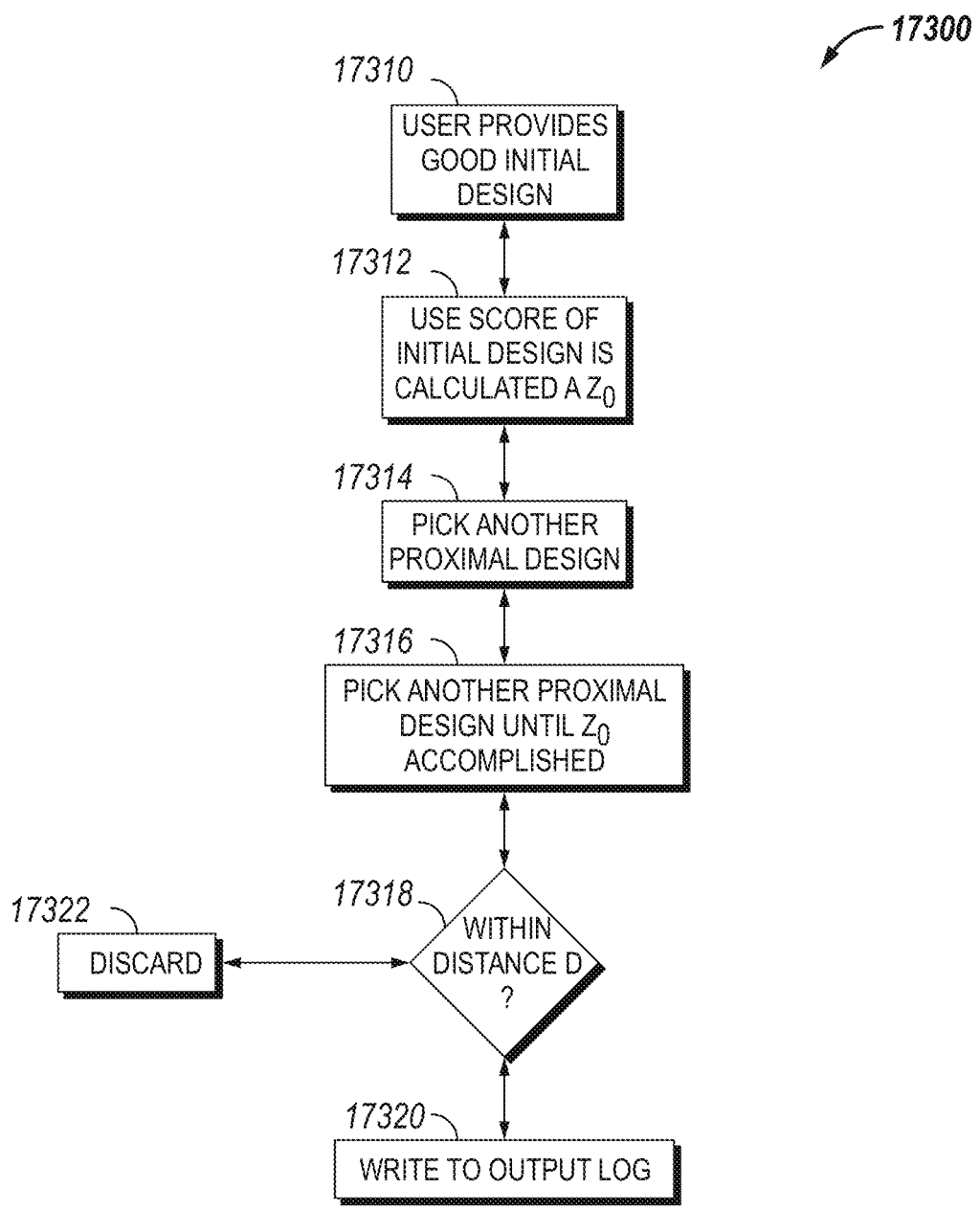
Figure 174:
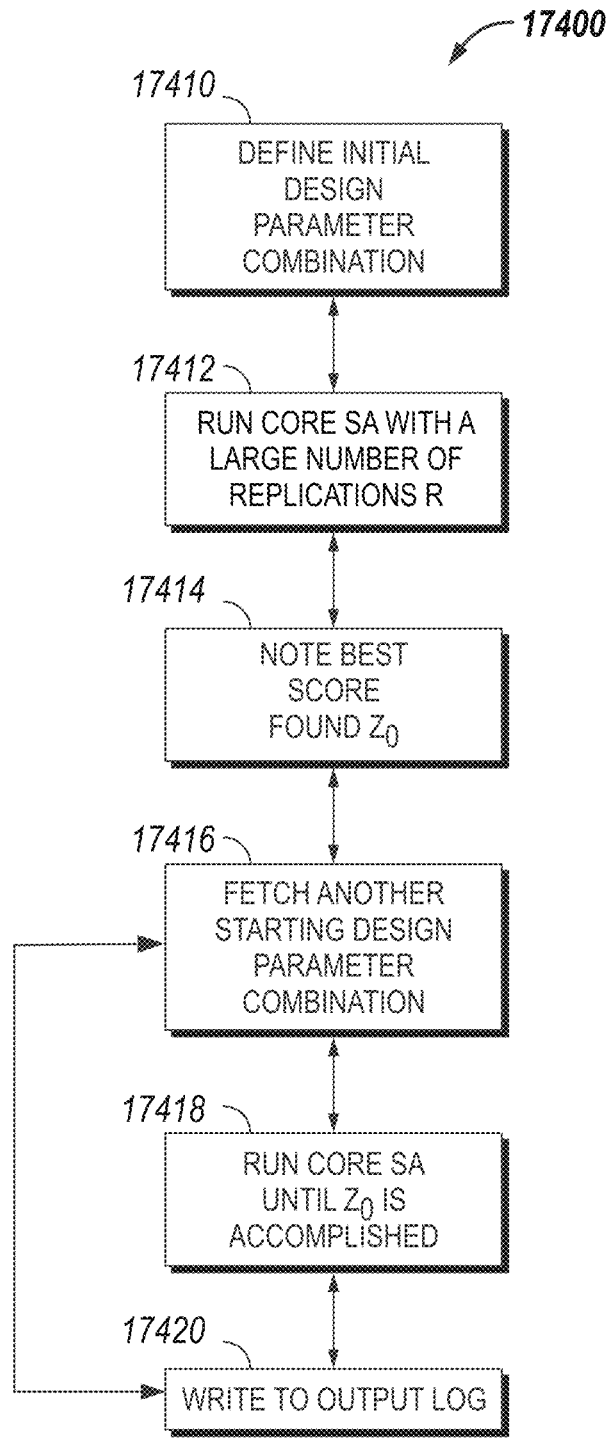
Figure 175:
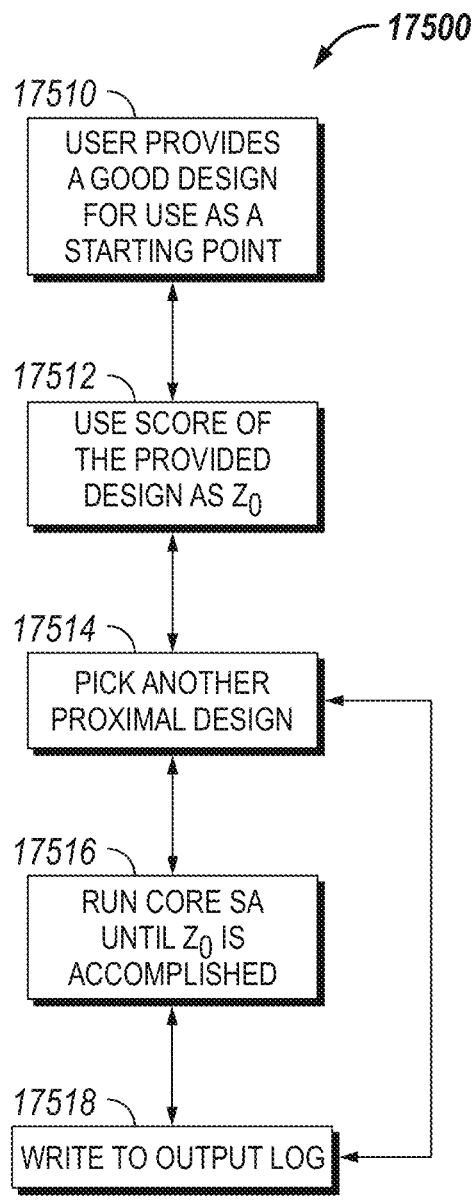
Figure 177:
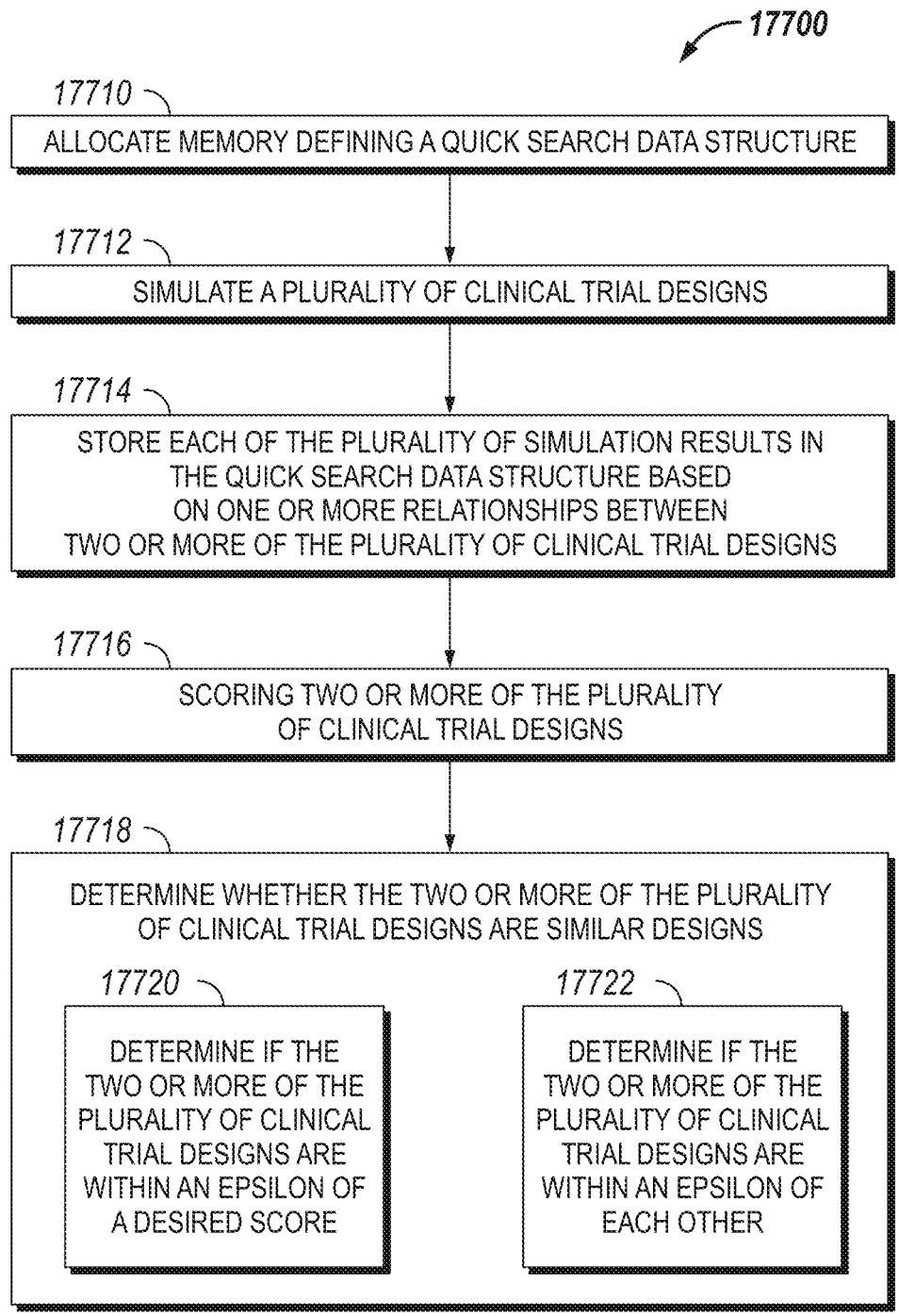
Figure 178:
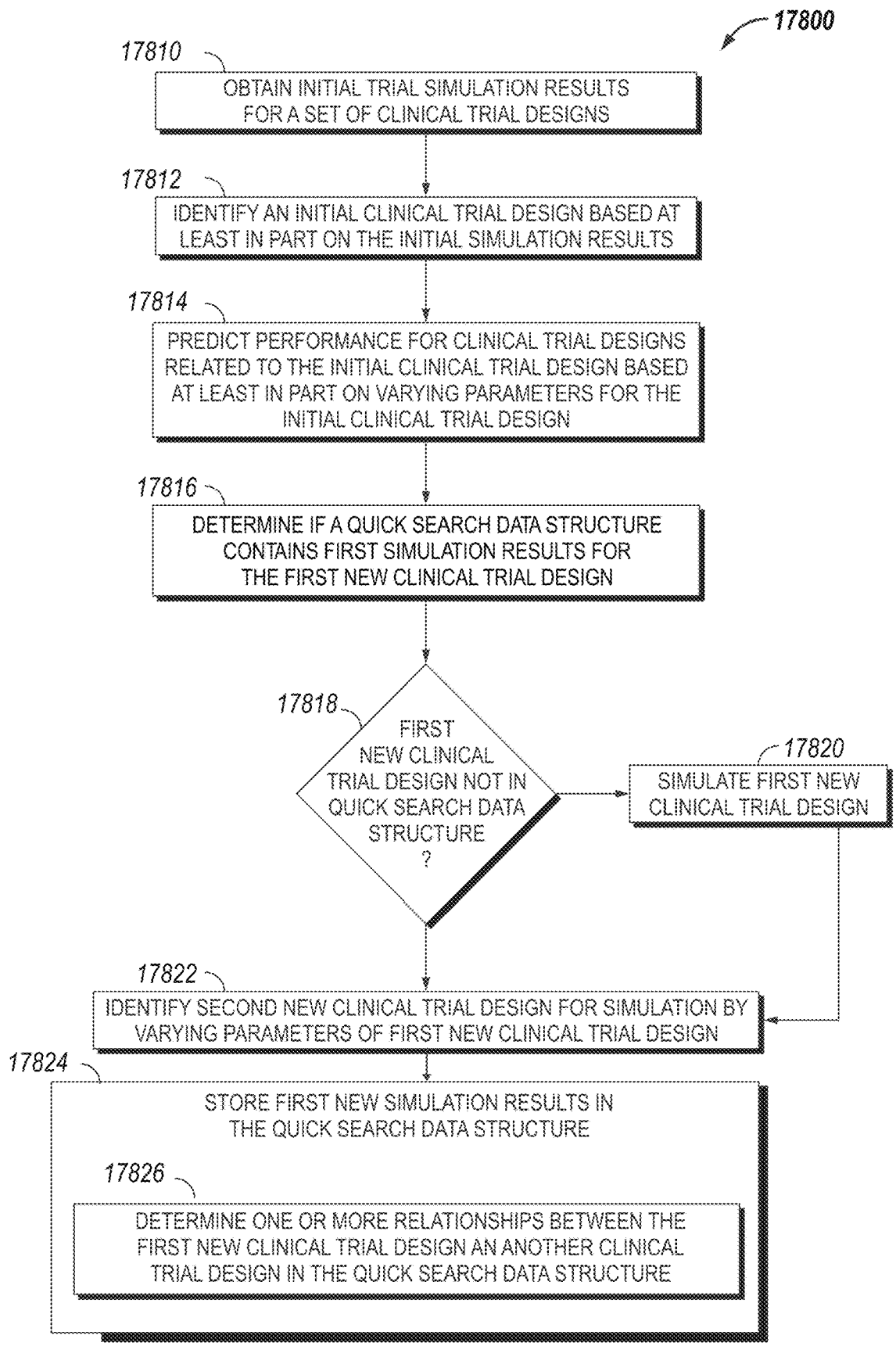
Figure 179:
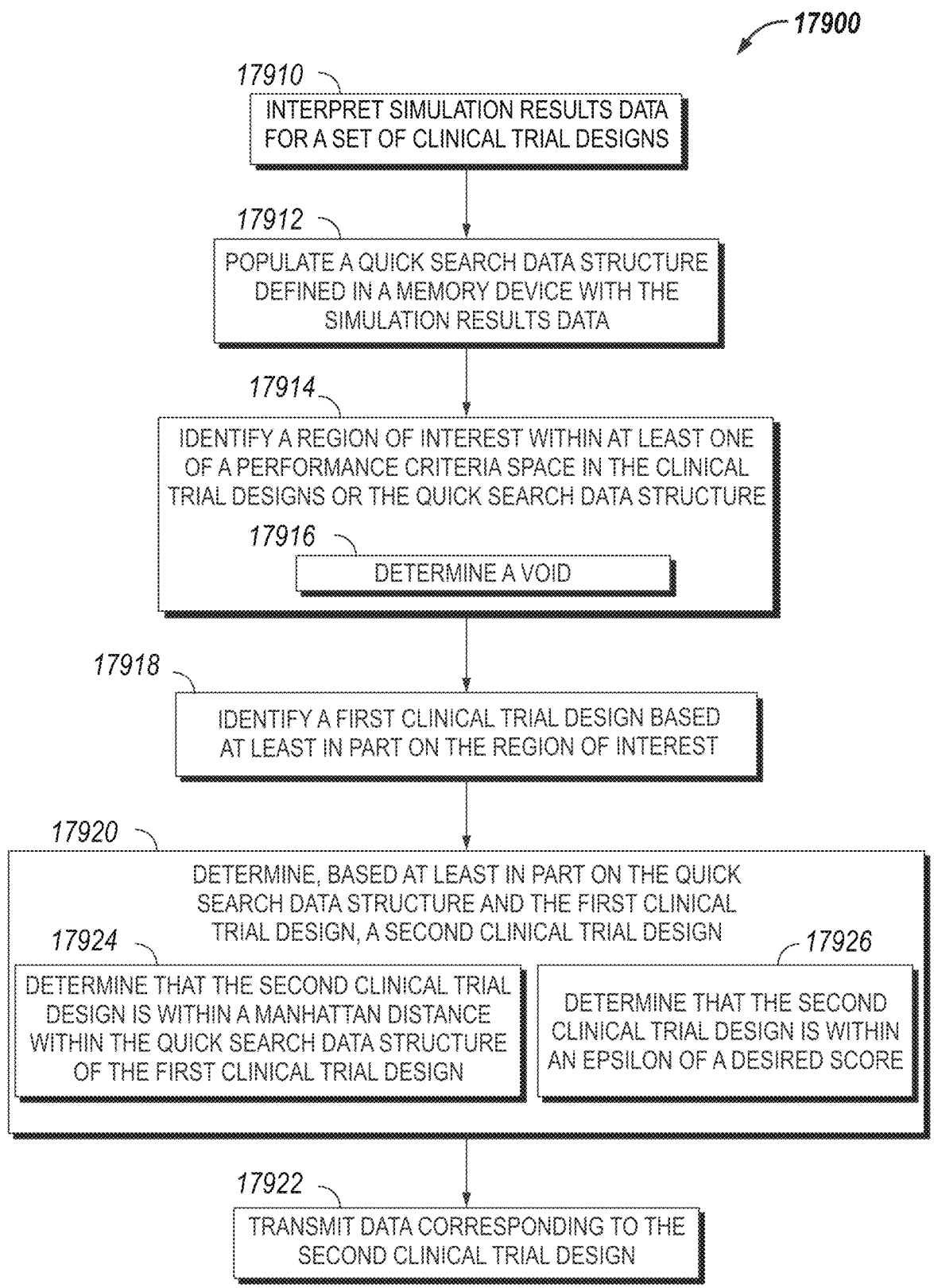
Figure 180:
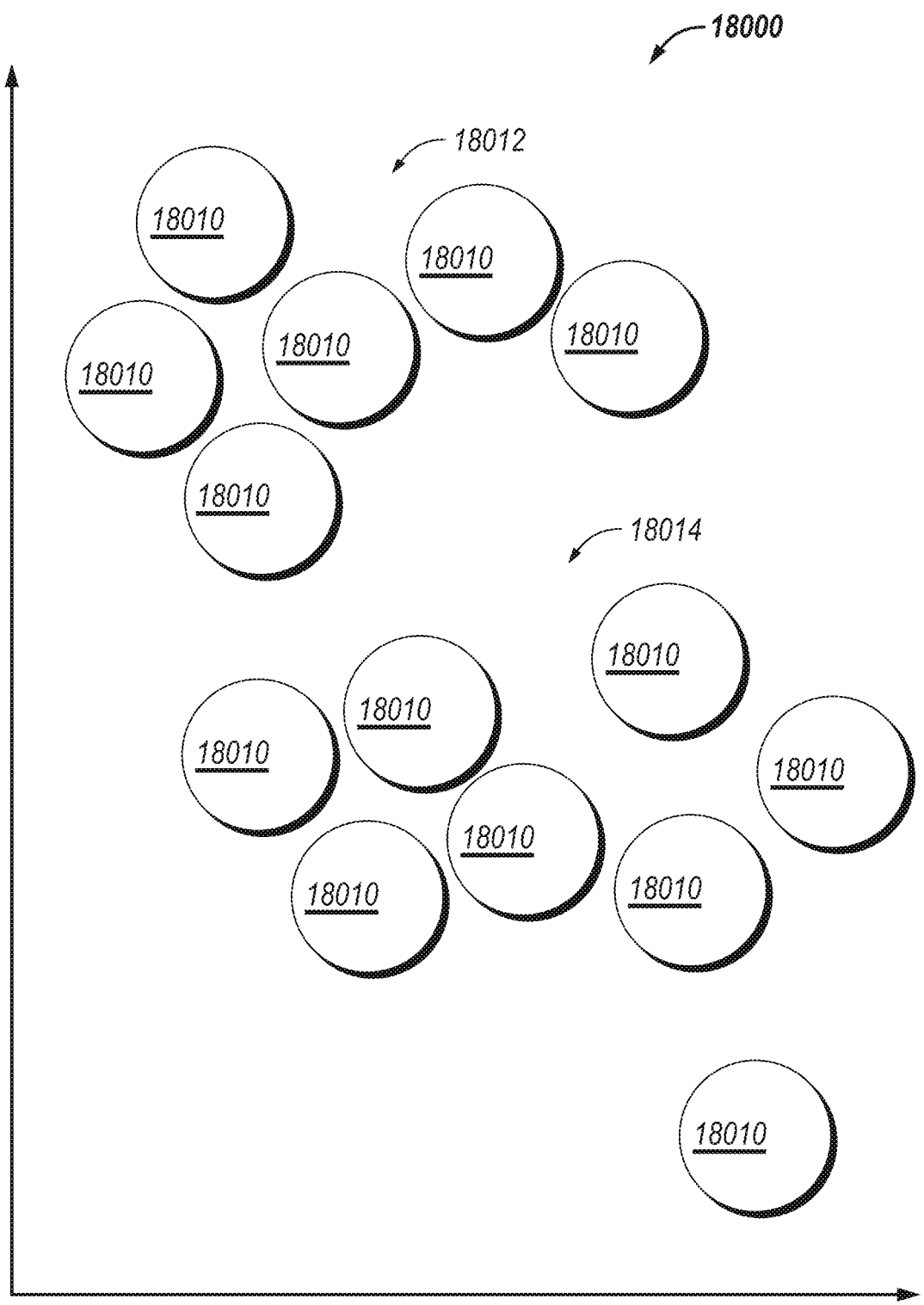
Figure 181A:
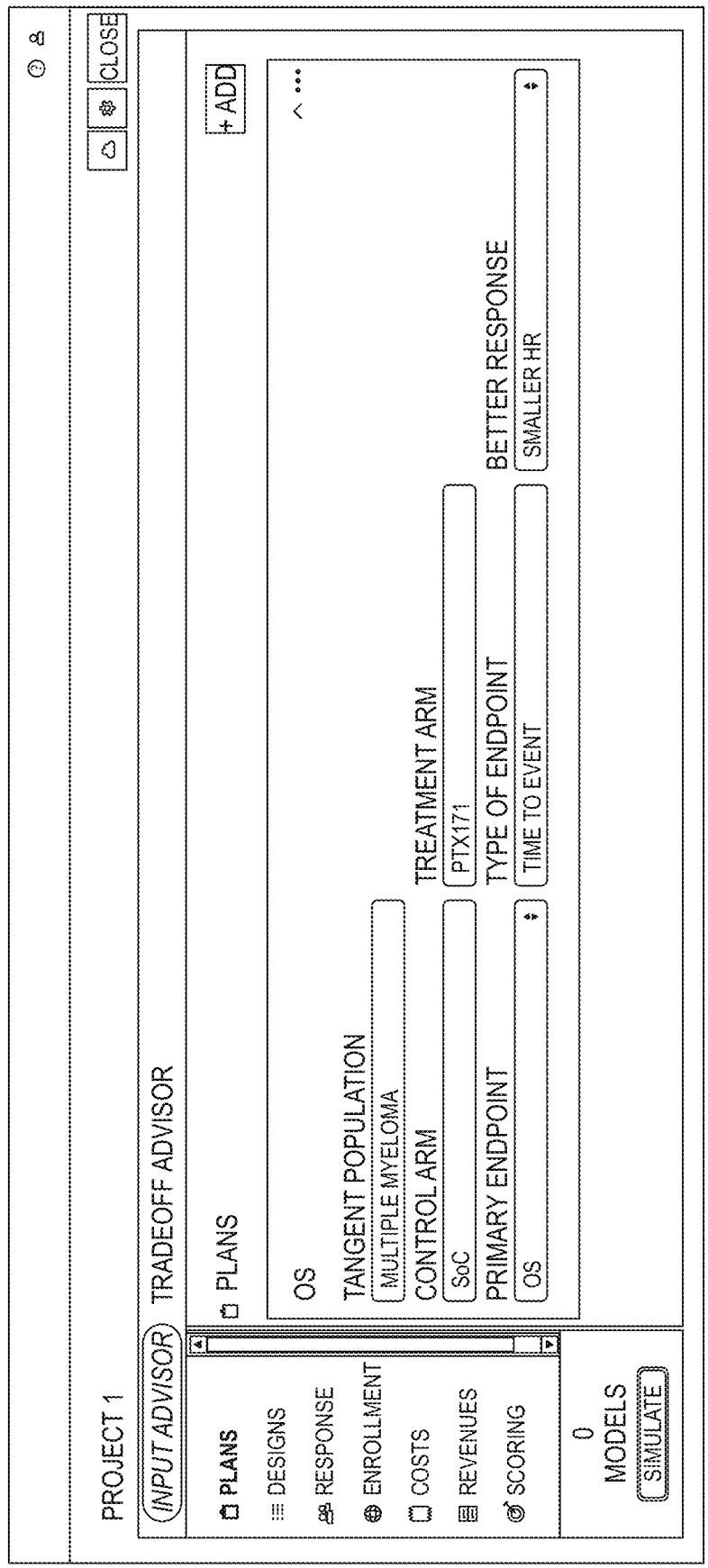
Figure 181B:
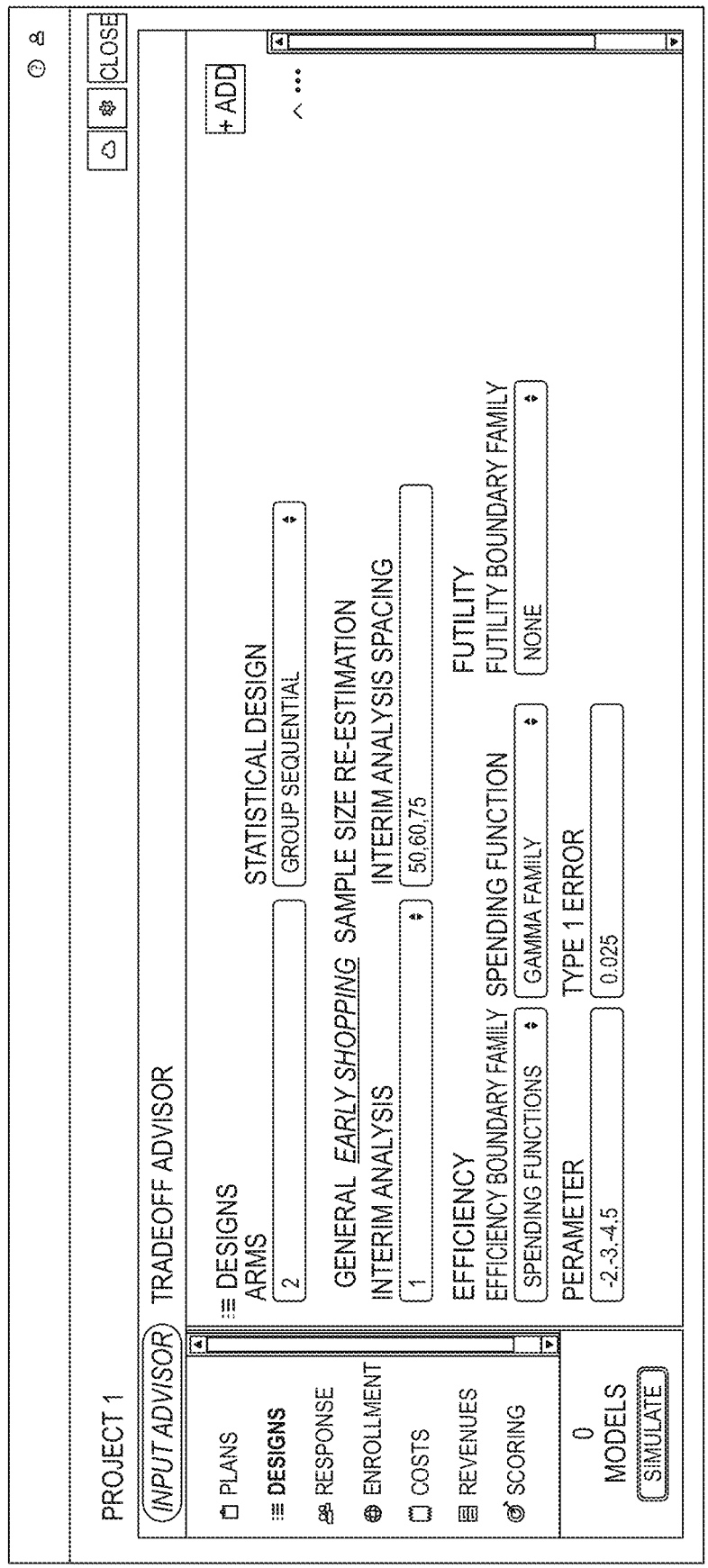
Figure 181D:
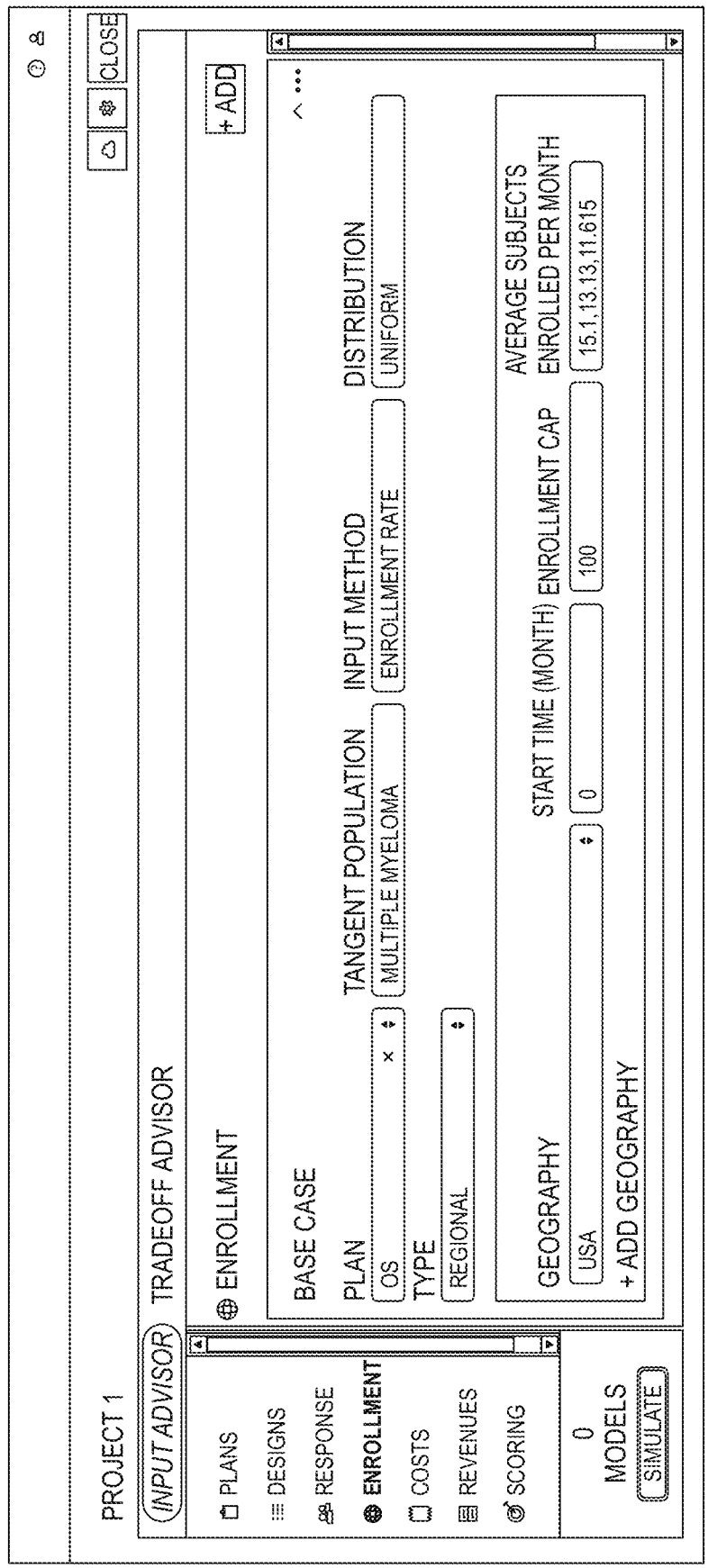
Figure 181E:
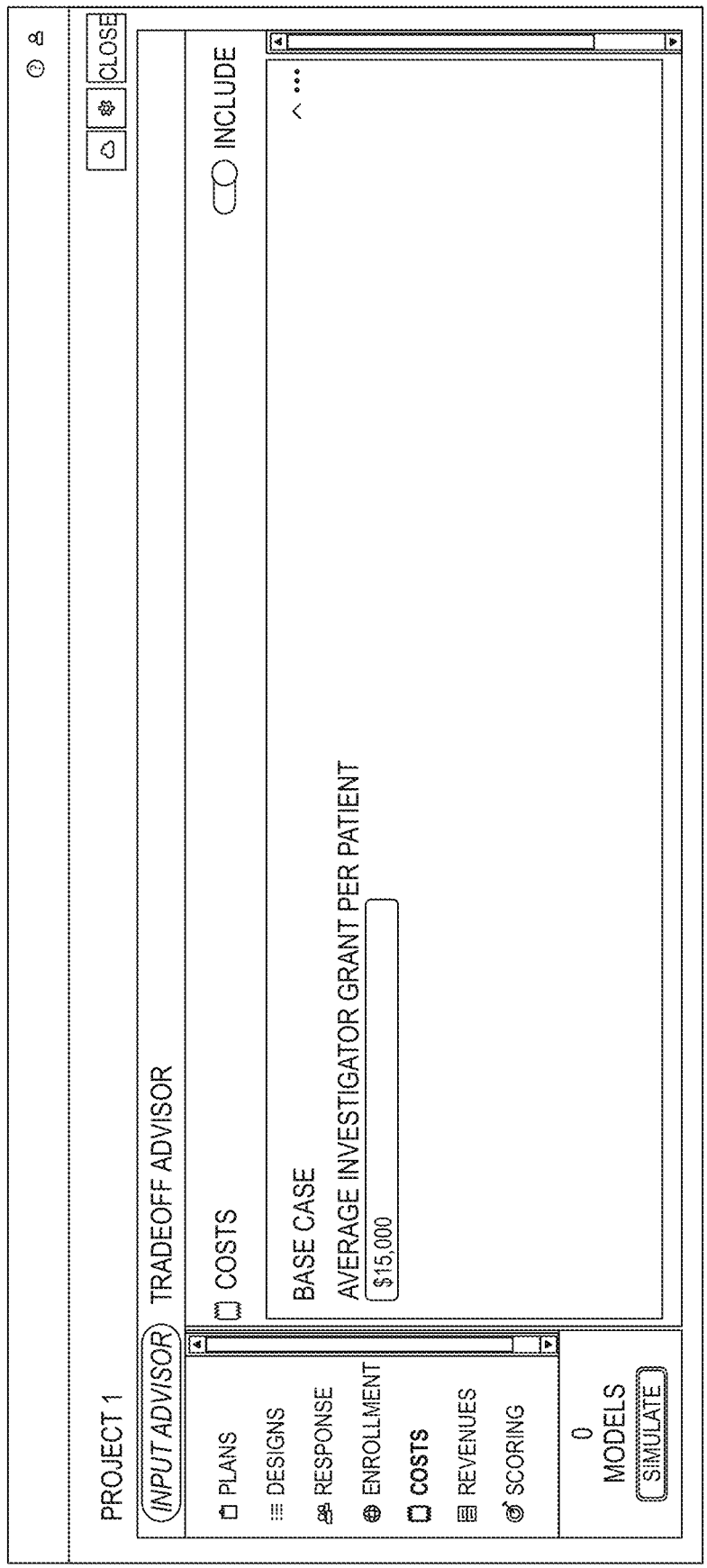
Figure 181F:
Figure 181I:
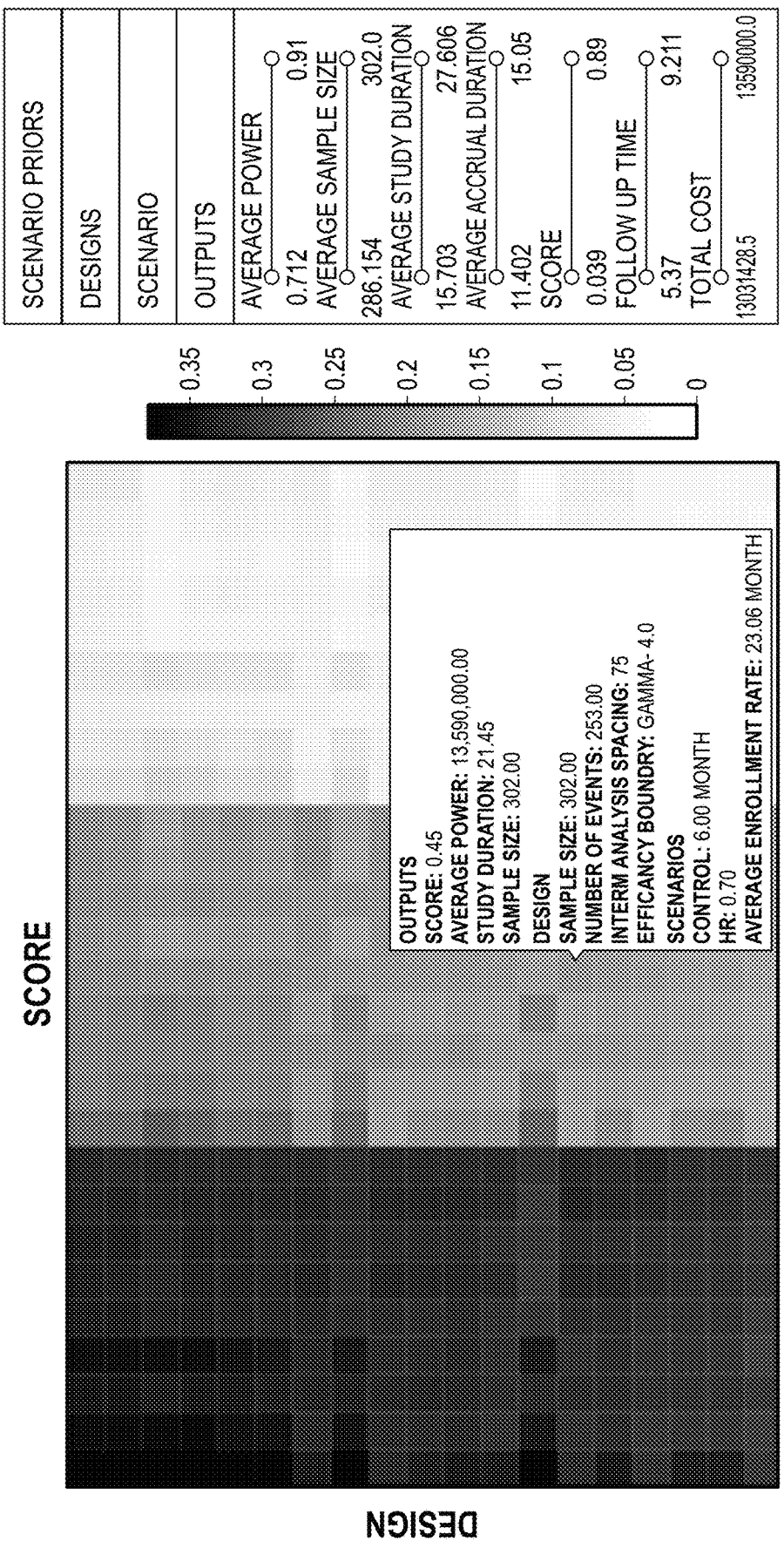
Figure 181J:
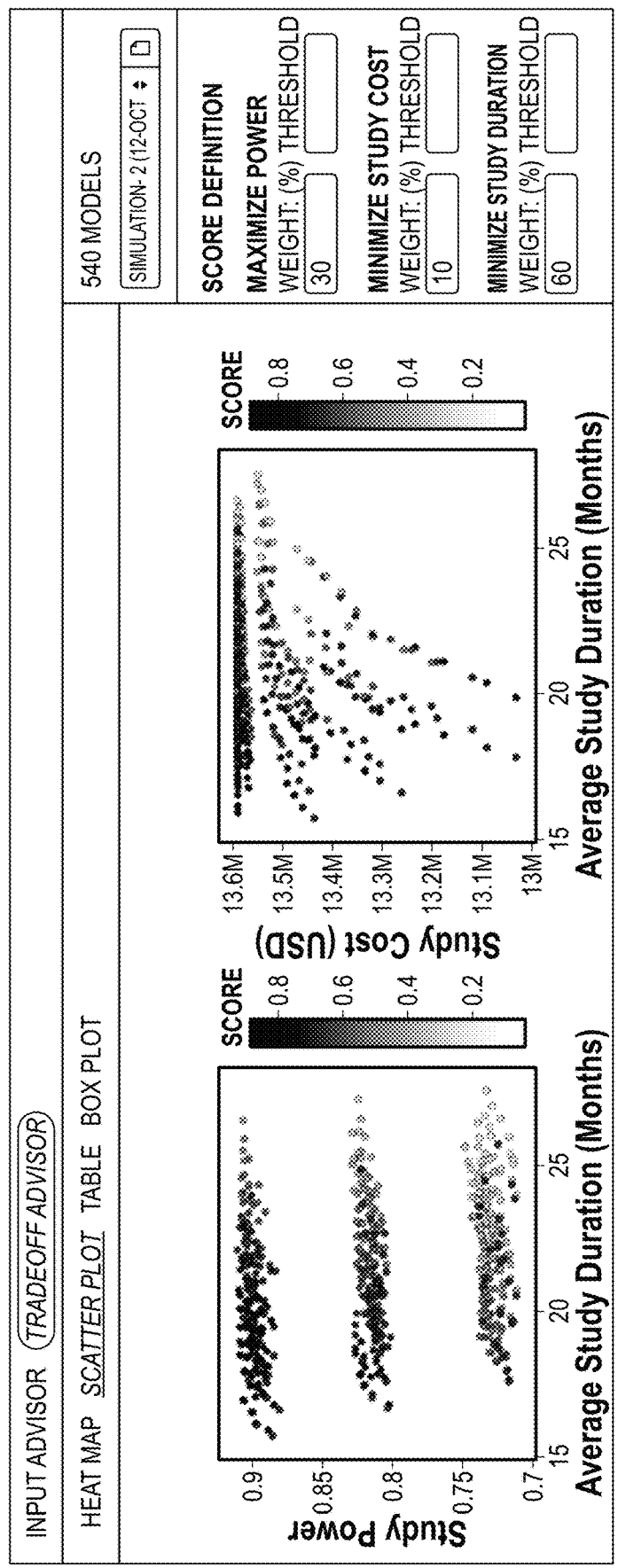
Figure 181K:
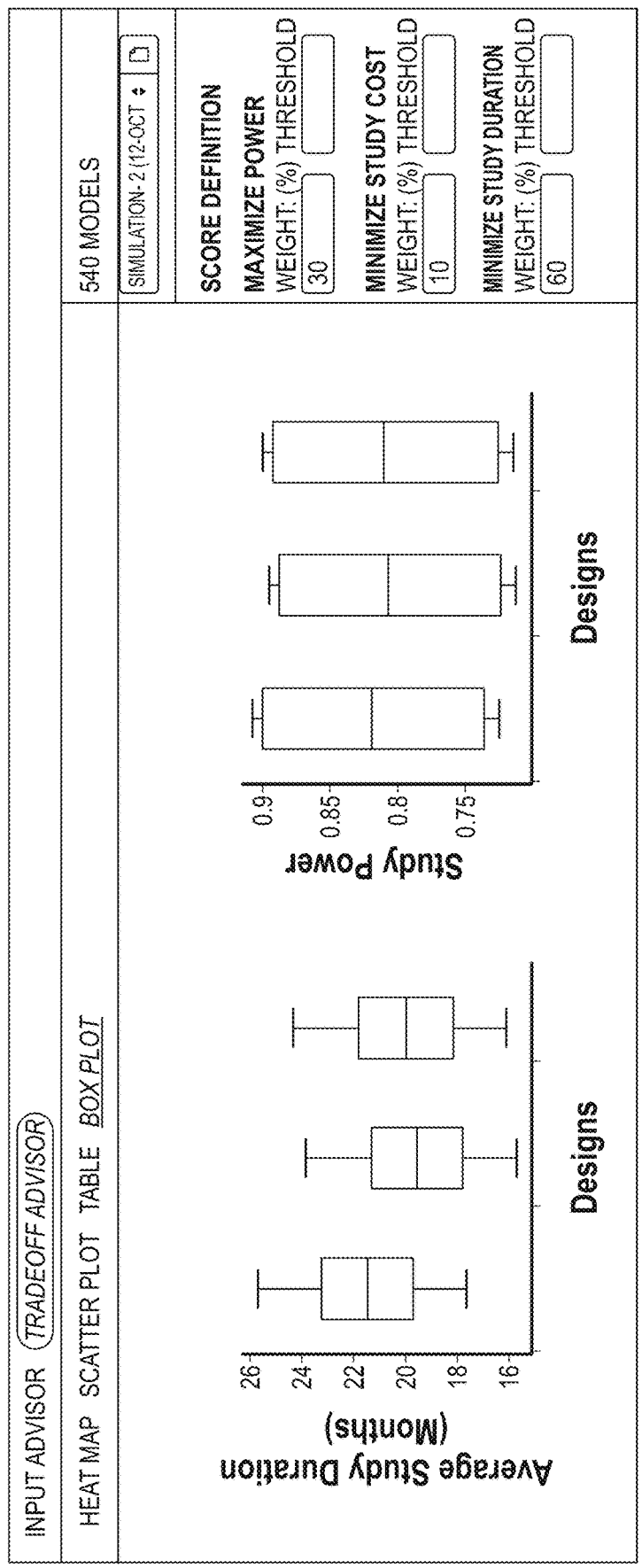

FIG. 132 is a flow chart depicting another method for determining a site selection to globally optimize available resources for a clinical trial, in accordance with an embodiment of the current disclosure;

FIG. 133 is a flow chart depicting an apparatus for determining a site selection to globally optimize available resources for a clinical trial, in accordance with an embodiment of the current disclosure;

FIG. 134 is a diagram of a platform with an interface for collaborative configuration of a site selection for optimization of availability of resources for a clinical trial, in accordance with an embodiment of the current disclosure;

FIG. 135 is a flow chart depicting a method for collaborative configuration of a site selection for optimization of availability of resources for a clinical trial, in accordance with an embodiment of the current disclosure;

FIG. 136 is a schematic diagram of an apparatus for collaborative configuration of a site selection for optimization of availability of resources for a clinical trial, in accordance with an embodiment of the current disclosure;

FIG. 137 is a flow chart depicting another method for collaborative configuration of a site selection for optimization of availability of resources for a clinical trial, in accordance with an embodiment of the current disclosure;

FIG. 138 is a diagram of a platform for configuring a system for globally optimizing availability of resources for a clinical trial, in accordance with an embodiment of the current disclosure;

FIG. 139 is a flow chart depicting a method for predicting an initial site selection with respect to optimizing available resources for a clinical trial, in accordance with an embodiment of the current disclosure;

FIG. 140 is a schematic diagram of an apparatus for predicting an initial site selection with respect to available resources for a clinical trial, in accordance with an embodiment of the current disclosure;

FIG. 141 is a diagram of a platform/system for generating an interactive interface for exploration/evaluation of spaces related to availability of resources for a clinical trial, in accordance with an embodiment of the current disclosure;

FIG. 142 is a flow chart depicting a method for generating an interactive interface for exploration/evaluation of spaces related to availability of resources for a clinical trial, in accordance with an embodiment of the current disclosure;

FIG. 143 is a schematic diagram of an apparatus for generating an interactive interface for exploration/evaluation of spaces related to availability of resources for a clinical trial, in accordance with an embodiment of the current disclosure;

FIG. 144 is a flow chart depicting a method for updating site selection according to available resources, in accordance with an embodiment of the current disclosure;

FIG. 145 is a flow chart depicting another method for updating site selection according to available resources, in accordance with an embodiment of the current disclosure;

FIG. 146 depicts aspects of a view of an organization of a platform, in accordance with an embodiment of the current disclosure;

FIG. 147 is a schematic diagram of a system for efficient resource allocation in accordance with an embodiment of the current disclosure;

FIG. 148 is a flow chart depicting a method for efficient resource allocation in accordance with an embodiment of the current disclosure;

FIG. 149 is a schematic diagram of a system for determining a score in accordance with an embodiment of the current disclosure;

FIG. 150 is a flow chart depicting a method for determining a score, in accordance with an embodiment of the current disclosure;

FIG. 151 is a flow chart depicting a method for score transformation, in accordance with an embodiment of the current disclosure;

FIG. 152 is a flow chart depicting a method for determining a collaborative session sequence, in accordance with an embodiment of the current disclosure;

FIG. 153 is a flow chart depicting a method for generating a collaborative interface, in accordance with an embodiment of the current disclosure;

FIG. 154 is a schematic diagram of a system for generating a collaborative interface in accordance with an embodiment of the current disclosure;

FIG. 155 is a diagram of a hierarchy of convex hulls in accordance with an embodiment of the current disclosure;

FIG. 156 is a flow chart depicting a method determining a design hierarchy based on convex hull peeling, in accordance with an embodiment of the current disclosure;

FIG. 157(a-e) is a diagram depicting a method for determining a convex hull for a scenario, in accordance with an embodiment of the current disclosure;

FIG. 158 is a flow chart depicting a method for determining a scenario convex hull, in accordance with an embodiment of the current disclosure;

FIG. 159 is a diagram depicting an apparatus for convex hull peeling, in accordance with an embodiment of the current disclosure;

FIG. 160 is a schematic diagram of a system for providing adaptive replication in clinical trial design simulation, in accordance with an embodiment of the current disclosure;

FIG. 161 is a schematic diagram for an apparatus for providing adaptive replication in clinical trial design simulation, in accordance with an embodiment of the current disclosure;

FIG. 162 is a flow chart depicting a method for providing adaptive replication in clinical trial design simulation, in accordance with an embodiment of the current disclosure;

FIG. 163 is a schematic diagram of a system for providing enhanced simulated annealing, in accordance with an embodiment of the current disclosure;

FIG. 164 is a schematic diagram of an apparatus for providing enhanced simulated annealing, in accordance with an embodiment of the current disclosure;

FIG. 165 is a diagram of a design space having neighboring clinical trial designs, in accordance with an embodiment of the current disclosure;

FIG. 166 is a diagram of a convex hull tunnel, in accordance with an embodiment of the current disclosure;

FIG. 167 is a flow chart depicting a method for providing enhanced simulated annealing, in accordance with an embodiment of the current disclosure;

FIG. 168 is a flow chart depicting another method for providing enhanced simulated annealing, in accordance with an embodiment of the current disclosure;

FIG. 169 is a flow chart depicting yet another method for providing enhanced simulated annealing, in accordance with an embodiment of the current disclosure;

FIG. 170 is a schematic diagram of a system for design exploration and search, in accordance with an embodiment of the current disclosure;

FIGS. 171(a-b) are diagrams of a quick search data structure, in accordance with an embodiment of the current disclosure;

FIG. 172 is a flow chart depicting a method for design exploration and search, in accordance with an embodiment of the current disclosure;

FIG. 173 is a flow chart of another method for design exploration and search, in accordance with an embodiment of the current disclosure;

FIG. 174 is a flow chart depicting another method for design exploration and search, in accordance with an embodiment of the current disclosure;

FIG. 175 is a flow chart depicting another method for design exploration and search, in accordance with an embodiment of the current disclosure;

FIG. 176 is a diagram of an interface for design exploration and search, in accordance with an embodiment of the current disclosure;

FIG. 177 is flow chart depicting another method for design exploration and search, in accordance with an embodiment of the current disclosure;

FIG. 178 is flow chart depicting another method for design exploration and search, in accordance with an embodiment of the current disclosure;

FIG. 179 is flow chart depicting another method for design exploration and search, in accordance with an embodiment of the current disclosure;

FIG. 180 is a diagram of a design space, in accordance with an embodiment of the current disclosure; and FIGS. 181(*a-k*) are diagrams of an example project, in accordance with an embodiment of the current disclosure.

DETAILED DESCRIPTION

Clinical trials (herein, also referred to as a "trial" or "study") may be used to assess, examine and evaluate drugs, devices, procedures, treatments, therapies, and the like. Clinical trials may be used to evaluate the efficiency, performance, and/or effectiveness of treatments for subjects. Embodiments of the current disclosure may also optimize for clinical trial resources, which may include drugs/drug supply subject to the trial, devices subject to the trial, administrative personnel, and/or equipment needed to administer a procedure/drug/device subject to the trial.

The success and the performance of a clinical trial depends on the design of the trial. In some cases, a wrong choice in the design of a trial may reduce the usefulness of the trial even if the trial is executed without error. In some cases, different choices for the design of a trial may result in very different costs, completion times, and/or other performance parameters for the trial.

The design of clinical trials may include considerations and tradeoffs between hundreds or even thousands of design options. Traditionally, the design of trials has been based on heuristics and experienced professionals to determine which set of parameters will result in a design that is likely to produce a successful trial. However, traditional approaches are not capable of evaluating more than a handful of design options and tradeoffs and may often miss design options that may result in better performance. The cost of a clinical trial may often exceed tens of millions or even hundreds of millions of dollars and may take years to complete, thus, small differences in the performance of a trial design may result in large impacts on the overall cost and time associated with corresponding trials.

The complexity of a trial design often requires aspects of statistical expertise, clinical design expertise, and software expertise, which may not be available in many organizations. As such, many organizations fallback on the use of generic study designs due to their inability to find optimal or near-optimal study designs.

A trial design platform, systems, and methods are described herein for evaluation and/or comparison of designs for a clinical trial. In embodiments, evaluation and/or comparison may include a large number of design options. In some embodiments, the platform, systems, and methods described herein may be used to evaluate hundreds, thousands, or even millions of design options for a clinical trial and may be used to find the optimal or near-optimal design for a trial.

The trial design platform may be used for trial design. In embodiments, a trial design platform may support a team in collaborating and surfacing all the inputs that are key to consider for preparing and selecting an optimal design. The trial design platform may use cloud and distributed computing so the team can simulate hundreds of millions of study design variants across all those inputs. The trial design platform may present the team with prioritized options and visualizations to enable the interrogation of the drivers of value. As used herein, a "team" may include a single individual or a group of individuals. Embodiments of the platforms disclosed herein may provide for collaboration within a single organization and/or across multiple organizations. In embodiments, an organization may be a business entity and/or a regulation authority, e.g., a governmental agency, and/or other entity charged with oversight and/or certification of clinical trials.

A trial design platform may enable a team to quickly identify optimal designs and the factors that most strongly drive performance factors, strategic goals, and the like. A trial design platform, as described herein, may leverage emerging technologies to provide options for advanced simulations, distributed computing, visualizations, and the like. The trial design platform may leverage methodological knowledge, analysis of the business value of different design choices, and/or analysis of regulatory risk and operational complexity to determine optimum or near optimum study designs. The trial optimization platform may determine optimum or near optimum study designs by leveraging a novel workflow, speed and/or computing innovations, and/or powerful visualizations for study analysis and optimization.

A trial design platform may improve how data and processes are used to make better decisions on clinical trial design. Improvements may result from recognizing which innovative designs might significantly increase goals. Improvements may be obtained by communicating the benefits of specific trial designs in a way that that intuitively allows a variety of team members to understand the design of a trial and/or possible options for the design of the trial. A trial design platform may support a team in collaborating and surfacing all the inputs that are key to consider for preparing and selecting an optimal design. The trial design platform may present the team with prioritized options and insightful visualizations to enable interrogation of the drivers of value.

Figure 1:
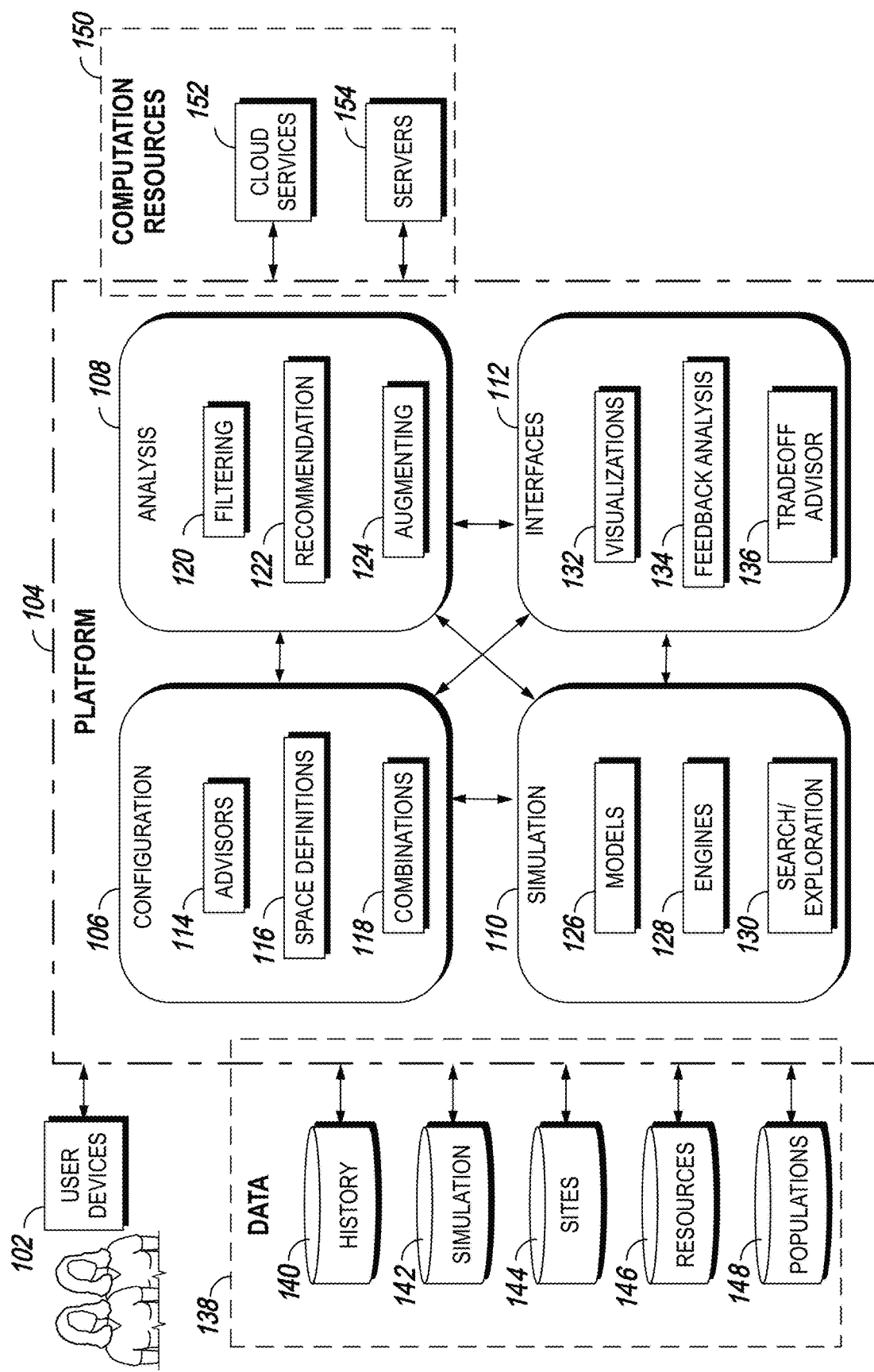
FIG. 1 is a block diagram of a platform for providing global optimization of clinical trial designs, in accordance with an embodiment of the current disclosure.

FIG. 1 shows an embodiment of a platform for evaluation and comparison of trial designs for treatments for subjects. As used herein, treatments may include procedures, diagnostic tests, devices, diets, placebos, drugs, vaccines, and the like. Treatments may include combinations of drugs, devices, procedures and/or therapies. References to subjects throughout this disclosure should also be understood to be references to people, animals, plants, organisms and other living elements.

The platform 104 may provide for a system for providing users with facilities and methods for designing, evaluating, and/or comparing designs. The facilities described herein may be deployed in part or in whole through a machine that executes computer software, modules, program codes, and/or instructions on one or more processors, as described herein, which may be part of or external to the platform 104. Users may utilize the platform 104 to identify trial designs for criteria, evaluate the designs, compare designs, determine optimal designs, and the like.

A user may interact with the platform 104 through one or more user devices 102 (e.g., computer, laptop computer, mobile computing device, and the like). The platform 104 may be implemented and/or leverage one or more computing resources 150 such as a cloud computing service 152, servers 154, software as a service (SaaS), infrastructure as a service (IaaS), platform as a service (PaaS), desktop as a Service (DaaS), managed software as a service (MSaaS), mobile backend as a service (MBaaS), information technology management as a service (ITMaaS), and the like. The platform 104 may be provided or licensed on a subscription basis and centrally hosted (e.g., accessed by users using a client (for example, a thin client) via a web browser or other application, accessed through or by mobile devices, and the like). In embodiments, elements of the platform 104 may be implemented to operate on various platforms and operating systems. In embodiments, interfaces for the user device 102 through which the users may interact with the platform may be served to the user device 102 through a webpage provided by a server of the platform 104, an application, and the like.

The platform 104 may include one or more facilities such as a configuration facility 106, simulation facility 110, analysis facility 108, interfaces facility 112, data facility 138, and computation resources 150.

The configuration facility 106 may include advisors 114, which may include one or more wizards, tools, algorithms, recommenders, configuration elements, questioners, and the like. Advisors may be used to receive data and/or define or develop space definitions 116. Space definitions 116 may include aspects of criteria space. As used herein, criteria space may include the set of parameters and values of the parameters that define goals for a design. Criteria space may define initial parameters for narrowing the design space before optimization. Parameters may include goals of designs, endpoints, primary objectives, secondary objectives, and the like. Criteria space may define values, ranges of values, types, ranges of types, and the like that may define general characteristics of a trial design.

Space definitions 116 may include aspects of design space. As used herein, design space may include the set of parameters and values of the parameters that define different options and variations of designs. Parameters may include design type, dose of drug, frequency of drug, maximum duration, patient inclusion/exclusion criteria, randomization type, and the like. The design space may include all possible permutations of the parameters. For example, one design type may be configured with different doses of a drug and different frequency of the administration of the drug. The design space may include all possible permutations of the different doses of the drug for all the different frequencies of the administration of the drug. The design space may include all the permutations of all the parameters associated with design. The design space may include millions of possible design variations. A trial design platform may evaluate all permutations of parameters of the design space. A trial design platform may evaluate a partial set of permutations of parameters of the design space. The partial set of permutations may be defined by a user. The partial set of permutations may be automatically defined, such as according to the criteria parameters.

Space definitions 116 may include aspects of scenario space. As used herein, scenario space may include the set of parameters and values of the parameters that define different options and variations of scenarios associated with designs. Scenario space may define the parameters of the environment associated with a design. Parameters may include population enrollment rate, dropout rate, population statistics, and the like. The scenario space may include all possible permutations of the parameters. For example, one scenario may be configured with a range of values for population enrollment rate and a range of values for patient dropout rate. The scenario space includes all possible permutations of the population enrollment rate and the patient dropout rate. The scenario space may include all the permutations of all the parameters associated with scenarios. The scenario space may include millions of possible scenario variations. A trial design platform may evaluate all permutations of parameters of the scenario space. A trial design platform may evaluate a partial set of permutations of parameters of the scenario space. The partial set of permutations may be defined by a user. The partial set of permutations may be automatically or semi-automatically defined, such as according to the criteria parameters.

Space definitions 116 may include aspects of performance space. As used herein, performance space may include the set of parameters and values of the parameters that define the evaluation criteria for a design. Parameters may include: net present value (NPV), expected NPV, incremental NPV, study cost, incremental study cost, study budget, incremental study budget, time to complete, incremental time to complete, time to market, incremental time to market, clinical utility, incremental clinical utility, probability of regulatory acceptance, incremental probability of regulatory acceptance, probability of success, incremental probability of success, statistical power, incremental statistical power, number of patients, incremental number of patients, number of sites, incremental number of sites, study complexity, incremental study complexity, operational complexity, incremental operational complexity, dose selected, incremental dose selected, statistical design, incremental statistical design, peak revenue, revenue at year five (5), other revenue numbers, incremental revenue, market introduction, whether market introduction beats competition entry, number of treatment arms, hypothesis superiority/equivalence/non-inferiority, other choices around statistical design, treatment effect, hazard ratio, and other choices around estimating the characteristics of the patient population, response, and safety profile, screening criteria, dropout rate, and other choices around modeling/estimating the characteristics and behaviors of the patient population and other factors that impact how the study evolves and its likelihood of achieving its goals (how slowly/quickly patients enroll, etc.), site payments and other choices around operational aspects of the study that can impact how the study evolves and its likelihood of achieving its goals, cost per patient, cost per site, or other cost factors, selections made in other projects (across users within customer companies or organizations and across all users of the platform), priorities set by the customer company or organization, and/or other user-defined filters based on available inputs and outputs of the platform or in the systems and methods described herein. In embodiments, any of the parameters and variables described herein may be incremental parameters and variables. Designs may be evaluated and compared against all of the parameters of the performance space or a subset of the parameters of the performance space. A set of designs may be evaluated for one or more of the performance parameters. The performance parameters and the values of the performance parameters of designs define the performance space of the set of designs.

The configuration facility 106 may include a combinations component 118. The combinations component 118 may automatically or semi-automatically define the design space and/or scenario space that may be evaluated by the platform.

The simulation facility 110 of the platform 104 may, based on the space definitions from the configuration facility 106, evaluate the trial designs. The simulation facility 110 may include models 126. As used herein, a model includes the combination of parameters and the values that describe a design and the scenario under which the design is evaluated. Models 126 may include hundreds or even thousands of models. Models 126 may include deviation specifications for one or more of the parameters of the models. Deviation specification may define a range of values, a distribution of values, and/or a function of values for one or more parameters of a model. The deviation specifications may be based on expected or previously measured distributions or variations in design parameters.

The simulation facility 110 may include engines 128. As used herein, engines may relate to the codification of a design that can receive model parameters and run a simulation to generate an output. The output of the engines 128 may be a predicted behavior for a design for one or more scenarios and/or conditions. Engines 128 may evaluate a design with analytical methods, mathematical methods, numerical methods, simulation, and/or the like. As used herein, simulation refers to the execution of a model using an engine. A simulation may be a single execution of model (one simulation instance) or a simulation run that includes more than one simulation instance. Evaluating a design may include a simulation run to determine performance of the design. Evaluating a design may include using a Monte Carlo approach to simulate a design for different values according to the deviation specifications and using statistical methods to determine the performance of the design from a simulation run.

The simulation facility 110 may include search/exploration component 130. The search/exploration component may facilitate modification of model parameters for simulation. The search/exploration component 130 may adaptively modify or generate models for simulations based on simulation results of other models/designs and/or based on triggers and data from other facilities of the platform 104.

The analysis facility 108 may be configured to analyze simulation results of designs. The analysis facility 108 may include a filtering component 120. The filtering component 120 may be configured to use one or more numerical and/or analytical methods to evaluate and compare the performance of evaluated designs. The filtering component may identify optimal or near-optimal designs for one or more performance parameters. The filtering component may search the performance space and identify a set of optimal and/or near optimal designs for one or more performance parameters.

The analysis facility 108 may include a recommendation component 122. The recommendation component 122 may provide design recommendations. The design recommendations may be based on optimal or near-optimal designs determined by the filtering component 120. Recommendations may be adaptive based on settings, feedback, selections, triggers, and the like from the user, and/or other facilities in the platform 104.

The analysis facility 108 may include an augmenting component, 124. The augmenting component may supplement simulation results with real-world data.

The interfaces facility 112 may be configured to provide visualizations and interfaces for comparing, searching, and evaluating simulated designs. Visualization component 132 may provide for one or more interfaces to visualize the performance of designs and facilitate comparison of designs by a user. The feedback analysis component 134 may track user actions associated with the interfaces and visualization to determine patterns and/or preferences for designs. The tradeoff advisor component 136 may analyze and provide data and guidance for evaluating tradeoffs between two more designs.

The platform 104 may include and/or provide access to one or more data facilities 138. Data in the data facilities may include design histories 140, simulation data 142, site data 144, resource data 146, population data 148, and the like.

Figure 2:
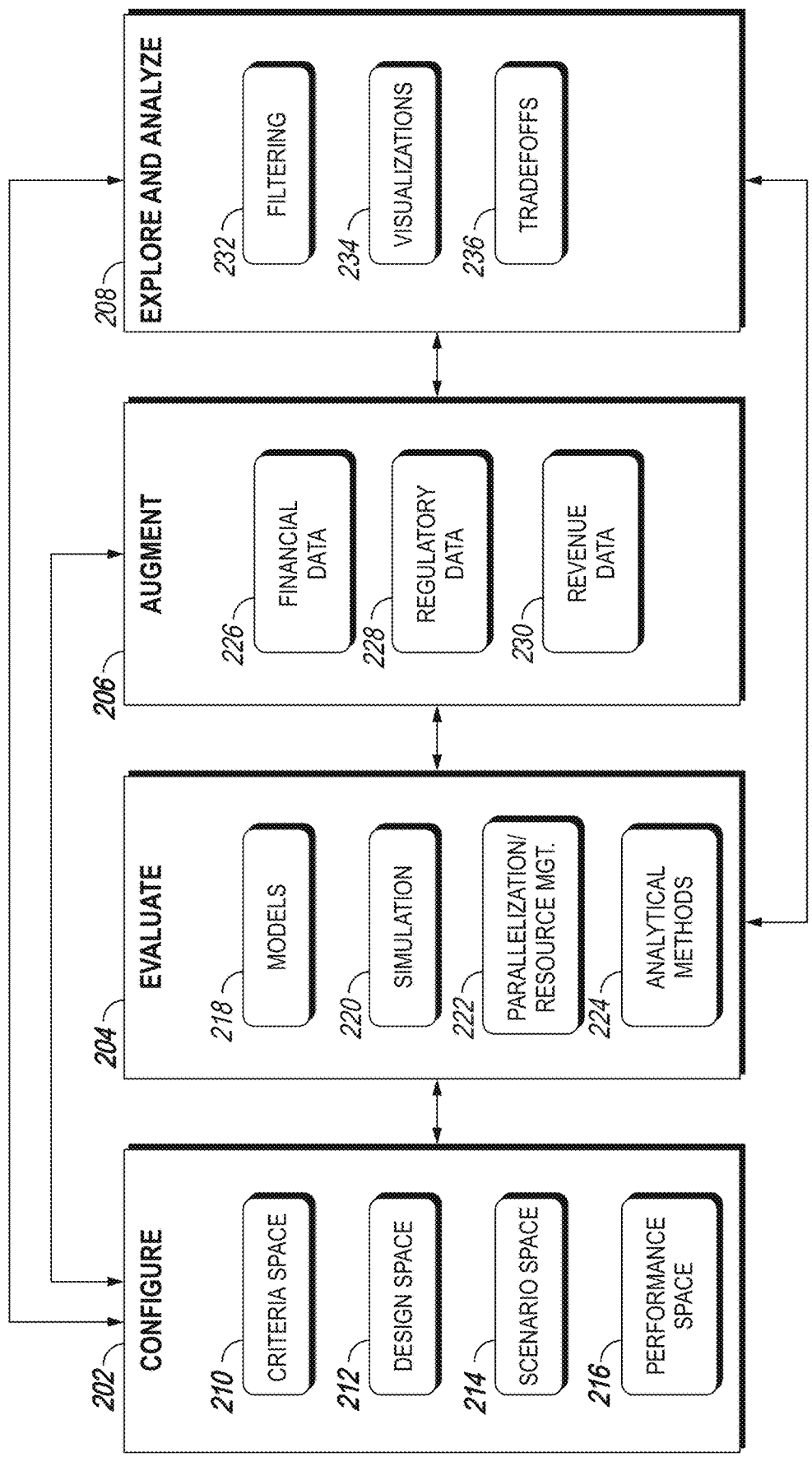
FIG. 2 is a diagram of a process for globally optimizing clinical trial designs, in accordance with an embodiment of the current disclosure.

FIG. 2 shows aspects of an embodiment of a process for trial design. The process may include four or more stages. Facilities of the platform 104 may be configured to implement the stages of the process. The stages of the process may include a configure stage 202. The configure stage 202 may define one or more the spaces associated with the trial design. The configure stage 202 may define one or more of criteria space 210, design space 212, scenario space 214, and/or performance space 216. The configure stage 202 may utilize one or more advisors, wizards, algorithms, and the like for defining the spaces. In some embodiments, the different spaces associated with the configuration stage 202 may be defined by different members of a team based on the expertise of the members. In some cases, members of a team may have different specializations. For example, some members may specialize in scenarios, while others may specialize in design definitions. Separating the inputs may allow different team members to independently optimize and improve specific models without affecting other inputs. In some embodiments, the inputs may be separated into two or more types based on convenience, expertise, flexibility, and the like.

The stages of the process may include an evaluate stage 204. The evaluate stage 204 may configure models 218 for evaluation using simulation 220 and analytical methods 224. The stage may include various methods of enhancing computation and simulation using parallelization and resource management 222.

The stages of the process may include an augment stage 206. The augment stage 206 may add real-world data to the simulation data. Financial data 226, regulatory data 228, revenue data 230, and the like may be added to the and used to augment data from simulations.

The stages of the process may include an explore and analyze stage 208. The explore and analyze stage 208 may include filtering methods and algorithms 232 for identifying optimal designs. The stage may include generating and interacting with visualizations 234 and tradeoff analysis tools 236 to compare and select designs.

In embodiments, the platform may be configured for identification and confirmation of globally optimal trial designs. Optimality of trial designs may be in relation to optimality criteria. Optimality criteria may be determined in relation to the performance space of designs. Optimality may be in relation to one or more performance parameters and the values of the performance parameters. An optimal design may be a design that achieves a most desirable value for one or more specific performance parameters. A most desirable value may depend on the performance parameter and may be different for each performance parameter. In some cases the most desirable value may be the highest value of a performance parameter. In some cases, the most desirable value may be the lowest value of a performance parameter. In some cases, the most desirable value may be a range of values, a specific value, a function of values, and the like. For example, in some cases an optimal design with respect to a cost performance parameter may be a design that has the lowest cost and achieves the goals of the clinical trial. As another example, an optimal design with respect to a time performance parameter may be a design that has the highest NPV and achieves the goals of the clinical trial. Optimality may be determined for different design types and/or different phases of a trial. In embodiments different optimality criteria may be used for different designs and/or different phase of a trial.

In embodiments, an optimum design is a design that achieves most desirable values for two or more specific performance parameters. In the case of optimality for multiple performance parameters, optimality may require a tradeoff between the parameter values. For example, a design that has the lower cost may have a low NPV and therefore may not be desirable. The optimality of a design may be based on a function of performance parameters. In some cases, a function may be a weighted sum of the performance parameters. A function, or a set of functions, may be used to generate an overall score (or a set of scores) and the score may be used to determine the optimality of the design. A highest score, a specific score, lowest score, and the like may be considered optimal depending on the function used to compute the score.

In embodiments, optimality may be evaluated according to Pareto optimality. Pareto optimal designs may be designs where no individual performance parameter can be better off without making at least one other individual performance parameter worse off. In some cases, optimality may be determined using convex hull analysis.

In some cases, one design may be globally optimum. In some cases, more than one design may be globally optimum. In some cases, no designs may be globally optimum. In some embodiments, optimality of designs may be relative to a benchmark. A known design, a set of historical designs, and/or the like may be used as a benchmark. Designs may be considered optimal if they meet, exceed, and/or are within a threshold distance of the benchmark design performance parameters.

Performance parameters that may be used to determine design optimality may be user defined, system defined, algorithmically defined, and/or the like. In some cases, users may specify a subset of performance parameters that should be used to identify optimal designs. A user may define optimality criteria by defining ranges, values, characteristics, and the like of the parameter values that may be considered desirable and/or optimal. Interactive graphical interfaces may be provided to a user to evaluate different designs based on one or more optimality criteria. Interactive interfaces may allow a user to explore different designs by changing scoring methods, weights associated with the criteria, and the like.

In embodiments, the characteristics of performance parameters for evaluated designs may be analyzed by the platform to determine if any of the parameters may be less important for optimality. For example, analysis may include evaluation of ranges, variability, and other statistical analysis. If one or more performance parameters for all evaluated designs is within a desirable range, or the performance parameter is almost equal for all of the evaluated designs, the performance parameter may be removed and identified as less significant for optimality and, in some cases, may not be factored in when determining optimality. Prior to determining optimality on based on performance parameters, the performance parameters and the values of the performance parameters may be grouped, filtered, normalized, and the like.

Optimality of designs may be redefined automatically, semi-automatically, in response to user input, and/or the like. The criteria for optimality of designs may change as designs are evaluated by the platform. For example, initial optimality criteria may produce no optimal designs. In response to no optimal designs being determined, the criteria may be changed (relaxed, increased, decreased, etc.) until at least one design is considered optimal. In another example, optimality criteria may change in response to user feedback. Users may evaluate initial designs found to be optimal and provide feedback (direct feedback and/or indirect feedback that can be derived from user actions and inactions). The feedback from the user may be used to change how optimality is determined, which performance parameters are used to determine optimality, the values of the performance parameters that are considered optimal, and/or the like.

In some embodiments, performance parameters may be grouped, ordered, and/or organized into one or more hierarchies, groups, and/or sets. Two or more different optimality criteria may be used in parallel to determine multiple sets of optimal designs under different criteria. Two or more different optimality criteria may be used sequentially to determine optimal designs. One criteria may first be used to identify a first set of optimal designs under first criteria. A second set of criteria may then be used on the first set to reduce the set of optimal designs.

In embodiments, a design may be globally optimum if the design is optimal with respect to all possible design options. In embodiments, a design may be globally optimum if the design is optimal with respect to possible design options for one or more criteria. In embodiments, a design may be globally optimum if the design is optimal with respect to a large percentage (such as 80% or more) of possible design options for one or more criteria. In embodiments, a design may be globally optimum if the optimality of the design is within a high confidence level (90% confidence) with respect to possible design options for one or more criteria.

Traditional methods for evaluating designs cannot determine global optimum designs since they evaluate one, several, or a small subset of design options. Traditional methods do not consider all or almost all of the design options and cannot find a global optimum.

Trial designs may involve numerous variables, parameters, considerations, tradeoffs, and the like resulting in a very large number of possible variations. A large number of possible variations makes study design and optimization using traditional methods difficult. In many cases, traditional methods may fail to explore or consider the complete space of possible trial design options and may miss or never consider globally optimal designs. Using traditional methods, the number of design variations that may be explored in a reasonable time is limited. In some cases, only one (1) statistical design and only three (3) clinical scenarios may be evaluated. The best design study of the limited number of variations may not result in a globally optimal design. A locally optimum design chosen from a limited number of considered designs may represent one (1) local maximum but may be far from the globally optimum design. When 10,000 or more clinical scenarios are considered, a globally optimum design may be distinguished from the many locally optimum designs. However, consideration of 10,000 clinical scenarios cannot be practically performed using traditional methods as it would require an estimated 50,000 hours or more to complete.

In embodiments, the platform and methods described herein may evaluate thousands or even millions of design options enabling a determination of a global optimum design. In many cases, the globally optimum design may have significant advantages over locally optimum designs. In one example, a globally optimum design may require less time to complete than other designs.

Referring again to FIG. 1, the platform 104 may receive and/or determine performance space using the configuration facility 106. Performance space may be defined in the space definitions component 116. The performance space may be configured based input from users and/or based on data 138 such as history data 140 and/or simulation data 142. In one instance, performance space may define optimality criteria. Optimality criteria may define performance parameters, performance values, functions, methods, and algorithms for evaluating optimality and/or global optimality of designs. In one instance optimality criteria may be configured by the user or determined from benchmark designs from history 140 and/or simulation 142 data. In another instance, optimality criteria may be defined from simulation data from the simulation facility 110. Optimality of designs may be determined in the analysis facility 108. The filtering component 120 may be used to determine one or more sets of globally optimum designs from the designs evaluated by the simulation facility 110.

Figure 3:
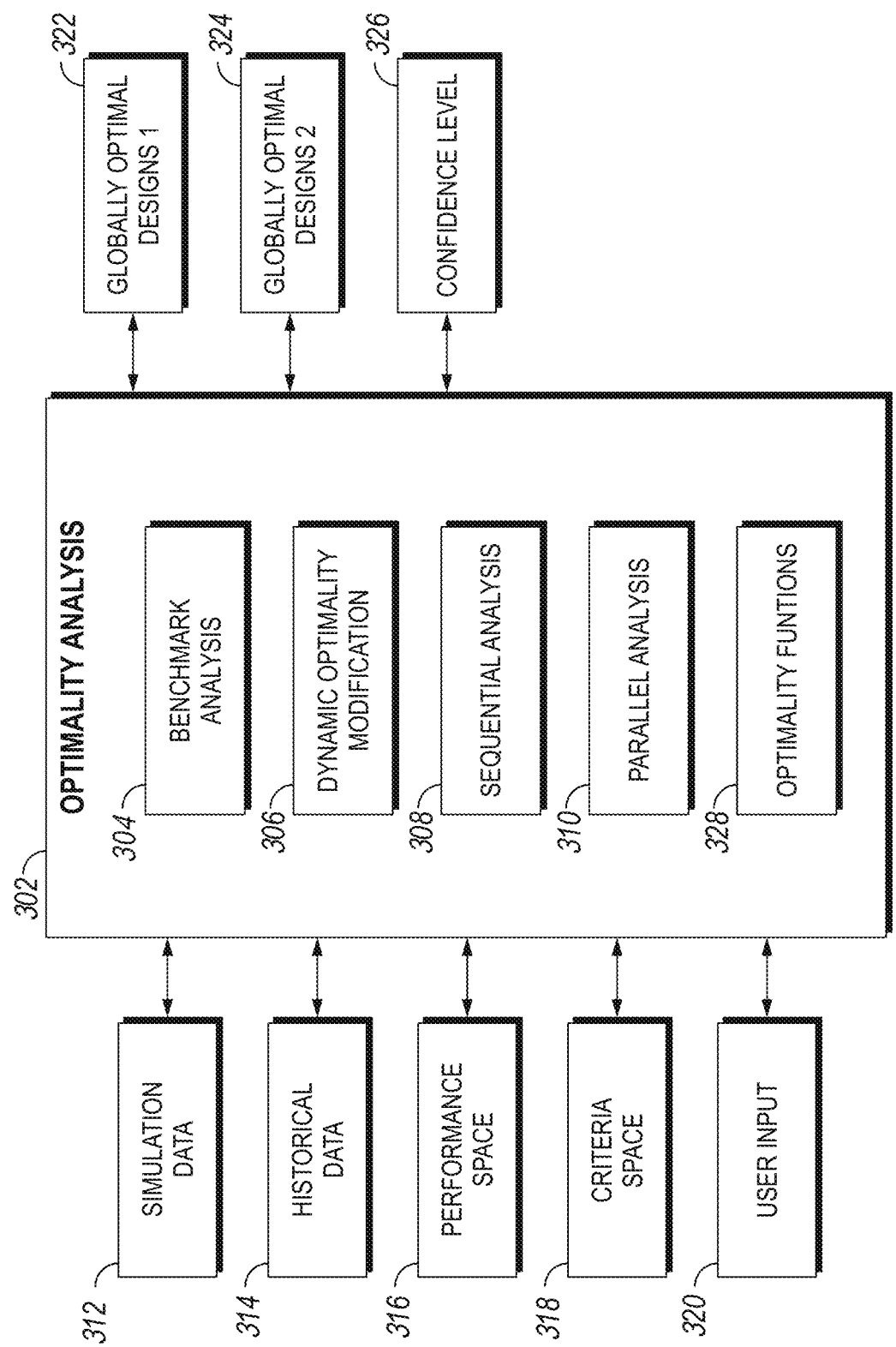
FIG. 3 is a schematic diagram of an apparatus for determining globally optimum designs, in accordance with an embodiment of the current disclosure.

FIG. 3 shows aspects of an apparatus for determining global optimality of designs. In embodiments, the optimality analysis component 302 may be part of the analysis facility 108 of the platform 104. The optimality analysis component 302 may receive data from simulated designs 312 and determine one or more sets of optimal designs 322, 324. The optimality analysis component 302 may include one or more circuits for determining optimality of designs. In embodiments, the optimality analysis component 302 may include circuits for determining optimality based on optimality functions 328. Optimality functions 328 may determine optimality of designs based on different weighting of performance factors of the simulated designs. In embodiments, the optimality analysis circuit 302 may include circuits for determining optimality based on benchmark analysis 304. Benchmark analysis circuit 304 may determine optimality of designs based on a comparison of performance parameter values to one or more benchmark designs such as from historical data 314 and/or simulation data 312. In embodiments, the optimality analysis circuit 302 may include circuits for determining optimality using sequential analysis 308 and/or parallel analysis 310. Sequential analysis circuit 308 and parallel analysis circuit 310 may use one or more different optimality functions 328 in parallel or sequentially to determine optimal designs. In embodiments, the optimality analysis circuit 302 may include circuits for dynamically modifying optimality criteria 306. User inputs 320, simulation data 312, and/or the determined sets of optimal designs may be monitored and analyzed to determine modifications to optimality criteria. In embodiments, the optimality analysis circuit 302 identifies a confidence level 326 associated with the optimality of sets of optimal designs. In the case where simulation data 312 may not include simulations of all design options for the criteria space 318, the optimality circuit 302 may determine, based on the simulated designs, a confidence level that the determined optimal designs are indeed optimal for a given optimality criteria.

Figure 4:
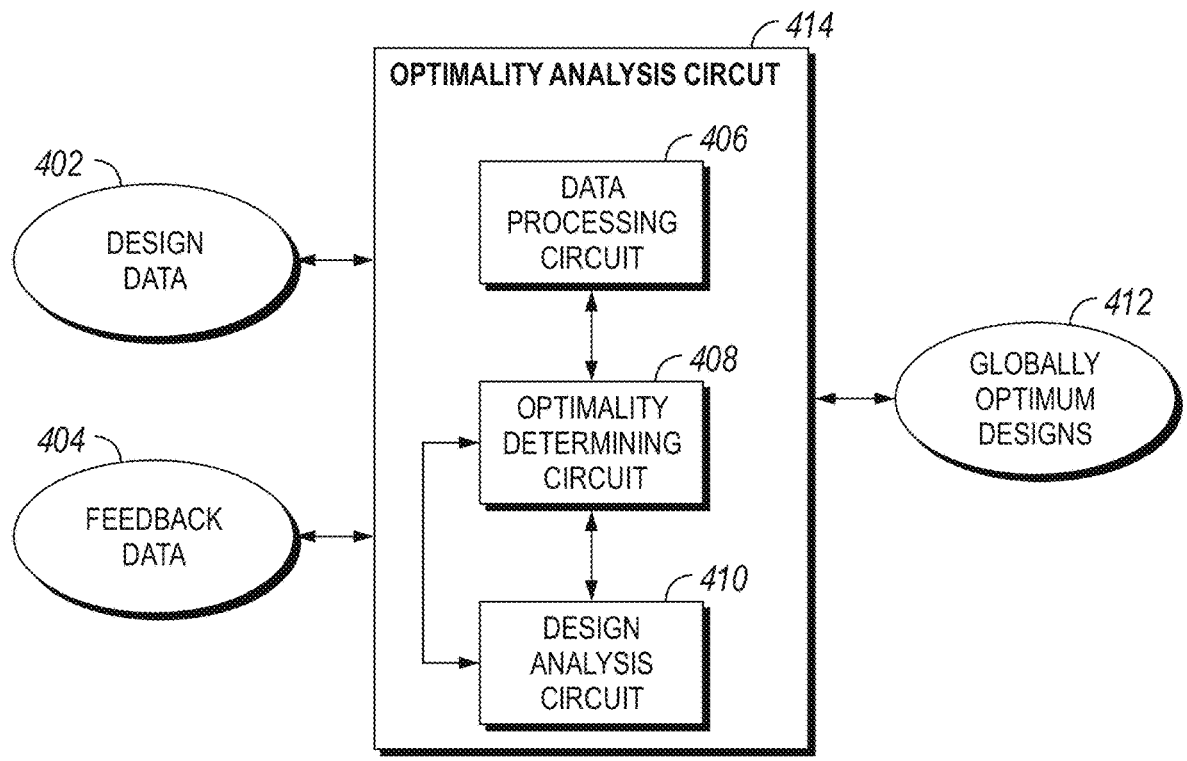
FIG. 4 is a schematic diagram of an apparatus for determining globally optimum designs, in accordance with an embodiment of the current disclosure.

FIG. 4 shows aspects of an apparatus for determining global optimality of designs. In embodiments, the apparatus may include an optimality analysis circuit 414 which may be part of the analysis facility 108 of the platform 104. In embodiments, the apparatus may include a data processing circuit 406 structured to interpret/obtain design data 402 of a clinical trial design. In some embodiments the design data 402 may be outputs of simulation data of trial designs. The data processing circuit 406 may transform the design data 402 into a format suitable for use by the various circuits in the apparatus. For example, the design data 402 may be received by the data processing circuit 406 and determine and identify performance parameters in the data. In some embodiments, some performance parameters may be grouped, filtered, converted, normalized, and the like.

The apparatus of FIG. 4 may further include an optimality determining circuit 408 structured to receive processed design data from the data processing circuit 406. The optimality determining circuit 408 may identify globally optimum designs 412 based on one or more optimality criteria. In some embodiments, the globally optimum designs 412 may be provided as an output of the apparatus. In some embodiments, globally optimum designs 412 may be further processed by the design analysis circuit 410. The design analysis circuit 410 may analyze the globally optimum designs 412, determine characteristics of the designs, and receive feedback data 404 about the designs. The design analysis circuit may, based on the determined characteristics, determine modifications for optimality criteria used in the optimality determining circuit 408. Using modified optimality criteria, the optimality determining circuit 408 may determine a new set of globally optimum designs 412.

Figure 5:
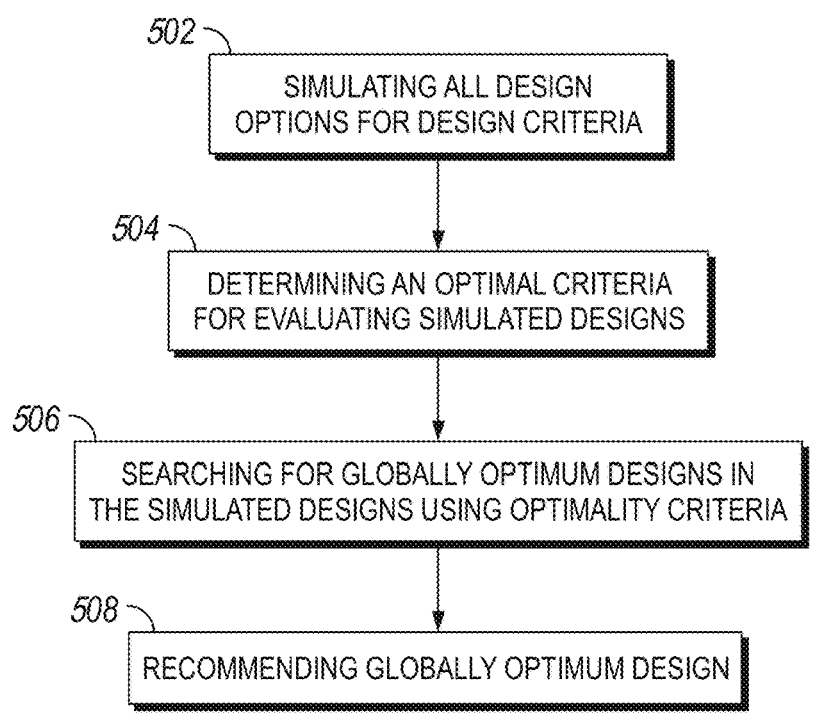
FIG. 5 is a flow chart depicting a method for determining globally optimum designs, in accordance with an embodiment of the current disclosure.

As shown in FIG. 5, a method for determining globally optimum designs may include simulating all design options for a design criteria 502. The method may further include determining an optimality criteria for evaluating simulated designs 504. Optimality criteria may be a function of one or more performance values for each design such as a weighted sum of the values, a comparison of the values, and the like. The method may include searching for globally optimum designs in the simulated designs using the determined optimality criteria 506. The globally optimum designs may be recommended to one or more users 508.

Figure 6:
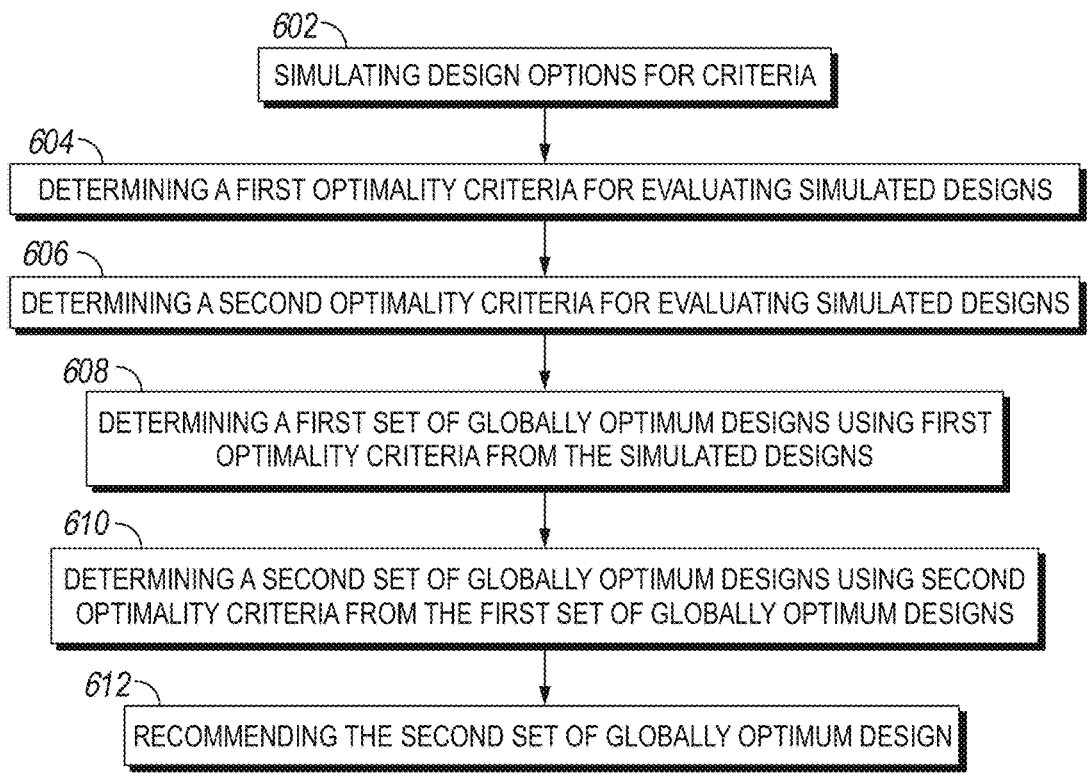
FIG. 6 is a flow chart depicting a method for determining globally optimum designs, in accordance with an embodiment of the current disclosure.

As shown in FIG. 6, a method for determining globally optimum designs may include simulating design options for a design criteria 602. The method may further include determining a first optimality criteria for evaluating simulated designs 604. The method may further include determining a first optimality criteria for evaluating simulated designs 606. In the next step, the method may include determining a first set of optimum designs using the first optimality criteria, the first set may be determined from the simulated designs 608. The method may further include determining a second set of optimum designs using the second optimality criteria, the second set may be determined from the first set of designs 610. The globally optimum designs may be recommended to one or more users 612.

Figure 7:
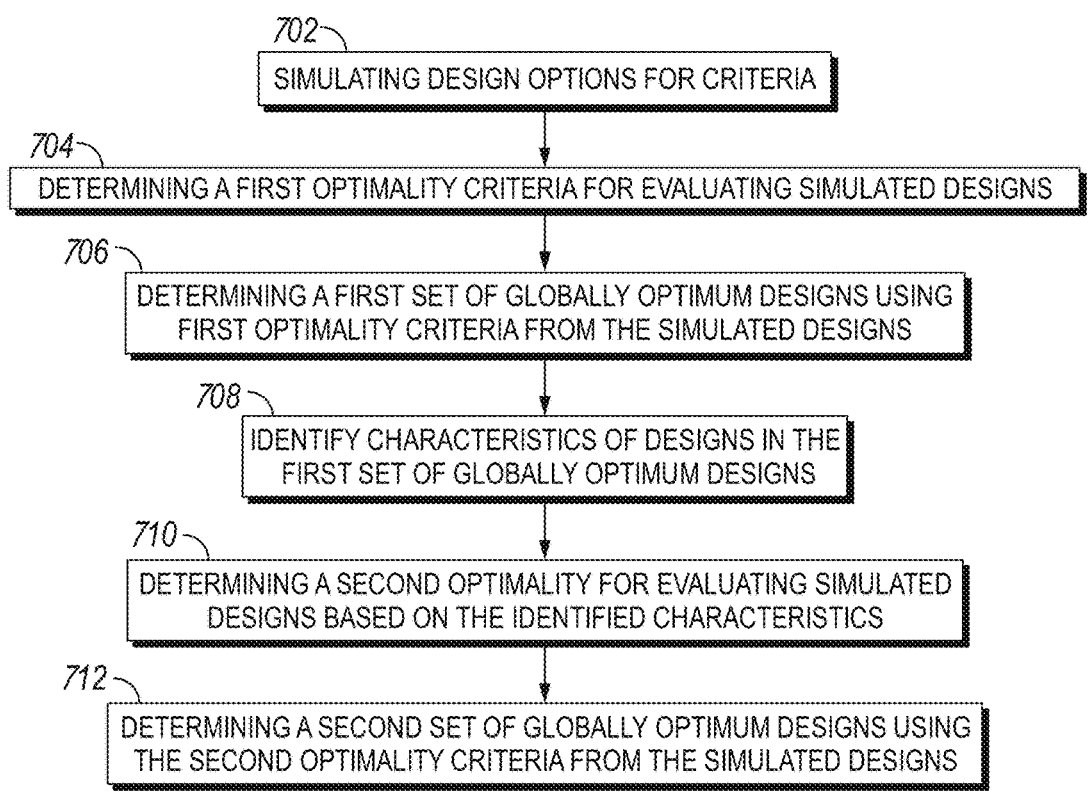
FIG. 7 is a flow chart depicting a method for determining globally optimum designs, in accordance with an embodiment of the current disclosure.

As shown in FIG. 7, a method for determining globally optimum designs may include simulating design options for a design criteria 702. The method may further include determining a first optimality criteria for evaluating simulated designs 704. In the next step, the method may include determining a first set of optimum designs using the first optimality criteria, the first set may be determined from the simulated designs 706. The method may further include identifying characteristics of designs in the first set of globally optimum designs 708. The method may further include determining a second optimality criteria for evaluating simulated designs based on the identified characteristics 710. The next step of the method may include determining a second set of globally optimum designs using the second optimality criteria from the simulated designs 712.

In embodiments, the platform may be configured for identification and confirmation of globally optimal trial designs across one or more of design space, scenario space, criteria space, or performance space. In embodiments, the determination of an optimum design requires a careful balance to ensure that relevant parameter permutations are considered but that time, cost, and the like are not wasted on needless simulations and evaluation of designs that are not relevant. In embodiments, the platform enables the surfacing and consideration of all relevant parameters for evaluating a design while not needlessly wasting resources.

In embodiments, the platform may support global optimization of clinical trial design by connecting criteria space, design space, scenario space and performance space. The platform may provide users with visualizations for interactive exploration of the spaces. The platform may support global optimization by enabling design optimization and exploration across different styles of explorations. Users of different experience, knowledge, and/or expertise may explore or optimize for elements that are within their expertise/knowledge and share and explore data with users of the same or different expertise/knowledge.

In embodiments, globally optimum trial design may include defining criteria space. In some embodiments, defining and configuring criteria space may be a prerequisite to defining and configuring other spaces. Configuration space may be at least partially defined and configured by a user. In some embodiments, expert users may define all or a large portion of the criteria space. In some embodiments, a user may directly define a portion of the criteria space and/or provide general aspects or goals for the study and the platform may use one or more advisors (such as the design advisor described herein), historical data, and AI/ML models of historical study data to define and configure the criteria space. In embodiments, the criteria space definitions may be used by the platform to determine parameters for design space, scenario space, and/or performance space. In embodiments, the scenario space parameters may be automatically reviewed for consistency and errors and any contradictions in parameters may be flagged for review by a user.

In embodiments, scenario space parameters may be analyzed to determine the breadth of the constraints of the parameters. In some cases, the platform may determine or estimate aspects such as size of the design space (for example, number of design options that will need to be simulated), complexity of the design space (for example, number of parameters) size of the scenario space (for example, number of scenarios that will need to be simulated), complexity of the scenario space (for example, number of parameters), size of the performance space (for example, number of performance parameters that need to be tracked in simulation), and the like based on the configuration of the criteria space. The estimates on sizes, complexity, and the like may provide a guide as to the breadth of the criteria space definitions. The estimates may be determined from historical data, may be algorithmically determined, and/or estimated via one or more tables that provide a correspondence between the criteria space parameters and other spaces.

In some cases, criteria space may be identified (automatically by the platform or by the user) as being too constricting (such as not resulting in a meaningful number of design options for simulation) or to broad (such as resulting in an extremely large number of design options to be simulated) and the platform may identify ways to broaden and/or narrow the criteria space. In one embodiment, parameters of the criteria space may include relations and dependencies. The platform may surface and identify criteria space parameters to add (typically to narrow the breadth) or to remove certain constraints from the criteria space (typically to increase the breadth) based on the relations and dependencies in the parameters.

In embodiments, the criteria space definitions may be used to define the design space. Design space definitions may include ranges of values for one or more design space parameters. The design space may be developed by defining design options by taking a cross product of all the permutations of the values of the design space parameters. Each of the resulting design options may be verified to determine if the permutation of parameters for the design resulted in a valid design option and/or consistent with the criteria space constraints. Invalid permutations may be removed or flagged to avoid needless simulation.

In embodiments, the criteria space definitions may be used to define the scenario space. Scenario space definitions may include ranges of values for one or more scenario space parameters. The scenario space may be developed by defining scenario options by taking a cross product of all the permutations of the values of the scenario space parameters. Each of the resulting scenario options may be verified to determine if the permutation of parameters for the scenario resulted in a valid scenario option and/or consistent with the criteria space constraints. Invalid permutations may be removed or flagged to avoid unnecessary simulation.

In embodiments, a cross product of all the valid scenario options from the scenario space and all the valid design options from the design space may be used to generate models for simulation. Each of the resulting scenario-design permutations may be verified to determine if the permutation resulted in a valid permutation and/or is consistent with the criteria space constraints. Invalid permutations may be removed or flagged to avoid unnecessary simulation.

In some embodiments, the set of scenario-design permutations may be pruned to remove permutations that are determined to have poor performance parameters or are predicted to not meet the criteria. In some cases, a database of previous simulations may be compared to the set of permutations to identify preliminary predictions.

Models for the valid scenario-design permutations may be simulated using one or more engines to determine performance of the designs. The simulations may track and evaluate performance space of each design according to the criteria space definitions. The simulated data may be analyzed to determine optimum designs. Various visualizations and analysis interfaces (such as card interfaces, heat maps, and tornado diagrams as described herein) may be provided by the platform for visualizing and identifying performance of designs. The systematic development of criteria, design, scenario, and performance spaces and their respective permutations ensures that all relevant design options are considered and evaluated for determining globally optimum design options.

Referring to FIG. 1, the configuration facility 106 of the platform 104 may include components for defining the criteria space, design space, scenario space, and performance space. In embodiments, advisor components 114 may be used to define criteria space and further define space definitions using the space definitions component 116. The combinations component 118 may determine permutations and combinations and may identify invalid or unnecessary combinations of parameters for a criteria. The combinations may be used to define models in the models component 126 for simulation. The models may be simulated by the simulation facility 110 and analyzed by the analysis facility 108.

Figure 8:
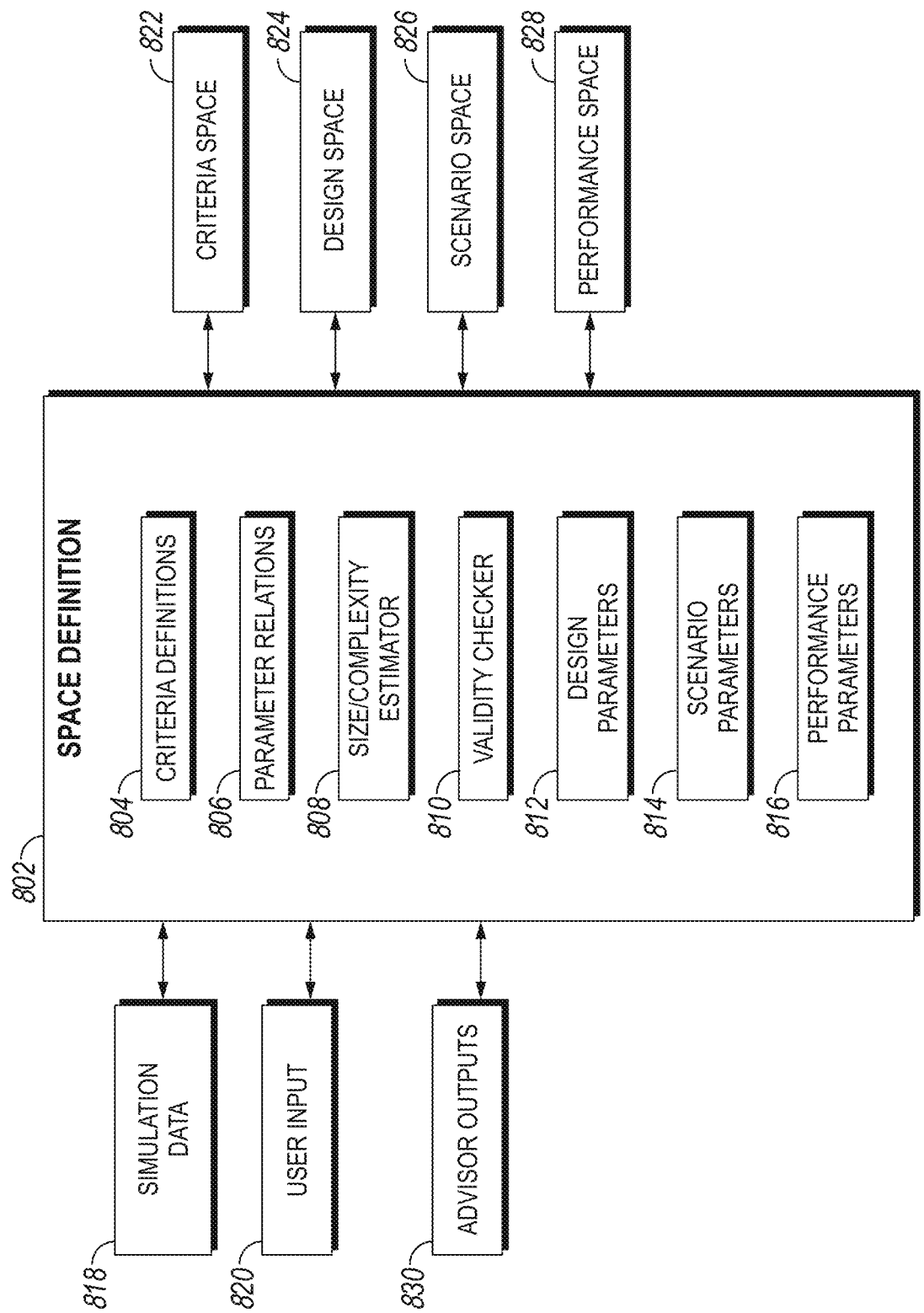
FIG. 8 is a schematic diagram of an apparatus for evaluating designs, in accordance with an embodiment of the current disclosure.

FIG. 8 shows aspects of an apparatus for defining criteria, design, scenario, and performance spaces for trial design. In embodiments, the space definition component 802 may be part of the configuration facility 106 of the platform 104. The space definition component 802 may receive specifications for user input 820 or from one or more input/design advisors 830. The inputs may identify definitions and constraints on one or more spaces. From the input, the criteria definitions component 804 may identify criteria parameters that may identify constraints on the study. In embodiments size/complexity estimator 808 may provide data and estimates with respect to how criteria definitions relate to the number of design options and scenario options that will be simulated for the criteria. Estimates may be determined from previous simulation data 818. The size/complexity estimator 808 may initiate criteria revisions. In some embodiments, parameter relations component 806 may surface settings and parameter relations to identify constraints and/or parameters that may be added, removed, or redefined in the criteria. A validity checker component 810 may verify that criteria space parameters are consistent and may flag any issues that should be addressed. Based on the criteria space definitions 822, the design parameters component 812 may determine ranges and values for one or more design parameters that meet the criteria. The design parameters component 812 may identify valid permutations of the design parameters and define the design space 824. Based on the criteria space definitions 822, the scenario parameters component 814 may determine ranges and values for one or more scenario parameters that meet the criteria. The scenario parameters component 814 may identify valid permutations of the scenario parameters and define the scenario space 826. The performance parameters component 816 may identify performance parameters that should be tracked based on the criteria and define the performance space 828.

Figure 9:
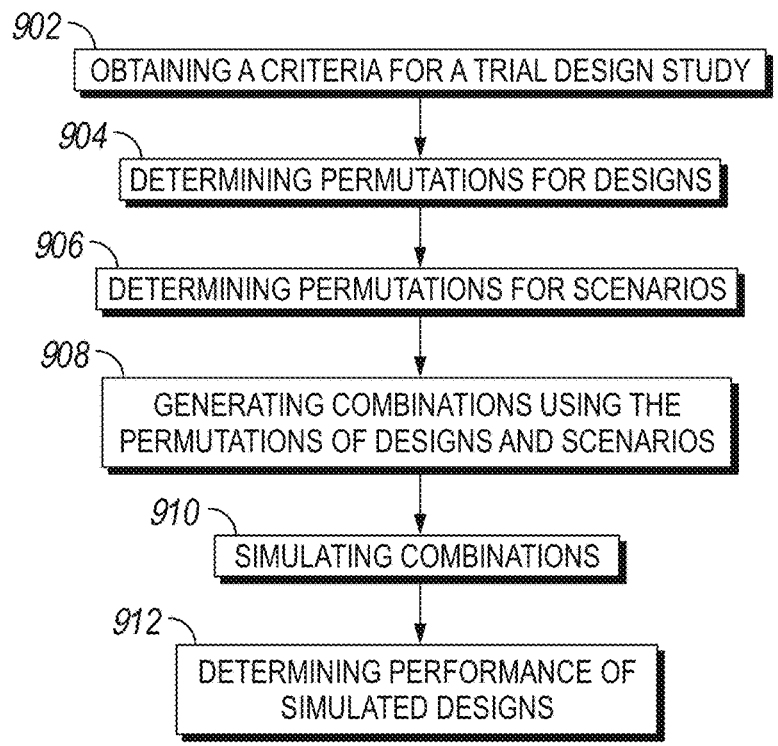
FIG. 9 is a flow chart depicting a method of evaluating designs, in accordance with an embodiment of the current disclosure.

As shown in FIG. 9, a method for evaluating a design may include obtaining a criteria for a trial design study 902. The criteria may be obtained from the user or from other parts of the platform based on a user input and/or historical data. The method may further include determining permutations for designs based on the criteria 904 and determining permutations for scenarios based on the criteria 906. For example, depending on the criteria, it may be possible to affirmatively determine design permutations or scenario permutations that are feasible in view of the criteria, and/or it may be possible to determine specific design permutations or scenario permutations that are not feasible in view of the criteria (e.g., cannot possibly provide a result that satisfies the criteria). For example, if a user inputs as a design criterion a specific maximum drug dose, then only design permutations having a dose of drug equal to or less than the specified maximum drug dose will be included (all other design permutations are infeasible in view of specified criterion, because it is not possible for them to achieve a drug dose that does not exceed the specified maximum). Alternatively or in addition, if a user inputs as a scenario criterion a specific range of patient dropout rates (for example), then only scenario permutations having a patient dropout rate within the specified range will be included. Furthermore, the method may include generating combinations using the permutations of designs and scenarios 908. In some embodiments, the combinations may be exhaustive, i.e., the combinations to be simulated include each possible design permutation combined with each possible scenario permutation (or, if infeasible permutations are first excluded, the combinations to be simulated include each feasible design permutation combined with each feasible scenario). Alternatively, in some embodiments, some combinations may be removed based on predicted performance. As discussed further below, a variety of heuristics, algorithms, filters, or the like may be used to predict that certain combinations are improbable or unlikely to achieve a desirable outcome. In some embodiments, analysis of data from past trials, or information input by one or more users, may indicate improbable combinations for which simulation would be of minimal value. For example, historical trial data and/or guidelines based on user experience may indicate a direct relationship between trial duration and patient dropout rates, such that a patient dropout rate below a certain level is unlikely to be achieved for a trial having a duration that exceeds a certain time period. Therefore, although combinations having certain patient dropout rates and certain trial durations may satisfy all selected criteria, it can be predicted that such combinations either cannot be achieved as a practical matter or cannot result in a satisfactory trial outcome. Therefore, such combinations can be removed prior to the simulation. As another example, analysis of past trial data may indicate that drug doses below a certain level are rarely effective in treatment of certain conditions, and combinations involving low drug doses may be predicted to perform poorly and therefore be removed prior to simulation. Also, as discussed further below, a scoring system may be implemented to predict performance and determine combinations that should be removed prior to simulation. The combinations that are determined to be appropriate for simulation (which may be all possible combinations in some embodiments or a subset of combinations in other embodiments) may be simulated 910 and the performance of the simulated designs may be determined and analyzed 912. The evaluated performance parameters may be based on the criteria and/or based on goals or performance objectives other than the obtained criteria.

Figure 10:
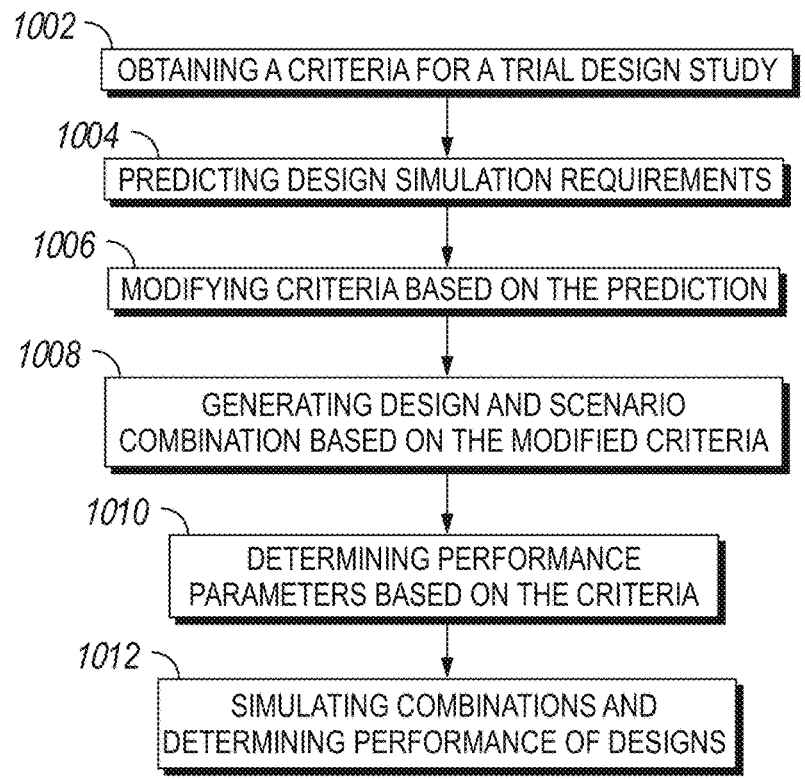
FIG. 10 is a flow chart depicting a method of evaluating design, in accordance with an embodiment of the current disclosure.

As shown in FIG. 10, a method of evaluating designs may include obtaining a criteria for trial design study 1002. The method may further include predicting design simulation requirements based on the criteria 1004. The predictions may include how many simulations will need to be performed, the cost of the simulations, the time for the simulations, and the like. For example, based on the obtained criteria, a number of potential design permutations may be determined, and a number of potential scenario permutations may be determined. A cross product of the number of design permutations and the number of scenario permutations can indicate the number of combinations to be simulated, and based on system parameters that number can be used to also determine, for example, the time required to simulate that number of combinations, the cost of the simulations, and the like. The method may include modifying the criteria based on the predictions 1006. The criteria may be modified to constrain the criteria to reduce the number of needed simulations or broaden the criteria to include more design options for simulation. As one example, if the predicted number of required simulations is very large for when an obtained criteria relates to a maximum trial duration, the criteria may be modified to include both a maximum and a minimum trial duration (in situations where a very short trial duration is deemed unlikely to provide a successful result). In some embodiments, controls (for example, slider bars) may be provided to a user to adjust values for selected criteria so that the user can quickly see the impact that changes to the criteria have on the predicted number of required simulations, the duration of the simulation, the cost of the simulation, etc. The method may include generating design and scenario combinations based on the modified criteria 1008 and determining performance parameters that should be determined based on the criteria 1010. The combinations may be simulated to obtain the performance parameters determined for each design. The method may further include simulating combinations and determining performance designs 1012.

Figure 11:
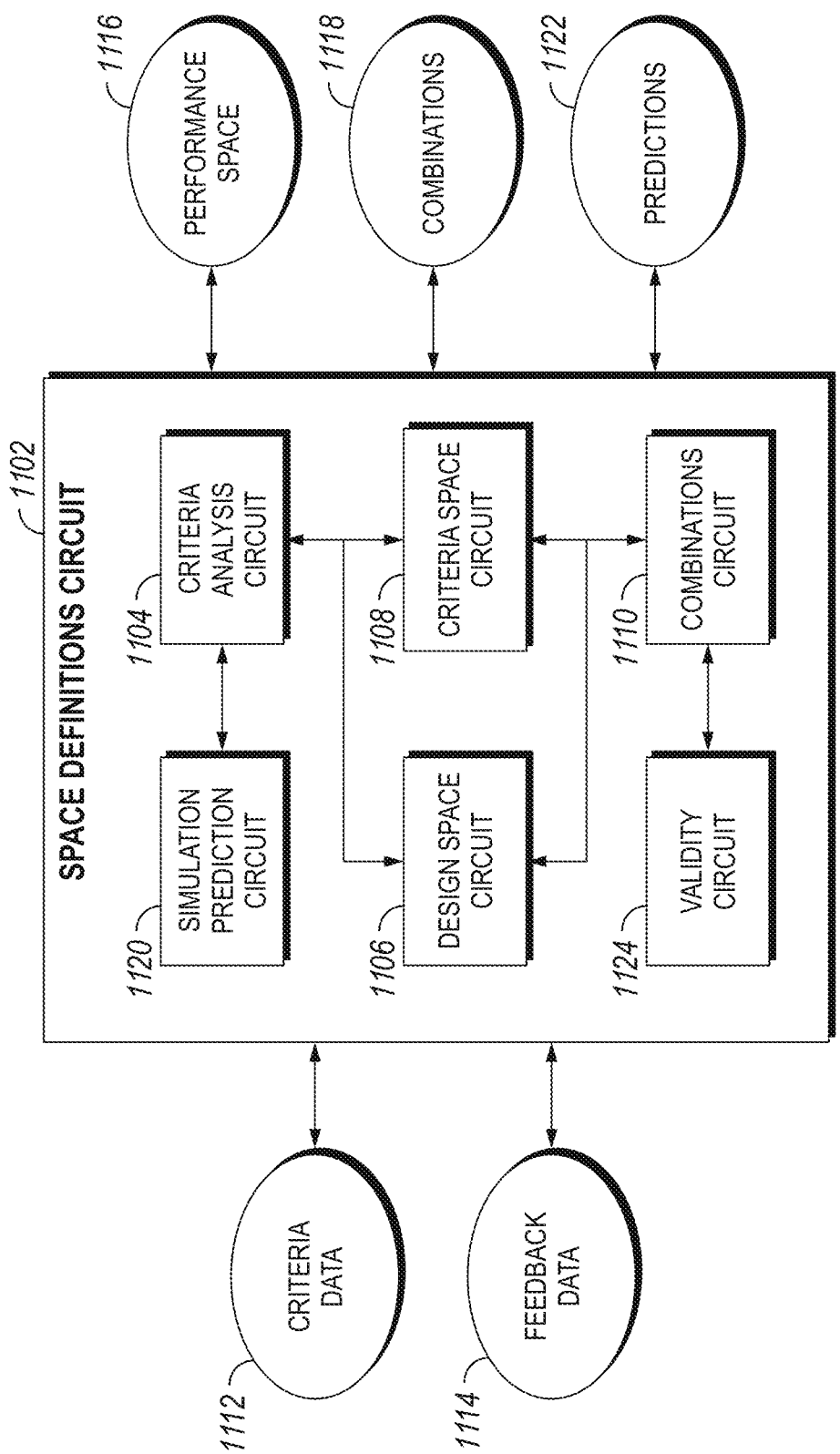
FIG. 11 is a schematic diagram of an apparatus for evaluating designs, in accordance with an embodiment of the current disclosure.

FIG. 11 shows aspects of an apparatus for determining designs. In embodiments, the apparatus may include a space definition circuit 1102 which may be part of the simulation facility 110 of the platform 104. In embodiments, the apparatus may include a criteria analysis circuit 1104 structured to interpret/obtain criteria data 1112. The criteria data may be analyzed by the simulation prediction circuit 1120 to determine aspects of simulation time, design options, and the like that are consistent with the criteria. The predictions 1122 from the simulation prediction circuit 1120 may be provided to a user and feedback 1114 may be received for modification of the criteria. The design space circuit 1106 and the criteria space circuit 1108 may generate the design and performance parameters from the criteria. The combinations circuit 1110 may generate design-scenario combinations 1118 for simulation. In some embodiments, a validity circuit 1124 may determine the validity of any combinations 1118 or any design space or scenario space parameters and the invalid options may be removed. The combinations 1118 and the performance space 1116 determined from the criteria by the space definition circuit 1102 may be used to simulate and analyze designs.

Figure 12:
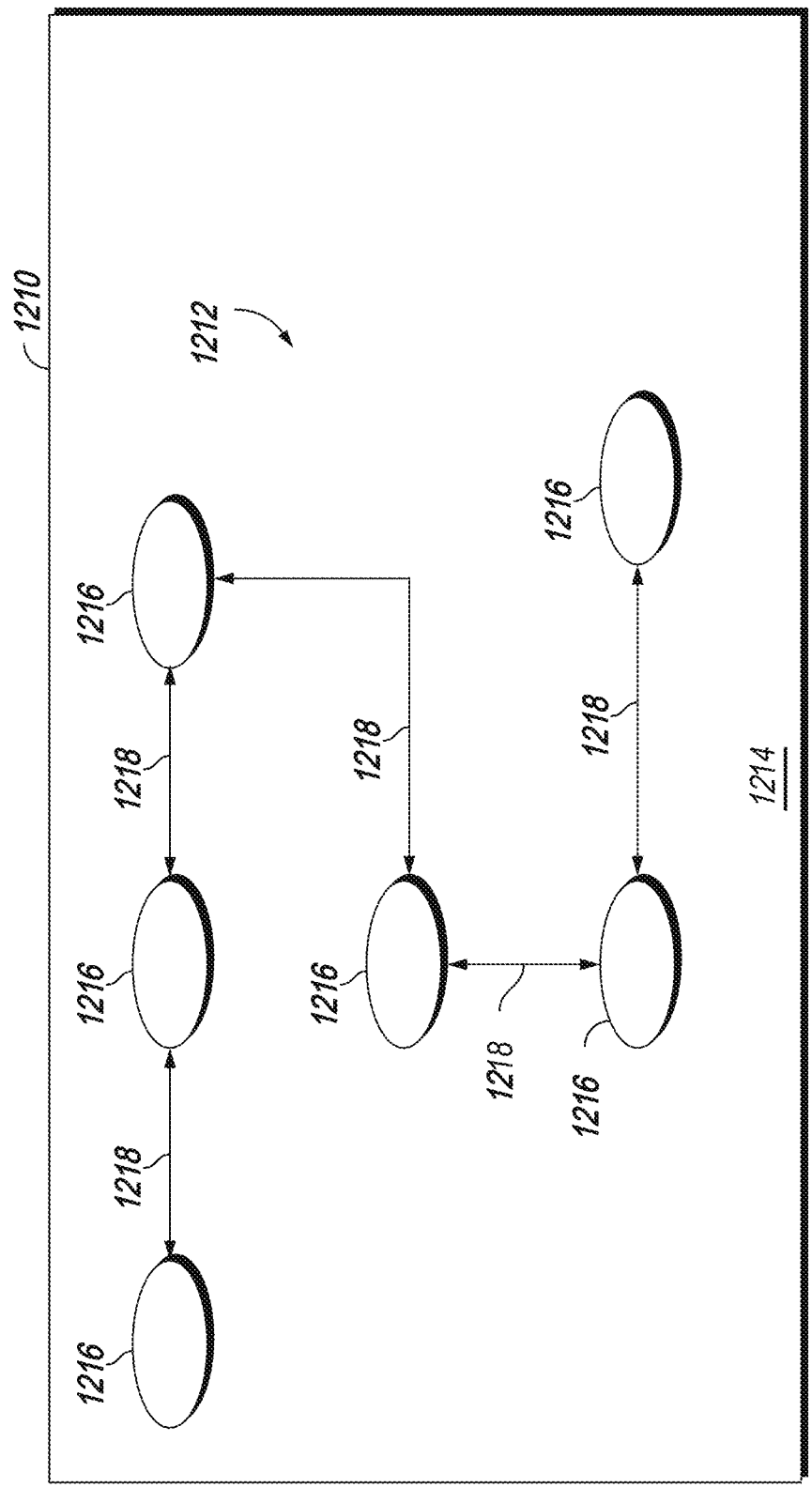
FIG. 12 is a block diagram of an interface for configuring and managing an execution flow for a clinical trial design evaluation, in accordance with an embodiment of the current disclosure.

Referring to FIG. 12, an embodiment of an interface 1210 for configuring and managing an execution flow 1212 for a clinical trial design evaluation is shown. In embodiments, the interface 1210 may form part of the configuration facility 106 (FIG. 1). The interface 1210 may also be provided by a system separate from the platform 104 (FIG. 1) and communicate with the platform 104 via one or more application programming interfaces (APIs) or otherwise. The interface 1210 may be provided as a graphical user interface on one or more user devices 102 (FIG. 1).

As can be seen in FIG. 12, the execution flow 1212 defines, in part, one or more processes and the order in which they occur for conducting one or more clinical trial design evaluations. The interface 1210 may include a canvas area 1214 for visualizing/editing/creating the execution flow 1212 using nodes 1216 and arcs 1218. For example, nodes 1216 and/or arcs 1218 may be dragged on and/or off the canvas area 1214, wherein the nodes 1216 and arcs 1218 on the canvas area 1214 define, in part, the execution flow 1212.

Each node 1216 may represent one or more modules and/or processes included in the execution flow 1212, wherein the arcs 1218, e.g., arrows, connect the nodes 1216 so as to define the flow of data from one node 1216 to another. Non-limiting examples of the types of processes the nodes 1216 may represent include: an execution engine from component 128 (FIG. 1); reception and/or obtaining one or more of design criteria, performance criteria/parameters, scenario criteria; a search/exploration module from component 130 (FIG. 1), e.g., simulated annealing; visualizations and/or interfaces to be presented from component 132 (FIG. 1); and/or any type of parameter, model/engine, and/or visualization described herein. Users of the interface 1210 may change the configuration of the execution flow 1212 by changing nodes 1216, adding nodes 1216, removing nodes 1216, moving arcs 1218 to change the flow of outputs from one node 1216 to the next, and/or the like.

Figure 13:
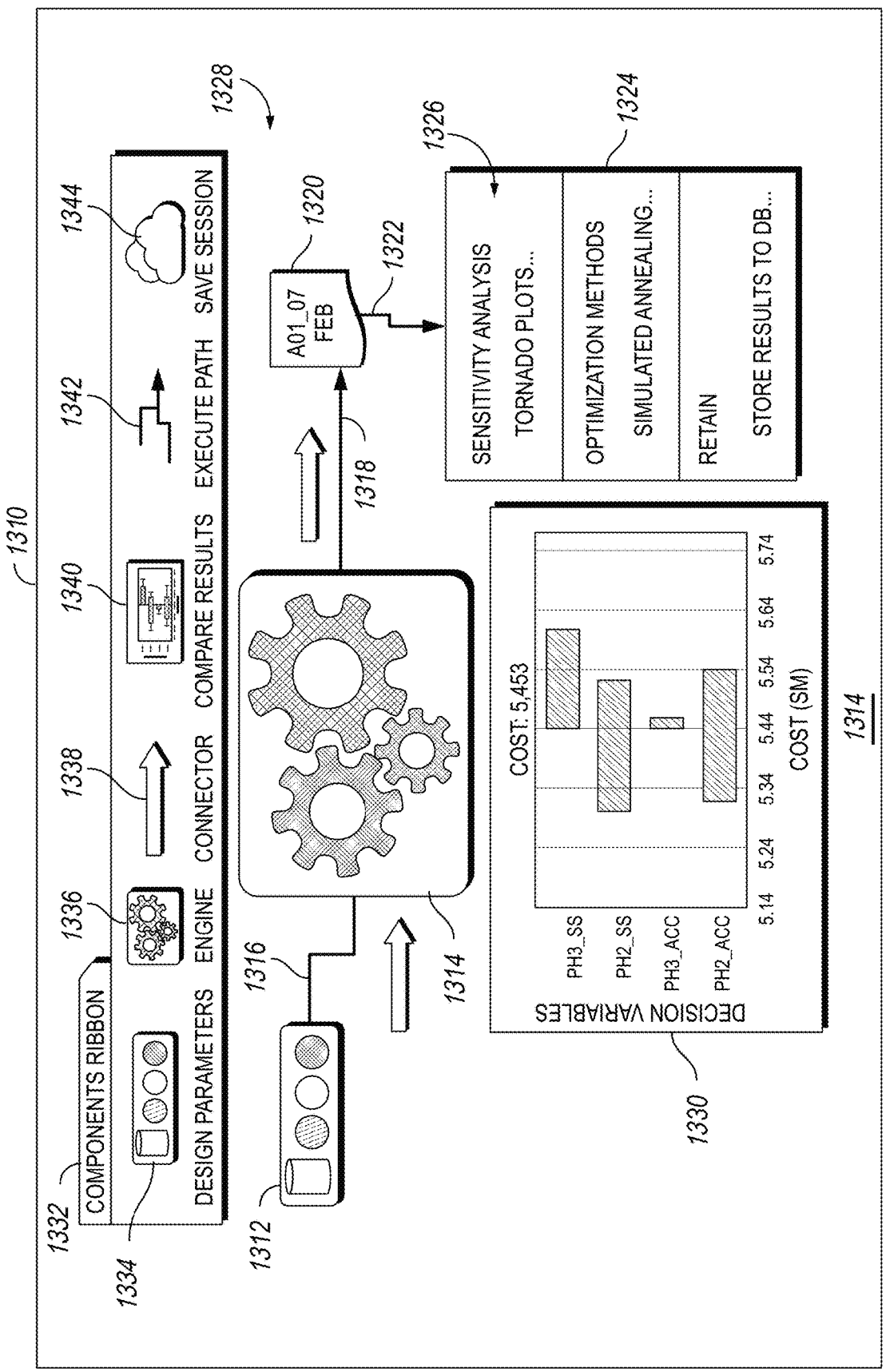
FIG. 13 is a schematic diagram of another embodiment of an interface for configuring and managing an execution flow for a clinical trial design evaluation, in accordance with an embodiment of the current disclosure.

Illustrated in FIG. 13 is another embodiment of an interface 1310 for configuring and managing an execution flow for a clinical trial design evaluation, in accordance with an embodiment of the current disclosure. A first node 1312 may represent a set of design parameters to be acquired/obtained and sent to a second node 1314, as indicated by arc 1316. Node 1314 may represent an engine that processes the set of design parameters to generate outputs as represented by arc 1318 and node 1320. Arc 1322 depicts the outputs being communicated to an unconfigured node 1324. As shown in FIG. 13, a menu 1326 may be generated within and/or near the unconfigured node 1324 and provide options for configuring the node 1324. For example, using the menu 1326 a user may configure the node 1324 to represent a sensitivity analysis, e.g., a tornado plot, a visualization, and/or an optimization method/engine, e.g., simulated annealing. The menu 1326 may also provide a general option to save the state of the interface 1310 and/or corresponding execution flow 1328. Node 1330 represents a visualization that has not yet been incorporated into the execution flow 1328, i.e., no arcs connect node 1330 into the execution flow 1328. In embodiments, the interface 1310 may include a menu 1332 that provides a user with options to add parameter input nodes 1334, engine nodes 1336, arcs 1338, visualizations 1340, complex arcs 1342, e.g., forks, a save option 1344, and/or the like.

Figure 14:
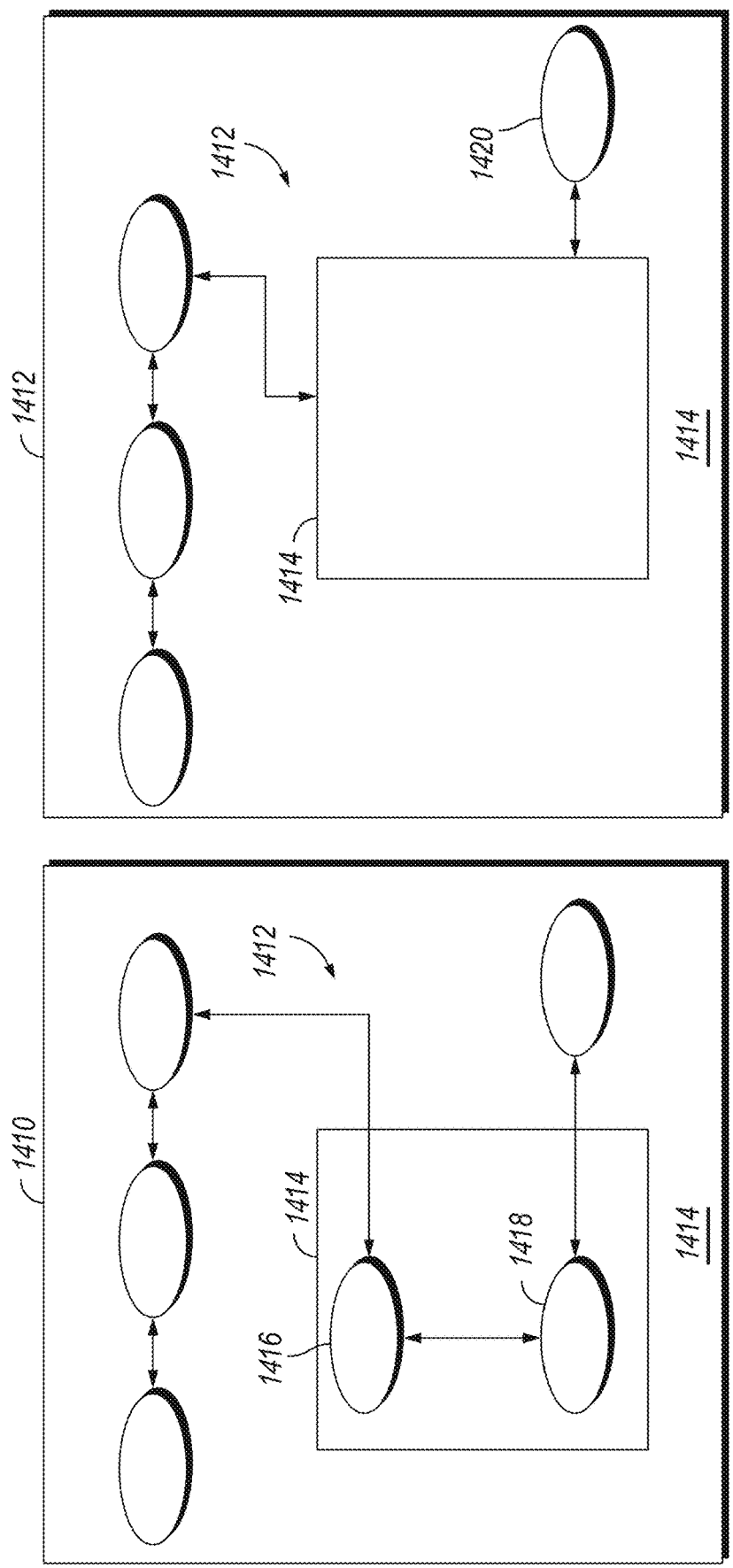
FIG. 14 is a block diagram of two distinct views of the interface of FIG. 12, in accordance with an embodiment of the current disclosure.

Referring now to FIGS. 14 and 15, in embodiments, the interface may be configured for different user types/target audiences. Distinct instances/views of the interface may be generated wherein each instance/view is tailored for a particular user type/role and/or a configuration level. In embodiments, an instance/view may be for defining analysis aspects and may include a focus, as well as additional interfaces and/or options for viewing and/or editing greater details of the execution flow, e.g., specifying algorithms, performance criteria, and the like. In embodiments, an instance/view may be for defining design and/or scenario aspects and may include, for example, additional interfaces and options for importing design parameters from a previous analysis. Analysis templates, e.g., collections of nodes 1216 and arcs 1218, may be used in the execution flow 1212 to provide a baseline configuration. Analysis templates may include templates for a low-cost analysis (i.e., use of low-cost engines), exhaustive analysis, and heatmap analysis (i.e., which visualizations are to be provided). In embodiments, different views may depict aspects of the same data to different users at the same time. For example, a user associated with a regulatory organization may see only results of the analysis, while another user may have access to additional features that provide for configuration of the analysis. Changes to the configuration of the analysis may propagate across multiple views in real-time.

User types may include simulation engine designers, visualization designers, optimization professionals and/or the like, and may be subdivided into skill levels, e.g., expert, intermediate, and/or novice. Configuration levels may provide for different levels of access over parts of an execution flow and may be categorized as high, medium, or low, wherein a high level provides for more access than a medium level which provides for more access than a low level. In embodiments, other classification schemes for user types and configuration levels are provided.

For example, a first instance/view of the interface 1410 may be configured for a first user type 1510 and a second instance/view of the user interface 1412 may be configured for a second user type 1512. In embodiments, the user types may correspond to skill levels and/or different specialties with respect to clinical trial design. For example, the first user type 1510 may be a subcategory of a user type 1514 corresponding to a simulation engine designer. User type 1510 may correspond to an expert simulation engine designer and have sibling types corresponding to intermediate simulation engine designer 1516 and/or novice simulation engine designer 1518. User type 1512 may be a subcategory of a user type 1520 corresponding to a visualization designer. User type 1512 may correspond to a novice visualization designer and have a sibling corresponding to an expert visualization designer 1522.

Accordingly, view 1410 provides user type 1510 access to more functionality and/or control over configuration of the execution flow 1212 within an engine 1414 as compared to view 1412 for user type 1512. For example, interface 1410 provides access to nodes 1416 and 1418 within the engine node 1414, while interface 1412 provides only high-level access to the engine node 1414. Thus, interface 1410 allows an expert simulation designer 1510 to configure the execution flow 1212 internal to an engine while interface 1412 prevents a non-expert simulation engine designer 1512 from doing the same.

In embodiments, different user types may define parts of the execution flow concurrently. In other words, embodiments may provide for users to collaborate (concurrently or asynchronously) to design, conduct simulations, and perform analysis on clinical trial designs during both pre-simulation and post-simulation stages. For example, user type 1510 may configure the internals of the engine node 1414 at the same time user type 1512 configures a visualization node 1420. Thus, as will be appreciated, users in different geographic regions, e.g., cities, states/provinces, and/or countries, may work together on the same execution flow 1212. In embodiments, authentication and access control may be used to identify and authenticate users and control access to one or more functions and/or resources accessible by the platform. In embodiments, users may have different permissions allowing different access and actions. For example, some users may be provided with the ability for configuring a flow but require another user or another authorization level to execute the flow.

Turning now to FIG. 16, a method 1600 for configuring an execution flow for a clinical trial design evaluation is provided. The method 1600 includes configuring an execution flow for a clinical trial design evaluation using a configurable interface 1610, as described herein. The configurable interface 1210 (FIG. 12) may include at least one node element 1216 and at least one arc element 1218. The execution flow 1212 may be defined, in part, via the at least one node element 1216 and the at least one arc element 1218 (FIG. 12), as disclosed herein. The method 1600 includes executing the clinical trial design evaluation using the execution flow 1612. The method 1600 includes reconfiguring at least one of the at least one node element or the at least one arc element in the execution flow 1614. Reconfiguring may include one or more of adding, removing, moving, and/or otherwise adjusting the at least one node element and/or the at least one arc element. The method 1600 further includes executing the clinical trial design evaluation using the reconfigured execution flow 1616.

FIG. 17 depicts another method 1700 for configuring an execution flow for a clinical trial design evaluation. The method 1700 includes configuring an execution flow for a clinical trial design evaluation using a configurable interface 1710, as disclosed herein. The execution flow 1212 may be defined using at least one node element 1216 and at least one arc element 1218, as described herein. The method 1700 further includes determining a first user type interacting with the execution flow 1712, e.g., attempting to and/or preparing to configure the execution flow 1212. The method 1700 further includes configuring a first view of the execution flow for the first user type 1714. The method 1700 further includes determining a second user type interacting with the execution flow 1716 e.g., attempting to and/or preparing to configure the execution flow 1212. The method 1700 further includes configuring a second view of the execution flow for the second user type 1718.

Figure 18:
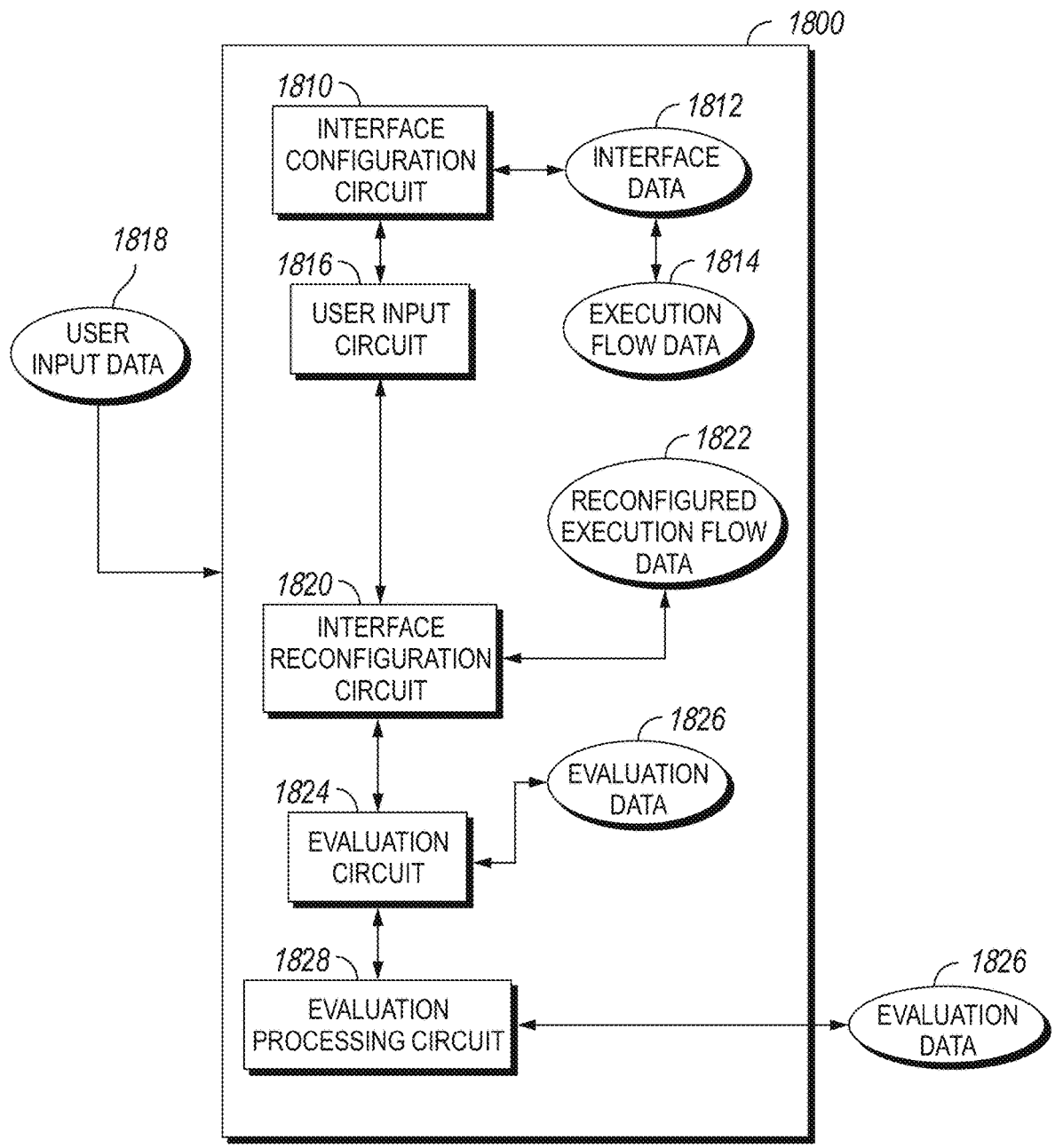
FIG. 18 is a schematic diagram of an apparatus for configuring and managing an execution flow for a clinical trial design evaluation, in accordance with an embodiment of the current disclosure.

Illustrated in FIG. 18 is an apparatus 1800 for configuring an execution flow for a clinical trial design evaluation. The apparatus 1800 includes an interface configuration circuit 1810 structured to generate interface data 1812 corresponding to a configurable interface having a node element 1216 (FIG. 12) and an arc element 1218 (FIG. 12). The node element 1216 and the arc element 1218 define execution flow data 1814 for a clinical trial design evaluation, i.e., the flow data 1814 corresponds to the execution flow 1212 (FIG. 12). The apparatus 1800 further includes a user input circuit 1816 structured to interpret user input data 1818 based at least in part on the node element 1216 and the arc element 1218. The apparatus 1800 further includes an interface reconfiguration circuit 1820 structured to reconfigure the execution flow data 1814 to generate, based at least in part on the user input data 1818, reconfigured execution flow data 1822. The apparatus 1800 may include an evaluation circuit 1824 structured to generate evaluation data 1826 via executing the clinical trial design evaluation based at least in part on the reconfigured execution flow data 1822. The apparatus 1800 may further include an evaluation processing circuit 1828 structured to transmit the evaluation data 1826.

In embodiments, apparatus for configuring execution flow may enable configuration and manipulation of scenario, design, performance, and criteria spaces. Each space may be separately configured by different users. Each space may be associated with one or more different nodes in the execution flow. The nodes corresponding to each space may be modified and/or replaced with a different version of the node to change aspects of any one of the spaces.

Figure 19:
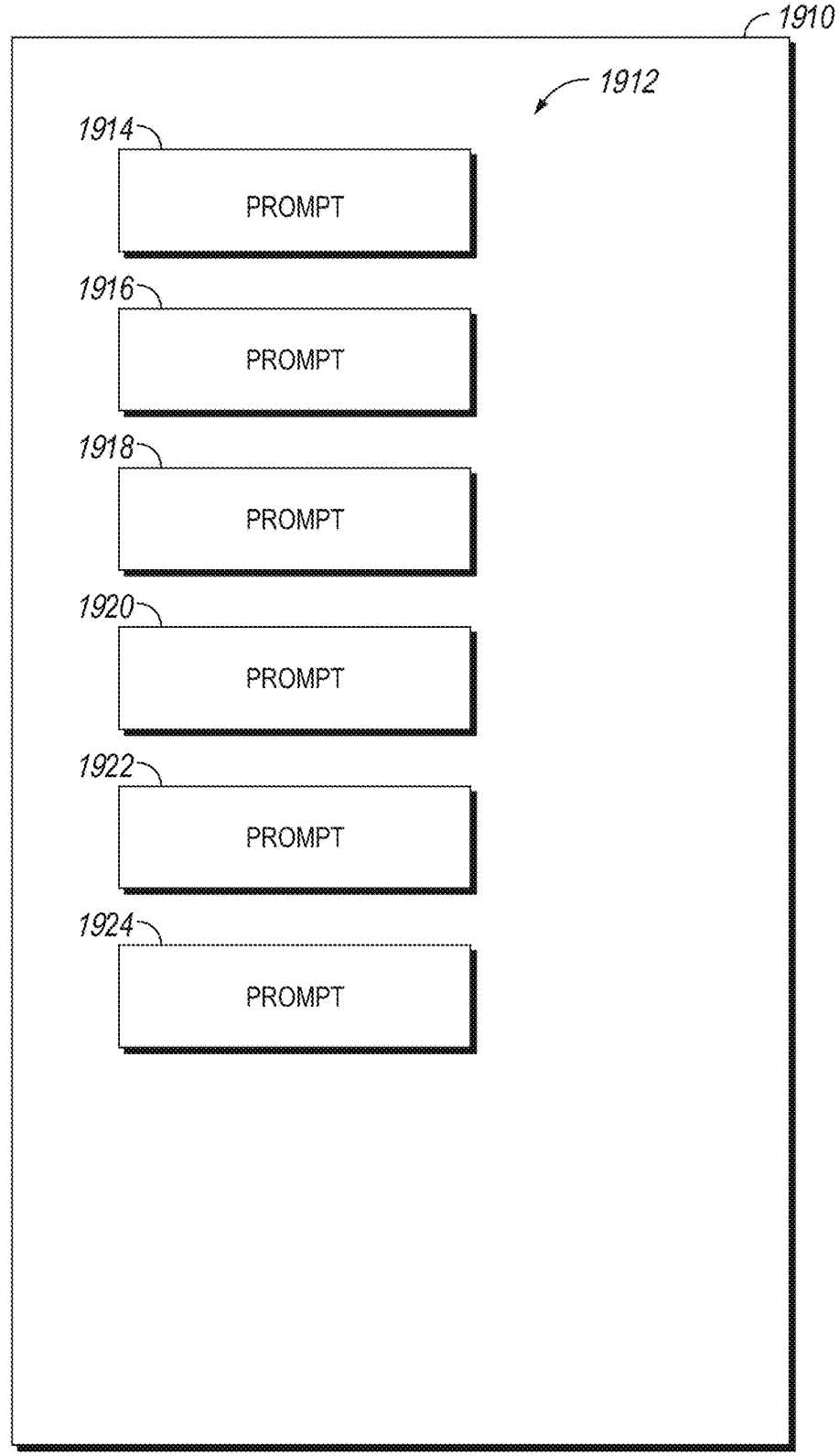
FIG. 19 is a schematic diagram of an interactive interface for an advisor for guiding a user through configuration of trial design simulations and/or systems for optimizing clinical trial design, in accordance with an embodiment of the current disclosure.

Referring to FIG. 19, an advisor 1900, e.g., an interactive wizard or algorithm, for guiding a user through configuration of trial design simulations, and/or systems for optimizing clinical trial design selection, is shown. In embodiments, the advisor 1900 may be used for pre-simulation configuration of the platform 104, updating of the platform 104 during simulation runs, and/or for configuring the platform 104 for post-simulation analysis, e.g., configuring searches such as those provided by the search/exploration component 130 (FIG. 1). For example, a user may first log on to the platform 104 and specify via a user interface, e.g., 112 (FIG. 1) that they wish to being a new design evaluation. The platform 104 may then launch an embodiment of the interactive wizard or algorithm which may then present the user with a series of initial questions/prompts designed to determine general design and/or performance criteria for one or more designs. The interactive wizard or algorithm may then ask additional questions/prompts to determine more specific ranges and/or values for the design and/or performance criteria. Based on the user's inputs/answers to the questions/prompts, the platform may affirmatively determine design permutations or scenario permutations that are feasible in view of the criteria, and/or it may be possible to determine specific design permutations or scenario permutations that are not feasible in view of the criteria (e.g., cannot possibly provide a result that satisfies the criteria). For example, if a user inputs as a design criterion a specific maximum drug dose, then only design permutations having a dose of drug equal to or less than the specified maximum drug dose will be included (all other design permutations are infeasible in view of specified criterion, because it is not possible for them to achieve a drug dose that does not exceed the specified maximum). Alternatively, or in addition, if a user inputs as a scenario criterion a specific range of patient dropout rates (for example), then only scenario permutations having a patient dropout rate within the specified range will be included.

In embodiments, the interactive wizard or algorithm may include a method of generating combinations that uses the permutations of designs and scenarios. In some embodiments, the combinations may be exhaustive, i.e., the combinations to be simulated include each possible design permutation combined with each possible scenario permutation (or, if infeasible permutations are first excluded, the combinations to be simulated include each feasible design permutation combined with each feasible scenario). Alternatively, in some embodiments, some combinations may be removed based on predicted performance. As discussed further below, a variety of heuristics, algorithms, filters, or the like may be used to predict that certain combinations are improbable or unlikely to achieve a desirable outcome. In some embodiments, analysis of data from past trials, or information input by one or more users, may indicate improbable combinations for which simulation would be of minimal value. For example, historical trial data and/or guidelines based on user experience may indicate a direct relationship between trial duration and patient dropout rates, such that a patient dropout rate below a certain level is unlikely to be achieved for a trial having a duration that exceeds a certain time period. Therefore, although combinations having certain patient dropout rates and certain trial durations may satisfy all selected criteria, it can be predicted that such combinations either cannot be achieved as a practical matter or cannot result in a satisfactory trial outcome. Therefore, such combinations can be removed prior to the simulation. As another example, analysis of past trial data may indicate that drug doses below a certain level are rarely effective in treatment of certain conditions, and combinations involving low drug doses may be predicted to perform poorly and therefore be removed prior to simulation. Also, as discussed further below, a scoring system may be implemented to predict performance and determine combinations that should be removed prior to simulation. The combinations that are determined to be appropriate for simulation (which may be all possible combinations in some embodiments or a subset of combinations in other embodiments) may be simulated and the performance of the simulated designs may be determined and analyzed. The evaluated performance parameters may be based on the criteria and/or based on goals or performance objectives other than the obtained criteria.

In embodiments, the advisor 1900 may be integrated into the platform 104, or the advisor 1900 may be a standalone system apart from the platform 104. In embodiments, the advisor 1900 may assist in obtaining input from a user to determine trial design criteria and/or trial design parameters, e.g., values for one or more of criteria space, design space, and/or scenario space, as described herein. User input may be obtained via one or more interactive interfaces, e.g., 1910, structured to generate one or more questions/user prompts, e.g., 1912. User inputs may be compared to historical data, such as data stored in data facility 138 (FIG. 1), e.g., previous designs, inputs, and/or outcomes, having similar criteria as that defined by the user input. As will be appreciated, assisting a user through the clinical trial design optimization process may reduce the amount of time and/or resources (including computing resources and/or associated costs) spent on research and/or simulating sub-optimal clinical trial designs for a given clinical trial. Further, the advisor 1900 may be able to make recommendations for trial design criteria and/or trial design parameters that may provide for improved efficiencies over similar trial design optimizations performed by a human.

Figure 20:
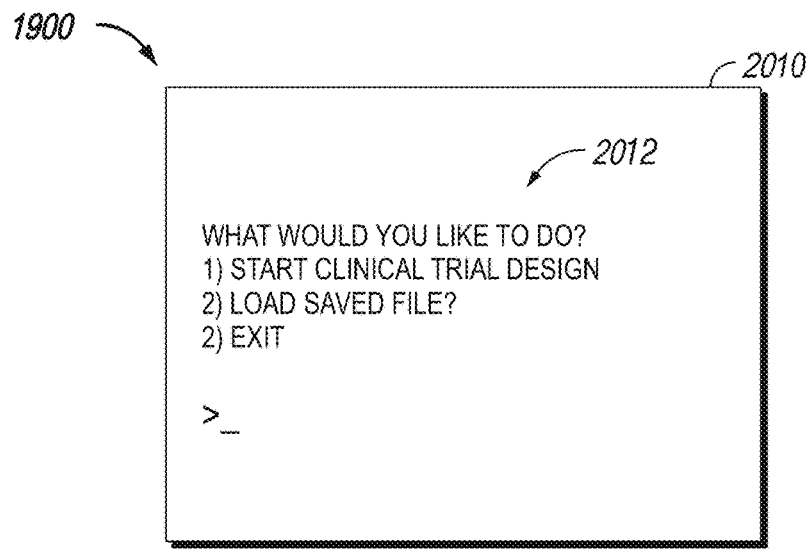
FIG. 20 is a schematic diagram of another embodiment of the interactive interface of FIG. 19, in accordance with an embodiment of the current disclosure.

Accordingly, in embodiments, the interactive interface 1910 may be a graphical user interface wherein the prompts 1912 may be textboxes, popup dialogue boxes, verbal questions played through a sound and/or video file, e.g., .mp4, .wav, etc. The interface 1910 may be provided though a web interface, e.g., provided through cloud services 152 (FIG. 1). The interface 1910 may be generated locally on a user device 102 (FIG. 1) and communicate with the platform 104 through one or more application programing interfaces (APIs). Further, while FIG. 19 depicts the interface 1910 as a graphical user interface, a non-limiting example of a command line version of the interface 2010 with textual prompts 2012 is shown in FIG. 20.

As shown in FIG. 19, in embodiments, the prompts 1912 may include one or more of: a prompt 1914 to determine a duration of a clinical trial; a prompt 1916 to determine a number of recommended designs to provide; a prompt 1918 to determine a type of a model to use for simulation and/or searching/exploration, e.g., whether Pareto and/or convex hull analysis should be performed; a prompt 1920 to determine whether simulated annealing should be performed; a prompt 1922 to determine total costs of a clinical trial; and/or other prompts 1924 for determining any other criteria relevant to determining a globally optimized design for a clinical trial.

Figure 21:
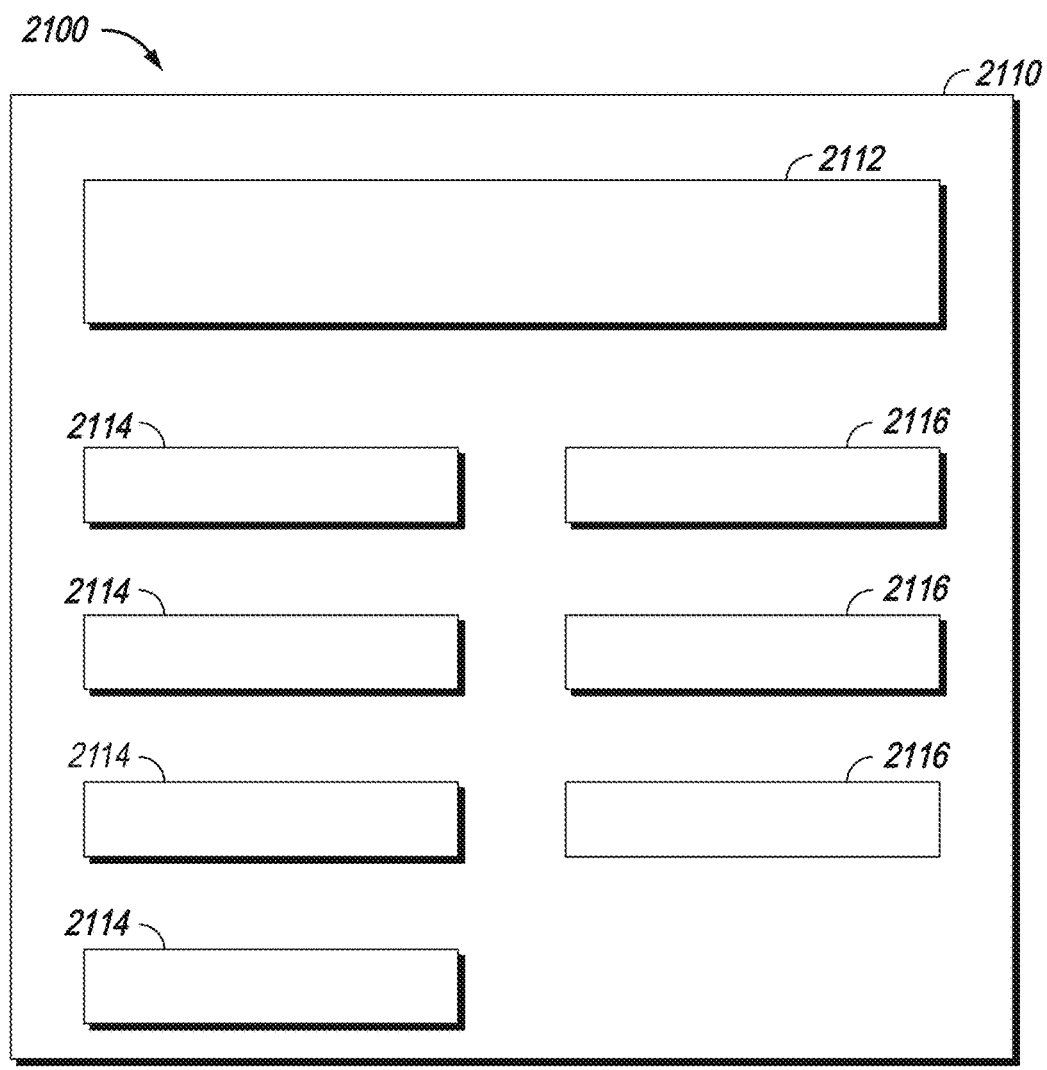
FIG. 21 is a schematic diagram of a prompt of the interactive interface of FIG. 19, in accordance with an embodiment of the current disclosure.

Turning now to FIG. 21, a non-limiting example of a prompt 2100 is shown. In embodiments, the prompt 2100 may include a presentation window 2110 having a message box 2112 which may display a textual question to the user, e.g., "What types of optimization engines would you like to use?" The prompt 2100 may also include one or more input fields 2114 for receiving the user input. The input fields 2114 may include text boxes, radio buttons, sliders, dropdown menus, checkboxes, and/or other suitable widgets for receiving user input.

In embodiments, the prompt 2100 may include recommendation fields 2116 which may present one or more recommended values to a user for one or more trial design criteria and/or design parameters. For example, a user may inform the interface 1910 that they intend to optimize a clinical trial of a titration design. The advisor 1900 may then query one or more databases in the data facility 138 (FIG. 1) and present the user with one or more recommendations 2116 for one or more trial design criteria and/or trial design parameters. For example, the advisor 1900 may recommend, for a particular trial design, that that a Pareto analysis be performed in conjunction with a convex hull analysis. The advisor 1900 may also provide a recommendation 2116 for an estimated cost of the clinical trial. In embodiments, the recommendations 2116 may be single values and/or ranges for values. In embodiments, a recommendation field 2116 may correspond to an input field 2114. For example, an input field 2114 may be structured to receive a user input defining a number of simulations to run, and a corresponding recommendation field 2116 may recommend a specific value or a range for the user to enter into the input field 2114. In embodiments, a recommendation 2116 may be in response to a user selection, e.g., users who select option "A" usually select option "B" and/or usually do not select option "C". For example, a user may select a first option "A" and then select a second option "C", wherein upon selecting option "C" a recommendation is generated informing the user that most users who pick option "A" select either options "B" or "D" instead of option "C".

In embodiments, the user inputs may be compared to historical clinical trial designs selected by traditional (human) experts. For example, the data facility 138 (FIG. 1) may include a history of past clinical trial design selections from a plurality of experts, e.g., humans who have extensive experience optimizing clinical trial designs. The advisor 1900 may receive one or more user inputs and query the data facility 138 for past trial designs having trial design criteria and/or trial design parameters that are the same, and/or nearly the same, as those defined by the user input. The advisor 1900 may then generate and present recommendations 2116 for other trial design criteria and/or trial design parameters, outside of the ones corresponding to the user input. In other words, in embodiments, the advisor 1900 may generate recommendations 2114 for design criteria and/or trial design parameters for which a user may not have yet specified and/or know. For example, past clinical trial designs may be categorized (based on type of trial, success of the trial, date of the trial, cost of the trial, and the like). Past clinical trials may be compared, clustered, analyzed, and the like to determine variations, similarities, and the like for trials in the same category. In some cases, based on one or more of the clustering, similarities, and/or variations the platform may generate statistics about the one or more features of past clinical trials in each category. The statistics may be used to determine features of trial designs that are common in a category and features that are uncommon. In some cases, common and uncommon features may correspond to desirable and undesirable features respectively. Features that are identified as common may be suggested to a user while features that are uncommon may be flagged for reconsideration. In another example, the platform may generate a dynamically changing score for the trial design configuration. The score may be a prediction of the likelihood that the study will results in a useful design for the study. As a user enters data about design details they wish to evaluate, the problem they study is meant to address, and the like, the platform may compare the inputs with a historical record of similar studies and the outcome of the studies (such as if the study resulted in a selected design, was the design implemented, how successful was the design when implemented, and the like). The system may compare the entered data to the database and develop a score according to the similarity of the entered parameters to historically successful studies. In some cases, similarity may be based on a function of all the parameters. The score may be updated in real time as users enter or change parameters, ranges of values, and the like. The score may provide a rough guide as to how close the study is to a successful study and what aspects of the parameters may be changed to make the study closer to a successful study.

In embodiments, artificial intelligence/machine learning approaches may be used to generate the prompts 1912 (FIG. 19) and/or other suggestions for a user. The artificial intelligence/machine learning may be trained via supervised learning. For example, in embodiments, the artificial neural network may be trained to estimate an expected cost, net present value (NPV), expected NPV, incremental NPV, study cost, incremental study cost, study budget, incremental study budget, time to complete, incremental time to complete, time to market, incremental time to market, clinical utility, incremental clinical utility, probability of regulatory acceptance, incremental probability of regulatory acceptance, probability of success, incremental probability of success, statistical power, incremental statistical power, number of patients, incremental number of patients, number of sites, incremental number of sites, study complexity, incremental study complexity, operational complexity, incremental operational complexity, dose selected, incremental dose selected, statistical design, incremental statistical design, peak revenue, revenue at year five (5), other revenue numbers, incremental revenue, market introduction, whether market introduction beats competition entry, number of treatment arms, hypothesis superiority/equivalence/non-inferiority, other choices around statistical design, treatment effect, hazard ratio, and other choices around estimating the characteristics of the patient population, response, and safety profile, screening criteria, dropout rate, and other choices around modeling/estimating the characteristics and behaviors of the patient population and other factors that impact how the study evolves and its likelihood of achieving its goals (how slowly/quickly patients enroll, etc.), site payments and other choices around operational aspects of the study that can impact how the study evolves and its likelihood of achieving its goals, cost per patient, cost per site, or other cost factors, selections made in other projects of a clinical trial design based on past examples. In embodiments, the artificial intelligence/machine learning may be trained on a training set that includes clinical trial designs created by experts and/or designs made by other non-expert users. Some embodiments of the training set may not account for the outcomes of past clinical trial designs. Some embodiments of the clinical trial training set may account for the outcomes of past clinical trial designs. In such embodiments, the artificial intelligence/machine learning may structure the prompts 1912 to guide a user towards a likely outcome, e.g., a likely global optimum design. In embodiments, the artificial intelligence may be trained via unsupervised learning, e.g., policy-based learning. For example, the artificial intelligence may be directed to make recommendations 2116 based on reducing the expected cost of a clinical trial.

Figure 22:
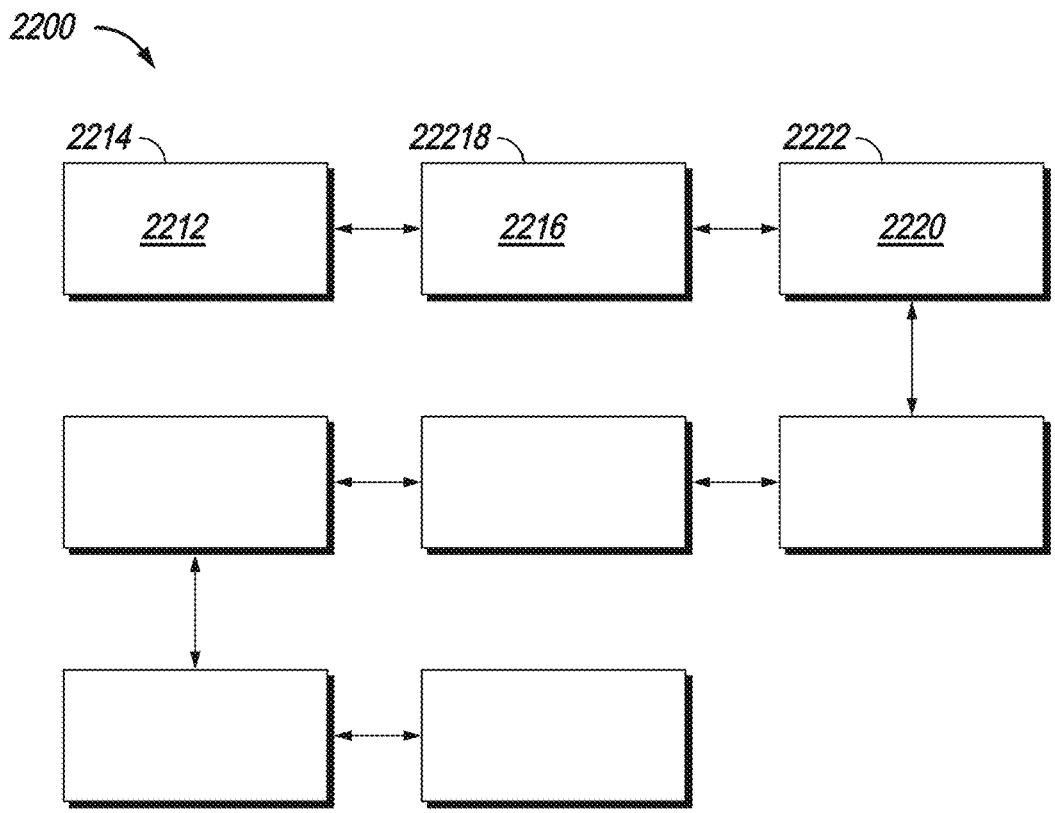
FIG. 22 is a block diagram depicting stages of configuring a clinical trial design optimization process, in accordance with an embodiment of the current disclosure.

Moving to FIG. 22, in embodiments, the advisor 1910 may generate and present the prompts 1912 based on one or more stages 2200. For example, a first plurality of prompts 2212 may correspond to a first stage 2214 of a clinical trial design configuration process, a second plurality of prompts 2216 may correspond to a second stage 2218 of the clinical trial design configuration process, a third plurality of prompts 2220 may correspond to a third stage 2222 of the clinical trial design process, and so on. One or more of the stages 2214, 2216, 2218, and/or 2220 may correspond to stages, of a clinical trial, e.g., "phase 0", "phase 1", "phase 2", "phase 3", etc., to include substages of a "phase". In embodiments, a user's inputs to a first plurality of prompts 2212 may determine the aspects of a subsequent plurality of prompts 2216. For example, a user may input a type of trial design in response to the first plurality of prompts 2212, and the second plurality of prompts 2216 may seek to elicit input from the user specific to the type of trial.

Figure 23:
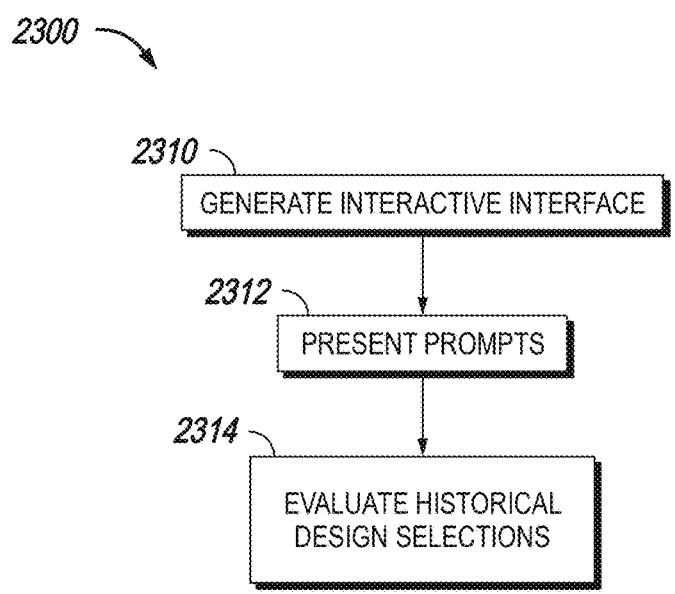
FIG. 23 is flow chart depicting a method for guiding a user through configuration of trial design simulations and/or systems for optimizing clinical trial design, in accordance with an embodiment of the current disclosure.

Illustrated in FIG. 23 is a method 2300 for guiding a user through configuration of the platform 104 (FIG. 1). The method 2300 may include generating an interactive interface 2310, presenting, via the interactive interface, one or more prompts to a user 2312. The prompts may be structured to determine one or more trial design criteria. The method 2300 may further include evaluating historical design selections 2314 to identify one or more trial design parameters based at least in part on or more trial design criteria.

In embodiments, the advisor may be configured to query and derive configurations for the designs, scenario, performance, and criteria space separately. The advisor and interfaces associated therewith may be configured to separate questions, wizards, and other interfaces such that configurations for the spaces are derived separately. The advisor may be configured to allow a first user configure the design space and another user configure the scenario space. In embodiments, user inputs such as type of therapeutic to be tested, budget, and the like may be used to configure the design space and or criteria space. In embodiments, user inputs such as number of patients may be used to configure the scenario space. In embodiments, user inputs such as desired cost or time to completion may be used to configure the performance space.

Figure 24:
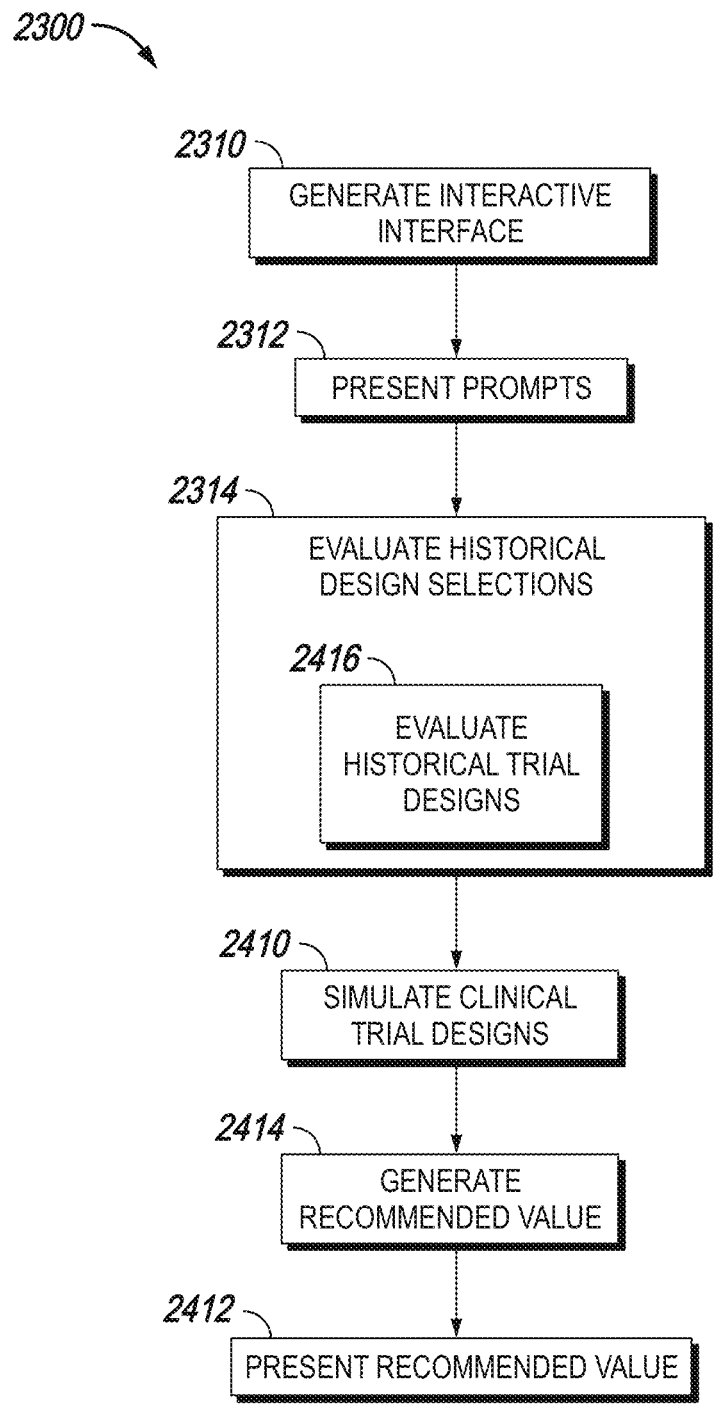
FIG. 24 is a flow chart depicting another embodiment of the method of FIG. 23, in accordance with an embodiment of the current disclosure.

Turning to FIG. 24, in embodiments, the method 2300 may further include simulating one or more clinical trial designs 2410. The simulations may be based at least in part on the one or more trial design parameters. The method 2300 may further include presenting, via at least one of the prompts, a recommended value for the one or more trial design criteria and/or the trial design parameters 2412. The method 2300 may further include generating the recommended values via artificial intelligence based at least in part on the historical trial design selections 2414. In embodiments, evaluating the historical trial design selections 2314 may include evaluating the historical trial design selections via artificial intelligence 2416.

Figure 25:
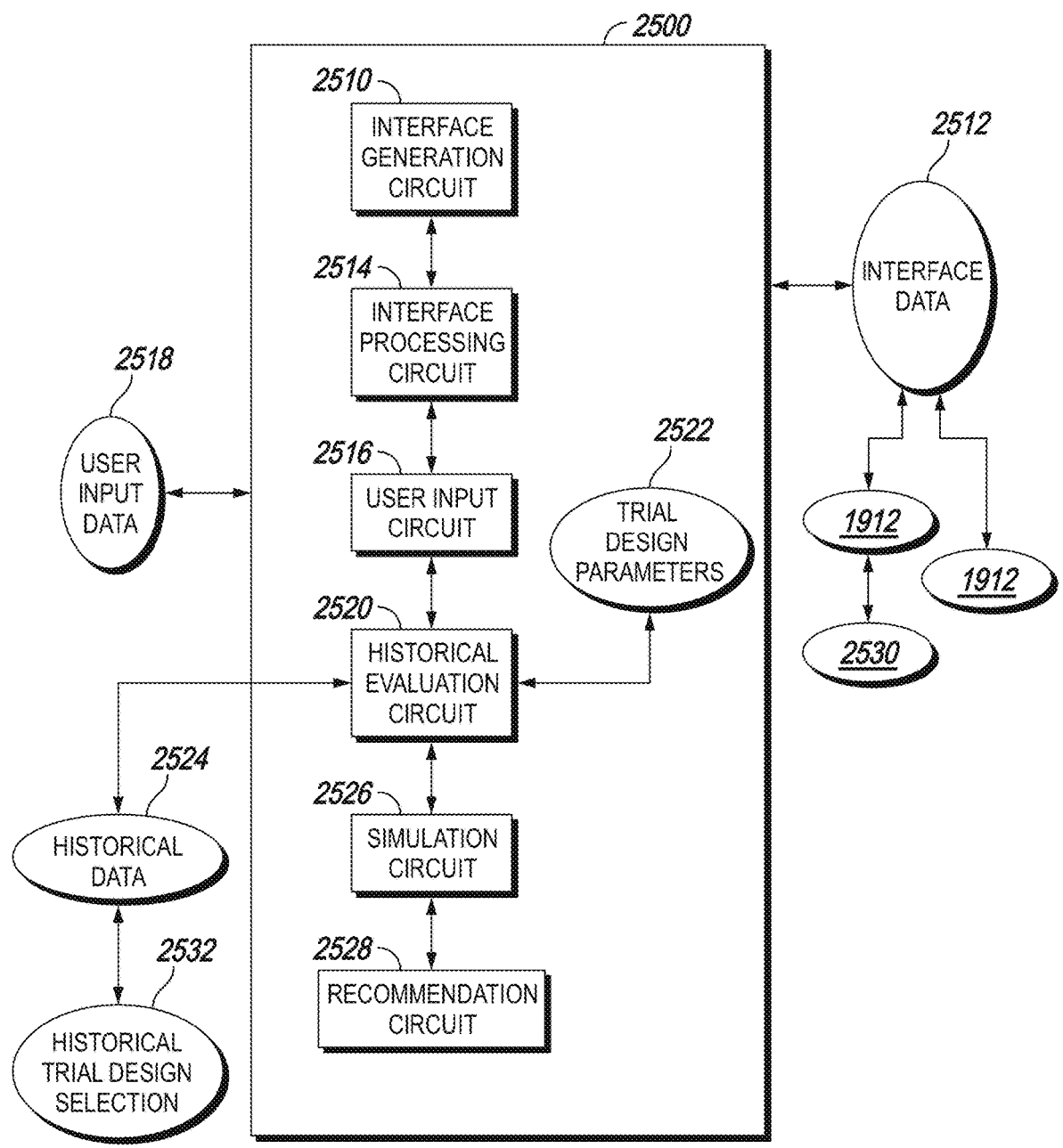
FIG. 25 is a block diagram of an apparatus for guiding a user through configuration of trial design simulations and/or systems for optimizing clinical trial design, in accordance with an embodiment of the current disclosure.

Illustrated in FIG. 25 is an apparatus 2500 for implementing the method 2300. The apparatus 2500 may be integrated into one or more servers 154, user devices 102, and/or other suitable computing devices. As shown in FIG. 25, the apparatus 2500 may include an interface generation circuit 2510 structured to generate interactive interface data 2512 that includes one or more user prompts 1912, in accordance with those described herein. The apparatus 2500 may include an interface processing circuit 2514 structured to transmit the interactive interface data 2512, and a user input circuit 2516 structured to receive user input data 2518 defining one or more trial design criteria and/or trial design parameters. The apparatus 2500 may include a historical evaluation circuit 2520 structured to identify one or more trial design parameters 2522 based at least on part on the trial design criteria via evaluating historical data 2524 corresponding to previously simulated clinical trial designs. The apparatus 2500 may further include a simulation circuit 2526 structured to simulate one or more clinical trial designs based at least in part on the trial design parameters. The apparatus 2500 may further include a recommendation circuit 2528 structured to generate a recommended value 2530 for the trial design criteria and/or the trial design parameters. In embodiments, the recommendation circuit 2528 may be further structured to generate the recommended value 2530 based at least in part on historical trial design selections 2532.

Figure 26:
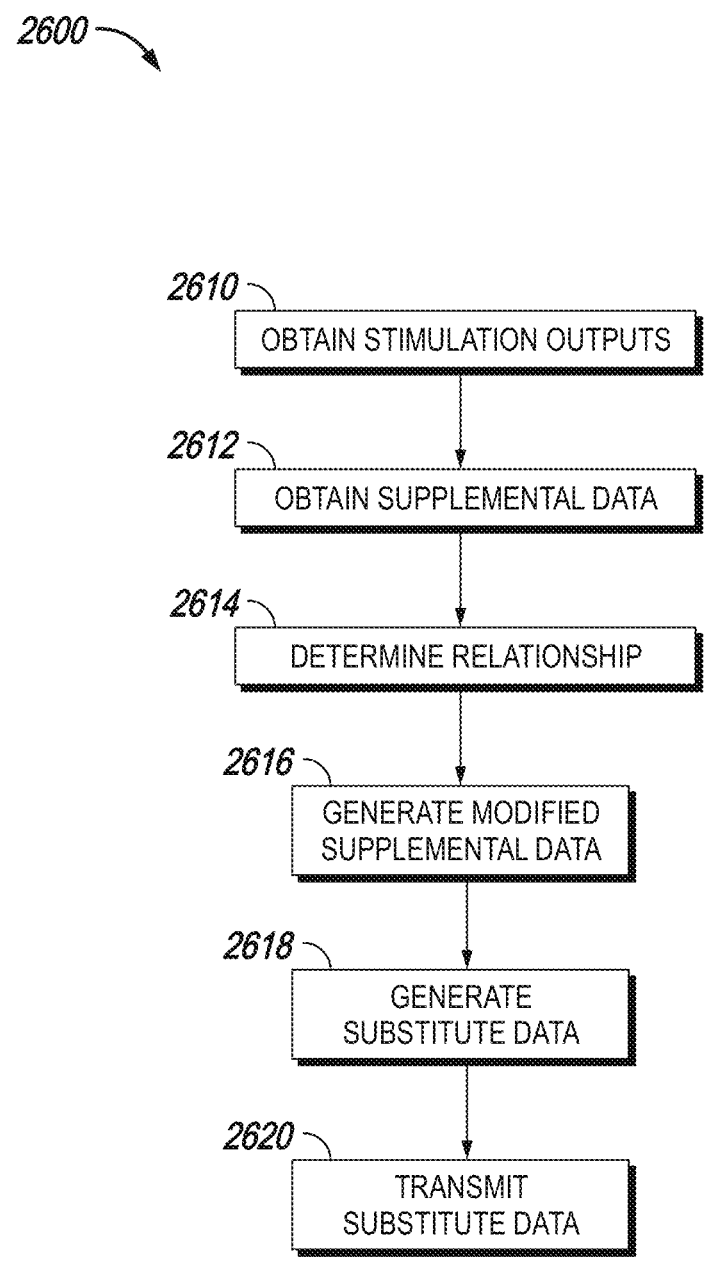
FIG. 26 is a flow chart depicting a method for augmenting simulated data, in accordance with an embodiment of the current disclosure.

Referring now to FIG. 26, embodiments of the current disclosure may provide for augmentation of simulated data with additional/supplemental data, e.g., real-world data. Real-world data may include actual data from clinical trial sites, patients, clinical trials, and/or other entities and aspects related to one or more parameters used to evaluate clinical trial designs as disclosed herein. For example, simulated data, also referred to herein as simulated outputs, may be generated via simulating one or more clinical trial designs. The simulated data may include relative and/or general values.

Relative values may include values related to an objective or subjective scale. Relative values may include a scale (i.e., 0-1, 1-10, 1-100) and/or designators (i.e., high, medium, low). For example, evaluation data may include a relative scale of a complexity of a trial which may be based on the number of personnel involved, the steps in a protocol of the trial, and the like. Real-world data such as regulatory approval times may be used to estimate how long it will take to receive regulatory approval for the study. Real world data may include a history of the time required to receive approval for studies with similar relative complexity rating. The relative values may be supplemented with the real-world data by substitution and evaluation with respect to historical data and real-world data.

General values may include values or placeholders that may be mapped or representative of other data. The mapping and placeholder may comprise metadata. For example, a simulation output of a design may specify general values such as number of sites and patients needed for a study. Real-world cost data may be used to determine the real-world cost (in a local currency such as dollars, for example) for the trial based on the number of sites and number of patients. Real-world data may include an average cost for a patient and an average cost per site. The general values may be supplemented with the real-world data by computing or substituting the real-world cost associated with the number of patients and sites.

The simulations of the clinical trial designs may be based on one or more design space parameters, criteria space parameters, scenario space parameters, and/or additional types of input parameters suitable for simulating clinical trial designs. In certain aspects, one or more of the input parameters to the simulations of the clinical trial designs may have an estimated and/or predicted value. For example, the manufacturing cost of a subject drug for an intended clinical trial may be unknown at the time the simulations of the possible clinical trial designs (for testing the subject drug) are first executed/run. In such a case, the initial simulations of the clinical trial designs may use an estimated (or predicted) price of the subject drug. The estimated price of the subject drug, and/or other input parameters, may be based at least in part on historical data. Real data may then be used in computations to relate the simulation data to real-world or current values. Thus, in the foregoing example, the actual price of the subject drug, when it becomes available, could be used to augment the initial simulations.

Real-world data may also be used to associate relative values with real-world absolute values. For example, simulation data may identify general or relative parameters that may influence cost. Additional data (such as current cost data) may be used to determine how these general parameters translate to real dollar values. Relative data may be substituted with additional data to provide current values for cost, time, and other performance data. Relative and absolute values may be tagged with metadata for marking for substitution.

As shown in FIG. 26, a method for augmentation of simulated data 2600 may include obtaining a set of simulation outputs for a set of clinical trial designs 2610. The method 2600 may further include obtaining a set of supplemental data 2612. The method 2600 may further include determining a relationship between at least one simulation output of the set to at least one supplemental data of the set 2614. The method 2600 may further include generating modified supplemental data based at least in part on the relationship 2616. The method 2600 may further include generating a substitute of the at least one simulation output based at least in part on the modified supplemental data 2618. The method 2600 may further include transmitting the substitute 2620.

Figure 27:
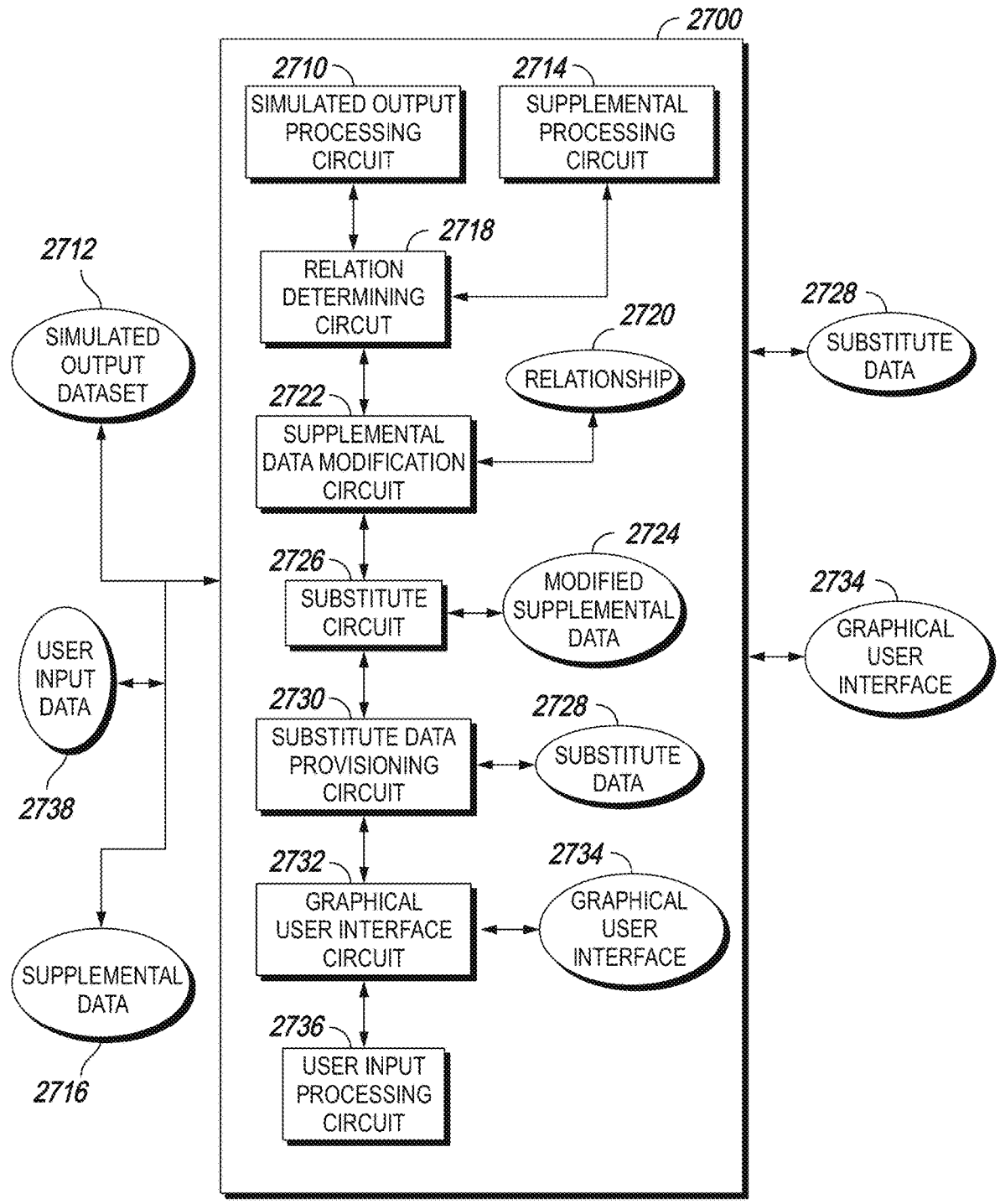
FIG. 27 is a schematic diagram of an apparatus for augmenting simulated data, in accordance with an embodiment of the current disclosure.

Illustrated in FIG. 27 is an apparatus 2700 for performing aspects of the method 2600 (FIG. 26). In embodiments, apparatus 2700 may be one or more processors, as described herein, that form part of the augmenting component 124 of the analysis facility 108 of the platform 104. In embodiments, the apparatus 2700 may be one or more processors of a mobile electronic device, e.g., a tablet or smart phone. The augmenting component 124 may receive data evaluation data such as from the simulation facility 110. The augmenting component 124 may analyze the data from the simulation facility 110 and identify elements in the data based on tags, values, locations, and the like. The augmenting component 124 may compile or group data that are related (such as data that is related to and/or may affect the cost of a trial). The augmenting component 124 may group data and determine relative scales or values for the data (such as 1-10 scale for complexity). The grouped and scaled data may be identified with tags or other identifiers for matching with real-world data during the substitution and/or supplementing process.

Accordingly, referring now to FIGS. 26 and 27, in embodiments, the apparatus 2700 may include a simulated output processing circuit 2710 structured to interpret/obtain 2610 a simulated output dataset 2712 of a clinical trial design. In certain aspects, the simulated output processing circuit 2710 may be in communication with (or integrated with) a network interface card, wherein the simulated output dataset 2712 is received over a corresponding network connection. The simulated output processing circuit 2710 may transform the simulated output dataset 2712 from a network transportation format into a different format suitable for use by the various circuits in the apparatus 2700. For example, the simulated output dataset 2712 may be received by the simulated output processing circuit 2710 as a series of packets, wherein the simulated output processing circuit 2710 may reassemble the packets into a complete data structure. In embodiments, the simulated output dataset 2712 may be distributed across multiple databases. In certain aspects, the simulated output dataset may include relative data and/or general data.

The apparatus 2700 may further include a supplemental processing circuit 2714 structured to interpret/obtain 2612 supplemental data 2716. Non-limiting examples of supplemental data include: costs of a clinical trial; time to completion of a clinical trial; NPV of a clinical trial; actual personnel costs of a clinical trial; or actual facility costs of a clinical trial. In embodiments, the supplemental data 2716 may be derived, e.g., collected, from one or more clinical trial sites 144. The apparatus 2700 may further include a relation determining circuit 2718 structured to determine 2614 a relationship 2720 between the simulated output dataset 2712 and the supplemental data 2716. Non-limiting examples of relationships include related units, related data tags, timestamps, user defined relationships, semantic analysis, and/or the like. In certain aspects, the relationship 2720 may be based at least in part on metadata, labels and/or unit values. The apparatus 2700 may further include a supplemental data modification circuit 2722 structured to generate 2616 modified supplemental data 2724 based at least in part on the relationship 2720. Non-limiting examples of modified supplemental data include financial data, regulatory data, revenue data, and the like. The apparatus 2700 may further include a substitute circuit 2726 structured to generate 2618, based at least in part on the modified supplemental data 2724, substitute data 2728 of/for the simulated output dataset 2712. Non-limiting examples of substitute data 2728 may include costs, time, number of personnel, available sites, number of enrolled patients, and/or the like. The apparatus 2700 may further include a substitute data provisioning circuit 2730 structured to transmit 2620 the substitute data 2728. The substitute data provisioning circuit 2730 may be in communication with, or integrated into, a network interface card that communicates with one or more remote devices via a network. The substitute data provisioning circuit 2730 may format the substitute data 2728 into a network specific format.

In certain aspects, the apparatus 2700 may further include a graphical user interface circuit 2732 structured to generate graphical user interface data 2734 for generating a graphical user interface that facilitates user control over augmentation of the simulated data. As such, the apparatus 2700 may further include a user input data processing circuit 2736 structured to interpret user data 2738 entered into the graphical user interface. For example, the graphical user interface may provide for the user to enter the supplemental data 2716 and/or provide instructions to the apparatus 2700 as to where and how the supplemental data 2716 may be acquired, e.g., downloaded from remote databases.

In embodiments, the substitute data 2728 may be used to replace corresponding parameters that were used to generate the simulated output dataset 2712 so that new simulations can be executed/run with more accurate data. In certain aspects, the substitute data 2728 may be included in one or more reports and/or displays, e.g., via the graphical user interface provided by the graphical user interface circuit 2732. For example, the graphical user interface may depict differences between the simulated output dataset 2712 and the substitute data 2728. In embodiments, the graphical user interface may depict differences between the simulated output dataset 2712 and an updated simulated output dataset derived from re-running the clinical trial design simulations, used to generate the simulated output dataset 2712, with the substitute data 2728.

As will be appreciated, use of supplemental data 2716, as described herein, may provide for improved accuracy with respect to simulating clinical trial designs. Further, by providing for the ability to augment simulated outputs, embodiments in accordance with method 2600 and/or apparatus 2700 may provide for earlier planning of a clinical trial, as possible clinical trial designs can be first simulated with estimated data, thus enabling other planning processes to begin and/or proceed, with the simulated data being adjusted based on real data at a later point in time.

In some embodiments the simulation models may include various parameters and data that are used by simulation engines to evaluate designs. Model parameters may be separated into different categories. Model parameters may be separated based on delineated expertise of teams. In some cases, members of a team may have different specializations. For example, some members may specialize in building human behavior models, while others may specialize in trial design models. Separating or grouping the parameters may allow different team members to independently optimize and improve specific aspects of models. In some embodiments, the model parameters may be separated into two or more types based on convenience, expertise, flexibility, and the like. Separation of parameters may provide for new and faster methods for simulation, analysis, optimization, and the like when the separation of parameters is at least partially maintained and propagated through the simulation and analysis components of the platform.

In embodiments, model parameters may be separated into at least two types or categories. Model parameters may be grouped to include parameters that define the trial design space and clinical scenario space. The trial design space may include one or more parameters that are related to protocol design, dosing algorithms, subject selection, demography, blinding of subjects, measurements to be performed, study length, and the like. The trial design space may include one or more trial design types with a combination of design variables. The trial design may specify how data will be analyzed. The design space may further include deviation models for one or more of the parameters of the design models. Deviation models may be based on expected or previously measured distributions or variations in the design.

Trial design space may further include experimental design data, adaptation rules data, and analysis model data. The experimental design data may include data, parameters, variables, and the like related to sample size, number of sites, accrual durations, allocation ratio, and the like. The adaptation rules data may include data, parameters, variables, and the like that specify the number of interim analyses, the timing of the interim analyses, boundaries, and the like. The analysis model data may include data, parameters, variables, and the like that specify test statistics, type one (1) error, and the like. In embodiments, each data, parameter, variable, and the like may have a set and/or a range of acceptable, realistic, or practical values. In embodiments, a set of trial designs may be generated wherein each trial design may have a different combination of data, parameters, variables, and the like. In some cases, the combination of different possible data values, parameters, and/or variables may result in thousands or millions of different trial design options.

Scenario space may include environmental and external factors that may affect trial design. In some embodiments, scenario data may include one or more mathematical or numerical models and methods that are related and/or describe one or more of human behavior, disease progress, drug behavior, and the like. Scenarios may include a combination of environmental variables that provide a specification or guidelines for generating virtual patient populations for a design study. Human behavior inputs may include trial execution characteristics, including how subjects adhere to regimen, dropout rates, and the like. Drug behavior may include models of drug behavior in a body and may include pharmacokinetic and pharmacodynamic models. The inputs may further include deviation models for one or more of the parameters of the models. Deviation models may be based on expected or previously measured distributions or variations in aspects such as human behavior, demographics, and the like. In embodiments, a plurality of different scenarios may be generated as potential inputs to the platform wherein each scenario may include different aspects of human behavior, disease progress, and drug behavior, and the like.

In embodiments, simulation models may be generated by combining two or more categories of inputs, such as by combining design space and scenario space. In embodiments, design space and scenario space may be defined separately and combined to generate models that include the two spaces. Generating the models from the two spaces may involve generating permutations of the two spaces. In one embodiment, a cross product between each scenario in the scenarios space and each design in the design space may be used to generate models. In this configuration, a large number of models may be generated from a much smaller set of designs and scenarios. In embodiments, millions of models may be created from design and scenario spaces that correspond to only thousands of designs and scenarios.

In some embodiments, the trial and clinical spaces models may be selectively combined, such that some instances of trial designs and clinical scenario models are not combined to create simulation models. The selective combination may reduce the number of simulation models that are simulated by the system, thereby reducing computation time. In some embodiments, a variety of heuristics, algorithms, filters, and the like may be used to select a subset of all possible combinations of trial and scenario spaces to reduce the number of simulation models, eliminate improbable combinations, and the like. In some embodiments, models may be scored before they are simulated. The scoring may be based, at least in part, on the feasibility, probability, practicality, or the like of the scenario-design combination for each model.

In embodiments scoring may be based on rating and/or priority associated with the design space parameters and/or scenario space parameters in each model. Ratings and/or priority may be provided by a user and/or other parts of the system. In some embodiments, rating and/or priority may be determined from historical data from previous simulations and design studies. The ratings and/or priority may be determined based on the number of occurrences of the parameter in the historical data in similar designs studies. In some embodiments the ratings and/or priority may be determined on the number of occurrences of the parameters in designs that were identified as optimal or desirable in previous designs studies. Ratings and/or priority score may be used to determine a relevancy score. The relevancy score may be computed as function of the ratings and priority score such that the higher the ratings and/or priority score the higher the relevancy score. Models that score below a threshold may be flagged or removed such that they are not simulated.

After the simulation models are created, the platform may execute and evaluate the simulation models. In embodiments, each simulation model (i.e., a specific combination of a trial design and scenario) may be evaluated over the course of numerous simulation runs, and the number of simulations may vary depending on the project stage. Each simulation run may be based on a different deviation of the trial design and/or scenario according to the respective deviation models. Results from multiple simulation runs for a particular simulation model may be analyzed to determine performance parameters.

In embodiments, results of simulations may be organized and grouped according to their relation to design and scenario space. Performance parameters of each model after simulation may be grouped to show relations of each parameter to one or more aspects of a design and/or scenario models. The relations may be used to refine aspects of the design space and/or scenario space for additional evaluation.

Figure 28:
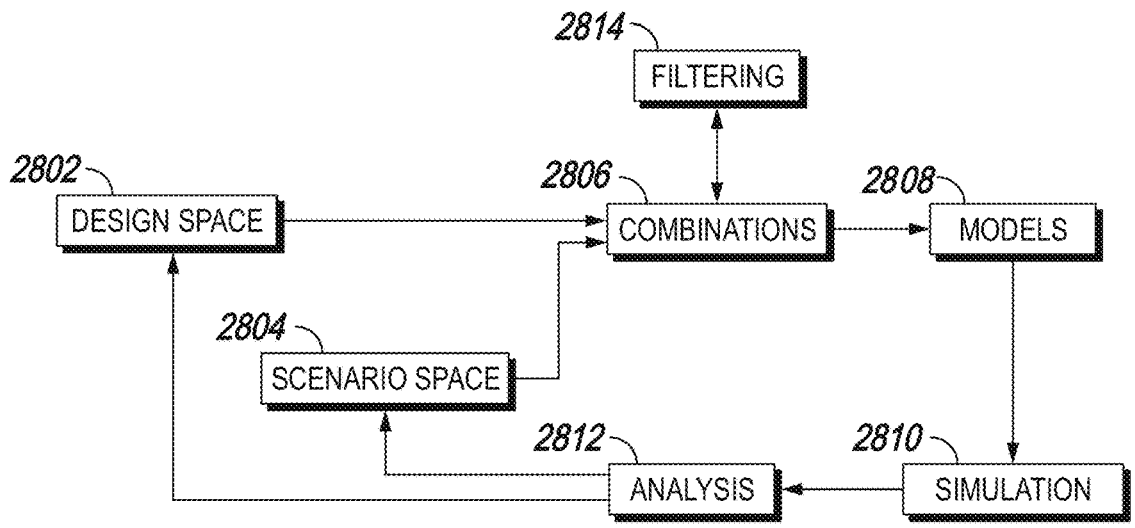
FIG. 28 is a is a flow chart for evaluating designs, in accordance with an embodiment of the current disclosure.

Referring to FIG. 28, a flow chart for the evaluating designs may include defining design space 2802 and scenario space 2804. The design space and scenario space may be used to determine combinations 2806 that are used to define models 2808 for simulation 2810. The combinations may be analyzed by one or more filtering components 2814 that may rate and rank the combinations. The simulation data may be analyzed to determine desirable and/or optimum designs. Based on the analysis, the design and/or scenario spaces may be modified to generate more combinations for simulation.

Figure 29:
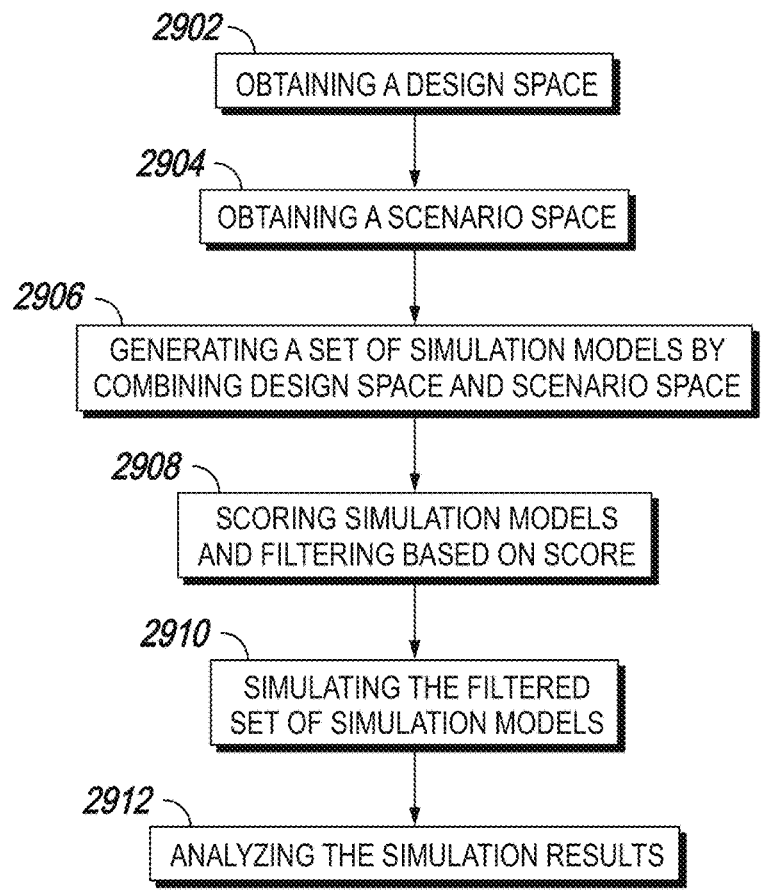
FIG. 29 is a flow chart depicting a method for evaluating designs, in accordance with an embodiment of the current disclosure.

As shown in FIG. 29, a method for evaluating designs may include obtaining a design space 2902 and a scenario space 2904. The set of simulation models may be generated by combing different permutations of the design space and scenario space 2906. The simulation models may be scored and filtered 2908. The method may further include simulating the filtered set of simulation models 2910 and analyzing the simulation results 2912.

In embodiments, simulations may require population models to evaluate a design for virtual subjects. Population models may define characteristics of subjects in a clinical trial. A trial design may define aspects of subjects that should be included in a trial. A trial design may define inclusion and exclusion criteria for subjects based on characterizations of demography, disease status, and the like.

In embodiments, for a simulation, virtual subjects may be selected from population models. A population model may include subject models that include various subject characteristics such as demography data, survival models (control and treatment), dropout rate (control and treatment), expected responses, and the like. Characteristics of subjects in a population model may be associated with different distributions. The distributions of parameters of the population model may correspond to real-world population models. In embodiments, when a subject is included in a simulation, a population model may be evaluated to determine characteristics for a subject for one simulation instance. For each simulation instance, the population model may be evaluated (with a random value for selection) to identify a new subject and the subject may be selected based on inclusion/exclusion criteria of the trial.

In embodiments, a virtual population may be pre-generated. The virtual population may be generated according to a population model and/or real-world population data. The virtual population may be a list or other data structure that includes thousands or even millions of different virtual subjects. Each subject in the virtual population may be associated with characteristics such as demography data, survival models, dropout rate, expected responses, and the like for each subject. For a simulation, a subject may be selected from the virtual population (randomly or based on another function) for simulation of a trial design.

Figure 30:
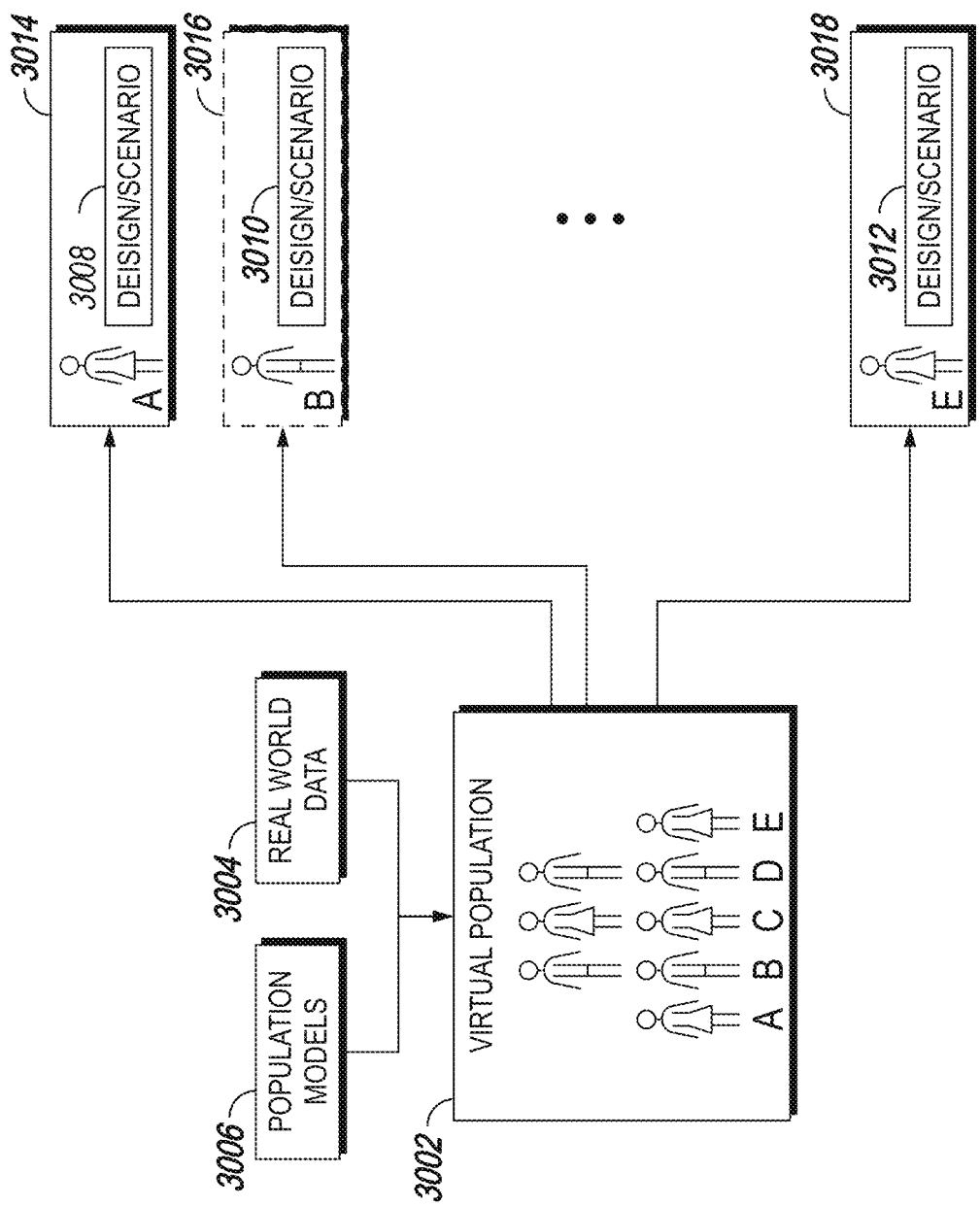
FIG. 30 is a flow chart showing aspects of utilizing virtual populations, in accordance with an embodiment of the current disclosure.

FIG. 30 shows aspects of utilizing virtual populations for simulation. A virtual population 3002 may be generated from population models 3006 and/or from real world population data 3004. The virtual population 3002 may include data representing individual subjects (virtual patients) and characteristics of the subjects. The virtual population may be generated to have a specific distribution of characteristics for the subjects. The distribution of characteristics may be consistent with real-world data for a specific population or sub-population. The virtual population may include data for hundreds, thousands, or even millions of subjects. In some embodiments, multiple different virtual populations may be generated with different distributions of characteristics for the subjects.

In embodiments, a virtual population 3002 may be pre-generated before simulation start or may be generated in real time during simulation. In some embodiments, subjects may be generated as they are needed and/or requested for simulation using population models and the subjects may be added to a virtual population each time it is generated. The virtual population may grow as simulations and analysis of designs progresses. The virtual population may be a data structure (such as a database, list, table, and the like) that may be configured to retrieve data for a subject or a group of subjects randomly, according to specific subject characteristics, according to an unique identifier of the subject, and the like. Subjects in the virtual population may be used for simulation of trials. Simulation instance 3014 may include characteristics of a subject. The subject for the simulation may be selected from the virtual population 3002. A simulation instance may evaluate a design for the subject for a specific design and scenario combination 3014. Simulations may include a plurality of simulation instances 3014, 3016, 3018 using different subjects from the virtual population and variations of design and scenario combinations 3008, 3010, 3012.

In embodiments a subject for a simulation instance 3008 may be selected from the virtual population 3002 randomly, based on a function of the characteristics of the subjects, by a unique identifier associated with each subject, and the like. In embodiments, each simulation instance may be associated with a unique identifier of a subject used for simulation. The virtual population may be used for all simulations of a study. Simulations instances may be reproduced with the same subject from the virtual population by saving a unique identifier associated with the subject with the simulation instance in a simulation history record.

In embodiments pre-generated virtual populations may have several benefits over subject selection from a population model. Subject selection from a virtual population may decrease computation time since a population model does not need to be evaluated for simulation instance and requires a simpler selection from a population (such as a selection from a list or table). Virtual populations provide for enhanced reproducibility given a constant population and improved accuracy of results across multiple simulations given constant population. In embodiments, due in part to the reproducibility aspects, pre-generated virtual populations may enable easier and faster computations of counterfactual data.

In embodiments, simulations may include determination of counterfactual data for a trial. Counterfactual data may relate to data that would have been observed under different (often conflicting) configurations of a trial. For example, if a trial provides data about an outcome of a patient that receives a therapy, counterfactual data may be data that relates to an outcome of the same patient if they did not receive a therapy. Normally, counterfactual data cannot be observed in a real-world trial. Continuing with the example, a patient, in a real-world trial can receive a therapy or not receive a therapy, but not both since the two configurations are conflicting. In a real-world trial, a patient can only be in one of two groups and therefore only one possible configuration of trial can be observed. The data related to a configuration that is not observed by a trial may be counterfactual data.

In another example, a trial may have missing data when patients drop out of the trial. The missing data is the data that would have been observed had the patient not dropped out of the trial. Missing data cannot be observed in a real-world trial but may be determined using simulation. Missing data (which may be a type of counterfactual data) may be determined by simulating a trial design configuration for when a patient drops out of the trial and a configuration where the same patient does not drop out of the trial.

A trial design simulation may determine what is expected to happen in a trial and what could have happened in a trial given a different configuration (such as counterfactual data). Counterfactuals may be used to determine estimands for a true effect of a treatment. In embodiments, counterfactual data may be used to determine how good a trial is at estimating the estimands of interest using the observables of a trial. In embodiments, estimands determined from counterfactual data may be used to configure a trial design parameter (such as population size) to enable a trial design to come close to estimating the estimands.

Figure 31:
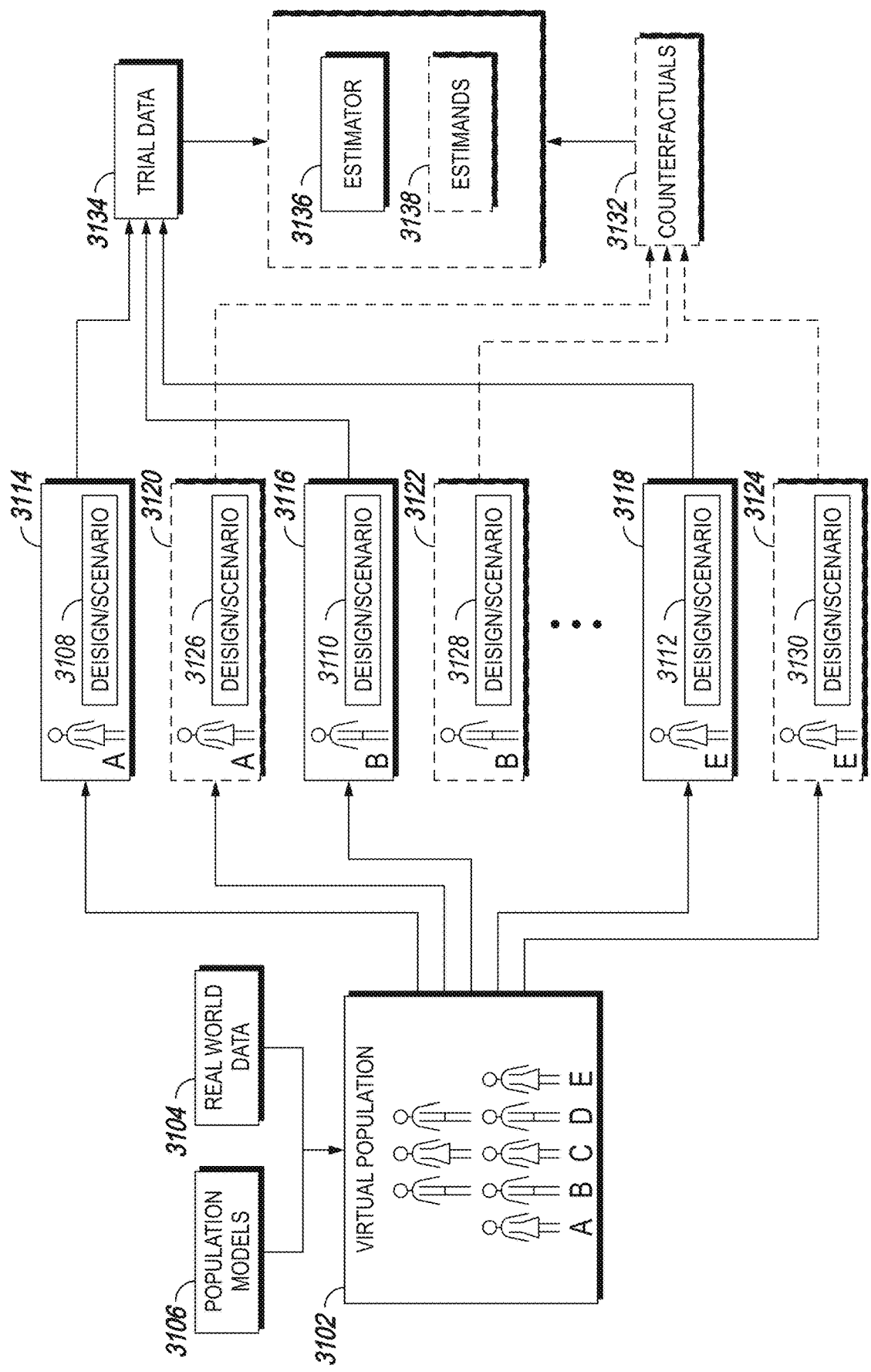
FIG. 31 is a flow chart for utilizing virtual populations and counterfactual data, in accordance with an embodiment of the current disclosure.

FIG. 31 shows aspects of a platform that utilizes counterfactual data in a simulation. In embodiments, simulations may include simulations 3114, 3116, 3118 to determine what is expected to happen in a trial 3134 and another set of counterfactual simulations 3120, 3122, 3124 to determine what could have happened in a trial given a different configuration. For example, one simulation 3114 may simulate an outcome if patient A received a treatment and another counterfactual simulation 3120 may simulate an outcome if patient A did not receive a treatment. In embodiments, the trial data 3134 may be used to determine the estimator 3136 of a design. In embodiments, the trial data 3134 may be compared to the counterfactual data 3132 to determine estimand for the trial 3138. A performance of a trial may be evaluated as to how close the estimator of trial is to the estimands. A trial for which the estimator is close to the estimands may be considered desirable.

Figure 32:
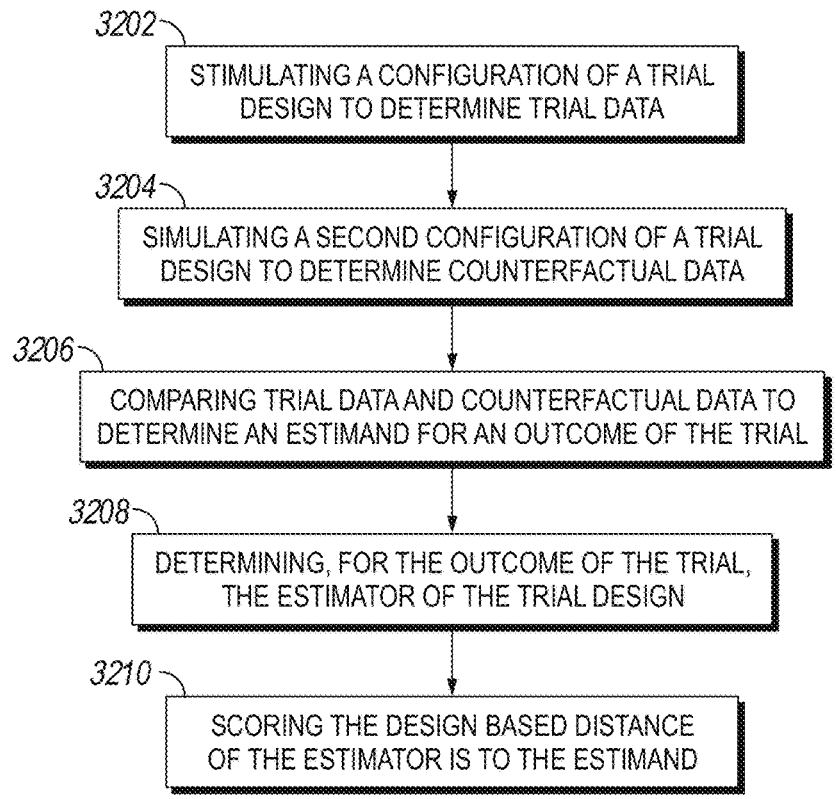
FIG. 32 is a flow chart depicting a method for evaluating designs with counterfactual data, in accordance with an embodiment of the current disclosure.

As shown in FIG. 32, a method for evaluating designs with counterfactual data may include simulating a configuration of a trial design to determine trial data 3202. The method may further include simulating a second configuration of a trial design to determine counterfactual data 3204. The trial data and the counterfactual data may be compared to determine an estimand for an outcome of the trial 3206. The method may further include determining, for the outcome of the trial, the estimator of the trial design 3208, and scoring the design based on a distance of the estimator to the estimand 3210.

Figure 33:
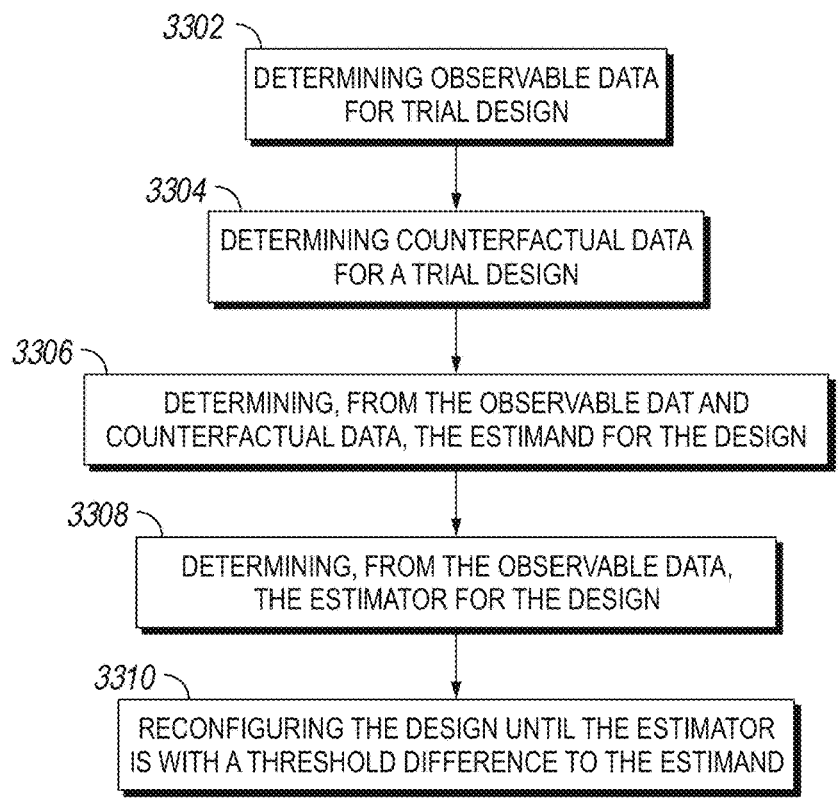
FIG. 33 is a flow chart depicting a method for evaluating designs with counterfactual data, in accordance with an embodiment of the current disclosure.

As shown in FIG. 33, a method for evaluating designs with counterfactual data may include determining observable data for a trial 3302. The method may further include determining counterfactual data for a trial design 3304. An estimand may then be determined from the observable data and the counterfactual data 3306. The method may also include determining, from the observable data, the estimator for the design 3308. The design may be modified or other variations of the design may be explored (such as a design with a different population) such that the difference between the estimator and estimand are within a threshold 3310.

Figure 34:
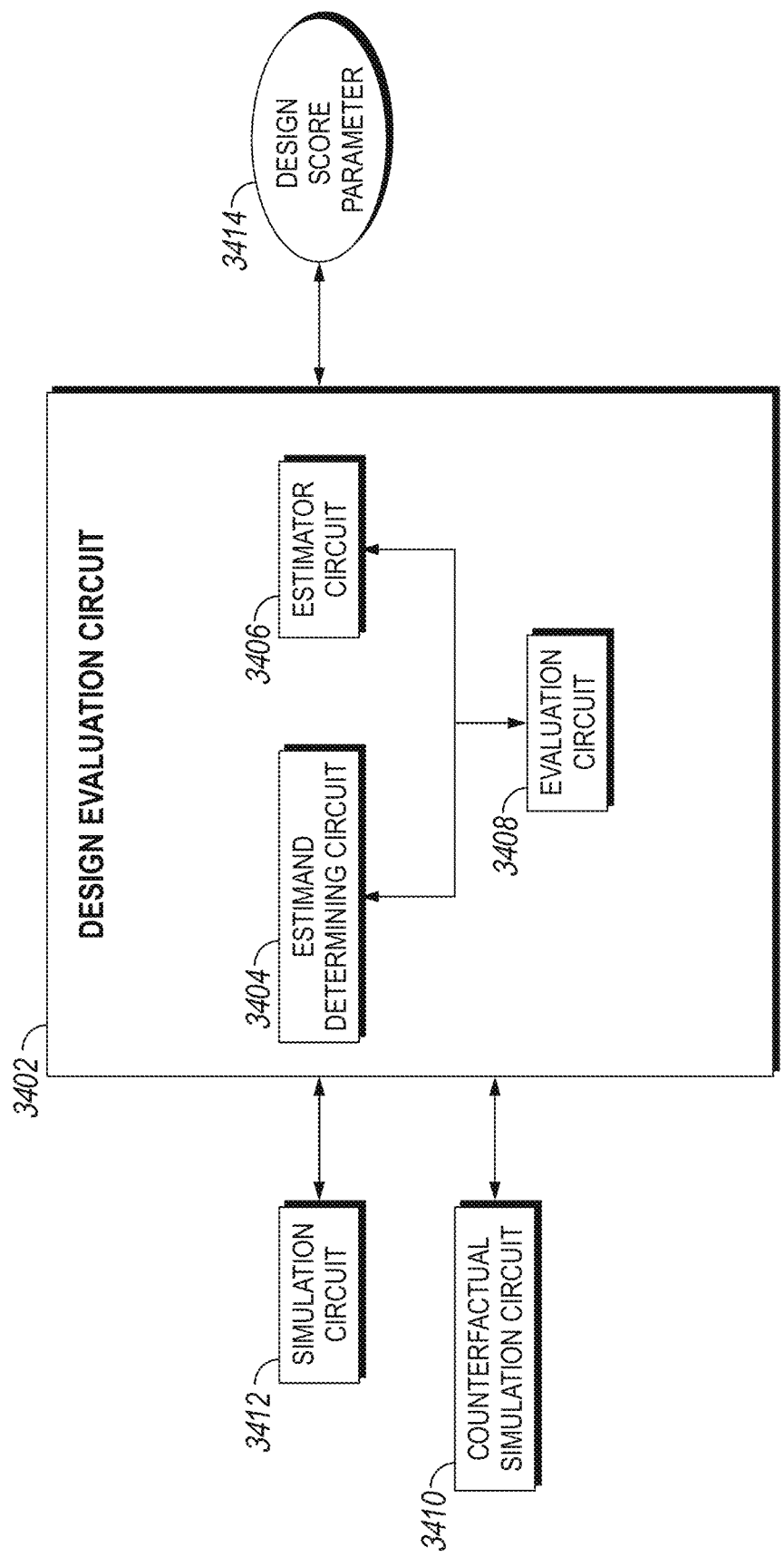
FIG. 34 is a schematic depicting a circuit for evaluating designs with counterfactual data, in accordance with an embodiment of the current disclosure.

FIG. 34 shows aspects of an apparatus for evaluating design with counterfactual data. In embodiments, the design evaluation circuit 3402 may receive simulation data from a simulation circuit 3412 and counterfactual simulation data from a counterfactual simulation circuit 3410 the data may be for a design. An estimand determining circuit 3404 may be configured to determine an estimand for an outcome using the input data. An estimator circuit 3406 may be used to determine the estimator for the design. An evaluation circuit 3408 may be configured to determine how well the estimator estimates the estimand. A distance measure, such as a difference or other statistical measure may be determined. Based on the measure the design may be scored and the design evaluation circuit 3402 may output a design score parameter 3414 based on the difference.

Interactive methods can be used in the process of evaluating designs, conducting simulations, configuring a design study (such as pre-simulation)s, and the like. Interactive methods may be methods in which a person or an alternate algorithm acts as a decision-maker and interacts with the methods, systems, and platform to indicate a preference for aspects of the outcomes and/or input. The preferences may be used to determine other inputs and/or outputs that relate to the preferences.

In embodiments, interactive methods may be used to identify preferences for trial designs. The preferences in trial designs may be used to identify optimum designs based on the preferences. The preferences in trial designs may be used to identify other designs that are similar to the preferences, surface design options that are complementary to the preferences, determine ranking of desired aspects of designs, determine unwanted features, and the like.

In embodiments, interactive methods may include providing a comparison and tracking selections in response to the comparison. In embodiments, configuration parameters may be presented to a user. Aspects of criteria space, design space, scenario space, and performance space may be presented before simulation. Parameters may be presented as a comparison between different parameters and/or values of the parameters. User input may an interaction between the values or parameters shown. Interactions may be used to identify preferences for parameters and/or values for parameters.

In embodiments, results of simulations may be presented to a user. Performance of simulated designs may be presented to a user via an interactive interface. In one embodiment, the interactive interface may present results of simulations as a comparison between two or more simulated designs. User input may include a selection of a preference between the designs, saving of one or more of the presented designs, indicating an interest in one or more parameters of the design and the like.

Interactive interfaces may be used to present two or more performance parameters of a simulated design to a user. In one embodiment the user may specify a preference for a design. Based on the tracking of the selection, one or more user preferences may be determined. User preferences may be identified from the user selecting a design, saving a design, dismissing a design, moving a design, and the like. In embodiments, preferences may be determined by identifying differences between the presented designs the designs associated with a user action.

In some embodiments, designs presented for consideration in an interactive interface may be selected based on results of optimality determination based on Pareto analysis and/or CH analysis. In some embodiments, designs presented for consideration in an interactive interface may be selected randomly from the set of designs.

Designs presented for consideration in an interactive interface may be selected such that an interaction with of one or more design in the interface provides useful information about preferences of a user. Designs may be selected for presentation may be selected such that they are substantially similar is most parameters and different with respect to a small number of parameters (such less than 10). Having substantially similar designs for comparison may provide a clear indication which parameters and/or values are preferrable to a user when an interaction with the designs is observed. In embodiments, designs may be selected such they represent very different designs. The designs may represent different ends of the spectrum with respect to the overall design (designs may differ in more than 10 parameters). Having designs that represent vastly different designs for comparison may provide a clear indication of the overall properties and types of designs that are preferred.

In embodiments, information inferred from interactions may be directly related to the parameters and values for which interactions were received. In some embodiments, information inferred from interactions may be derived for parameters and values for which interactions were received. Interactions related to one parameter or a design may provide additional information about other parameters. For example, interactions related to cost of a study may be used to determine preferences for the cost and/or other related parameters such a duration (longer studies may typically be more expensive), number of patients (more patients may require more sited and more cost), and the like.

In embodiments, interactive interfaces for identifying preferences for designs may be iterative and may require multiple interactions from a user to determine preferences. In the case of an interactive interface based on a comparison, the interface may iterate over multiple cycles of presenting designs and receiving user selections. In each iteration, the interactive interface may present a different set of designs for consideration and monitor user interactions with the designs. In each iteration, the set of designs may be strategically selected to determine different aspects of preferences from user interactions. For example, in first iteration the designs shown on the interface may be selected to identify preference for design type, in the second iteration, the designs may be selected to identify preference for a first parameter.

Once preferences are identified designs, such as optimal designs, may be determined for the preferences.

In embodiments, interactive methods may be used to identify regions of interest and/or identify additional designs for simulation. Initial simulations may be coarse grained simulations. Coarse grained simulations may not be exhaustive but may be used to provide a course grid of designs that provides an overview of the designs and performance for identified criteria by simulating subset of the possible combinations. Some of the simulated designs from the coarse set of simulations may be presented to a user. User interactions with the presented designs may be used to identify types of designs and parameters of the designs that may be further explored with simulation.

In embodiments, an interactive method for identifying regions of interest may include an interface such as a map that shows relative and/or absolute performance of designs and their parameters. The interactive interface may be used to visualize the locations of designs in the performance space. Users may select regions of interest and the platform may be directed to identify designs that may be in the regions of interest for further simulation and evaluation.

In embodiments, an interactive method for identifying regions of interest may include an interface that identifies one or more designs from the coarse grid of designs. The designs and the properties and performance of the designs may be presented to a user and the user interactions with aspects related to the design may be tracked. Based on the interactions, user preference for the design may be determined. Additional designs may be presented to the user to determine preference for additional designs. Based on the interactions and preferences for designs, a region or an area in the design space may be identified as being an area of interest. An area of interest may include an area around a design (such as all designs within an ε-distance of a design). An area of interest may be an area between two designs. An area of interest may be an area bounded by three or more designs (such as a triangular area bounded by three designs). The area of interest may be used as a guide for additional simulations. Additional simulations may be conducted on the designs that are in the area of interest.

In embodiments, interactive interfaces may be in connection with sensitivity analysis of designs. Interactions with the interface may be monitored to determine preferences for designs with respect to sensitivity and/or robustness of the designs. User interactions with interfaces for interacting with graphical elements for specifying filters, designs, regions, and the like may be tracked to determine which aspects of a design the user analyzes the most with respect to sensitivity of the design. The interactions may be tracked to determine minimum and/or maximum acceptable values for one or more parameter variations.

In embodiments, user interactions with interactive interfaces may be recorded and saved. In some embodiments, interactions with interactive interfaces may be processed to derive relevant data from the interaction and only the derived relevant data may be stored. In some embodiments, the derived data and the raw interaction data may be stored. Aspects of presented data in the interactive interfaces, interactions from users, sequence of interactions to achieve an outcome, and other aspects related to interactive interfaces may be saved. Interactions data, along with design data, design data, scenario data, and the like may be used to train one or more AI and/or ML models for identifying user preferences from interactions. The models may be trained on the previous interactions, presented data, and other aspects of the design study relevant to the interaction such as the criteria space, design space, scenario space, and performance space definitions. The trained models may be used to predict which designs should be presented to the user to maximize information obtained from the interactions from the user with the presented designs. The models may be trained to determine user preferences based on the interactions and the final selections. The use of trained models may reduce the number of iterations and amount of interactions that need to be observed to identify preferences and/or identify other designs or regions of interest.

Figure 35:
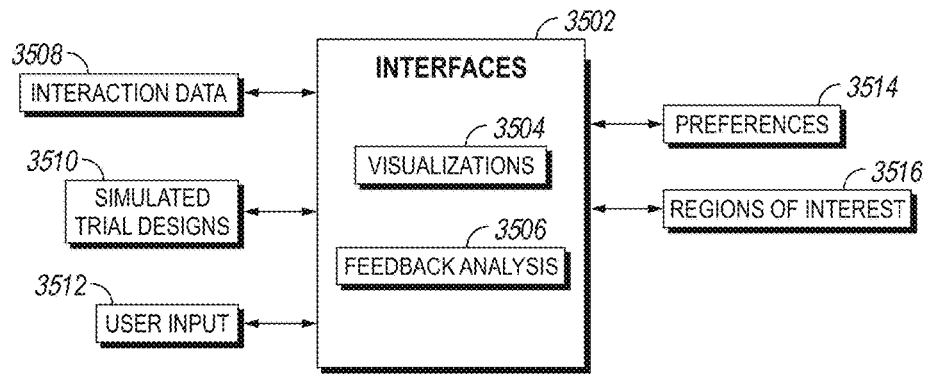
FIG. 35 is a is a schematic diagram of an apparatus for determining designs from user interactions, in accordance with an embodiment of the current disclosure.

As shown in FIG. 35, the interfaces component 3502 may include component for generating visualizations 3504. The visualizations may include data related to simulated trial designs 3510. The visualizations may present data related to trials and receive user input data 3512 that is indicative of user interactions with the interface and the presented data on the interface. The apparatus may include a feedback analysis component 3506 for tracking and analyzing the user input and interactions 3512. The feedback analysis component 3506 may analyze interactions to determine design preferences, regions of interest, and the like. In some embodiments, the feedback analysis component 3506 may receive data related to user interactions which may include AI/ML model trained on the previous interaction data 3508. The feedback analysis component 3506 may determine preferences 3514 for designs, parameters of designs, regions of interest 3516 for designs and the like based on the interactions.

Figure 36:
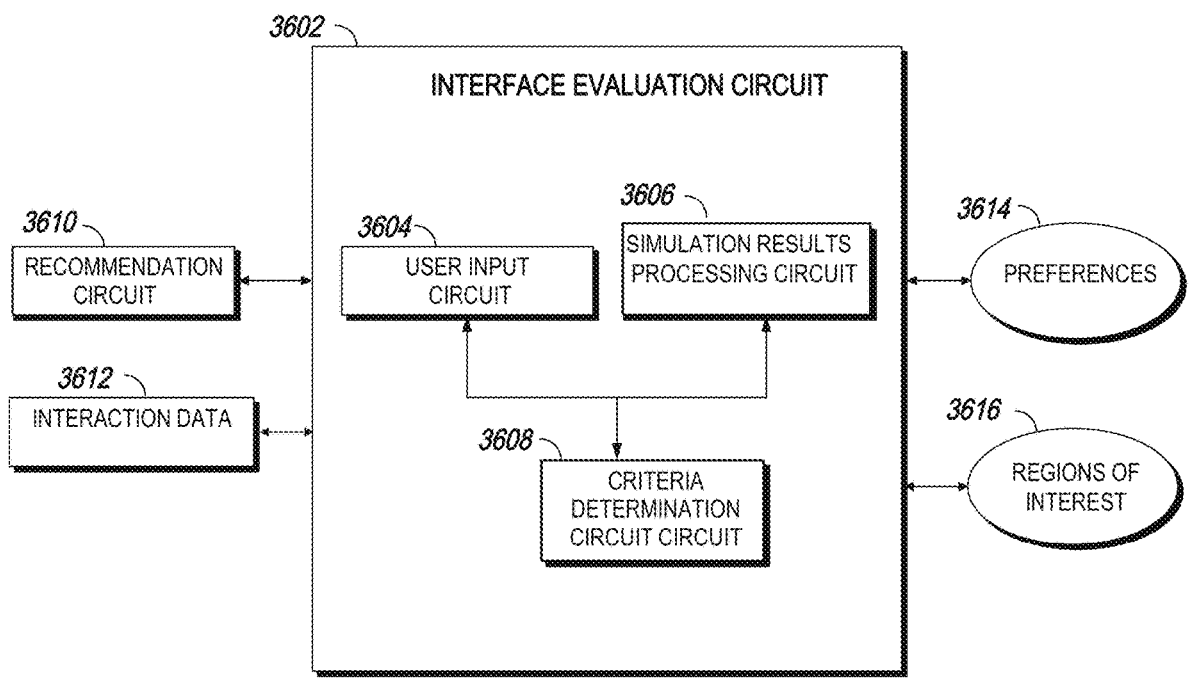
FIG. 36 is a is a schematic diagram of an apparatus for determining designs from user interactions, in accordance with an embodiment of the current disclosure.

FIG. 36 shows aspects of an apparatus for determining preferences from user interactions. In embodiments, the interfaces circuit 3602 may include a user input circuit 3604 and a simulation results processing circuit 3606. The user input circuit 3604 may process interaction data 3612 from a user. The interaction data 3612 may relate to user interactions with data and components of an interactive interface. The interface may, during the interaction, display design data that is received from a recommendation circuit 3610. The simulation processing circuit 3606 may further include a criteria determination circuit 3608 that may be configured to analyze processed user interaction data from the user input circuit 3604 and data provided in the interface from the simulation results processing circuit 3606 and determine user preferences. The preferences may include design preferences 3614 and/or regions of interest 3616.

Figure 37:
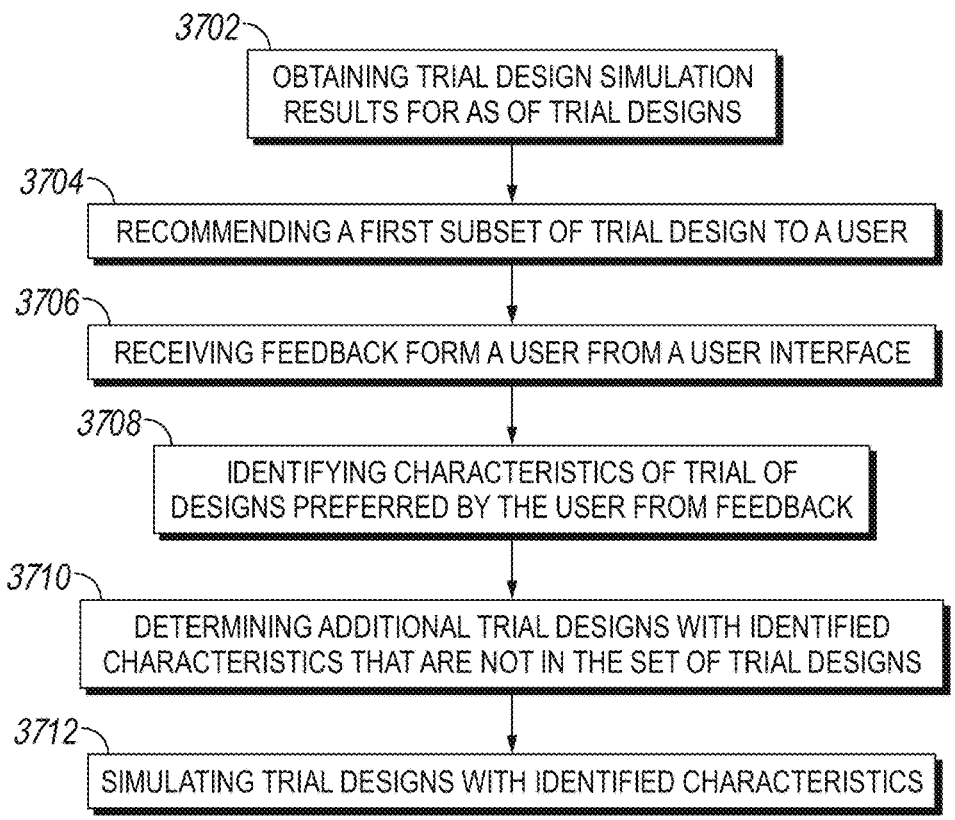
FIG. 37 is a flow chart depicting a method for determining designs from user interactions, in accordance with an embodiment of the current disclosure.

As shown in FIG. 37, a method for determining design using user interactions may include obtaining trial design simulation results from a set of trial designs 3702 and recommending a first subset of trial designs to a user 3704. The recommendations may be via one or more interactive graphical interfaces. The method may include receiving feedback from the user via the interface 3706. The feedback may include interaction data that relates to one or more of the recommended designs. The method may further include identifying characteristics of trial designs preferred by the user from the feedback 3708. Using the determined characteristics, the method may determine new trials with the identified characteristics that have not been presented to the user 3710. The new trials may be simulated 3712. The method may be repeated at least some of the recommended designs being the new simulated designs.

Figure 38:
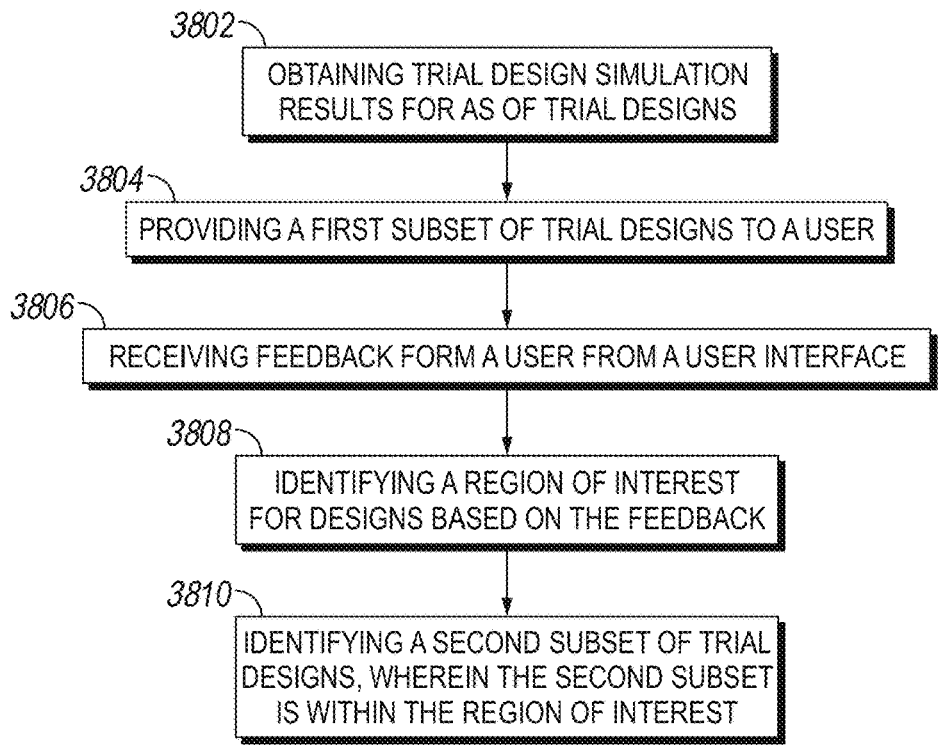
FIG. 38 is a flow chart depicting a method for determining designs from user interactions, in accordance with an embodiment of the current disclosure.

Shown in FIG. 38 is a method for determining a design using user interactions. The method may include obtaining trial design simulations results for a set of trial designs 3802. The method may further include providing a first subset of trial designs to a user 3804 and feedback from the user may be received from an interface 3806. Based on the feedback, one or more regions of interest from the design space may be identified 3808. The method may further include identifying a second set of trial designs that are within the region of interest 3810.

In embodiments, the interactive graphical interfaces may include a card interface. A In embodiments, a card interface may be used to evaluate or determine aspects the criteria space, design space, scenarios space, and/or performance space.

In embodiments, a card interface may be used to evaluate simulated designs. The card interface may be configured to identify, based on user interactions with the interface, user preferences for designs, preferences for design parameters, optimality of designs, and the like. The card interface may be configured to identify, based on user interactions with the interface, regions or areas of interest in the design space that appear to have desirable designs. These areas may be further explored with further simulations and analysis.

In embodiments, the card interface may include depictions of elements referred herein as "cards" that represent one or more of the simulated trial options. Depictions of cards may include rectangular shapes that may group data or parameters associated with a simulated design. The cards may be depicted as rectangles, squares, circles, polygons, or other shapes. The graphical interface depicting cards may include one or more cards that are associated with different trial designs.

In embodiments, an initial set of cards may be populated on the graphical interface, such as when simulations are completed. In some embodiments, an initial set of cards may be populated on the graphical interface during the simulation before all of the simulations are finished based on available or intermediate data. A card may provide an intuitive grouping of data for a trial design allowing a user to easily determine the parameters and qualities of the trial design the card is associated with.

In many situations, the number of simulated trial designs may be large such as a thousand or even millions of simulated trial designs. In embodiments, the number of cards shown on the graphical interface may be less than the number of simulated trial designs. In some embodiments, the number of cards initially shown on the interface may be less than fifty (50) or may be less than ten (10). The number of cards initially shown may be determined based on the total number of simulated trial designs, a user preference, historical preference, or the like.

A number of cards may be initially shown on the interface. Each card may be associated with and show data related to a particular trial design of the set of simulated trial designs. The selection of the initial trial designs that are represented by the cards may be selected using an initial card selection criteria.

In some embodiments, the initial card selection criteria may be a random criteria wherein random trial designs from the set of simulated trial designs are selected. In some embodiments, the initial card selection criteria may be based on a selection of trial designs that have the best value for one or more parameters. In some cases, each card shown on the interface may represent a trial design that has a maximum value for a different parameter. In embodiments, initial cards shown may represent the trial design that is associated with the trial design that has the best value for each strategic goal. Depending on the parameter, the best value may be the maximum value, a minimum value, a median value, and the like and may depend on the parameter and the goals of the parameter.

In some embodiments, the initial card selection criteria may be based at least in part on historical data (such as associated with a particular user or organization). Trial designs may be selected that have similar parameters to trial designs that were ultimately selected or were finalists in other clinical trials.

In embodiments, the selection of trial designs for cards may be based on a function of one or more parameters and variables. In some embodiments, the selection of trial design candidates for cards may be based on a weighted value sum of one or more parameters and variables. The weighting may be based on a specific goal of the study or other design parameters or requirements. In some cases, two or more different functions may be used. In some cases, each card or some cards may be associated with a different selection function. In embodiments, selection of trial designs for cards may be based on Pareto and/or CH analysis. Pareto designs and/or CH-designs may be used to populate data in the cards.

FIG. 39 shows one embodiment of a graphical interface with cards associated with trial designs. The figure shows four cards elements 3902, 3904, 3906, 3908 with each card showing seven parameter values of different trial designs. In this case, the four initial cards represent a trial design that has the best value for four (4) different strategic goals. The first card 3902 is representative of a trial design that maximizes the expected net present value (eNPV) of all the simulated design studies. The first card 3902 shows parameters of the trial design that maximizes the eNPV for the simulated trial designs. Other cards are representative of trial designs that maximize or minimize other design goals, such as the probability of success (POS), discounted cost, and study duration.

In embodiments, colors, shading, saturation, background color, and the like may be used to represent information regarding values of the parameters of a trial design shown on each card. In embodiments colors, shading, saturation, background color, and the like may be used to represent the relative value of a parameter with respect to all of the simulated trial designs. For example, a low relative value may be shown with a blue color, while a large relative value may be shown with a red color. In embodiments, colors, shading, saturation, background color, and the like may be used to represent the relative value of a parameter with respect to the values shown on the cards.

In embodiments, the graphical card interface may include designs for specifying filters 3910 for one or more parameters of the trial designs. Filters 3910 may affect which trial designs are displayed by the cards. In embodiments, the filters may affect the number of cards shown. Filters may be used to set global limits on specific parameters for all the displayed cards or may be applied differently to each card.

In embodiments, filters may be applied to cards that are configured to display cards that maximize or minimize a strategic goal. An applied filter may cause the card to display a trial design that provides the maximum or minimum for a strategic goal but also satisfies the bounds of the filter.

In embodiments, filters may be applied via one or more graphical controls. The controls may be different based on the type of parameter or variable the filter is being applied to. Parameters or variables that have real numbers, for example, may have different controls than parameters or variables that have Boolean values. In some embodiments, the filter controls may include sliders, dials, input boxes, and the like. The behavior of a control may depend on the values for the respective parameters or variables in the set of simulated trial designs. The behavior of the control may depend on the distribution of the values of the respective parameter or variable. For example, in the case of a slider control, the behavior of the slider control may be nonlinear with respect to the value the slider represents with respect to the position of the slider. The behavior of the slider may be different when the slider is in a position where there are many values for a variable or a parameter versus where there are no values for a variable or a parameter.

In embodiments, filter settings may be analyzed with respect to the one or more distributions, values, desired values, expected values, goals, trial goals, trial parameters, trial values, distribution of values, distributions or parameters, and the like. Filter settings may be analyzed to determine how adjusting one or more filters may impact what trial designs are displayed on one or more cards. For example, filter settings may be set to filter out all trial designs below a specific value of a parameter of the trial designs. However, the setting of the filter may filter out many trial designs that meet one or more strategic goals. In embodiments, the sensitivity of filter settings may be identified, and their sensitivity may be communicated to a user. In embodiments, a user may be provided with information to indicate that the user may consider adjusting one or more filter settings. The user may be provided with information as to how the settings may be changed. In some embodiments, the platform may adjust filters when the filters are determined to be too aggressive or determined to cause filtering of trial designs that would otherwise be good candidates for a trial or that a user should otherwise review. In some embodiments, the filters may be set to approximate values, and the platform may be configured to automatically set the filters to an actual value based on analysis of the trial designs and/or design objectives.

In some embodiments, filter settings may be analyzed with respect to a distribution of the values related to the filter. Users may be provided with information regarding the setting of the filter with respect to the distribution of the values. For example, in some cases, a variable may have a binomial distribution. The user may be provided with information regarding the setting of the filter and how the setting may be adjusted to consider a cluster or a specific distribution of values. In some cases, filters may be associated with one or more graphs or graphics that identify the distribution of the values associated with the filter. In some cases, a user may be provided with a graph or other indicators that provide information about the relation between a value associated with a filter and one or more strategic goals.

In embodiments graphics on a displayed card, around a displayed card, the like may provide additional information regarding the trial design displayed compared to other simulated trial designs not displayed. Graphics may be used to provide information regarding how many other trial designs are within a specified distance to the displayed trial design. Graphics such as variable shadows, lines, colors, and the like may provide a quick visual indication as to the number of similar trial designs are available to the trial design displayed on the card. In embodiments, graphics may indicate a depth of a deck of cards, the number of trial designs related to a card, the number of trial designs in the same category as a card, and the like.

In embodiments, cards in the card interface may be manipulated by a user. User interactions with the card interface may be tracked. Interactions may include manipulation of cards. Manipulation of cards may include actions that are performed by a user in the process of examining and selecting one or more trial designs. Manipulations may include selecting, ranking, moving, putting into a "shopping cart" or "favorites" category, comparing, and the like. The manipulations of the cards may be tracked by the platform to determine the preferences and/or goals of the user.

In embodiments, the platform may use the history of the interactions, such as the manipulations, to provide suggestions for filter settings and/or provide new cards that show additional trial designs for consideration. For example, the platform may identify a trend that cards with data related to trial designs with a cost exceeding a specific value are removed from consideration by a user. The platform may use the identified trend to determine additional trial designs below the cost and provide the designs for consideration to the user.

In embodiments, data related to objectives of an organization, historical data, customer data, and the like may be used to identify trial designs automatically. In embodiments, the automatically identified trial designs may be displayed to a user with a card for consideration. In embodiments, manipulation of cards may be used to identify preferences such as absolute values or variables or parameters, relative values, and correlations. In embodiments, the platform may find trial designs that are similar to those selected as "favorites" and present them as cards for consideration.

In embodiments, cards that were tagged as a favorite, saved in a shopping cart, or highly ranked by a user may be selected for display in a comparison table. Data related to the trial designs of the cards may be displayed in a table format, and the data may be compared by the user or exported for comparison or other purposes. In embodiments, the interface may include visual effects such as highlighting or emphasized (such as a darker border, a different color of border, a flickering of colors, and the like) to confirm user interactions and/or provide feedback that an interaction was analyzed to determine preferences.

In embodiments, the platform may determine preferences for characteristics of trial designs by presenting various trial designs in the form of cards for considerations. The trial designs may be strategically selected to explore preferences between tradeoffs between one or more parameters. In some embodiments, cards with selected values may be presented to a user allowing the user to select the card or provide other indications of interest in the card. Based on the responses, the platform may determine which variables or parameters are important, as well as acceptable ranges for those variables and parameters. In another embodiment, the platform may simultaneously present two or more cards with contrasting values for parameters allowing the user to choose a favorite card or rate the relative interest in the cards. Based on the rating and selection, the platform may determine which parameters, variables, values, and the like the user is most interested in or that are more important to the trial. Cards presented to the user may reflect values of specific trial designs or may not be selected to explore preferences and may not be directly related to any specific trial design.

In embodiments, the platform may determine preferences for characteristics of trial designs by presenting various combinations of parameters. The platform may show parameter values that represent corner cases of one or more parameters. The platform may show values that represent a spectrum of values of one or more parameters or a combination of parameters to determine a user preference. For example, the platform may display cards to a user that represent different ranges of parameters such as a high cost or low cost. Based on user interactions with the cards, the platform may determine a user's preference for cost. In another example, the platform may determine user preferences for a tradeoff between parameters by presenting cards with two or more parameter values. For example, the user may be presented with one card that represents high cost and low time values. The user may be further presented with another card that represents low cost and high time values. Based on user selection of the cards, the platform may determine the user preferences for tradeoffs between cost and time for a study.

In embodiments, the platform may determine a trial design through one or more processes that may use various graphical interfaces for determining user preferences, user selections, refining results, receiving feedback, and/or the like. In some embodiments, a series of scripts, programs, algorithms, and wizards may analyze data, patterns in the data, user preferences from the data, and/or the like without direct or other use of a graphical user interface. In some embodiments, any combination of data analysis and graphical user interfaces may be used to narrow down a set of trial designs to one or more selected trial designs.

In embodiments, one or more, artificial intelligence algorithms, neural network, statistical analysis, and the like may be used to track user selections, analyze the history of trial design selections to suggest one or more filters and trial designs in view strategic goals, preferences, constraints, and the like.

Figure 40:
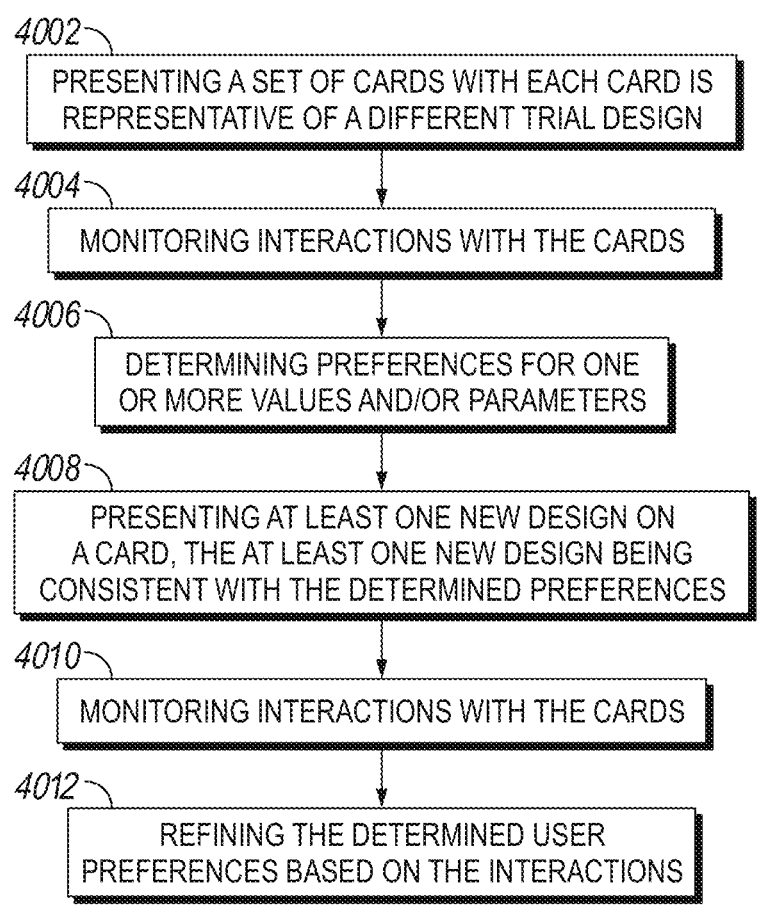
FIG. 40 is a flow chart depicting a method for design analysis using a card interface, in accordance with an embodiment of the current disclosure.

As shown in FIG. 40, a method for evaluating designs with user interactions in a card interface may include presenting a set of cards wherein each card is representative of a different trial design 4002. Each card may include graphics that display one or more parameters associated with the card. The designs represented by the cards may be derived by Pareto analysis, CH analysis, and/or simulated annealing. The designs presented by the cards may be selected at least in part based on filters. In embodiments, filters may be configured by user input to select bounds and/or values on one or more parameters. The method may further include monitoring user interactions with the cards 4004. Interactions may include selecting cards, moving cards, deleting cards, saving cards, changing filters, adjusting filter, and the like. Based on the interactions, the method may determine preferences for one or more values and/or parameters of designs 4006. The method may further include presenting at least one new design based on the determined preferences 4008. The new design may be presented on a new card that is added to the set of cards. The new design may be shown as a replacement for a previously shown design. The method may further include monitoring user interactions with the cards that include the new design 4010. The interactions may be used to refine the determined user preferences 4012. The new interactions, such as for example, a user selecting the new design, may indicate that the parameters of the new design are desirable.

Figure 41:
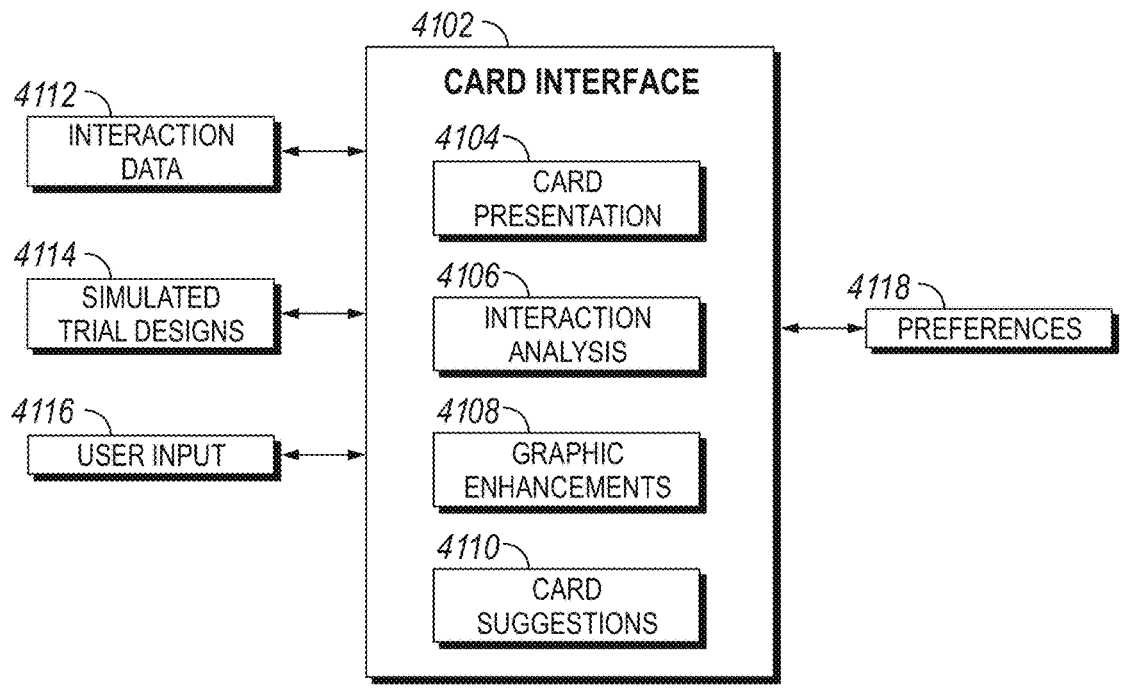
FIG. 41 is a schematic diagram of an apparatus for design analysis using a card interface, in accordance with an embodiment of the current disclosure.

FIG. 41 shows aspects of an apparatus for evaluating design with user interaction using a card interface. The apparatus may include a card interface component 4102. The card interface component 4102 may be part of the interfaces facility 112 of the platform 104. The card interface component 4102 may display and monitor an interactive card interface that enables interactive evaluation of designs. The card interface may include a card presentation component 4104 that may generate a card display for one or more simulated designs 4114. The card presentation component 4104 may identify which values or parameters should be displayed for a design on a card. The card interface component 4102 may include an graphic enhancement component 4108 which may be configured to change the display of one or more aspects of a card to highlight a property, value, rating, ranking, and the like of the design displayed by the card. For example, the highlighting may be relative to other designs shown on the cards. Designs that have a parameter higher than the other designs displayed may have the parameter highlighted on the card of the design. The card interface component 4102 may include an interaction analysis component 4106 configured to monitor user input 4116 with the interface. Interaction analysis component 4106 may be configured to infer one or more preferences 4118 for one or more parameters of the designs based on the interactions. The interaction analysis component 4106 be configured to receive historical interaction data 4112 to identify patterns or trends in previous interactions and preferences to identify how interactions with the present interface relate to preferences. The preferences may be used by the card suggestion component 4110 to identify new designs to be displayed in a card. The new design may be consistent with the determined preferences 4118. In some embodiments the new design may be selected to provide new information about preferences and may not be consistent with the preferences 4118.

Figure 42:
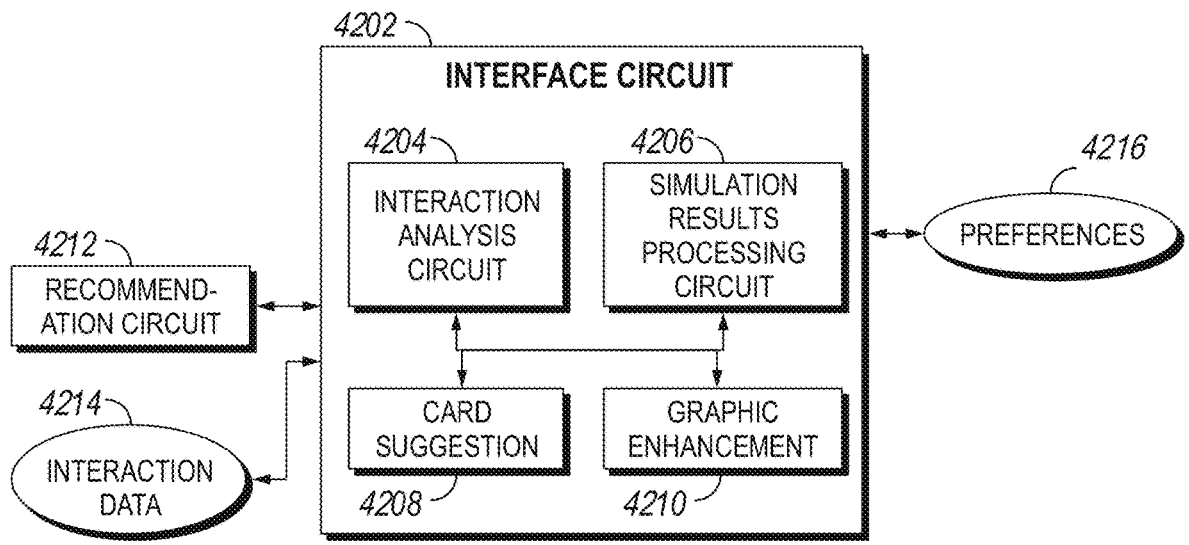
FIG. 42 is a schematic diagram of an apparatus for design analysis using a card interface, in accordance with an embodiment of the current disclosure.

FIG. 42 shows aspects of an apparatus for evaluating design with user interaction using a card interface. In embodiments, the interfaces circuit 4202 may include an interaction analysis circuit 4204 and a simulation results processing circuit 4206. The interaction analysis circuit 4204 may process interaction data 4214 from a user. The interaction data 4214 may relate to user interactions with data and components of an interactive interface. The interface may, during the interaction, display design data in a card interface. The design data may be received from a recommendation circuit 4212. The interface circuit 4202 may further include a suggestion circuit 4208 that may be configured to analyze processed user interaction data from the interaction analysis circuit 4204 and data provided in the interface from the simulation results processing circuit 4206 and determine user preferences 4216 for designs. The interface circuit 4202 may include a graphic enhancement circuit for highlighting or emphasizing one or more parameters or values displayed on the card. The emphasizing may be due to the value being substantially (such as 10% or more) higher or lower than the other designs. The card suggestion circuit 4208 may identify which designs to present using the card interface. The card suggestion circuit 4208 may determine designs based on the determined preferences 4216. The card suggestion circuit 4208 may determine designs to display on the card interface in order to determine new preferences.

In embodiments, the interactive graphical interfaces may include a tornado diagram interface that may be used to evaluate simulated designs. In embodiments, designs may be evaluated for their sensitivity to changes in scenarios and/or other parameters. A tornado chart is a type of sensitivity analysis that provides a graphical representation of the degree to which the result is sensitive to the specified independent variables. Tornado visualization may be configured for viewing trade-offs and obtain answers to what-if questions in real-time. In embodiments, an interactive tornado diagram for sensitivity analysis of promising designs may use categorization of design parameters, including: decision variable vector, scenario vector, performance criteria, and the like. The tornado diagrams may be configured to help in visually analyzing the effect of change in design and scenario vectors on the performance, and to identify the desirable design space combination to have optimum performance criteria values.

Figure 43:
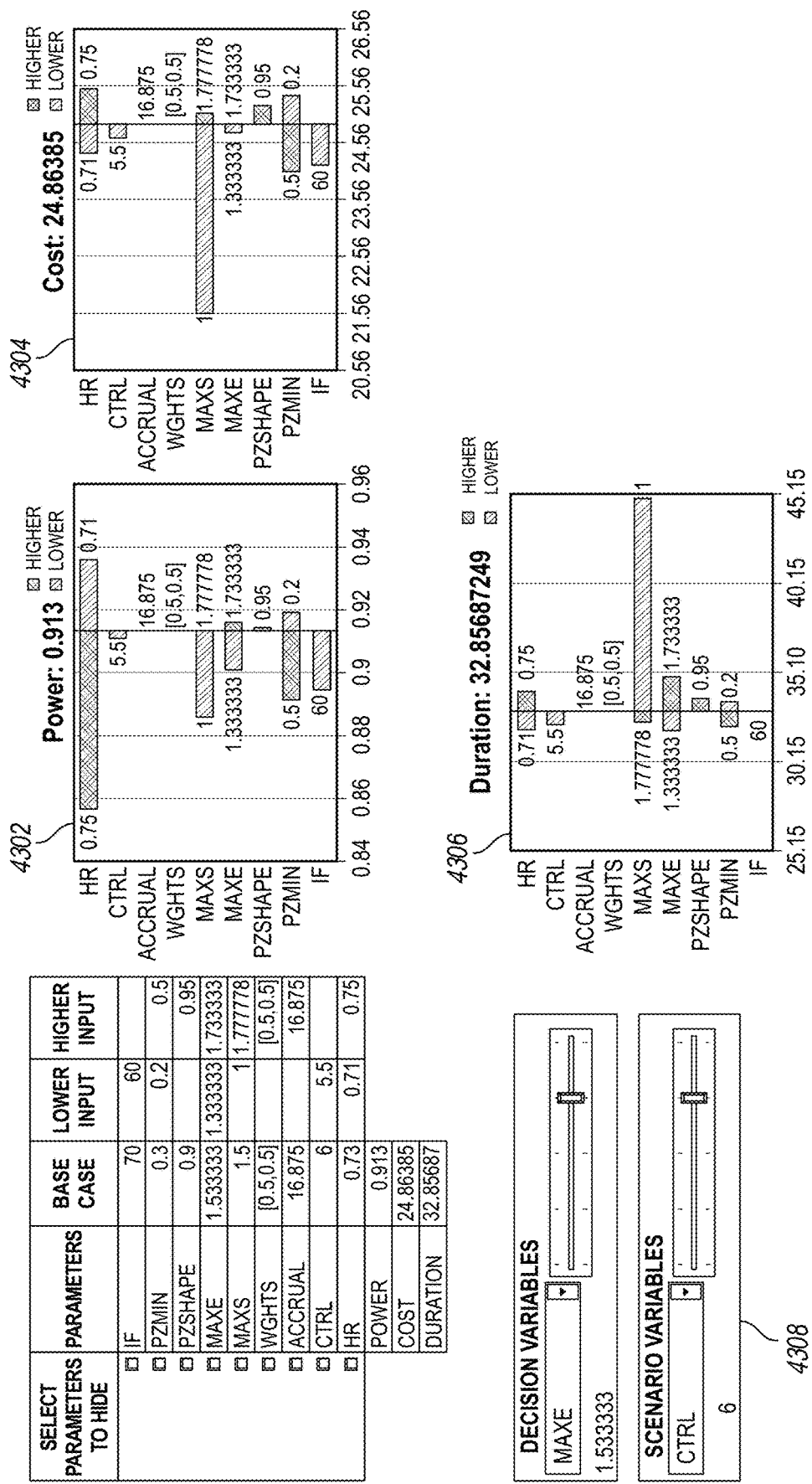
FIG. 43 shows aspects of a tornado interface, in accordance with an embodiment of the current disclosure.

FIG. 43 shows example aspects of a tornado dashboard for evaluating sensitivity of design. In embodiments, the dashboard may include one or more tornado diagrams (three tornado diagrams are shown 4302, 4304, 4306). In embodiments, tornado plots may be used to analyze the sensitivity of designs and decision variables with respect to performance criteria. A set of tornado plots that may be used to assess and compare the sensitivity of various designs and decision variables. In embodiments, an interface may be presented to a user allowing comparison of sensitivity designs and variables with respect to two or more performance criteria. In some embodiments, input elements 4308, such as slides, text boxes, checkboxes, and the like, may be provided to change values of variables and options that are shown in the plots.

In embodiments, the interactive graphical interfaces may include a heatmap interface that may be used to evaluate simulated designs. A heatmap interface may show a magnitude of a performance parameters for different designs using colors and shading. The heatmap may be arranged in a grid or a matrix. The heatmap may be arranged such that one dimension may list designs while the other dimension may list parameters. In embodiments, the heatmaps may be clustered heatmaps where the parameters may be clustered according to different criteria.

A heatmap provides an interface to quickly visually compare, evaluate, and select designs. In embodiments a heatmap may provide for tens, hundreds, or even thousands of different designs with respect to tens, hundreds, or even thousands of different parameters or scenarios. In embodiments, a heatmap may be configured or configurable to show different relations and allow a user to compare and evaluate different designs against different parameters and/or scenarios. In embodiments, a heatmap may be configured or configurable to show different parameters for the designs. The heatmap elements may be filtered according to one or more filters. In embodiments, the elements may be reordered based on one or more criteria. Users may zoom or select a subsection of a heatmap.

In embodiments, users may evaluate designs by changing views of a heatmap or showing more than one heatmaps with different configurations. In embodiments, users may mark one or more designs in one heatmap or one configuration of a heatmap. The marking of a design in one heatmap or one configuration of a heatmap may be propagated to other heatmaps or configurations of heatmaps with the same design. The selected design may be highlighted or emphasized (such as a darker border, a different color of border, a flickering of colors, and the like) as a heatmap is reconfigured to show the selected design. In embodiments, a two or more designs may be selected and tracked between different heatmaps or heatmap configurations.

In embodiments, heatmaps may provide an option to display or emphasize optimal designs, Pareto designs, CH-designs, and/or other recommended designs. The designs may be highlighted and/or emphasized to show their location in the heatmap and may show animations or other indicators to show changes in locations of the designs in the heatmap when a heatmap is reconfigured. Designs and/or cells that are highlighted or emphasized may be deselected, dismissed, flagged, marked, and the like by the user. Designs that are dismissed may be deemphasized and no longer tracked in the heatmap. User interactions with the heatmap may be tracked to identify user preferences for designs. In some embodiments, a user may identify regions of the heatmap (such as by drawing or indicating an area such as a circle, square, or other shape) to indicate an area of interest or to indicate an area that does not include relevant designs. The areas that are indicated to not have designs may be filtered from the heatmap. Areas that are indicated as areas of interest may trigger additional simulations. For example, marking an area as an area of interest may trigger simulated annealing analysis to identify other designs that may be similar to those in the area of interest. In embodiments, selections of elements in the heatmap may trigger automatic updates to definitions of the criteria space, design space, scenario space, and/or performance space and may trigger additional simulations and/or additional analysis (such as recomputing P-designs, CH-designs, and the like).

In embodiments, heatmaps may provide features to emphasize some designs. In heatmaps with a large number of designs, the color and/or shading that represents a value of a design with respect to a parameter may have a small area on the interface. The small area of the color may make it difficult to distinguish the value represented by the color from nearby or neighboring colors. In some embodiments, the heatmap interface may identify cells that may be of interest to a user (such as representative of a high or desirable value) but may not be clearly visible due to small size or the colors of neighboring cells. In embodiments the cells may be emphasized with changing colors, flickering, distinguished borders, or other effects to distinguish the cell from surrounding cells.

Figure 44:
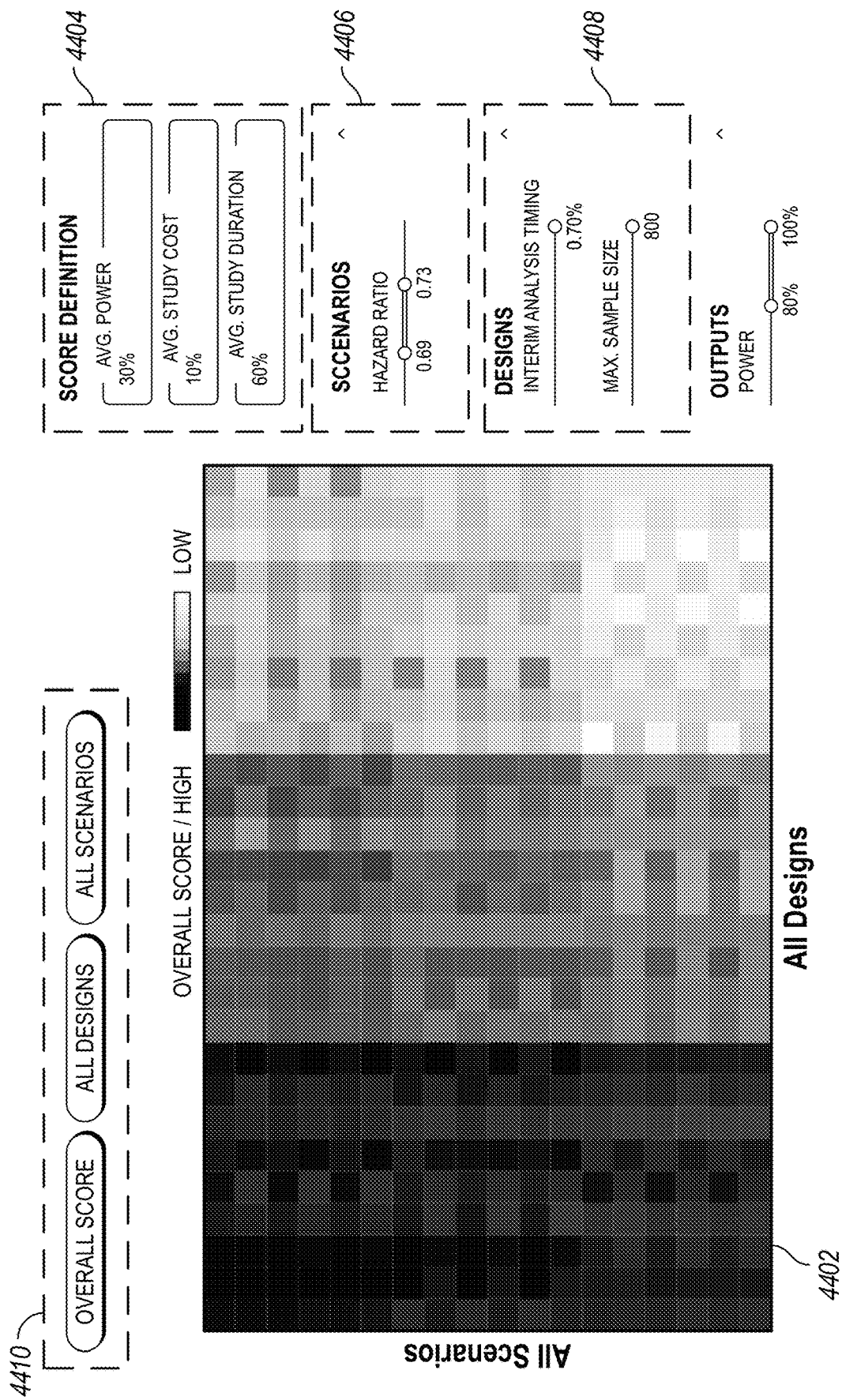
FIG. 44 shows aspects of a heatmap interface, in accordance with an embodiment of the current disclosure.

FIG. 44 shows aspects of a heatmap. A heatmap 4402 may be displayed as a grid of cells. The rows of the grid may correspond to different designs and the columns may be representative of different scenarios. Each cell may be colored or shaded to be representative of a value (such as a score) of the design for a scenario. The configuration of heatmap may be changed by changing aspects of the score, aspects of what designs and scenarios are represented, the ordering of the designs and scenarios, and the like. The score shown for each cell may be configured in a score definition part of the interface 4404. The score definition part 4404 may provide for a configuration of the weights used for computing the score and/or the parameters used to calculate the score. The interface may include components to filter scenarios 4406 and components to filter designs 4408. The interface may include options 4410 to configure the heatmap for displaying different aspects such as what score is shown, which design and scenarios are shown. The component 4410 may include preset options for filtering and configuring the heatmap. In embodiments, users may mark one or more cells in the heatmap. The marked heatmaps may be visually emphasized and may be tracked as the heatmap is reconfigured.

In embodiments, the interactive graphical interfaces may include a tradeoff advisor. A tradeoff advisor may include a graphical interface may provide one or more displays for selecting data for comparison and graphing. The tradeoff advisor may provide a display of heatmaps, scatter plots, tornado plots, and other graphs for visualizing relationships between aspects of the designs. In embodiments, relationships between strategic goals, variables, parameters, values, and the like may be automatically determined for a set of simulated trial options. In some cases, users may choose to select a parameter and/or strategic goal, and the platform may determine two (2) or three (3) or more variables and/or parameters that have the biggest impact on the selected parameter and/or strategic goals. The platform may generate one or more graphs showing the relationship between the parameters. For example, a user may select one output of interest (duration, cost, eNPV, probability of success, etc.). The platform may use sensitivity analysis to automatically put the two (2) or three (3) biggest drivers for that output on the two (2) or three (3) axes for a display chart. In embodiments, a user may select to show parameters or variables that have the biggest impact, lower impact, average impact, variable impact, and the like. The relationships may be used to set filters, rank importance of variables or parameters, and the like.

In embodiments, interactive interfaces (such as the card interface, heatmap interface, tornado interface and the like described herein) may be used to evaluate and configure parameters and/or criteria before simulation. Parameters and values of the parameters for design space, scenario space, criteria space, and/or performance space may be displayed using one or more interactive interfaces. Interactions may be received to configure one or more of the spaces. For example, heatmaps may be used to visualize scenario parameter values that have been determined for simulation. Regions in the heatmap may be identified using the interface to exclude some scenarios. In some cases regions in interest in the heatmaps may be identified to add additional parameters or ranges of values to the spaces.

In embodiments, interactive interfaces may include reporting and alert features. In embodiments, outputs of interfaces may be provided in report format for users. In embodiments, reports may be automatically generated and stored for documentation of design and analysis methodologies. In embodiments reporting may be based on the types and/or number of interactions observed. In some cases reporting may provide a summary of how interactions were interpreted and used to determine preferences and/or recommended designs.

Figure 45:
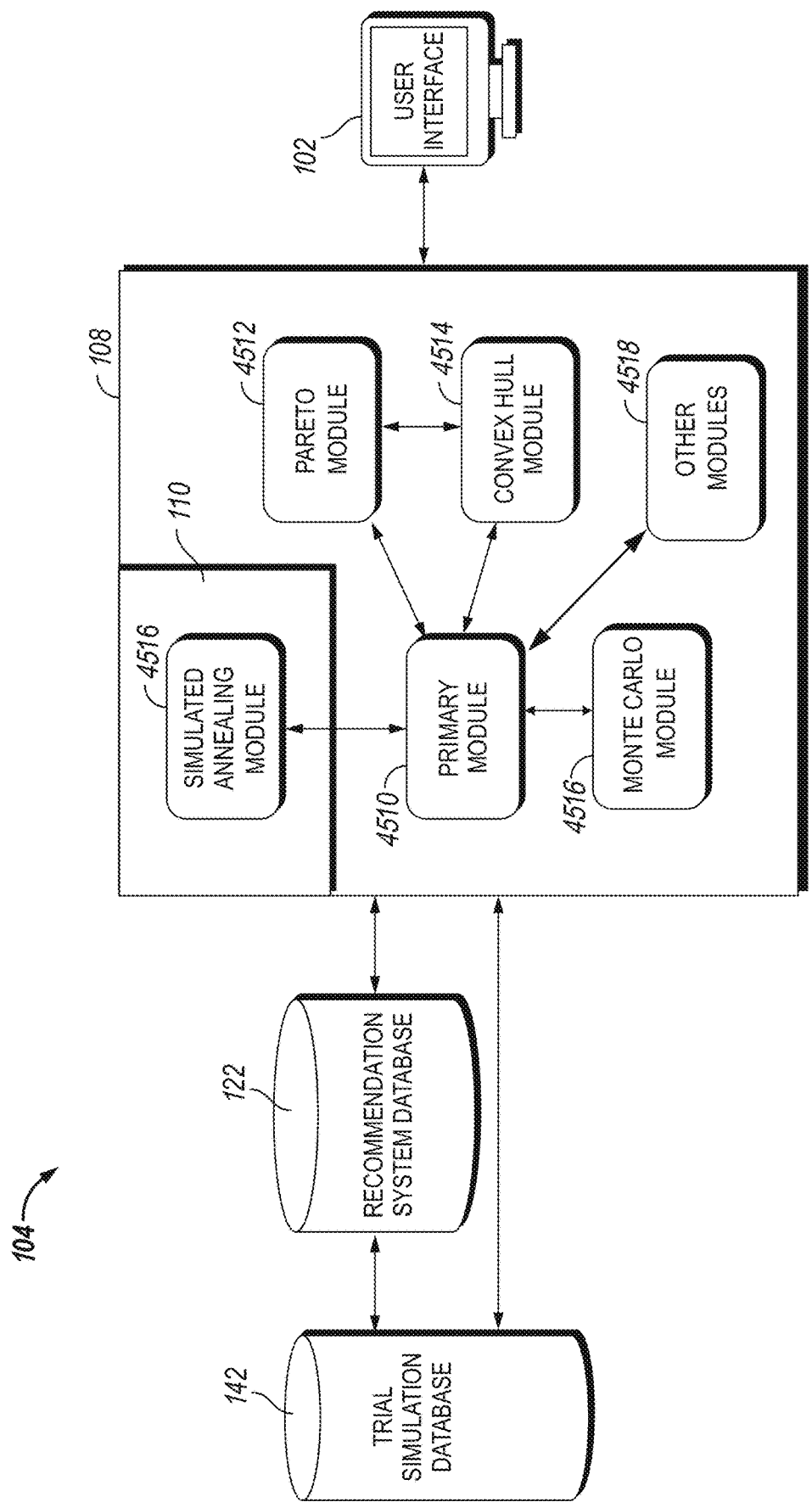
FIG. 45 is a schematic diagram of an embodiment of the platform 104 having a primary algorithm, in accordance with the current disclosure.

Referring now to FIG. 45, an embodiment of the architecture/analysis platform 104 (also shown in FIG. 1) is depicted. The platform 104 may include a primary algorithm 4510 that controls and/or monitors the workflow of the platform 104, e.g., queuing (ordering), cueing (invoking), starting and/or stopping execution of one or more algorithms and/or engines; procurement of inputs; delivery of outputs, performance, progress updates; and/or the like. While FIG. 45 depicts the primary algorithm 4510 as being within the analysis facility 108, it is to be understood that, in embodiments, the primary algorithm 4510 may form part of, extend, and/or have access to one or more other components of the platform 104, e.g., the configuration facility 106, simulation facility 110, interface facility 112, data facility 138, computing resources 150, and/or the like. In certain aspects, the primary algorithm 4510 may interface with other algorithms/engines/modules and techniques such as simulated annealing 4516 modules, Pareto modules 4512, convex hull modules 4514, Monte Carlo modules 4516, visualization tools/engines, recommendation algorithms/engines, and/or the like 4518. As described in greater detail herein, embodiments of the primary algorithm 4510 may structure and/or control the flow of data through the platform 104. Data flow through the platform 104 may be facilitated by data records that are stored and retrieved from one or more databases in data facility 138. In other words, embodiments of the primary algorithm 4510 may provide for a configuration of the platform 104, also referred to herein as a platform configuration. A data record may include one or more variable types, e.g., string, integer, long, scalar, etc., in rows and columns. Data records may conform to a relational schema so that several data records collectively represent a higher-level data object. As used herein with respect to the platform 104, the terms "configuration" and "platform configuration" include the arrangement, sequencing, and/or manipulation of one or more components of the platform 104, e.g., sequencing of models and/or engines, sequencing and/or configuration of algorithms, control of data flow and/or the like. In certain aspects, the platform configuration may be based on data analysis, user inputs, and/or the like.

Figure 46:
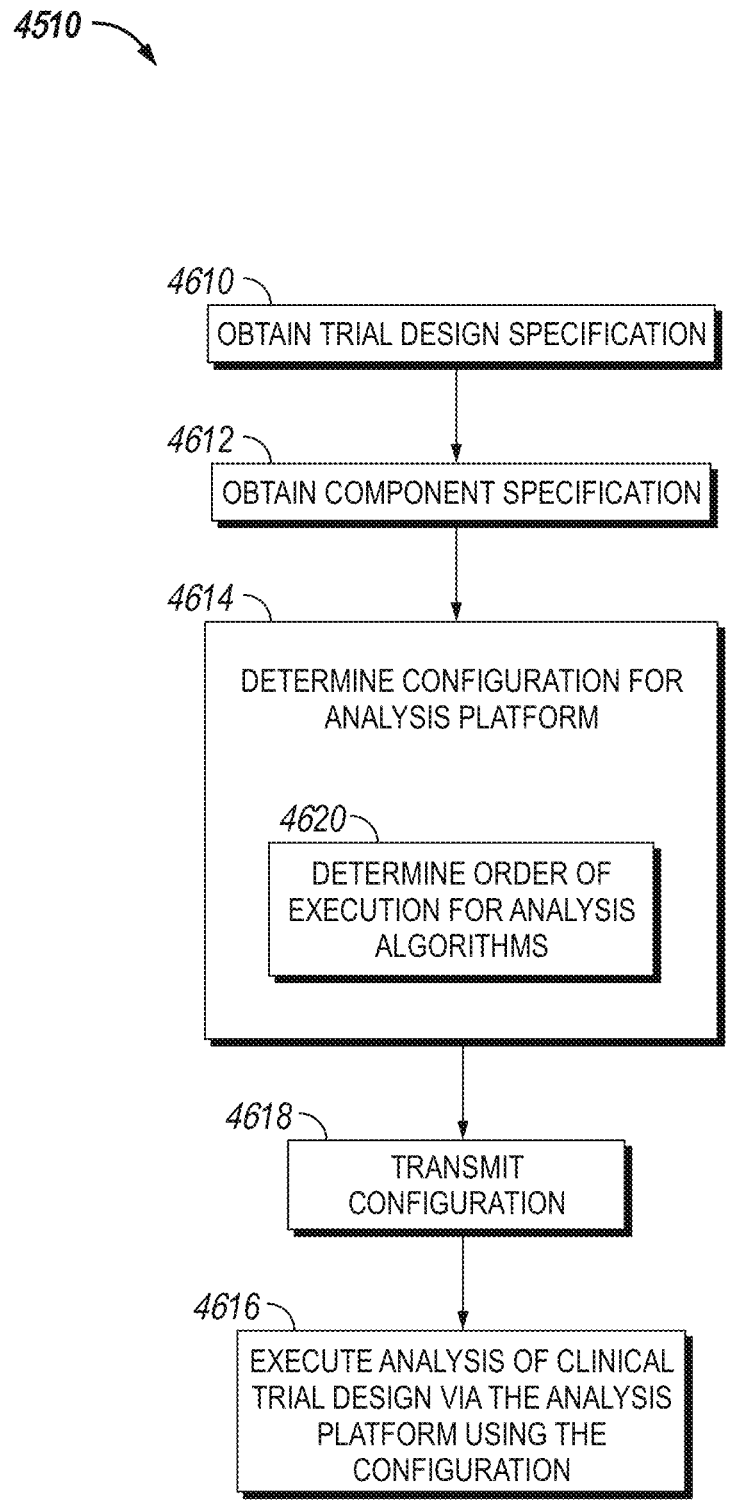
FIG. 46 is a flow chart depicting a workflow of the primary algorithm of FIG. 45, in accordance with an embodiment of the current disclosure.

For example, FIG. 46 depicts a method/workflow execution control structure of an embodiment of the primary algorithm 4510. The primary algorithm 4510 may include obtaining a trial design specification for a clinical trial design 4610 and obtaining one or more component specifications for one or more components of the platform 4612. A component specification may include one or more levels of specification. For example, in one level, the component specification may include specific configurations of components such as which algorithms will be used, order of execution, the types and versions of simulation engines, and/or the like. In another level, the component specification may include high-level, and/or generalized, descriptions/objectives that may specify how long a design study should take and/or a cost of performing the design study. In the case of a high-level description, the component specification may be used to automatically, or semi-automatically, identify details of a configuration to achieve the high-level description. For example, based on a high-level specification of a cost, a configuration may limit the number of designs simulated, the number of simulation runs for each design, the fidelity of the simulations, number of analysis algorithms executed, and the like. The one or more components may include an engine, one or more algorithms, models, databases, computing resources, storage resources, and/or any other component of the platform 104 described herein. The algorithms may include Pareto analysis algorithms, convex hull algorithms, simulated annealing algorithms, Monte Carlo algorithms, recommendation algorithms, and/or the like. The trial design specification may include a simulation time, a runtime, a type of analysis, a performance criteria, and/or the like. In embodiments, the trial design specification may include a preference for a number of recommended designs, a type of visual output, a type of interactive interface, and/or the like. The one or more component specifications may include a cost, a runtime, a required resource, a version, and/or the like.

The primary algorithm 4510 may further include determining, based at least in part on the trial design specification and the one or more component specifications, a configuration for the analysis platform 4614. The configuration may be a data file and/or other type of data structure that defines various aspects of the platform 104, e.g., sequencing and/or type of algorithms, location of inputs, and/or any other type of configurable property of the platform 104 described herein. For example, in embodiments, the configuration may call for filtering simulated trial designs by first applying a Pareto algorithm followed by applying a convex hull algorithm. The configuration may then call for the results of the convex hull algorithm to be assessed via simulated annealing to detect if the current results are a local maxima or minima with respect to the desired performance criteria. In embodiments, the primary algorithm 4510 may include executing an analysis of the clinical trial design 4616 via the analysis platform 104, as described herein, using the configuration. As further shown in FIG. 45, in certain aspects, the primary algorithm 4510 may include transmitting the configuration 4618. Determination of the configuration 4614 may include determining an order of execution for one or more analysis algorithms 4620. In certain aspects, the configuration may be based on historical data and/or derived/predicted via machine learning. For example, artificial intelligence may be used to recognize and/or recommend particular configurations as being suitable for a particular type of clinical trial.

In one example, the primary algorithm may determine a configuration of the analysis platform based in part on the number of designs that are expected to be simulated for a study. The primary algorithm, may, before simulations are executed, analyze the configuration for simulation to determine or estimate the number of designs for which performance parameters will be determined. The number of designs may be estimated based on the number of design/scenario parameters (the number of parameters may correlate to the number of designs that will be simulated), based on the types of simulations scheduled (exhaustive simulations, partial simulations, or based on simulated annealing). The primary algorithm may determine which analysis algorithms should be executed to provide the user with sufficient (not too many) recommended designs. In one instance, if exhaustive simulations are scheduled, the primary algorithm may configure the analysis platform for the convex hull algorithms to reduce the number of design suggestion. In another instance, if partial simulations are scheduled, the primary algorithm may configure the analysis platform for Pareto algorithms in order to provide for a sufficient number of recommended designs.

Figure 47:
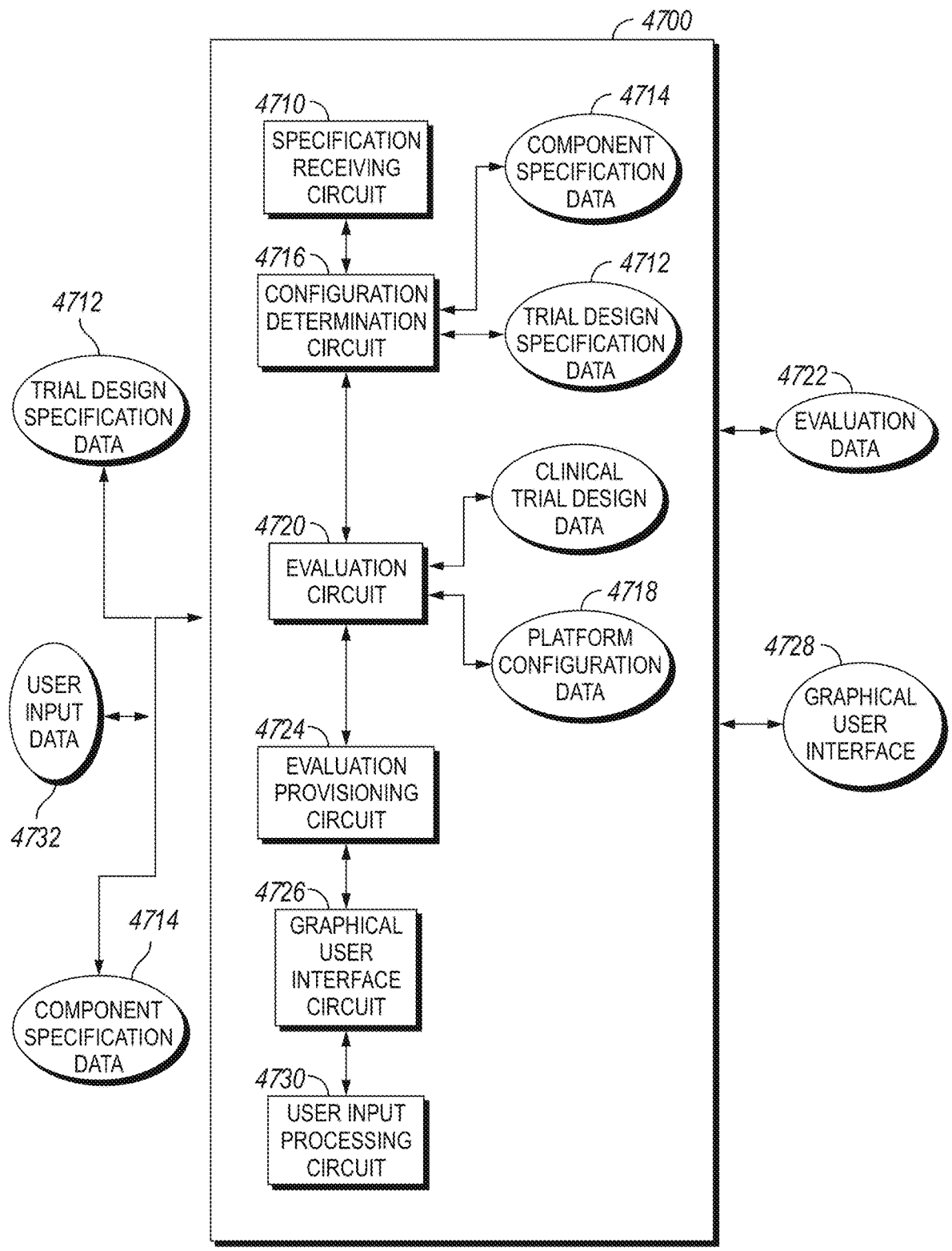
FIG. 47 is a schematic diagram of an apparatus that implements the primary algorithm of FIG. 45, in accordance with an embodiment of the current disclosure.

Turning to FIG. 47, an apparatus 4700 for implementing the primary algorithm 4510 is shown. The apparatus 4700 may be one or more processors, as described herein, that form part one or more servers, e.g., computing resources 150 (FIG. 1). The apparatus 4700 may include a specification receiving circuit 4710 structured to interpret trial design specification data 4712 and one or more component specification data 4714. The apparatus 4700 may further include a configuration determination circuit 4716 structured to generate platform configuration data 4718 based at least in part on the trial design specification data 4712 and the one or more component specification data 4714. The apparatus 4700 may further include an evaluation circuit 4720 structured to analyze the clinical trial design via the analysis platform 104, as described herein. In embodiments, the evaluation circuit 4720 may generate evaluation data 4722 which may be transmitted by the apparatus 4700 via an evaluation data provisioning circuit 4724. The apparatus 4700 may further include a graphical user interface circuit 4726 structured to generate graphical user interface data 4728 configured to provide a graphical user interface. The apparatus 4700 may further include a user input processing circuit 4730 structured to interpret user input data 4732.

In certain aspects, the apparatus 4700 may provide for results and/or intermediate data of the analysis of one or more clinical trials to be transmitted and/or accessed by a user interface (which may be provided by the graphical user interface circuit 4726) for review, analysis, visualization, and manipulation. The user interface may receive user input data 4732 for design selections, parameters, and/or the like. The apparatus 4700 may provide an interface (which may be provided by the graphical user interface circuit 4726) for interacting with external tools and/or engines for simulation and/or analysis. In some embodiments, the apparatus 4700 may record and/or track the processes and/or inputs for a session and/or design study. The apparatus 4700 may track the sequence of steps and/or algorithms/engines used for the analysis of data and may further record and/or track user selections and/or actions. The apparatus 4700 may analyze recorded sequences of processes, user actions, and/or selections to learn from past actions and results to determine the most appropriate (i.e., the fastest, the most accurate, etc.) sequence of algorithms for providing user recommendations. In embodiments, the apparatus may learn via artificial intelligence, e.g., a neural network, as disclosed herein. In embodiments, the primary algorithm 4510 may facilitate communication between any two or more of the algorithms described herein. For example, the platform may track and record which platform configurations resulted in a faster design consensus. The platform may track which platform configuration and which combination of analysis configuration resulted in less time between when designs were presented/recommended to a user and when a final design was selected. Faster time for selection may be indicative that the platform provided the user with recommended designs that were acceptable since the user spent less time considering other options or performing additional simulations and/or analysis. The system configuration that was related to faster consensus may be tagged as more favorable. Based on the tags, the platform may analyze a configuration of simulation configurations and analysis configurations.

In embodiments, analysis of design options may include a Pareto analysis. A Pareto optimal analysis may be used for algorithmic generation of design recommendations. Pareto analysis may be used to determine one or more Pareto optimal designs (also referred herein as "Pareto designs" or "P-designs"). Initial selections of a set of candidates for best or optimal designs may be selected using a Pareto frontier that is generated by the Pareto designs.

Pareto analysis may identify designs that are Pareto optimal for the one or more performance parameters. Pareto optimal designs may be designs where no individual performance parameter can be better off without making at least one other individual performance parameter worse off. The set of Pareto optimal designs may form a Pareto frontier. Pareto optimality may be used as an optimality criteria.

Referring again to FIG. 1, the filtering component 120 (FIG. 1) may include Pareto analysis. The filtering component 120 may include circuits, components, and algorithms for enabling Pareto analysis. The filtering component 120 may receive simulation data from the simulation facility 110 and analyze the simulated data to identify one or more designs using Pareto analysis techniques. The identified designs may be recommended to a user.

Figure 48:
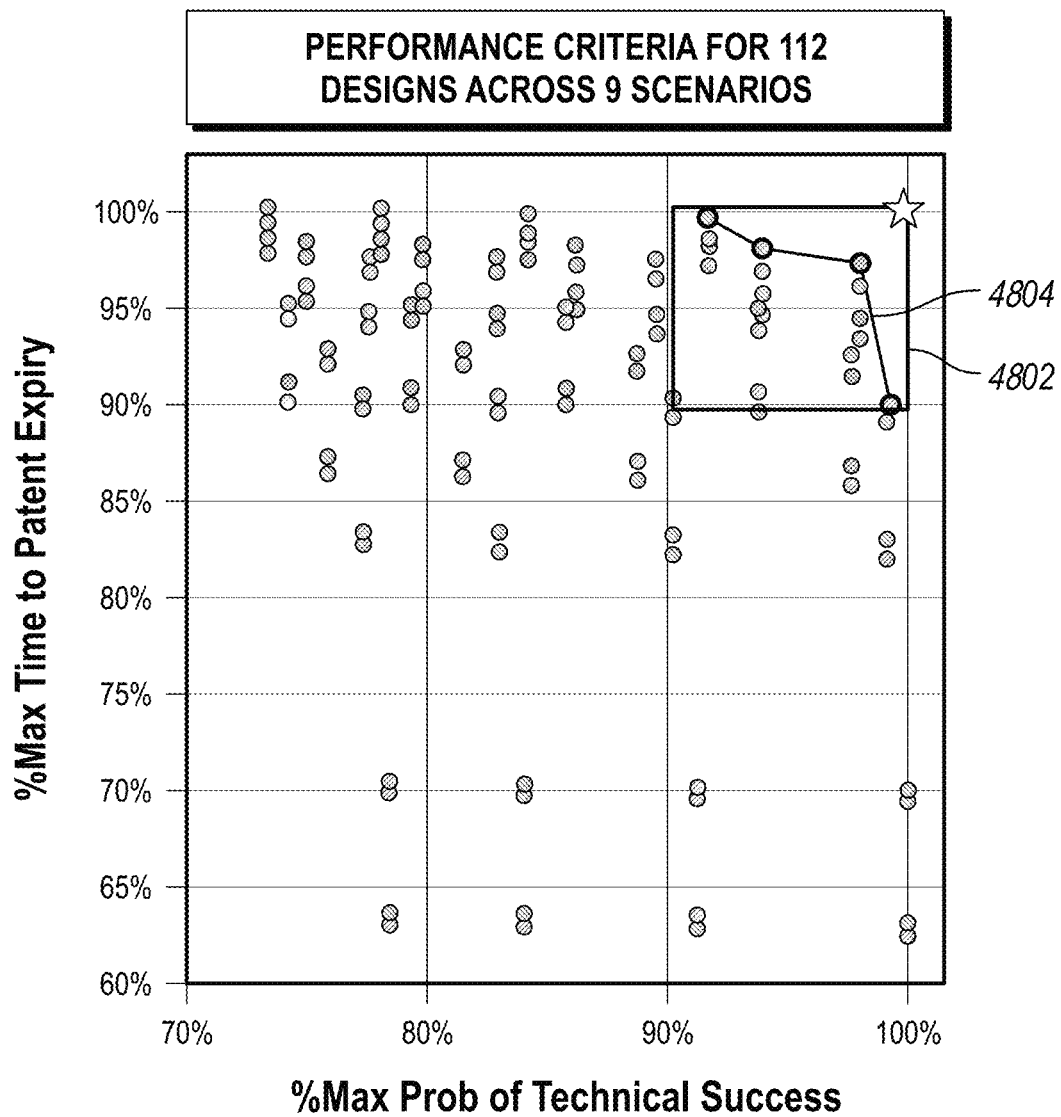
FIG. 48 is a graph showing aspects of Pareto analysis in accordance with an embodiment of the current disclosure.

FIG. 48 shows a graphical representation of aspects of Pareto analysis. FIG. 48 further shows a graph with points wherein each point corresponds to a trial design. The graph shows the performance of each trial design with respect to two trial design parameters (e.g., maximum probability of technical success and maximum time to patent expiry) that may have been determined by simulation. As depicted in 48, it may be the case that the higher the number of the parameter, the more desirable the parameter is. Points in the top right quadrant (represented by box 4802) of the graphs may relate to designs having more desirable performance parameter values. In the illustrated example, Pareto analysis is used to determine Pareto optimum designs in the top right quadrant 4802. As further shown, the Pareto designs are connected by a line that is the Pareto frontier 4804. As will be appreciated, the Pareto designs represent designs where no individual performance parameter can be better off without making at least one other individual performance parameter worse off.

The Pareto frontier may be computed for a subset of all the trial designs. In some cases, the Pareto frontier may be computed for trial designs that have at least a threshold value for one or more performance parameters. In the example of FIG. 48, the Pareto frontier is determined only for the trial designs that are in the top right section/quadrant 4802 of the graph and relate to a threshold of at least 90% in both the two performance parameters considered. The thresholds may be based on the goals considered, may be set by a user, algorithmically determined, and/or the like. FIG. 48 also shows trial designs that do not meet the 90% threshold for the two performance parameters are omitted from consideration, and a Pareto frontier is determined only for the designs that meet the thresholds.

In embodiments, the Pareto designs (and, hence, the Pareto frontier) may be determined using various methods such as, but not limited to, a scalarization algorithm, a skyline query, weighted sums, and/or the like.

In embodiments, Pareto designs may be identified as globally optimum designs and the Pareto designs may be recommended to a user. In some embodiments, Pareto designs may be identified as initial globally optimum designs and they may be used to refine the optimality criteria to identify other globally optimum designs for the new criteria. In some embodiments, interactive methods can be used in which a person, or an alternate algorithm, acts as a decision-maker and interacts with the method to indicate a preference for designs (such as preference among initial Pareto designs). In such embodiments, the method may use the preference information to determine other trial designs (and modify optimality criteria) based on the preference of designs. In embodiments, the Pareto designs can be used to elicit the user's preferences by interactively querying the user to make comparisons between designs.

Trial designs that are on or near the Pareto frontier may be selected as initial choices for evaluation by a user. One or more of the designs may be presented to a user to evaluate and provide feedback. Feedback may include data related to acceptance of a trial design, rejection of a trial design, identification of one or more parameters or features of a trial design, and/or the like. In embodiments, the one or more trial designs from the Pareto frontier may be presented to a user using cards, tornado diagrams, heatmaps, and/or other similar interfaces as described herein.

In some cases, the platform may receive feedback, e.g., user feedback, regarding recommended Pareto designs. Based on the feedback, optimality criteria may be changed. Changes in optimality criteria may include eliminating designs from consideration. When designs are eliminated from considerations, a Pareto analysis may be performed on the remaining designs which may result in new Pareto designs. In some cases, a change in optimality criteria may include a new and/or modified criteria that provides for a "second best" Pareto frontier to be computed. A "second best" Pareto frontier may include designs that are Pareto optimal when the initial Pareto designs are eliminated. The second best Pareto designs may represent a second "level" of a Pareto frontier. In some cases, multiple "levels" of Pareto frontiers may be computed. In some cases, recommendations to users may include designs from the second best Pareto frontier and/or other levels, e.g., "third best", "fourth best", etc. Recommendations to designs in other levels may identify other design types that may be preferrable. Recommendations to designs in other levels may identify design that are more robust than designs in the first level and may be more desirable due to their robustness even if they have worse performance with respect to other performance parameters. In embodiments, interfaces such as tornado diagrams, card interfaces, heatmaps, and the like (including as described herein) may be used to evaluate initial recommendations determined using initial optimality criteria. Received feedback regarding the designs may be used to refine recommendations and optimality criteria used to determine globally optimum designs.

In embodiments, the optimality criteria may be modified according to the number of Pareto designs that are identified. Pareto designs may sometimes cluster. Some Pareto designs may be very close to other Pareto designs. Differences in the designs may be small and/or within the expected simulation error of the designs. In some cases, the Pareto designs which are close together may be filtered or grouped together. In some cases, a first Pareto design may be used to temporarily represent one or more other Pareto designs that are close to the first Pareto design to reduce the number of Pareto designs that are considered.

Pareto analysis may be configured to separate Pareto designs that are twins (designs that have equal or nearly equal performance parameters or observables such as cost, power, and/or time, twins may be designs that are within simulation error for example) and/or siblings (designs that are similar with respect to performance parameters or observables). In some cases, similarity for twin and/or sibling determination may be based on thresholds, such as designs that are within an $\varepsilon$-box of each other. In embodiments, one or more first designs may be considered within an $\varepsilon$-box of a second design when the one or more first designs are within a ball of radius $\varepsilon$ from the second design. Designs that are twins or siblings may be flagged or marked for further analysis if they are deemed to have desired performance as the twins or siblings may represent different design options that can be used to achieve similar performance criteria.

In embodiments, the Pareto analysis may further identify dominated designs. Dominated designs may be designs that are dominated by one or more other Pareto designs. Dominating Pareto designs may be better for one or more of the dominated designs for one or more design criteria. From the dominated designs, Pareto analysis may identify designs that are clustered by the dominating Pareto designs. The designs that are clustered may be identified using $\varepsilon$-criteria. The $\varepsilon$-criteria may be a threshold as to how far the dominated designs may be from the dominating Pareto designs to be included in the set of clustered designs. The $\varepsilon$-criteria may be a measure as to how similar designs should be to be clustered together. The threshold and similarity measures may be directed to the performance parameters of each design, such as the cost, duration, etc., of each design. For example, for performance parameter p, a design may be within $\varepsilon$-criteria if a design is within $p\pm\varepsilon$.

Pareto designs may be filtered or grouped, and one or more other Pareto designs that are within $\varepsilon$ of another Pareto design may be represented by one Pareto design. In other words, a dominating Pareto design may represent one or more dominated Pareto designs. In one example, the set of Pareto designs may be filtered to a smaller set of $\varepsilon$-filtered designs. The size of the set of $\varepsilon$-filtered designs may be adjusted, e.g., made larger or smaller, by selecting the value of $\varepsilon$. In some cases, $\varepsilon$ may be selected to be about 0.001, and/or about 0.055, and/or about 0.15. The $\varepsilon$-filtered designs may remove designs that are within $\varepsilon$-distance of another design. In some cases, the $\varepsilon$ may be selected such that the number of $\varepsilon$-filtered designs is less than a predetermined and/or desired number such as one hundred (100), ten (10), or less than ten (<10). The $\varepsilon$-filtering may be performed with respect to performance parameters, design parameters, scenario parameters, and the like. In embodiments, $\varepsilon$-filtering may reduce the number of designs recommended to a user, and may increase the range or variety of designs that are recommended to a user by eliminating designs that are close to one another. In embodiments, ε-filtering may reduce clutter on a user interface and/or the number of computations performed.

In some embodiments, ε-filtered designs may be recommended and/or evaluated by a user to determine if the set includes designs with design criteria that are desirable. When a design from the ε-filtered designs is selected, the Pareto designs that were ε-filtered may be provided to the user for further evaluation. The ε-filtered designs may have similar design criteria to the selected design but may relate to different types of designs. The user may evaluate different design types and design options that are within ε of the desired/selected design criteria.

Pareto analysis often requires new configurations and considerations when applied to clinical trial design optimization. In one aspect, clinical trial simulation (CTS) data is usually different from data in other applications. For example, in many other applications, points in criterion space are continuous or form a lattice while, in the current application, points correspond to discrete designs. In many other applications, there may be a very large number of points on the Pareto frontier and the focus may be to produce a handful of well spread out points on the Pareto frontier for a decision-maker to study closely to determine and/or select the best solution. CTS data, on the other hand, is typically highly clustered in certain regions of criterion space with substantial parts of the space being empty due to practical limits and constraints, e.g., continuous adaptation after each subject) and/or due to there being a handful of design types for a particular trial (fixed SS, SSR, Group Sequential, tailored innovative designs and the like).

Pareto analysis for the clinical trial optimization applications may be designed to cluster dominated designs into Pareto clusters and provide an input consisting of only Pareto designs to convex hull algorithms in preparation for creating convex hull clusters with a simple geometrical structure in the criterion space. Additional unique aspects, of some embodiments, include a focus on interactive clinical trial simulations linked with visualizations of performance criteria space, design factors space, and/or scenarios. Links between Pareto designs and close but dominated designs may be generated as a byproduct of finding the Pareto set. Dominated designs may be preferred for qualitative reasons (e.g., complexity in trial execution, sensitivity to extreme downside scenarios). Pareto points that are close to other points may be automatically suppressed in a corresponding visualization (e.g., because they are unimportant due to being in the area within the margin of model error). Dominated designs can be unmasked when needed (e.g., when the designs are qualitatively different). Hierarchical level two (2), level three (3), etc. Pareto sets may be generated by rerunning the analysis. In embodiments, the analysis may accommodate constraints on design parameters, and dynamically updating the Pareto set by removing designs, adding new designs and scenarios, and/or changing prior probabilities of scenarios. In embodiments, the analysis may be applied in stages to first find Pareto points in clusters of similar design sets (e.g., changes of one parameter change, qualitatively different). In embodiments, the analysis may be useful for gaining insight into design improvements. In embodiments, clustering points in design space distances are natural and may be efficient for users to gain insights. In embodiments, the analysis may be integrated with a simulated annealing engine that uses weights and/or target criteria points in unexplored regions.

Pareto analysis may provide for organization and/or analysis of data that is comprehensible and/or provides for a focus to designs that are optimal or near-optimal. The Pareto analysis may determine the hierarchies of design sets for consideration. In embodiments, one set in the hierarchy may be ε-filtered Pareto designs, another may be all Pareto designs, and/or another hierarchy may be designs that are within ε of the Pareto designs. The design space may be explored using the hierarchies to find designs that have the desired criteria and further to find designs that achieve the desired criteria with desired or acceptable design types.

In embodiments, Pareto analysis may be a two-pass analysis. In the first pass, the simulation records (e.g., summary records) may be sorted by maximum and/or minimum values of the performance parameters. Various sorting algorithms (including those described herein) may be used. In the second pass, after the records are sorted, each record may be compared with all the records that follow in the ordered set to identify which records are ε-dominated by the record. After the second pass, the algorithm may provide a set of Pareto designs which are not ε-dominated by any other design and/or Pareto clusters of dominated designs linked to one-or-more Pareto designs. If ε=0 for all performance criteria, then the full set of Pareto designs may be produced. If ε>0 for some performance criteria, then the set of t-filtered Pareto designs may be produced, which is a subset of the full set of Pareto designs since some of the Pareto designs from the full set may be ε-dominated by other Pareto designs.

FIG. 49 shows aspects of the Pareto analysis using numerical examples. As shown in FIG. 49, each row in the table represents a design with the performance parameter values listed in the columns. In the depicted example, all of the designs are Pareto designs identified by a unique "PSet" number. In the first pass of the algorithm/engine, the P-designs are sorted, and the designs with the highest power, the lowest cost, and the lowest duration are determined (PSet 1, 2, 3, respectively). In the second pass, the top three (3) P-designs (PSet 1, 2, 3) are compared to all remaining designs according to the selected ε for each performance parameters. Based on the values of δ, some of the remaining designs may be classified dominated by one of the first three (3) P-designs. As further shown in the example of FIG. 49, PSet 7, 13, and 19 are determined to be dominated by PSet 1 for the ε values chosen (denoted by "−1" in the EPSet column). The algorithm may proceed to the next Pareto design after all the ε designs for the first Pareto design were determined. The next Pareto design considered may be a design that has not been identified as ε-dominated design. In this example, PSet 2 is next determined to dominate PSet 8, 11, 17, and 20 designs (denoted by "−2" in the EPSet column). The analysis may proceed to iteratively process all the Pareto designs that are not dominated by other designs to determine the set of ε-filtered Pareto designs. In this example, the ε-filtered Pareto designs (designs denoted by positive numbers by the EPSet column) are a subset of the Pareto designs and includes nine (9) designs. The algorithm may be iterated multiple times, and some designs may be dominated by more than one Pareto design.

In embodiments, the ε-filtered Pareto designs may be used for initial recommendations and/or consideration for users. The designs dominated by each ε-filtered design may be further recommended or provided for consideration when a design from the ε-filtered set if selected for further analysis by a user.

In embodiments, the Pareto analysis may be configured to quickly update the identified Pareto designs when new designs are introduced as inputs to the algorithm. The set of identified Pareto designs may be augmented incrementally by the algorithm as new designs are identified/simulated and added to the design space.

Figure 50:
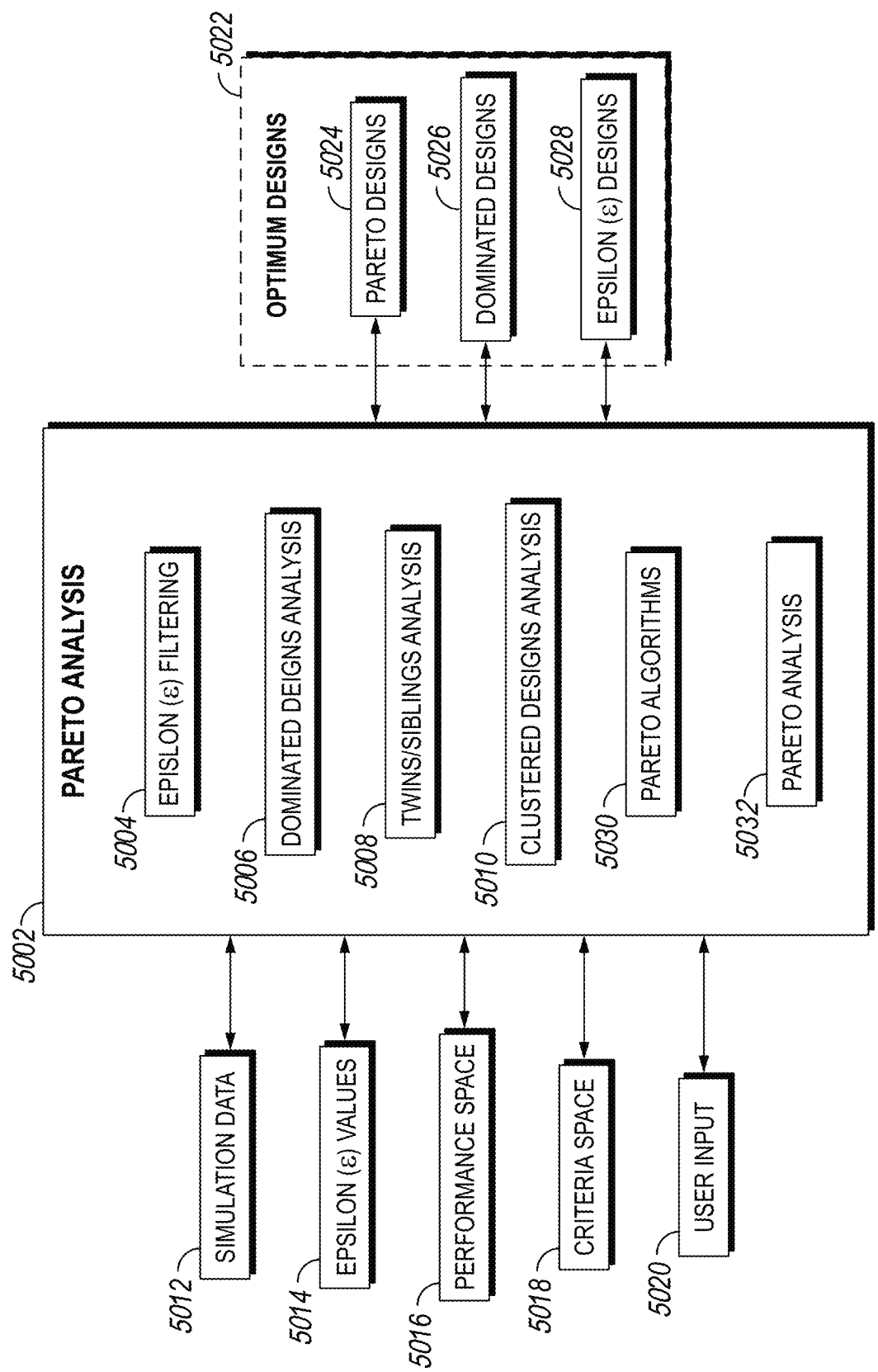
FIG. 50 is a schematic diagram of an apparatus for determining optimum designs using Pareto analysis, in accordance with an embodiment of the current disclosure.

FIG. 50 shows aspects of an apparatus for determining globally optimum designs using Pareto analysis. In embodiments, the Pareto analysis component 5002 may be part of the analysis facility 108 of the platform 104. The Pareto analysis component 5002 may receive data from simulated designs 5012 and determine one or more sets of optimal designs 5022 which may include Pareto designs 5024, dominated designs 5026 (designs that are dominated by Pareto designs), ε designs 5028 (designs that are within a distance ε of Pareto designs). The Pareto analysis component 5002 may include one or more circuits for determining recommended designs. The circuits in the Pareto analysis 5002 may be selectively enabled according to user input 5020, ε values 5014, and other inputs. In embodiments, the Pareto analysis component 5002 may include circuits for determining Pareto optimality using Pareto algorithms 5030. In embodiments, the Pareto analysis component 5002 may include circuits for determining optimality using ε filtering 5004. Epsilon filtering circuit 5004 may determine designs that are within epsilon of Pareto designs. The Pareto analysis component 5002 may include Pareto level analysis circuit 5032. Pareto level analysis circuit 5032 may determine one or different levels of Pareto designs and Pareto frontiers. In embodiments, the Pareto analysis circuit 5002 may include circuits for dominated designs analysis 5006. Dominated designs analysis circuit 5006 may identify designs that are dominated by one or more Pareto designs and filter the designs and/or recommend the designs according to user input 5020 and/or epsilon values 5014. In embodiments, the Pareto analysis circuit 5002 may include circuits for twins/siblings analysis 5008. Twins/siblings analysis circuit 5008 may identify designs that are twins and/or siblings to one or more Pareto designs and filter the designs and/or recommend the designs according to user input 5020. In embodiments, the Pareto analysis circuit 5002 may include circuits for clustered design analysis 5010. Clustered design analysis circuit 5010 may identify designs that are clustered with one or more Pareto designs and filter the designs and/or recommend the designs according to user input 5020.

Figure 51:
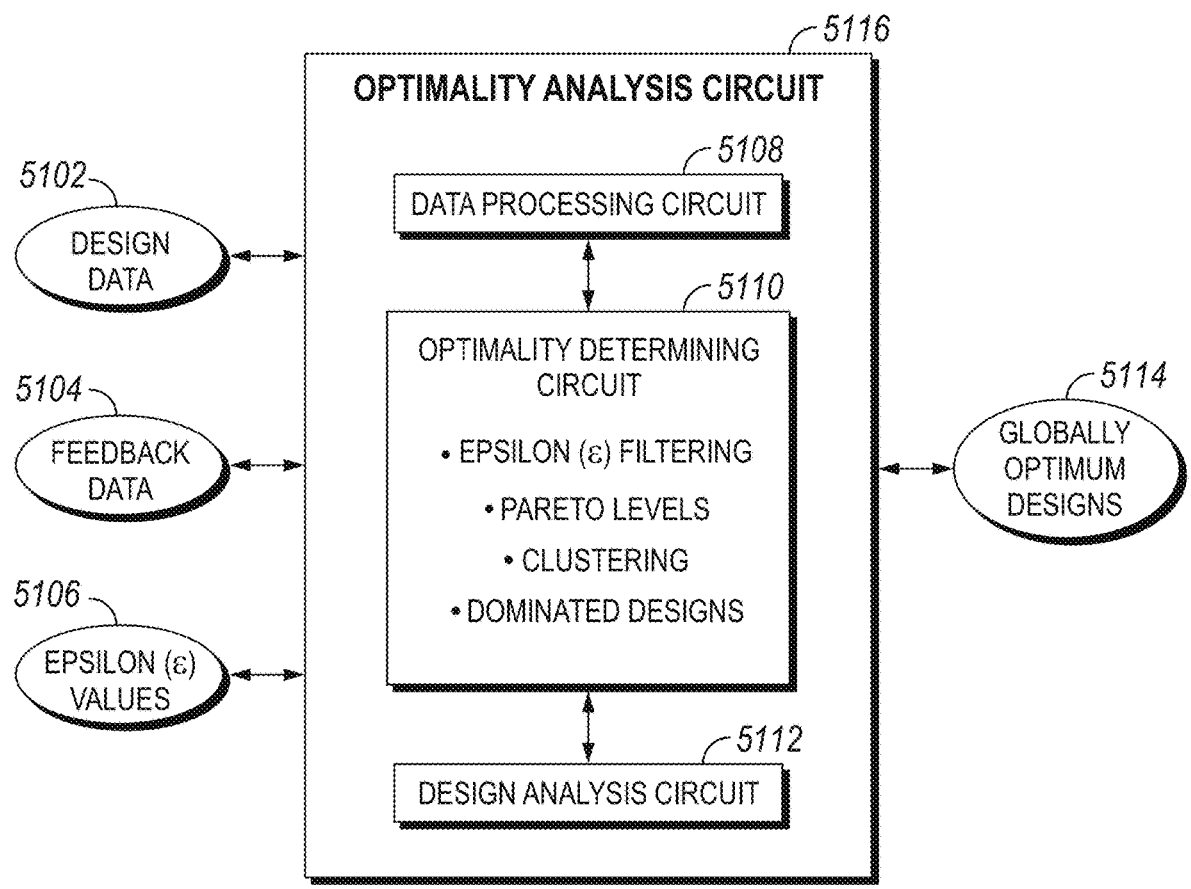
FIG. 51 is a is a schematic diagram of an apparatus for determining optimum designs using Pareto analysis, in accordance with an embodiment of the current disclosure.

FIG. 51 shows aspects of an apparatus for determining global optimality of designs. In embodiments, the apparatus may include an optimality analysis circuit 5116 which may be part of the analysis facility 108 of the platform 104. In embodiments, the apparatus may include a data processing circuit 5108 structured to interpret/obtain design data 5102 of a clinical trial design. In some embodiments the design data 5102 may be outputs of simulation data of trial designs. The output processing circuit 5108 may transform the design data 5102 into a format suitable for use by the various circuits in the apparatus. For example, the design data 5102 may be received by the data processing circuit 5108 and determine and identify performance parameters in the data. In some embodiments, some performance parameters may be grouped, filtered, converted, normalized, and the like.

The apparatus of FIG. 51 may further include an optimality determining circuit 5110 structured to receive processed design data from the data processing circuit 5108. The optimality determining circuit 5110 may identify globally optimum designs 5114 based on Pareto analysis. In some embodiments, the globally optimum designs 5114 may be provided as an output of the apparatus. In some embodiments, globally optimum designs 5114 may be further processed by the design analysis circuit 5112. The design analysis circuit 5112 may analyze the globally optimum designs 5114 and determine characteristics of the designs, receive feedback data 5104 about the designs. The design analysis circuit may, based on the determined characteristics determine modifications for optimality criteria used in the optimality determining circuit 5110. The optimality determining circuit 5110 may modify optimality criteria of Pareto analysis. The modifications may include epsilon filtering of Pareto designs, determining multiple levels of Pareto designs, clustering of Pareto designs, determining dominated Pareto designs, and/or the like. Using modified optimality criteria, the optimality determining circuit 5108 may determine a new set of globally optimum designs 5114.

Figure 52:
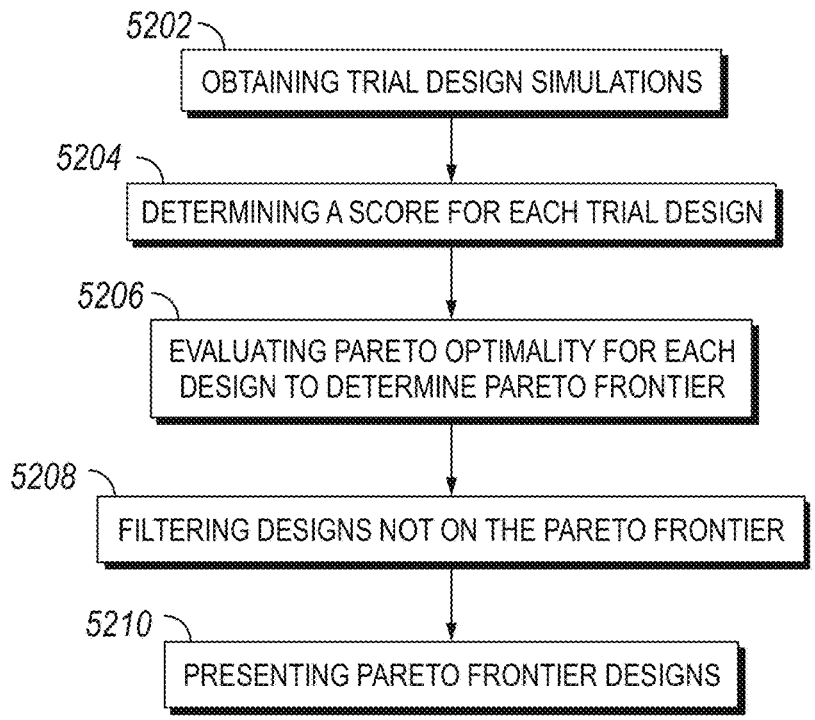
FIG. 52 is a flow chart depicting a method for determining globally optimum designs with Pareto analysis, in accordance with an embodiment of the current disclosure.

As shown in FIG. 52, a method for determining optimum designs using Pareto analysis may include obtaining trial design simulations 5202. The method may further include determining one or more score for each trial design based on the performance parameters 5204. The method may include evaluating Pareto optimality for each design to determine Pareto frontier 5206. Designs not on the Pareto frontier may be filtered 5208. Designs on the Pareto frontier may be presented for further analysis 5210.

Figure 53:
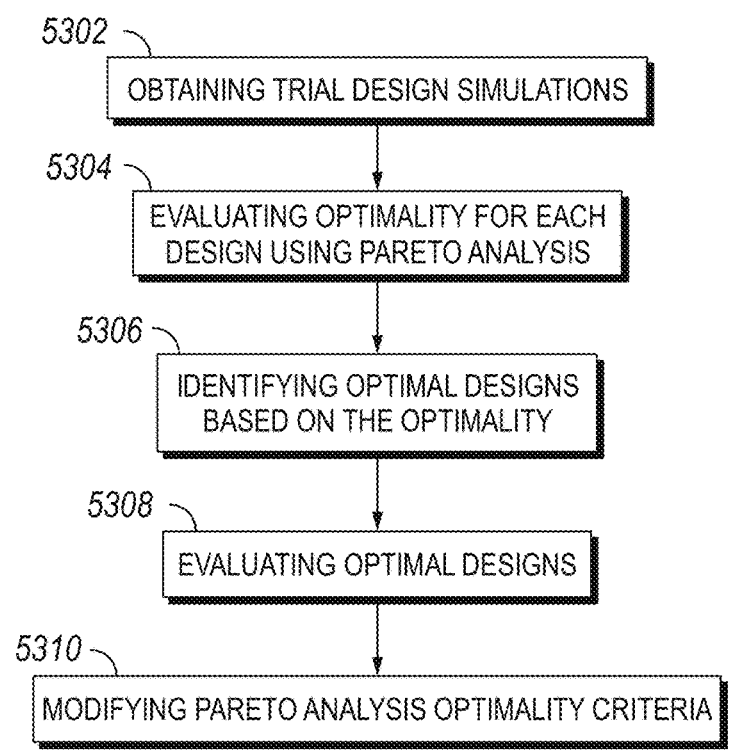
FIG. 53 is a flow chart depicting a method for determining globally optimum designs with Pareto analysis, in accordance with an embodiment of the current disclosure.

As shown in FIG. 53, a method for determining optimum designs using Pareto analysis may include obtaining trial design simulations 5302. The method may further include evaluating optimality for each design using Pareto analysis 5304. The method may include identifying optimal designs based on the Pareto analysis 5306. The optimum designs may be evaluated 5308. Evaluation may include feedback from user, statistical analysis, and the like. Based on the evaluation, the Pareto analysis may be modified 5310. Modifications may include determining epsilon-distance designs, clustering, determining second level Pareto designs, filtering sibling and twin designs, and the like.

In embodiments Pareto analysis includes consideration of performance, design, scenario, and criteria spaces. Pareto optimality is determined with respect to performance parameters of the performance space. The performance parameters may be evaluated using simulation for different designs defined by the design space. Each design in the design space is evaluated for different scenarios of the scenario space. The performance, design, and scenario spaces are defined according to the criteria space definitions.

In embodiments, analysis of design options may include convex hull (CH) analysis. A convex hull analysis may be used for algorithmic generation of design recommendations. Convex hull analysis may be used to determine one or more designs that are on a convex hull (also referred herein as convex hull designs or CH-designs). Initial selections of a set of candidates for best or optimal designs may be selected using a convex hull that is generated with convex hull analysis. Convex hull analysis may determine the smallest convex polygon shape that contains the designs.

Referring again to FIG. 1, the filtering component 120 may include convex hull analysis. The filtering component 120 may include circuits, components, and algorithms for enabling convex hull analysis. The filtering component 120 may receive simulation data from the simulation facility 110 and analyze the simulated data to identify one or more designs using convex hull analysis techniques. The identified designs may be recommended to a user.

Figure 54:
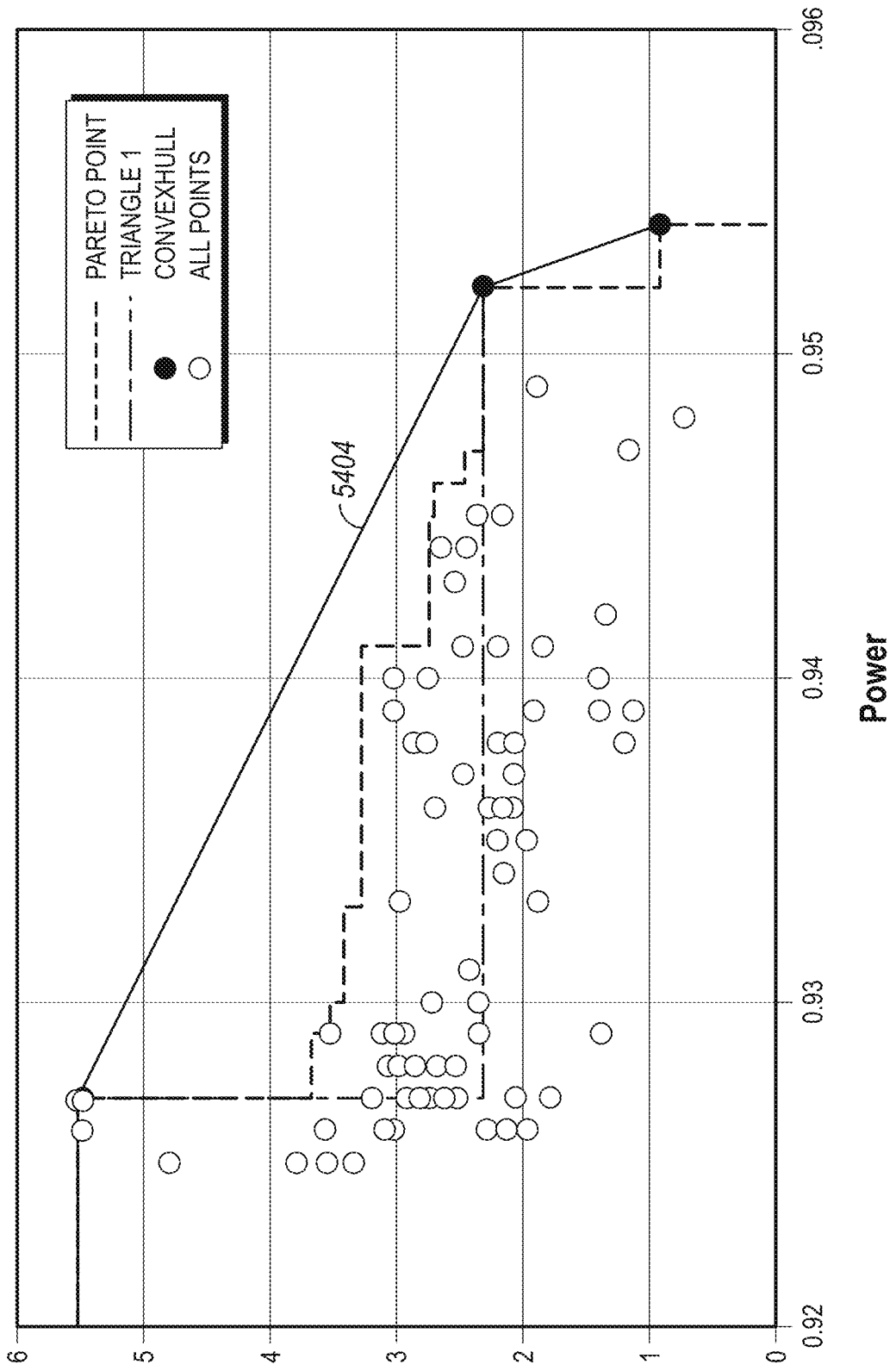
FIG. 54 depicts aspects of convex hull (CH) analysis in accordance with an embodiment of the current disclosure.
Figure 55:
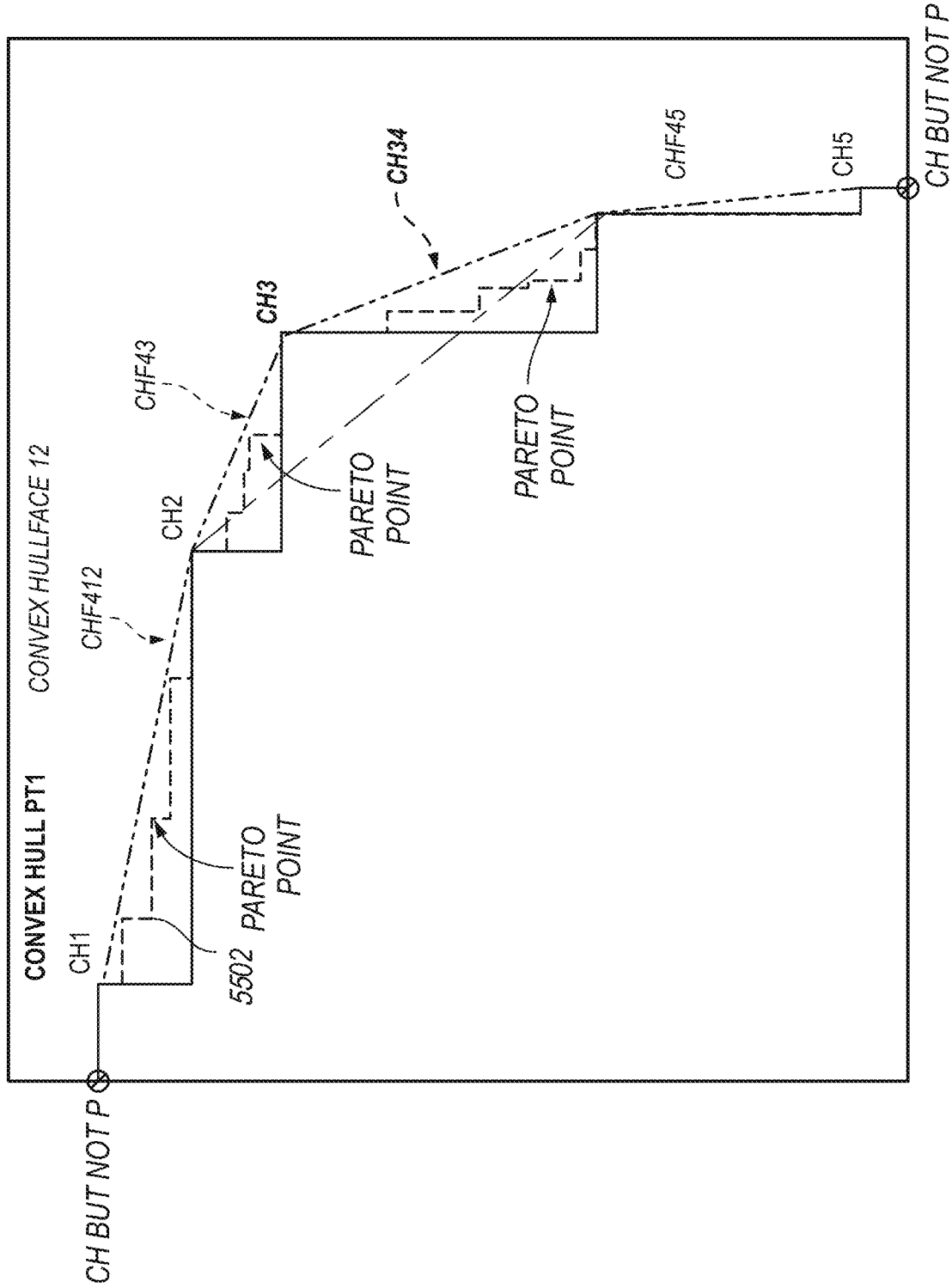
FIG. 55 depicts aspects of convex hull analysis in accordance with an embodiment of the current disclosure.

FIG. 54 shows a graphical representation of aspects of convex hull analysis. FIG. 54 shows a graph with points wherein each point corresponds to a trial design. The graph shows the performance of each trial design with respect to two trial design parameters (power and minimum study cost) that may have been determined by simulation. For these two performance parameters, the higher the number the more desirable. Points in the top right quadrant of the graphs relate to designs with the more desirable performance parameter values. In the example, convex hull analysis is used to determine CH-designs. The convex hull is a line 5404 and CH-design are vertices of the line 5404. The convex hull contains or envelopes the other designs.

In embodiments, convex-hull designs are a subset of Pareto designs. They are often a fraction of the size of the set of Pareto designs. An important property of convex-hull designs is that they are that can be optimal with respect to a performance criteria that is a linear weighted criterion of the components of the multivariate performance parameters.

The convex hull of design may be computed for a subset of all the trial designs. In some cases, the convex hull may be computed for trial designs that have at least a threshold value for one or more performance parameters.

In embodiments, various algorithms/engines may be used to compute convex hull points and may include brute force, gift wrapping, Graham scan, Jarvis, QuickHull, Qhull algorithms/engines, and/or the like. Computation of the convex hull of the designs may include additional data such as facet area and volume of the hull, facet normal vectors (weights for which the facet is optimal). Additional outputs may include triangular facets (such as Delaunay) or polygon (polyhedral) facets. In embodiments, outputs related to the facet area may be indicative of the number of designs from the CH-designs that are in the design space. Large facet areas may indicate that there are few design options in the design space area of the facet. Facet area information may be used as a basis for the exploration of the design space using simulated annealing algorithms/engines and/or the like.

In embodiments, CH-designs may be identified as desirable or optimum designs and the CH-designs may be recommended to a user. In some embodiments, CH-designs may be identified as initial globally optimum designs and they may be used to refine the optimality criteria to identify other globally optimum designs for the new criteria. In some embodiments, interactive methods can be used in which a person or an alternate algorithm acts as a decision-maker and interacts with the method to indicate a preference for designs (such as preference among initial CH-designs), and the method may use the preference information to determine other trial designs (and modify optimality criteria) based on the preference of designs. In embodiments, the CH-designs can be used to elicit the user's preferences by interactively querying the user to make comparisons between designs.

Trial designs that are on or near the convex hull may be selected as initial choices for evaluation by a user. One or more of the designs may be presented to a user to evaluate and provide feedback. Feedback may include data related to acceptance of the trial design, rejection of the trial design, identification of one or more parameters or features of the trial design, and the like. In an embodiment, the one or more trial designs from the convex hull may be presented to a user using the card, tornado, heatmaps, and similar interfaces described herein.

Convex hull analysis may output two or more sets of designs and may include the convex hull designs and clustered convex hull designs (such as designs that are non-reachable by weighting criteria). The sets of designs determined by convex hull analysis may represent a hierarchy of designs for recommendation and/or consideration by a user. The convex hull designs may be the first in the hierarchy and may be the first designs to be recommended or provided for consideration. The clustered convex hull designs may be below the convex hull designs on the hierarchy of designs for recommendation and/or consideration. The clustered convex hull designs may be provided for recommendation and/or consideration after the set of convex hull designs or if no designs in the set of convex hull designs are acceptable to a user. In some cases, the set of clustered convex hull designs may be larger than the set of convex hull designs.

Convex hull analysis may be configured to separate CH-designs that are have equal or nearly equal performance parameters or observables such as cost, power, and/or duration. In embodiments, designs that are within an $\varepsilon$-box of a design may be designs that are within a ball of radius $\varepsilon$ from a design. Designs that are twins or siblings may be flagged or marked for further analysis if they are deemed to have desired performance as the twins or siblings may represent different design options that can be used to achieve similar performance criteria.

CH-designs may be grouped, and one or more other designs that are within $\varepsilon$ of a CH-design design may be represented by one CH-design. The size of the set of $\varepsilon$-filtered designs may be larger or smaller by selecting the value for $\varepsilon$. In some cases, $\varepsilon$ may be selected to be 0.001, and/or 0.055, and/or 0.15.

Convex hull analysis for the clinical trial optimization applications may be designed to cluster dominated designs into convex hull clusters (CH-clusters). In embodiments, the analysis may accommodate constraints on design parameters, and dynamically updating the CH-design by removing designs, adding new designs and scenarios, and/or changing prior probabilities of scenarios.

Convex hull analysis may provide for organization and/or analysis of data that is comprehensible and/or provides for a focus to designs that are optimal or near-optimal. The convex hull analysis may determine the hierarchies of design sets for consideration. In embodiments, one set in the hierarchy may be CH-design, another may be clustered CH-designs. In some embodiments, on CH-design hierarchy level may be the initial CH-designs. The next hierarchy level may be CH-designs that are determined when the initial CH-designs are not deleted and so on. Platform may drill down into the hierarchies when initial levels do not provide acceptable designs.

In embodiments, inputs to convex hull analysis may include simulated trial designs. In some embodiments, inputs may be P-designs determined by the Pareto algorithm/engine. In some embodiments, the inputs may be a set of trial design simulation records from a simulation database. Inputs may further include levels of minimum meaningful difference for performance parameters ($\varepsilon 1$, $\varepsilon 2$, $\varepsilon 3$, ... ) specified by users or default values that are fixed or dynamic (data dependent). The values for ($\varepsilon 1$, $\varepsilon 2$, $\varepsilon 3$, ... ) may depend on the stage of design exploration (e.g., larger values in early stages and smaller values in later stages, when more accurate information has been obtained), user perspective/choice, and/or the like. In some cases, inputs may include upper and lower bounds for each performance parameter value.

FIG. 54 shows a graphical representation of aspects of convex hull analysis. In embodiments, outputs of convex hull analysis may include the set of convex hull designs (designs on vertices CH1, CH2, CH3, CH4, CH5). In the case where the inputs were Pareto designs, CH-design may be a subset of the Pareto designs. In the figure, Pareto designs correspond to vertices of line 5502 (the Pareto frontier). Some vertices of the Pareto frontier correspond to the CH-designs (such as CH2 and CH3). In embodiments, outputs may further include clusters of P-designs for each convex hull facet (CHF), e.g., (CHF12, CHF23, CHF45) of the convex hull. Clusters may be determined by a right triangle formed by the ends of each facet forming convex hull facet clusters (CHF clusters). Convex hull facet clusters may be non-overlapping (i.e., each P-design belongs to exactly one CHF cluster). Each CH-design may be at the intersection of several facets so CHF clusters can be combined into a convex hull Pareto cluster (CHP cluster) for each CH-design. CHP clusters may be overlapping. As will be appreciated, this may provide a decomposition for the global problem of optimization into smaller local problems defined for a CHF or CHP clusters.

In embodiments, outputs of convex hull analysis may include facet area, volume of the hull, facet normal vectors (weights for which the facet is optimal). In embodiments, facet area, volumes of the hull, and normal vectors may be used by search algorithms such as simulated annealing to determine search trajectories and parameters. In embodiments convex hull analysis may be parallelized. Input designs may be partitioned into two or more sets and a CH-designs may be determined for each set in parallel. The CH-designs of each set may be combined and overall CH-designs may be determined. In some embodiments, convex hull analysis may support batch updating in collaborative environments.

Figure 56:
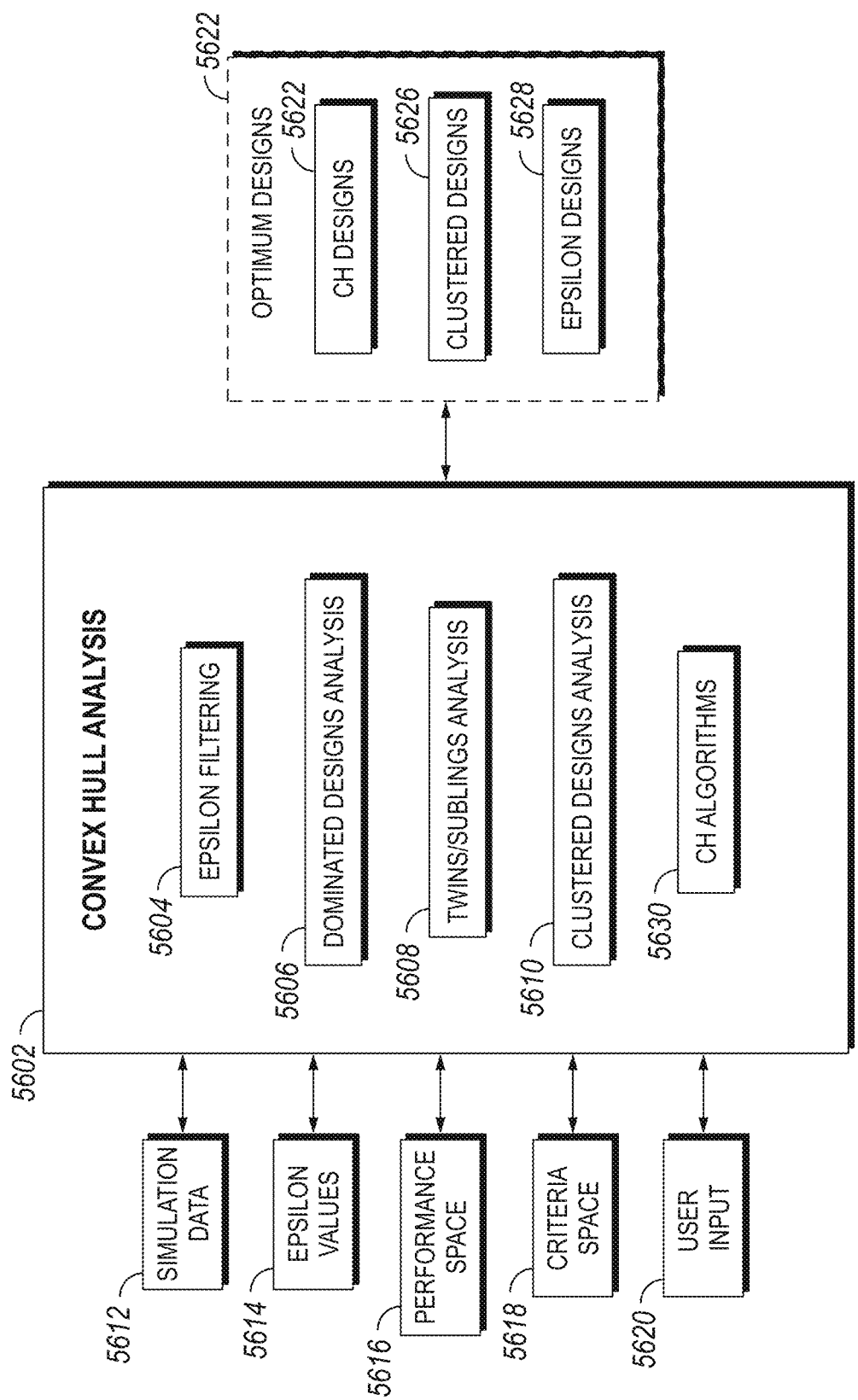
FIG. 56 is a is a schematic diagram of an apparatus for determining optimum designs using convex hull analysis, in accordance with an embodiment of the current disclosure.

FIG. 56 shows aspects of an apparatus for determining designs using convex hull analysis. In embodiments, the convex hull analysis component 5602 may be part of the analysis facility 108 of the platform 104. The convex hull analysis component 5602 may receive simulated design data 5612 (which may include just P-designs from Pareto analysis) and determine one or more sets of optimal designs 5622 which may include CH-(designs that are within a distance epsilon of CH-designs). The convex hull analysis component 5602 may include one or more circuits for determining recommended designs. The circuits in the convex hull analysis component 5602 may be selectively enabled according to user input 5620, epsilon values 5614, and other inputs. In embodiments, the convex hull analysis component 5602 may include circuits for determining convex hull optimality using convex hull algorithms 5630. In embodiments, the convex hull analysis component 5602 may include circuits for determining optimality using epsilon filtering 5604. Epsilon filtering circuit 5604 may determine designs that are within epsilon of CH-designs. In embodiments, the convex hull analysis circuit 5602 may include circuits for dominated designs analysis 5606. Dominated designs analysis circuit 5606 may identify designs that are dominated by one or more CH-designs and filter the designs and/or recommend the designs according to user input 5620 and/or epsilon values 5614. In embodiments, the convex hull analysis circuit 5602 may include circuits for twins/siblings analysis 5608. Twins/siblings analysis circuit 5608 may identify designs that are twins and/or siblings to one or more CH-designs and filter the designs and/or recommend the designs according to user input 5620. In embodiments, the convex hull analysis circuit 5602 may include circuits for clustered design analysis 5610. Clustered design analysis circuit 5610 may identify designs that are clustered with one or more CH-designs and filter the designs and/or recommend the designs according to user input 5620.

Figure 57:
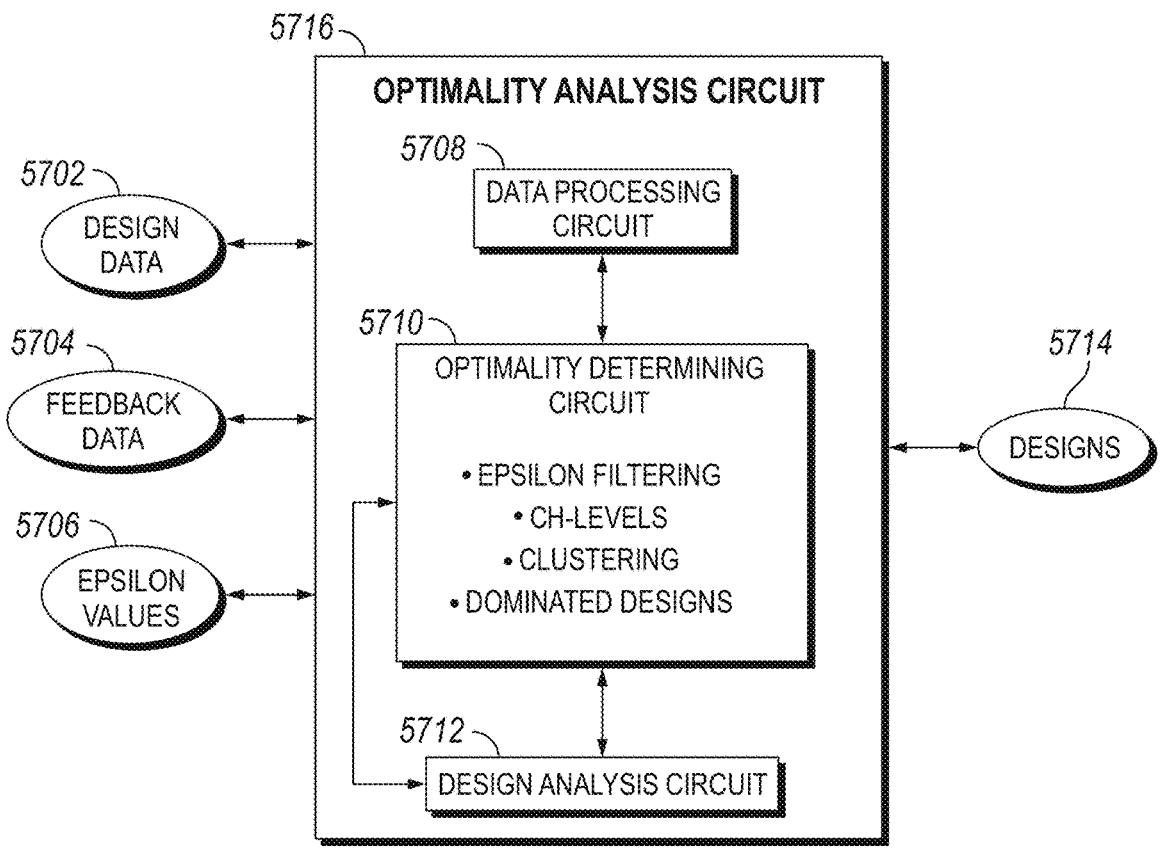
FIG. 57 is a is a schematic diagram of an apparatus for determining optimum designs using convex hull analysis, in accordance with an embodiment of the current disclosure.

FIG. 57 shows aspects of an apparatus for determining global optimality of designs using convex hull analysis. In embodiments, the apparatus may include an optimality analysis circuit 5716 which may be part of the analysis facility 108 of the platform 104. In embodiments, the apparatus may include a data processing circuit 5708 structured to interpret/obtain design data 5702 of a clinical trial design. In some embodiments the design data 5702 may be outputs of simulation data of trial designs. The output processing circuit 5708 may transform the design data 5702 into a format suitable for use by the various circuits in the apparatus. For example, the design data 5102 may be received by the data processing circuit 5708 and determine and identify performance parameters in the data. In some embodiments, some performance parameters may be grouped, filtered, converted, normalized, and the like. The apparatus of FIG. 57 may further include an optimality determining circuit 5710 structured to receive processed design data from the data processing circuit 5708. The optimality determining circuit 5710 may identify designs 5714 based on convex hull analysis. In some embodiments, the designs 5714 may be provided as an output of the apparatus. In some embodiments, designs 5714 may be further processed by the design analysis circuit 5712. The design analysis circuit 5712 may analyze the designs 5714 and determine characteristics of the designs, receive feedback data 5704 about the designs. The design analysis circuit may, based on the determined characteristics determine modifications for optimality criteria used in the optimality determining circuit 5710. The optimality determining circuit 5710 may modify optimality criteria of convex hull analysis. The modifications may include epsilon filtering designs, determining multiple levels of CH-designs, clustering of designs, determining dominated CH-designs, and the like. Using modified optimality criteria, the optimality determining circuit 5708 may determine a new set of designs 5714 which may be recommended to a user.

Figure 58:
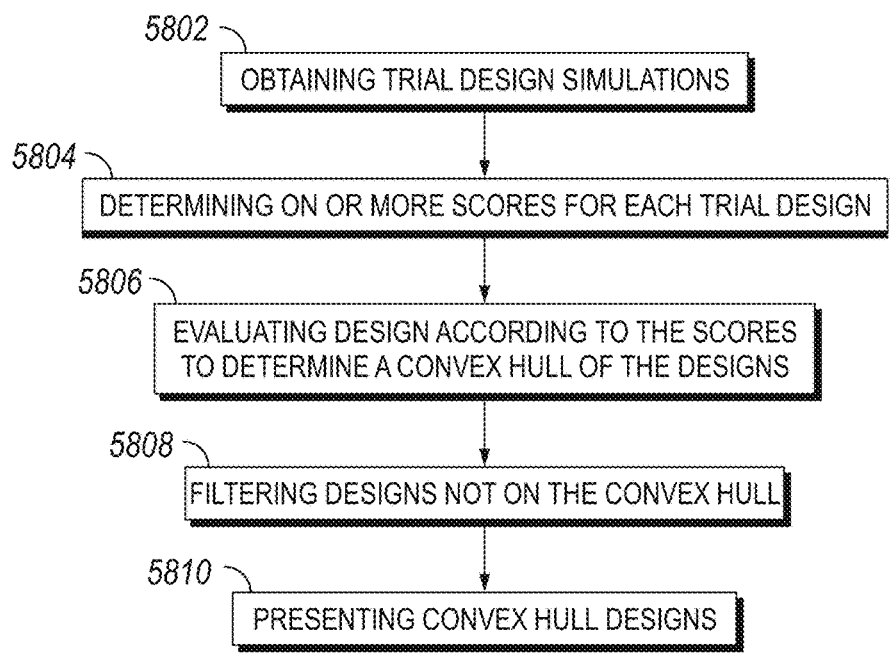
FIG. 58 is a flow chart depicting a method for determining globally optimum designs with convex hull analysis, in accordance with an embodiment of the current disclosure.

As shown in FIG. 58, a method for determining optimum designs using convex hull analysis may include obtaining trial design simulations 5802. The method may further include determining one or more scores for each trial design based on the performance parameters 5804. The method may include the convex hull for the designs 5806. Designs not on the convex hull may be filtered 5808. Designs on the convex hull may be presented for further analysis 5810.

Figures 59, 60:
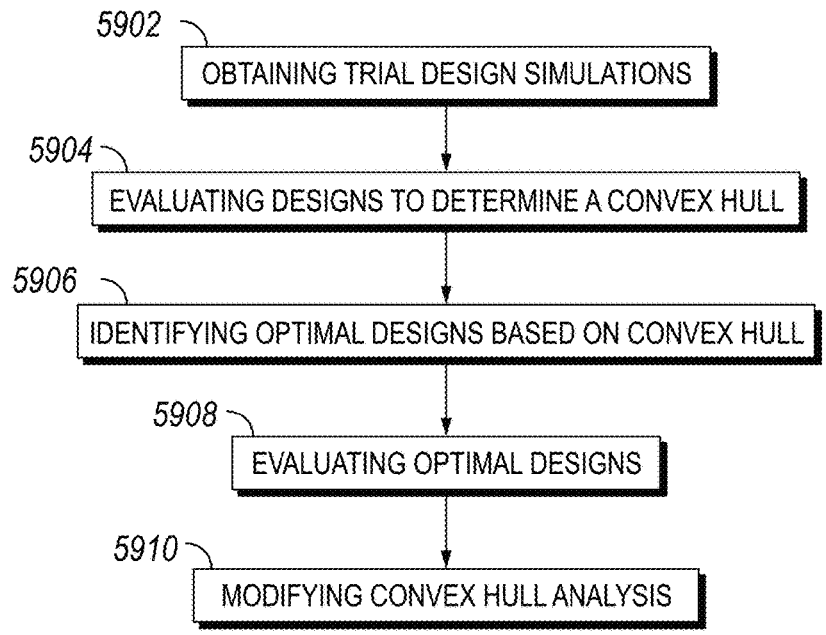
FIG. 59 is a flow chart depicting a method for determining globally optimum designs with convex hull analysis, in accordance with an embodiment of the current disclosure.
FIG. 60 shows aspects of robustness analysis in accordance with an embodiment of the current disclosure.

As shown in FIG. 59, a method for determining optimum designs using convex hull analysis may include obtaining trial design simulations 5902. The method may further include evaluating the designs to determine a convex hull 5904. The method may include identifying optimal designs based on the convex hull 5906. The optimum designs may be evaluated 5908. Evaluation may include feedback from user, statistical analysis, and the like. Based on the evaluation, aspects of the convex hull analysis may be modified 5910. Modifications may include determining epsilon-distance designs, clustering, determining second level CH-designs, and the like. New optimal designs may be identified using the modifications to the convex hull analysis.

In embodiments convex hull analysis includes consideration of performance, design, scenario, and criteria spaces. Convex hull may be determined with respect to performance parameters of the performance space. The performance parameters may be evaluated using simulation for different designs defined by the design space. Each design in the design space is evaluated for different scenarios of the scenario space. The performance, design, and scenario spaces are defined according to the criteria space definitions.

In embodiments, the platform 104 may be configured to explore different scenarios and perform "what if" analysis. The platform may be configured to automatically or semi-automatically explore the robustness of different designs. Trial designs may be evaluated, for example, respective to a range of treatment effects. As depicted in FIG. 29, a trial design may be evaluated to determine the outcomes of the trial based on whether the treatment effect is optimistic, base, or pessimistic, for example. In some embodiments, the analysis may include changes to assumptions of the trial to determine how a change in assumptions may change the usefulness of the trial.

In embodiments, the platform may further provide additional sensitivity analysis for designs. Models and designs may include assumptions about behaviors, parameters, and the like of a study. Sensitivity analysis may be used to determine behavior or trial designs in view of perturbations and variations in the model assumptions and/or parameters. Sensitivity analysis may be used to determine the robustness of designs. In some embodiments, the robustness of designs provides for a measure of what variations of assumptions a design can tolerate and still provide a useful result.

In embodiments, designs may be scored or evaluated based on multiple criteria. In some cases, a series of different tests that evaluate a sensitivity, robustness, and/or risk associated with a design may be computed. In some cases, an overall composite score that takes into account the multiple tests that can be computed.

FIG. 60 shows aspects of sensitivity analysis. In some embodiments, the separation of trial design inputs and scenario inputs, as described herein, may enable efficient sensitivity analysis. In embodiments, a framework for sensitivity analysis may compare how different combinations of design choices and scenarios affect performance criteria. In one embodiment, a vector of scenarios ($SV_1 \ldots SV_j \ldots SV_{57}$) may be arranged against each combination of designs ($DV_1 \ldots DV_i \ldots DV_{1120}$). For each combination of a designs and scenario ($SV_i$ $DV_i$ combination) performance parameters may be determined, such as by simulating the design and scenario combination. In embodiments, for each combination of a design and scenario, a weighted sum of performance parameters may be determined from simulation data. The arrangement of combinations and a weighted sum of performance criteria may provide for a measure of how performance parameters for each design change or are affected by variations in scenarios. Each row of the table shown in FIG. 60, when populated with simulation data, would show how performance parameters (or a function of the performance parameters) change over the scenarios. Each row of the table may show for which scenarios and/or what values of scenarios results in acceptable levels of performance (such as performance values above a threshold value). In embodiments, a span of acceptable parameter values may be related to the robustness or sensitivity of the design. In embodiments, a span may be the number of scenarios for which a design or a design parameter generates acceptable parameter values. In embodiments, a span may be a range of scenario parameter values a design or a design parameter that generates acceptable parameter values. In embodiments a larger span may be associated with a higher robustness of a design (i.e. the design or design parameter results in an acceptable performance for many scenarios). In embodiments, robustness may be a function of a span and probabilities associated with each scenario ($Pr_i \ldots Pr_j \ldots Pr_{57}$).

In embodiments robustness and/or sensitivity of a design and/or design parameters may be determined by determining design and scenario performance parameters as depicted in FIG. 60. The performance parameters may be evaluated via simulation. In some cases, simulations may be exhaustive such that each design scenario combination may be simulated to determine performance parameters. In some embodiments, only a partial set of designs and/or scenarios may be simulated. Based on the simulation the robustness and/or sensitivity of each design may be determined across all the scenarios or a partial set of the scenarios. The results of the robustness and/or sensitivity analysis may be provided to a user via tables, lists, and/or interactive interfaces such as tornado diagrams described herein. For example, tables and visual interfaces may provide information about the performance of a design over various scenarios. The interfaces may provide information regarding how close the performance of each design was to an acceptable threshold for each scenario or a subset of scenarios. The data may be used to get a more complete view of the risks associated with a design and possibilities to reduce the risks. The data may be used to infer or calculate the robustness, risk, and/or potential costs associated with a design. The data may be used to reduce the risk or and/or potential costs associated with a design. For example, in some cases, probability of some scenarios may be reduced or eliminated with inexpensive or common precautions or risk mitigation techniques. A user or the platform may identify scenarios for which a performance of a design was below a threshold and analyze or prompt the user to analyze possible mitigation techniques. If inexpensive mitigation techniques are possible the some negative scenarios for a design may be removed from robustness evaluations.

In some embodiments, a Pareto analysis may provide for a measure of robustness for designs. In embodiments, the Pareto analysis may be used to determine Pareto optimal designs. As described herein, Pareto optimal designs may define the Pareto frontier. In embodiments, robustness of Pareto designs may be determined based on the separation between Pareto designs.

Figure 61:
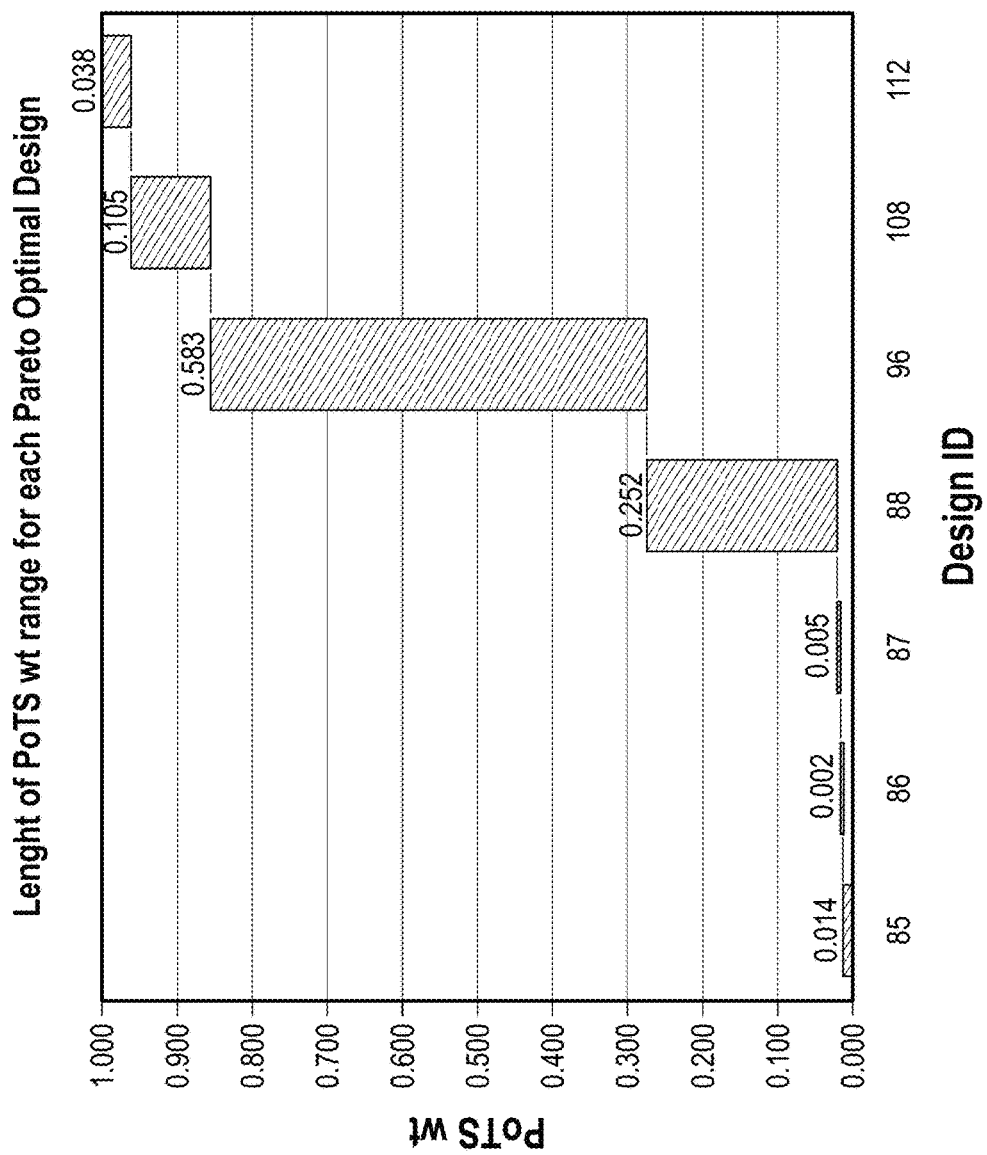
FIG. 61 shows aspects of robustness analysis in accordance with an embodiment of the current disclosure.

FIG. 61 shows aspects of measuring the robustness of the design based on Pareto analysis. The table FIG. 61 shows data for seven (7) Pareto designs determined for a set of simulated designs for one performance criteria of probability of technical success (PoTS). For each design, a PoTS weight can be determined. The PoTS weight indicates the interval of PoTS for which each design is optimal according to the Pareto analysis. For example, design with DesignID "88" is optimal from a PoTS value of 0.022 to 0.274 (corresponding to 2.2% and 27.4% respectively). The range of optimality for design "88" is, therefore, 0.252 (25.2%). In another example, design with DesignID "96" is optimal from a PoTS value of 0.274 to 0.857 (corresponding to 27.4% and 85.7% respectively). The range of optimality for design "96" is, therefore, 0.583 (58.3%). The ranges of optimality of the performance parameter are shown in the graph of the figure. The size of the bar in the graph indicates the range for the performance parameter that each design is optimal for. The designs with the largest ranges of optimality (the most robust designs), such as designs with Design IDs "88" and "96", may make good candidates for recommendation by the system. These designs with the largest range of optimality provide the designs that are typically most likely to be selected by a user, such as a decision-maker selecting the study. For example, in the case of the design corresponding to Design ID "96", if two or more decision-makers had different weight preferences for PoTS, as long as their preferences were between 0.274 and 0.857, they would all prefer design "96" above all other designs. In the selection of the designs to recommend, unless there are other factors that would dictate a bias towards the importance of one or more criteria, selecting the most robust designs is often a good starting point for analysis and design recommendation. In some cases, Pareto analysis of simulations may result in a large number P-designs for initial consideration. In some cases, initial suggestions of P-designs may be limited to the most robust P-designs.

In embodiments, robustness and/or sensitivity may be defined with respect to types of scenarios. In embodiments, scenarios may be categorized based on properties of the scenarios such as their probabilities. In one example, scenarios may be categorized into four (4) types of scenarios: Optimistic, Base, Pessimistic, Very pessimistic. In embodiments, a performance score for a design or design parameters may be determined for each scenario. The scores for each scenario may be used to determine a composite score for each type of scenario (by computing an average for example). A composite score may provide a measure of robustness. The score may provide a measure of a performance for a design for scenarios that are likely to happen, unlikely to happen, and the like. Robustness may be determined based on the number of scenario categories for which a design exhibits acceptable performance. For example, designs that have acceptable performance for scenarios that are only likely to happen may not be considered robust, while designs that have acceptable performance for scenarios that likely to happen and unlikely to happen may be considered robust.

Referring to FIG. 1, the analysis facility 108 of the platform 104 may include robustness and sensitivity analysis. The analysis facility 108 may include circuits, components, and algorithms for enabling robustness analysis. The analysis facility 108 may receive simulation data from the simulation facility 110 and analyze the simulated data to identify robustness of designs. The identified designs may be recommended to a user.

Figure 62:
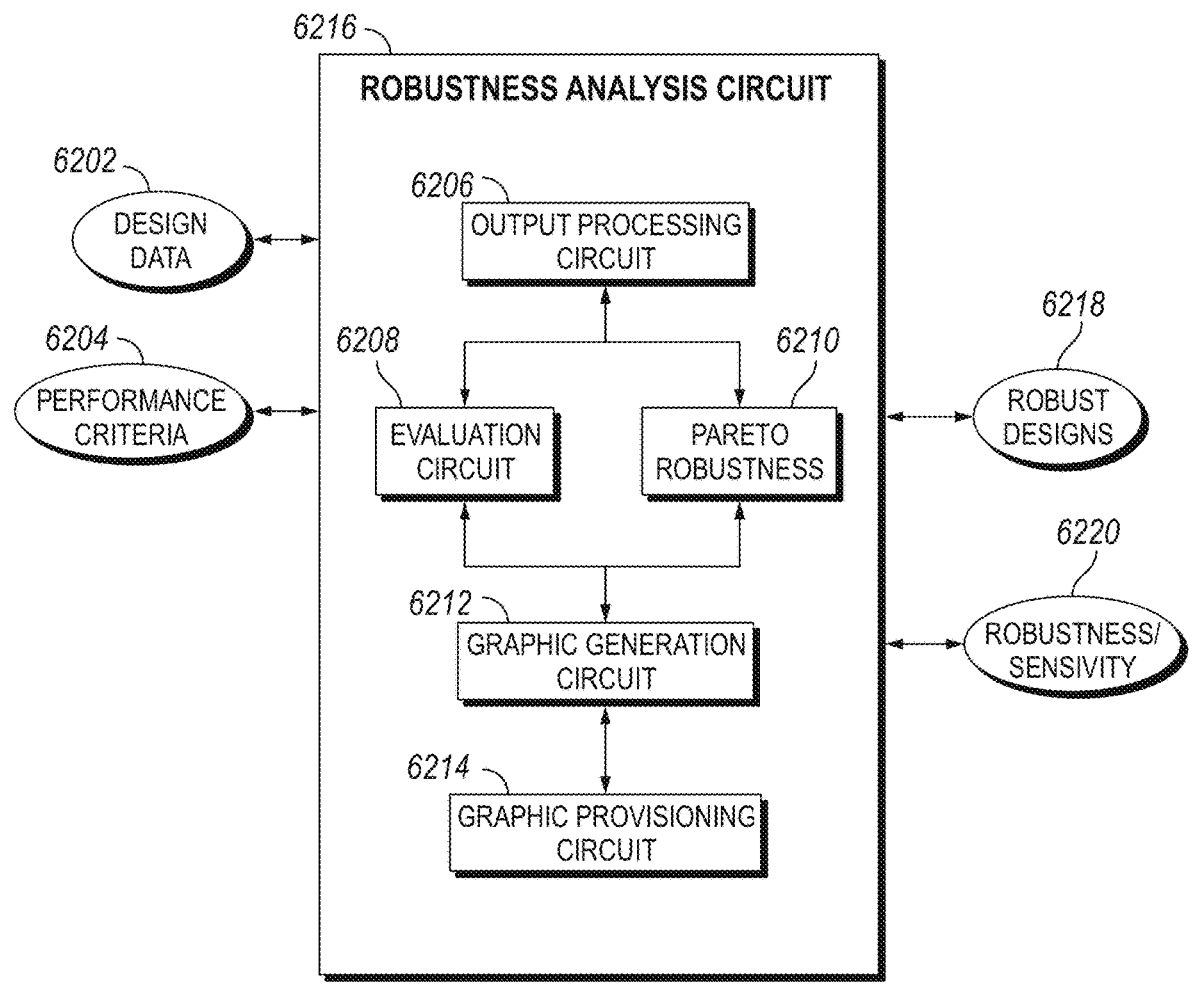
FIG. 62 is a schematic diagram of an apparatus for determining robustness of designs, in accordance with an embodiment of the current disclosure.

FIG. 62 shows aspects of an apparatus for determining robustness of designs. In embodiments, the apparatus may include a robustness analysis circuit 6216 which may be part of the analysis facility 108 of the platform 104. In embodiments, the apparatus may include an output processing circuit 6206 structured to interpret/obtain design data 6202 of a clinical trial design. In some embodiments the design data 6202 may be outputs of simulation data of trial designs. The design data may include simulation data for designs for various scenarios. The output processing circuit 6208 may transform the design data 6202 into a format suitable for use by the various circuits in the apparatus. The apparatus of FIG. 62 may further include an evaluation circuit 6208 structured to receive processed design data from the output processing circuit 6206. The evaluation circuit 620810 may identify robustness 6220 and/or robust designs 6218 based on analysis of performance for designs for different scenarios. In some embodiments, the robustness analysis circuit 6216 may include a Pareto robustness determining circuit 6210. The Pareto robustness determining circuit 6210 may determine Pareto designs from the design data 6202 and determine robustness for the Pareto designs based on the separations of the Pareto designs. The robustness and/or sensitivity of the designs may be compiled into a graphical interface such as a tornado diagram using the graphic generation circuit 6212 and may be provided to a user with the graphic provisioning circuit 6214.

Figure 63:
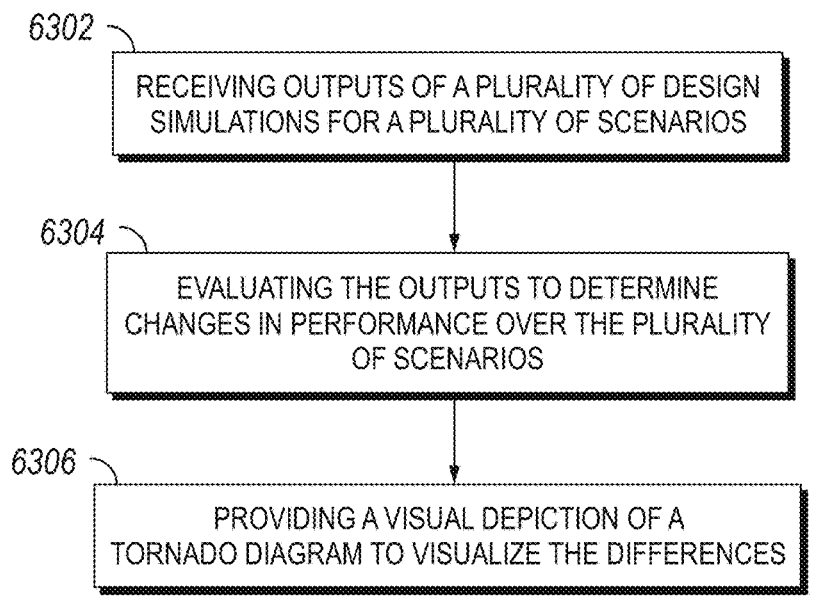
FIG. 63 is a flow chart depicting a method for determining robustness of designs, in accordance with an embodiment of the current disclosure.

As shown in FIG. 63, a method for determining robustness of designs may include receiving outputs of a plurality of design simulations for a plurality of scenarios 6302. The method may further include evaluating the outputs to determine changes in performance for the designs over the plurality of scenarios 6304. The method may also include providing a visual depiction of a tornado diagram to visualize the differences 6306.

Figure 64:
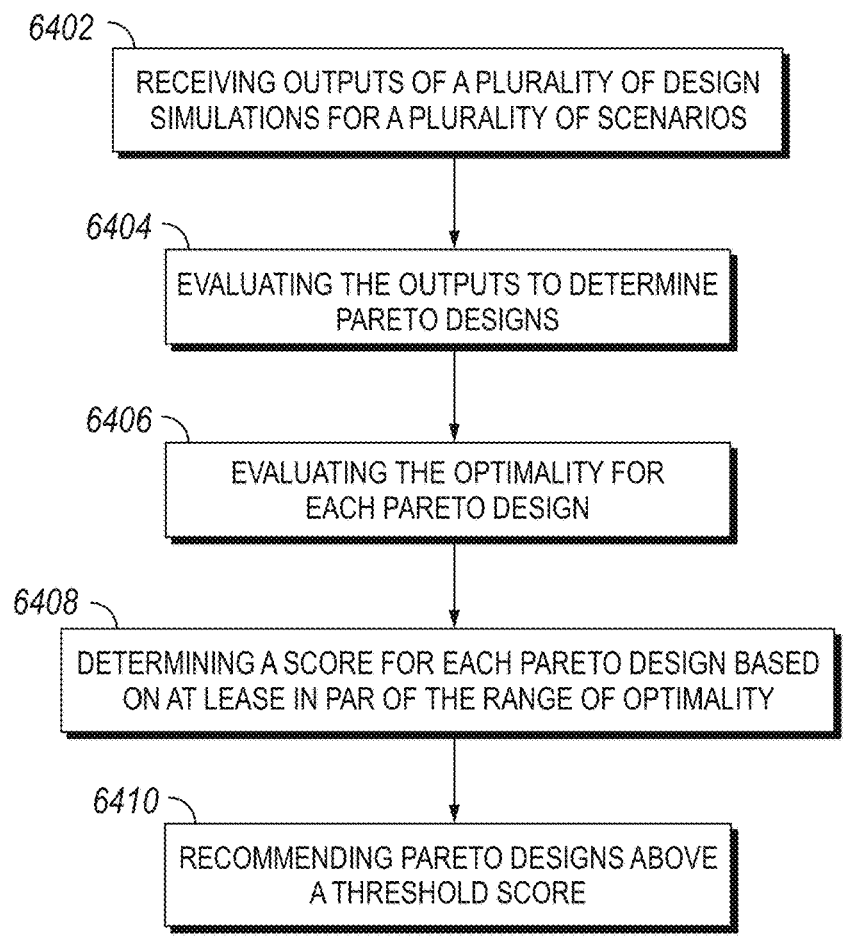
FIG. 64 is a flow chart depicting a method for determining robustness of designs, in accordance with an embodiment of the current disclosure.

As shown in FIG. 64, a method for determining robustness of designs may include receiving outputs of a plurality of trial design simulations for a plurality of scenarios 6402. The method may further include evaluating the outputs to determine Pareto designs 6404. The method may also include evaluating the range of optimality for each Pareto design 6406 and determining a score for each Pareto design based on at least in part on the range of optimality 6408. The method may include recommending Pareto designs above a threshold score 6410.

In some embodiments, one or more optimization algorithms may be used to explore the global design space or a localized subspace of possible designs. Simulated annealing algorithms may be used to explore a subspace of possible designs. In some embodiments, simulated annealing may be used to explore the design space around an initial selected trial design to determine if there are any additional design options near the selected design that provide an improvement to one or more criteria or parameters. Simulated annealing may reduce the number of designs that are simulated while providing high confidence that optimum or near optimum designs are determined.

In embodiments, design simulations may be non-exhaustive and the platform may simulate a partial set of possible design options. When a partial set of possible design options for a design criteria is simulated best/optimal designs may be missed. When only partial set of design options has been simulated, designs of interest (such as designs with the best and/or optimal performance for the set of simulated designs) may be identified (such as by a user or by other components of the platform), simulated annealing may be used to search for additional designs that may have similar or better performance than the designs of interest. In embodiments, when only a partial set of design options has been simulated, regions of interest (such as regions of the performance space that are identified as having designs of interest) may be identified (such as by a user or by other components of the platform), simulated annealing may be used to search for additional designs that may have similar or better performance than the designs of interest.

Simulating annealing of trial designs may involve an initial starting design and iterations that consider neighboring design options. Adaptive logic may be used to move the system between different neighboring design options. Adaptive logic may control which parameters of the design options are modified, how much they are modified, conditions for taking different paths, conditions for retreating towards the initial design, conditions for cooling schedules, and the like. Adaptive logic may predict which parameter modification may results in an improvement in performance compared to the initial design. In embodiments, predictions may be based on historical data. Previous simulation data may be used to generate ML and/or AI models to predict the effects of changes of design on performance. For each modification from the initial design, the design modification may be simulated to determine the performance of the design to determine if the modification resulted in an improved design option. Changes in performance may be used by the control logic to determine the path of exploration and other parameters of simulated annealing.

Referring to FIG. 1, the search/exploration component 130 of the simulation facility 110 of the platform 104 may include components for simulated annealing. The search/exploration component 130 may include circuits, components, and algorithms for enabling simulated annealing. The search exploration component 130 may interact with the models 126 and engines 128 components to explore design space. In embodiments the analysis facility 108 may provide analysis data to simulated annealing components to identify designs or regions of interest. The search/explorations component 130 may use simulated annealing to determine designs around designs of interest and/or in or around regions of interest and simulate the designs. The analysis facility 108 may provide analysis of the simulated designs to determine parameters (such as cooling cycles, parameter changes, directions, and the like) for simulated annealing.

In embodiments, simulated annealing may be used in a workflow where initial design simulations are selected to provide a coarse representation/overview of the performance space of the design options. The coarse representation may be used to identify designs or regions of the performance space, scenario space, and/or design space of interest. The designs or regions of interest may be used as initial starting points for simulated annealing to search for designs near the identified designs or in the regions of interest that have improved performance compared to the initial designs. In some embodiments, initial coarse design simulation may represent 50% or 30% or less of the total design options for a criteria. The use of coarse initial design simulation may reduce initial simulation time and resources. In embodiments, the designs of interest or the regions of interest from the initial simulations may be determined by a user via user interface. In embodiments, the designs of interest or the regions of interest from the initial simulations may be determined by other elements of the system. For example, designs of interest that can be identified using Pareto analysis, convex hull analysis, and the like. Simulated annealing may be used to fill in gaps between initial simulated designs.

In embodiments, simulated annealing analysis may be configured to fill gaps in a convex hull within a CHP cluster. Simulated annealing may be configured to reduce simulation runs required by the Cartesian product approach. Simulation may start with a coarse cartesian grid (or replications of trials of random samples of designs randomly, possibly stratified) as input and incrementally develop P-designs and CH-designs that are identical or close to the P-designs and CH-designs of the full Cartesian sample using simulated annealing.

Simulated annealing may be configured to find designs that are optimal for given weights or a design that is nearest in performance to specified desired criteria. In some embodiments, the simulated annealing may use a weighted sum of squares or of absolute differences as the distance from the desired point to iterate to a design if there is a feasible design in a specified elliptical or box neighborhood around the point. The simulated annealing may be configured to use starting points that are designs closest to designs that are in the criteria space. In embodiments, the simulated annealing algorithm/engine may explore the design space around a criteria by exploring the effects of altering parameters of a design. Simulated annealing may be configured to explore all the parameters of a design or preferentially manipulate or explore a subset of the parameters. In some embodiments, users may specify preferences with respect to which parameters to prioritize for the exploration using simulated annealing. In some cases, the user may specify which directions the simulated annealing should explore the design space. The constraints may be based on which areas of the design space already have many designs, for example. In embodiments, historical data related to simulated annealing search may be used to prioritize one or more design parameters for the search using the algorithm.

In embodiments, inputs to simulated annealing may include a weight vector for criteria, an objective function specification (e.g., normal vector for CHFs), design variable ranges (discretized) numeric or categorical, design simulation engines (with control of a number of simulations and in future feedback of intermediate results as engine decreases replications at inferior designs to exploit simulation efficiency), engines for design simulations or other engines equipped with interfacing wrappers, set of starting designs from which simulated annealing will iteratively attempt to improve using probabilistic search. Inputs may further include cooling schedules with defaults, constraints on design variables (e.g., upper and lower bounds, rules of inadmissible combinations and the like). In embodiments, outputs may include parameters and criteria values for best design found, best design for each start, visualization of paths, cooling schedules, visualization through parallel designs interface, and the like. The output of the simulated annealing analysis may be used to update the set of CH designs and P-designs. The simulated annealing analysis may be configured and/or modified using one or more interactive interfaces (such as from feedback from card interface, heatmap interface, tornado diagram interface).

In some embodiments, a simulated annealing algorithm/engine may be configured for multicriteria objectives where no weights for performance criteria are specified and the algorithm/ending may search for Pareto points directly. In some embodiments, the simulated annealing algorithm/engine may start a search with P-designs and/or siblings of P-designs. In embodiments, the simulated annealing algorithm/engine may be parallelized. Parallelization may be configured based on convex hull facets and/or different data sets which can be computed in parallel. In embodiments, the simulated annealing algorithm/engine may include bounds and/or improvement cut-off criteria in the search. In embodiments, the simulated annealing algorithm/engine may use a flexible grid structure and may use different step sizes when exploring the design space. In embodiments, the step/grid size may be initially coarse (relatively large steps) and set to finer logic (relatively smaller steps) as the design space is explored. In embodiments, search algorithms/engines may include genetic and/or integer programming algorithms/engines. In some embodiments, smart Monte Carlo methods (including as described herein) may be further used to reduce the number of simulated designs.

Figure 65:
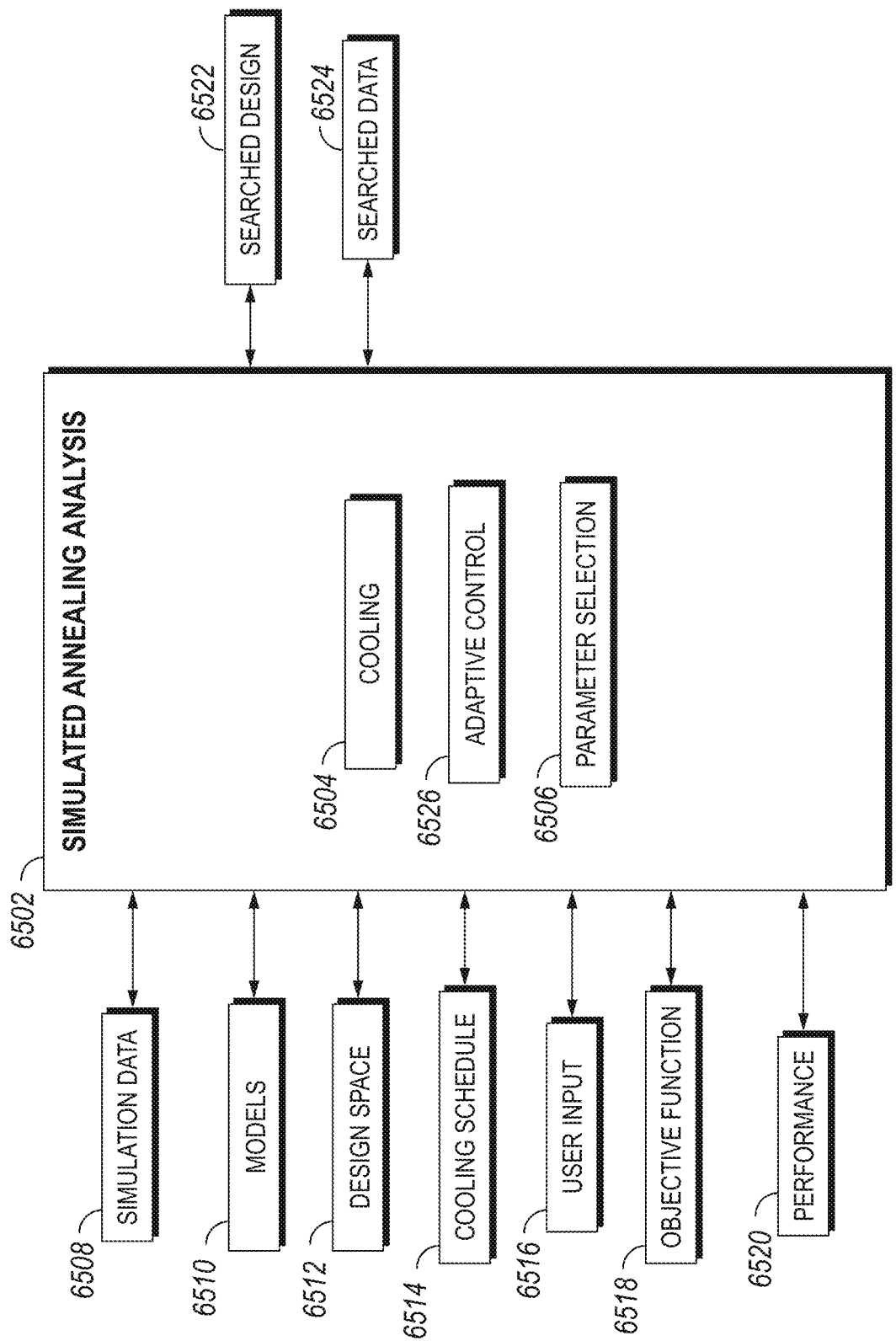
FIG. 65 is a is a schematic diagram of an apparatus for evaluating design with simulated annealing, in accordance with an embodiment of the current disclosure.

FIG. 65 shows aspects of an apparatus for determining designs using simulated annealing. In embodiments, the simulated annealing component 6502 may be part of the simulation facility 110 of the platform 104. The simulated annealing analysis component 6502 may receive data for simulated designs 6508. The simulated design may identify designs of interest or regions of interest that may be used as a starting point for simulated annealing analysis. The parameter selection circuit 6506 of the simulated annealing analysis component 6502 may identify parameters of a design that is neighboring or close to the design of interest or is in the region of interest. In embodiments, parameter selection may be defined by a user from user input 6516 and/or based on input from other components of the platform. Parameter selection circuit 6506 may determine designs parameters from an objective function 6518, cooling schedule definitions 6514, and other data. Objective function 6518 may include data from the analysis facility 108 and may provide data regarding locations of Pareto design, CH designs, facets of convex hull, normals of facets, distance between CH designs and Pareto designs, and the like. Parameter selection circuit 6506 may identify feasible designs from the design space 6512 that have the identified parameters. The parameter selection circuit 6506 may verify that the parameters of the design to be evaluated are feasible under defined criteria based on the design space 6512 data. Once the design to be simulated is defined according to the parameter selection circuit 6506 the design definition may be provided to engines component 128 of the simulation facility 110 for simulation and the performance data 6520 of the simulated design may be received after simulation. The adaptive control circuit 6526 may evaluate the performance data 6520 to determine the next direction, step size, set of parameters to manipulate, and the like. The adaptive control circuit 6526*f* may identify trends and correlations between changes in parameters of designs and the resulting performance parameters of the design. The trends and correlations may be used to by the parameter selection circuit 6506 to identify new design options to evaluate. The adaptive control circuit 6526 may further interact with the cooling circuit 6504 to determine if the selection of parameters should return to a previous state. The simulated annealing analysis component 6502 may provide search data 6524 and data related to paths and changes in parameters that may be analyzed and/or visualized by users. The search data 6524 may be used to change or update objective functions 6518, cooling schedule 6514 and other settings related to the simulated annealing analysis component 6502.

Figure 66:
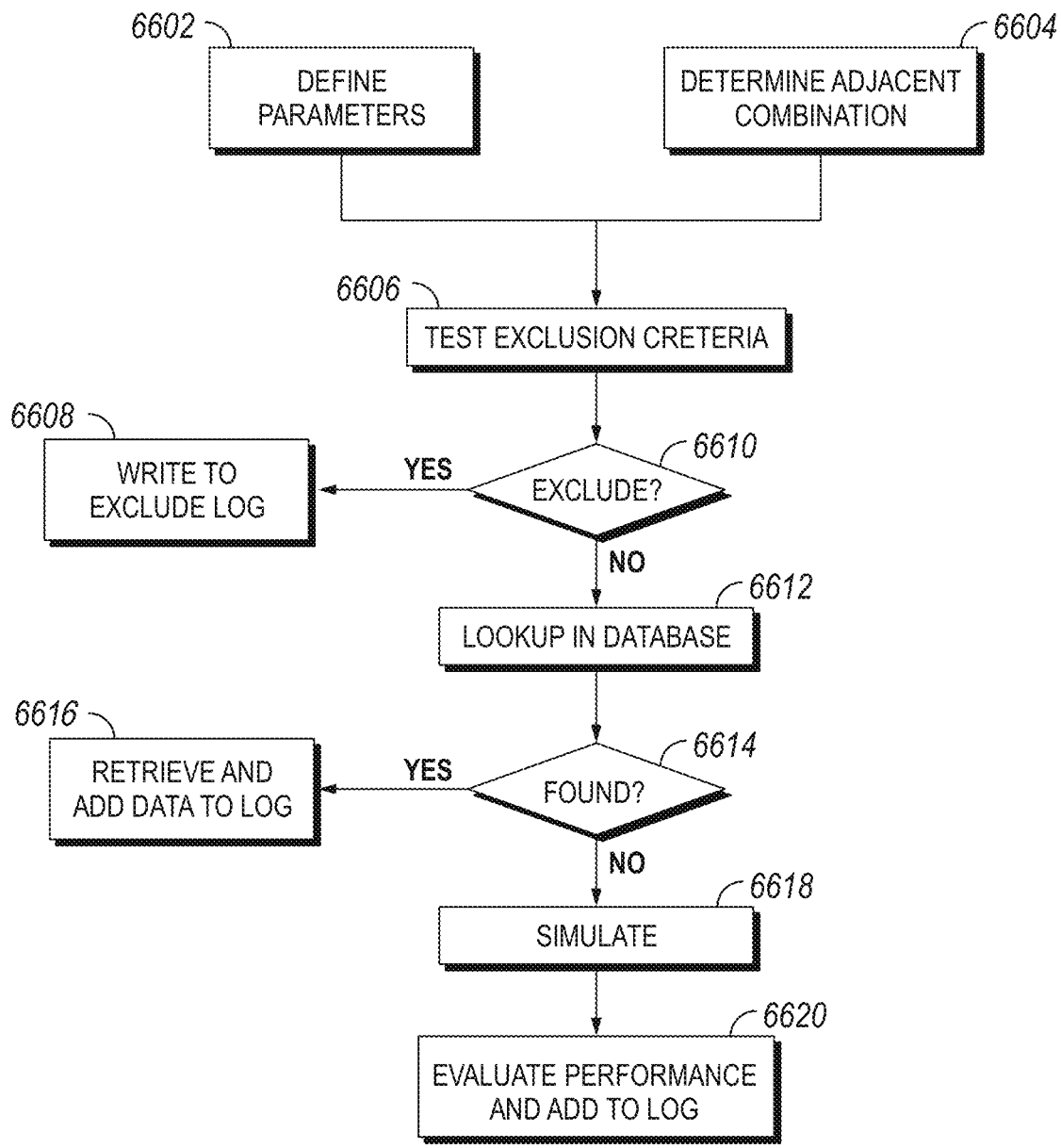
FIG. 66 is a is a flow chart evaluating design with simulated annealing, in accordance with an embodiment of the current disclosure.

FIG. 66 shows an example flowchart for simulated annealing which may be implemented by the simulated annealing component 6502. Simulated annealing may start with a definition of parameters 6602 and/or determination of adjacent combinations 6604 for a design to be simulated. The definition of parameters may include receiving design parameters 6602 or determining parameter variations to a design to identify a new adjacent design 6604. The parameters of the design to be simulated may be tested for exclusion criteria 6606. In some cases, the parameters may generate an invalid combination for a design for a criteria of the study. If the design is excluded 6610, the exclusion may be recorded in an exclusion log 6608 and a new set of parameters may be determined 6602, 6604. If the design is not excluded, the design may be searched in a database 6612 of previously simulated designs (such as from previous design studies). If the design is found in the database 6614, the data for the design may be retrieved and added to the log 6614 and new parameters may for a new design may be determined 6602, 6604. If the design is not found in the database, the design may be simulated 6618 and the performance of the design may be evaluated 6620. Based on the performance, new designs may be selected 6602, 6604 and the processes repeated.

Figure 67:
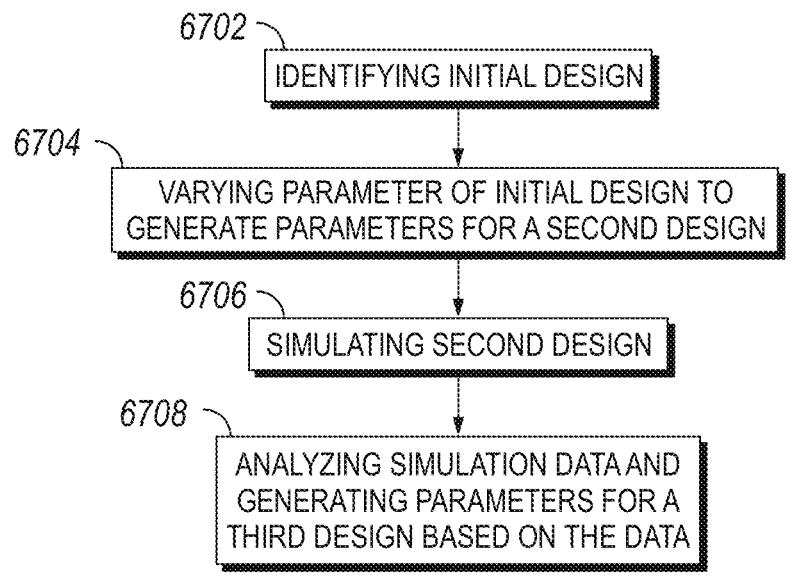
FIG. 67 is a flow chart depicting a method for evaluating a design with simulated annealing, in accordance with an embodiment of the current disclosure.

As shown in FIG. 67, a method evaluating designs using simulated annealing may include identifying an initial design 6702. The method may further include varying the parameter of the initial design to generate parameters for a second design 6704. The method may include simulating the second design 6706 and analyzing the simulation data to determine parameters for a third design 6708.

Figure 68:
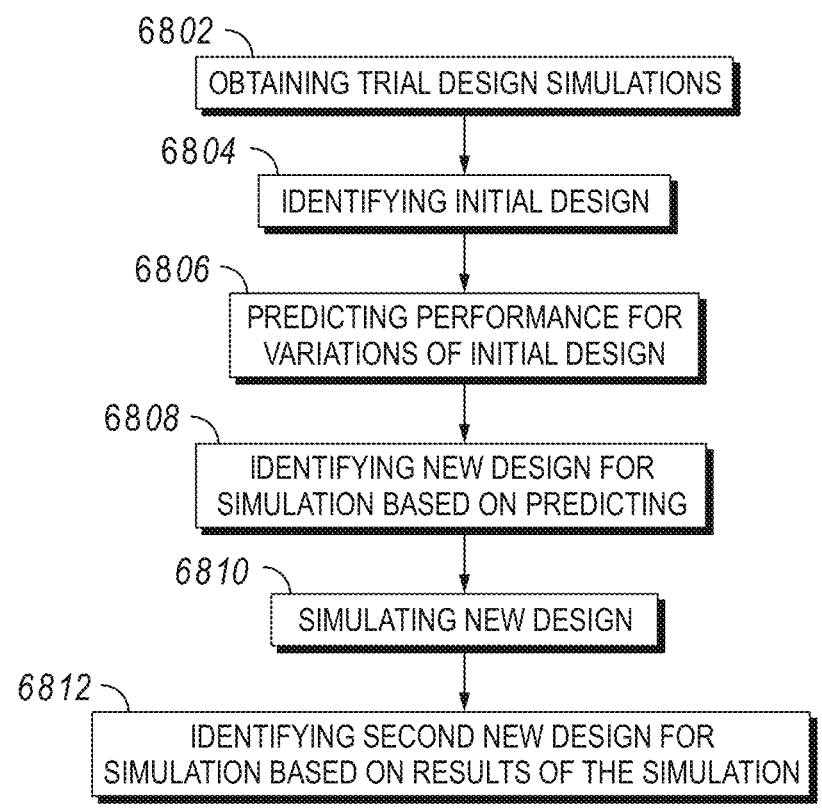
FIG. 68 is a flow chart depicting a method for evaluating a design with simulated annealing, in accordance with an embodiment of the current disclosure.

As shown in FIG. 68, a method for evaluating designs using simulated annealing may include obtaining trial design simulations 6802. The method may further include identifying an initial design from the trial design simulations 6804. The initial design may be an optimum design with respect to the trial design simulation. The method may include predicting performance for variation of the initial design 6806. Predictions may be based on historical data such as previous simulations. AI and ML algorithms may be used to determine how changes in parameters may affect the performance of a design. Based on the predictions, parameters for a new design may be identified. The new design may be a design that has favorable predictions such as an improvement in one or more performance parameter values compared to the initial design. The method may include simulating the new design 6810 and identifying a second new design for simulation 6812. The second new design may be identified based on the simulation results. For example, if the simulation results matched the predictions the second new design may be on the same trajectory from the initial design as the new design.

In embodiments simulated annealing includes consideration and analysis of performance, design, scenario, and criteria spaces. Simulated annealing analysis searches for designs that show improvements in the performance space. Searching comprises generating variation in the design parameters (design space) and scenarios (scenario space) parameters of an initial design. The performance, design, and scenario spaces are defined according to the criteria space definitions.

Figure 69:
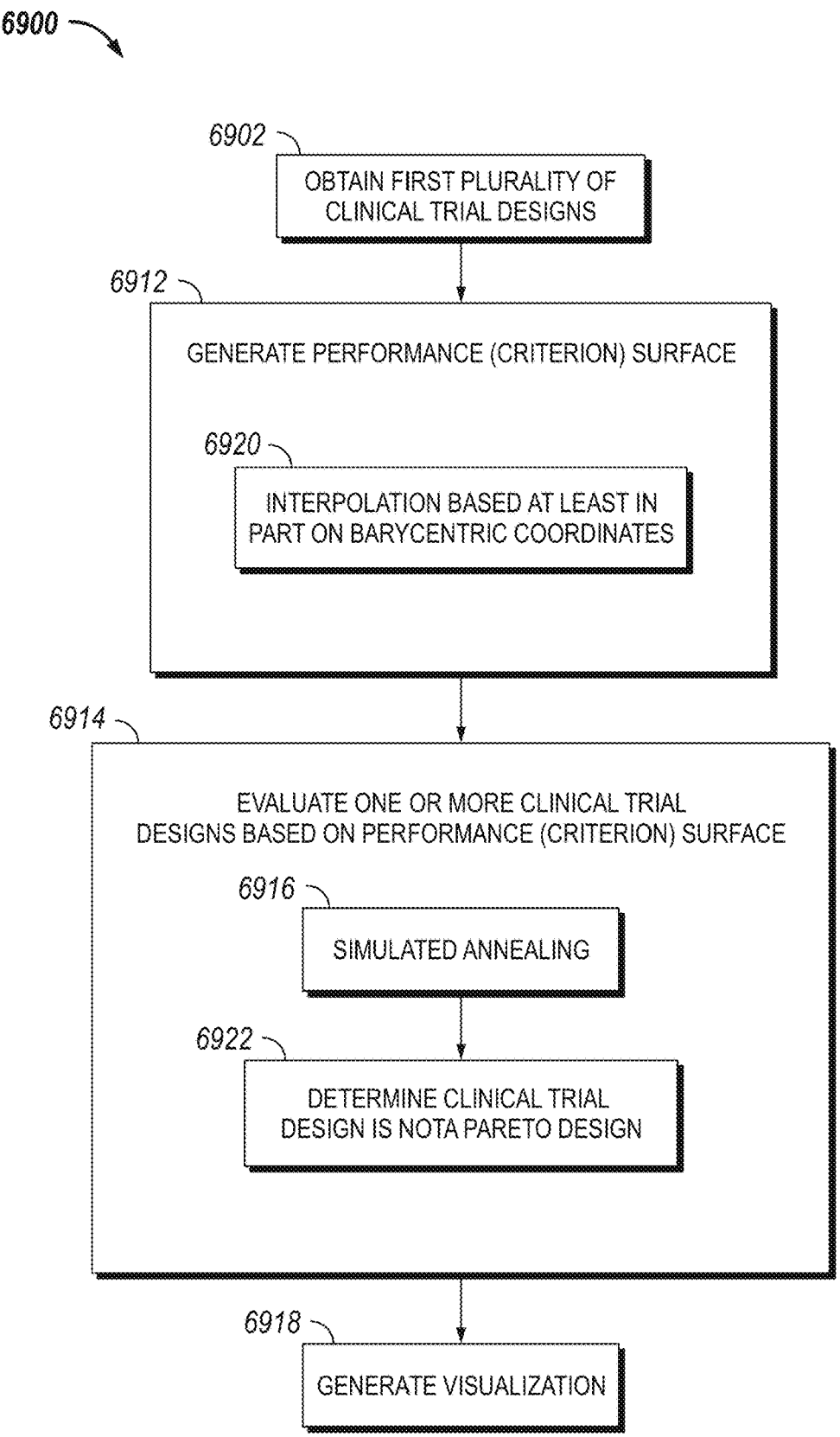
FIG. 69 is a flow chart depicting a method of simulating clinical trial designs based in part on a Delaunay interpolation, in accordance with an embodiment of the current disclosure.

Referring to FIG. 69, embodiments of the present disclosure may employ Delaunay triangulation, or other interpolation methods, e.g., clustering, to reduce the number of simulated clinical trial designs. In particular, the number of initial simulations may be non-exhaustive and Delaunay triangulation may be used to determine what additional designs should be simulated and/or which areas of the design space should be explored (such as with simulated annealing). For example, an embodiment of a method that uses Delaunay triangulation may start with a number of initial clinical trial designs for which the design parameters and/or performance parameters are known, either through simulation or historical data. The method may construct a piecewise linear criterion surface via Delaunay triangulation, wherein each point on the surface, minus the initial designs, represents interpolated criteria for possible designs. Thus, the criteria for a clinical trial design may be determined (estimated) before the design is simulated.

Accordingly, the time required to perform simulated annealing may be decreased by testing variations of a clinical trial design without having to simulate the variations by locating the variations on the surface. Interpolation may be computed using the barycentric coordinates of a point within its enclosing simplex. The surface may be used to generate visualizations of the weighted criteria functions over the design space. The visualizations may include a weighted criteria surface generated via the weighted sum of the individual criteria surfaces, which may provide for rapid estimation of the design value for a large set of criteria weights. Embodiments may use linear programming or network formulation as the "simplex finder" for a given design point. The surface may also be used to determine most promising and least promising directions or parameter variations in simulated annealing therefore reducing the number of simulations. Use of the criterion surface may provide for the early detection that a clinical trial design is not likely to be a Pareto design and, therefore, simulation of the clinical trial design may be skipped.

In particular, embodiments of the current disclosure may use a simulated annealing engine to leverage the criteria values from past clinical trial designs that have been simulated for a scenario vector to estimate design performance under an adjacent scenario. As such, some embodiments may take advantage of the fact that: 1) the edges in a Delaunay triangulation contain all shortest paths between any two design points; and/or 2) minimum spanning trees of all subsets of the design points are subgraphs of the Delaunay triangulation.

For example, consider a set of clinical trial designs that have been simulated and have known performance parameter values. The clinical trial designs may be treated as a scatter of points in the K dimensional design space of design vectors (e.g., K=5). Each clinical trial design may be associated with its performance parameter vector of dimension J (e.g., J=3). A Delaunay triangulation of these clinical trial design vectors may be constructed, wherein the surface of any criterion at any point is the interpolation of the criterion values of the K Delaunay simplex vertices containing the point. The interpolation may be computed using the barycentric coordinates of the point within its enclosing simplex. The weighted criteria surface is then the weighted sum of the individual criteria surfaces. As will be appreciated, this approach may provide for rapid estimation of a design's values for a large set of performance parameter weights. As will be further appreciated, Delaunay triangulation also has the advantage of creating simplexes that are not "long and skinny" so that vertices are "reasonably" close to any interior point. This is particularly true where, as in some embodiments of the present disclosure, the design points belong to a rectangular grid. Embodiments of the present disclosure may utilize linear programming or network formulation as the "simplex finder" for a given design point. A cache of recent simplexes since, apart from visualization may then be used to quickly approximate the criterion value.

Accordingly, as shown in FIG. 69, a method 6900, in accordance with the current disclosure, may include obtaining a first plurality of clinical trial designs with determined performance parameters 6910; and generating a criterion surface 6912, also referred to herein as a performance surface, based at least in part on the first plurality of clinical trial designs. As discussed herein, the points on the performance surface represent interpolated performance parameters for a second plurality of clinical trial designs (which may not have been simulated, as described herein). One or more clinical trial designs may then be evaluated based at least in part on the performance surface 6914. In certain aspects, the performance surface may be based at least in part on Delaunay triangulation, though other methods of interpolating a surface may be used. In certain aspects, evaluating may include simulated annealing 6916. The method 6900 may further include generating a visualization based at least in part on the criterion surface 6918. In embodiments, the visualization may be of weighted criteria functions over the corresponding design space. In embodiments, generating the performance surface may include interpolation based at least in part on the barycentric coordinates of a point 6920. In embodiments, the evaluating may further include determining that a clinical trial design of the second plurality is not a Pareto design 6922.

Figure 70:
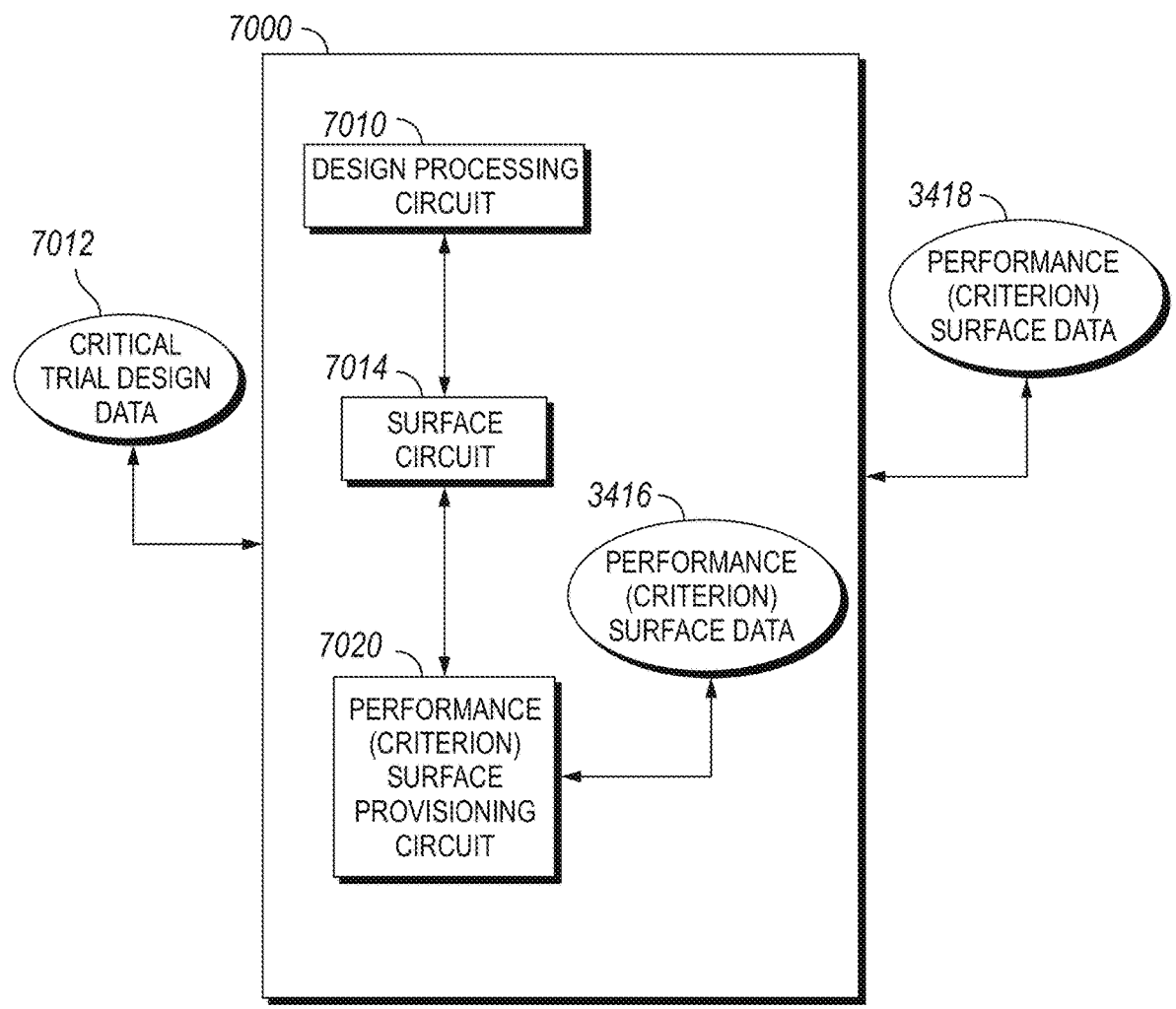
FIG. 70 is a schematic diagram of an apparatus for implementing the method of FIG. 69, in accordance with an embodiment of the current disclosure.

Turning to FIG. 70, an apparatus 7000 for implementing one or more aspects of the method 6900 is shown. The apparatus 7000 may form part of one or more computing devices in the platform 104, to include the computing resources 150. The apparatus 7000 may include a design processing circuit 7010 structured to interpret clinical trial design data 7012 corresponding to a first plurality of clinical trial designs with determined performance parameters. The apparatus 7000 may further include a surface circuit 7014 structured to generate a performance surface data object 7016 based at least in part on the clinical trial design data 7012. The performance surface data object 7016 may include data points representing interpolated performance parameters for a second plurality of clinical trial designs. The apparatus 7000 may further include a performance surface provisioning circuit 7020 structured to transmit the performance surface data object 7016.

Figure 71:
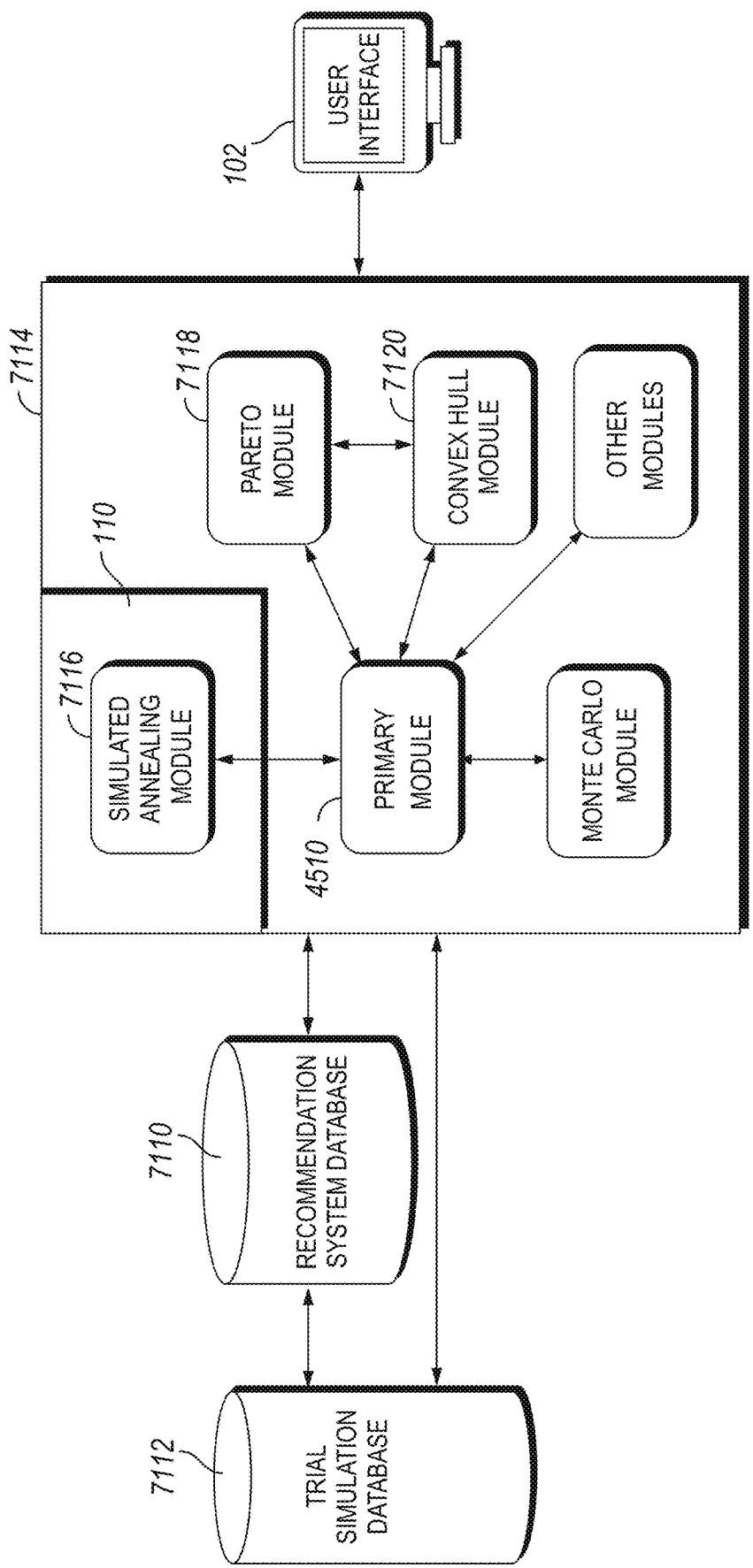
FIG. 71 is a schematic diagram of a recommendation component for recommending clinical trial designs, in accordance with an embodiment of the current disclosure.

Referring now to FIG. 71, a non-limiting embodiment of the recommendation component/system 7100 (also referred to herein as recommendation system architecture) is shown. In embodiments, the recommendation component 7100 may be, and/or be part of, the recommendation component 122 (FIG. 1). In other embodiments, the recommendation component 7100 may be a separate system from the recommendation component 122. The recommendation component 7100 may be configured to identify and provide one or more clinical trial designs for recommendation to a user via an interface, e.g., interface of a user device 102. In some embodiments, the recommendation component 7100 may receive feedback from a user via the interface of a user device 102 for evaluating recommended designs and revise or update recommendations based on the feedback. As shown in FIG. 71, the recommendation component 7100 may include a recommendation database 7110, a simulation database 7112, and/or a recommendation algorithm/engine 7114.

The trial simulation database 7112 may form part of the data facilities 138 and be a large repository of previous, current, and/or selected clinical trial design simulations. The trial simulation database 7112 may include simulations, as described herein, merged from different databases, groups, users, and the like. The trial simulation database 7112 may include data related to each simulation, such as engines used to run the simulation, date, time, and/or the like. In embodiments, the trial simulation database 7112 may include input data such as: id number, version, scenario id, design id, user id associated with a clinical trial design, the running status, number of interim analyses, time units, performance of events observed, treatment arm information, treatment control name, and/or the like. In embodiments, the trial simulation database 7112 may include output data such as accrual duration, average power, events data, net present value, insufficient count data, follow-up time data, expected net present value, probability of efficiency, probability of favorability, probability of futility, probability of success, study cost, study duration, time required, discounted study cost, total sales, a score, a total score, and/or the like. The inputs and/or outputs may be organized in a hierarchy that includes labels and/or other identifiers that label the items as pertaining to scenarios, clinical trial designs, primary criteria, secondary criteria, stimulation control, and the like. The trial simulation database 7112 may include temporal data for each simulation and may include data related to the beginning phase of a clinical trial design, the middle of a clinical trial design, progress data of virtual patients, and/or the like. In some cases, the trial simulation database 7112 may include raw simulation data from each simulation run. In some cases, the simulation database 7112 may include summary records associated with each clinical trial design simulation and include averages, endpoints, overall statistics, and/or the like. The trial simulation database 7112 may include data that relates each clinical trial simulation to the design space, scenario space, criteria space, and/or performance space, as described herein.

The recommendation database 7110 may include a subset of the trial simulation database 7112 that has been analyzed or flagged to be applicable to design criteria.

The recommendation engine 7114 may include and/or interact with one or more components and/or algorithms/engines, e.g., a Pareto engine 7118, a convex hull engine 7120 and/or any other engines/components described herein, for simulation, global optimization, visualization, analysis of clinical trial designs, control, and/or the like. For example, the recommendation engine 7114 may interact with, e.g., exchange data with and/or invoke procedure calls to, the simulation facility 110 (FIG. 1). For example, embodiments of the recommendation engine 7114 may utilize a simulated annealing component/algorithm/engine 7116 which may be provided by the search/exploration component 130 (FIG. 1) of the simulation facility 110. In embodiments, the recommendation engine 7114 may include and/or interact with a primary algorithm 4510, as described herein, that controls and/or monitors the workflow of the algorithms and/or engines 7114, 7116, 7118, and/or 7120.

In embodiments, the Pareto algorithm/engine 7118 and/or the convex hull algorithm/engine 7120 may be run or executed sequentially such that the output of the Pareto algorithm/engine 7118 may be an input to the convex hull algorithm/engine 7120. In this scenario, the Pareto engine 7118 may be used to first identify Pareto designs (also referred to herein as "P-designs") from the design space (which may be a subset of the design space), and the convex hull algorithm 7120 may further separate the P-designs and identify convex hull designs (also referred to herein as "CH-designs"), which may be a subset of the P-designs. In embodiments, the convex hull engine 7120 may be the first executed engine and may identify a set of CH-designs from the design space, wherein the Pareto engine 7118 may be used to further identify P-designs from the set of CH-designs. In embodiments, the convex hull engine 7120 may be configured to quickly update the identified CH-designs when new designs are introduced as inputs to the convex hull engine 7120. The set of identified CH-designs may be augmented incrementally by the Pareto engine 7118 as new designs are identified/simulated and added to the design space.

In embodiments, the Pareto engine 7118 may be executed without the convex hull engine 7120, wherein the outputs of the Pareto algorithm/engine 7118 may be used for design recommendations. In some embodiments, the convex hull engine 7120 may be executed without executing the Pareto engine 7118, wherein the outputs of the convex hull engine 7120 may be used for design recommendations.

In embodiments, the recommendation engine 7114 may be configured to provide a user with a limited number of recommended designs. The recommendation engine 7114 may provide recommendations that are a subset of the P-designs or the CH-designs. In some cases, the recommendation engine 7114 may be configured to limit the number of designs recommended to between about five (5) and about nine (9) designs. Recommended designs may be presented in small sets (such as between about five (5) and about nine (9) designs), allowing a user to compare the designs in the set. The set of recommended designs may be interactively augmented or updated based on user input or feedback. For example, the recommendation algorithm 7114 may present a set of initial recommended designs and ask a user to select a favorite design. Based on the favorite design, the recommendation engine 7114 may augment a next set of recommended designs. For example, based on the selection of one design, the engine 7114 may further present siblings of the selected design and/or designs that are dominated by the design.

Figure 72:
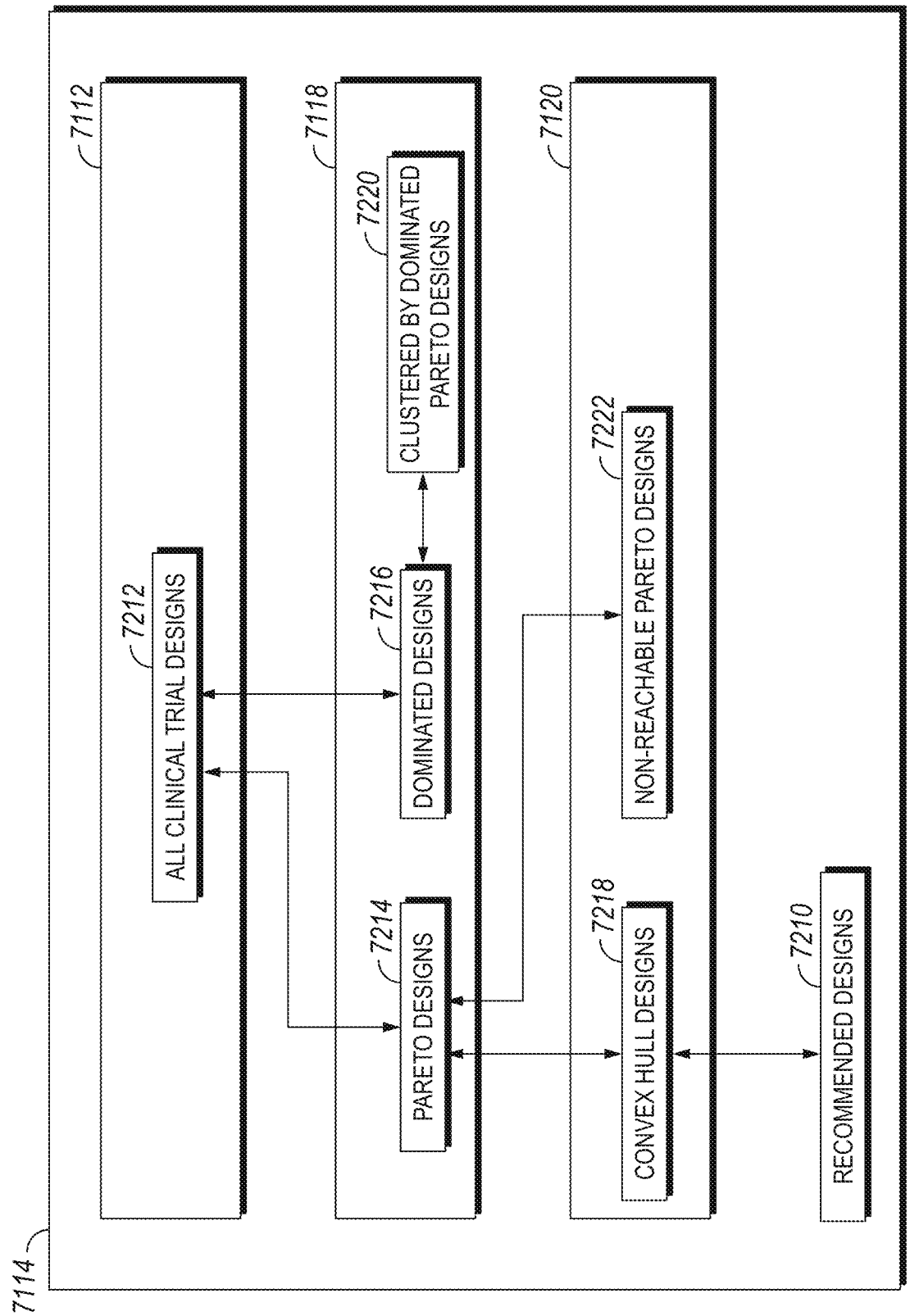
FIG. 72 is a schematic diagram of a recommendation engine, in accordance with an embodiment of the current disclosure.
Figure 73:
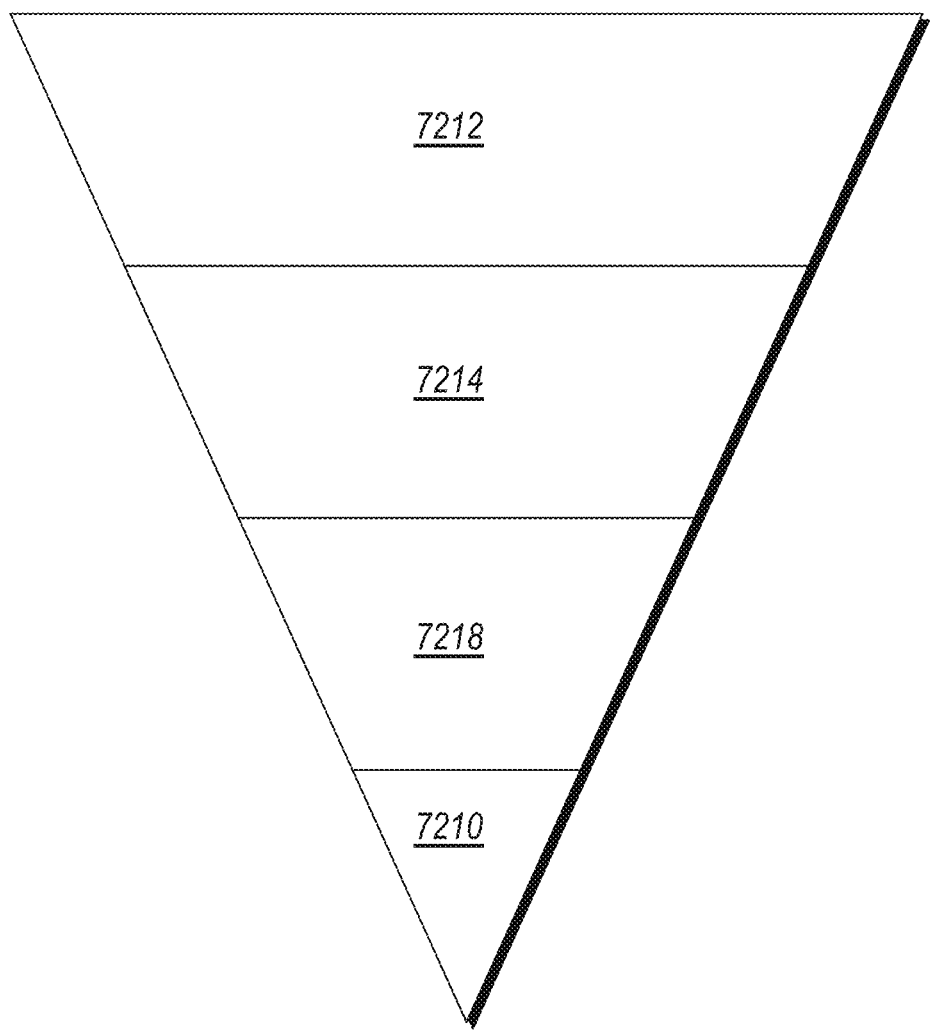
FIG. 73 is a diagram depicting a relationship between sets of clinical trial designs, Pareto designs, convex hull designs, and recommended designs, in accordance with an embodiment of the current disclosure.

Referring now to FIGS. 72 and 73, in embodiments, the recommendation engine 7114 may determine clinical trial designs 7210 to recommend (also referred to herein as "a set of recommended designs" or "recommended designs") to the user by processing a set of simulated designs 7212, which may be retrieved from the database 7112. Processing of the simulated designs 7212 may involve use one or more algorithms/engines, such as the Pareto engine 7118 and/or convex hull engine 7120. For example, in one configuration, the set of clinical trial designs 7212 may be first processed using the Pareto engine 7118 to identify a set of Pareto designs 7214 (P-designs) and/or a set of dominated designs 7216. As represented in FIG. 73 by the inverse triangle, in embodiments, the set of Pareto designs 7214 may be much less than the set of all designs 7212, e.g., 10× or 100× smaller, the set of convex hull designs 7218 may be smaller than the set of Pareto designs 7214, and the set of recommended designs 7210 may be smaller than the set of convex hull designs 7218. For example, the set of Pareto designs 7214 may be further processed using the convex hull engine 7120 to identify, from the set of P-designs 7214, convex hull designs 7218, wherein the convex hull designs 7218 are, generally, Pareto designs 7214 that can be reached by weighting criteria as described herein. In embodiments, non-reachable pareto designs 7222 may not be considered for use by the convex hull engine 7120 and/or recommendation.

Figure 74:
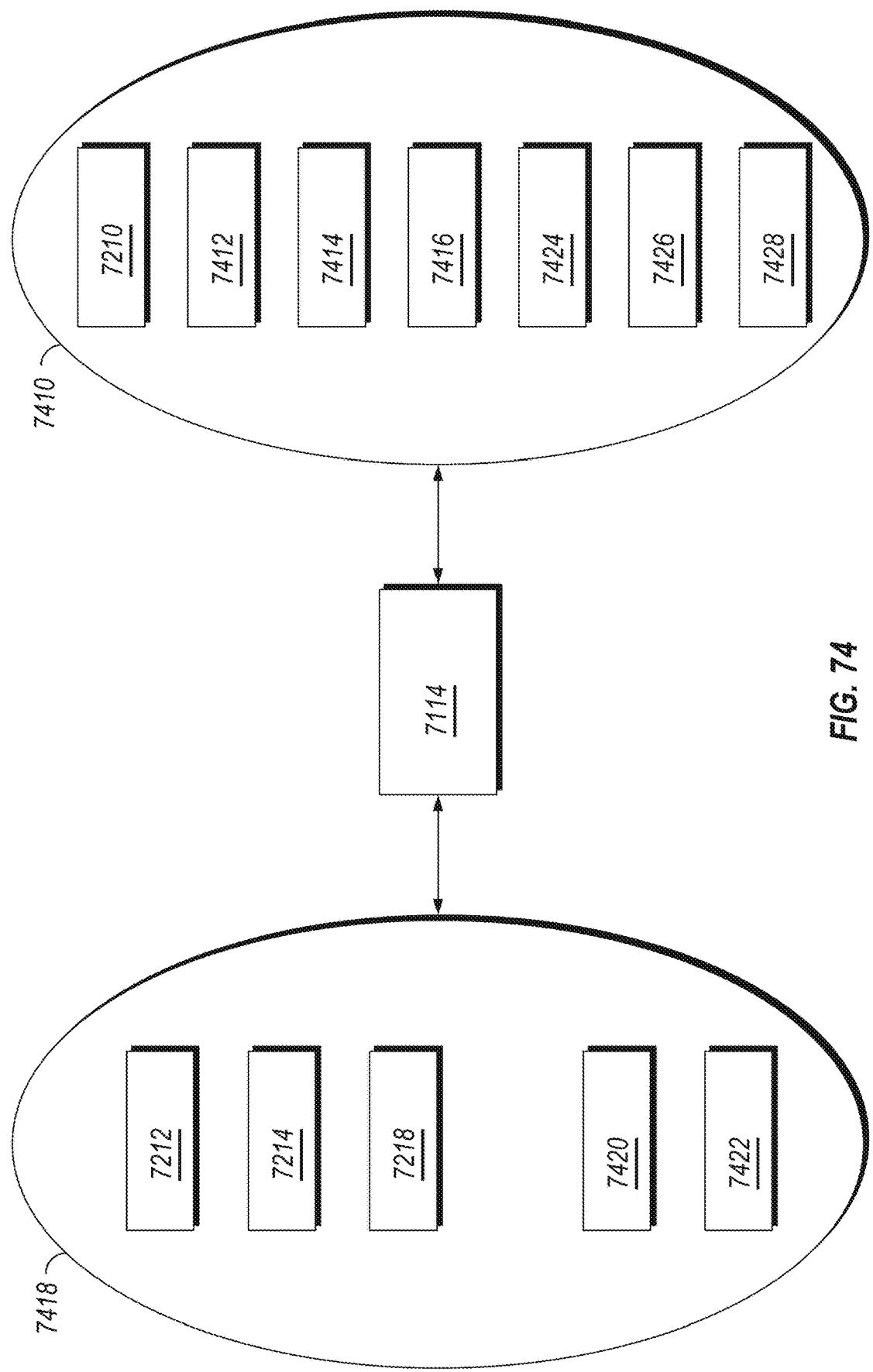
FIG. 74 is another diagram of the recommendation engine of FIG. 72, in accordance with an embodiment of the current disclosure.

Referring to FIG. 74, in embodiments, the design recommendation engine 7114 may generate one or more outputs 7410, including a list or a set of the recommended designs 7210. The list of recommended designs 7210 may be provided with criterion values 7412, scenario parameters 7414, and/or trial design parameters 7416. A non-limiting example of a list of recommended designs is shown in FIG. 75. As shown, the list may include design ID, power, costs, and/or duration for each listed design. The term "power", as used herein with respect to a clinical trial design may represent a measure of one or more properties and/or statistics of the clinical trial, e.g., statistical power. For example, power may provide an indication of how many patients are required to avoid a type I (false positive) or type II (false negative) error.

Inputs 7418 to the recommendation engine 7114 may include the clinical trial design results 7212, wherein the engine 7114 generates the Pareto 7214 and convex hull 7218 designs via the corresponding engines 7118 and 7120. In some embodiments, however, the Pareto designs 7214 and/or the convex hull designs 7218 may be fed to the engine 7114 as inputs 7418. The inputs 7418 may also include any other type of output from the Pareto 7118 and/or convex hull 7110 engines (facets, normal, etc.). In embodiments, the inputs 7418 to the recommendation engine 7114 may also include the set or a subset of all the designs simulated 7212 in addition to the P-designs 7214 and/or CH-designs 7218. Inputs 7418 may also include user settings 7420 and/or parameters 7422, such as the number of recommendations the recommendation engine 7114 should provide. The recommendation engine 7114 may receive user selections and other inputs 7418 that may provide guidance to the engine 7114 as to which designs are preferred by the user or which other designs the user wants to explore.

Figure 76:
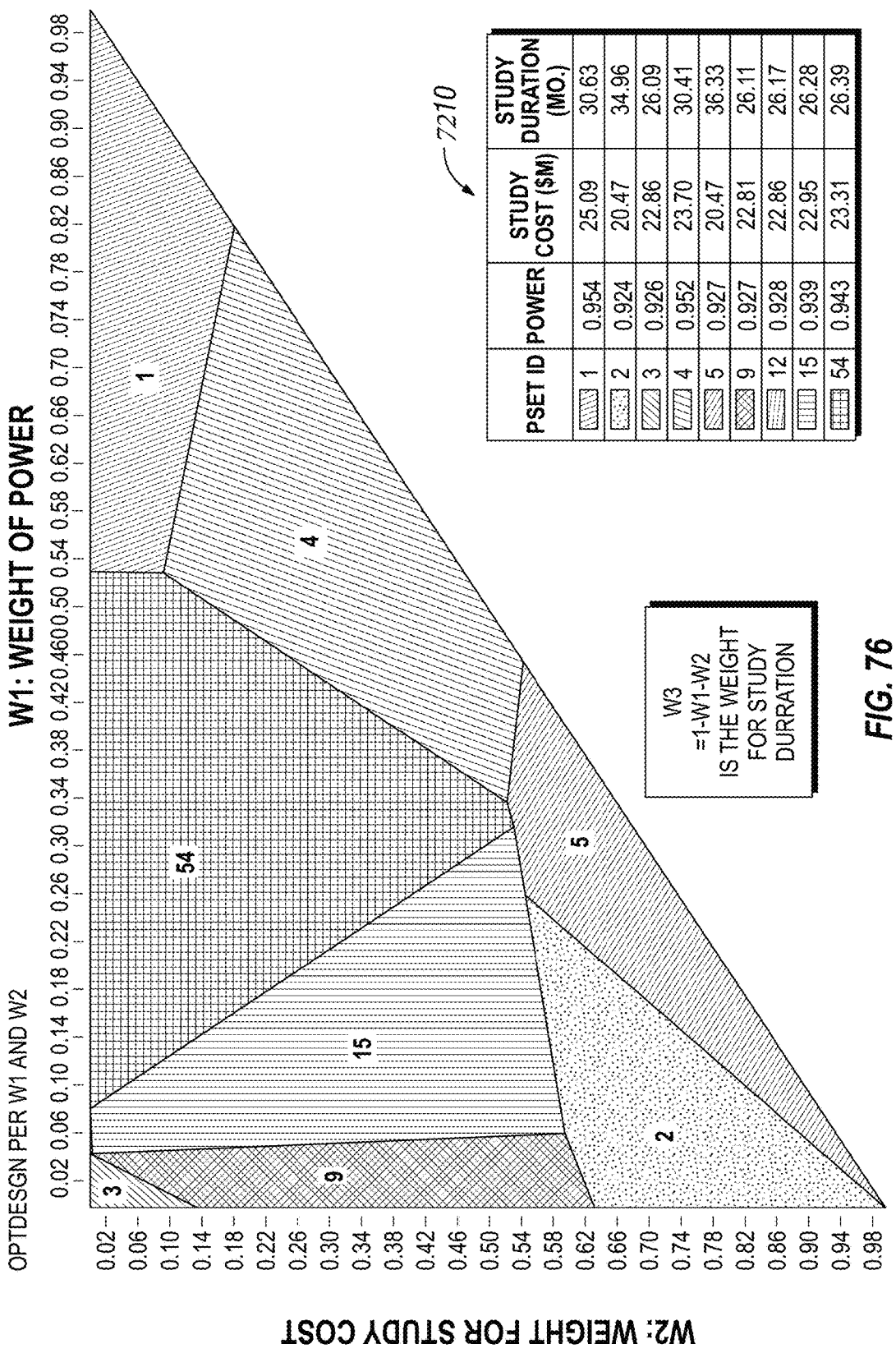
FIG. 76 is a diagram of a visualization of recommended clinical trial designs, in accordance with an embodiment of the current disclosure.
Figure 77:
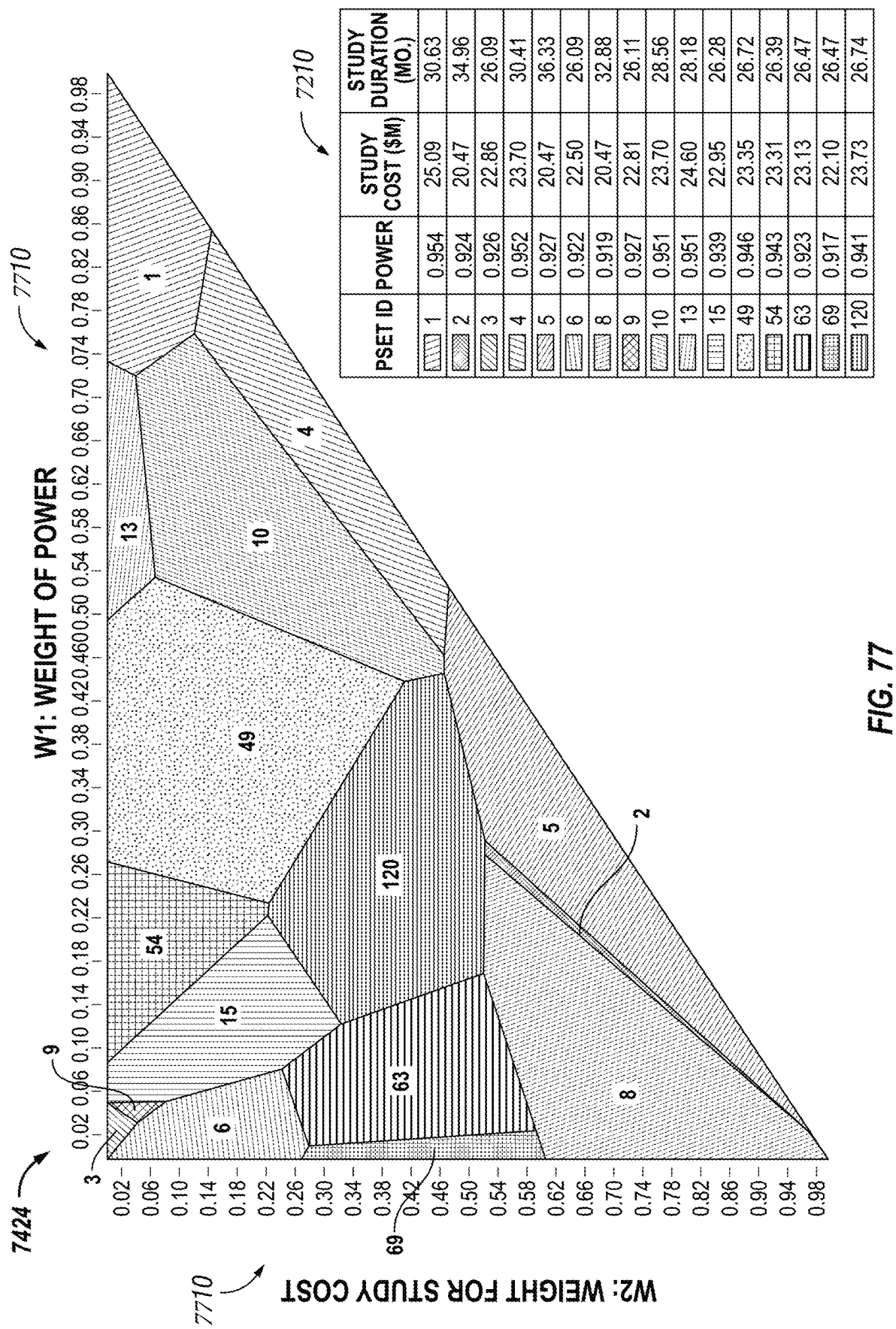
FIG. 77 is a diagram of another visualization of recommended clinical trial designs, in accordance with an embodiment of the current disclosure.

In embodiments, the algorithm/engine 7114 may generate or output visualizations and/or interfaces (collectively shown as 7424) to compare two or more recommended designs 7210. Non-limiting examples of the visualizations 7424 are depicted in FIGS. 76 and 77 and may be configured for performing sensitivity analysis on the recommended designs 7210, as described herein. Visualizations 7424 may also include other types of graphs and/or other visual representations that depict preference weights regions (polygons in three (3) criteria models), barycentric coordinate graphics, and/or the like. As shown in FIG. 76, visualizations may depict relationships between recommended designs 7210 with respect to weightings (W1—power and W2—costs) for performance criteria. As will be understood, the numbered polygons in FIG. 76 represent the range of weighting values for each of the recommended designs 7210, which may be optimal. As shown in 77, a visualization may depict the relationship of recommended designs, e.g., sixteen (16) different designs (numbered "1-6", "8-10", "13", "15", "19" "54", "63", "69", and "120"), with respect to weightings 7710 for performance criteria. Polygons may be used to represent the range of weighting values for each of the recommended designs which may be optimal.

The recommendation engine 7114 may also output lists or sets of designs, referred to herein as "related designs" 7426 (FIG. 74), that are close to the recommended designs 7210 in the criterion space (which may or may not be P-designs or CH-designs). Related designs 7426 may be determined using various distance measures. For example, one distance measure may be related to the steps needed for a simulated annealing algorithm 7116 (FIG. 71) to go from one design to another. In embodiments, the recommendation engine 7114 may provide recommendations for designs 7210 (based on the Pareto 7118 and/or the convex hull 7120 engine outputs) and allow a user to compare and analyze the recommended designs 7210 (sensitivity analysis, weigh graphs, etc.). The recommendation engine 7114 may provide lists of twin or sibling designs 7428 (FIG. 74) that are related to a selected design and show/highlight different types of designs that are available or close to a selected/recommended design.

In embodiments, design siblings 7428, and/or other different clinical trial designs that have similar performance criteria, may have different complexity. In some embodiments, types of clinical trial designs may be arranged and/or marked according to the complexity, ratings, historical preference, and/or the like. In some cases, clinical trial designs may be arranged in a hierarchy according to a preference such that, for example, designs that have lower complexity for a performance criteria are provided first. For example, in a case where multiple clinical trial designs have the same or nearly the same performance criteria, the multiple clinical trial designs may be ordered based on the properties of the designs when providing recommendations.

In embodiments, the recommendation algorithm/engine 7114 may include logic to reduce the set of CH-designs 7218 by a user-specified number by dropping CH-designs within the set 7218 with the objective of minimizing the maximum reduction of criteria values over the weight space. The recommendation engine 7114 may include logic to expand the CH-design set 7218 by choosing subsets of Pareto designs 7214 that are closest to the convex hull facet of the CHF cluster (facets may be Delaunay triangulations as described herein). The recommendation engine 7114 may include logic to fill gaps between recommended designs 7210. For example, Pareto designs 7214 in CHF clusters may be selected to fill large gaps (e.g., large facets and/or distances from a recommended design and a target point on the facet according to different metrics (e.g., multiple of criteria value differences ($\varepsilon_1, \varepsilon_2, \varepsilon_3, \ldots$))). The clusters may also be based on default and/or user-defined parameters, and/or average overall weights in a facet of the distance from a target point. The recommendation engine 7114 may include logic to calculate distances in design space to search for designs that are siblings, e.g., close in criterion space but distant in design.

In some embodiments, the recommendation engine 7114 may provide initial recommendations that cover all possible weightings of performance criteria. In such embodiments, the recommended designs 7210 may serve as anchor designs that facilitate further exploration of the simulated designs. Anchor designs may serve as initial points for design searches, e.g., simulated annealing, as described herein. The recommended designs 7210 may be designs that best approximated the performance (with respect to performance criteria) of the CH-designs 7218 and/or P-designs 7214. In embodiments, one or more cluster designs 7220 (FIG. 72) may be associated with each of the CH-designs 7218. The cluster designs 7220 may be generated by the Pareto engine 7118. In embodiments, the cluster designs 7220 may be used to provide rapid recommendations when more than a threshold number, e.g., twenty-four (24), of recommended clinical trial designs 7210 are desired, and/or when designs in a certain range of weights are desired. In embodiments, the cluster designs 7220 may include all of the Pareto designs 7214.

As will be understood, embodiments of the recommendation engine 7114 may present different types of designs within the recommended set of designs 720 that are similar in performance criteria. In certain aspects, the different types of designs may have similar performance criteria but different design parameters that may be more favorable for certain situations.

As will be further understood, in some embodiments, simulations of designs may not be exhaustive, i.e., the set of initial designs 7212 may be incomplete. For example, not every possible combination of clinical trial designs may be initially simulated, and/or a partial set of all clinical trial design combinations may be simulated and processed using one or more of the Pareto, convex hull, and recommendation algorithms/engines. In such cases, when a recommended design 7210 is provided, it may be true that a better, i.e., more optimal, design for the desired performance criteria exists in the space. In some cases, when a design is recommended 7212, the recommendation engine 7114 (and/or primary algorithm 4510, may further explore if there are designs that have better or similar performance to the recommended designs 7210 that have not been simulated. In embodiments, the simulated annealing algorithm/engine 7116 may be used to explore the design space around recommended 7210 and/or selected designs.

Figure 78:
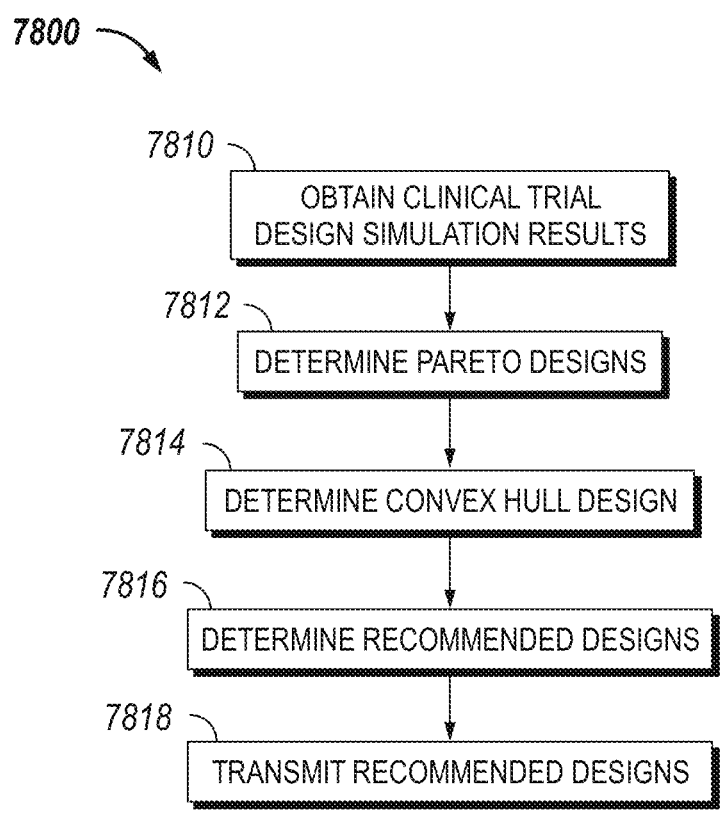
FIG. 78 is a flow chart depicting an embodiment of a method of recommending clinical trial designs, in accordance with the current disclosure.

Accordingly, turning now to FIG. 78, a non-limiting example of a method 7800 for recommending clinical trial designs in accordance with the current disclosure is shown. The method 7800 may include obtaining clinical trial design simulation results for a set of clinical trial designs 7810, and determining a set of Pareto designs 7812 based at least in part on the clinical trial design simulation results and one or more performance parameters of the kind described herein. The method 7800 may further include determining a set of convex hull designs 7814 based at least in part on the clinical trial design simulation results 7212 and/or the Pareto designs 7214. The method 7800 may further include determining a set of recommended designs 7816 based at least in part on the set of Pareto designs 7214 and/or the set of convex hull designs 7218. In embodiments, the method 7800 may further include transmitting the set of recommended designs 7818.

Figure 79:
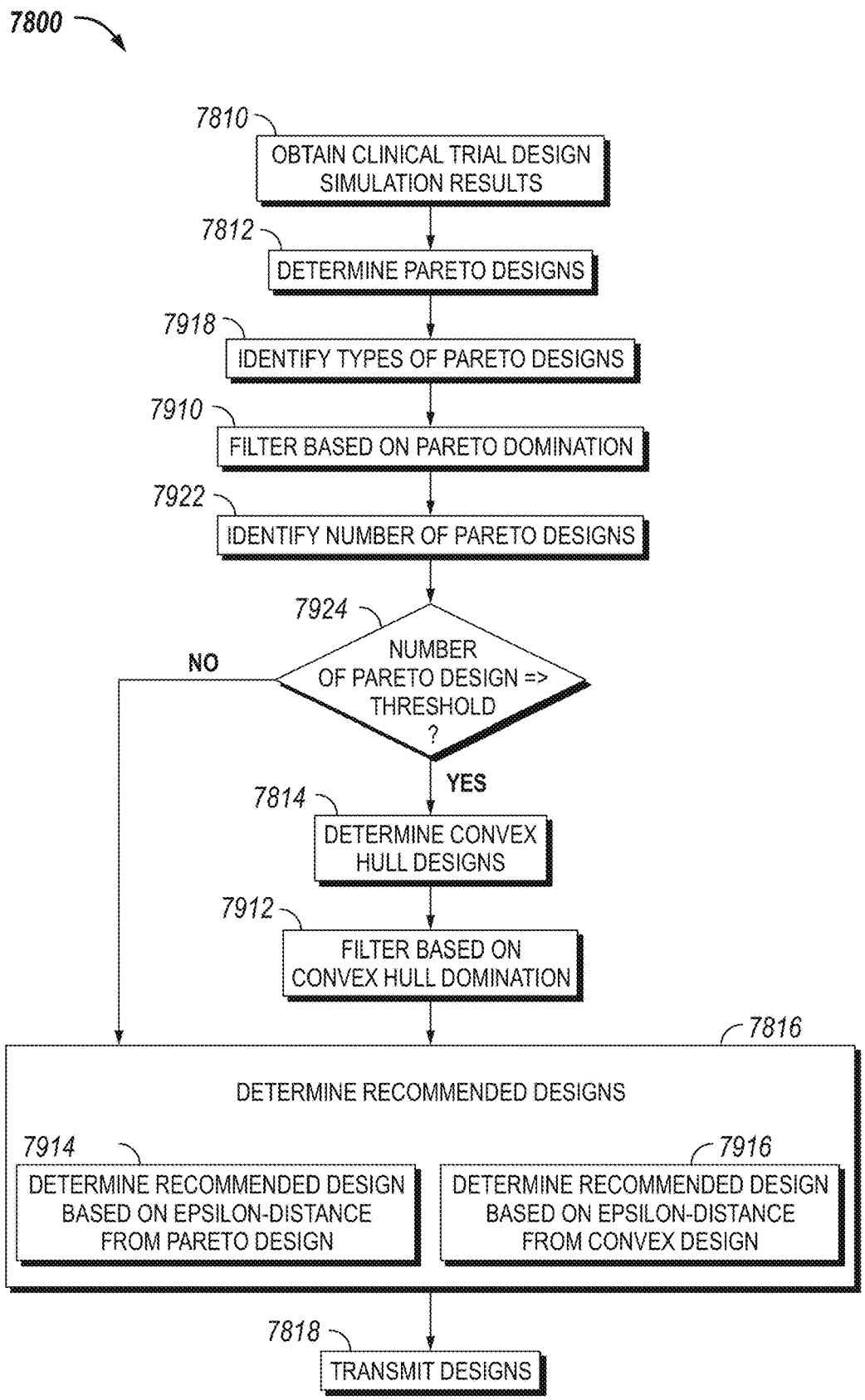
FIG. 79 is a flow chart depicting another embodiment of the method of FIG. 78, in accordance with the current disclosure.
Figure 80:
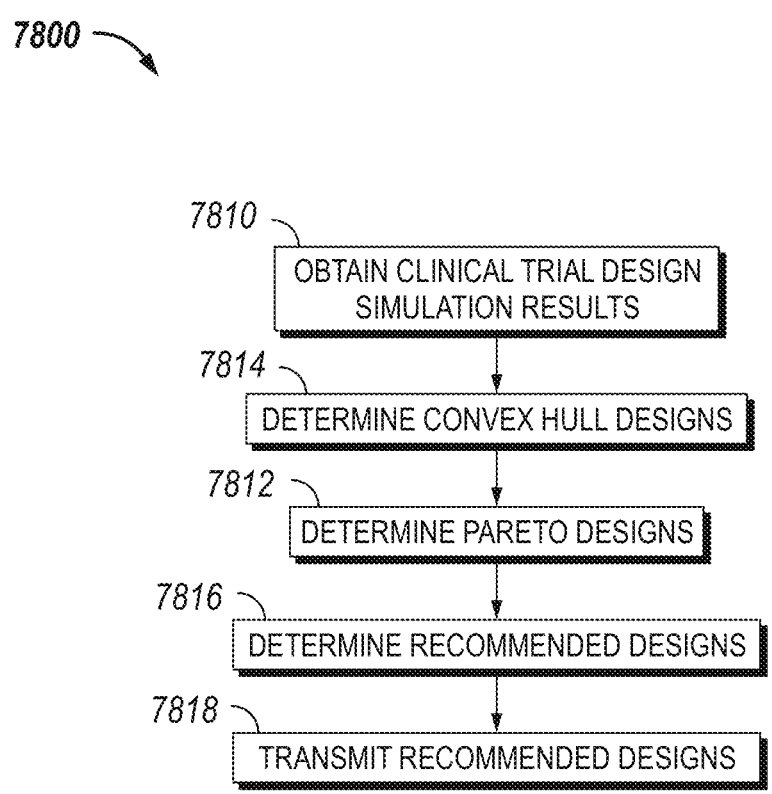
FIG. 80 is a flow chart depicting another embodiment of the method of FIG. 78, in accordance with the current disclosure.

Referring to FIG. 79, in embodiments, the method 7800 may further include filtering clinical trial designs which are dominated by Pareto designs 7910. The method 7800 may further include filtering clinical trial designs which are dominated by convex hull designs 7912. In embodiments, determining the recommended designs 7210 may include determining that at least one of the recommended designs 7210 is within an epsilon-distance from at least one of the Pareto designs 7914. In embodiments, determining the recommended designs 7210 may include determining that at least one of the recommended designs is within an epsilon-distance from at least one of the convex hull designs 7916. In embodiments, the method 7800 may further include identifying different design types in the set of Pareto designs 7918. As shown in FIGS. 78 and 79, the Pareto designs 7214 may be determined prior to determination the set of convex hull designs. In such embodiments, the convex hull designs 7218 may be derived from the Pareto designs 7214 such that each of the set of convex hull designs 7218 is one of the Pareto designs 7214, and such that at least one of the recommended designs 7210 is a convex hull design 7218. As shown in FIG. 80, in embodiments, the convex hull designs 7218 may be determined prior to determination of the Pareto designs. In such embodiments, the Pareto designs 7214 may be derived from convex hull designs 7218 such that each of the set of Pareto designs 7214 is a convex hull design 7218, and such that at least one of the recommended design 7810 is a convex hull design 7218.

Returning back to FIG. 79, the method 7800 may include identifying 7922 a number of clinical trial designs in the Pareto designs 7214, where the convex hull designs 7218 are determined 7814 when the number is greater-than-or-equal to a threshold 7924.

Figure 81:
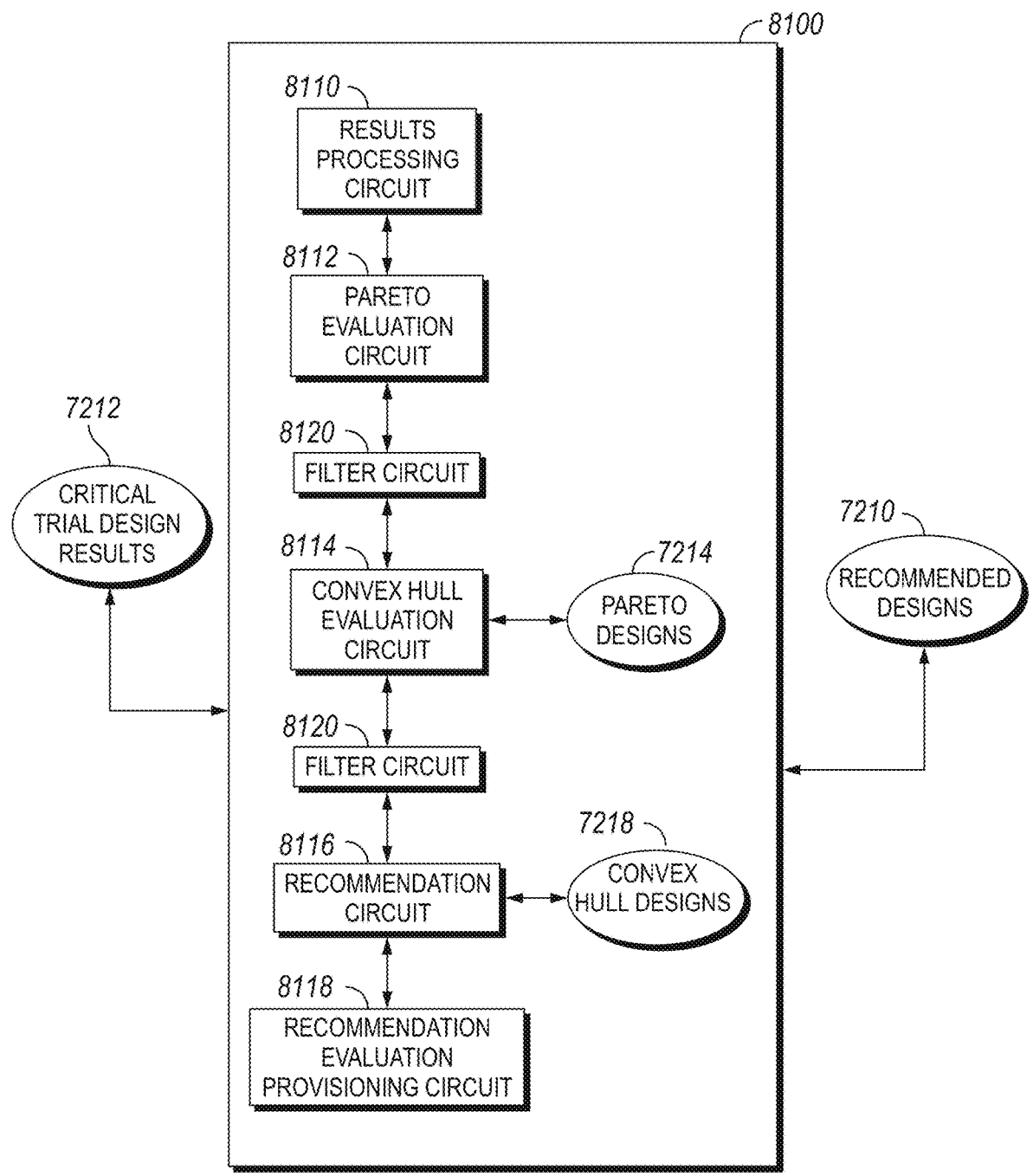
FIG. 81 is a schematic diagram of an apparatus for implementing the method of FIG. 78.

Referring now to FIG. 81, an apparatus 8100 for implementing the method 7800 is shown. The apparatus 8100 may include a results processing circuit 8110, a Pareto evaluation circuit 8112, a convex hull evaluation circuit 8114, a recommendation evaluation circuit 8116, and/or a recommendation evaluation provisioning circuit 8118. The results processing circuit 8110 is structured to interpret/obtain 7810 the clinical trial design simulation results 7212. The Pareto evaluation circuit 8112 is structured to determine 7812 the Pareto designs 7214 based at least in part on the clinical trial design simulation results 7212 and one or more performance criteria, as described herein. The convex hull evaluation circuit 8114 is structured to determine 7814 the convex hull designs 7218. The recommendation evaluation circuit 8116 is structured to determine 7816 the recommended designs 7210. The recommendation provisioning circuit 8118 is structured to transmit 7818 the recommended designs 7210. The apparatus 8100 may further include one or more filtering circuits, collectively represented by 8120, that perform filtering of the clinical trial designs 7212, Pareto designs 7214, and/or convex hull designs 7218, as described herein.

Figure 82:
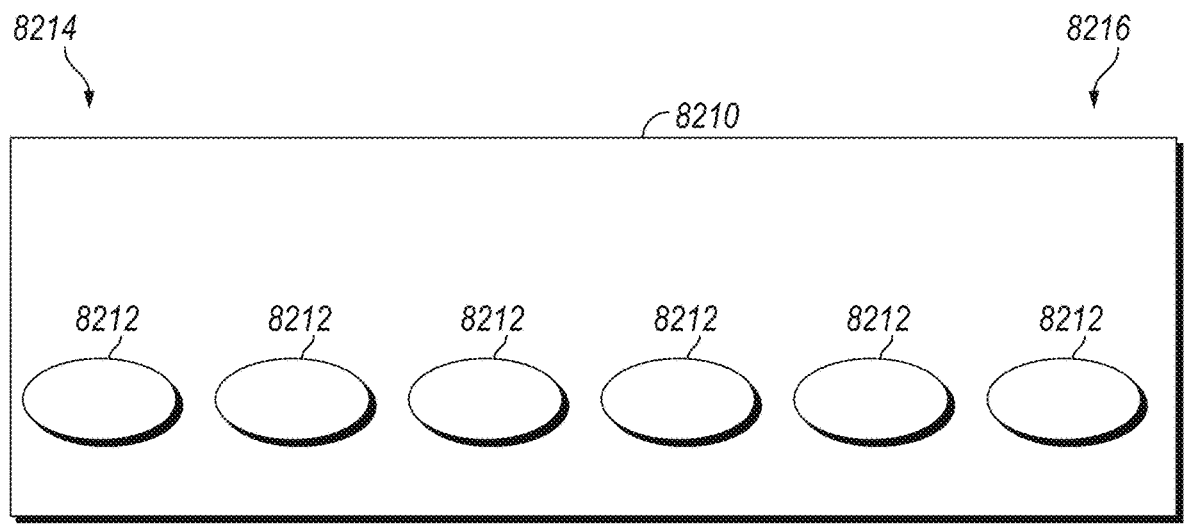
FIG. 82 is a diagram of a simulation queue, in accordance with an embodiment of the current disclosure.

Referring now to FIG. 82, a non-limiting example of a simulation queue 8210 for management and optimization of clinical trial designs 8212 is provided. The queue 8210 and/or corresponding methods described herein for operating the queue 8210, may implemented by the simulation facility 110, analysis facility 108, and/or other components of the platform 104 (FIG. 1). As shown in FIG. 82, the queue 8210 may have an entrance 8214, where yet to be simulated clinical trial designs 8212 are accepted, and an exit 8216, where the next to be simulated clinical trial design 8212 is pulled from.

In embodiments, simulations of clinical trial designs 8212 may be executed according to input queues, e.g., queue 8210, of individual simulation runs 8212, as described herein. Queues may be organized based on factors associated with the simulation runs, expected outputs of the simulation runs, and/or relationships between simulation runs. Non-limiting examples of such factors may include similarity, priority, costs, and/or complexity. The relationships may be discovered/identified using machine learning, e.g., artificial intelligence. For example, the simulation runs in a queue may be organized based on time required to run the simulations. In another example, the simulation runs in the queues may be organized to process the most promising designs first, thus facilitating quick access to most the promising designs.

Most promising designs may be identified from historical data and/or machine learning. A most promising design may be a clinical trial design that has a moderate-to-high chance, e.g., greater than 50%, of being a global optimal for a particular set of performance criteria. Historical data may be acquired from one or more data sources in the data facility 138 (FIG. 1). In one example, simulation runs in the queues may be organized based on user identified parameters. In one instance, simulation runs in the queues may be populated to provide an initial non-exhaustive sampling of the design space to provide of an overview of the performance of the clinical trial designs. The initial results may be used to populate queues for designs that are near designs that are in the desirable areas of the performance space. Simulated annealing, which may be provided by the search/exploration component 130 (FIG. 1) may be used to populate the queues with simulation runs for designs that are near initial simulated designs that are determined to be promising. The order of simulation runs in the queues may be revised based on results from initial simulations. Queues may also be organized to prioritize simulation runs to provide real-time results.

In certain aspects, queues, e.g., queue 8214, may be organized based on time and/or costs. For example, results of a first simulation run may be needed before results of a second simulation run. Additionally, a simulation run may be given a lower priority in a queue, and/or scheduled, so that it runs on a processing system during off-peak hours, thus, lowering costs. Queues may also be organized to execute simulation runs across different hosting providers, e.g., across multiple cloud computing systems. For example, higher priority simulation runs may be queued to run on a first cloud computing system, where the hosting provider charges a premium price for fast results, and lower priority simulation runs may be queued to run on a second cloud computing system, where the hosting provider charges a non-premium price for slower results. In certain aspects, queues may be organized by customer and/or across customers. For example, simulation runs for a first customer may be prioritized over simulation runs of a second customer. Queues may also be organized based on workload and/or work type. Queues may also be organized to assign simulation runs to either a binary computing system or a quantum computing system. For example, simulation runs that fall into the bounded error, quantum, polynomial time class, but outside of P, may be assigned to a quantum computing system, while P class problems may be assigned to a binary computing system. Artificial intelligence, e.g., machine learning, may also be used to organize queues, to include populating and distributing simulation runs. For example, in embodiments, a neural network training set may include a variety of clinical trial designs and whether they were previously selected as being a global optimum design for a particular scenario. Using such a scenario, the neural network may learn to identify promising clinical trial designs and prioritize them in one or more queues. In embodiments queue organization may be based at least in part on metadata associated with the models and/or engines. Metadata may include data regarding what engines, run times, resources, and the like are necessary for simulation.

While FIG. 82 depicts a single queue 8210, embodiments of the current disclosure may include multiple queues executing on multiple machines, e.g., computing resources 150 (FIG. 1).

Figure 83:
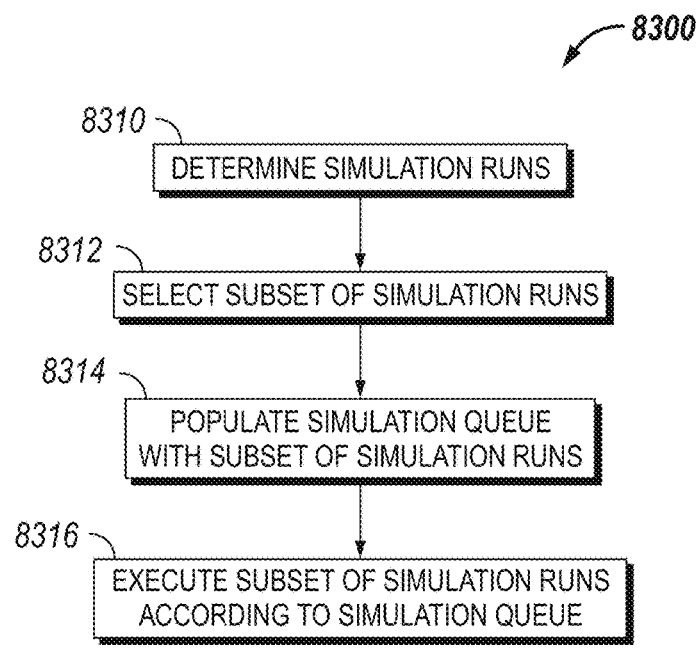
FIG. 83 is a flow chart depicting a method for management and optimization of clinical trial designs, in accordance with an embodiment of the current disclosure.

Illustrated in FIG. 83 is a method 8300 for management and optimization of clinical trial designs. The method 8300 may include determining simulation runs for a trial design study 8310. The method 8300 may further include selecting a subset of the simulation runs 8312. The method 8300 may further include populating a simulation queue with the subset of the simulation runs 8314. The method may further include executing the subset of simulation runs according to the simulation queue 8316.

Figure 84:
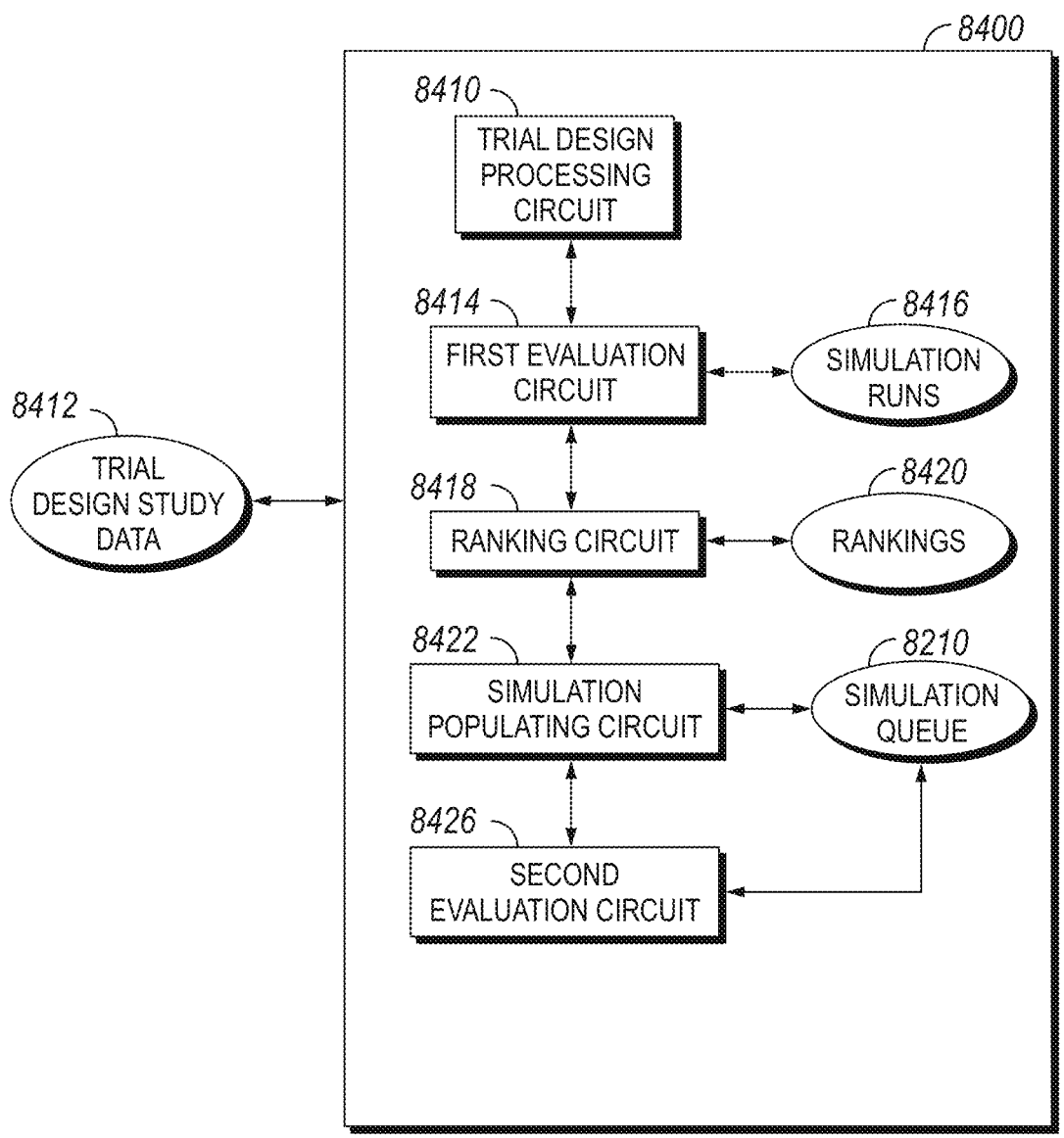
FIG. 84 is a schematic diagram of an apparatus for management and optimization of clinical trial designs, in accordance with an embodiment of the current disclosure.

Illustrated in FIG. 84 is an apparatus 8400 for management and optimization of clinical trial designs. The apparatus 8400 includes a trial design processing circuit 8410 structured to interpret trial design study data 8412. The apparatus 8400 includes a first evaluation circuit 8414 structured to execute simulation runs 8416 of clinical trial designs defined, in part, by the trial design study data 8412. The apparatus 8400 includes a ranking circuit 8418 structured to, in response to executing the simulation runs 8416, rank the simulation runs 8416 according to expected performance, i.e., generate rankings 8420 for the simulation runs 8416. In certain aspects, the expected performance data may be based on data derived from a database of simulated designs. The apparatus 8400 includes a simulation populating circuit 8422 structured to populate a simulation queue 8210 according to the simulation run rankings 8420. The apparatus 8400 includes a second evaluation circuit 8426 structured to execute simulation runs from the simulation queue 8210. In embodiments, the rankings 8420 may be revised based at least in part on the outputs of simulated runs.

Figure 85:
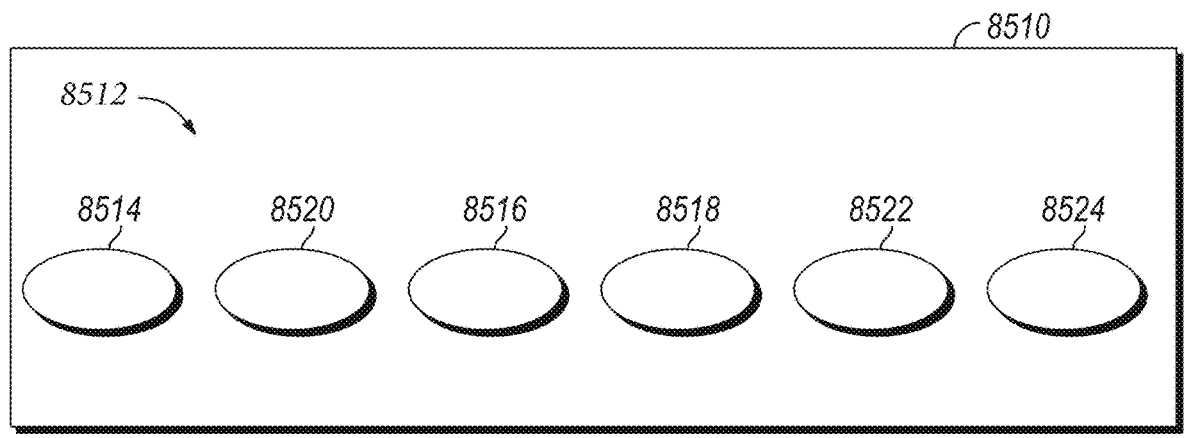
FIG. 85 is a block diagram of a simulation engine marketplace, in accordance with an embodiment of the current disclosure.

As described herein, simulations of trial designs may use simulation engines. Accordingly, referring now to FIG. 85, a marketplace 8510 for simulation engines 8512 is shown. The marketplace 8510 may form part of the engines component 128 (FIG. 1) and/or computing resources 150 (FIG. 1), or the marketplace 8510 may be a stand-alone system that communicates with the platform 104 via one or more application programming interfaces (APIs). The marketplace 8510 may serve as a repository/library which users can browse and/or search for engines suited to a particular need/scenario. Engines 8512 may be selected based on different criteria including, cost, run time, complexity of model, outputs of model, etc. As explained in greater detail herein, selected engines 8512 may be incorporated into the platform 104, e.g., via the engine component 128, for subsequent use in clinical trial design simulations, as described herein. For example, in embodiments, the simulation facility 110 (FIG. 1) may use two or more different engines 8512 from the marketplace 8510.

Entities, e.g., third party and/or in-house developers, may create simulation engines 8512 for use with different design types, design complexity, and/or the like. The created engines 8512 may then be uploaded into the marketplace 8510 via a web interface, an application programming interface, a File Transfer Protocol (FTP) interface or other suitable technology for transferring data and/or software files. The marketplace 8510 may include one or more filters which a user can use to limit and/or control which engines 8512 are displayed based on one or more properties. For example, a user may only want to view engines are configured for a particular clinical trial type (engines 8514, 8516, and 8518) and/or may only want to view engines that have been authored by a trusted developer (engines 8520, 8522, 8524). For example, trial type X, e.g., a cluster randomized design, may require a different type of engine than trial type Y, e.g., an adaptive randomization design.

Figure 86:
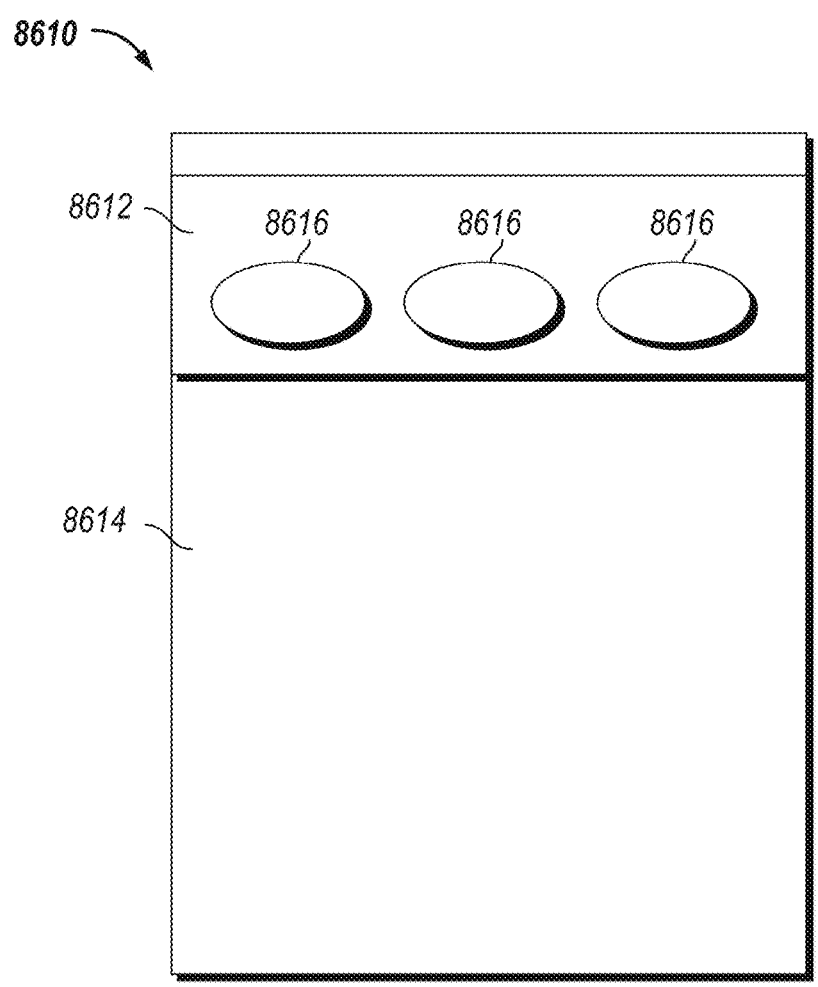
FIG. 86 is a block diagram of a simulation engine, in accordance with an embodiment of the current disclosure.

Turning to FIG. 86, a non-limiting example of a simulation engine 8610 is shown. In embodiments, the simulation engine 8610 may include a header section 8612 and a main body 8614. The main body 8614 may include one or more modules for performing a clinical trial simulation, or aspects thereof. The header section 8612 may include one or more definitions 8616 that identify the various inputs used by one or more modules of the main body 8614. One or more of the definitions 8616 may define an expected output of the engine 8610. One or more definitions 8616 may define the developer of the engine 8610 and/or a version number of the engine 8610.

Upon being selected, the header section 8612 may be registered with an engine registry of the platform 104, e.g., the engine component 128. Registration of an engine 8610 may include the registry interrogating the header section 8612 to determine one or more required inputs and/or expected outputs of the engine 8610. Registration of an engine 8610 may make the engine 8610 available as a selectable option in one or more of the interfaces of the platform 104, such as in the advisors 114. Registration of the engine 8610 may also include the registry determining one or more values for the inputs to the engine 8610 based on known settings and/or values for various components of the platform 104. For example, an input of an engine 8610 specifying how many trial designs can be simulated concurrently by the engine 8610 may be set to a particular value based on known available memory and/or processing resources the platform 104 can make available to the engine 8610.

Figure 87:
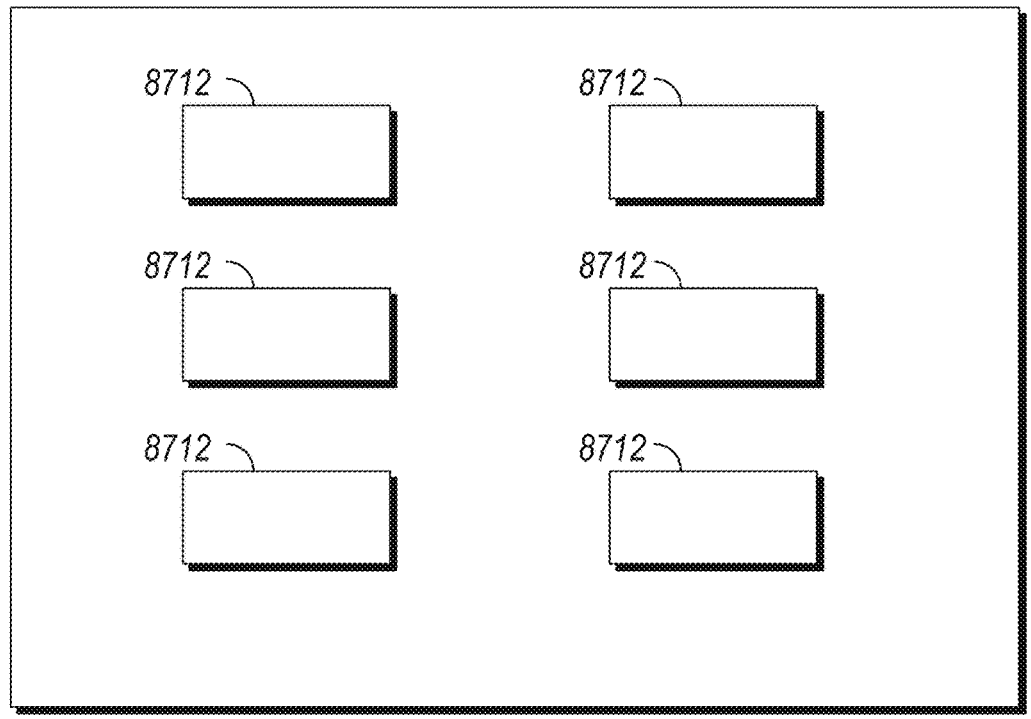
FIG. 87 is a diagram of an interface with fields populated based at least in part on a header section of a simulation engine in accordance with an embodiment of the current disclosure.

Turning to FIG. 87, the header section 8612, to include the definitions 8616, may be used by one or more of the interfaces of the platform 104, as described herein and represented generally by 8710, to populate one or more fields 8712. The fields 8712 may include dialogue boxes, text fields, input fields, and/or other suitable widgets for conveying one or more of: current values/settings for inputs to the engine 8610; requested values/setting for inputs to the engine 8610; recommended value/settings for inputs to the engine 8610; and/or other information regarding the engine 8610.

In embodiments, inputs to the engine 8610 defined by the user may be saved for later use, which may include system audits and/or replication of past outputs. For example, a simulation may track the version number and/or inputs of each engine used in the simulation such that the simulation may be reproduced. Versions of each engine and inputs associated with each engine (such as a seed value) may be recorded, stored and/or associated with each trial design, including for purposes of audit or replication.

Figure 88:
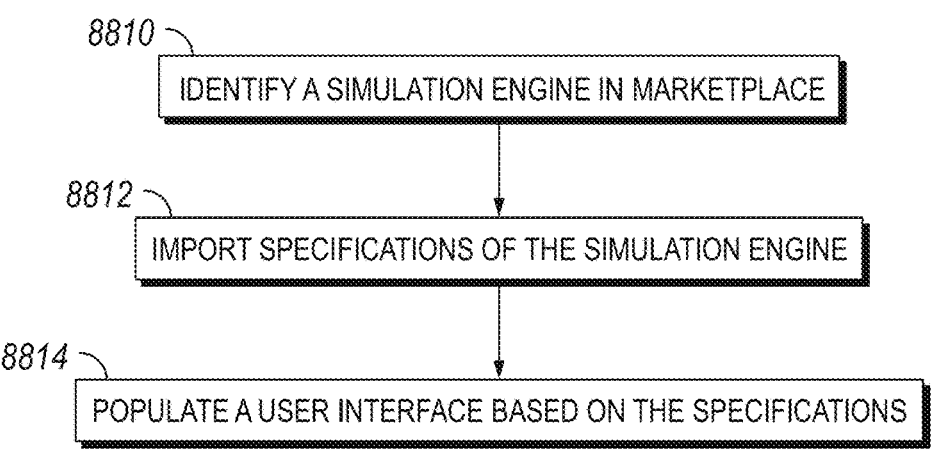
FIG. 88 is a flow chart depicting a method for using a simulation marketplace in accordance with an embodiment of the current disclosure.

Moving to FIG. 88, a method 8800 for using a simulation engine marketplace is shown. The method 8800 includes identifying, in the marketplace, a simulation engine for simulating a clinical trial design 8810. The method 8800 further includes importing specifications, e.g., definitions 8616 (FIG. 86), of the simulation engine 8812, and populating a user interface based on the specification 8814.

Figure 89:
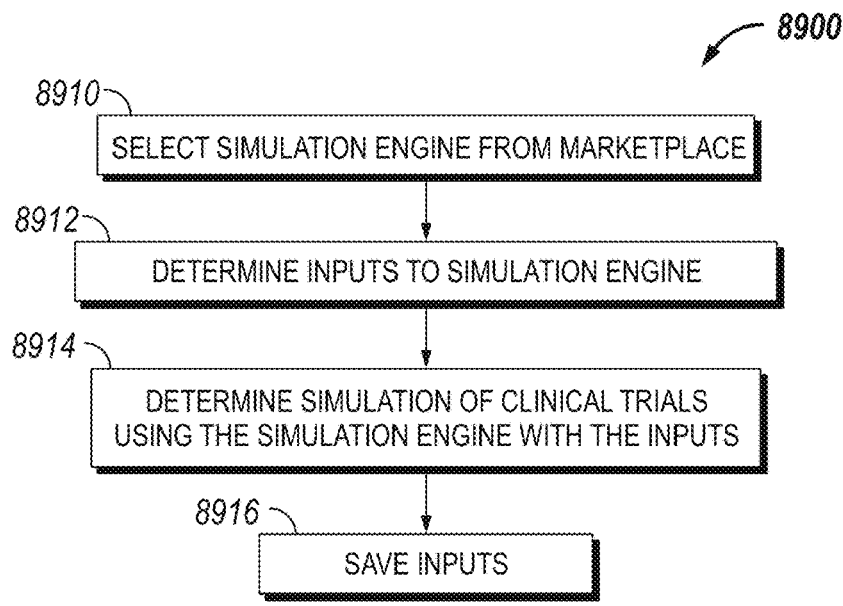
FIG. 89 is a flow chart depicting another method for using a simulation marketplace in accordance with an embodiment of the current disclosure.

FIG. 89 depicts another method 8900 for using a simulation engine marketplace. The method 8900 includes selecting a simulation engine from a marketplace 8910, the simulation engine for simulating a clinical trial design. The method 8900 further includes determining inputs to the simulation engine 8912 and executing a simulation of the clinical trial design using the simulation engine with the inputs 8914. The method 8900 may include saving the inputs 8916.

Figure 90:
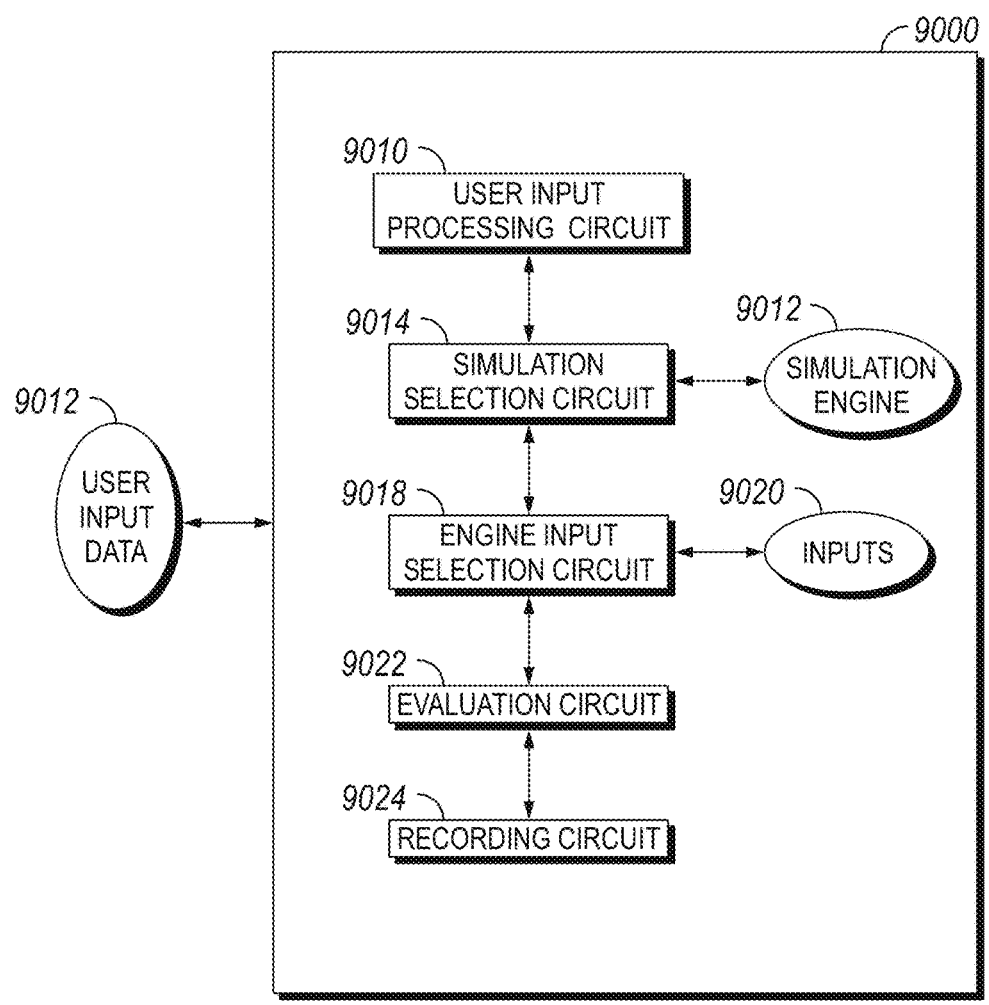
FIG. 90 is a schematic diagram of an apparatus for using a simulation marketplace in accordance with an embodiment of the current disclosure.

FIG. 90 depicts an apparatus 9000 for using a simulation engine marketplace. The apparatus 9000 includes a user input processing circuit 9010 structured to interpret user input data 9012. The apparatus 9000 includes a simulation selection circuit 9014 structured to determine a simulation engine 8512 based at least in part on the user input data 9012. The apparatus 9000 further includes an engine input selection circuit 9018 structured to determine inputs 9020 to the simulation engine 8512 based at least in part on the user input data 9012. The apparatus 9000 further includes an evaluation circuit 9022 structured to execute/conduct a simulation using the determined simulation engine 8512 and determined inputs 9020. In embodiments, the apparatus 9000 may further include a recording circuit 9024 structured to save the determined inputs 9020 and the determined simulation engine 8512 to a memory device, e.g., data component 138 (FIG. 1).

Embodiments of the current disclosure may provide for one or more methods and apparatuses for evaluating seemingly disparate simulation engines so that a user can determine the most effective and/or efficient engine(s) to use for a particular simulation. As described herein, simulations may use different design models 126 (FIG. 1) and/or simulation engines 128 (FIG. 1). In embodiments, the simulation facility 110 (FIG. 1) may use various engines to simulate different design types, including different design types within one overall clinical trial design simulation. Non-limiting examples of differences in engines and/or engine types include: different underlying purposes, e.g., convex hull analysis vs. simulated annealing, etc.; different creators, e.g., in-house development teams, vendors, suppliers, etc.; versioning, e.g., an update to an existing engine of "version 1.0" to "version 1.5", etc.; and/or other variations.

As will be understood, different engines may not be uniform in how they evaluate performance criteria. For example, engines created by different entities may make different assumptions and/or use different logic flows to determine performance criteria for a given simulation. Evaluation of simulated designs often requires that the determined performance of an engine can be correctly and/or practically compared against the determined performance of other engines. As such, embodiments of the current disclosure provide for benchmarking of engines so that their outputs can be normalized to reduce and/or eliminate variations and/or scale the outputs. Reducing variations between engines, in turn, provides for engines to be accurately compared against one another. In embodiments, benchmarking may include simulating one or more designs using various engines. Benchmarking may also include varying one or more parameters common across several different engines/design models and monitoring for corresponding variations/changes in performance criteria, e.g., engine outputs. Based on the changes, a normalizing factor for one or more engines may be determined. Benchmarking may also include providing a set of inputs with a corresponding set of expected outputs, feeding the inputs to one or more engines to generate actual outputs, and comparing the actual outputs to the expected outputs.

Figure 91:
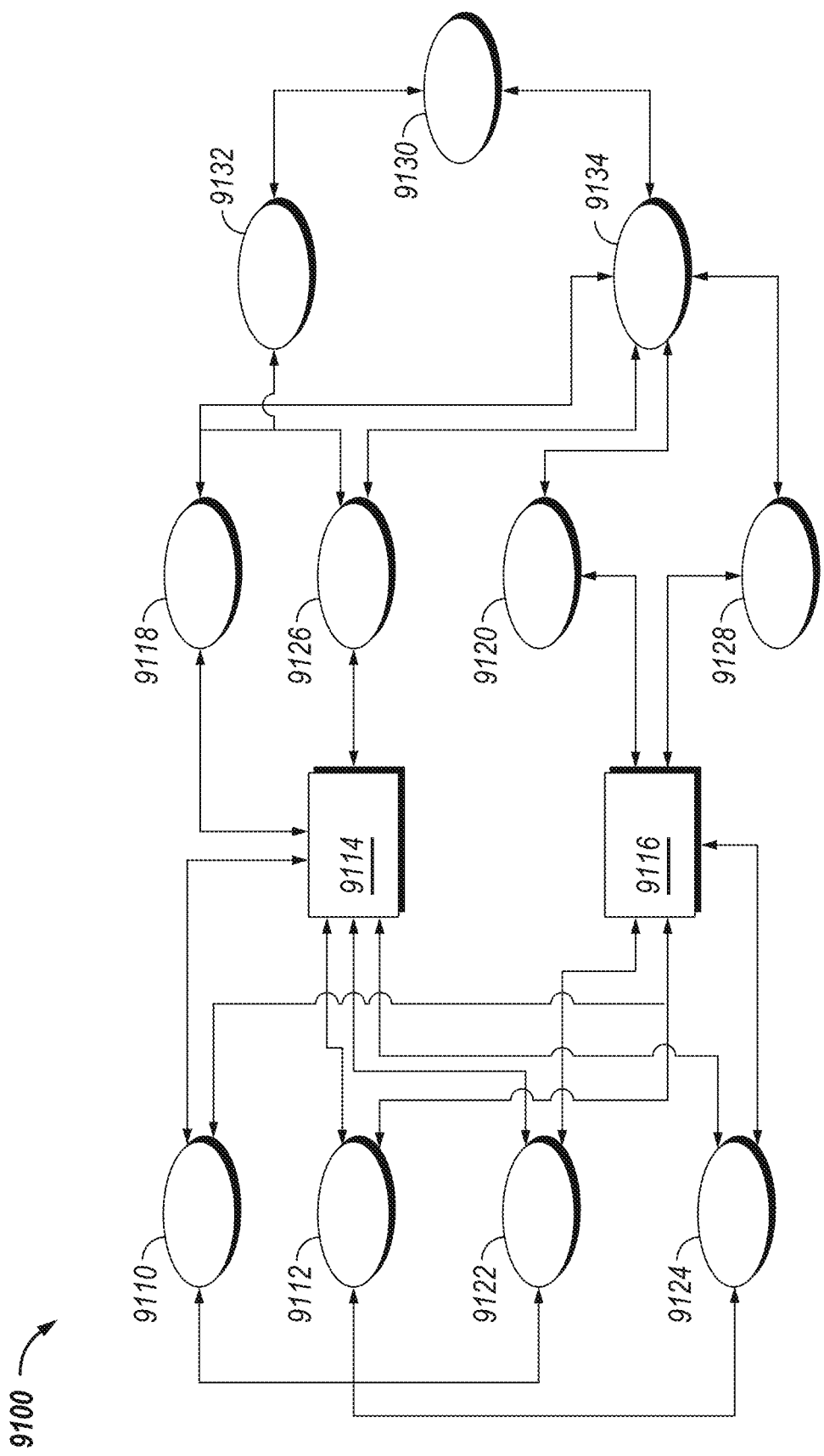
FIG. 91 is a diagram for a process for benchmarking and/or normalizing simulation engines, in accordance with an embodiment of the current disclosure.

Accordingly, referring now to FIG. 91, a block diagram of a process 9100 for benchmarking and/or normalizing simulation engines, in accordance with an embodiment of the current disclosure, is shown. The process 9100 may provide a plurality of inputs 9110 and 9112 to a plurality of clinical trial design simulation engines 9114 and 9116. The clinical trial design engines 9114 and 9116 may then generate first outputs 9118 and 9120 based on the inputs 9110 and 9112. Variations 9122 and 9124 of the inputs 9110 and 9112, respectively, may be generated and provided to the engines 9114 and 9116 so that second outputs 9126 and 9128 are generated. In embodiments, the variations 9122 and/or 9124 may include single item changes, e.g., a single parameter value, from their corresponding inputs 4510 and/or 9112. In embodiments, the variations 9122 and 9124 may be structured to test specific functions of the engines 9114 and 9116. For example, the only difference between variation 9122 and input 9110 may be a value for an expect cost of a clinical trial design. Non-limiting examples of variations may also include difference in number of expected recruited patients, expected drug costs, expected administrative costs, site availability, drug availability, duration of the trial, and/or any other type of performance criteria and/or parameter for simulating a clinical trial design.

The set of outputs 9118, 9120, 9126 and/or 9128 may then be evaluated to determine one or more normalization factors 9130. In embodiments, the normalization factors 9130 may be based on delta values 9132 and 9134 generated by comparing one or more of the outputs to each other. For example, in embodiments, the outputs 9118 and 9126 of an engine 9114 may be compared to generate delta value 9132, wherein the delta value 9132 may represent effects that varying the input 9110 had on engine 9114. In embodiments, output 9118 could be compared to outputs 9126, 9120, and 9128 to determine delta value 9134, wherein the delta value 9134 may reflect differences between how engines 9114 and 9116 handles variance to the inputs 9110 and 9112.

In embodiments, the normalization factors 9130 may provide for a common metric by which to measure the performance of one or more of the plurality of engines 9114 and 9116 against each other. In certain aspects, the normalization factors 9130 may be multiplied against one or more of the outputs 9118, 9120, 9126, and/or 9128. In embodiments, the normalization factors 9130 may differ with respect to differences between the inputs 9110 and 9112 and their corresponding variations 9122 and 9124.

In embodiments, a first clinical trial design simulation engine 9114 of the plurality may be structured to simulate a first clinical trial design that is of a different type than a second clinical trial design which a second clinical trial design simulation engine 9116 of the plurality is structured to simulate. For example, engine 9114 may be structured to simulate trial designs comparing two different drugs to each other, while engine 9116 may be structured to simulate trial designs for evaluating non-drug related therapies. In embodiments, a first clinical trial design simulation engine 9114 of the plurality may be of a different version of a second clinical trial design simulation engine 9116 of the plurality. For example, engine 9116 may be an updated version of the engine 9114, wherein 9116 may utilize different logic and/or other programmatic changes. In embodiments, a first clinical trial design simulation engine 9114 of the plurality may have been generated by a first entity and a second clinical trial design simulation engine 9116 of the plurality may have been generated by a second entity of the plurality distinct from the first entity. For example, engine 9114 may be structured to simulate the same type of clinical trial designs for which engine 9116 is structured to simulate, but engine 9114 may have been built by an in-house development team while engine 9116 may have been built by a user of the platform, third-party contractor or separate company. In embodiments, the outputs 9118, 9120, 9126, and/or 9128 may include metadata.

Non-limiting examples of metadata may include version number of the engine used, authorship of the engine used, creation/simulation date of the output, and/or other types of properties.

In embodiments, the delta values 9132 and/or 9134 may represent output variability between one or more of the engines 9114 and 9116 for similar inputs, e.g., input 9110, or between the same engine 9114 across an input 9110 and the corresponding variation 9122. In embodiments, the delta values 9132 and 9134 and/or the normalization factors 9130 may be used, in part, to determine valid ranges for the output values of an engine 9114 and 9116. The valid ranges, in turn, may be used to determine whether an engine is providing faulty information, e.g., the engine may have incorrect logic and/or coding errors.

Figure 92:
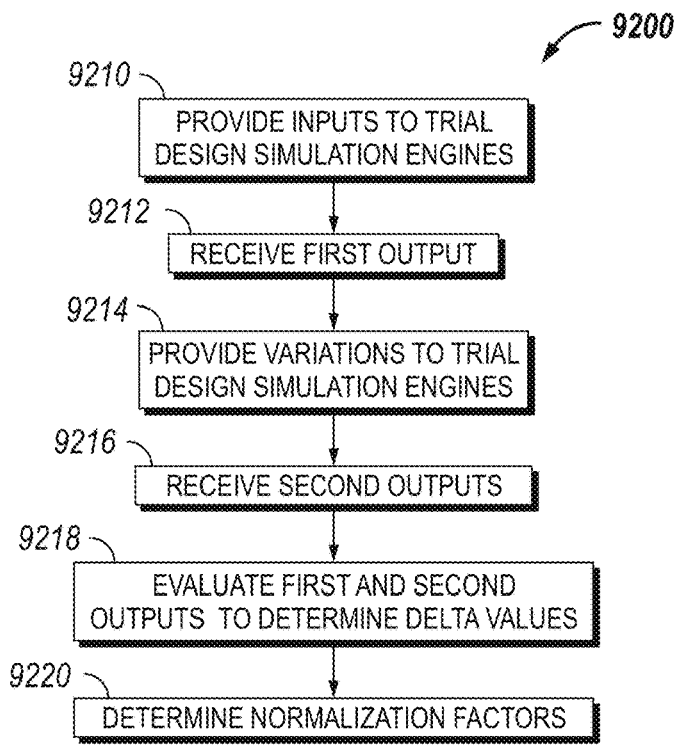
FIG. 92 is a flow chart depicting a method for benchmarking and/or normalizing simulation engines, in accordance with an embodiment of the current disclosure.

Illustrated in FIG. 92 is a method 9200 for benchmarking and/or normalizing clinical trial design simulation engines. The method 9200 includes providing inputs to a plurality of clinical trial design simulation engines 9210. The method 9200 includes receiving first outputs of the plurality of clinical trial design simulation engines in response to the inputs 9212. The method 9200 includes providing variations of the inputs to the plurality of clinical trial design simulation engines 9214. The method 9200 further includes receiving second outputs of the plurality of clinical trial design simulation engines in response to the variations 9216. The method 9200 includes evaluating the first and the second outputs to determine delta values 9218. The method 9200 includes determining, based in part on the delta values, a plurality of normalization factors for the plurality of clinical trial design simulation engines 9220.

In embodiments, engine variability may be confined to small number of parameters or values. For example, variations in engine versions (such as from one version to another) may be confined to minor algorithm changes related to corner cases, extreme values or the like. In some cases, various versions of engines may perform exactly the same except for a small range of values at extreme ends or specific values. Engines may be evaluated for exact ranges of inputs and/or outputs for which engines are comparable, ranges of inputs and/or outputs for which engines differences exhibit acceptable error, and range of inputs and/or outputs for which engines are not comparable. Configuration data may be used to indicate for which values and/or ranges of values engines are comparable. Data that is in the comparable range may be marked as comparable. Data in other ranges may be flagged as not comparable or marked with an estimated error for user review. In some cases, a user may specify threshold for acceptable error values.

Figure 93:
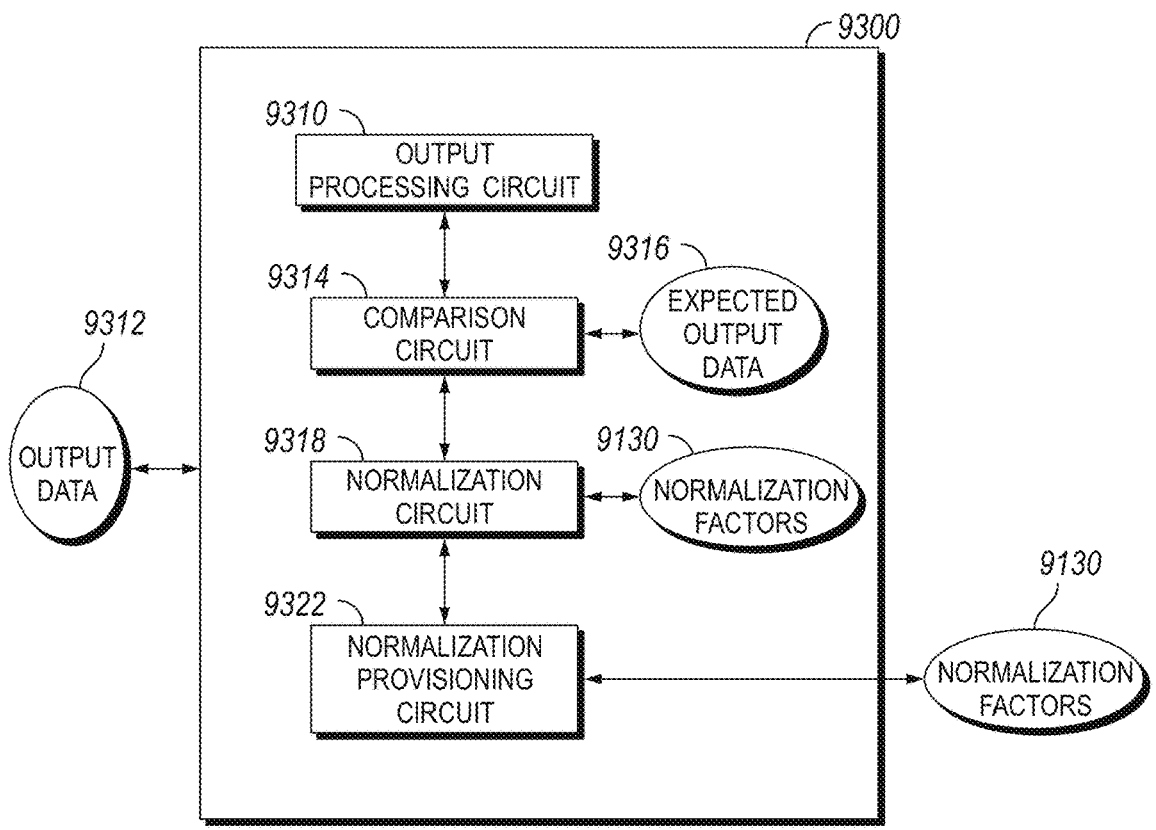
FIG. 93 is a schematic diagram of an apparatus for benchmarking and/or normalizing simulation engines, in accordance with an embodiment of the current disclosure.

Referring to FIG. 93, an apparatus 9300 for benchmarking and/or normalizing clinical trial design simulation engines is shown. The apparatus 9300 includes an output processing circuit 9310 structured to interpret output data 9312 from a plurality of clinical trial design simulation engines, e.g., 9114 and 9116 (FIG. 91). Output data 9312 may correspond to one or more of output data 9118, 9120, 9126, and/or 9128 (FIG. 91). The apparatus 9300 includes a comparison circuit 9314 structured to compare the interpreted output data 9312 to expected output data 9316. Expected output data 9316 may include previously calculated outputs for the engines 9114 and/or 9116 and/or outputs, calculated using engines outside of the plurality of engines 9114 and 9116, for the inputs 4510 and/or 9112 (FIG. 91), e.g., an agreed upon benchmark standard. The apparatus 9300 includes a normalization circuit 9318 structured to determine a plurality of normalization factors 9130 for the plurality of clinical trial design simulation engines 9114 and 9116. The apparatus 9300 further includes a normalization provisioning circuit 9322 structured to transmit the plurality of normalization factors 9130.

Figure 94:
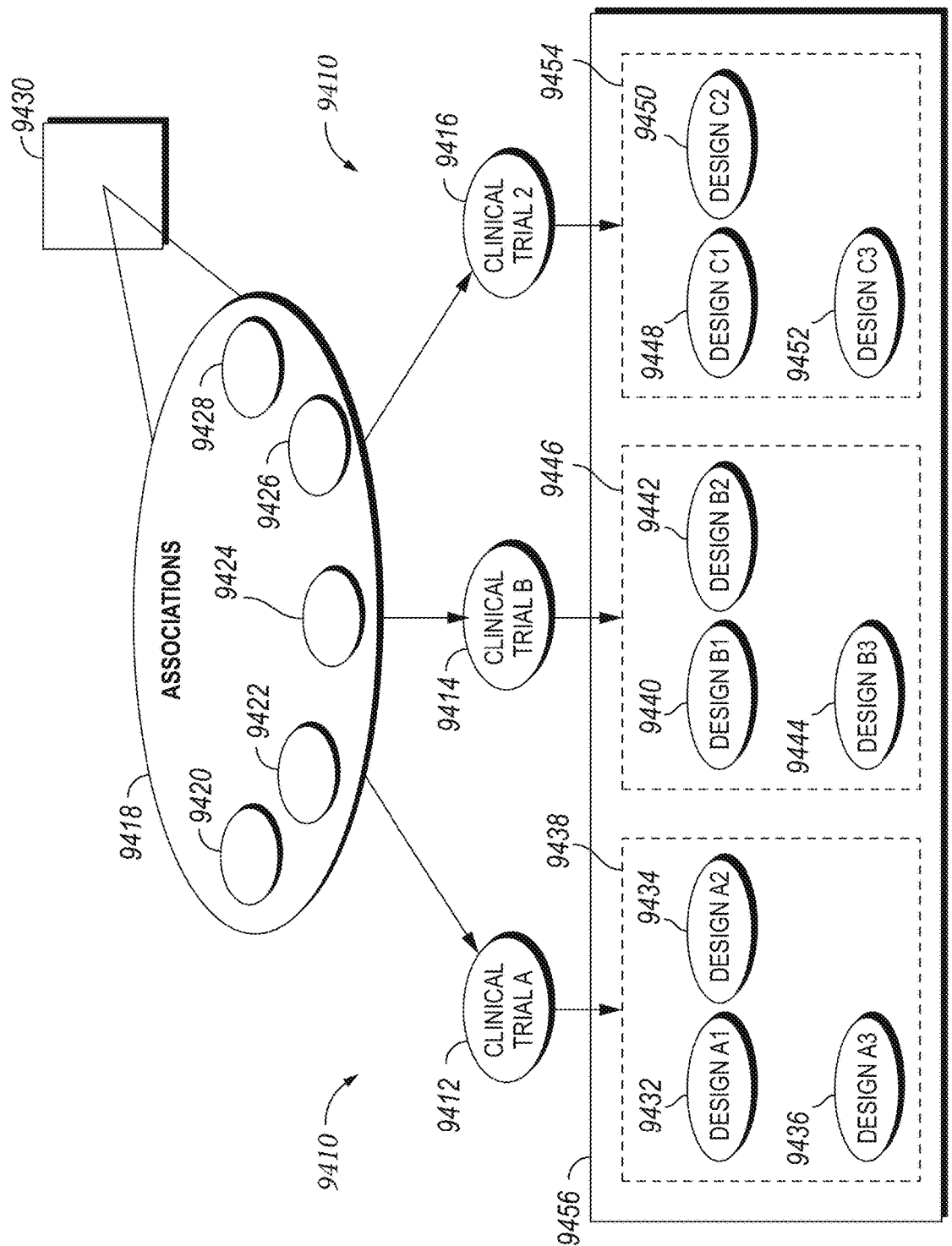
FIG. 94 is a block diagram of a plurality of clinical trials and corresponding clinical trial designs for optimization, in accordance with an embodiment of the current disclosure.

Referring now to FIG. 94, in addition to optimizing a design for a single clinical trial, embodiments of the platform 104 (FIG. 1) may provide for optimization of clinical trial designs across a plurality/set of clinical trials 9410 and/or aspects of the clinical trials. As will be appreciated, optimization over a set of related clinical trials may result in better overall performance for the set, as compared to optimizing each element, aspect, or clinical trial in the set individually and combining the results. For example, two clinical trial designs A and B may impact each other such that conducting clinical trials A and B concurrently is more efficient, with respect to a given performance criteria, than conducting A and B at different times. As another example, conducting clinical trials A and B, whether successively or concurrently, may be more efficient, with respect to a given performance criteria, than conducting one of clinical trial A or clinical trial B without conducting the other.

Improving the performance of a set may, in turn, improve the effectiveness and/or cost efficiencies of the related clinical trials.

As shown in FIG. 94, two or more of the clinical trials, e.g., clinical trial A 9412, clinical trial B 9414, and/or clinical trial C 9416 may be related to each other through one or more associations 9418. Non-limiting examples of associations 9418 include: trial sites 9420; an order of execution and/or dependencies 9422; shared resources 9424; clinical trial phases 9426; test subjects 9428, and/or other aspects of design space, scenario space and performance space. Trial sites 9420 may include any facility that participates in and/or performs a service related to execution of a clinical trial and/or any other type of facility, as described herein, with respect to the term "site" and/or "clinical trial site". An order of execution 9422 and/or dependency may include the sequencing of the conduction/execution of one or more clinical trials. For example, clinical trial A 9412 may execute before clinical trial B 9414 which may execute before clinical trial C 9416. An order of execution 9422 may also specify that two more clinical trials execute concurrently, e.g., have overlapping time periods. For example, clinical trial A 9412 may execute concurrently, e.g., at the same time, as clinical trial B 9414. Non-limiting examples of shared resources 9424 may include administrative personnel, medical practitioners, and/or drug availability/supply. Clinical trial phases 9426 may include phases 0-4, which may be performed sequentially. In embodiments, the platform 104 may simulate all, or a large percentage, of the feasible clinical trial designs/variations for each of clinical trials (and corresponding phases) and determine the optimal or near optimal combination of trial variations for each phase. Test subjects 9428 may include a drug and/or treatment that is the subject/purpose of a clinical trial 9410. In embodiments, the set of clinical trials 9410 may include trials that are performed in parallel but are related to different aspects of the same drug/treatment or related drugs/treatments.

In embodiments, a specification 9430, e.g., a data file (to include one or more records in a relational and/or object database) and/or written document, may record and/or define the one or more associations 9418. The specification 9430 may be stored in one or more databases within the data facility 138 (FIG. 1) where it may be retrieved from and/or updated as needed.

As will be explained in greater detail below, one or more clinical trial designs 9432, 9434, 9436, 9440, 9442, 9444, 9448, 9450 and 9452 (collectively referred to as 9456) may be generated for each of the clinical trials 9410 based at least in part on the specification 9430 and/or associations 7118. For example, three (3) clinical trial designs 9432, 9434, and 9436 (collectively referred to herein as 9438) may be generated for clinical trial A 9412, three (3) clinical trial designs 9440, 9442, and 9444 (collectively referred to herein as 9446) may be generated for clinical trial B 9414, and three (3) clinical trial designs 9448, 9450, and 9452 (collectively referred to herein as 9454) may be generated for clinical trial C 9416. While the foregoing example includes three (3) clinical trials each having three (3) corresponding clinical trial designs, it will be understood that any number of two or more (>2) clinical trials 9410 may be used with any number of corresponding clinical trial designs 9456.

Figure 95:
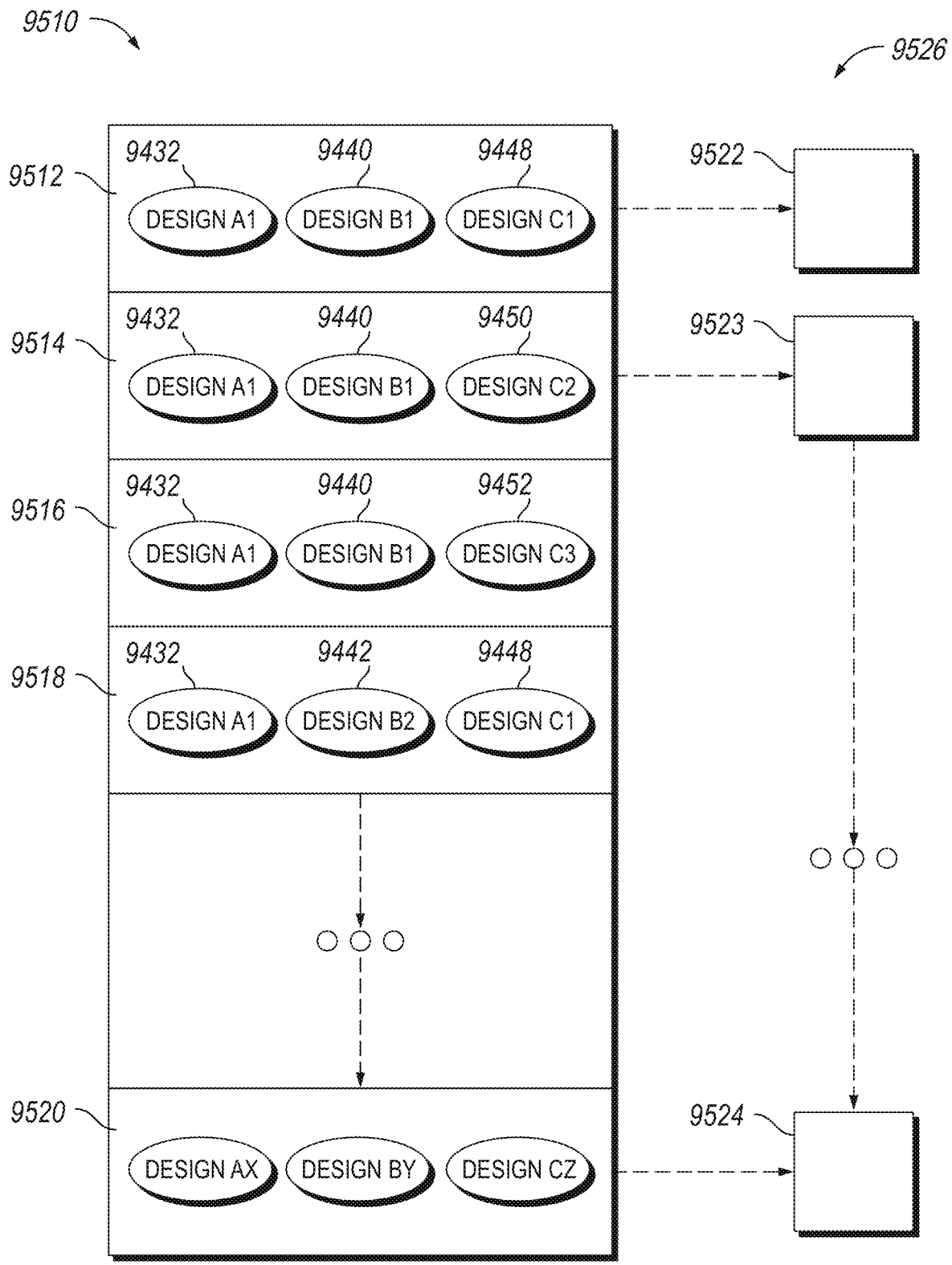
FIG. 95 is a block diagram of a permutation set of the clinical trial designs of FIG. 94 and corresponding combined performance criteria, in accordance with an embodiment of the current disclosure.

Turning to FIG. 95, a permutation set 9510 may be determined from the clinical trial designs 9456 (FIG. 94). The permutation set 9510 may be a collection of the possible combinations of the clinical trial designs 9456. In embodiments, each item in the permutation set 9510 may include at least one clinical trial design from each of the subgroups 9438, 9446, and/or 9454 corresponding to the clinical trials 9412, 9414, and 9416. In the case of three (3) clinical trials, as shown in FIG. 94, each of the combinations in the permutation set 9510 may associate a clinical trial design from group 9438 (derived from clinical trial A 9412) with two other clinical trial designs, one from group 9446 (derived from clinical trial B 9414) and one from group 9454 (derived from clinical trial C 9416). For example, as shown in FIG. 95, a first item 9512 of the permutation set 9510 may include design A1 9432, design B1 9440, and design C1 9448. A second item 9414 of the permutation set 9510 may include design A1 9432, design B1 9440, and design C2 9450. A third item 9516 of the permutation set 9510 may include design A1 9432, design B1 9440, and design C3 9452. A fourth item 9518 of the permutation set 9510 may include design A1 9432, design B2 9442, and design C1 9448. As will be understood, the permutations may continue so that the set 9510 contains all possible permutations/combinations as represented by the final item 9020. In embodiments, the permutation set 9510 may include only a subset of the possible permutations/combinations. In embodiments, the permutation set 9510 may include variations of a permutation/combination based on the one or more associations 9418 (FIG. 94). For example, where the order of the clinical trials in item 9512 from left to right represents the execution order of the clinical trials, the permutation set 9410 could include variations of item 9412, e.g., clinical trial design C1 9448, clinical trial design B1 9440, and clinical trial design A1 9432, representing a case where trial C1 9448 executes before trial B1 9440 which executes before trial A1 9432.

Combined performance criteria 9526 may be generated for each item of the permutation set 9510 where the combined performance criteria represents the collective performance criteria of the clinical trials within the item. For example, as shown in FIG. 95, combined performance criteria 9522 may be generated for item 9512, combined performance criteria 9523 may be generated for item 9514 and so on until all items have a corresponding combined performance criteria, as represented by combined performance criteria 9524 and corresponding item 9520. In embodiments, the platform 104 may simulate all, or a large percentage, of the feasible trial options for each of the parallel trials to determine the optimal or near optimal combination of trial variations. In some cases, optimization of clinical trials, as disclosed herein, may also include other aspects of trials such as patient recruitment and clinical trial resources (including drug supply). Simulations of trials may include determinations of requirements for drug supply and other aspects.

Analysis of the combined performance criteria 9526 may provide for determination of which set/permutation/combination of designs is the optimal combination to use for the set of clinical trials 9410.

Figure 96:
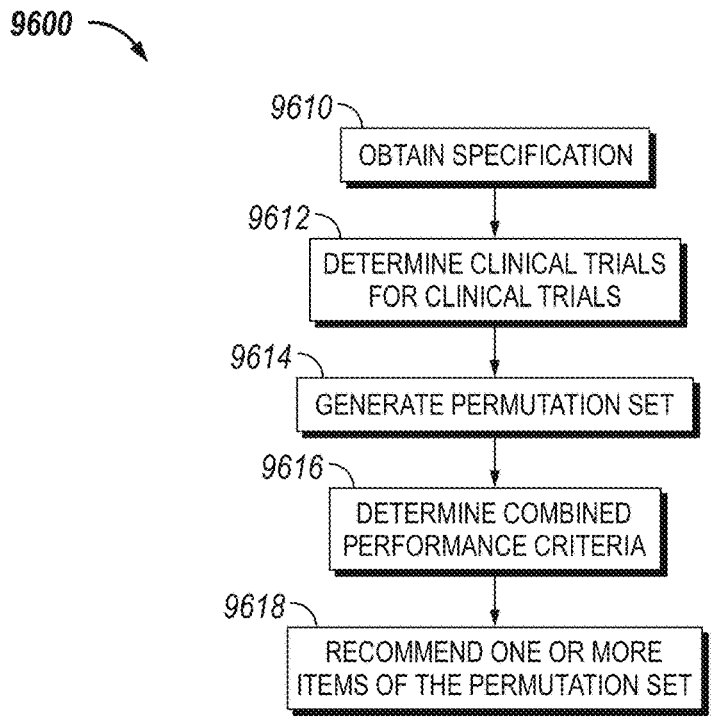
FIG. 96 is a flow chart depicting a method for optimization of clinical trial designs across a plurality of clinical trials, in accordance with an embodiment of the current disclosure.

Accordingly, turning to FIG. 96, a method 9600 for optimization of clinical trial designs across a plurality/set of clinical trials 9410 (FIG. 94) and/or aspects of the clinical trials is shown. The method 9600 includes obtaining a specification 9610. The specification 9430 (FIG. 94) may define one or more associations 9418 (FIG. 94) between two or more clinical trials 9410. The method 9600 further includes determining clinical trial designs for each of the two or more clinical trials 9612. In embodiments, the clinical trial designs may be based at least in part on the specification 9430 and/or the associations 9418. The method 9600 further includes generating a permutation set of the clinical trial designs 9614. The method 9600 further includes determining combined performance criteria for each item of the permutation set 9616. The method 9600 may further include recommending one or more items of the permutation set 9618. The recommendation may be based at least in part on the combined performance criteria 9526 (FIG. 95).

Figure 97:
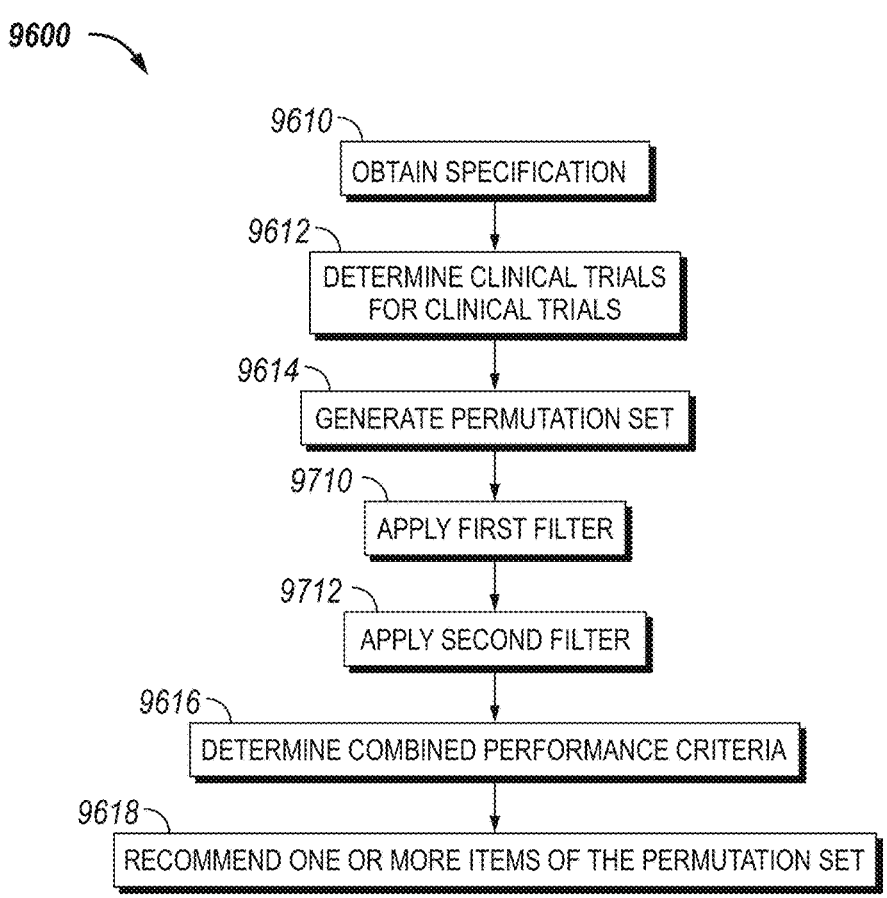
FIG. 97 is a flow chart depicting another embodiment of the method of FIG. 96, in accordance with the current disclosure.

Moving to FIG. 97, in embodiments, the method 9600 may include applying a first filter to the permutation set 9710. In embodiments, the first filter may be based at least in part on a Pareto analysis, as described herein. For example, a combination Pareto set may be generated by applying a Pareto analysis to the permutation set 9510, wherein the combination Pareto set is a subset of the permutation set 9510. In such embodiments, the recommended items from the permutation set may be members of the combination Pareto set.

In embodiments, the method 9600 may include applying a second filter to the permutation set 9712 and/or the combination Pareto set. In embodiments, the second filter may be based at least in part on a convex hull analysis, as described herein. In such embodiments, the second filter may be applied to the combination Pareto set wherein the recommended items of the permutation set are on a convex hull of the combination Pareto set.

Figure 98:
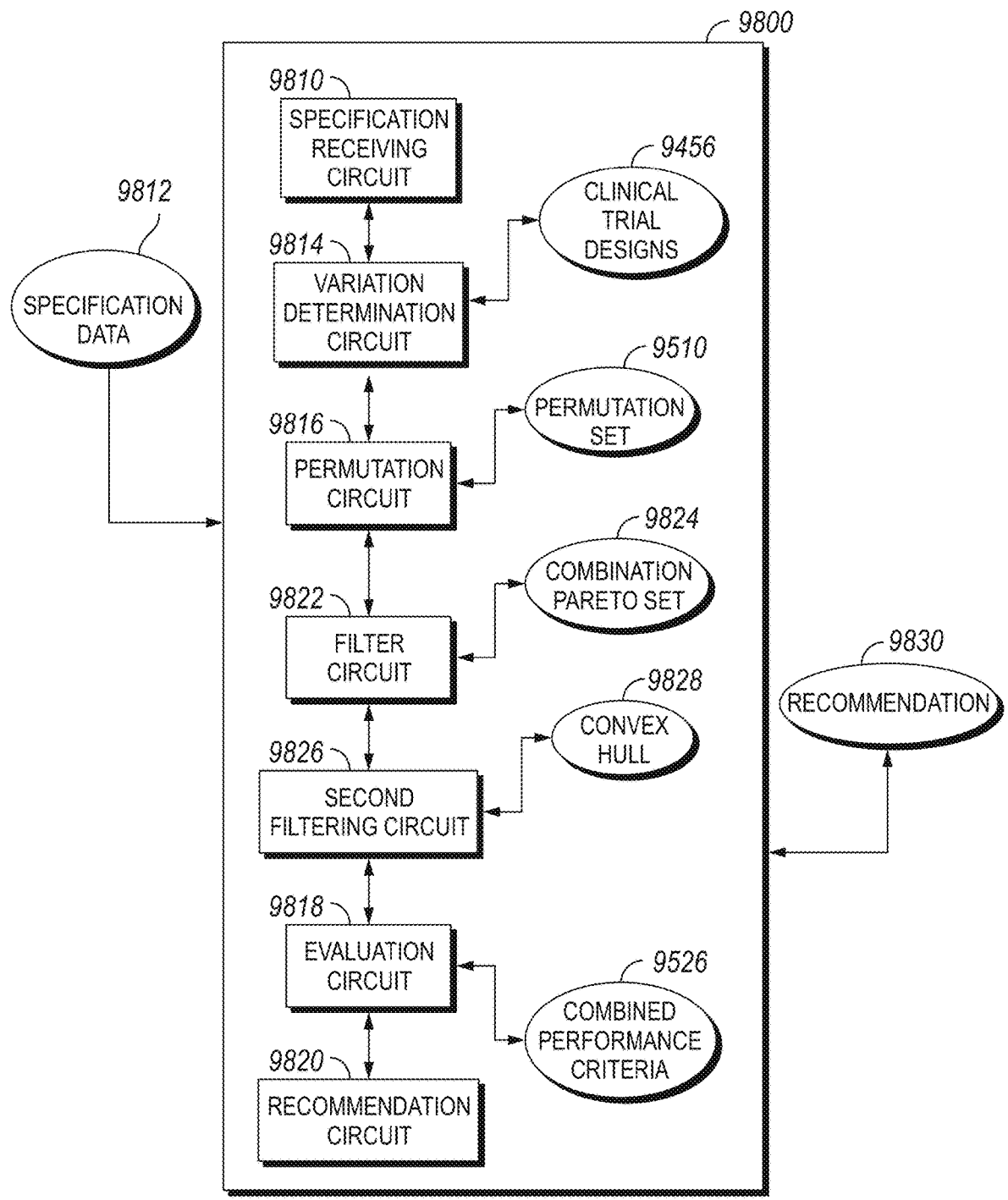
FIG. 98 is a schematic diagram of an apparatus for optimization of clinical trial designs across a plurality of clinical trials, in accordance with an embodiment of the current disclosure.

Illustrated in FIG. 98 is an apparatus 9800 for implementing the method 9600. The apparatus 9800 includes a specification receiving circuit 9810 to obtain and/or interpret specification data 9812 corresponding to a specification 9430 (FIG. 94). In embodiments, the specification may be based at least in part on a globally optimum clinical trial design determined in accordance with the systems and methods described herein. The apparatus 9800 further includes a variation determining circuit 9814 structured to determine clinical trial designs 9456. Determination of the clinical trial designs 9456 may be based at least in part on the specification data 9812. The apparatus 9800 further includes a permutation circuit 9816 structured to generate a permutation set 9510 of combinations of the clinical trial designs 9456. The apparatus 9800 further includes an evaluation circuit 9818 structured to determine combined performance criteria 9526 for each item of the permutation set 9510. The apparatus 9800 may further include a recommendation circuit 9820 structured to recommend one or more of the permutation set, e.g., select a recommended permutation 9830. The recommendation 9830 may be based at least in part on the combined performance criteria 9526.

In embodiments, the apparatus 9800 may include a first filtering circuit 9822 structured to filter the permutation set 9510. The first filter 9822 may be based at least in part on a Pareto analysis and generate a combination Pareto set 9824, as discussed herein. In such embodiments, the recommendation circuit 9820 may be further structured to select the recommendation 9830 from the combination Pareto set 9824.

In embodiments, the apparatus 9800 may include a second filtering circuit 9826. The second filtering circuit 9826 may be based at least in part on a convex hull analysis. In embodiments, the second filtering circuit may filter the combination Pareto set 9824. In such embodiments, the recommendation circuit 9820 may be further structured to select the recommendation 9830 from the set of points within the combination Pareto set that fall on the convex hull 9828. Embodiments of the apparatus 9800 may include additional circuits that may perform other types of analysis, e.g., simulated annealing, Monte Carlo, and/or the like.

As will be appreciated, by generating permutations based on associations 7118, as described herein, embodiments of the disclosure may determine optimized combinations and/or execution orderings for two or more clinical trials. For example, it may be the case that clinical trial A and clinical trial C can execute at the same facility at the same time with the same administrative staff, while clinical trial B needs to execute after clinical trial C due to dependencies. Embodiments of the current disclosure may also determine whether certain portions/subparts of two or more clinical trials should be executed together (either in time and/or location) or separately (either in time and/or location). In other words, some embodiments of the current disclosure may provide for an overall ordering and/or sequencing of multiple clinical trials, to include ordering of portions/subparts of the clinical trials. Further, filtering the permutation set, as described herein, may reduce the number of non-optimal combinations that need to be considered, thus reducing the amount of time to determine the optimal combination.

In embodiments, the platform's 104 (FIG. 1) infrastructure, e.g., components 106, 108, 110, 112, 138, and/or 150, includes engines 128, models 126 and/or the underlying algorithms, and may be used to optimize clinical designs for robustness against variations in prior probability assessments. In other words, instead of determining optimal clinical trial designs for a given set of scenarios and/or design parameters, some embodiments of the current disclosure may provide for determining robustness for a particular clinical trial design.

As such, embodiments of the platform 104 may operate in a forward mode of operation and/or an inverse mode of operation. In "forward" operation mode, the platform 104 may be used to provide design recommendations for fixed scenario probabilities over a user selected range of criteria weights, as disclosed herein. In "inverse" operation mode (also referred to herein as "backwards" operation mode), however, the platform 104 may be used to assess the impact of departures from the assumed probabilities of the scenarios (e.g., a departure modeled by multinomial distribution with n=1). In embodiments, the inverse operation mode may be used to compute design performance on multiple criteria for a vector of criteria weights, which may be fixed, while varying multinomial probability vectors. This may be done using algorithms for the forward operation mode by interchanging the role of the multinomial probabilities and the weights. As will be appreciated, this interchanging of roles is possible, in part, due to the mathematical models of the forward and backward modes of operation being duals of each other, in the sense that fixing either the weights or the scenario probabilities typically leads to the same linear model structure for the design performance value.

A measure of the robustness, also referred to herein as a "robustness value", of a clinical trial design may correspond to a size of the range of scenario probabilities for which the design is optimal. In embodiments, this range is convex, thus providing for the application of Pareto analysis/optimality, convex hull analysis, and/or simulated annealing. In embodiments, the dimension of the vector of the multinomial distribution for scenarios may be reduced by exploiting uniformity of probabilities over subsets of scenarios (e.g., using three (3) or five (5) ordered categories of likelihood) and/or functional relations between scenario probabilities. This may result in reductions in the number of multinomial vectors and speeds up computations.

In embodiments, if a user, e.g., 102 (FIG. 1) provides a prior (e.g., a Dirichlet distribution) over the multinomial probability vector for scenarios the inverse mode of operation computes the posterior distribution for the weighted criterion vector to provide summary measures of robustness such as one or more of the posterior means, standard deviation, and/or credible intervals. As will be appreciated, in embodiments, the forward and inverse modes of operation can be reversed in sequence if there is certainty around weights for criteria and optimal robustness to scenario assumptions is of concern.

Figure 99:
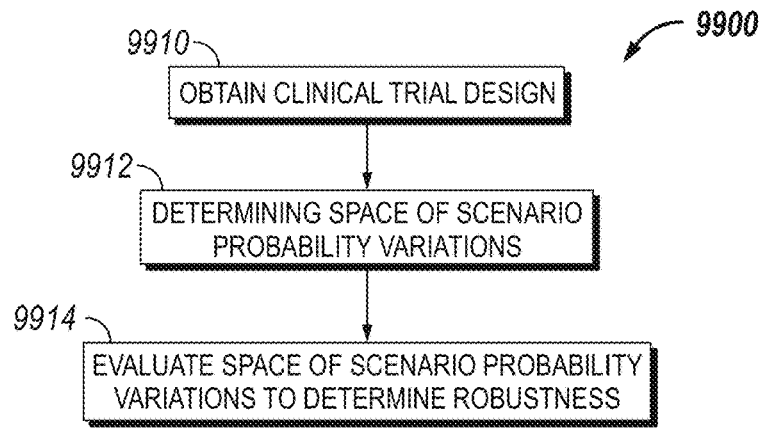
FIG. 99 is a flow chart depicting a method for determining robustness of a clinical trial design, in accordance with an embodiment of the current disclosure.

Accordingly, illustrated in FIG. 99, a method 9900 for determining robustness of a clinical trial design. The method 9900 may provide for operation of the platform 104 in an "inverse" mode of operation, as described herein. As such, the method 9900 includes obtaining a clinical trial design 9910. In embodiments, the clinical trial design may have been generated in accordance with the "forward" mode of operation of the platform 104, as described herein. The method 9900 further includes determining a space of scenario probability variations for the clinical trial design 9912, and evaluating the space of scenario probability variations to determine a robustness of the clinical trial design 9914.

Figure 100:
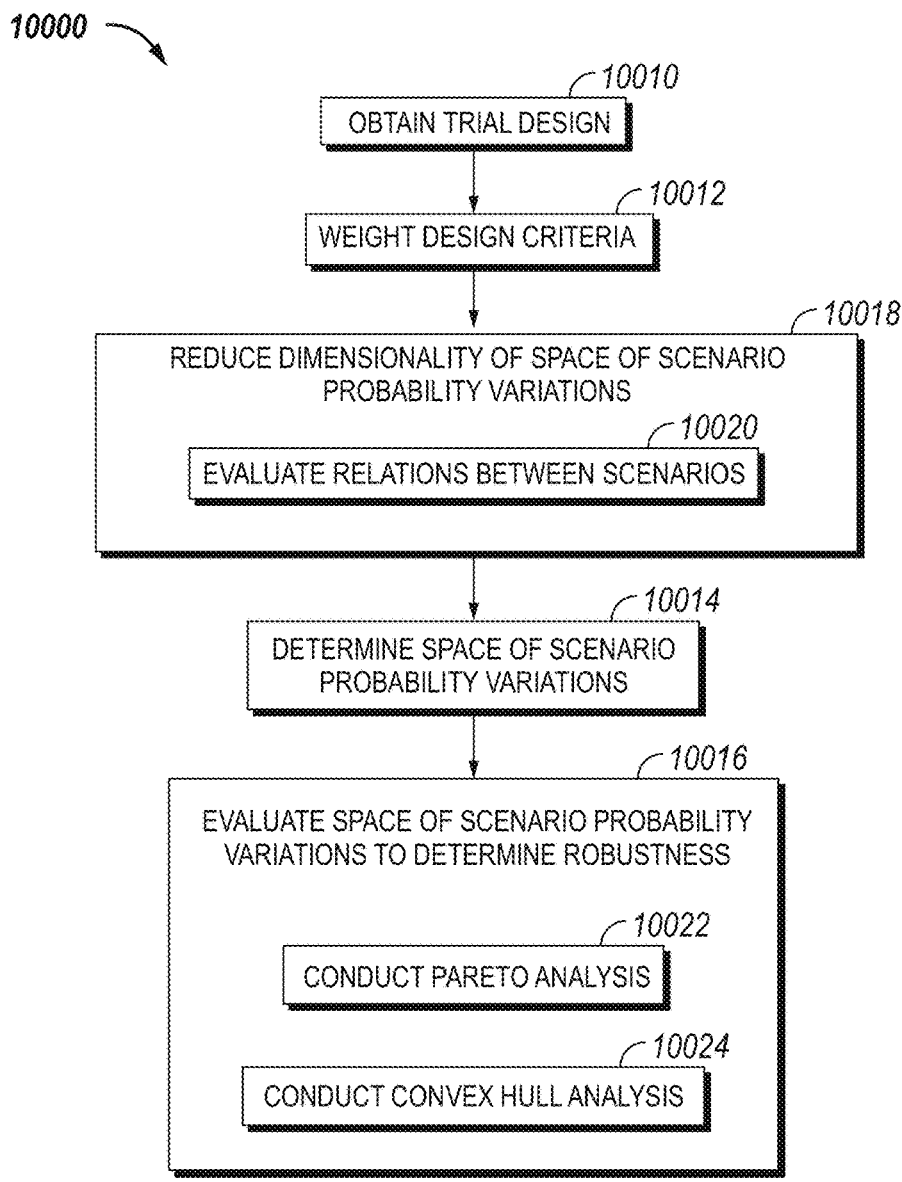
FIG. 100 is a flow chart depicting another method for determining robustness of a clinical trial design, in accordance with an embodiment of the current disclosure.

Turning to FIG. 100, another method 10000 for determining robustness of a clinical trial design is shown. The method 10000 may provide for operation of the platform 104 in an "inverse" mode of operation, as described herein. As such, the method 10000 includes obtaining a clinical trial design 10010. In embodiments, the clinical trial design may have been generated in accordance with the "forward" mode of operation of the platform 104, as described herein. The method 10000 may include weighting one or more design criteria for the clinical trial design 10012. The method 10000 may include reducing a dimensionality of the space of scenario probability variations 10018 by evaluating relations between two or more scenarios within the space 10020. The method 10000 further includes determining a space of scenario probability variations for the clinical trial design 10014. In embodiments, determining the space of scenario probability variations 10014 is based at least in part on the one or more weighted design criteria. In embodiments, the weights of the design criteria may be fixed. The method further includes evaluating the space of scenario probability variations to determine a robustness of the clinical trial design 10016. In embodiments, evaluating the space of scenario probabilities 10016 includes conducting a Pareto analysis 10022 and/or a convex hull analysis 10024.

Figure 101:
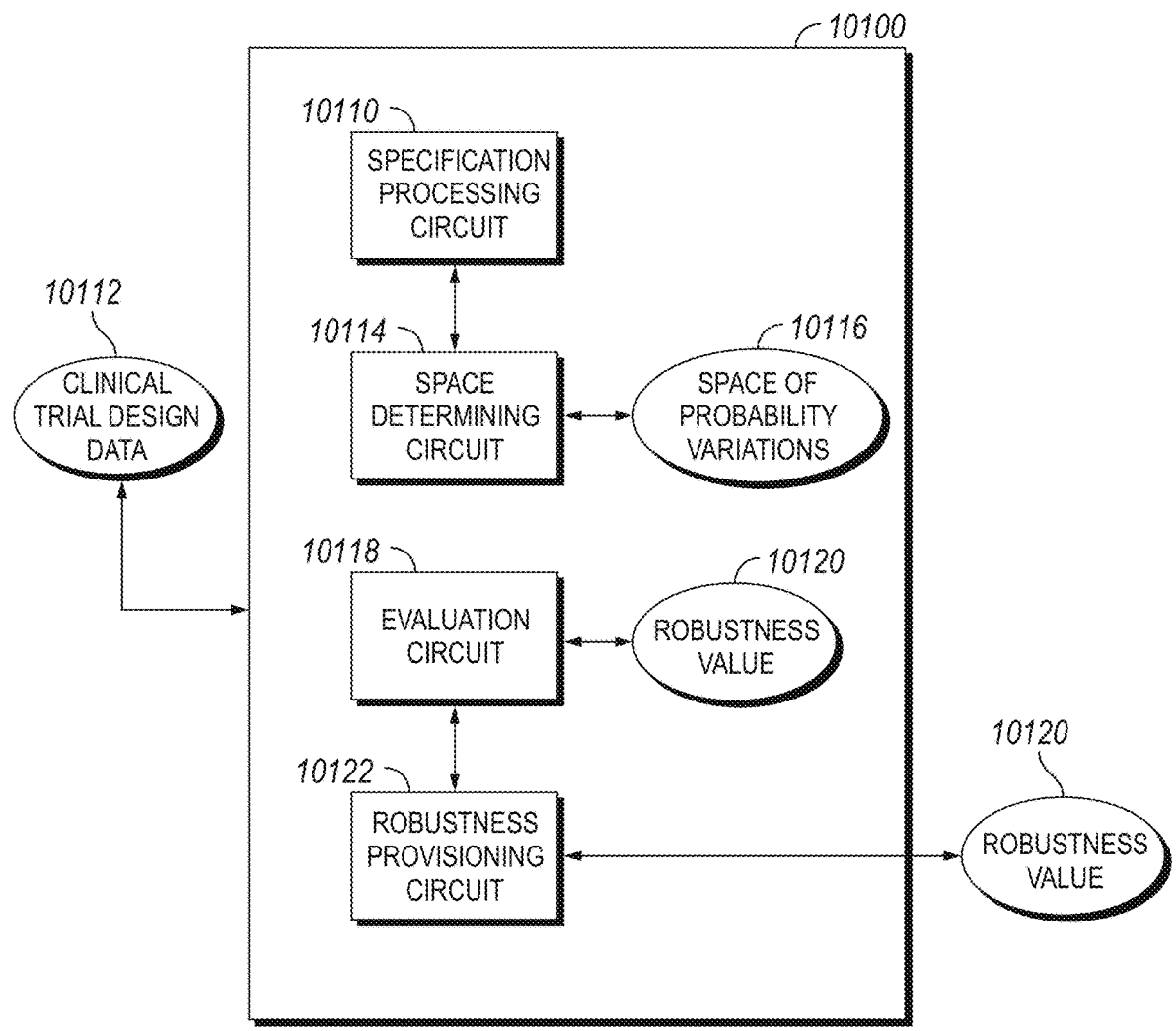
FIG. 101 is a schematic diagram of an apparatus for determining a robustness of a clinical trial design, in accordance with an embodiment of the current disclosure.

Illustrated in FIG. 101 is an apparatus 10100 for determining robustness of a clinical trial design is shown. The apparatus 10100 may form part of the platform 104 and provide for operation of the platform 104 in an "inverse"

mode of operation, as described herein. As such, the apparatus 10100 includes a specification processing circuit 10110 structured to interpret clinical trial design data 10112 corresponding to a clinical trial design. In embodiments, the clinical trial design data may have been generated in accordance with the "forward" mode of operation of the platform 104, as described herein. The apparatus 10100 further includes a space determining circuit 10114 structured to determine, based at least in part on the clinical trial design data 10112, a space of scenario probability variations 10116 for the clinical trial design. The apparatus 10100 further includes an evaluation circuit 10118 structured to determine, based at least in part on the space of scenario probability variations 10116, a robustness value 10120 of the clinical trial design. The apparatus 10100 further includes a robustness provisioning 10122 circuit structured to transmit the robustness value 10120.

In embodiments, the forward and inverse modes of operations can be executed sequentially over a plurality of iterations. In some examples, designs may be evaluated in the forward mode of operation to evaluate designs. Designs may be evaluated for different performance parameter weights to determine one or more designs of interest for the weights. The designs of interest for the determined weights may be further evaluated to determine the robustness of the designs for scenario. For each design, the platform may be operated in reverse mode for each design of interest to determine the robustness of each design. In some cases, the robustness results may reveal that the design of interest has unsatisfactory robustness. In response to unsatisfactory robustness the platform may be operated in forward mode to find new designs of interest. In some cases, the operation of platform in the forward mode may be modified based on the robustness results. Modifications may include changing weighting of performance criteria, changing design criteria, changing scenario criteria, and the like. Forward mode of operation may be used to find new designs of interest and the platform may be again operated in reverse mode to identify robustness of the new designs of interest. The cycles of forward and reverse operation may be repeated until design with acceptable robustness and performance are found.

Figure 102:
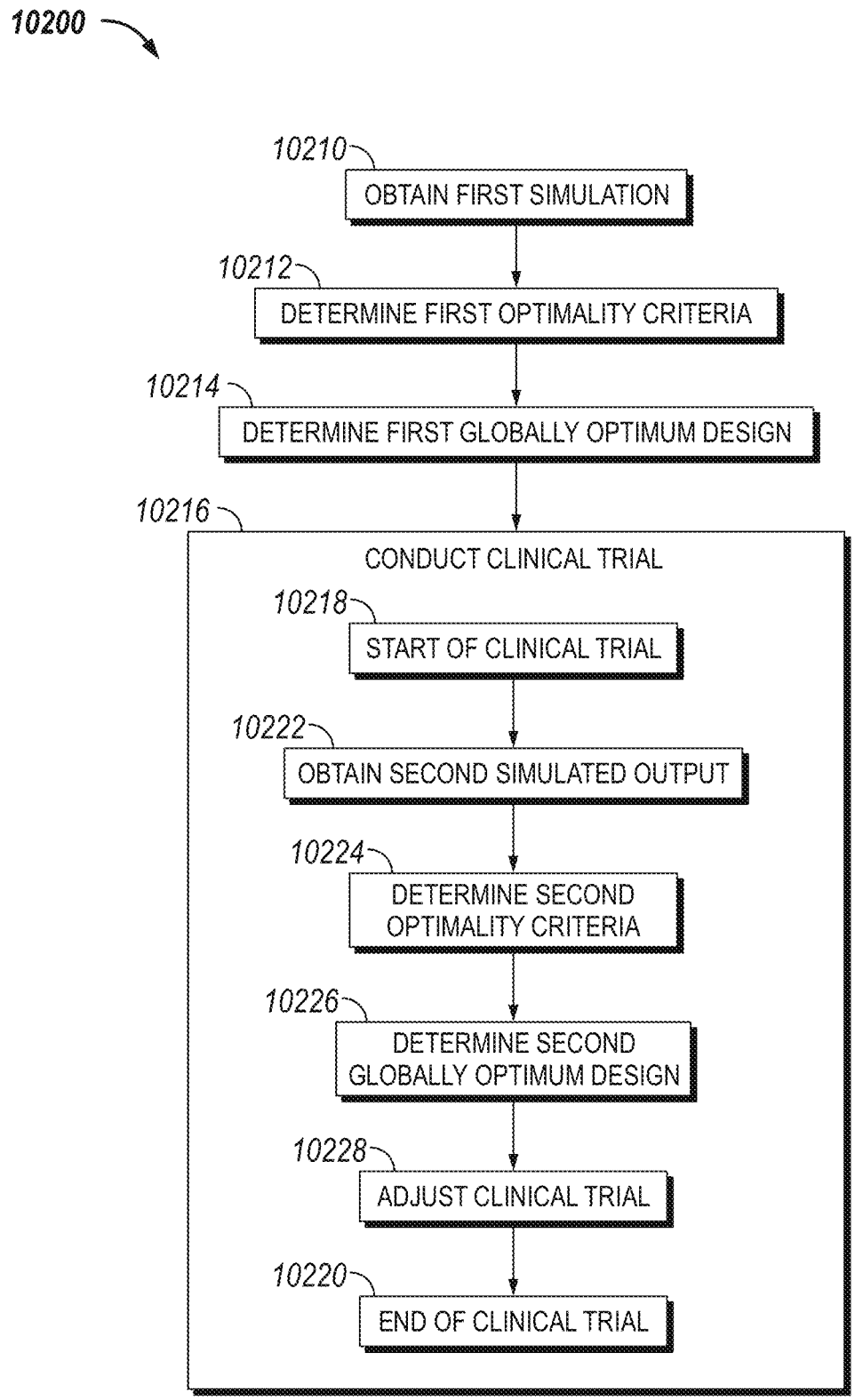
FIG. 102 is a flow chart depicting a method for updating a clinical trial, in accordance with an embodiment of the current disclosure.

Referring to FIG. 102, a method 10200 for updating a clinical trial is shown. Since recommendation of globally optimal designs, as disclosed herein, are generally predictive, it is possible that one or more parameters used to determine a globally optimum design for a clinical trial may deviate from what actually occurs during conduction/execution of the trial, i.e., while the trial is underway. For example, a globally optimum design may have been determined based on a scenario where no major worldwide health emergencies occur during the duration of the clinical trial, when, in actuality, a global pandemic emerges shortly after the start of a clinical trial based on the globally optimum design. In such a case, the original globally optimum design may no longer be the optimum design. Updating of a clinical trial, as described herein, may occur multiple times through the course/duration of the clinical trial. In some embodiments, updating of the clinical trial, as described herein, may be performed on a continuous basis throughout the duration of the clinical trial.

Accordingly, the method 10200 includes obtaining a first simulation output for a first set of clinical trial designs for the clinical trial 10210. The first simulation output includes first performance parameters, as disclosed herein, associated with each design in the first set of clinical trial designs for a first set of criteria. The method 10200 further includes determining, from the first set of criteria, a first optimality criteria for evaluating the first set of clinical trial designs 10212. The method 10200 further includes determining, within the first set of clinical trial designs, a first globally optimum design based at least in part on the first optimality criteria and the first performance parameters 10214. The clinical trial may then be configured based at least in part on the first globally optimum design, e.g., the clinical trial may be made to conform to the globally optimum design.

As further shown in FIG. 102, the method 10200 may include conducting/executing the clinical trial based at least in part on the first globally optimum design 10216. Conduction of the clinical trial may be defined by a start/beginning 10218 of the clinical trial and a stop/end 10220 of the clinical trial. In embodiments, the start 10218 may be the occurrence of the first patient recruitment. In embodiments, the start 10218 may be the occurrence of the first interaction between administrative personnel (for the clinical trial) and a patient or recruitment site, in respect of the trial. In embodiments, the start 10218 may be the first occurrence of a patient receiving a treatment (including receiving a drug). In embodiments, the stop 10220 may be the last occurrence of patient receiving a treatment (including receiving a drug). In embodiments, the stop 10220 may be the occurrence of the last interaction between administrative personnel (for the clinical trial) and a patient or recruitment site, in respect of the trial. The time between the start 10218 and the stop 10220 may constitute the duration of the clinical trial as that term is user herein. In embodiments, conduction of the clinical trial may include commencement of any portion and/or process of the clinical trial whether performed in succession and/or intermittently.

After the start 10218 of the clinical trial, but before the stop 10220, the globally optimum design may be reassessed. As such, the method 10200 includes obtaining, during conduction of the clinical trial, a second simulation output for a second set of clinical trial designs for the clinical trial 10222. The second simulation output includes second performance parameters associated with each design in the second set of clinical trial designs for a second set of criteria. In embodiments, the second simulation output may be different than the first simulation output. For example, the second simulation output may be from another evaluation of the clinical trial designs. In embodiments, the second simulation output may be the same as the first simulation output. For example, the first simulation output may be reused. In embodiments, the second performance parameters may be different than the first performance parameters. For example, the second performance parameters may include more or fewer parameters than the first performance parameters. In embodiments, the second performance parameters may be the same as the first performance parameters. In embodiments, the second set of designs may be the same or different than the first set of designs. For example, the second set of designs may include additional designs and/or have removed designs as compared to the first set of designs. In embodiments, the second set of criteria may be the same or different than the first set of criteria. For example, constraints on the clinical trial may have changed since the start 10218.

The method 10200 further includes determining, from the second set of criteria, a second optimality criteria for evaluating the second set of clinical trial designs 10224. In embodiments, the second optimally criteria may be the same or different from the first optimally criteria. For example, a user may have previously determined the globally optimum design with respect to shortest duration and wish to do so again for the second globally optimum design. As another example, a user may have previously determined the globally optimum design with respect to shortest duration and may now wish to determine the globally optimum design with respect to costs.

The method 10200 further includes determining, within the second set of clinical trial designs, a second globally optimum design 10226. Determination of the second globally optimum design may be based at least in part on the second optimality criteria and the second performance parameters. The method 10200 may further include adjusting the clinical trial based at least in part on the second globally optimum design 10228. Adjustment of the clinical trial may include conforming the clinical trial to the second globally optimum design.

Figure 103:
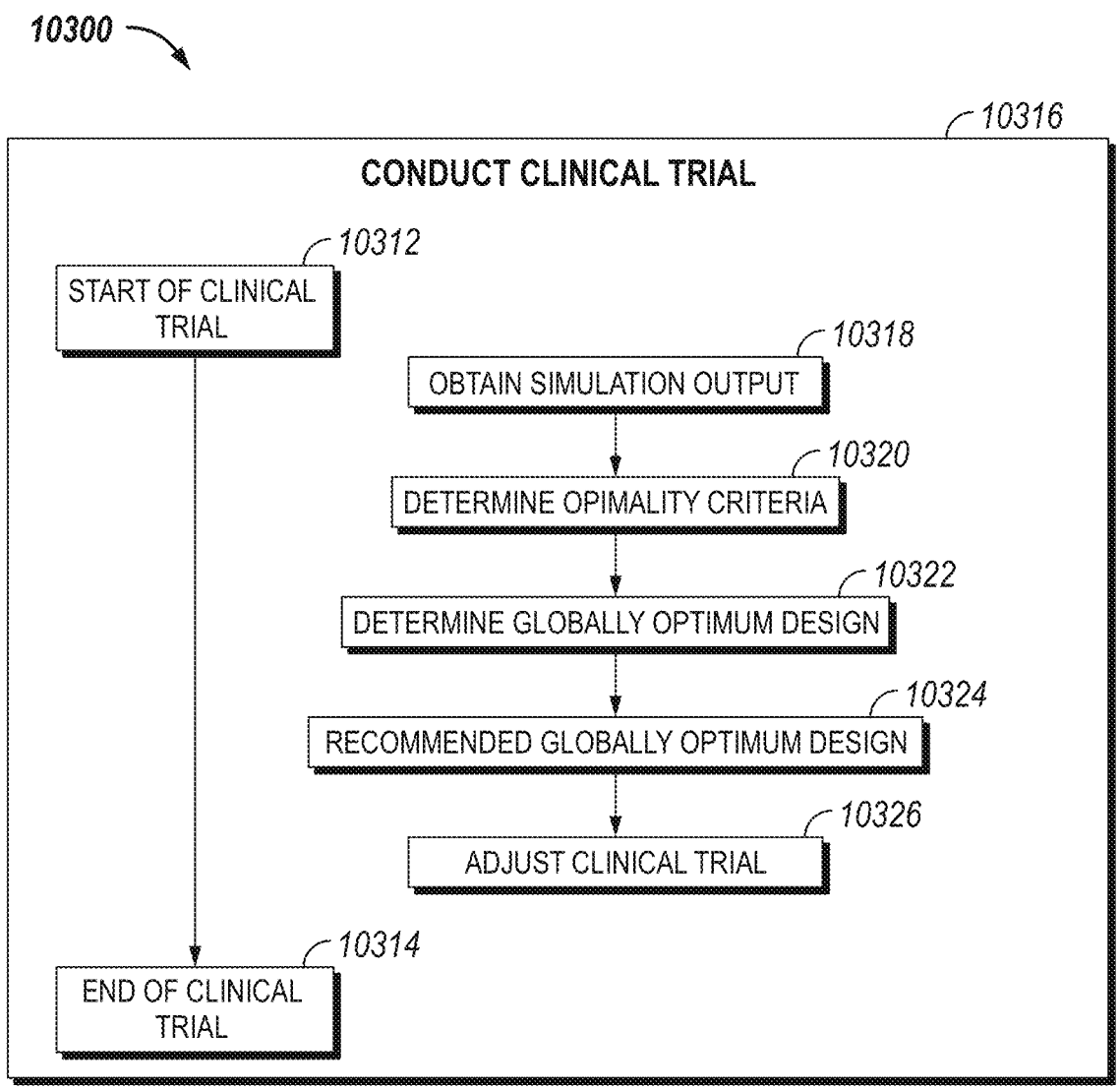
FIG. 103 is a flow chart depicting another method for updating a clinical trial, in accordance with an embodiment of the current disclosure.

Illustrated in FIG. 103 is another method 10300 for updating a clinical trial. In particular, method 10300 identifies a globally optimum design for a clinical trial after the start 10312 of the clinical trial, but before the end 10314 of the clinical trial, where an initial globally optimum design may not have been determined, or was not determined by an entity performing method 10300. Accordingly, the method 10300 includes obtaining, during conduction of the clinical trial 10316, a simulation output for a set of clinical trial designs for the clinical trial 10218. The simulation output includes performance parameters associated with each design in the set of clinical trial designs for a set of criteria. The method 10300 further includes determining, from the set of criteria, an optimality criteria for evaluating the first set of clinical trial designs 10320. The method 10300 further includes determining, within the set of clinical trial designs, a globally optimum design based at least in part on the optimality criteria and the performance parameters 10322. The method 10300 may further include recommending the globally optimum design 10324. Recommendation may include transmitting the globally optimum design to an entity performing the clinical trial. The recommended globally optimum design may be the first time a globally optimum design was calculated/determined for the clinical trial, or the globally optimum design may be an update to a previously calculated/determined globally optimum design. In embodiments, the method 10300 may not include recommending the globally optimum design, but rather may include adjusting the clinical trial based at least in part on the globally optimum design 10326. It is to be understood, however, that embodiments of the method 10300 may not include adjusting the clinical trial based at least in part on the globally optimum design. In embodiments, the method 10300 may include both recommending and adjusting the clinical trial based at least in part on the globally optimum design.

In addition to the design of a clinical trial, the success of the clinical trial often depends on the ability to recruit a satisfactory number of patients, also referred to herein as "subjects", suitable to participate in the clinical trial. The number of suitable patients available to be recruited for a clinical trial is, in turn, typically a function of the sites selected for the clinical trial, also referred to herein as a "site selection".

In some cases, a wrong choice in the selection of sites for a clinical trial may reduce the usefulness of the trial even if the trial is executed without error. In some cases, a wrong choice in the selection of sites for a clinical trial may inhibit and/or prevent completion of the clinical trial, e.g., not enough suitable patients are recruited to satisfy applicable guidelines and/or industry requirements. In some cases, different choices in site selection for a clinical trial may result in very different costs, completion times, and/or other performance parameters for the clinical trial.

The selection of sites for a clinical trial may include considerations and tradeoffs between hundreds or even thousands of site selections, also referred to herein as site selection options, e.g., different groupings/sets of selected sites. For example, different site selection options, often have different values for performance criteria, e.g., the type of clinical trial being conducted, the minimum and/or maximum number of suitable patients available to be recruited, the time required to complete the clinical trial, the costs associated with conducting the clinical trial, and/or the like. Traditionally, site selection for clinical trials has been based on heuristics and experienced professionals to determine a set of parameters likely to result in a site selection that produces a successful clinical trial. However, traditional approaches are not capable of evaluating more than a handful of site selection options and corresponding tradeoffs. As a result, traditional approaches to site selection often miss site selection options that may result in better performance. As the cost of a clinical trial may exceed tens of millions or even hundreds of millions of dollars and/or may take years to complete, small differences in the performance between site selections for a clinical trial may result in large impacts on the overall cost and/or time associated with the clinical trial.

The complexity of site selection often requires aspects of statistical expertise, clinical design expertise, and software expertise, which may not be available in many organizations. As such, many organizations fallback on the use of generic site selection methodologies due to their inability to find optimal or near-optimal site selections for a particular clinical trial.

Accordingly, embodiments of the current disclosure may provide for a site selection platform, systems, and methods for evaluation and/or comparison of site selection options for a clinical trial. In embodiments, evaluation and/or comparison may include a large number of site selection options. In some embodiments, the platform, systems, and methods described herein may be used to evaluate hundreds, thousands, or even millions of site selection options for a clinical trial and may be used to find the optimal or near-optimal site selection for a trial.

The site selection platform may be used for site selection. In embodiments, a site selection platform may support a team, as described herein, in collaborating and surfacing all the inputs that are key to consider for preparing and selecting an optimal site selection. The site selection platform may use cloud and distributed computing so the team can simulate hundreds of millions of site selection variants/options across all those inputs. The site selection platform may present the team with prioritized options and visualizations to enable the interrogation of the drivers of value.

A site selection platform may enable a team to quickly identify optimal site selections and the factors that most strongly drive performance factors, strategic goals, and the like. A site selection platform, as described herein, may leverage emerging technologies to provide options for advanced simulations, distributed computing, visualizations, and the like. The site selection platform may leverage methodological knowledge, analysis of the business value of different design choices, and/or analysis of regulatory risk and operational complexity to determine optimum or near optimum site selections. The site selection platform may determine optimum or near optimum site selections by leveraging a novel workflow, speed and/or computing innovations, and/or powerful visualizations for study analysis and optimization.

A site selection platform may improve how data and processes are used to make better decisions on site selections. Improvements may result from recognizing which innovative options might significantly increase goals. Improvements may be obtained by communicating the benefits of specific site selections in a way that that intuitively allows a variety of team members to understand a particular site selection and/or possible options for the site selection of a clinical trial. A site selection platform may support a team in collaborating and surfacing all the inputs that are key to consider for preparing and selecting an optimal site selection. The site selection platform may present the team with prioritized options and insightful visualizations to enable interrogation of the drivers of value.

Figure 104:
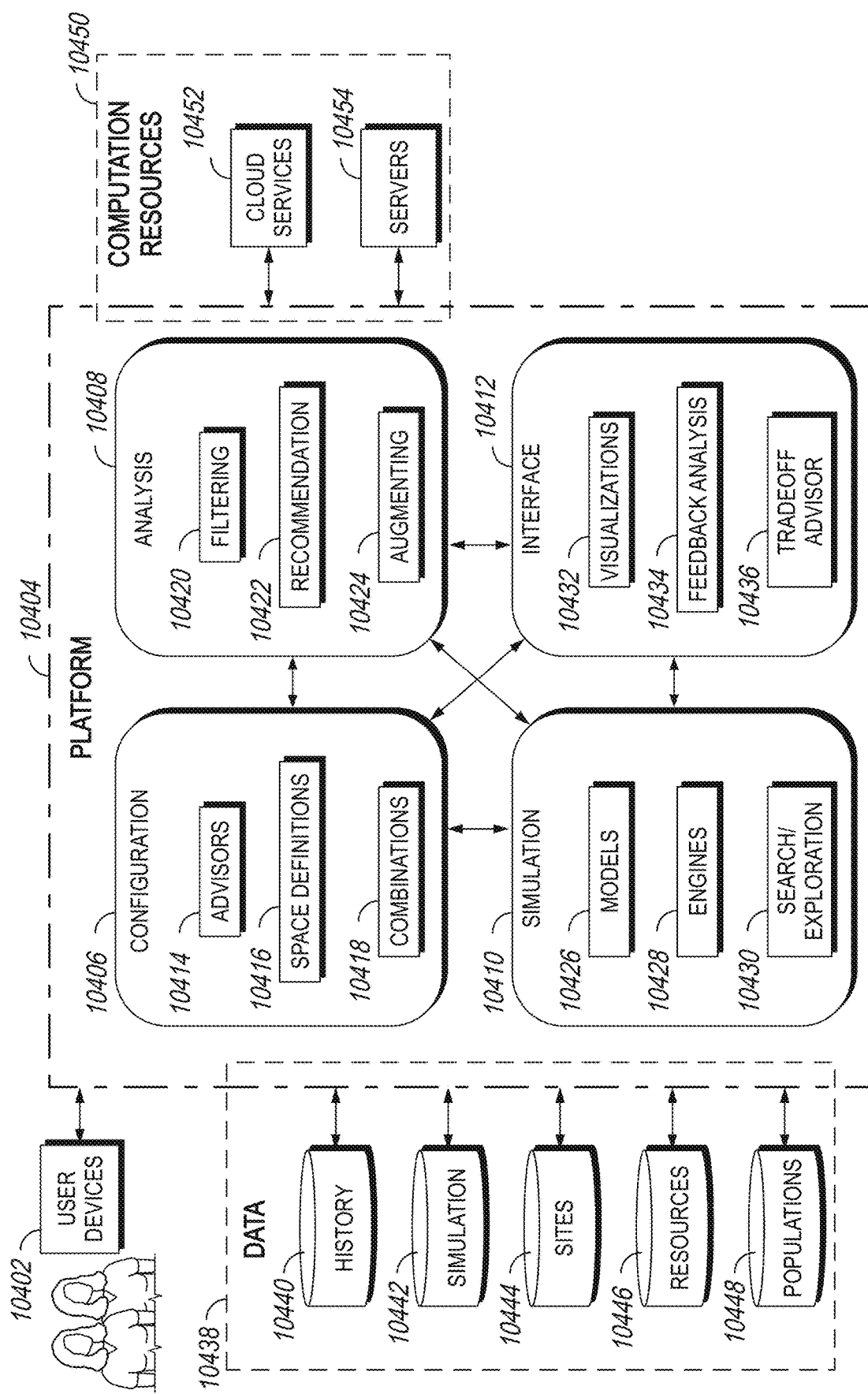
FIG. 104 is a block diagram of a platform for providing global optimization of site selection for clinical trial designs, in accordance with an embodiment of the current disclosure.

FIG. 104 shows an embodiment of a platform/system for evaluation and comparison of site selections for a clinical trial. The platform 10404 may form part of the platform 104 (FIG. 1) or the platform 10404 may be stand-alone from the platform 104. In embodiments, the platform 10404 may communicate with the platform 104 via one or more application programming interfaces (APIs). The platform 10404 may provide for a system for providing users with facilities and methods for determining, evaluating, and/or comparing site selections. The facilities described herein may be deployed in part or in whole through a machine that executes computer software, modules, program codes, and/or instructions on one or more processors, as described herein, which may be part of or external to the platform 10404. Users may utilize the platform 10404 to identify site selections for criteria, evaluate the site selections, compare site selections, determine optimal site selections, and the like.

A user may interact with the platform 10404 through one or more user devices 10402 (e.g., computer, laptop computer, mobile computing device, and the like). The platform 10404 may be implemented and/or leverage one or more computing resources 10450 such as a cloud computing service 10452, servers 10454, software as a service (SaaS), infrastructure as a service (IaaS), platform as a service (PaaS), desktop as a Service (DaaS), managed software as a service (MSaaS), mobile backend as a service (MBaaS), information technology management as a service (ITMaaS), and the like. The platform 10404 may be provided or licensed on a subscription basis and centrally hosted (e.g., accessed by users using a client (for example, a thin client) via a web browser or other application, accessed through or by mobile devices, and the like). In embodiments, elements of the platform 10404 may be implemented to operate on various platforms and operating systems. In embodiments, interfaces for the user device 10402 through which the users may interact with the platform may be served to the user device 10402 through a webpage provided by a server of the platform 10404, an application, and the like.

The platform 10404 may include one or more facilities such as a configuration facility 10406, simulation facility 10410, analysis facility 10408, interfaces facility 10412, data facility 10438, and computation resources 10450.

The configuration facility 10406 may include advisors 10414, which may include one or more wizards, tools, algorithms, recommenders, configuration elements, questioners, and the like. Advisors may be used to receive data and/or define or develop space definitions 10416.

Figure 105:
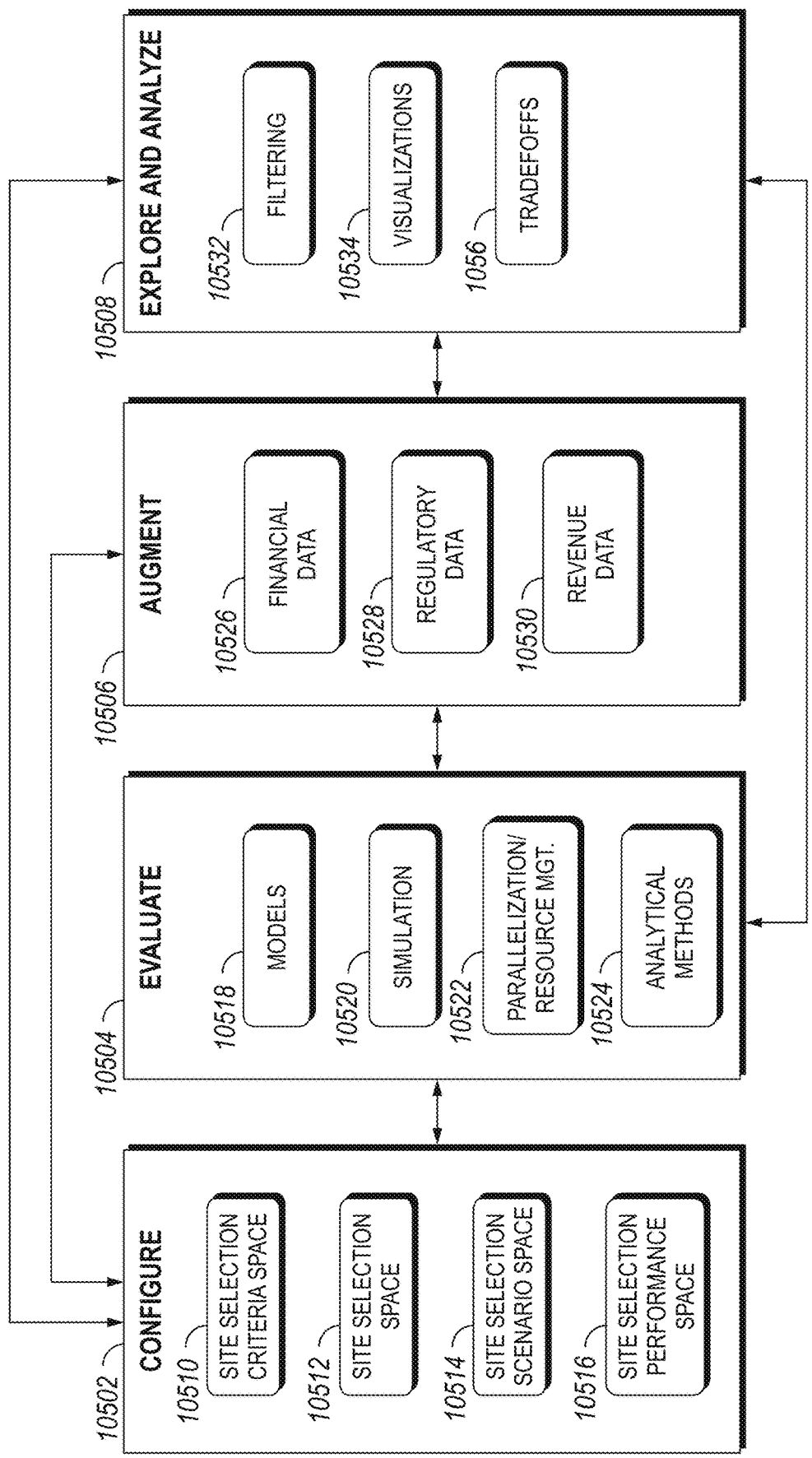
FIG. 105 is a diagram of a process for globally optimizing site selection for clinical trial designs, in accordance with an embodiment of the current disclosure.

Space definitions 10416 may include aspects of site selection criteria space 10510 (FIG. 105). Site selection criteria space may define values, ranges of values, types, ranges of types, and the like that may define general required characteristics of a site selection, as required by a clinical trial. Non-limiting examples of site selection criteria include: maximum and/or minimum duration of the clinical trial, maximum and/or minimum costs of the clinical trial, a minimum and/or maximum number of required patients to complete the trial, and/or the like. In embodiments, site selection criteria space may also include critical dates (the start, stop, duration, and/or milestones of a clinical trial), required protocols, geographic distribution of patients, demographics of patients, and/or the like.

Space definitions 10416 may include aspects of site selection space 2412 (FIG. 105). Site selection space 2412 may include the set of parameters and values of the parameters that define different options and variations of sites for implementation of clinical trials. Non-limiting examples of site selection space may include expected patient recruitment, expected patient dropout rate, geographical locations, patient demographics, expected costs, and/or the like. The site selection space may include all possible permutations of the parameters. For example, one site selection may be configured with different expected patient recruitment and different patent dropout rates. The site selection space may include all possible permutations of the different expected costs of the clinical trial for all the different expected patient dropout rates. The site selection space may include all the permutations of all the parameters associated with a site selection. The site selection space may include millions of possible site selection variations. A site selection platform may evaluate all permutations of parameters of the site selection space. A site selection platform may evaluate a partial set of permutations of parameters of the site selection space. The partial set of permutations may be defined by a user. The partial set of permutations may be automatically defined, such as according to the site selection criteria parameters.

Space definitions 10416 may include aspects of site selection scenario space 2414 (FIG. 105). Site selection scenario space may include the set of parameters and values of the parameters that define different options and variations of scenarios associated with site selections. Site selection scenario space may define the parameters of the environment associated with one or more sites. Non-limiting examples of site selection scenario space include: expected weather conditions, expected pandemics; expected economic conditions; expected resource availability, to include administrative personnel; and/or the like. The site selection scenario space may include all possible permutations of the parameters. For example, one scenario may be configured with a range of values for average patient age and a range of values for average weather conditions, e.g., how will varying weather conditions affect the ability of patients of varying age to participate in a clinical trial. The site selection scenario space may include all the permutations of all the parameters associated with scenarios. The site selection scenario space may include millions of possible scenario variations. A site selection platform may evaluate all permutations of parameters of the site selection scenario space. A site selection platform may evaluate a partial set of permutations of parameters of the site selection scenario space. The partial set of permutations may be defined by a user. The partial set of permutations may be automatically or semi-automatically defined, such as according to the site selection criteria parameters.

Space definitions 10416 may include aspects of site selection performance space 2416 (FIG. 105). Site selection performance space may include the set of parameters and values of the parameters that define the evaluation criteria for a site selection. Parameters may include: predicted patient recruitment (as estimated by simulation), net present value (NPV), expected NPV, incremental NPV, study cost, incremental study cost, study budget, incremental study budget, time to complete, incremental time to complete, time to market, incremental time to market, clinical utility, incremental clinical utility, probability of regulatory acceptance, incremental probability of regulatory acceptance, probability of success, incremental probability of success, statistical power, incremental statistical power, number of patients, incremental number of patients, number of sites, incremental number of sites, study complexity, incremental study complexity, operational complexity, incremental operational complexity, dose selected, incremental dose selected, statistical design, incremental statistical design, peak revenue, revenue at year five (5), other revenue numbers, incremental revenue, market introduction, whether market introduction beats competition entry, number of treatment arms, hypothesis superiority/equivalence/non-inferiority, other choices around statistical design, treatment effect, hazard ratio, and other choices around estimating the characteristics of the patient population, response, and safety profile, screening criteria, dropout rate, and other choices around modeling/estimating the characteristics and behaviors of the patient population and other factors that impact how the study evolves and its likelihood of achieving its goals (how slowly/quickly patients enroll, etc.), site payments and other choices around operational aspects of the study that can impact how the study evolves and its likelihood of achieving its goals, cost per patient, cost per site, or other cost factors, selections made in other projects (across users within customer companies or organizations and across all users of the platform), priorities set by the customer company or organization, and/or other user-defined filters based on available inputs and outputs of the platform or in the systems and methods described herein. In embodiments, any of the parameters and variables described herein may be incremental parameters and variables. Site selections may be evaluated and compared against all of the parameters of the performance space or a subset of the parameters of the performance space. A set of site selections, e.g., one or more groups each including one or more possible sites, may be evaluated for one or more of the performance parameters. The performance parameters and the values of the performance parameters of site selection and/or clinical trial design define the performance space of the set of site selections.

The configuration facility 10406 may include a combinations component 10418. The combinations component 10418 may automatically or semi-automatically define the design space and/or scenario space that may be evaluated by the platform 10404.

The simulation facility 10410 of the platform 10404 may, based on the space definitions from the configuration facility 10406, evaluate the site selections. The simulation facility 10410 may include models 10426. As used herein with respect to site selection, a model includes the combination of parameters and the values that describe a site selection and/or corresponding clinical trial designs and the scenario under which the site selection is evaluated. Models 10426 may include hundreds or even thousands of models. Models 10426 may include deviation specifications for one or more of the parameters of the models. A deviation specification may define a range of values, a distribution of values, and/or a function of values for one or more parameters of a model. The deviation specifications may be based on expected or previously measured distributions or variations in design parameters.

The simulation facility 10410 may include engines 10428. As used herein, engines may relate to the codification of a site selection and/or corresponding clinical trial design that can receive model parameters and run a simulation to generate an output. The output of the engines 10428 may be a predicted behavior for a site selection for one or more corresponding clinical trial designs and/or one or more scenarios and/or conditions. Engines 10428 may evaluate a site selection with analytical methods, mathematical methods, numerical methods, simulation, and/or the like. Evaluating a site selection may include a simulation run to determine performance of the site selection. Evaluating a site selection may include using a Monte Carlo approach to simulate a site selection for different values according to the deviation specifications and using statistical methods to determine the performance of the site selection from a simulation run.

The simulation facility 10410 may include search/exploration component 10430. The search/exploration component may facilitate modification of model parameters for simulation. The search/exploration component 10430 may adaptively modify or generate models for simulations based on simulation results of other models/site selections and/or based on triggers and data from other facilities of the platform 10404.

The analysis facility 10408 may be configured to analyze simulation results of site selections. The analysis facility 10408 may include a filtering component 10420. The filtering component 10420 may be configured to use one or more numerical and/or analytical methods to evaluate and compare the performance of evaluated site selections. The filtering component may identify optimal or near-optimal site selections for one or more performance parameters. The filtering component may search the performance space and identify a set of optimal and/or near optimal site selections for one or more performance parameters.

The analysis facility 10408 may include a recommendation component 10422. The recommendation component 10422 may provide site selection recommendations. The site selection recommendations may be based on optimal or near-optimal site selections determined by the filtering component 10420. Recommendations may be adaptive based on settings, feedback, selections, triggers, and the like from the user, and/or other facilities in the platform 10404.

The analysis facility 10408 may include an augmenting component, 10424. The augmenting component may supplement simulation results with real-world data.

The interfaces facility 10412 may be configured to provide visualizations and interfaces for comparing, searching, and evaluating simulated site selections. Visualization component 10432 may provide for one or more interfaces to visualize the performance of site selections and facilitate comparison of site selections by a user. The feedback analysis component 10434 may track user actions associated with the interfaces and visualizations to determine patterns and/or preferences for site selections. The tradeoff advisor component 10436 may analyze and provide data and guidance for evaluating tradeoffs between two more site selections.

The platform 10404 may include and/or provide access to one or more data facilities 10438. Data in the data facilities may include design histories 10440, simulation data 10442, site data 10444, resource data 10446, population data 10448, and the like.

FIG. 105 shows aspects of an embodiment of a process for site selection. The process may include four or more stages. Facilities of the platform 10404 may be configured to implement the stages of the process. The stages of the process may include a configure stage 10502. The configure stage 10502 may define one or more of the spaces associated with the site selection. The configure stage 10502 may define one or more of site selection criteria space 10510, site selection design space 10512, site selection scenario space 10514, and/or site selection performance space 10516. The configure stage 10502 may utilize one or more advisors, wizards, algorithms, and the like for defining the spaces. In some embodiments, the different spaces associated with the configuration stage 10502 may be defined by different members of a team based on the expertise of the members. In some cases, members of a team may have different specializations. For example, some members may specialize in scenarios, while others may specialize in site selection and/or design definitions. Separating the inputs may allow different team members to independently optimize and improve specific models without affecting other inputs. In some embodiments, the inputs may be separated into two or more types based on convenience, expertise, flexibility, and the like.

The stages of the process may include an evaluate stage 10504. The evaluate stage 10504 may configure models 10518 for evaluation using simulation 10520 and analytical methods 10524. The stage may include various methods of enhancing computation and simulation using parallelization and resource management 10522.

The stages of the process may include an augment stage 10506. The augment stage 10506 may add real-world data to the simulation data. Financial data 10526, regulatory data 10528, revenue data 10530, and the like may be added to the and used to augment data from simulations.

The stages of the process may include an explore and analyze stage 10508. The explore and analyze stage 10508 may include filtering methods and algorithms 10532 for identifying optimal site selections. The stage may include generating and interacting with visualizations 10534 and tradeoff analysis tools 10534 to compare and select site selections.

Figure 106:
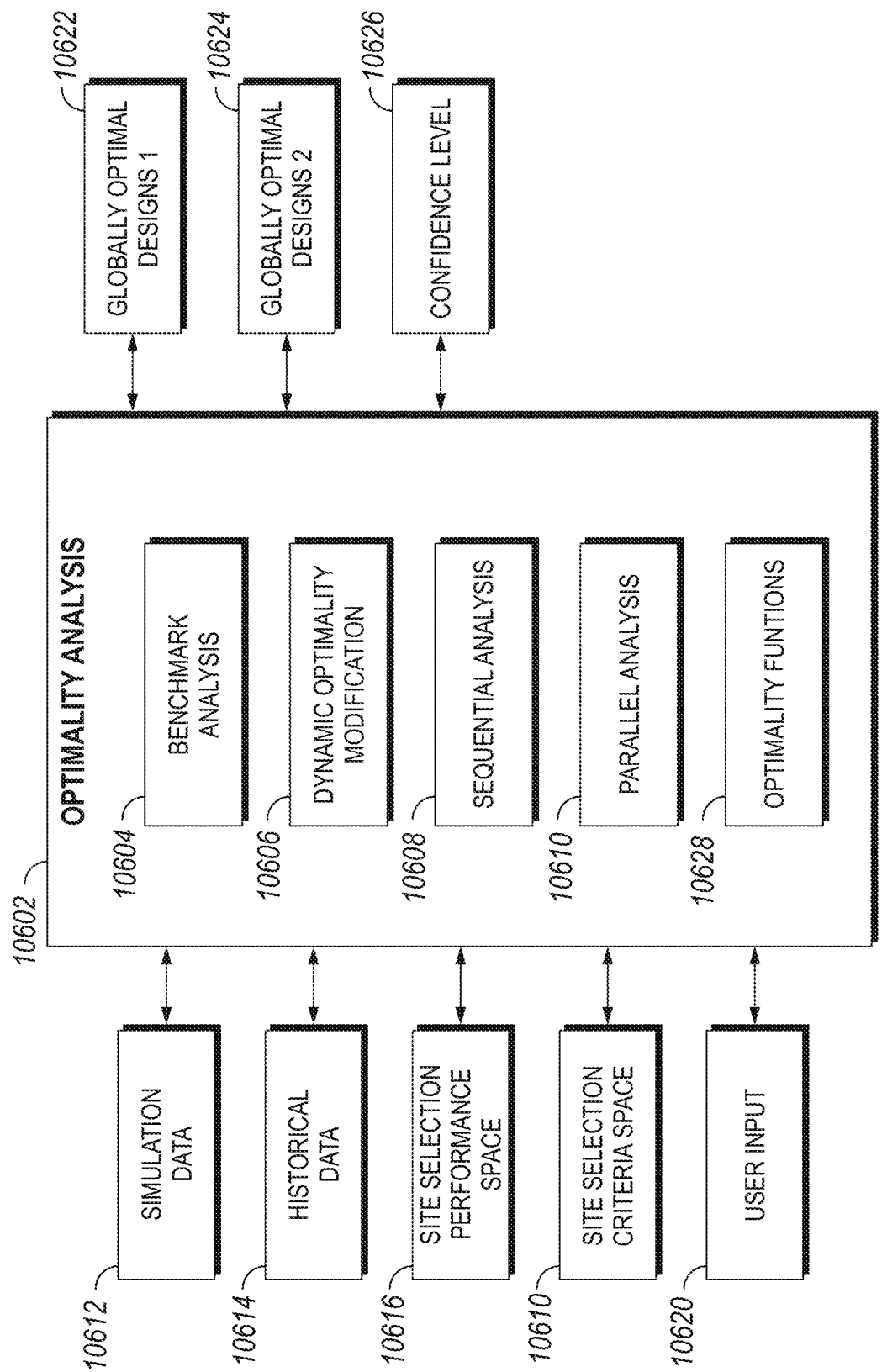
FIG. 106 is a schematic diagram of an apparatus for determining a site selection to globally optimize patient recruitment for a clinical trial, in accordance with an embodiment of the current disclosure.

In embodiments, the platform 10404 (FIG. 104) may be configured for identification and confirmation of optimal site selections for a clinical trial. Optimality of site selection may be in relation to site selection criteria, e.g., a parameter within site selection criteria space 10510 (FIGS. 105 and 106). For example, embodiments of the current disclosure may provide for the determination of a site selection for a clinical trial as being the most likely site selection to result in the highest number of diabetic patients being recruited to participate in the clinical trial. Site selection criteria may be determined in relation to the site selection performance space 10514 (FIGS. 105 and 106). Optimality of the site selection criteria may be in relation to one or more site selection performance parameters, e.g., a parameter within site selection performance space 2414, and the values thereof An optimal site selection may be a site selection that achieves a most desirable value for one or more specific site selection performance parameters. A most desirable value may depend on the site selection performance parameter and may be different for each site selection performance parameter. In some cases, the most desirable value may be the highest value of a site selection performance parameter. In some cases, the most desirable value may be the lowest value of a site selection performance parameter. In some cases, the most desirable value may be a range of values, a specific value, a function of values, and the like. For example, in some cases an optimal site selection with respect to a cost site selection performance parameter may be a site selection that has the lowest cost and achieves the goals of the clinical trial. As another example, an optimal site selection with respect to a time site selection performance parameter may be a site selection that has the highest NPV and achieves the goals of the clinical trial.

In embodiments, an optimum site selection is a site selection that achieves most desirable values for two or more specific site selection performance parameters. In the case of optimality for multiple site selection performance parameters, optimality may require a tradeoff between the parameter values. For example, a site selection that has a lower cost may have a low NPV and therefore may not be desirable. The optimality of a site selection may be based on a function of site selection performance parameters. In some cases, a function may be a weighted sum of the site selection performance parameters. A function, or a set of functions, may be used to generate an overall score (or a set of scores) and the score may be used to determine the optimality of the site selection. A highest score, a specific score, lowest score, and the like may be considered optimal depending on the function used to compute the score.

In embodiments, optimality may be evaluated according to Pareto optimality. Pareto optimal site selections may be site selections where no individual site selection performance parameter can be better off without making at least one other individual site selection performance parameter worse off. In some cases, optimality may be determined using convex hull analysis.

In some cases, one site selection may be globally optimum. In some cases, more than one site selection may be globally optimum. In some cases, no site selections may be globally optimum. In some embodiments, optimality of site selection may be relative to a benchmark. A known site selection, a set of historical site selections, and/or the like may be used as a benchmark. Site selections may be considered optimal if they meet, exceed, and/or are within a threshold distance of the benchmark site selection performance parameters.

Site selection performance parameters that may be used to determine site selection optimality may be user defined, system defined, algorithmically defined, and/or the like. In some cases, users may specify a subset of site selection performance parameters that should be used to identify optimal site selections. A user may define optimality criteria by defining ranges, values, characteristics, and the like of the parameter values that may be considered desirable and/or optimal. Interactive graphical interfaces may be provided to a user to evaluate different site selections based on one or more optimality criteria. Interactive interfaces may allow a user to explore different site selections by changing scoring methods, weights associated with the criteria, and the like.

In embodiments, the characteristics of site selection performance parameters for evaluated site selections may be analyzed by the platform to determine if any of the parameters may be less important for optimality. For example, analysis may include evaluation of ranges, variability, and other statistical analysis. If one or more site selection performance parameters for all evaluated site selections is within a desirable range, or the site selection performance parameter is almost equal for all of the evaluated site selections, the site selection performance parameter may be removed and identified as less significant for optimality and, in some cases, may not be factored in when determining optimality. Prior to determining optimality based on site selection performance parameters, the site selection performance parameters and the values of the site selection performance parameters may be grouped, filtered, normalized, and the like.

Optimality of site selections may be redefined automatically, semi-automatically, in response to user input, and/or the like. The criteria for optimality of site selections may change as site selections are evaluated by the platform. For example, initial optimality criteria may produce no optimal site selections. In response to no optimal site selections being determined, the criteria may be changed (relaxed, increased, decreased, etc.) until at least one site selection is considered optimal. In another example, optimality criteria may change in response to user feedback. Users may evaluate initial site selections found to be optimal and provide feedback (direct feedback and/or indirect feedback that can be derived from user actions and inactions). The feedback from the user may be used to change how optimality is determined, which site selection performance parameters are used to determine optimality, the values of the site selection performance parameters that are considered optimal, and/or the like.

In some embodiments, site selection performance parameters may be grouped, ordered, and/or organized into one or more hierarchies, groups, and/or sets. Two or more different optimality criteria may be used in parallel to determine multiple sets of optimal site selections under different criteria. Two or more different optimality criteria may be used sequentially to determine optimal site selections. One criteria may first be used to identify a first set of optimal site selections under first criteria. A second set of criteria may then be used on the first set to reduce the set of optimal site selections.

In embodiments, a site selection may be globally optimum if the site selection is optimal with respect to all possible site selection options. In embodiments, a site selection may be globally optimum if the site selection is optimal with respect to possible site selection options for one or more criteria. In embodiments, a site selection may be globally optimum if the site selection is optimal with respect to a large percentage (such as 80% or more) of possible site selection options for one or more criteria. In embodiments, a site selection may be globally optimum if the optimality of the site selection is within a high confidence level (90% confidence) with respect to possible site selection options for one or more criteria.

Traditional methods for evaluating site selections cannot determine global optimum site selections since they evaluate one, several, or a small subset of site selection options. Traditional methods do not consider all or almost all of the site selection options and cannot find a global optimum.

Trial site selections may involve numerous variables, parameters, considerations, tradeoffs, and the like resulting in a very large number of possible variations. A large number of possible variations makes study site selections and optimization using traditional methods difficult. In many cases, traditional methods may fail to explore or consider the complete space of possible trial site selection options and may miss or never consider globally optimal site selections. Using traditional methods, the number of site selection variations that may be explored in a reasonable time is limited. In some cases, only one (1) statistical site selection and only three (3) clinical scenarios may be evaluated. The best site selection study of the limited number of variations may not result in a globally optimal site selection. A locally optimum site selection chosen from a limited number of considered site selections may represent one (1) local maximum but may be far from the globally optimum site selection. When 10,000 or more clinical scenarios are considered, a globally optimum site selection may be distinguished from the many locally optimum site selections. However, consideration of 10,000 clinical scenarios cannot be practically performed using traditional methods as it would require an estimated 50,000 hours or more to complete.

In embodiments, the platform and methods described herein may evaluate thousands or even millions of site selection options enabling a determination of a global optimum site selection. In many cases, the globally optimum site selection may have significant advantages over locally optimum site selection. In one example, a globally optimum site selection may require less time to complete than other site selections.

In embodiments optimization of trial site selections may occur sequentially after optimization of trial design. In one embodiment, a globally optimum trial design may be determined using the techniques described herein. After the globally optimum trial design is determined a globally optimum trial site selection may be determined for the determined trial.

Referring again to FIG. 104, the platform 10404 may receive and/or determine performance space using the configuration facility 10406. Performance space may be defined in the space definitions component 10416. The performance space may be configured based on input from users and/or based on data 10438 such as history data 10440 and/or simulation data 10442. In embodiments data 10438 may include external data from external data sources and providers. In one instance, performance space may define optimality criteria. Optimality criteria may define site selection performance parameters, performance values, functions, methods, and algorithms for evaluating optimality and/or global optimality of site selections. In one instance optimality criteria may be configured by the user or determined from benchmark site selections from history 10440 and/or simulation 10442 data. In another instance, optimality criteria may be defined from simulation data from the simulation facility 10410. Optimality of site selections may be determined in the analysis facility 10408. The filtering component 10420 may be used to determine one or more sets of globally optimum site selections from the site selections evaluated by the simulation facility 10410.

FIG. 106 shows aspects of an apparatus/optimality analysis component 10602 for determining global optimality of site selections. In embodiments, the optimality analysis component 10602 may be part of the analysis facility 10408 of the platform 10404. The optimality analysis component 10602 may receive data from simulated site selections 10612 and determine one or more sets of optimal site selections 10622, 10624. The optimality analysis component 10602 may include one or more circuits for determining optimality of site selection. In embodiments, the optimality analysis component 10602 may include circuits for determining optimality based on optimality functions 10628. Optimality functions 10628 may determine optimality of site selections based on different weighting of performance factors of the simulated site selections. In embodiments, the optimality analysis circuit 10602 may include circuits for determining optimality based on benchmark analysis 10604. A benchmark analysis circuit 10604 may determine optimality of site selections based on a comparison of site selection performance parameter values to one or more benchmark site selections such as from historical data 10614 and/or simulation data 10612. In embodiments, the optimality analysis circuit 10602 may include circuits for determining optimality using sequential analysis 10608 and/or parallel analysis 10610. The sequential analysis circuit 10608 and parallel analysis circuit 10610 may use one or more different optimality functions 10628 in parallel or sequentially to determine optimal site selections. In embodiments, the optimality analysis circuit 10602 may include circuits for dynamically modifying optimality criteria 10606. User inputs 10620, simulation data 10612, and/or the determined sets of optimal site selections may be monitored and analyzed to determine modifications to optimality criteria. In embodiments, the optimality analysis circuit 10602 identifies a confidence level 10626 associated with the optimality of sets of optimal site selections. In the case where simulation data 10612 may not include simulations of all site selection options for the criteria space 10618, the optimality circuit 10602 may determine, based on the simulated site selections, a confidence level that the determined optimal site selections are indeed optimal for a given optimality criteria.

Figure 107:
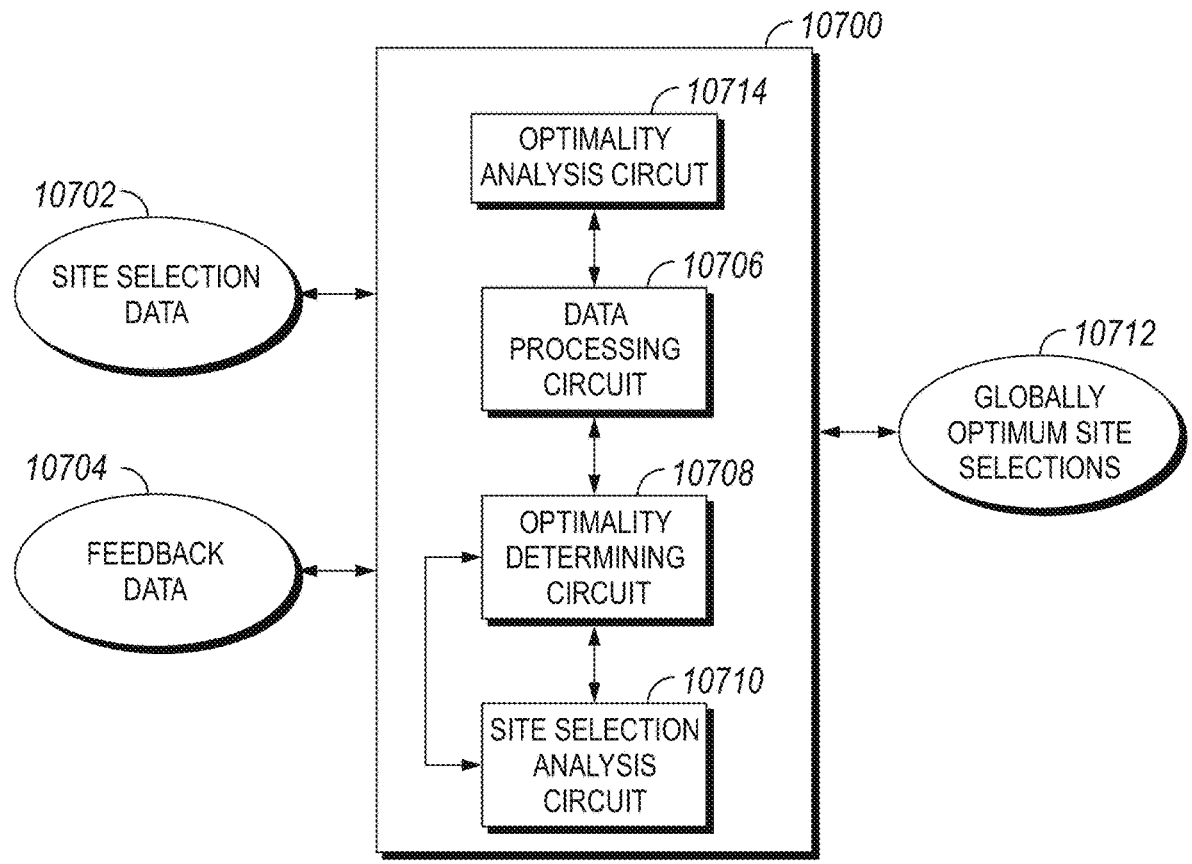
FIG. 107 is a schematic diagram of another apparatus for determining a site selection to globally optimize patient recruitment for a clinical trial, in accordance with an embodiment of the current disclosure.

FIG. 107 shows aspects of an apparatus 10700 for determining global optimality of site selections. In embodiments, the apparatus 10700 may include an optimality analysis circuit 10714 which may be part of the analysis facility 10408 of the platform 10404 (FIG. 104). In embodiments, the apparatus 10700 may include a data processing circuit 10706 structured to interpret/obtain site selection data 202 of a clinical trial site selection. In some embodiments the site selection data 202 may be outputs of simulation data of trial site selections. The output processing circuit 10706 may transform the site selection data 10702 into a format suitable for use by the various circuits in the apparatus. For example, the site selection data 10702 may be received by the data processing circuit 10706 and determine and identify site selection performance parameters in the data. In some embodiments, some site selection performance parameters may be grouped, filtered, converted, normalized, and the like.

The apparatus 10700 of FIG. 107 may further include an optimality determining circuit 10708 structured to receive processed site selection data from the data processing circuit 10706. The optimality determining circuit 10708 may identify globally optimum site selections 10712 based on one or more optimality criteria. In some embodiments, the globally optimum site selections 10712 may be provided as an output of the apparatus. In some embodiments, globally optimum site selections 10712 may be further processed by the site selection analysis circuit 10710. The site selection analysis circuit 10710 may analyze the globally optimum site selections 10712, determine characteristics of the site selections, and receive feedback data 10704 about the site selections. The site selection analysis circuit may, based on the determined characteristics, determine modifications for optimality criteria used in the optimality determining circuit 10708. Using modified optimality criteria, the optimality determining circuit 10708 may determine a new set of globally optimum site selections 10712.

Figure 108:
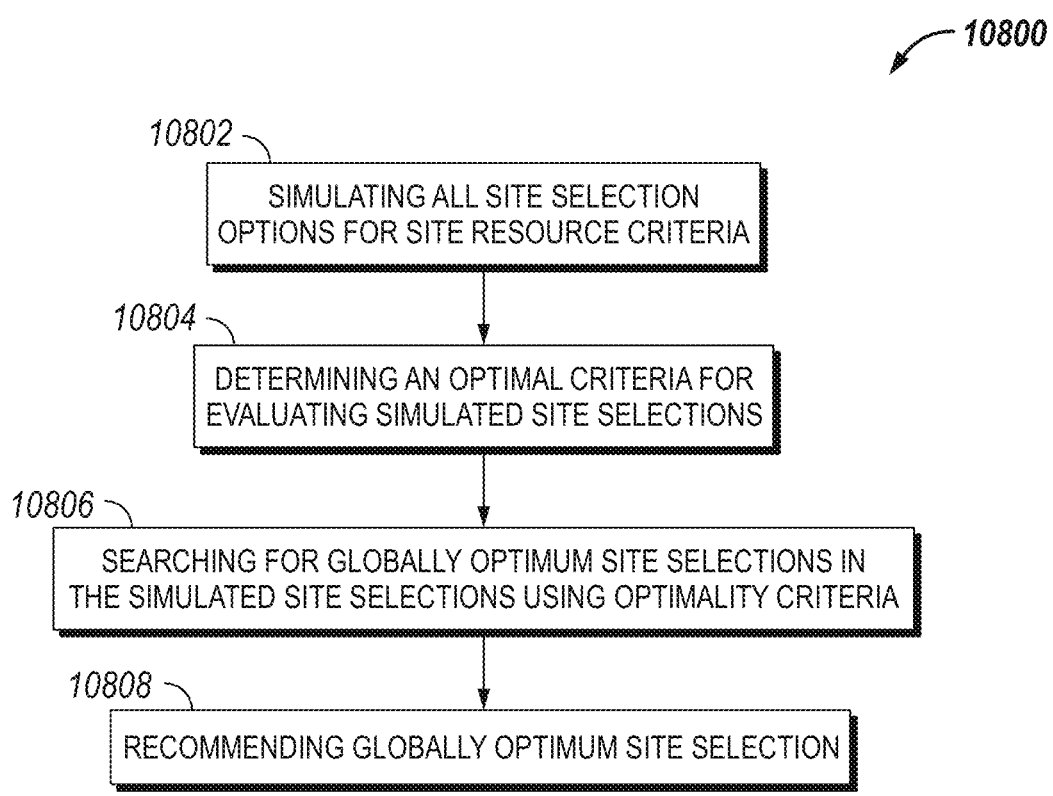
FIG. 108 is a flow chart depicting a method for determining a site selection to globally optimize patient recruitment for a clinical trial, in accordance with an embodiment of the current disclosure.

As shown in FIG. 108, a method 10800 for determining globally optimum site selections may include simulating all site selection options for a site selection criteria 10802. The method 10800 may further include determining an optimality criteria for evaluating simulated site selections 10804. Optimality criteria may be a function of one or more performance values for each site selection such as a weighted sum of the values, a comparison of the values, and the like. The method 10800 may include searching for globally optimum site selections in the simulated site selections using the determined optimality criteria 10806. The globally optimum site selections may be recommended to one or more users 10808.

Figure 109:
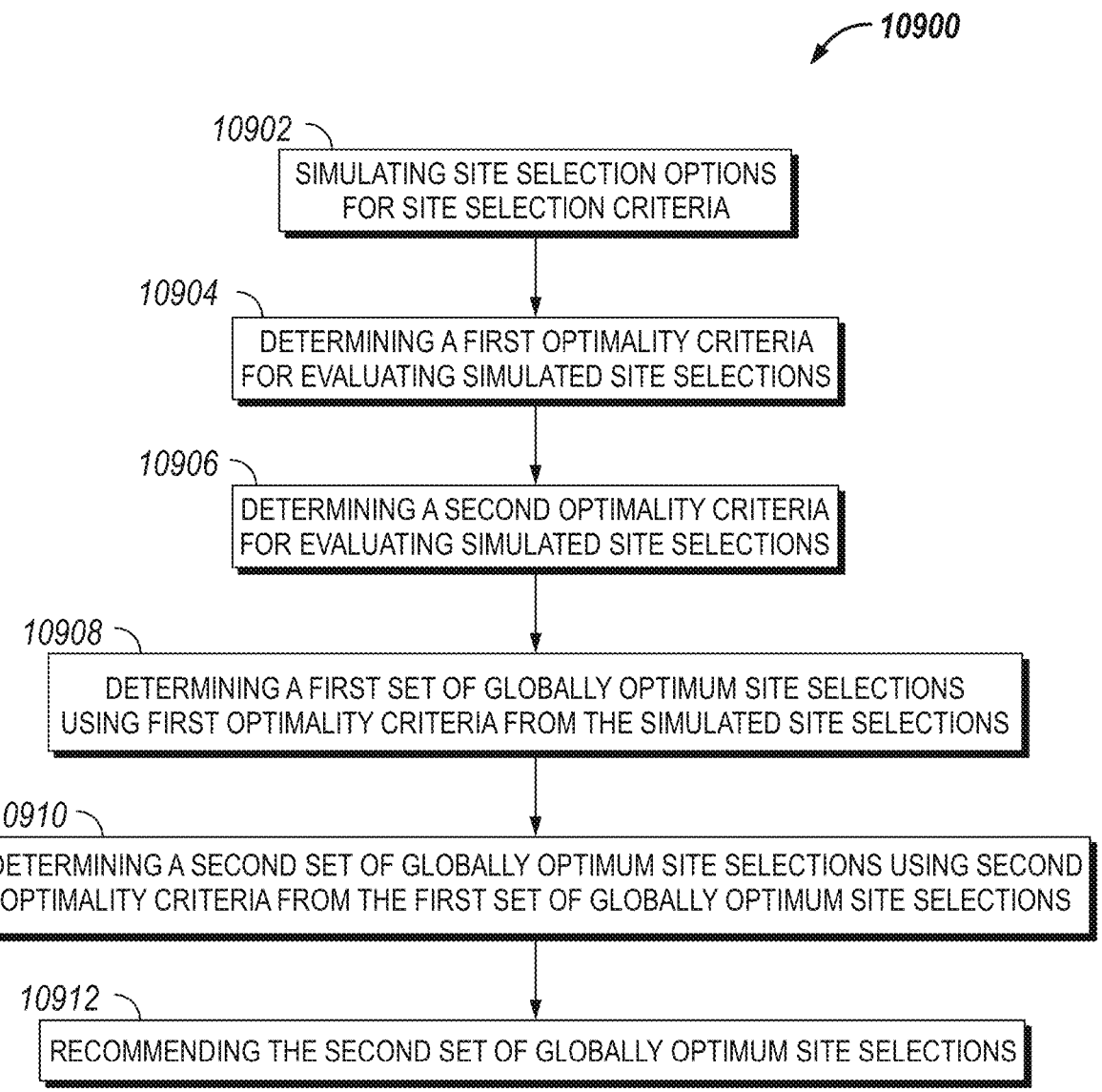
FIG. 109 is a flow chart depicting another method for determining a site selection to globally optimize patient recruitment for a clinical trial, in accordance with an embodiment of the current disclosure.

As shown in FIG. 109, a method 10900 for determining globally optimum site selections may include simulating site selection options for a site selection criteria 10902. The method 10900 may further include determining a first optimality criteria for evaluating simulated site selections 10904. The method 10900 may further include determining a second optimality criteria for evaluating simulated site selection(s) 10906. The method 10900 may include determining a first set of optimum site selections using the first optimality criteria, the first set may be determined from the simulated site selections 10908. The method 10900 may further include determining a second set of optimum site selections using the second optimality criteria, the second set may be determined from the first set of site selections 10910. The globally optimum site selections may be recommended to one or more users 10912.

Figure 110:
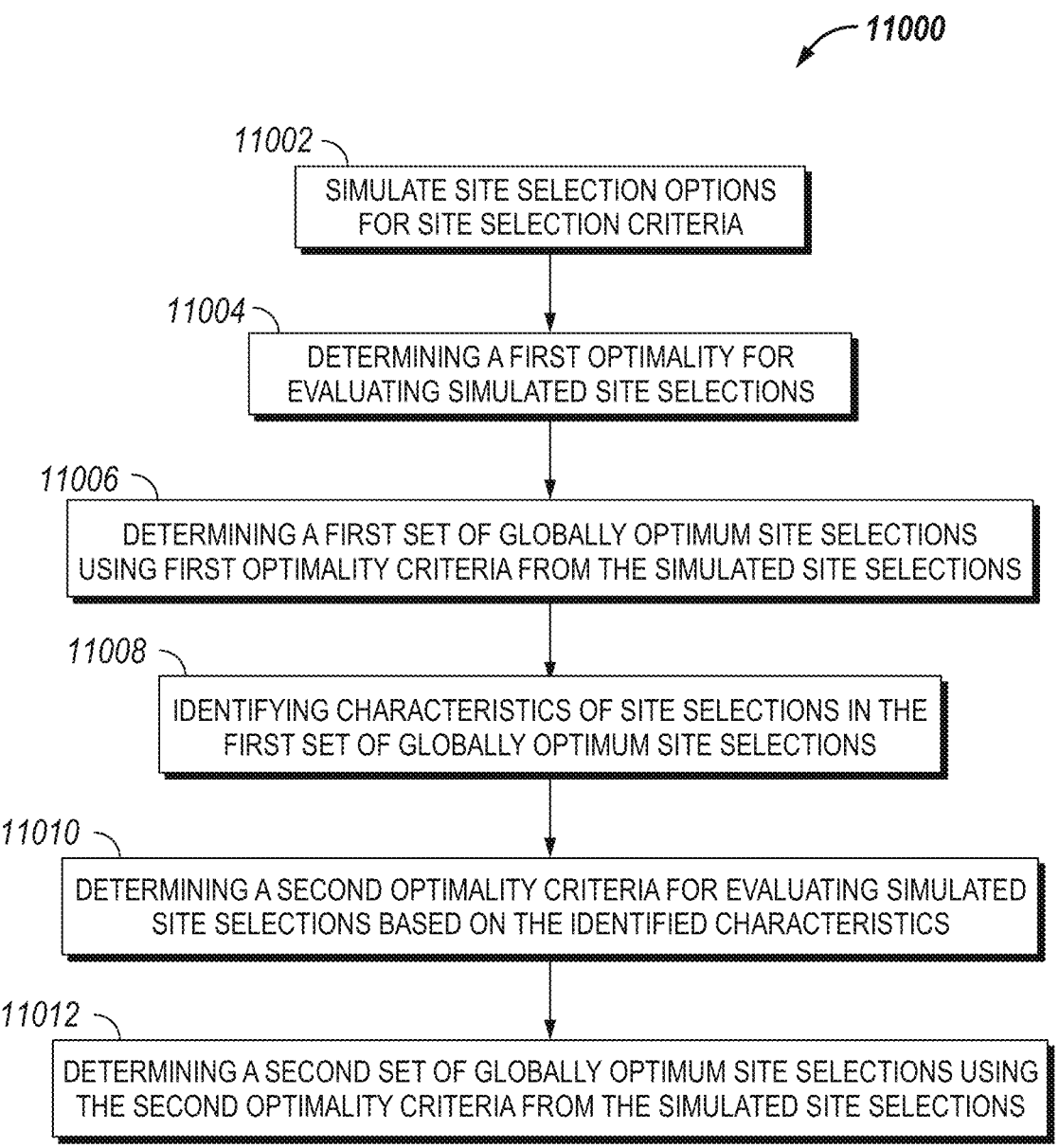
FIG. 110 is a flow chart depicting another method for determining a site selection to globally optimize patient recruitment for a clinical trial, in accordance with an embodiment of the current disclosure.

As shown in FIG. 110, a method 11000 for determining globally optimum site selections may include simulating site selection options for a site selection criteria 11002. The method 11000 may further include determining a first optimality criteria for evaluating simulated site selections 11004. The method 11000 may include determining a first set of optimum site selections using the first optimality criteria, the first set may be determined from the simulated site selections 10906. The method 11000 may further include identifying characteristics of site selections in the first set of globally optimum site selections 11008. The method 11000 may further include determining a second optimality criteria for evaluating simulated site selections based on the identified characteristics 11010. The method 11000 may include determining a second set of globally optimum site selections using the second optimality criteria from the simulated site selections 11012.

Figure 111:
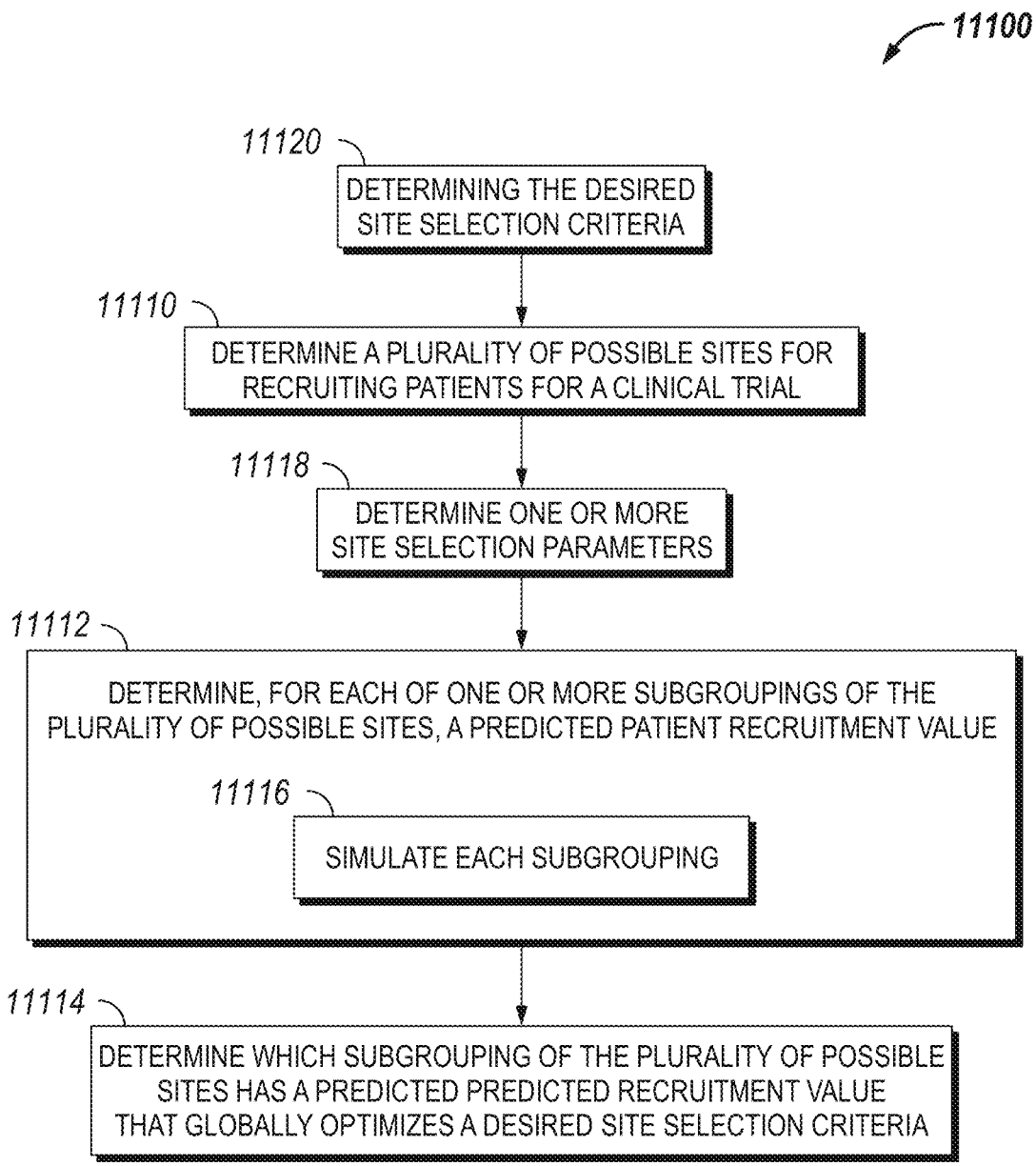
FIG. 111 is a flow chart depicting another method for determining a site selection to globally optimize patient recruitment for a clinical trial, in accordance with an embodiment of the current disclosure.

Illustrated in FIG. 111 is a method 11100 for determining a site selection to globally optimize patient recruitment for a clinical trial, in accordance with an embodiment of the current disclosure. The method 11100 includes determining a plurality of possible sites for recruiting patients from for a clinical trial 11110. The method 11100 further includes determining, for each of one or more subgroupings of the plurality of possible sites, a predicted patient recruitment value 11112. The method 11100 further includes determining which subgrouping of the plurality of possible sites has a predicted patient recruitment value that globally optimizes a desired site selection criteria 11114. In embodiments, determining the predicted patient recruitment value for each of the subgroupings of the plurality of possible sites includes simulating each of the subgroupings 11116. In embodiments, simulating each of the one or more subgroupings may be based at least in part on use of different types of engines, e.g., engines with different version numbers and/or developed by different entities, e.g., in-house vs third-party vendor. In embodiments, the differences in types of engines may include underlying types of algorithms and/or assumptions, e.g., rounding rules. In embodiments, the method 11100 may further include determining one or more site selection parameters 11118. In such embodiments, simulating each of the one or more subgroupings 11116 may be based at least in part on the one or more site selection parameters. In embodiments, the one or more site selection parameters may be based at least in part on: a country; a state/province; a county; a city; a zip code; and/or a patient enrollment matriculation number. In embodiments, the method 11100 may further include determining the desired site selection criteria 11120. In such embodiments, simulating each of the one or more subgroupings 11116 may be based at least in part on the determined site selection criteria. In embodiments, the determined site selection criteria may be based at least in part on: a number of required patients; a start date of the clinical trial; an end date of the clinical trial; and/or a total cost of the clinical trial. In embodiments, determining which subgrouping of the plurality of possible sites has a predicted patient recruitment value that globally optimizes the desired site selection criteria 11114 may include and/or be based at least in part on: a convex hull engine; a Pareto engine; a Monte Carlo engine; and/or a simulated annealing engine. In embodiments, determining which subgrouping of the plurality of possible sites has a predicted patient recruitment value that globally optimizes the desired site selection criteria 11114 may be based at least in part on a machine learning engine, as described herein. For example, in embodiments, a neural network may be trained to look at past site selections and their outcomes and predict one or more site selection criteria. In embodiments, the neural network may be trained via supervised learning and/or by unsupervised learning, e.g., cost-based policies.

Figure 112:
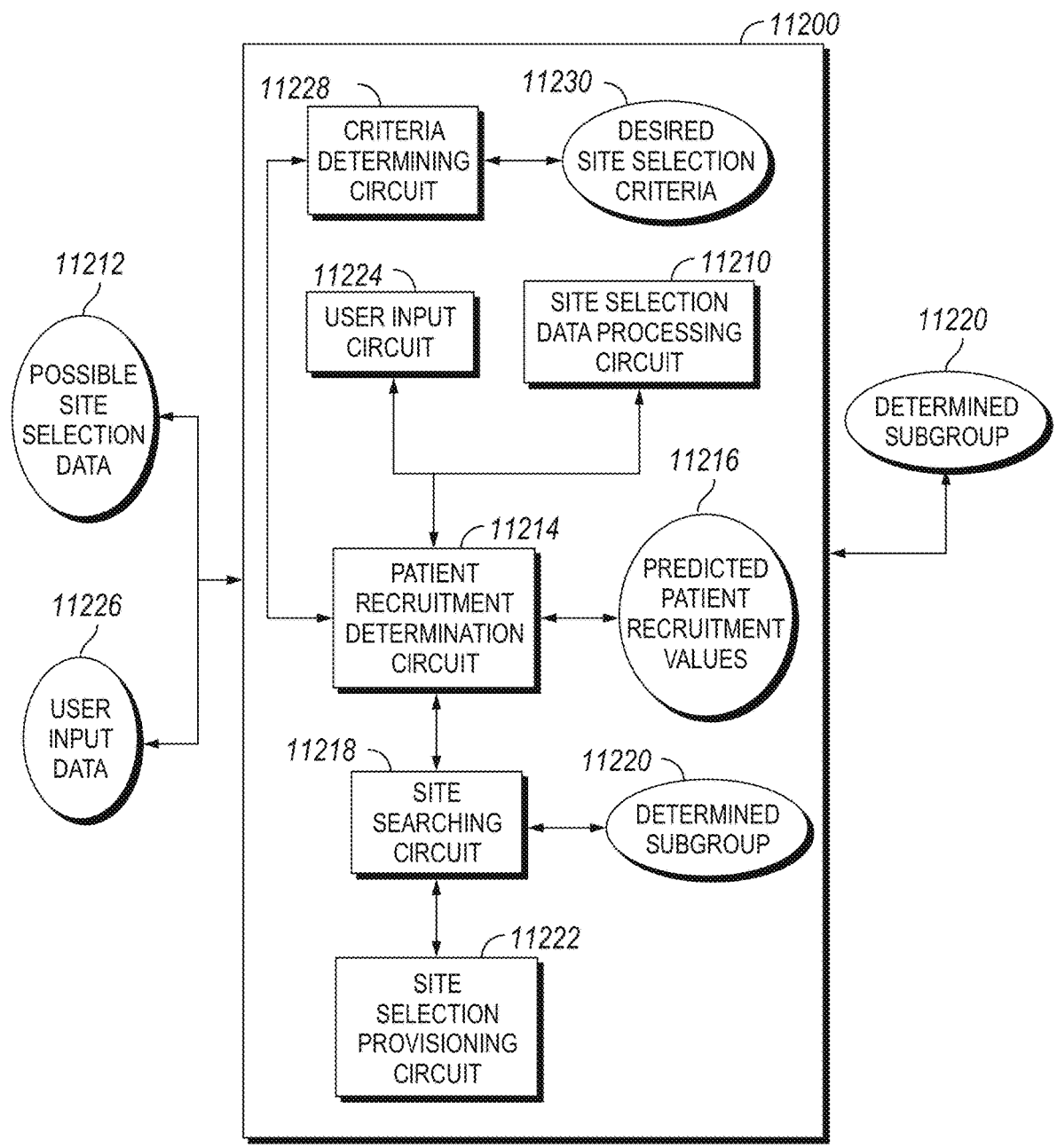
FIG. 112 is a flow chart depicting an apparatus for determining a site selection to globally optimize patient recruitment for a clinical trial, in accordance with an embodiment of the current disclosure.

Turning to FIG. 112, an apparatus 11200 for determining a site selection to globally optimize patient recruitment for a clinical trial, in accordance with an embodiment of the current disclosure, is shown. The apparatus 11200 may form part of the platform 10404 or it may be stand-alone from the platform 10404 and/or communicate with the platform 10404 via one or more application programming interfaces (APIs). The apparatus 11200 includes a site selection data processing circuit 11210 structured to interpret possible site selection data 11212 identifying a plurality of possible sites for recruiting patients from for a clinical trial. The apparatus 11200 further includes a patient recruitment determination circuit 11214 structured to determine a predicted patient recruitment value 11216 for each of one or more subgroupings of the plurality of possible sites. The apparatus 11200 further includes a site searching circuit 11218 structured to determine which subgrouping 11220 of the plurality of possible sites has a predicted patient recruitment value that globally optimizes a desired site selection criteria 11230. The apparatus 11200 further includes a site selection provisioning circuit 11222 structured to transmit the subgrouping 11220 of the plurality of possible sites that has the predicted patient recruitment value that globally optimizes the desired site selection criteria. In embodiments, the patient recruitment determination circuit 11214 is further structured to determine the predicted patient recruitment value for each of the one or more subgroupings of the plurality of possible sites by simulating each of the subgroupings. In embodiments, simulating each of the one or more subgroupings is based at least in part on use of different types of engines, as described herein. In embodiments, the apparatus 11200 may include a user input circuit 11224 structured to interpret user input data 11226 and a criteria determining circuit 11228 structured to determine the desired site selection criteria 11230 based at least in part on the user input data 11226. In embodiments, the site searching circuit 11218 may include a convex hull engine; a Pareto engine; a Monte Carlo engine; and/or a simulated annealing engine.

Figure 113:
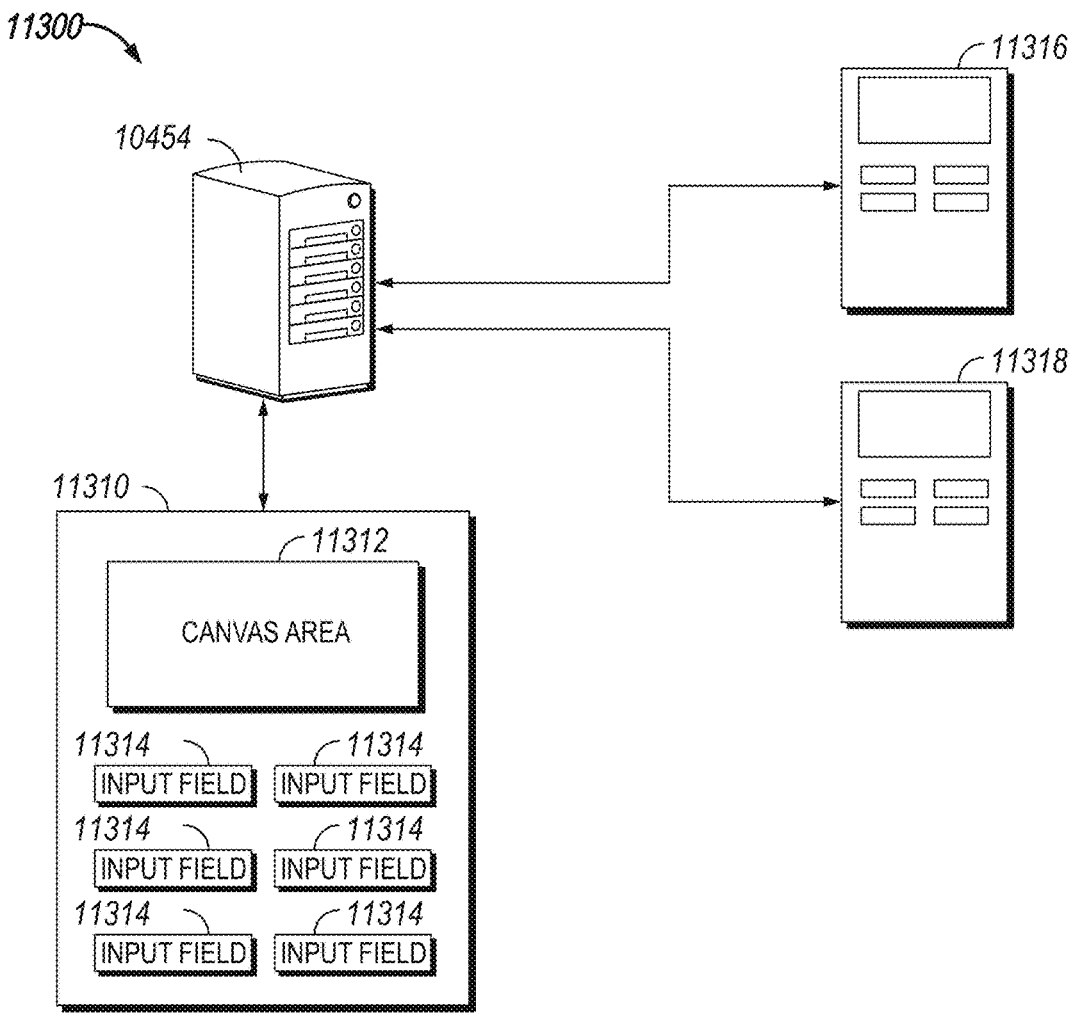
FIG. 113 is a diagram of a platform with an interface for collaborative configuration of a site selection for optimization of patient recruitment for a clinical trial, in accordance with an embodiment of the current disclosure.

Referring to FIG. 113, embodiments of the current disclosure may provide for a design platform 11300 with an interface 11310 for configuring and managing the platform 10404 with respect to optimizing site selection for patient recruitment for a clinical trial. The design platform 11300 may provide for pre-simulation determination of one or more selection parameters, e.g., values within site selection criteria space 10510, site selection space 10512, site selection scenario space 10514 and/or site selection performance space 10516. Some embodiments may provide for adjustment of selection parameters during a simulation. The interface 11310 may include a canvas area 11312 for visualizing/editing/creating selection parameters for use by the platform 10404 (FIG. 104). Embodiments of the interface 11310 may be a graphical user interface (GUI) that has one or more input fields 11314 for inputting or selecting selection parameters. The input fields 11314 may be sliders, text boxes, moveable components, and/or other GUI user input widgets. The graphical user interface may also provide for a heat map for selecting possible sites. The heat map may provide for filtering of the possible sites. In embodiments, the platform 11300 may provide, via servers 10454 (FIG. 104) multiple interfaces, e.g., interfaces 11310, 11316, 11318, for collaborative configuration of the platform 10404 by one or more users. In embodiments, the interfaces 11310, 11316, 11318 may be configured differently for different users, e.g., an interface may be tailored to a type of user and/or target audience, e.g., clinical trial experts, novices, and/or other types of users of varying skill levels in clinical trial designs and/or site selection. Tailoring of an interface to a user type may include enabling and/or disabling certain features and/or options on the interface. In embodiments, collaboration between users may involve a first user operating on a first interface 11310 receiving inputs from a second interface 11316 operated by a second user. In embodiments, the interface 11310 may provide for weighting of one or more selection parameters. In embodiments, the interface 11310 may provide for configuration of the simulation component 10410 (FIG. 104). For example, a user operating the interface 11310 may configure the simulation component 10410 to perform an exhaustive search and/or simulation of site selection options. In embodiments, a user operating the interface 11310 may configure the simulation component 10410 to perform a non-exhaustive search and/or simulation of site selection options. In embodiments, the interface 11310 may provide for a user to configure the platform 10404 to user one or more of a convex hull engine, a Pareto engine, a Monte Carlo engine, and/or simulated annealing engine. In embodiments, the interface 11310 may provide for a user to configure a training set for a machine learning engine to learn how to optimize site selections with respect to patient recruitment, as disclosed herein.

Figure 114:
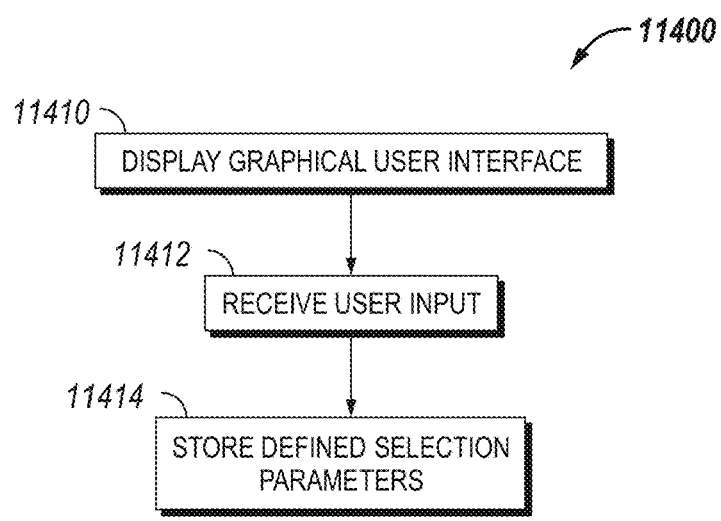
FIG. 114 is a flow chart depicting a method for collaborative configuration of a site selection for optimization of patient recruitment for a clinical trial, in accordance with an embodiment of the current disclosure.

Turning to FIG. 114, a method 11400 for collaborative configuration of a site selection platform 10404 for optimization of patient recruitment for a clinical trial is shown. The method 11400 includes displaying a graphical user interface structured to configure a system for determining which subgrouping, of a plurality of possible sites for recruiting patients from for a clinical trial, globally optimizes a desired criteria 11410. The method further includes receiving, via the graphical user interface, one or more user inputs that define one or more selection-parameters used by the system 11412. The method further includes storing the defined selection-parameters in a memory device 11414.

Figure 115:
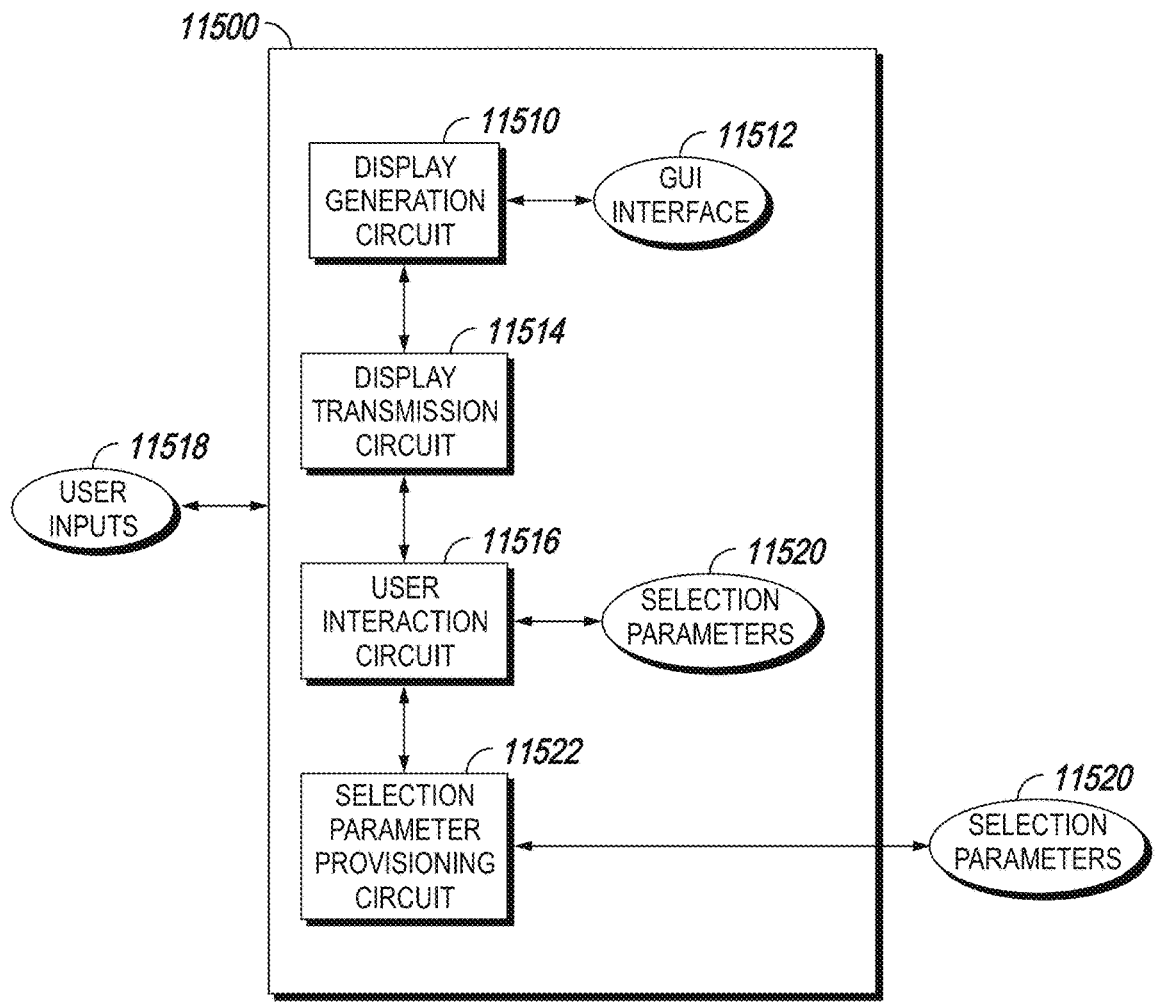
FIG. 115 is a schematic diagram of an apparatus for collaborative configuration of a site selection for optimization of patient recruitment for a clinical trial, in accordance with an embodiment of the current disclosure.

Shown in FIG. 115 is an apparatus 11500 for providing collaborative configuration of a site selection platform 10404 for optimization of patient recruitment for a clinical trial is shown. The apparatus 11500 includes a display generation circuit 11510 structured to generate a graphical user interface 11512 for configuring a system 10404 for determining which subgrouping, of a plurality of possible sites for recruiting patients from for a clinical trial, globally optimizes a desired criteria. The apparatus 11500 further includes a display transmission circuit 11514 structured to transmit the graphical user interface 11512 to an electronic device for display, e.g., 10402 (FIG. 104). The apparatus 11500 further includes a user interaction circuit 11516 structured to: interpret user inputs 11518 received by the graphical user interface 11512; and in response to, and based at least in part on, interpreting the user inputs 11518, define selection parameters 11520 used by the system 10404. The apparatus 11500 further includes a selection-parameter provisioning circuit 11522 structured to store the defined selection-parameters 11520 in a memory device, e.g., 10438 (FIG. 104).

Figure 116:
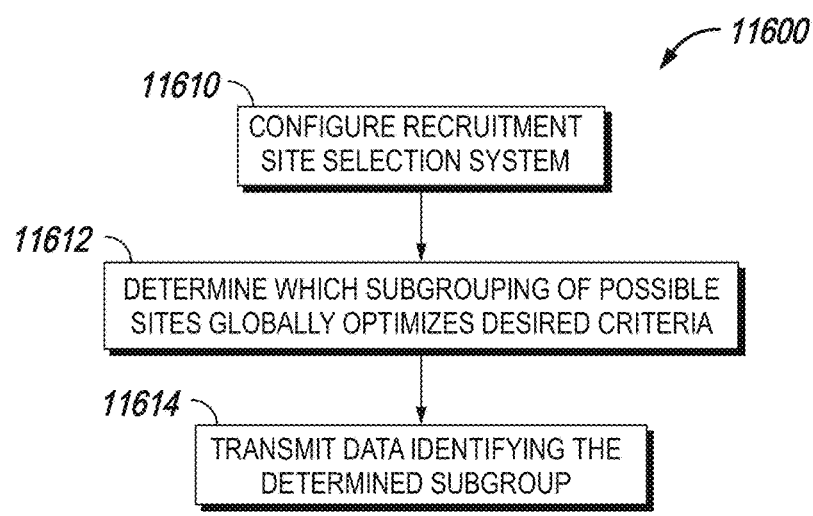
FIG. 116 is a flow chart depicting another method for collaborative configuration of a site selection for optimization of patient recruitment for a clinical trial, in accordance with an embodiment of the current disclosure.

Shown in FIG. 116 is another method 11600 for collaborative configuration of a site selection platform 10404 for optimization of patient recruitment for a clinical trial. The method 11600 includes configuring, via a graphical user interface, a recruitment site selection system via entering one or more user inputs into the graphical user interface that define one or more selection-parameters 11610. The method 11600 further includes determining, via the recruitment site selection system, which subgrouping, of a plurality of possible sites for recruiting patients from for a clinical trial, globally optimizes a desired criteria 11612. The method further includes transmitting data identifying the determined subgrouping 11614.

Figure 117:
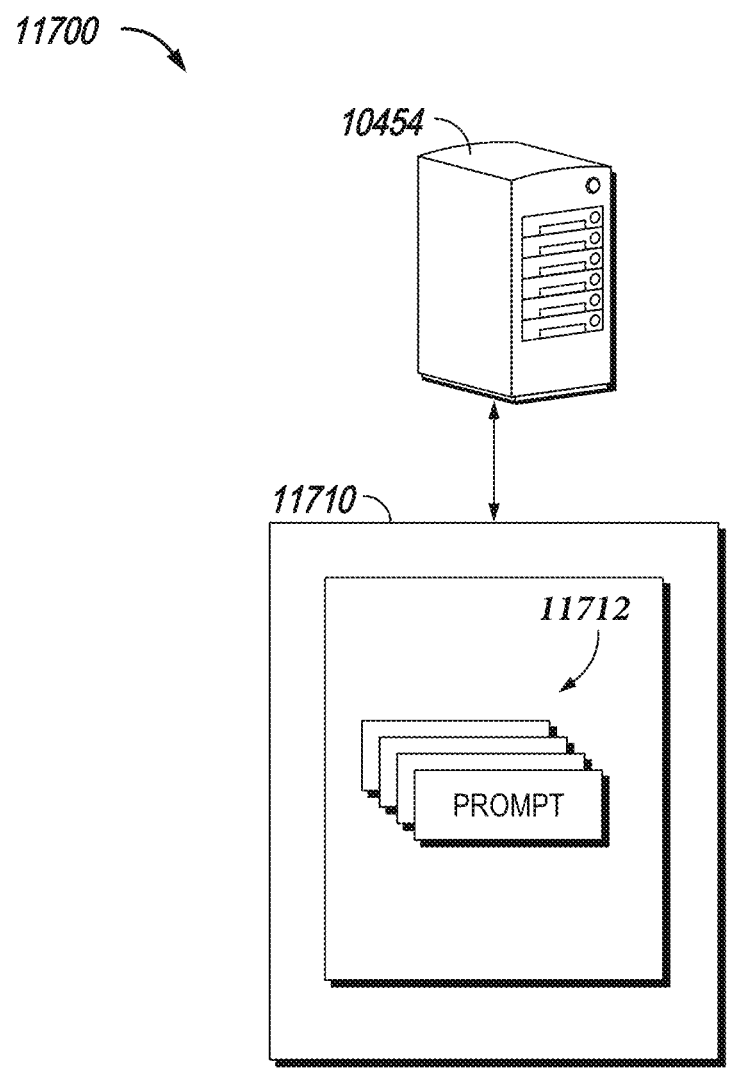
FIG. 117 is a diagram of a platform for configuring a system for globally optimizing patient recruitment for a clinical trial, in accordance with an embodiment of the current disclosure.

Referring to FIG. 117, embodiments of the disclosure may provide for a platform/system 11700 with an interface 11710, e.g., a wizard, for guiding a user through configuring a site grouping/selection system/platform 10404 (FIG. 104) for optimizing site selection for patient recruitment for a clinical trial. In embodiments, the interface 11710 may be generated by a server 10454 (FIG. 104). The interface 11710 may be command line based or graphical user interfaced based. The interface 11710 may generate a plurality of prompts 11712 that assist in obtaining initial selection parameters, e.g., criteria, from users to determine parameters for site selection criteria space 10510, site selection space 10512, site selection scenario space 10514, and/or site selection performance space 10516. The plurality of prompts 11712 may ask for a variety of static inputs or ranges. The inputs may include the type of engine 10428 to use in the simulation 10410. The inputs may also include the type of search algorithm 10430 used. The inputs may include the type of sensitivity analysis algorithms or tools that are preferred. The inputs may include the type of clinical trial. The interface 11710 may recommend one or more site groupings/selections based on the type of clinical trial. The recommended site groupings/selections may serve as a starting base for further modification by a user. Artificial intelligence/machine learning approaches may be used to generate the prompts 11712 and/or suggestions for the user through the configuration process. As will be appreciated, the suggestions and/or guiding by the interface 11710 may allow a user to avoid (or reduce) spending time and resources (including computing resources and the costs of those resources) on sub-optimal simulations.

In an embodiment, a method for guiding a user through configuring a site grouping/selection system/platform for optimizing site selection for patient recruitment for a clinical trial is provided. The method includes generating an interactive interface. The method further includes presenting, via the interactive interface, a plurality of prompts to a user structured to configure a site selection system for determining which subgrouping, of a plurality of possible sites for recruiting patients from for a clinical trial, globally optimizes a desired criteria. The method further includes for each of the plurality of prompts, receiving a responsive user input, and configuring the site selection system based at least in part on the responsive user inputs.

In another embodiment, a system for guiding a user through configuring a site grouping/selection system/platform for optimizing site selection for patient recruitment for a clinical trial is provided. The system includes a server structured to determine which subgrouping of a plurality of possible sites for recruiting patients from for a clinical trial globally optimizes a desired criteria. The system further includes an electronic device, e.g., 10402, structured to: display an interactive interface that presents a plurality of prompts to a user for configuring the server; for each of the plurality of prompts, receive a responsive user input; and configure the server based at least in part on the responsive user inputs.

In another embodiment, a non-transitory computer readable medium storing instructions is provided. The stored instructions, when loaded into at least one processor, adapt the at least one processor to: generate an interactive interface; and present, via the interactive interface, a plurality of prompts to a user. The plurality of prompts are structured to configure a site selection system for determining which subgrouping, of a plurality of possible sites for recruiting patients from for a clinical trial, globally optimizes a desired criteria. The stored instructions further adapt the at least one processor to, for reach of the plurality of prompts, receive a responsive user input; and configure the site selection system based at least in part on the responsive user inputs.

Embodiments of the current disclosure may provide for prediction of an initial site grouping/selection with respect to patient recruitment of a clinical trial. In embodiments, the initial site selection may be structured to maximize (globally optimize) one or more desired criteria, e.g., one or more parameters within site selection criteria space 10510, site selection space 10512, site selection scenario space 10514, and/or site selection performance space 10516, based on historical data. For example, in embodiments, a predicted initial site selection may correspond to maximizing a number of patients with a particular medical condition. In other embodiments, the predicted initial site selection may correspond to maximizing the number of recruited patients who are likely to complete the clinical trial.

In embodiments, the historical data may include data from previously conducted clinical trials and/or it may include data from prior simulated clinical trials. In embodiments, the data may be stored in data facility 10438 and/or be generated by the simulation component 10410 and/or the analysis components 10408. Data from past trials may be used to directly predict aspects of sites. Data from past trials may be used as a guide to determine parameters of the trials that were successful since in many cases, past indicators of success may translate to future success. For example, sites identified as having a high historical recruitment rate may generally be expected to have high recruitment rate for a future study. However, in some cases, depending on the parameter, a high success rate in historical data may translate to a negative or less favorable prediction for the current site selection. For example, a site as having a historical high recruitment for patients with a rare disease may translate to a prediction for low recruitment of the same type of patients for a new study. In some cases, depending on the therapeutic tested, a waiting period for the patients involved in the previous study may be required before they are allowed to participate in a new study making the patients unavailable for a new study. Therefore, an indication of high success in historical data may indicate that the patients will not available and may indicate a low performance for a planned study in the site. In embodiments, models for site selection may be evaluated for negative and positive associations between historical performance and expected current performance.

The prediction may be generated prior to receiving user input or after receiving some user input e.g., via user device 10402. The predicted initial site grouping/selection may be displayed in a graphical user interface, e.g., interface component 10412, for adjustment by a user. The predicted initial site grouping/selection may be the grouping/selection actually used in the clinical trial, or it may serve as a starting point which the user can configure/tweak as desired. The predicted initial site grouping/selection may be the global optimal, with respect to the desired site selection criteria; or it may be close to the global optimal, wherein a user can tweak it, i.e., make adjustments, to be the global optimal. The initial prediction may reduce the amount of time to find the global optimum by providing the user (or computer) with a good starting point based on knowledge gained from historical data. Simulated annealing, e.g., via the search/exploration modules/engines 10430, may be applied to the initial prediction to test the surrounding subgroupings. Artificial intelligence may be used to analyze the historical data based on known desired criteria for the clinical trial. For example, in embodiments, a neural network may be trained on historical data to identify patterns in site selections that result in particular values for one or more site selection criteria. The neural network may then process site selection data, i.e., data regarding possible sites for a clinical trial, and then generate a predicted initial site selection.

Figure 118:
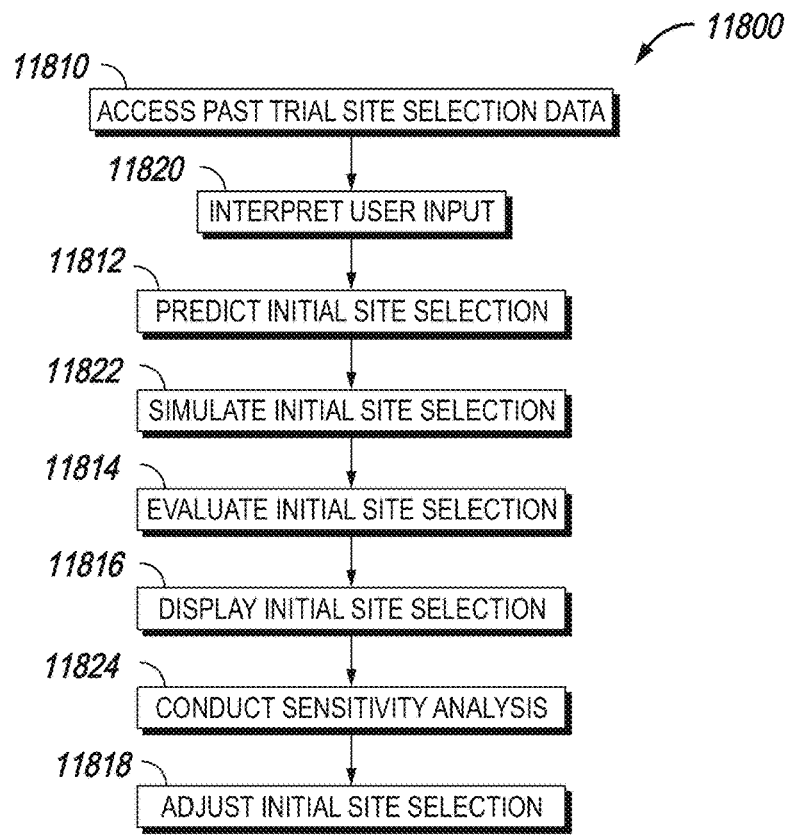
FIG. 118 is a flow chart depicting a method for predicting an initial site selection with respect to patient recruitment for a clinical trial, in accordance with an embodiment of the current disclosure.

Accordingly, referring to FIG. 118, a method 11800 for prediction of an initial site grouping/selection with respect to patient recruitment of a clinical trial is shown. The method 11800 includes accessing past trial site selection data stored in a database 11810. The method 11800 further includes predicting, based at least in part on the past trial site selection data, the initial site selection 11812. In embodiments, predicting the initial site selection may be based at least in part on artificial intelligence, as disclosed herein. The initial site selection may correspond to a global optimization of a desired site selection criteria. The method 11800 further includes evaluating the initial site selection with respect to being the global optimization (with respect to the desired site selection criteria) 11814. Such evaluation may be based at least in part on a convex hull engine, a Pareto engine, a Monte Carlo engine, or a simulated annealing engine, as disclosed herein. The method 11800 may further include displaying the initial site selection in a graphical user interface 11816. In embodiments, the desired site selection criteria may include a number of required patients; a start date of the clinical trial; an end date of the clinical trial; and/or a total cost of the clinical trial. In embodiments, the desired site selection criteria may be based at least in part on a patient recruitment related number, e.g., a minimum and/or maximum number of patients required to be recruited by the clinical trial guidelines, a minimum number of patients required to complete the clinical trial, and/or the like. In embodiments, the method 11800 further includes adjusting the initial site selection via the graphical user interface 11818. In embodiments, the method 11800 may further include interpreting one or more user inputs, wherein the prediction of the initial site selection is based at least in part on the one or more user inputs 11820. In embodiments, the method 11800 may further include simulating the initial site selection to determine performance criteria 11822. In embodiments, the method 11800 may further include conducting a sensitivity analysis of the initial site selection 11824, e.g., via analysis component 10408.

Figure 119:
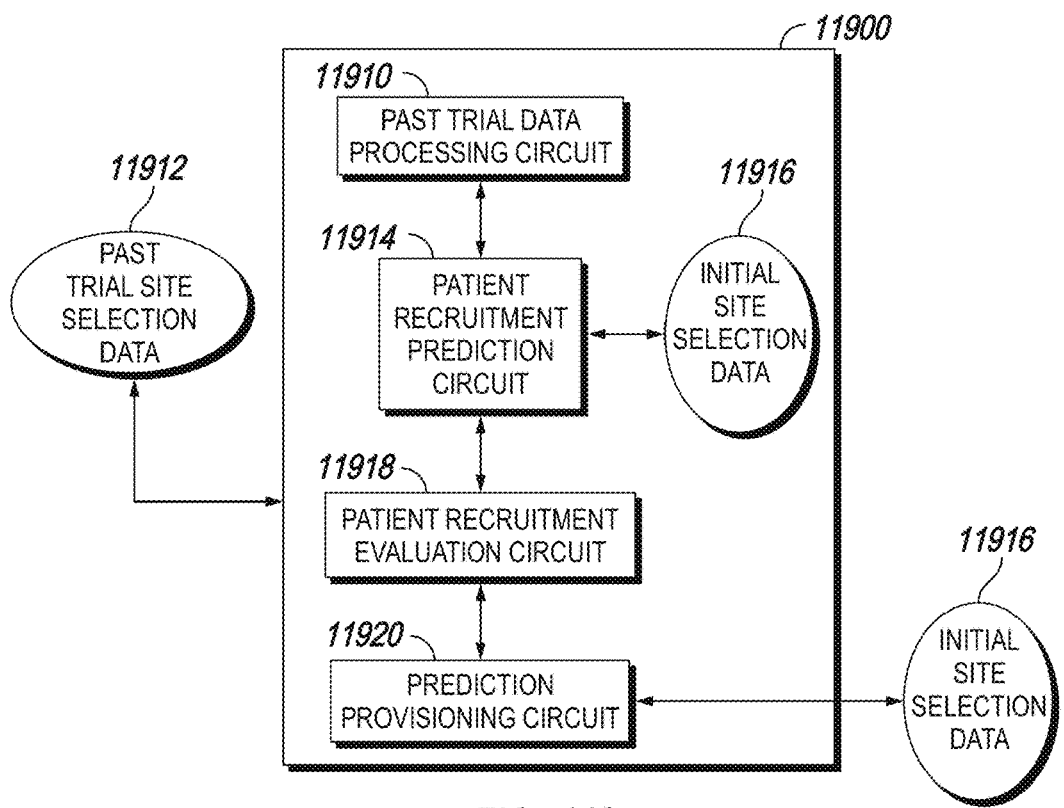
FIG. 119 is a schematic diagram of an apparatus for predicting an initial site selection with respect to patient recruitment for a clinical trial, in accordance with an embodiment of the current disclosure.

Illustrated in FIG. 119 is an apparatus 11900 for prediction of an initial site grouping/selection with respect to patient recruitment of a clinical trial. The apparatus 11900 includes a past trial data processing circuit 11910 structured to interpret past trial site selection data 11912. The apparatus 11900 further includes a patient recruitment prediction circuit 11914 structured to generate, based at least in part on the past trial site selection data 11912, initial site selection data 11916 for recruiting patients for a clinical trial. The initial site selection data corresponds to a global optimization of a desired site selection criteria. The apparatus 11900 further includes a patient recruitment evaluation circuit 11918 structured to evaluate the initial site selection data with respect to the global optimization. The apparatus 11900 further includes a prediction provisioning circuit 11920 structured to transmit the initial site selection data 11916.

Embodiments of the current disclosure may also provide for a method for using the initial site selection. The method may include receiving an initial site selection for recruiting patients for a clinical trial; and conducting a clinical trial based as least in part on the initial site selection. The initial site selection may correspond to a global optimization of a desired criteria, wherein the initial site selection was predicted from past trial site selection data. For example, a first entity may generate initial site selection data and send it to a second entity that conducts a clinical trial based at least on part on the initial site selection data.

Figure 120:
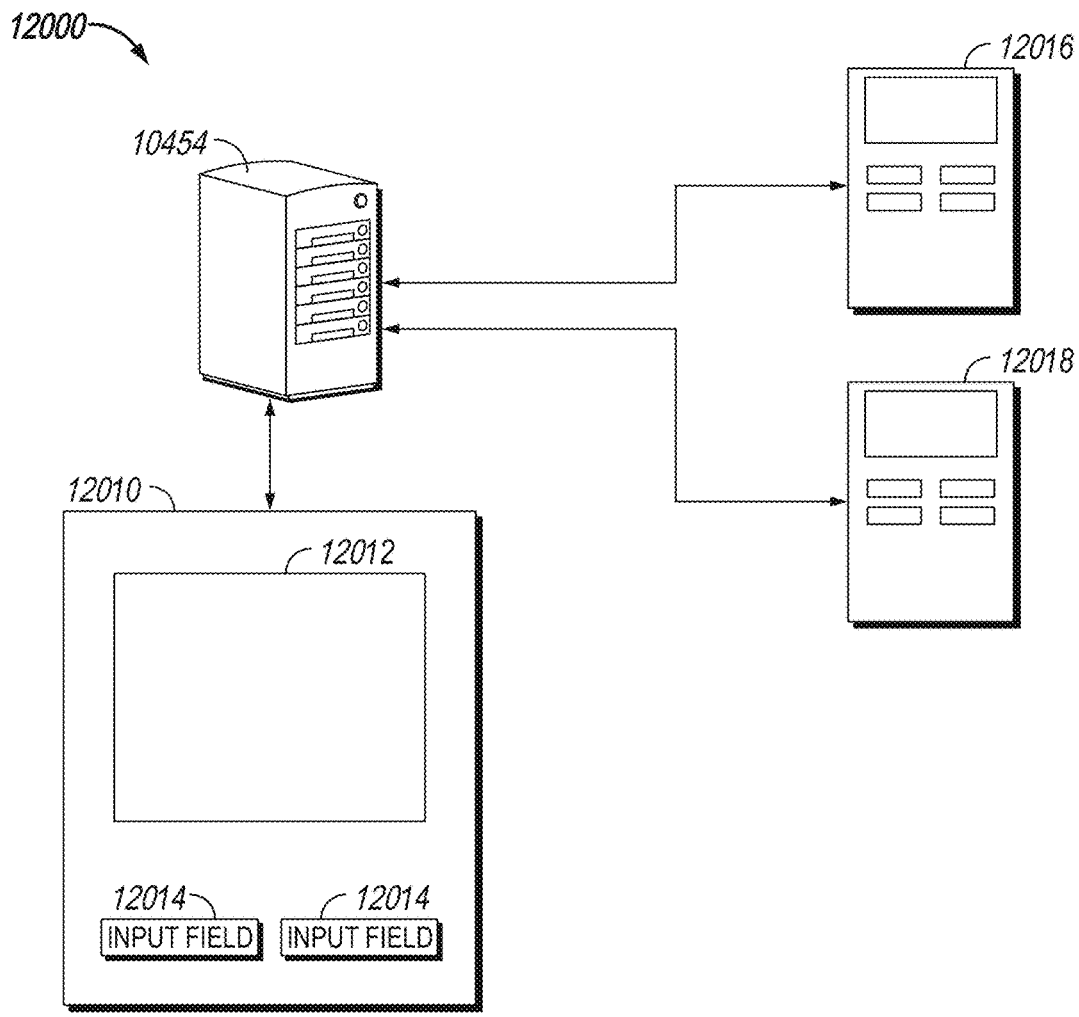

Referring now to FIG. 120, embodiments of the current disclosure may provide for a platform/system 12000 that generates an interactive interface 12010, e.g., a GUI, for exploration/evaluation of spaces related to patient recruitment for a clinical trial, as opposed to merely facilitating selection of proposed sites, for the purpose of globally optimizing site selection for a clinical trial to achieve a desired patient recruitment, e.g., a maximum number of recruited patients. The spaces may include site selection criteria space 10510, site selection space 10512, site selection scenario space 10514, and/or site selection performance space 10516. In embodiments, generation of the site selections and/or evaluation of the spaces may be based at least in part on convex hull, Pareto frontiers, Monte Carlo, simulated annealing, and/or machine learning, e.g., artificial intelligence, as described herein.

Exploration/evaluation of the spaces may provide insights to a user regarding known and/or unknown constraints on site selection and/or the impact a particular selection parameter, e.g., a parameter within one of the spaces, may have on patient recruitment.

Exploration of the spaces may be facilitated via visualizations of the spaces. The visualizations may include, and/or be based at least in part on, heatmaps and/or tornado graphs. The interface 12010 may include a canvas area 12012 for rendering (or rasterizing) the visualizations.

The interface 12010 may provide for users to adjust one or more selection parameters and/or adjust sites within one or more proposed site selections/groupings and see the effect on the predicted patient recruitment. Adjustment of the selection parameters may be facilitated by one or more interactive widgets 12014, e.g., text boxes, buttons, sliders, and/or the like. In embodiments, adjustment of the selection parameters may be facilitated via the canvas 12012. In embodiments, the interface 12010 may allow users to evaluate and compare possible site selections/groupings side-by-side.

In embodiments, exploration of the spaces may provide for sensitivity analysis. For example, embodiments of the interface 12010 may incorporate simulated annealing engines, as described herein.

In embodiments, platform/system 12000 may include a server, e.g. server 10454 in the computation resources 10450 of platform 10404. The server 10454 may generate the interface 12010 as a web application, remote desktop, and/or other suitable architecture for providing the interface 12010 to users and/or user devices 10402.

The platform may support collaboration among different users. For example, the server 10454 may generate multiple interfaces 12010, 12016, and 12018. In embodiments, the interfaces 12010, 12016, and 12018 may be configured/tailored to different types of user/target audience, e.g., users with different levels of experience and/or knowledge with respect to evaluating site groupings/selection for various criteria. For example, a first interface 12010 for an expert user may have more functionality, e.g., access to more options and/or features, than a second interface 12016 for a novice user.

Figure 121:
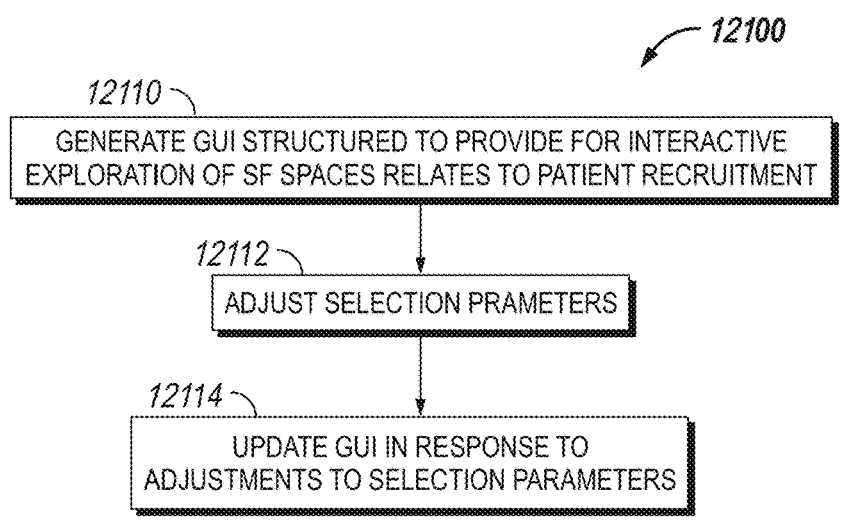

Turning to FIG. 121, a method 12100 for exploring/evaluating spaces related to patient recruitment for a clinical trial is shown. The method 12100 includes generating a graphical user interface structured to provide for interactive exploration of one or more spaces corresponding to one or more selection parameters for determining which subgrouping, of a plurality of possible sites for recruiting patients from for a clinical trial, globally optimizes a desired site selection criteria 12110. The method 12100 further includes adjusting at least one of the selection parameters via the graphical user interface 12112. The method 12100 further includes updating the graphical user interface in response to adjusting the at least one selection parameter 12114. In embodiments, the desired selection criteria may be based at least in part on a patient recruitment related number. In embodiments, generating the graphical user interface occurs prior to simulating, as disclosed herein, any one of the possible sites. In embodiments, generating the graphical user interface occurs after simulation of one or more of the possible sites.

Figure 122:
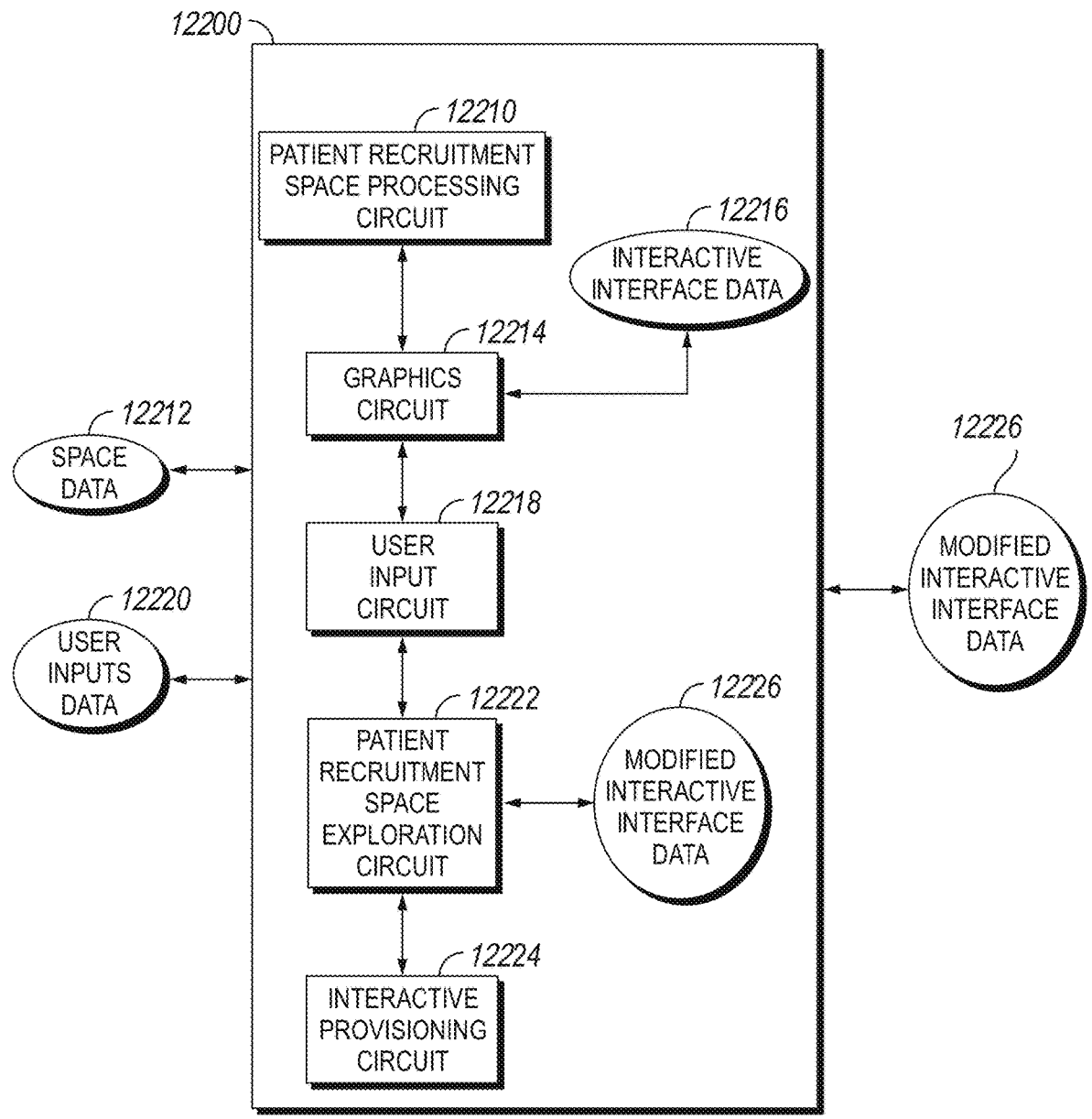

Illustrated in FIG. 122 is a non-limiting embodiment of an apparatus 12200 for exploring/evaluating spaces related to patient recruitment for a clinical trial. The apparatus 12200 includes a patient recruitment space processing circuit 12210 structured interpret space data 12212 corresponding to one or more spaces, e.g., 10510, 10512, 10514, and/or 10516, related to subgroupings of possible sites for use in conducting a clinical trial. The apparatus 12200 further includes a graphics circuit 12214 structured to generate interactive interface data 12216 in response to the space data 12212. The interactive interface data 12216 may correspond to a computerized interface 12010 for globally optimizing a desired site selection criteria. The apparatus 12200 further includes a user input circuit 12218 structured to receive user input data 12220 responsive to the presentation of the interactive interface data 12216. The apparatus 12200 further includes a patient recruitment space exploration circuit 12222 structured to modify the interactive interface data 12226 in response to the user input data 12220. The apparatus 12200 further includes an interactive provisioning 12224 circuit structured to transmit the modified interactive interface data 12226.

Figure 123:
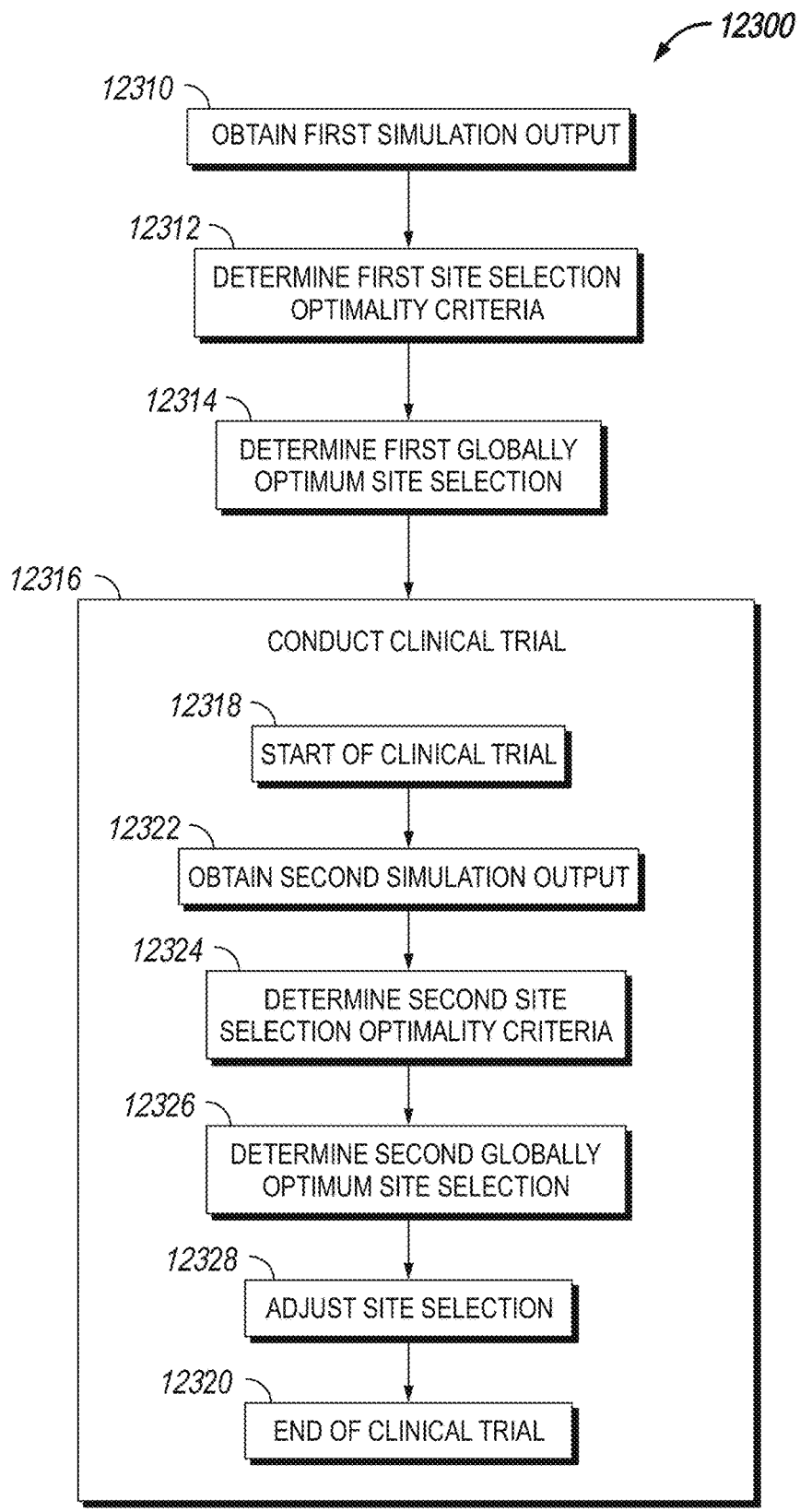

Referring to FIG. 123, a method 12300 for updating patient recruitment is shown. Since recommendation of globally optimal site selection, as disclosed herein, are generally predictive, it is possible that one or more parameters used to determine a globally optimum site selection for a clinical trial may deviate from what actually occurs during conduction/execution of the trial, i.e., while the trial is underway. For example, a globally optimum site selection may have been determined based on a recruitment scenario where no major worldwide health emergencies occur during the duration of the clinical trial, when, in actuality, a global pandemic emerges shortly after the start of a clinical trial. In such a case, the original globally optimum site selection may no longer be the optimum. Updating of a site selection, as described herein, may occur multiple times through the course/duration of the clinical trial. In some embodiments, updating of the site selection, as described herein, may be performed on a continuous basis throughout the duration of the clinical trial.

Accordingly, the method 12300 includes obtaining a first simulation output for a first set of site selections for a clinical trial 12310. The first simulation output includes first site selection performance parameters, as disclosed herein, associated with each design in the first set of site selections for a first set of site selection criteria. The method 12300 further includes determining, from the first set of site selection criteria, a first optimality criteria for evaluating the first set of site selections 12312. The method 12300 further includes determining, within the first set of site selections, a first globally optimum site selection based at least in part on the first site selection optimality criteria and the first site selection performance parameters 12314. Optimum site selections may be determined using one or more of Pareto analysis, convex hull analysis, and/or simulated annealing analysis. The site selection may then be configured based at least in part on the first globally optimum site selection, e.g., the site selection may be made to conform to the globally optimum site selection.

As further shown in FIG. 123, the method 12300 may include conducting/executing the clinical trial based at least in part on the first globally optimum site selection 12316. Conduction of the clinical trial may be defined by a start/beginning 12318 of the clinical trial and a stop/end 12320 of the clinical trial. In embodiments, the start 12318 may be the occurrence of the first patient recruitment. In embodiments, the start 12318 may be the occurrence of the first interaction between administrative personnel (for the clinical trial) and a patient or recruitment site, in respect of the trial. In embodiments, the start 12318 may be the first occurrence of a patient receiving a treatment (including receiving a drug). In embodiments, the stop 12320 may be the last occurrence of patient receiving a treatment (including receiving a drug). In embodiments, the stop 12320 may be the occurrence of the last interaction between administrative personnel (for the clinical trial) and a patient or recruitment site, in respect of the trial. The time between the start 12318 and the stop 12320 may constitute the duration of the clinical trial as that term is user herein. In embodiments, conduction of the clinical trial may include commencement of any portion and/or process of the clinical trial whether performed in succession and/or intermittently.

After the start 12318 of the clinical trial, but before the stop 12320, the globally optimum site selection may be reassessed. As such, the method 12300 includes obtaining, during conduction of the clinical trial, a second simulation output for a second set of site selections for the clinical trial 12322. The second simulation output includes second site selection performance parameters associated with each design in the second set of site selections for a second set of site selection criteria. In embodiments, the second simulation output may be different than the first simulation output.

For example, the second simulation output may be from another evaluation of the site selections. In embodiments, the second simulation output may be the same as the first simulation output. For example, the first simulation output may be reused. In embodiments, the second site selection performance parameters may be different than the first site selection performance parameters. For example, the second site selection performance parameters may include more or fewer parameters than the first site selection performance parameters. In embodiments, the second site selection performance parameters may be the same as the first site selection performance parameters. In embodiments, the second set of site selections may be the same or different than the first set of site selections. For example, the second set of site selections may include additional sites selections and/or have removed site selections as compared to the first set of site selections. In embodiments, the second set of site selection criteria may be the same or different than the first set of site selection criteria. For example, constraints on the clinical trial and/or site selections may have changed since the start 12318.

The method 12300 further includes determining, from the second set of site selection criteria, a second site selection optimality criteria for evaluating the second set of site selections 12324. In embodiments, the second site selection optimally criteria may be the same or different from the first site selection optimally criteria. For example, a user may have previously determined the globally optimum site selection with respect to shortest duration and wish to do so again for the second globally optimum site selection. As another example, a user may have previously determined the globally optimum site selection with respect to shortest duration and may now wish to determine the globally optimum site selection with respect to costs.

The method 12300 further includes determining, within the second set of site selections, a second globally optimum site selection 12326. Determination of the second globally optimum site selection may be based at least in part on the second site selection optimality criteria and the second site selection performance parameters. The method 12300 may further include adjusting the site selection based at least in part on the second globally optimum site selection 12328. Adjustment of the site selection may include conforming the site selection to the second globally optimum site selection.

Figure 124:
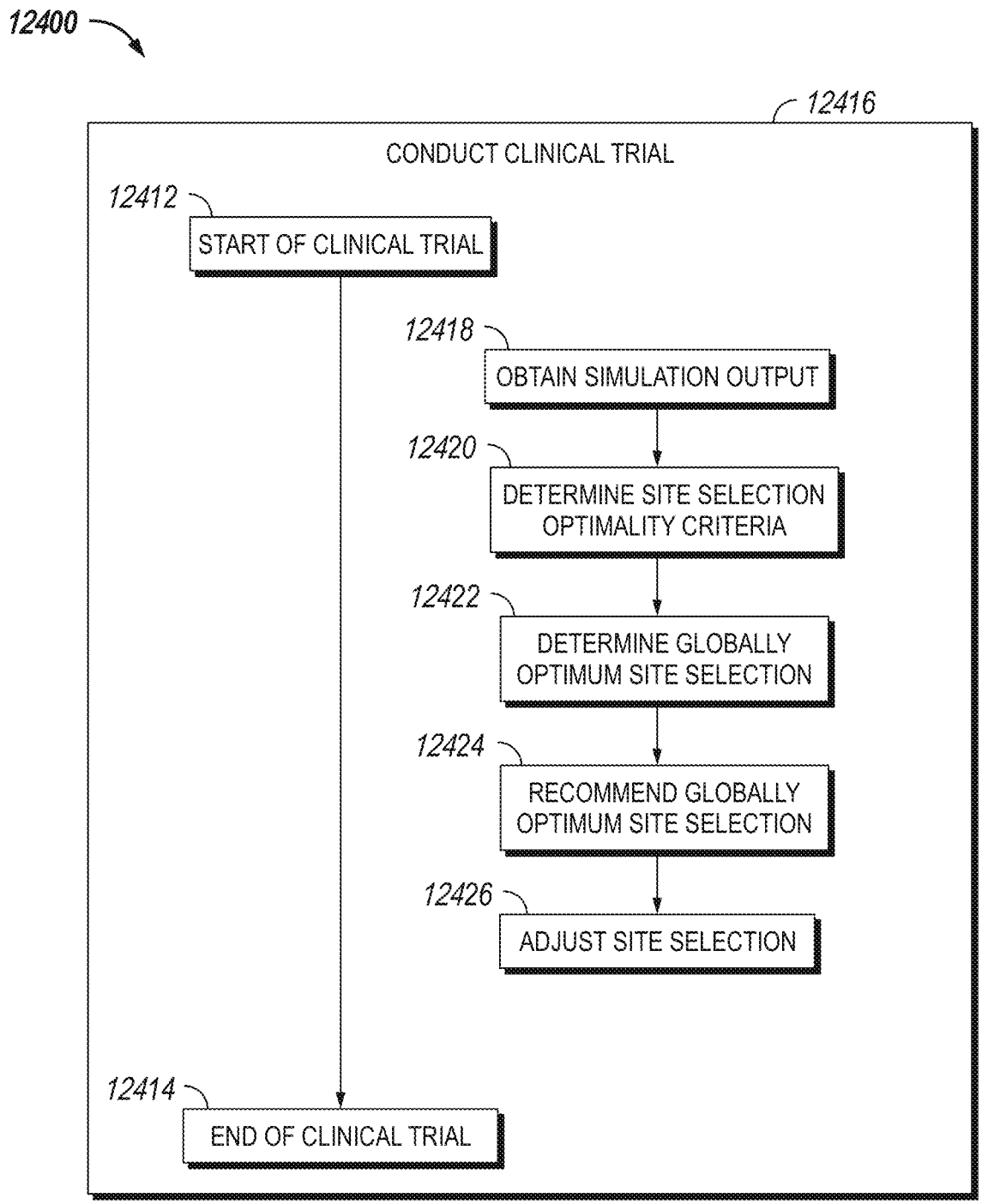

Illustrated in FIG. 124 is another method 12400 for updating site selections. In particular, method 12400 identifies a globally optimum site selection for a clinical trial after the start 12412 of the clinical trial, but before the end 12414 of the clinical trial, where an initial globally optimum site selection may not have been determined, or was not determined by an entity performing method 12400. Accordingly, the method 12400 includes obtaining, during conduction of the clinical trial 12416, a simulation output for a set of site selections for the clinical trial 12418. The simulation output includes site selection performance parameters associated with each site selection in the set of site selections for a set of site selection criteria. The method 12400 further includes determining, from the set of site selection criteria, a site selection optimality criteria for evaluating the first set of site selections 12420. The method 12400 further includes determining, within the set of site selections, a globally optimum site selection based at least in part on the site selection optimality criteria and the site selection performance parameters 12422. The method 12400 may further include recommending the globally optimum site selection 12424. Recommendation may include transmitting the globally optimum site selections to an entity performing and/or planning the clinical trial. The recommended globally optimum site selections may be the first time a globally optimum site selection was calculated/determined for the clinical trial, or the globally optimum site selection may be an update to a previously calculated/determined globally optimum site selection. In embodiments, the method 12400 may not include recommending the globally optimum site selection, but rather may include adjusting the site selection based at least in part on the globally optimum site selection 12426. It is to be understood, however, that embodiments of the method 12400 may not include adjusting the site selection trial based at least in part on the globally optimum site selection. In embodiments, the method 12400 may include both recommending and adjusting the site selection based at least in part on the globally optimum site selection.

In addition to the design of a clinical trial, the success of the clinical trial often depends on the availability of resources needed to conduct the clinical trial, also referred to herein as "resource availability". Non-limiting examples of trial resources include: drugs/drug supply, medical devices, procedures, administrative personnel, and/or equipment/devices needed to conduct a clinical trial, and/or the like. Resource availability, in turn, is typically a function of a site selection.

In some cases, a wrong choice in the selection of sites for a clinical trial may reduce resource availability which, in turn, may impact and/or prevent completion of the clinical trial. In some cases, difference in available resources between different site selections may result in very different costs, completion times, and/or other performance parameters for the clinical trial.

The selection of sites for a clinical trial, with respect to optimizing available resources, may include considerations and tradeoffs between hundreds or even thousands of site selections. For example, different site selection options, often have different values for resource availability, e.g., the sites of a first site selection may be closer to medical supply distribution centers than the sites of a second site selection. Traditionally, consideration of resource availability for clinical trials has been based on heuristics and experienced professionals to determine a set of parameters likely to result in a site selection that produces adequate access to resources. However, traditional approaches are not capable of evaluating more than a handful of site selection options and corresponding tradeoffs. As a result, traditional approaches to resource availability often miss site selection options that may result in greater resources availability. As the cost of a clinical trial may exceed tens of millions or even hundreds of millions of dollars and/or may take years to complete, small differences in resources availability between site selections for a clinical trial may result in large impacts on the overall cost and/or time associated with the clinical trial.

The complexity of site selection with respect to resource availability often requires aspects of statistical expertise, clinical design expertise, and software expertise, which may not be available in many organizations. As such, many organizations fallback on the use of generic site selection methodologies due to their inability to find optimal or near-optimal site selections with respect to resource availability for a particular clinical trial.

Accordingly, embodiments of the current disclosure may provide for a resource optimization platform, systems, and methods for evaluation and/or comparison of site selection options with respect to optimizing resource availability for a clinical trial. In embodiments, evaluation and/or comparison may include a large number of site selection options. In some embodiments, the platform, systems, and methods described herein may be used to evaluate hundreds, thousands, or even millions of site selection options for a clinical trial and may be used to find the optimal or near-optimal resource availability for a trial.

The resource optimization platform may be used for site selection. In embodiments, a resource optimization platform may support a team, as described herein, in collaborating and surfacing all the inputs that are key to consider for preparing and selecting a site selection to optimize available resources. The resource optimization platform may use cloud and distributed computing so the team can simulate hundreds of millions of site selection variants/options across all those inputs. The resource optimization platform may present the team with prioritized options and visualizations to enable the interrogation of the drivers of value. In an embodiment, available clinical trial resources may have an initial distribution across one or more sites. For example, a first site may have forty (40) kg of a drug and a second site may have twenty (20) kg of a drug. In embodiments, the platform may determine a site selection based on the initial distribution of one or more available clinical trial resources. In embodiments, the platform may determine one or more adjustments to the initial distribution to optimize availability of the one or more clinical trial resources and/or site selection. In embodiments, the adjustments to the initial distribution may facilitate a different clinical trial design and/or a different type of clinical trial design that was not previously possible given the initial distribution of the one or more available clinical trial resources. In embodiments, the platform may recommend adjustments to the initial distribution.

A resource optimization platform may enable a team to quickly identify site selections that optimize available resources and the factors that most strongly drive performance factors, strategic goals, and the like. A resource optimization platform, as described herein, may leverage emerging technologies to provide options for advanced simulations, distributed computing, visualizations, and the like. The resource optimization platform may leverage methodological knowledge, analysis of the business value of different design choices, and/or analysis of regulatory risk and operational complexity to determine optimum or near optimum site selections with respect to resource availability. The resource optimization platform may determine optimum or near optimum site selections by leveraging a novel workflow, speed and/or computing innovations, and/or powerful visualizations for study analysis and optimization.

A resource optimization platform may improve how data and processes are used to make better decisions on site selections. Improvements may result from recognizing which innovative options might significantly increase goals. Improvements may be obtained by communicating the benefits of specific site selections in a way that that intuitively allows a variety of team members to understand a particular site selection and/or possible options for the site selection of a clinical trial. A resource optimization platform may support a team in collaborating and surfacing all the inputs that are key to consider for preparing and selecting an optimal site selection. The resource optimization platform may present the team with prioritized options and insightful visualizations to enable interrogation of the drivers of value.

Figure 125:
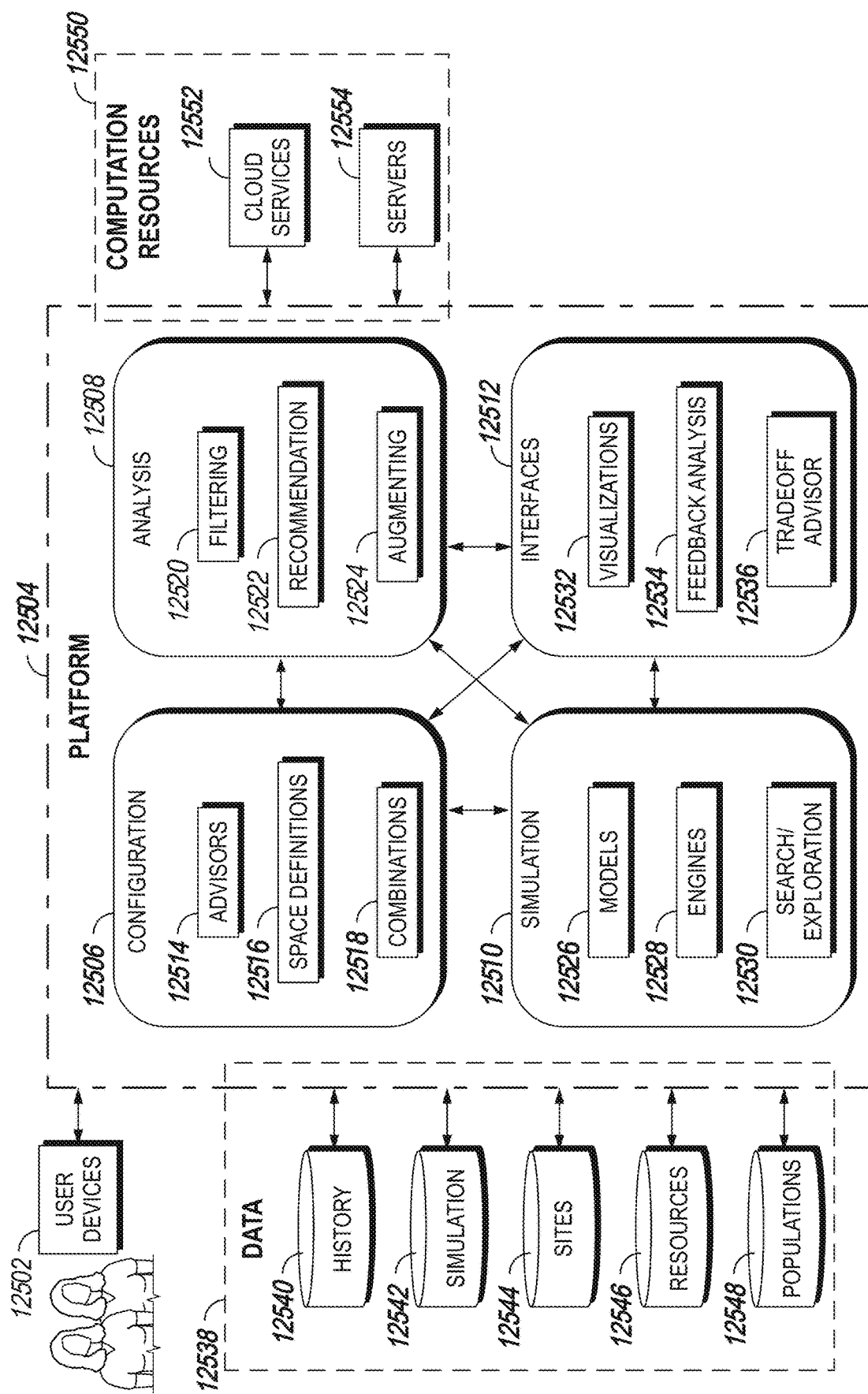

FIG. 125 shows an embodiment of a platform/system for evaluation and comparison of site selections with respect to optimizing resource availability for a clinical trial. The platform 12504 may form part of the platform 104 (FIG. 1) or the platform 12504 may be stand-alone from the platform 104. In embodiments, the platform 12504 may communicate with the platform 104 via one or more application programming interfaces (APIs). The platform 12504 may provide for a system for providing users with facilities and methods for determining, evaluating, and/or comparing site selections with respect to resource availability. The facilities described herein may be deployed in part or in whole through a machine that executes computer software, modules, program codes, and/or instructions on one or more processors, as described herein, which may be part of or external to the platform 12504. Users may utilize the platform 12504 to, with respect to optimization of resource availability for a clinical trial, identify site selections for criteria, evaluate the site selections, compare site selections, determine optimal site selections, and the like.

A user may interact with the platform 12504 through one or more user devices 12502 (e.g., computer, laptop computer, mobile computing device, and the like). The platform 12504 may be implemented and/or leverage one or more computing resources 12550 such as a cloud computing service 12552, servers 12554, software as a service (SaaS), infrastructure as a service (IaaS), platform as a service (PaaS), desktop as a Service (DaaS), managed software as a service (MSaaS), mobile backend as a service (MBaaS), information technology management as a service (ITMaaS), and the like. The platform 12504 may be provided or licensed on a subscription basis and centrally hosted (e.g., accessed by users using a client (for example, a thin client) via a web browser or other application, accessed through or by mobile devices, and the like). In embodiments, elements of the platform 12504 may be implemented to operate on various platforms and operating systems. In embodiments, interfaces for the user device 12502 through which the users may interact with the platform may be served to the user device 12502 through a webpage provided by a server of the platform 12504, an application, and the like.

The platform 12504 may include one or more facilities such as a configuration facility 12506, simulation facility 12510, analysis facility 12508, interfaces facility 12512, data facility 12538, and computation resources 12550.

The configuration facility 12506 may include advisors 12514, which may include one or more wizards, tools, algorithms, recommenders, configuration elements, questioners, and the like. Advisors may be used to receive data and/or define or develop space definitions 12516.

Figure 126:
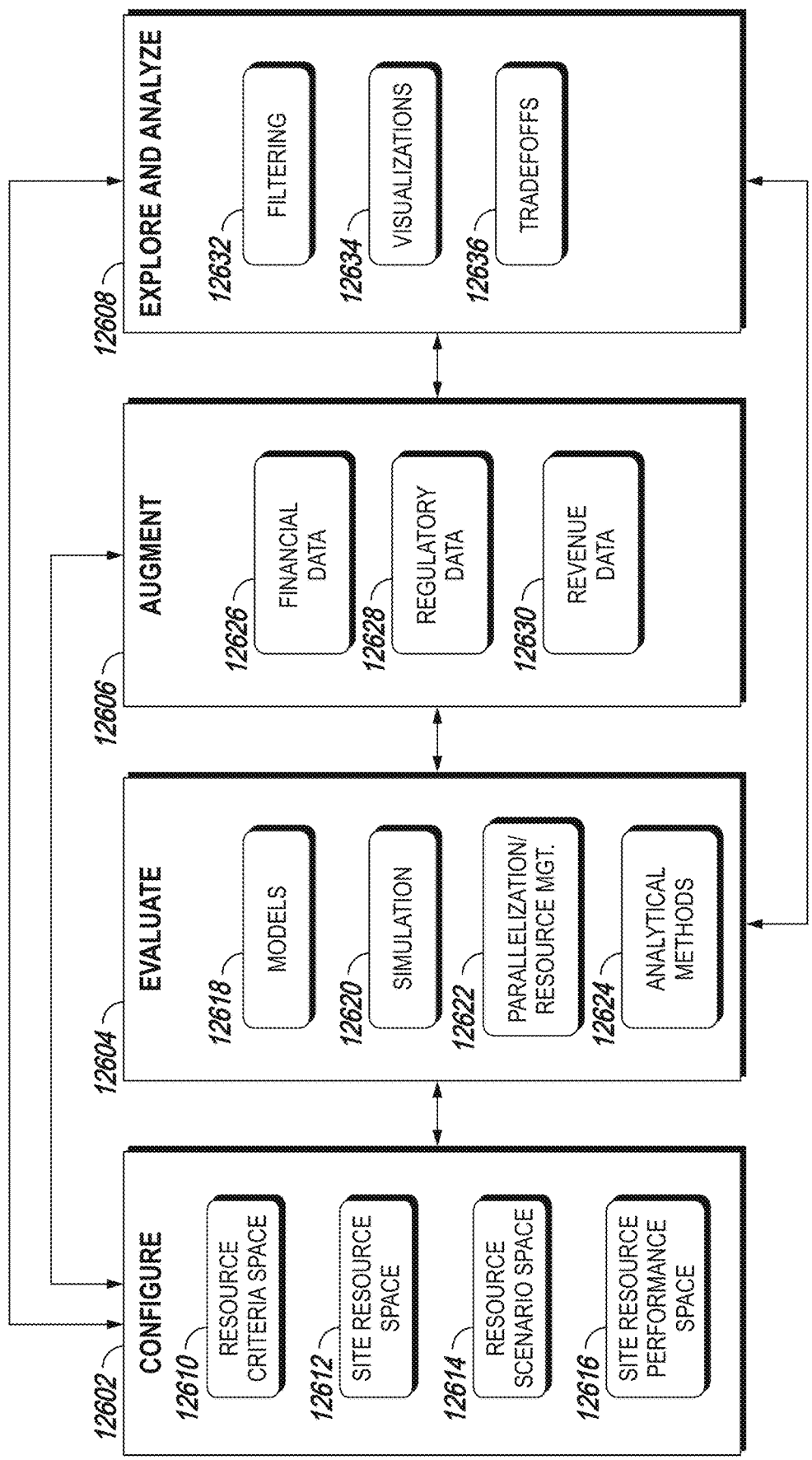

Space definitions 12516 may include aspects of site resource criteria space 12610 (FIG. 126). Resource criteria space may define values, ranges of values, types, ranges of types, and the like that may define general required characteristics of the resources required by a clinical trial. Non-limiting examples of resource criteria include: maximum and/or minimum numbers of administrative personnel; maximum and/or minimum price points for subject drugs; a minimum and/or maximum number of required patients to complete the trial; maximum and/or minimum price points for equipment, to include equipment purchase and/or lease; and/or the like.

Space definitions 12516 may include aspects of site resource space 12612 (FIG. 126). Site resource space 12612 may include the set of parameters and values of the parameters that define different options and variations of resources available at a particular site and/or group of sites for implementation of clinical trials. Non-limiting examples of site resource space may include: expected drug and/or price points; expected access to drugs and/or equipment; expected patient recruitment, expected patient dropout rate; geographical locations; patient demographics; expected availability of administrative and/or medical personnel; and/or the like. The site resource space may include all possible permutations of the parameters. For example, one site selection may be configured with different expected drug costs and different administrative personnel availabilities. The site resource space may include all the permutations of all the parameters associated with the resources available at individual sites and/or site selections. The site resource space may include millions of possible site selection variations. A resource optimization platform may evaluate all permutations of parameters of the site resource space. A resource optimization platform may evaluate a partial set of permutations of parameters of the site resource space. The partial set of permutations may be defined by a user. The partial set of permutations may be automatically defined, such as according to the resource criteria parameters.

Space definitions 12516 may include aspects of site selection resource scenario space 12614 (FIG. 126). Resource scenario space may include the set of parameters and values of the parameters that define different options and variations of scenarios associated with site selections and resource availability. Resource scenario space may define the parameters of the environment associated with one or more sites. Non-limiting examples of resource selection scenario space include: expected flow through drug and/or equipment supply chains; expected weather conditions; expected pandemics; expected economic conditions; and/or the like. The resource scenario space may include all possible permutations of the parameters. For example, one scenario may be configured with a range of values for average drug costs and a range of values for average weather conditions, e.g., how will varying weather conditions affect the price point and/or availability of a drug. The resource scenario space may include all the permutations of all the parameters associated with scenarios. The resource scenario space may include millions of possible scenario variations. A resource optimization platform may evaluate all permutations of parameters of the resource scenario space. A resource optimization platform may evaluate a partial set of permutations of parameters of the resource scenario space. The partial set of permutations may be defined by a user. The partial set of permutations may be automatically or semi-automatically defined, such as according to the resource criteria parameters.

Space definitions 12516 may include aspects of site resource performance space 12616 (FIG. 126). Site resource performance space may include the set of parameters and values of the parameters that define the evaluation criteria for a site selection with respect to resource availability. Parameters may include: net present value (NPV), expected NPV, incremental NPV, study cost, incremental study cost, study budget, incremental study budget, time to complete, incremental time to complete, time to market, incremental time to market, clinical utility, incremental clinical utility, probability of regulatory acceptance, incremental probability of regulatory acceptance, probability of success, incremental probability of success, statistical power, incremental statistical power, number of patients, incremental number of patients, number of sites, incremental number of sites, study complexity, incremental study complexity, operational complexity, incremental operational complexity, dose selected, incremental dose selected, statistical design, incremental statistical design, peak revenue, revenue at year five (5), other revenue numbers, incremental revenue, market introduction, whether market introduction beats competition entry, number of treatment arms, hypothesis superiority/ equivalence/non-inferiority, other choices around statistical design, treatment effect, hazard ratio, and other choices around estimating the characteristics of the patient population, response, and safety profile, screening criteria, dropout rate, and other choices around modeling/estimating the characteristics and behaviors of the patient population and other factors that impact how the study evolves and its likelihood of achieving its goals (how slowly/quickly patients enroll, etc.), site payments and other choices around operational aspects of the study that can impact how the study evolves and its likelihood of achieving its goals, cost per patient, cost per site, or other cost factors, selections made in other projects (across users within customer companies or organizations and across all users of the platform), priorities set by the customer company or organization, and/or other user-defined filters based on available inputs and outputs of the platform or in the systems and methods described herein. In embodiments, any of the parameters and variables described herein may be incremental parameters and variables. Site selections may be evaluated and compared against all of the parameters of the performance space or a subset of the parameters of the performance space. A set of site selections, e.g., one or more groups each including one or more possible sites, may be evaluated for one or more of the performance parameters.

The configuration facility 12506 may include a combinations component 12518. The combinations component 12518 may automatically or semi-automatically define the resource criteria design and/or resource scenario space that may be evaluated by the platform 12504.

The simulation facility 12510 of the platform 12504 may, based on the space definitions from the configuration facility 12506, evaluate the site selections. The simulation facility 12510 may include models 12526. As used herein with respect to site selection, a model includes the combination of parameters and the values that describe a site selection and/or corresponding clinical trial designs and the scenario under which the site selection is evaluated with respect to resource availability. Models 12526 may include hundreds or even thousands of models. Models 12526 may include deviation specifications for one or more of the parameters of the models. A deviation specification may define a range of values, a distribution of values, and/or a function of values for one or more parameters of a model. The deviation specifications may be based on expected or previously measured distributions or variations in clinical trial design parameters, site selection parameters, and/or resource availability parameters.

The simulation facility 12510 may include engines 12528. As used herein, engines may relate to the codification of a site selection and/or corresponding resource availabilities that can receive model parameters and run a simulation to generate an output. The output of the engines 12528 may be a predicted behavior, e.g., resource availability, for a site selection for one or more corresponding clinical trial designs, one or more scenarios, and/or conditions. Engines 12528 may evaluate a site selection with analytical methods, mathematical methods, numerical methods, simulation, and/or the like. Evaluating a site selection may include a simulation run to determine performance of the site selection. Evaluating a site selection may include using a Monte Carlo approach to simulate a site selection for different values according to the deviation specifications and using statistical methods to determine the performance of the site selection from a simulation run.

The simulation facility 12510 may include search/exploration component 12530. The search/exploration component may facilitate modification of model parameters for simulation. The search/exploration component 12530 may adaptively modify or generate models for simulations based on simulation results of other models/site selections and/or based on triggers and data from other facilities of the platform 12504.

The analysis facility 12508 may be configured to analyze simulation results of site selections. The analysis facility 12508 may include a filtering component 12520. The filtering component 12520 may be configured to use one or more numerical and/or analytical methods to evaluate and compare the performance of evaluated site selections. The filtering component may identify optimal or near-optimal site selections for one or more performance parameters. The filtering component may search the performance space and identify a set of optimal and/or near optimal site selections for one or more performance parameters, e.g., availability of resources.

The analysis facility 12508 may include a recommendation component 12522. The recommendation component 12522 may provide site selection recommendations. The site selection recommendations may be based on optimal or near-optimal site selections determined by the filtering component 12520. Recommendations may be adaptive based on settings, feedback, selections, triggers, and the like from the user, and/or other facilities in the platform 12504.

The analysis facility 12508 may include an augmenting component, 12524. The augmenting component may supplement simulation results with real-world data.

The interfaces facility 12512 may be configured to provide visualizations and interfaces for comparing, searching, and evaluating simulated site selections. Visualization component 12532 may provide for one or more interfaces to visualize the performance of site selections and facilitate comparison of site selections by a user. The feedback analysis component 12534 may track user actions associated with the interfaces and visualizations to determine patterns and/or preferences for site selections. The tradeoff advisor component 12536 may analyze and provide data and guidance for evaluating tradeoffs between two more site selections.

The platform 12504 may include and/or provide access to one or more data facilities 12538. Data in the data facilities may include design histories 12540, simulation data 12542, site data 12544, resource data 12546, population data 12548, and the like.

FIG. 126 shows aspects of an embodiment of a process for site selection. The process may include four or more stages. Facilities of the platform 12504 may be configured to implement the stages of the process. The stages of the process may include a configure stage 12602. The configure stage 12602 may define one or more of the spaces associated with the site selection. The configure stage 12602 may define one or more of site selection criteria space 12610, site selection design space 12612, site selection scenario space 12614, and/or site selection performance space 12616. The configure stage 12602 may utilize one or more advisors, wizards, algorithms, and the like for defining the spaces. In some embodiments, the different spaces associated with the configuration stage 12602 may be defined by different members of a team based on the expertise of the members. In some cases, members of a team may have different specializations. For example, some members may specialize in scenarios, while others may specialize in site selection and/or design definitions. Separating the inputs may allow different team members to independently optimize and improve specific models without affecting other inputs. In some embodiments, the inputs may be separated into two or more types based on convenience, expertise, flexibility, and the like.

The stages of the process may include an evaluate stage 12604. The evaluate stage 12604 may configure models 12618 for evaluation using simulation 12620 and analytical methods 12624. The stage may include various methods of enhancing computation and simulation using parallelization and resource management 12622.

The stages of the process may include an augment stage 12606. The augment stage 12606 may add real-world data to the simulation data. Financial data 12626, regulatory data 12628, revenue data 12630, and the like may be added to the and used to augment data from simulations.

The stages of the process may include an explore and analyze stage 12608. The explore and analyze stage 12608 may include filtering methods and algorithms 12632 for identifying optimal site selections. The stage may include generating and interacting with visualizations 12634 and tradeoff analysis tools 12636 to compare and select site selections.

Figure 127:
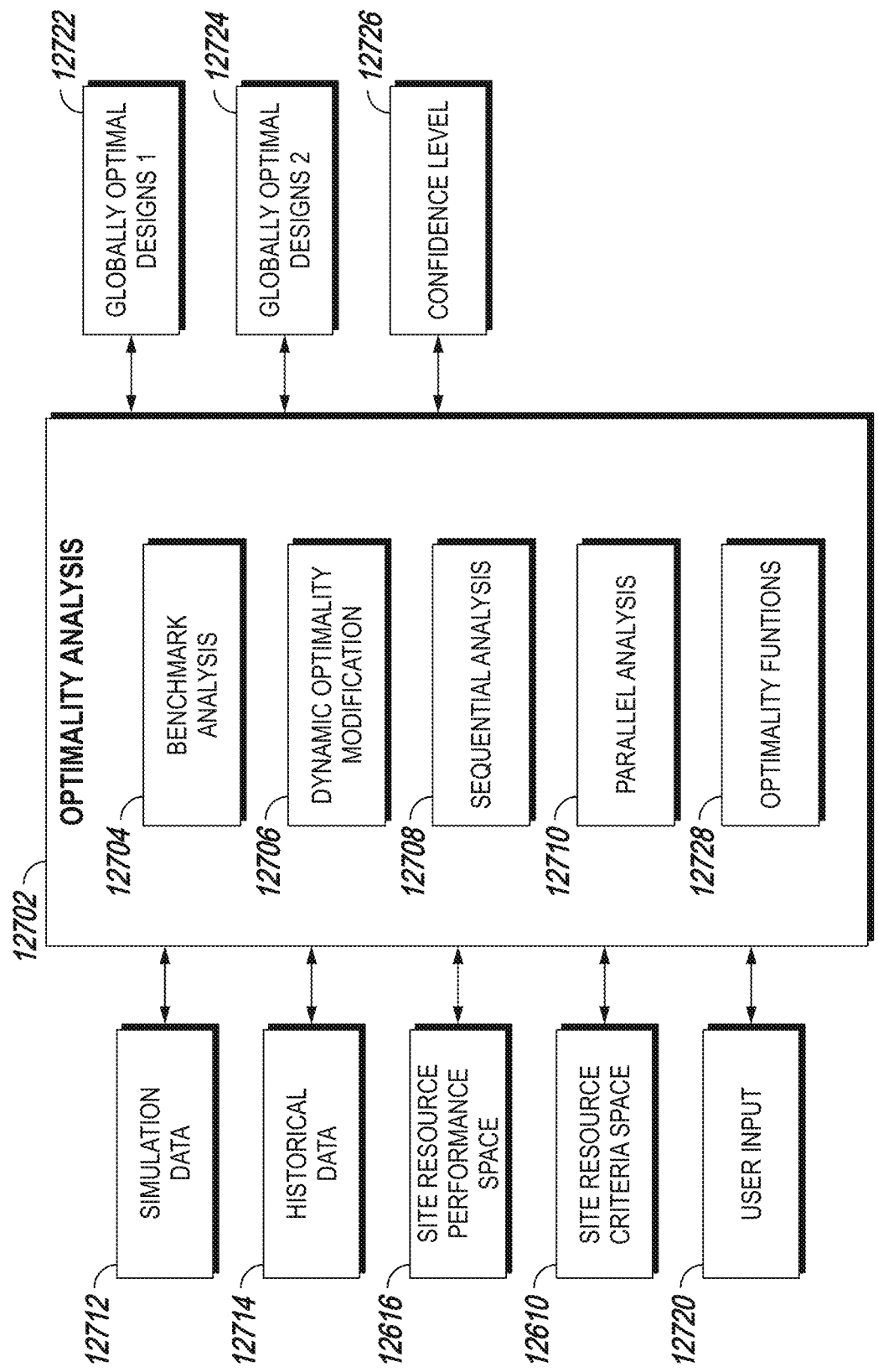

In embodiments, the platform 12504 (FIG. 125) may be configured for identification and confirmation of optimal site selections for a clinical trial. Optimality of site selection may be in relation to site resource criteria, e.g., a parameter within site resource criteria space 12610 (FIGS. 126 and 127). For example, embodiments of the current disclosure may provide for the determination of a site selection for a clinical trial as being the least likely site selection to experience a drug shortage during the duration of the clinical trial. Site resource criteria may be determined in relation to the site resource performance space 12614 (FIGS. 126 and 127). Optimality of the site resource criteria, via site selection, may be in relation to one or more site resource performance parameters, e.g., a parameter within site resource performance space 12616, and the values thereof. An optimal site selection may be a site selection that achieves a most desirable value for one or more specific site resource performance parameters. A most desirable value may depend on the site resource performance parameter and may be different for each site resource performance parameter. In some cases, the most desirable value may be the highest value of a site resource performance parameter. In some cases, the most desirable value may be the lowest value of a site resource performance parameter. In some cases, the most desirable value may be a range of values, a specific value, a function of values, and the like. For example, in some cases an optimal site selection with respect to a drug availability site resource performance parameter may be a site selection that has the lowest risk of drug supply interruption and achieves the goals of the clinical trial. As another example, an optimal site selection with respect to an equipment resource performance parameter may be a site selection wherein all sites within the selection have duplicate/redundant equipment, e.g., multiple Magnetic Resonance Imaging (MIR) systems on site.

In embodiments, an optimum site selection is a site selection that achieves most desirable values for two or more specific site resource performance parameters. In the case of optimality for multiple site resource performance parameters, optimality may require a tradeoff between the parameter values. For example, a site selection that has a lower risk of drug supply interruption may have a low NPV and therefore may not be desirable. The optimality of a site selection may be based on a function of site resource performance parameters. In some cases, a function may be a weighted sum of the site resource performance parameters.

A function, or a set of functions, may be used to generate an overall score (or a set of scores) and the score may be used to determine the optimality of the site selection. A highest score, a specific score, lowest score, and the like may be considered optimal depending on the function used to compute the score.

In embodiments, optimality may be evaluated according to Pareto optimality. Pareto optimal site selections may be site selections where no individual site resource performance parameter can be better off without making at least one other individual site resource performance parameter worse off. In some cases, optimality may be determined using convex hull analysis.

In some cases, one site selection may be globally optimum. In some cases, more than one site selection may be globally optimum. In some cases, no site selections may be globally optimum. In some embodiments, optimality of site selection may be relative to a benchmark. A known site selection, a set of historical site selections, and/or the like may be used as a benchmark. Site selections may be considered optimal if they meet, exceed, and/or are within a threshold distance of the benchmark site resource performance parameters.

Site resource performance parameters that may be used to determine site selection optimality may be user defined, system defined, algorithmically defined, and/or the like. In some cases, users may specify a subset of site resource performance parameters that should be used to identify optimal site selections. A user may define optimality criteria by defining ranges, values, characteristics, and the like of the parameter values that may be considered desirable and/or optimal. Interactive graphical interfaces may be provided to a user to evaluate different site selections based on one or more optimality criteria. Interactive interfaces may allow a user to explore different site selections by changing scoring methods, weights associated with the criteria, and the like.

In embodiments, the characteristics of site resource performance parameters for evaluated site selections may be analyzed by the platform to determine if any of the parameters may be less important for optimality. For example, analysis may include evaluation of ranges, variability, and other statistical analysis. If one or more site resource performance parameters for all evaluated site selections is within a desirable range, or the site resource performance parameter is almost equal for all of the evaluated site selections, the site resource performance parameter may be removed and identified as less significant for optimality and, in some cases, may not be factored in when determining optimality. Prior to determining optimality based on site resource performance parameters, the site resource performance parameters and the values of the site resource performance parameters may be grouped, filtered, normalized, and the like.

Optimality of site selections may be redefined automatically, semi-automatically, in response to user input, and/or the like. The criteria for optimality of site selections may change as site selections are evaluated by the platform. For example, initial optimality criteria may produce no optimal site selections. In response to no optimal site selections being determined, the criteria may be changed (relaxed, increased, decreased, etc.) until at least one site selection is considered optimal. In another example, optimality criteria may change in response to user feedback. Users may evaluate initial site selections found to be optimal and provide feedback (direct feedback and/or indirect feedback that can be derived from user actions and inactions). The feedback from the user may be used to change how optimality is determined, which site resource performance parameters are used to determine optimality, the values of the site resource performance parameters that are considered optimal, and/or the like.

In some embodiments, site resource performance parameters may be grouped, ordered, and/or organized into one or more hierarchies, groups, and/or sets. Two or more different optimality criteria may be used in parallel to determine multiple sets of optimal site selections under different criteria. Two or more different optimality criteria may be used sequentially to determine optimal site selections. One criteria may first be used to identify a first set of optimal site selections under first criteria. A second set of criteria may then be used on the first set to reduce the set of optimal site selections.

In embodiments, a site selection may be globally optimum if the site selection is optimal with respect to all possible site selection options. In embodiments, a site selection may be globally optimum if the site selection is optimal with respect to possible site selection options for one or more criteria. In embodiments, a site selection may be globally optimum if the site selection is optimal with respect to a large percentage (such as 80% or more) of possible site selection options for one or more criteria. In embodiments, a site selection may be globally optimum if the optimality of the site selection is within a high confidence level (90% confidence) with respect to possible site selection options for one or more criteria.

Traditional methods for evaluating site selections cannot determine global optimum site selections since they evaluate one, several, or a small subset of site selection options. Traditional methods do not consider all or almost all of the site selection options and cannot find a global optimum.

Trial site selection may involve numerous variables, parameters, considerations, tradeoffs, and the like resulting in a very large number of possible variations. A large number of possible variations makes study site selections and optimization using traditional methods difficult. In many cases, traditional methods may fail to explore or consider the complete space of possible site selection options and may miss or never consider globally optimal site selections. Using traditional methods, the number of site selection variations that may be explored in a reasonable time is limited. In some cases, only one (1) statistical site selection and only three (3) clinical scenarios may be evaluated. The best site selection study of the limited number of variations may not result in a globally optimal site selection. A locally optimum site selection chosen from a limited number of considered site selections may represent one (1) local maximum but may be far from the globally optimum site selection. When 10,000 or more clinical scenarios are considered, a globally optimum site selection may be distinguished from the many locally optimum site selections. However, consideration of 10,000 clinical scenarios cannot be practically performed using traditional methods as it would require an estimated 50,000 hours or more to complete.

In embodiments, the platform and methods described herein may evaluate thousands or even millions of site selection options enabling a determination of a global optimum site selection with respect to availability of resources for a clinical trial. In many cases, the globally optimum site selection may have significant advantages over locally optimum site selection. In one example, a globally optimum site selection may require less time to complete than other site selections.

In embodiments optimization of trial site selections for resource availability may occur sequentially after optimization of trial design. In one embodiment, a globally optimum trial design may be determined using the techniques described herein. After the globally optimum trial design is determined a globally optimum trial site selection for resource availability may be determined for the determined trial.

Referring again to FIG. 125, the platform 12504 may receive and/or determine performance space using the configuration facility 12506. Performance space may be defined in the space definitions component 12516. The performance space may be configured based on input from users and/or based on data 12538 such as history data 12540 and/or simulation data 12542. In embodiments, data 12538 may include external data from external data sources and providers. In one instance, performance space may define optimality criteria. Optimality criteria may define site resource performance parameters, performance values, functions, methods, and algorithms for evaluating optimality and/or global optimality of site selections. In one instance optimality criteria may be configured by the user or determined from benchmark site selections from history 12540 and/or simulation 12542 data. In another instance, optimality criteria may be defined from simulation data from the simulation facility 12510. Optimality of site selections may be determined in the analysis facility 12508. The filtering component 12520 may be used to determine one or more sets of globally optimum site selections from the site selections evaluated by the simulation facility 12510.

FIG. 127 shows aspects of an apparatus/optimality analysis component 12702 for determining global optimality of site selections with respect to availability of resources for a clinical trial. In embodiments, the optimality analysis component 12702 may be part of the analysis facility 12508 of the platform 12504. The optimality analysis component 12702 may receive data from simulated site selections 12712 and determine one or more sets of optimal site selections 12722, 12724. The optimality analysis component 12702 may include one or more circuits for determining optimality of site selection. In embodiments, the optimality analysis component 12702 may include circuits for determining optimality based on optimality functions 12728. Optimality functions 12728 may determine optimality of site selections based on different weighting of performance factors of the simulated site selections. In embodiments, the optimality analysis circuit 12702 may include circuits for determining optimality based on benchmark analysis 12704. A benchmark analysis circuit 12704 may determine optimality of site selections based on a comparison of site resource performance parameter values to one or more benchmark site selections such as from historical data 12714 and/or simulation data 12712. In embodiments, the optimality analysis circuit 12702 may include circuits for determining optimality using sequential analysis 12708 and/or parallel analysis 12710. The sequential analysis circuit 12708 and parallel analysis circuit 12710 may use one or more different optimality functions 12728 in parallel or sequentially to determine optimal site selections. In embodiments, the optimality analysis circuit 12702 may include circuits for dynamically modifying optimality criteria 12706. User inputs 12720, simulation data 12712, and/or the determined sets of optimal site selections may be monitored and analyzed to determine modifications to optimality criteria. In embodiments, the optimality analysis circuit 12702 identifies a confidence level 12726 associated with the optimality of sets of optimal site selections. In the case where simulation data 12712 may not include simulations of all site selection options for the criteria space 12610, the optimality circuit 12702 may determine, based on the simulated site selections, a confidence level that the determined optimal site selections are indeed optimal for a given optimality criteria.

Figure 128:
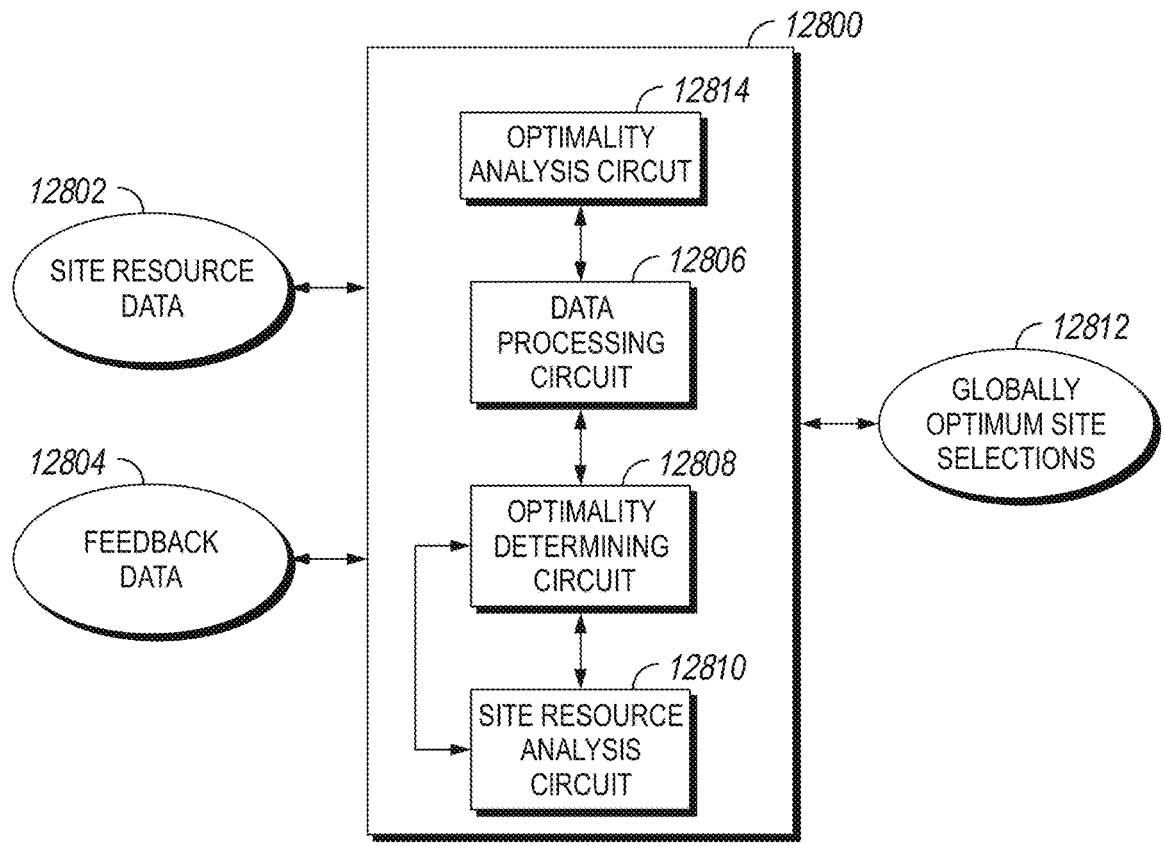

FIG. 128 shows aspects of an apparatus 12800 for determining global optimality of site selections with respect to availability of resources for a clinical trial. In embodiments, the apparatus 12800 may include an optimality analysis circuit 12814 which may be part of the analysis facility 12508 of the platform 12504 (FIG. 125). In embodiments, the apparatus 12800 may include a data processing circuit 12806 structured to interpret/obtain site resource data 12802 of a clinical trial site selection. In some embodiments the site resource data 12802 may be outputs of simulation data of trial site selections. The data processing circuit 12806 may transform the site resource data 12802 into a format suitable for use by the various circuits in the apparatus. For example, the site resource data 12802 may be received by the data processing circuit 12806, which may then determine and identify site resource performance parameters in the data. In some embodiments, some site resource performance parameters may be grouped, filtered, converted, normalized, and the like.

The apparatus 12800 of FIG. 128 may further include an optimality determining circuit 12808 structured to receive processed site resource data from the data processing circuit 12806. The optimality determining circuit 12808 may identify globally optimum site selections 12812 based on one or more optimality criteria. In some embodiments, the globally optimum site selections 12812 may be provided as an output of the apparatus 12800. In some embodiments, globally optimum site selections 12812 may be further processed by the site resource analysis circuit 12810. The site resource analysis circuit 12810 may analyze the globally optimum site selections 12812, determine characteristics of the site selections, and receive feedback data 12804 about the site selections. The site resource analysis circuit may, based on the determined characteristics, determine modifications for optimality criteria used in the optimality determining circuit 12808. Using modified optimality criteria, the optimality determining circuit 12808 may determine a new set of globally optimum site selections 12812.

Figure 129:
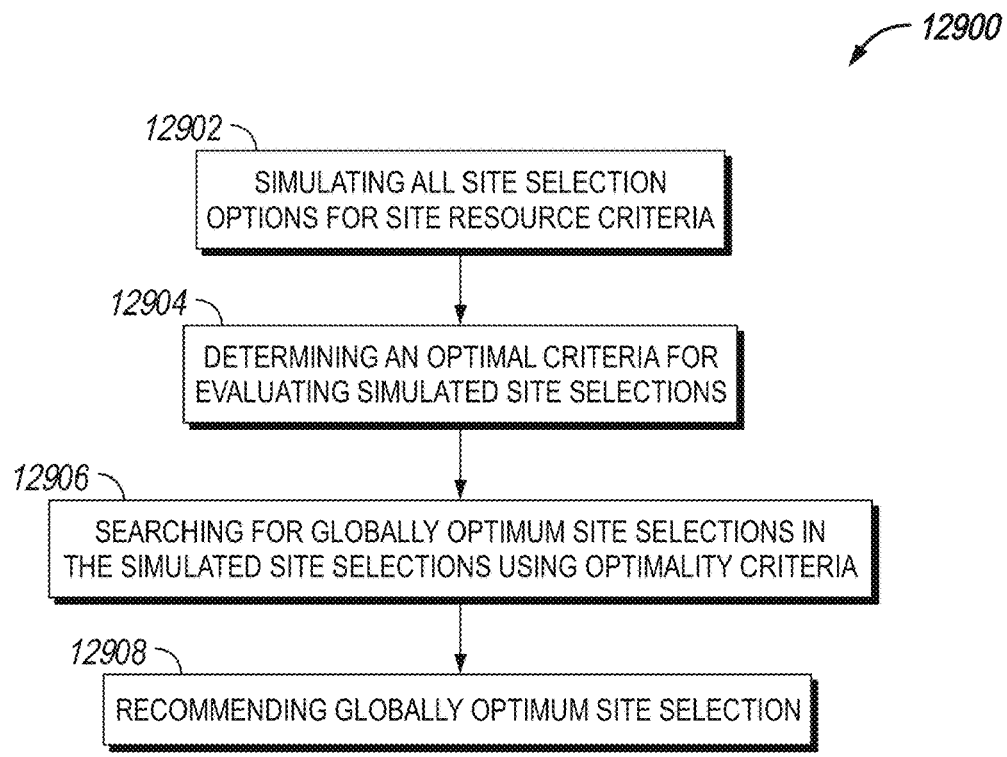

As shown in FIG. 129, a method 12900 for determining globally optimum site selections with respect to availability of resources for a clinical trial may include simulating all site selection options for a site resource criteria 12902. The method 12900 may further include determining an optimality criteria for evaluating simulated site selections 12904. Optimality criteria may be a function of one or more performance values for each site selection such as a weighted sum of the values, a comparison of the values, and the like. The method 12900 may include searching for globally optimum site selection(s) in the simulated site selections using the determined optimality criteria 12906. The globally optimum site selections may be recommended to one or more users 12908.

Figure 130:
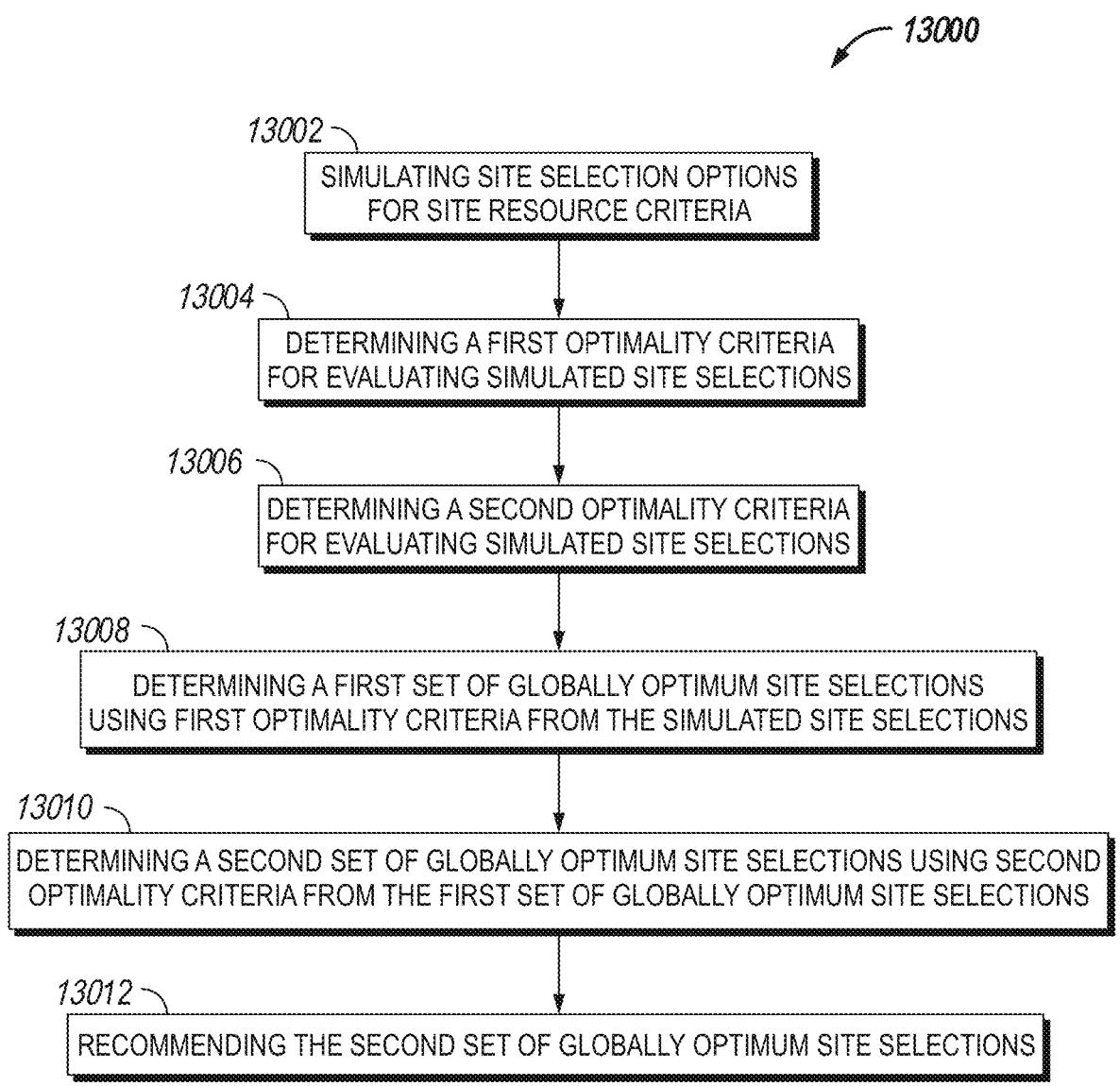

As shown in FIG. 130, a method 13000 for determining site selections to globally optimize available resources for a clinical trial may include simulating site selection options for a site resource criteria 13002. The method 13000 may further include determining a first optimality criteria for evaluating simulated site selections 13004. The method 13000 may further include determining a second optimality criteria for evaluating simulated site selections 13006. The method 13000 may include determining a first set of optimum site selections using the first optimality criteria, the first set may be determined from the simulated site selections 13008. The method 13000 may further include determining a second set of optimum site selections using the second optimality criteria, the second set may be determined from the first set of site selections 13010. The globally optimum site selections may be recommended to one or more users 13012.

Figure 131:
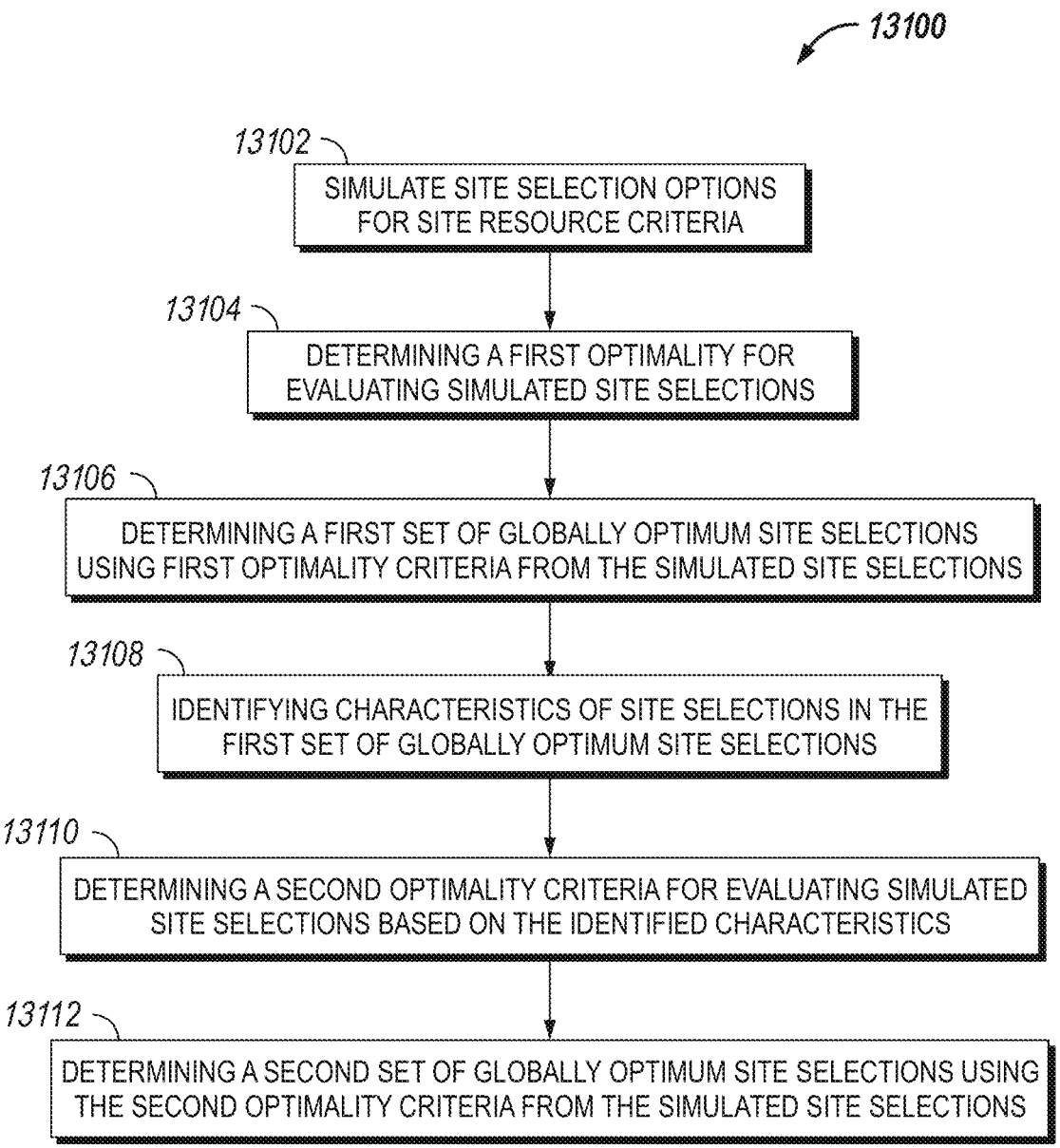

As shown in FIG. 131, a method 13100 for determining a site selection to globally optimize available resources for a clinical trial may include simulating site selection options for a site resource criteria 13102. The method 13100 may further include determining a first optimality criteria for evaluating simulated site selections 13104. The method 13100 may include determining a first set of optimum site selections using the first optimality criteria, the first set may be determined from the simulated site selections 13006. The method 13100 may further include identifying characteristics of site selections in the first set of globally optimum site selections 13108. The method 13100 may further include determining a second optimality criteria for evaluating simulated site selections based on the identified characteristics 13110. The method 13100 may include determining a second set of globally optimum site selections using the second optimality criteria from the simulated site selections 13112.

Illustrated in FIG. 132 is a method 13200 for determining a site selection to globally optimize available resources for a clinical trial, in accordance with an embodiment of the current disclosure. The method 13200 includes determining a plurality of possible sites for recruiting patients from for a clinical trial 13210. The method 13200 further includes determining, for each of one or more subgroupings of the plurality of possible sites, a predicted available resources value 13212. The method 13200 further includes determining which subgrouping of the plurality of possible sites has a predicted available resources value that globally optimizes a desired site resource criteria 13214. In embodiments, determining the predicted available resources value for each of the subgroupings of the plurality of possible sites includes simulating each of the subgroupings 13216. In embodiments, simulating each of the one or more subgroupings may be based at least in part on use of different types of engines, e.g., engines with different version numbers and/or developed by different entities, e.g., in-house vs third-party vendor. In embodiments, the differences in types of engines may include underlying types of algorithms and/or assumptions, e.g., rounding rules. In embodiments, the method 13200 may further include determining one or more site resource parameters 13218. In such embodiments, simulating each of the one or more subgroupings 13216 may be based at least in part on the one or more site resource parameters. In embodiments, the one or more site resource parameters may be based at least in part on: a supply of a drug; administrative personnel; and/or equipment. In embodiments, the method 13200 may further include determining the desired site resource criteria 13220. In such embodiments, simulating each of the one or more subgroupings 13216 may be based at least in part on the determined site resource criteria. In embodiments, the determined site resource criteria may be based at least in part on: a supply of a drug; administrative personnel; and/or equipment. In embodiments, determining which subgrouping of the plurality of possible sites has a predicted available resources value that globally optimizes the desired site resource criteria 13214 may include and/or be based at least in part on: a convex hull engine; a Pareto engine; a Monte Carlo engine; and/or a simulated annealing engine. In embodiments, determining which subgrouping of the plurality of possible sites has a predicted available resources value that globally optimizes the desired site resource criteria 13214 may be based at least in part on a machine learning engine, as described herein. For example, in embodiments, a neural network may be trained to look at past site selections and their outcomes and predict one or more site resource criteria. In embodiments, the neural network may be trained via supervised learning and/or by unsupervised learning, e.g., cost-based policies.

Turning to FIG. 133, an apparatus 13300 for determining a site selection to globally optimize available resources for a clinical trial, in accordance with an embodiment of the current disclosure, is shown. The apparatus 13300 may form part of the platform 12504 or it may be stand-alone from the platform 12504 and/or communicate with the platform 12504 via one or more application programming interfaces (APIs). The apparatus 13300 includes a site selection data processing circuit 13310 structured to interpret possible site selection data 13312 identifying a plurality of possible sites for recruiting patients from for a clinical trial. The apparatus 13300 further includes an available resources determination circuit 13314 structured to determine a predicted available resource value 13316 for each of one or more subgroupings of the plurality of possible sites. The apparatus 13300 further includes a site searching circuit 13318 structured to determine which subgrouping 13320 of the plurality of possible sites has a predicted available resources value that globally optimizes a desired site resource criteria 13330. The apparatus 13300 further includes a site selection provisioning circuit 13322 structured to transmit the subgrouping 13320 of the plurality of possible sites that has the predicted available resources value that globally optimizes the desired site resource criteria. In embodiments, the available resources determination circuit 13314 is further structured to determine the predicted available resources value for each of the one or more subgroupings of the plurality of possible sites by simulating each of the subgroupings. In embodiments, simulating each of the one or more subgroupings is based at least in part on use of different types of engines, as described herein. In embodiments, the apparatus 13300 may include a user input circuit 13324 structured to interpret user input data 13326 and a criteria determining circuit 13328 structured to determine the desired site resource criteria 13330 based at least in part on the user input data 13326. In embodiments, the site searching circuit 13318 may include a convex hull engine; a Pareto engine; a Monte Carlo engine; and/or a simulated annealing engine.

Referring to FIG. 134, embodiments of the current disclosure may provide for a design platform 13400 with an interface 13410 for configuring and managing the platform 12504 with respect to optimizing site selection for availability of resources for a clinical trial. The design platform 13400 may provide for pre-simulation determination of one or more resource selection parameters, e.g., values within resource criteria space 12610, site resource space 12612, resource scenario space 12614 and/or site resource performance space 12616. Some embodiments may provide for adjustment of resource selection parameters during a simulation. The interface 13410 may include a canvas area 13412 for visualizing/editing/creating resource selection parameters for use by the platform 12504 (FIG. 125). Embodiments of the interface 13410 may be a graphical user interface (GUI) that has one or more input fields 13414 for inputting or selecting resource selection parameters. The input fields 13414 may be sliders, text boxes, moveable components, and/or other GUI user input widgets. The graphical user interface may also provide for a heat map for selecting possible sites. The heat map may provide for filtering of the possible sites. In embodiments, the platform

13400 may provide, via servers 12554 (FIG. 125) multiple interfaces, e.g., interfaces 13410, 13416, 13418, for collaborative configuration of the platform 12504 by one or more users. In embodiments, the interfaces 13410, 13416, 13418 may be configured differently for different users, e.g., an interface may be tailored to a type of user and/or target audience, e.g., clinical trial experts, novices, and/or other types of users of varying skill levels in clinical trial designs and/or site selection. Tailoring of an interface to a user type may include enabling and/or disabling certain features and/or options on the interface. In embodiments, collaboration between users may involve a first user operating on a first interface 13410 receiving inputs from a second interface 13416 operated by a second user. In embodiments, the interface 13410 may provide for weighting of one or more resource selection parameters. In embodiments, the interface 13410 may provide for configuration of the simulation component 12510 (FIG. 125). For example, a user operating the interface 13410 may configure the simulation component 12510 to perform an exhaustive search and/or simulation of site selection options. In embodiments, a user operating the interface 13410 may configure the simulation component 12510 to perform anon-exhaustive search and/or simulation of site selection options. In embodiments, the interface 13410 may provide for a user to configure the platform 12504 to user one or more of a convex hull engine, a Pareto engine, a Monte Carlo engine, and/or simulated annealing engine. In embodiments, the interface 13410 may provide for a user to configure a training set for a machine learning engine to learn how to optimize site selections with respect to resource availability, as disclosed herein.

Turning to FIG. 135, a method 13500 for collaborative configuration of a site selection platform 12504 for optimization of availability of resources for a clinical trial is shown. The method 13500 includes displaying a graphical user interface structured to configure a system for determining which subgrouping, of a plurality of possible sites for a clinical trial, globally optimizes available clinical trial resources 13510. The method 13500 further includes receiving, via the graphical user interface, one or more user inputs that define one or more resource selection parameters used by the system 13512. The method 13500 further includes storing the defined resource selection parameters in a memory device 13514.

Shown in FIG. 136 is an apparatus 13600 for providing collaborative configuration of a site selection platform 12504 for optimization of availability of resources for a clinical trial is shown. The apparatus 13600 includes a display generation circuit 13610 structured to generate a graphical user interface 13612 for configuring a system 12504 for determining which subgrouping, of a plurality of possible sites for a clinical trial, globally optimizes available clinical trial resources. The apparatus 13600 further includes a display transmission circuit 13614 structured to transmit the graphical user interface 13612 to an electronic device for display, e.g., 12502. The apparatus 13600 further includes a user interaction circuit 13616 structured to interpret user inputs 13618 received by the graphical user interface 13612; and in response to, and based at least in part on, interpreting the user inputs 13618, define resource selection parameters 13620 used by the system 12504. The selection parameter provisioning circuit 13622 is structured to store the defined selection-parameters 13620 in a memory device, e.g., 12538.

Shown in FIG. 137 is another method 13700 for collaborative configuration of a site selection platform 12504 for optimization of availability of resources for a clinical trial.

The method 13700 includes configuring, via a graphical user interface, a recruitment site selection system via entering one or more user inputs into the graphical user interface that define one or more selection-parameters 13710. The method 13700 further includes determining, via the recruitment site selection system, which subgrouping, of a plurality of possible sites for recruiting patients from for a clinical trial, globally optimizes available clinical trial resources 13712. The method 13700 further includes transmitting data identifying the determined subgrouping 13714.

Referring to FIG. 138, embodiments of the disclosure may provide for a platform/system 13800 with an interface 13810, e.g., a wizard, for guiding a user through configuring a site grouping/selection system/platform 12504 (FIG. 125) for optimizing site selection with respect to availability of resources for a clinical trial. In embodiments, the interface 13810 may be generated by a server 12554 (FIG. 125). The interface 13810 may be command line based or graphical user interfaced based. The interface 13810 may generate a plurality of prompts 13812 that assist in obtaining initial resource selection parameters, e.g., criteria, from users to determine parameters for resource criteria space 12610, site resource space 12612, resource scenario space 12614, and/or site resource performance space 12616. The plurality of prompts 13812 may ask for a variety of static inputs or ranges. The inputs may include the type of engine 12528 to use in the simulation 12510. The inputs may also include the type of search algorithm 12530 used. The inputs may include the type of sensitivity analysis algorithms or tools that are preferred. The inputs may include the type of clinical trial. The interface may recommend one or more site groupings/selections based on the type of clinical trial. The recommended site groupings/selections may serve as a starting base for further modification by a user. Artificial intelligence/machine learning approaches may be used to generate the prompts 13812 and/or suggestions for the user through the configuration process. As will be appreciated, the suggestions and/or guiding by the interface 13800 may allow a user to avoid (or reduce) spending time and resources (including computing resources and the costs of those resources) on sub-optimal simulations.

In an embodiment, a method for guiding a user through configuring a site grouping/selection system/platform for optimizing site selection for resource availability for a clinical trial is provided. The method includes generating an interactive interface. The method further includes presenting, via the interactive interface, a plurality of prompts to a user structured to configure a site selection system 12504 for determining which subgrouping, of a plurality of possible sites for recruiting patients from for a clinical trial, globally optimizes a desired resource criteria, e.g., one or more parameters within resource criteria space 12610. The method further includes for each of the plurality of prompts, receiving a responsive user input, and configuring the site selection system based at least in part on the responsive user inputs.

In another embodiment, a system for guiding a user through configuring a site grouping/selection system/platform for optimizing site selection for resource availability for a clinical trial is provided. The system includes a server structured to determine which subgrouping of a plurality of possible sites for recruiting patients from for a clinical trial globally optimizes a desired resource criteria. The system further includes an electronic device, e.g., 12502, structured to: display an interactive interface that presents a plurality of prompts to a user for configuring the server; for each of the plurality of prompts, receive a responsive user input; and configure the server based at least in part on the responsive user inputs.

In another embodiment, a non-transitory computer readable medium storing instructions is provided. The stored instructions, when loaded into at least one processor, adapt the at least one processor to: generate an interactive interface; and present, via the interactive interface, a plurality of prompts to a user. The plurality of prompts are structured to configure a site selection system for determining which subgrouping, of a plurality of possible sites for recruiting patients from for a clinical trial, globally optimizes a desired resource criteria. The stored instructions further adapt the at least one processor to, for reach of the plurality of prompts, receive a responsive user input; and configure the site selection system based at least in part on the responsive user inputs.

Embodiments of the current disclosure may provide for prediction of an initial site grouping/selection with respect to resource availability of a clinical trial. In embodiments, the initial site selection may be structured to maximize (globally optimize) access to clinical trial resources and/or other criteria, e.g., one or more parameters within resource criteria space 12610, site resource space 12612, resource scenario space 12614, and/or site resource performance space 12616. For example, in embodiments, a predicted initial site selection may correspond to minimizing interruptions in supply of a drug used in the clinical trial. In other embodiments, the predicted initial site selection may correspond to maximizing the number of administrative personnel or healthcare providers available to conduct the clinical trial. In yet other embodiments, the predicted initial site selection may correspond to maximizing the availability of medical equipment used in the clinical trial.

In embodiments, the initial site selection may be based at least in part on historical data. The historical data may include data from previously conducted clinical trials and/or it may include data from prior simulated clinical trials. In embodiments, the data may be stored in data facility 12538 and/or be generated by the simulation component 12510 and/or the analysis components 12508.

The prediction may be generated prior to receiving user input or after receiving some user input e.g., via user device 12502. The predicted initial site grouping/selection may be displayed in a graphical user interface, e.g., interface component 12512, for adjustment by a user. The predicted initial site grouping/selection may be the grouping/selection actually used in the clinical trial, or it may serve as a starting point which the user can configure/tweak as desired. The predicted initial site grouping/selection may be the global optimal, with respect to the desired resource; or it may be close to the global optimal, wherein a user can tweak, i.e., make adjustments, it to be the global optimal. The initial prediction may reduce the amount of time to find the global optimum by providing the user (or computer) with a good starting point based on knowledge gained from historical data. Simulated annealing, e.g., via the search/exploration modules/engines 12530, may be applied to the initial prediction to test the surrounding subgroupings. Artificial intelligence may be used to analyze the historical data based on known desired criteria for the clinical trial. For example, in embodiments, a neural network may be trained on historical data to identify patterns in site selections that result in particular values for the availability of a resource at one or more sites. The neural network may then process site selection data, i.e., data regarding possible sites for a clinical trial, and then generate a predicted initial site selection.

Accordingly, referring to FIG. 139, a method 13900 for prediction of an initial site grouping/selection for optimizing resource availability for a clinical trial is shown. The method 13900 includes accessing past trial site selection data stored in a database 13910. The method 13900 further includes predicting, based at least in part on the past trial site selection data, the initial site selection 13912. In embodiments, predicting the initial site selection may be based at least in part on artificial intelligence, as disclosed herein. The initial site selection corresponds to a global optimization of access to a desired resource for the clinical trial, as disclosed herein. The method 13900 further includes evaluating the initial site selection with respect to being the global optimization 13914. Such evaluation may be based at least in part on a convex hull engine, a Pareto engine, a Monte Carlo engine, or a simulated annealing engine, as disclosed herein. The method 13900 may further include displaying the initial site selection in a graphical user interface 13916. In embodiments, the desired resource may be based at least in part on a drug supply, administrative personnel, and/or equipment. In embodiments, the method 13900 further includes adjusting the initial site selection via the graphical user interface 13918. In embodiments, the method 13900 may further include interpreting one or more user inputs, wherein the prediction of the initial site selection is based at least in part on the one or more user inputs 13920. In embodiments, the method may further include simulating the initial site selection to determine performance criteria 13922. In embodiments, the method 13900 may further include conducting a sensitivity analysis of the initial site selection 13924, e.g., via analysis component 12508.

Illustrated in FIG. 140 is an apparatus 14000 for prediction of an initial site grouping/selection for optimizing resource availability for a clinical trial. The apparatus 14000 includes a past trial data processing circuit 14010 structured to interpret past trial site selection data 14012. The apparatus 14000 further includes a resource prediction circuit 14014 structured to generate, based at least in part on the past trial site selection data 14012, initial site selection data 14016 for a clinical trial. The initial site selection data 14016 may correspond to a global optimization of access to one or more resources for the clinical trial. The apparatus 14000 further includes a resource evaluation circuit 14018 structured to evaluate the initial site selection data 14016 with respect to the global optimization. The apparatus 14000 further includes a prediction provisioning circuit 14020 structured to transmit the initial site selection data 14016.

Embodiments of the current disclosure may also provide for a method for using the initial site selection. The method may include receiving an initial site selection for a clinical trial, and conducting a clinical trial based as least in part on the initial site selection. The initial site selection may correspond to a global optimization of access to one or more resources for the clinical trial, wherein the initial site selection was predicted from past trial site selection data. For example, a first entity may generate initial site selection data and send it to a second entity that conducts a clinical trial based at least on part on the initial site selection data.

Referring now to FIG. 141, embodiments of the current disclosure may provide for a platform/system 14100 that generates an interactive interface 14110, e.g., a GUI, for exploration/evaluation of spaces related to availability of resources for a clinical trial, as opposed to merely facilitating selection of proposed sites, for the purpose of globally optimizing site selection for a clinical trial to optimize availability of resources. The spaces may include site resource criteria space 12610, site resource space 12612, resource site scenario space 12614, and/or site resource performance space 12616. In embodiments, generation of the site selections and/or evaluation of the spaces may be based at least in part on convex hull, Pareto frontiers, Monte Carlo, simulated annealing, and/or machine learning, e.g., artificial intelligence, as described herein.

Exploration/evaluation of the spaces may provide insights to a user regarding known and/or unknown constraints on site selection and/or the impact a particular selection parameter, e.g., a parameter within one of the spaces, may have on resource availability.

Exploration of the spaces may be facilitated via visualizations of the spaces. The visualizations may include, and/or be based at least in part on, heatmaps and/or tornado graphs. The interface 14110 may include a canvas area 14112 for rendering (or rasterizing) the visualizations.

The interface 14110 may provide for users to adjust one or more selection parameters and/or adjust sites within one or more proposed site selections/groupings and see the effect on the predicted resource availability. Adjustment of the selection parameters may be facilitated by one or more interactive widgets 14114, e.g., text boxes, buttons, sliders, and/or the like. In embodiments, adjustment of the selection parameters may be facilitated via the canvas 14112. In embodiments, the interface 14110 may allow users to evaluate and compare possible site selections/groupings side-by-side.

In embodiments, exploration of the spaces may provide for sensitivity analysis. For example, embodiments of the interface 14110 may incorporate simulated annealing engines, as described herein.

In embodiments, platform/system 14100 may include a server, e.g. server 12554 in the computation resources 12550 of platform 12504. The server 12554 may generate the interface 14110 as a web application, remote desktop, and/or other suitable architecture for providing the interface 14110 to users and/or user devices 12502.

The platform 14100 may support collaboration among different users. For example, the server 12554 may generate multiple interfaces 14110, 14116, and 14118. In embodiments, the interfaces 14110, 14116, and 14118 may be configured/tailored to different types of user/target audience, e.g., users with different levels of experience and/or knowledge with respect to evaluating site groupings/selection for various criteria. For example, a first interface 14110 for an expert user may have more functionality, e.g., access to more options and/or features, than a second interface 14116 for a novice user.

Turning to FIG. 142, a method 14200 for exploring/evaluating spaces related to resource availability for a clinical trial is shown. The method 14200 includes generating a graphical user interface structured to provide for interactive exploration of one or more spaces corresponding to one or more selection parameters for determining which subgrouping, of a plurality of possible sites for recruiting patients from for a clinical trial, globally optimizes clinical trial resources 14210. The method 14200 further includes adjusting at least one of the selection parameters via the graphical user interface 14212. The method 14200 further includes updating the graphical user interface in response to adjusting the at least one selection parameter 14214. In embodiments, the clinical trial resources may be based at least in part on a supply of a drug, administrative personnel, and/or equipment. In embodiments, generating the graphical user interface occurs prior to simulating, as disclosed herein, any one of the possible sites. In embodiments, generating the graphical user interface occurs after simulation of one or more of the possible sites.

Illustrated in FIG. 143 is a non-limiting embodiment of an apparatus 14300 for exploring/evaluating spaces related to patient recruitment for a clinical trial. The apparatus 14300 includes a resource space processing circuit 14310 structured interpret space data 14312 corresponding to one or more spaces, e.g., 12610, 12612, 12614, and/or 12616, related to subgroupings of possible sites for use in conducting a clinical trial. The apparatus 14300 further includes a graphics circuit 14314 structured to generate interactive interface data 14316 in response to the space data 14312. In embodiments, the interactive interface data 14316 corresponds to a computerized interface 14110 for globally optimizing site selection for clinical trial resource availability. The apparatus 14300 further includes a user input circuit 14318 structured to receive user input data 14320 responsive to the presentation of the interactive interface data 14316. The apparatus 14300 further includes a resource space exploration circuit 14322 structured to modify the interactive interface data 14326 in response to the user input data 14320. The apparatus 14300 further includes an interactive provisioning 14324 circuit structured to transmit the modified interactive interface data 14326.

Referring to FIG. 144, a method 14400 for updating site selection according to available resources is shown. Since recommendation of globally optimal site selection, as disclosed herein, are generally predictive, it is possible that one or more parameters used to determine a globally optimum site selection for a clinical trial may deviate from what actually occurs during conduction/execution of the trial, i.e., while the trial is underway. A globally optimum site selection may have been determined based on an initial availability of resources, when, in actuality, a global pandemic emerges shortly after the start of a clinical trial affecting the availability of resources. In such a case, the original globally optimum site selection may no longer be the optimum. Updating of a site selection, as described herein, may occur multiple times through the course/duration of the clinical trial. In some embodiments, updating of the site selection, as described herein, may be performed on a continuous basis throughout the duration of the clinical trial.

Accordingly, the method 14400 includes obtaining a first simulation output for a first set of site selections for a clinical trial based on the availability of resources 14410. The first simulation output includes first resource availability, as disclosed herein, associated with each site in the first set of site selections. The method 14400 further includes determining a first resource availability 14412. The method 14400 further includes determining, within the first set of site selections, a first globally optimum site selection based at least in part on the availability of resources 14414. Optimum site selections may be determined using one or more of Pareto analysis, convex hull analysis, and/or simulated annealing analysis. The site selection may then be configured based at least in part on the first globally optimum site selection, e.g., the site selection may be made to conform to the globally optimum site selection.

As further shown in FIG. 144, the method 14400 may include conducting/executing the clinical trial based at least in part on the first globally optimum site selection 14416. Conduction of the clinical trial may be defined by a start/beginning 14418 of the clinical trial and a stop/end 14420 of the clinical trial. In embodiments, the start 14418 may be the occurrence of the first patient recruitment. In embodiments, the start 14418 may be the occurrence of the first interaction between administrative personnel (for the clinical trial) and a patient or recruitment site, in respect of the trial. In embodiments, the start 14418 may be the first occurrence of a patient receiving a treatment (including receiving a drug). In embodiments, the stop 14420 may be the last occurrence of patient receiving a treatment (including receiving a drug). In embodiments, the stop 14420 may be the occurrence of the last interaction between administrative personnel (for the clinical trial) and a patient or recruitment site, in respect of the trial. The time between the start 14418 and the stop 14420 may constitute the duration of the clinical trial as that term is user herein. In embodiments, conduction of the clinical trial may include commencement of any portion and/or process of the clinical trial whether performed in succession and/or intermittently.

After the start 14418 of the clinical trial, but before the stop 14420, the globally optimum site selection may be reassessed in view of changes to availability of resources. As such, the method 14400 includes obtaining, during conduction of the clinical trial, a second simulation output for a second set of site selections for the clinical trial based on a second resource availability 14422. The second simulation output includes second site selection performance parameters associated with each design in the second set of site selections for a second set of site selection criteria. In embodiments, the second simulation output may be different than the first simulation output. For example, the second simulation output may be from another evaluation of the site selections according to a second resource availability. In embodiments, the second simulation output may be the same as the first simulation output. For example, the first simulation output may be reused. In embodiments, the second site selection performance parameters may be different than the first site selection performance parameters. For example, the second site selection performance parameters may include more or fewer parameters than the first site selection performance parameters. In embodiments, the second site selection performance parameters may be the same as the first site selection performance parameters. In embodiments, the second set of site selections may be the same or different than the first set of site selections. For example, the second set of site selections may include additional sites selections and/or have removed site selections as compared to the first set of site selections. In embodiments, the second set of site selection criteria may be the same or different than the first set of site selection criteria. For example, availability of a resource such as a drug for the clinical trial and/or site selections may have changed since the start 14418.

The method 14400 further includes determining, within the second set of site selections, a second globally optimum site selection 14426. Determination of the second globally optimum site selection may be based at least in part on the second resource availability 1424. The method 14400 may further include adjusting the site selection based at least in part on the second globally optimum site selection 14428. Adjustment of the site selection may include conforming the site selection to the second globally optimum site selection.

Illustrated in FIG. 145 is another method 14500 for updating site selections based on resource availability. In particular, method 14500 identifies a globally optimum site selection for a clinical trial for a first resource availability after the start 14512 of the clinical trial, but before the end 14514 of the clinical trial, where an initial globally optimum site selection may not have been determined, or was not determined by an entity performing method 14500. Accordingly, the method 14500 includes obtaining, during conduction of the clinical trial 12416, a simulation output for a set of site selections for the clinical trial for a resource availability 14518. The simulation output includes site selection performance parameters associated with each site selection in the set of site selections for a resource availability. The method 14500 further includes determining, from the set of site selection criteria, a site selection optimality criteria for evaluating the first set of site selections 14520. The method 14500 further includes determining, within the set of site selections, a globally optimum site selection based at least in part on the site selection optimality criteria and the availability of resources 14522. The method 14500 may further include recommending the globally optimum site selection for the available resources 14524. Recommendation may include transmitting the globally optimum site selections to an entity performing and/or planning the clinical trial. The recommended globally optimum site selections may be the first time a globally optimum site selection was calculated/determined for the clinical trial, or the globally optimum site selection may be an update to a previously calculated/determined globally optimum site selection. In embodiments, the method 14500 may not include recommending the globally optimum site selection, but rather may include adjusting the site selection based at least in part on the globally optimum site selection 14526. It is to be understood, however, that embodiments of the method 14500 may not include adjusting the site selection trial based at least in part on the globally optimum site selection. In embodiments, the method 14500 may include both recommending and adjusting the site selection based at least in part on the globally optimum site selection.

FIG. 146 shows aspects of another view or organization of a platform 14606 as discussed herein. In one embodiment, entities such as users may interact with the platform 14606 with a user device such as an application in a browser 14604. The browser application 14604 may receive content from a content management system 14602. The browser application 14604 may communicate with an authentication module 14610 to authenticate the entity and enable access to the services 14618 and other elements of the platform 14606. In embodiments, the access and interaction with the platform 14606 may include interaction with the application programming interface 14612 of the platform 14606. The API interface 14612 may provide an interface to the services 14618 of the platform. The services of the platform may provide services provided by the configuration facility 106, analysis facility 108, simulation facility 110, and/or the interfaces facility 112 shown with respect to the platform configuration of FIG. 1. The services of the platform 14606 may include services such as an engine registry service 14624, query service 14626, subscription service 14628, simulation service 14630, project service 14632, statistical service 14634, and augmentation service 14636.

In embodiments, one or more of the services may interact with other services and interact with the compute component 14638. The compute component 14638 may include components for executing simulations. The compute component may include one or more components that provide the functionality of the simulation facility 110 of the configuration of the platform shown in FIG. 1. The compute component 14638 may include queues 14640, 14642, 14644 that provide data to and/or receive data from engines 14650. The queues may sort and manage simulation models for simulation by the simulation engines 14650. Data from the queues and/or engines 14650 may be stored and received by the data storage and data management components such as a data lake 14651, storage service 14646, and databases 14648.

In embodiments, the platform 14606 may include one or more cloud services 14616 provided by one or more cloud providers. Cloud services may include code management services 14652, deployment pipeline services 14654, container services 14656, and the like. In embodiments, one or more monitors 14620 may monitor the operation of the platform 14606 and identify errors, faulty components, completions of operations or processing and the like. The monitors 14620 may cause alerts or other notifications for the browser app 14604. In some embodiments, the platform 14606 may include an application insights 14622 module which may provide performance monitoring and management of applications and components associated with the platform 14606.

In embodiments, elements of the platform may include a quantum computer. In embodiments, one or more algorithms and/or methods described herein may be implemented using a quantum computer that may be executing a quantum algorithm. A quantum computer may be a computer that is based on quantum mechanical phenomena such as superposition and entanglement to perform operations on data. A computing system may include a hybrid system that includes a quantum computer and a classical computer. The methods and systems described herein may be deployed such that they are distributed among the classical and quantum computers. A quantum computer may execute one or more quantum algorithms for solving one or more quantum computing tasks, and a classical computer may execute one or more classical algorithms for solving one or more classical computing tasks. In embodiments, parts of the platform may use quantum computing and quantum algorithms to speed up computations for algorithms or parts of algorithms that are difficult for classical computers. In some embodiments, algorithms for quantum search, quantum simulation, quantum annealing, and the like may be used in parts of the platform for implementing aspects of the methods and systems described herein.

In embodiments, one or more algorithms and/or methods described herein may be implemented with artificial intelligence algorithms such as machine learning algorithms and neural network algorithms. Artificial intelligence algorithms may be used to build mathematical models based on training data to make predictions or decisions. In embodiments, training data may include any one or subset of: interface interactions, simulated annealing inputs and results, pareto analysis inputs and results, convex hull analysis inputs and results, recommendation algorithm inputs and results, orchestrating algorithm inputs and results, design advisor inputs and trade-off advisor inputs and outputs, and other data received or determined by the platform described herein. In embodiments artificial intelligence may include supervised machine learning, unsupervised machine learning, reinforcement machine learning, and the like. In embodiments artificial intelligence algorithms may be used to identify design optimality, identify optimal designs, identify analysis flow and methods to reduce computation and analysis time, and the like.

In embodiments, the system and methods described herein may be include one or more computing resources such as a cloud computing service. The cloud computing service may provide on demand availability of computer system resources. Computing and/or storage resources may be allocated based on demand, cost, timing requirements, and the like. The computing resources may be distributed across multiple locations. Computing resources may be allocated on demand during operation of the platform. Different stages of operation may require different computing resources. Simulations, for example, may require an increase in computing and storage resources. The amount, locations, and the like of the computing resources may be selected based on timing and cost considerations. High priority design studies may be allocated more resources for example. In embodiments, cloud computing may be used for platform and functions to optimize trial design, site selection, and/or clinical trial resources.

In embodiments, the system and methods described herein may utilize one or more external data sources. External data sources may include databases of data, federated data sources, government data, real-time data, and the like. In some cases, external data sources may be queried for data from a single source. In some cases, external data may require data harvesting from multiple locations or resources using one or more crawlers, queries, bots, and the like. For example, financial data used for augmenting data in the platform described herein may require querying or multiple resources to determine current costs for sites, doctors, drugs, and the like. External data sources may be updated using data calculated, compiled, or determined by the platform or parts of the platform. Data may be written to multiple locations while using one or more write-back methods to maintain data coherency.

In embodiments, the system and methods described herein may include authentication and/or provide conditional access. The platform, resources associated with the platform, and the like may require establishing and confirming identities of entities that interact with the platform and associated resources thereof. Entities may be persons and/or other resources. Identities may be associated with account and may track usage for billing and accounting. Identities may be associated with access or capabilities restrictions. Some aspects of the platform may be enabled for some entities associate with specific accounts based on subscription level. Conditional access may be provided to specific algorithms, models, engines, data, analysis interfaces, and the like. Data and communications may be secured with one or more encryption and data security methods for maintaining data security and confidentiality.

In embodiments, the system and methods described herein may include metadata. Metadata may include descriptive metadata, structural metadata, administrative metadata, reference metadata, and/or statistical metadata. Metadata may be associated with stored data, data as it progresses through the platform, elements of the platform (for example elements that may self-identify and register to the platform). Metadata may be associated with major data structures and elements of the system. Metadata may be associated with and/or accompany data related to the design space, criteria space, performance space and the like. The metadata may provide information about where the data originated, who or what created the data, when the data was created, assumptions and limitations of the data and the like. For example, simulated data may include metadata that relates to the engines and algorithms that were used for the computations. The metadata may identify what version of engines, what random number seeds were used, known limitations and compatibility of the engines and data generated by the engines with other engines and data produced by other engines.

In embodiments, the system and methods described herein may include reporting functionality. Reporting may include charts, spreadsheets and other tools used to present the results of the optimization process and/or the data fed into the optimization process. Reporting may include heat maps and tornado graphs. Reporting may be generated for user review and analysis. In some cases reporting may be generated for machine analysis. User report and machine reports may include different formatting and amounts of data. Reporting may be system initiated or user initiated. In some cases reporting may be triggered by an event, such as in an analysis. Reporting may include data and documentation for audit or methods, procedures, and the like used by the platform and parts thereof. Reporting may be necessary for compliance and regulatory approval.

In embodiments, the system and methods described herein include integrations with one or more databases, third party systems, sources of data, marketplaces, computational resources, and the like.

In embodiments, the systems, methods, and platform described herein may include aspects of application programming interfaces (APIs). APIs may include software interfaces that provide for communications between various components of the overarching clinical trial framework, e.g., backend servers, frontend graphical user interfaces, querying of historical data, available resource data, and the like. APIs may be exposed (such as software hooks) for expanding, controlling, and/or modifying functionality of the platform. APIs may include libraries and frameworks for interacting and integrating third party simulation and analysis systems. Third party simulation engines may consume platform APIs to control or use system resources. In embodiments, the systems, methods, and platform described herein may consume APIs of external or internal software and systems.

In embodiments, the system and methods described herein may include alerts. The platform or components thereof may include components for generation and transmission of data messages to an end user (human or machine). Alerts may be generated for notifying an end user of analysis results, status of processes (such as simulation, analysis, configuration, and the like), errors (delays in processing, unavailability of platform or external resources, unauthorized access, and the like), time of completions of simulations and/or analysis, and the like. Alerts may be logged for system audit and used for predictions. Alerts may be pushed or pulled to user devices, such as mobile devices and may wake a device from a sleep or low power mode. Alerts may be provided to other platform elements which may be used as a trigger to initiate and/or abort other processes of the platform. For example, simulated annealing analysis may provide alerts when improved designs are observed. The alerts may be provided to a user and used to trigger an update of interfaces that display analyzed designs.

In embodiments, the system and methods described herein may include collaboration features. Collaboration may include collaboration among users. Components of the various interfaces may provide for users to collaborate with respect to trial design and/or site selection. Collaboration may include: messaging/commenting systems, screen sharing, and/or platforms that merge various elements that are created/edited by different users. Users may be able to post, view, edit and/or download simulation results. Collaboration may include collaboration across sites. Users at different locations may use and collaborate with the same system. Collaboration may include collaboration across time. Settings, analysis, results, and the like may be saved and modified by different users at different times. Changing settings from analysis performed in the past may automatically trigger analysis based on new setting and a comparison against previous results.

In embodiments, the systems and methods described herein may include design and optimization or various clinical trial types and may include: parallel group design, cluster randomized design, crossover design, titration design, enrichment design, group sequential design, placebo-challenging design, blinder reader designs, single-stage up-and-down phase 1 design, two-stage up-and-down phase 1 design, continual reassessment method phase 1 design, optimal/flexible multiple-stage designs, randomized phase II designs, dose-escalating design, biomarker-adaptive design, adaptive randomization design, pick the winner design.

In embodiments, the system and methods described herein may include trial design and optimization for different phases of trials. In embodiments, different phases of trials (such as preclinical, phase 0, phase 1, phase 2, phase 3, phase 4) may use different considerations and, in some cases, use different simulation engines, analysis algorithms, interfaces, wizards, and the like. In embodiments, the scenario space, design space, criteria space, and/or performance space may be modified or different based on the phase of the trial and/or type of trial.

In embodiments, the systems and methods described herein may include consideration and analysis of trial resources. Trial resources may include resources to prepare, conduct, and evaluate a clinical trial. Examples include drugs/drug supply subject to the trial, devices subject to the trial, and/or administrative personnel and/or equipment needed to administer a procedure/drug/device subject to the trial. Resources may include test equipment to analyze and certify results. Availability, cost, time for acquisition and the like of resources may be a factor in performance space, design space, scenario space, and/or criteria space during design and evaluation of clinical trials.

Computational resources (such as servers and cloud services) used for simulation or analysis during trial design may operate in batch mode or may operate with a time delay between when the resources are requested and when they are available for use. Batch mode and a time delay may reduce responsiveness of an interactive design simulation. In embodiments, a platform may predict when a request for computation resources should be issued such that they are available when needed. Triggers, such as progress in the interface, time of day, amount of data entered, meeting schedules, and the like may be used to predict when simulations or analysis will be ready for execution or computation. In embodiments, machine learning models may be used to predict when computational resources should be requested such that they are ready when simulations are ready for execution. Models may use historical data. Computation resources may be requested ahead of time before they are needed in anticipation of a future request.

In embodiments, the size of a batch of computation (which may be correlated with the time of computation) may be sized based on predicted computational requirements for the project. Predictions may be based on history of similar projects, users, and the like. In embodiments, the size of a batch may be related to when computation resources are expected to be available, a prediction of when simulations or analysis will be ready for execution or computation and how long the execution or computation is expected to take.

FIG. 147 shows aspects of an apparatus for determining resource allocation in accordance with an embodiment of the current disclosure. The apparatus may include a resource allocation engine 14706. The resource allocation engine 14706 may include a resource response data component 14708 configured to identify and/or maintain data related to resource capabilities, costs, allocation delay, computing power and the like. The resource response data component 14708 may include one or more tables or databases that identify available or authorized resources for performing batch computations for simulation, analysis, and other platform tasks. The resource response data component 14708 may be configured to trigger the polling engine 14712 to determine data for computational resources. The polling engine 14712 may be configured to periodically or upon a trigger event, identify a list of available resources, their availability, cost, computational capability, time to availability and the like. The polling engine 14712 may transmit a data request directly to one or more resources to determine their availability. In some cases, the polling engine 14712 may transmit a data request to a central database to determine data for the resources. The polling engine 14712 may update, with the resource response data, the component with the determined data. The resource allocation engine may receive data related to the design progress 14702 within the platform. The design progress may indicate what data has been entered for a design study, how quickly data is entered, what part of the interface the user is currently interacting with, and the like. The resource allocation engine may receive data related to the study parameters 14704. The study parameters 14704 may identify how many designs and/or scenarios are being considered for simulation, types of simulations required, the types of computation engines related to the simulations, and the like. The prediction engine 14710, may, based on the design progress data 14702 and/or study parameter data 14704, predict when resources will be required and how much of the resources are required for the study. The prediction engine 14710, may, using resource response data and the required resource predictions determine when the resources should be requested such that they are available when needed. The prediction engine 14710 may factor in the allocation delay, costs of resources, and the like to determine when a request for resources should be made and how many resources should be requested. In some cases, the prediction engine 14710 may determine, based on the predictions, a trigger in the design progress data 14702 that when reached will cause the resource allocation engine to issue a resource request 14714 to allocate resources in anticipation of need.

In embodiments, the prediction engine may determine when resources should be allocated or determine progress triggers for allocation based on historical data of design progress and time of resource request. In embodiments, one or more machine learning models may be trained on the historical data to train the model to predict when resources will be needed. The prediction when the resources will be needed may then be used to request resources ahead of when they are needed according to the time delay associated with each resource. In some embodiments, additional data such as calendar data, meeting data, and the like may be used to make or supplement the prediction process. Meeting data may indicate that resources may be required for computation during the meeting.

In embodiments a prediction engine may determine triggers such as a specific location in the interface that indicate that the study is almost ready for simulation and resources should be requested. Triggers may include when specific data is entered, when one or more locations in the interface progression are reached, and the like.

As shown in FIG. 148, a method for determining a trigger for requesting computational resources may include monitoring design specification progress 14802 and determining resource allocation parameters 14804. Resource allocation parameters may include data related to the time delay between when a resource is requested and when the allocation is available for use. The method may further include predicting when computation resources will be required based on the design specification progress 14806. Predicting may be based on historical data, trained machine learning models, external data, and the like. Based on the predicting, a design specification progress trigger point may be determined 14808. The trigger point may be identified to correspond to the time delay associated with obtaining a resource and expected requirement of the resource. The design specification progress may be monitored for the determined trigger and in response to the trigger being observed, the computational resources may be requested such that they are allocated and ready when they are predicted to be needed 14810.

In embodiments, computing resources may be allocated in anticipation of collaborative sessions for trial design. For example, embodiments of the current disclosure may detect that one or more users are in, or are about to enter, a collaborative session and spool computing resources. The spooling of computing resources may be based on one or more aspects of the platforms, disclosed herein, that the users are likely to use. In embodiments, where it is detected that one or more uses are about to enter a collaborative session with interactive interfaces, as described herein, one or more computationally expensive but highly interactive interfaces may be spooled up to improve overall responsiveness of the interfaces to the users.

In certain aspects, allocating of resources may be based on one or more triggers, e.g., a user location in an interface, embodiments of the platform may provide an alert and/or message dialogue box to a user confirming that the user's wishes to proceed with the allocation.

Embodiments of the current disclosure may provide for a score for comparing simulated designs. The score may be a proxy or an indicator of metrics that may not be directly determined from available or simulated data. The score may be used as a guide to identify interesting or valuable designs during design analysis or exploration. The score may be used as an initial design ranking score. As will be understood, embodiments of the analysis facility 108 (FIG. 1) may compute the score (herein also referred to as a "proxy score" or a "comparison score").

The comparison score may be a score based on one or more score components. The score may be a function of one or more score components. Score components may include one or more simulated, predicted, and/or calculated performance metrics of a design such as cost, time to completion, success, and the like. Score components may include one or more elements of the design space such as properties of a design that are not dependent on simulation and may be related to the type of a design and/or specified by a user. For example, score components may include aspects of design type, dose of drug, frequency of drug, maximum duration, patient inclusion/exclusion criteria, randomization type, and the like.

The score may be computed based on a weighted sum or other function of a plurality of score components. Score components and/or functions for a score may be configured by a user. A user may configure a score via one or more interfaces or may provide a specification by other means (such as via a specification or configuration file that is accessible by the platform). A user (using an interface, specification files, etc.) may specify or select one or more score components for computing the score, the function used to compute the score, weighting of score components, normalization of score component values, and the like. In some cases, a set of preconfigured scores that have preconfigured score components, weights, functions, and the like may be selected from a list of predefined scores.

In some cases, score configuration may include an input or a specification of the type of score the user would like to compute. The type may include that the score is a proxy score for NPV, duration, robustness, and the like. Each of the types may be associated with a set of score components. Based on the selection of type and the associated score components for each type, the platform may identify a list of available score components that are related to a computation of the type of score selected. In some cases, not all score components associated with the type of score selected may be available in the simulated data. The available score components for the selected score type may be automatically used to compute the score. In some cases, the available score components may be presented to a user and the user selects one or more of the score components for inclusion in the score.

In some cases, the score components may be normalized or transformed before the score component is used in the computation of a score. Score components may be normalized according to the type of data (i.e. Boolean, integer, float, string, etc.), number of possible values (i.e. a set of possible values, continuous values), range of values (i.e. difference between maximum and minimum values in the simulation data), and the like. For example, score components that are of a string data type may be normalized to an integer value wherein each string is represented by a different integer value. In another example, score components that are of a string data type may be normalized to a value between 0 and 1. In another example, score component values that are larger than 1 or less than 0 may be normalized such that each score component value is within the range between 0 and 1. Normalization may be configured such that the maximum value of a score component is normalized to the value 1, the minimum value of a score component is normalized to a value of 0, and all other values of the score component are normalized to a value between 0 and 1 where the normalized value is based on how far the value was from the maximum. For example, a score component x may be normalized to a score component x' according to $x'=(x-x_{min})/(x_{max}-x_{min})$. In embodiments, normalization may include normalization techniques that include and/or are based on linear scaling, clipping, log-scaling, z-score, and the like. In embodiments, normalization may include normalization techniques including substitution, rounding, mapping, and the like. In some cases, normalization techniques that normalize each score component value to a value between 0 and 1 may be preferable as they can be easier to manipulate and compare numerically.

A score may be a function of one or more score component values. In one embodiment, a score may be a sum of the values of a plurality of score components. In another embodiment, a score may be a sum of the normalized values of a plurality of score components. In yet another embodiment, a score may be a weighted sum of the normalized values of a plurality of score components. For example, a score $s_1$ for a design may be computed as a weighted sum of the normalized score components $c_1, c_1, \ldots, c_n$ according to $s_1 = w_1 c_1 + w_2 c_1 + \ldots + w_n c_n$ wherein $w_1, w_1, \ldots, w_n$ are weighting values associated with each normalized score component. The weights associated with each score component for the computation of the score may be based on relative importance of the score component. Score components that are more important for a score may be multiplied by a larger weighting value.

A score may be computed for each simulated design. In some cases a plurality of scores based on different score components, functions, weights, and the like may be computed for each simulated design. The score may be used to filter designs such that only designs that are larger than the score, lower than the score, between some values, and/or the like are shown. The score may be used to rank or order designs such that designs with the highest score are shown first to a user.

In embodiments, the score may be computed before simulation (a score that is not based on simulation results), during simulation (scores may be computed using one or more simulated score components in real time as simulation results are obtained), and/or after simulation.

In embodiments, a score computed using normalized score component values may be a relative score. The score may provide a relative value of a design with respect to other designs that are computed according to the same normalization. In some cases, scores may not be absolute and scores from different simulation runs may not be comparable. For example, if a score is normalized with respect to the minimum and maximum score component values of a simulation, the score will not be comparable with a score from a different simulation that has different minimum and maximum score component values.

In some cases, score values may be stored or associated with the data used to determine the score. A score may be associated or stored with data that identifies which score components were used to compute the score, the values of the score components, the function for computing the score, the normalize score components, normalization function, and/or the like. The associated data may be a vector or array of data that is stored or associated with each score or simulation run and may be used to determine if scores from different simulation runs are comparable. The associated score data from two different simulation runs for different designs may be compared to determine if the scores are based on the same score function, normalization function, score components, and the like to determine if they can be used to accurately compare designs from different simulations. In some cases, when the scores from different simulation runs are identified as not comparable based on the comparison of the associated data, the mismatch between the associated data may be identified. In some cases, the mismatch between the data may be used to identify functions or methods to recalculate or modify one or more of the scores to make the scores comparable.

For example, one set of scores for designs simulated in a first simulation run may be based on the same score function, score components, and normalization functions for the score component values as a second set of scores for designs in a second simulation run. The first set of scores and the second of scores may still not be comparable since the minimum and/or maximum values of the score components for the first simulation run and the second simulation may be different which may result in a different normalization of values (such as when the normalization is based on the minimum and maximum values as described herein). In one example, identification of the minimum and maximum values for the score components for each simulation run may allow a modification of the scores such that they are based on the minimum and maximum scores of the two simulation runs. In embodiments, the associated data for scores from two or more simulation runs may be compared. The platform may determine if the scores are comparable. If they are not comparable the platform may determine if the associated data includes enough information to transform or renormalize the score component values such that they are comparable.

FIG. 149 shows aspects of an apparatus for determining a score in accordance with an embodiment of the current disclosure. The apparatus may include a scoring engine component 14908. The scoring engine component 14908 may be part of the analysis facility 108 of the platform 104. The scoring engine component 14908 may determine a score for design that may be used to compare the designs. The scoring engine component 14908 may receive one or more simulation data 14902 that may include simulated performance characteristics of designs and the design definitions. The scoring engine component 14908 may receive one or more score selections 14904 that may define which score should be computed, how a score is computed, the type of score that is computed and the like. The score selections 14904 may be defined by user input 14906 or other data input or files that are accessible to the scoring engine 14908. The scoring engine component 14908 may include a scoring definitions component 14920 that provides definitions or mappings between score selections 14904 and operations, score components, and calculations that are needed to determine a score. The score definitions 14920 may include data that defines what score components should be included for one or more score type calculations.

The scoring engine component 14908 may include a simulation data analysis component 14912 that may identify score components that are used for computing a score and may determine if and how they should be normalized. The simulation data analysis component 14912 may analyze the range of the data, data type, number of values, and the like to identify the normalization operations for the score components. The normalization component 14910 may be configured to perform normalization operations on the score component values from the simulation data according to the results of the simulation data analysis 14912 component. The normalization component 14910 may perform any number of normalization functions including, substitution, mapping, rounding, clipping, and the like. The calculation module 14914 of the scoring engine 14908 may determine one or more scores of the designs according to the score definition 14920 and normalized data from the normalization component 14910. The score and associated data 14918 may be stored in a database that is local to the scoring engine 14908, in other parts of the platform 104 or external to the platform. The score and associated data 14918 may include the score, score definitions used to determine the score, normalization functions used to normalize values of the score components, results of simulation data analysis (such as min and max values), and/or the like.

The scoring engine component 14908 may further include a comparison component 14916. The comparison component 14916 may be configured to receive score and associated data 14918 from one or more simulation runs and determine if the scores are comparable. Scores may be comparable if the scores are based on the same score definitions, calculations, normalization functions, and the like. The comparison component 14916 may compare the scores and associated data from one or more simulation runs and determine if the scores may be modified to make them comparable. In embodiments, the comparison component 14916 may identify differences in the associated data (such as differences in normalization functions) and determine how one or more of the scores or score components may be modified or mapped to new values to make scores comparable. In some cases, the comparison component 14916 may cause one or more of the calculation components 14914, normalization components 14910, and/or simulation data components 14912 to recalculate or modify the score based on the determined differences in the associated data between scores.

As shown in FIG. 150, a method for determining a score for a design may include obtaining trial design simulation results for a set of trial designs 15002 and receiving a score selection 15004. The score selection may be a definition of a score, a type of a score, a framework of a score (such as what weights and type information), and the like. Based on the score selection, the score components for the score selection may be identified 15006. The score components may be identified according to the type of score that the user specified. A lookup table may be used to provide a listing of all score components that are related to a score type. The identifying of step 15006 may include searching the simulation results to find which score components are available. The method may further include determining a normalization function for each score component 15008. The normalization function may be based on the type of data, ranges of data, and the like as described herein. Each score component may have different normalization functions. In some cases two or more normalization functions may be applied to a score component. The normalization functions may be used to normalize the score components 15010 and the normalized score components may be used to determine a score 15012. The score may be based on a function of the score components. The function may be a weighted sum of the normalized score components. The weights may be specified by the user or determined based on the type of score. Scored designs may be presented and/or recommended to a user and ranked or filtered according to the score.

As shown in FIG. 151, a method for score transformation may include obtaining design scores and associated score data for designs from a plurality of simulation runs 15102. The simulation runs may be from parallel simulations or simulations at different times. The associated score data may include data as to how the score was computed, normalization functions, score functions, weighting of score components, aspects of the data values (such as ranges, min/max values, etc.) of the score components, and the like. The method may include comparing the associated score data to determine if the scores from the plurality of simulation runs are comparable 15104. If the associated score data indicates that the scores are based on the same or comparable functions, normalization functions, and the like the scores may be determined as comparable and otherwise determined as not comparable 15106. When the scores are not comparable, the method may include determining a normalization function for one or more scores to make the scores comparable 15108. For example, the normalization function may be taken into account the minimum and maximum values for score components across all of the simulation runs and determine a multiplications factor or other function to make the scores comparable. Designs with scores that are comparable may be presented and/or recommended to a user and ranked or filtered according to the score. In embodiments, the proxy score may be computed during one or more collaborative session for design analysis. In such embodiments, the proxy score may be based at least in part on one or more user preferences detected through one or more interactive interfaces. In embodiments, the proxy score may be generated in part via machine learning, e.g., a neural network. For example, a neural network can be trained to generate a proxy score from one or more design parameters and/or scenario parameters.

In embodiments, the platform may be configured for collaboration. Collaboration features may be enabled via one or more methods and/or interfaces for design specification, filtering, and selection. Collaboration features may be configured to allow multiple users to work together to determine, develop, analyze, and/or select a trial design. In some embodiments interfaces and methods may be configured such that multiple users may view and interact with design and analysis tools for group evaluation of simulated designs. Collaboration features may be used to facilitate collaboration between users at different locations (or simply users that use separate computers and interfaces) and/or users that are at one location and can view the same interface. Collaboration may occur in one or more collaboration sessions. Collaboration sessions may include sessions where multiple users work on different or the same tasks concurrently. Collaboration sessions may include sessions where multiple users work and collaborate on different tasks sequentially. Collaboration sessions may occur in a continuous time block or may include two or more disjoint or asynchronous time blocks that may occur at different times of the day, different days, and the like.

In some embodiments, a collaboration session may include one or more users collaborating in real time. A real-time collaboration session may include a session in which multiple users may work together to reach a consensus on one or more aspects of a trial design. The real-time collaboration session may include a session in which users may work together to evaluate and select one or more trial designs based on evaluation of simulated trial designs. The real-time collaboration session may include a session in which users may work together to specify design and evaluation parameters for a simulation for a trial.

During a collaboration session, the interface may step through one or more tasks for accomplishing the goals of the session. Tasks may be associated with a sequence of different graphical interfaces, a sequence of computations, and/or a combination thereof. The sequences of interfaces and/or computations may be at least partially preconfigured providing for a framework of sequences for accomplishing a task. The framework of sequences may include divergent or a tree like framework allowing users to tailor or dynamically change the sequences based on decisions made during the session, results from previous operations, and the like.

For example, in one case, a goal of a collaboration session may include selection of one or more trial designs from a set of simulated trial designs. Based on the specified goal, a platform may load or determine a proposed starting point for the session (such as which interface to show) and what interfaces may be shown and/or computations may be performed as a result of selections or actions in the first interface. As an example, the starting point for the session in this example may be a list of top or optimum design as determined from the simulated data using convex hull analysis. The interface may show the top designs along with their parameters. The top designs may be shown with options for selection, further analysis, comparison, and the like. Based on the selections the sequence may be configured to provide additional analysis or comparison of the top designs or provide additional suggested designs (such as twins or siblings of the top designs). The design may further be compared against one another or against the space of all available designs (such as using heatmaps, tornado diagrams, and the like). In one example, the general sequence for the session may include design selection, design comparison, evaluation of twin designs, a drill down of performance parameters, and the like. The sequence of interfaces may be configured to ensure the top designs are considered, as well as alternative designs that are close to selected designs are considered during the session.

In another example, a sequence of interfaces and/or computations in a session may be configured to surface, in real time, similar designs such as twins, siblings, Pareto designs, and the like to one or more selected or top designs. A user or a group of users may be guided to explore/consider a range of different design types and/or design parameters. Design alternatives (such as different design types, siblings, twins, etc. that may have similar performance to selected designs) may be automatically identified (such as by using one or more Pareto, Convex Hull, and other algorithms) and provided for consideration. Parameters of the alternative design that complement or diverge from previous designs and selections may be emphasized and users may be guided to make evaluations and selections of the alternative parameters.

In another example, a sequence of interfaces and/or computations in a session may be configured to allow designs to be compared with respect to robustness of the designs. Robustness of the designs may indicate the range of parameters for which designs have acceptable or good performance. Interfaces may be used to indicate design performance over a range of parameters in addition to the best possible performance thereby allowing users to visualize/evaluate and debate the risks associated with the designs.

In some embodiments, collaboration interfaces in a collaboration session may be tailored or customized based on the type of the user. Users may be provided with a different interface according to their expertise, authority, tasks, roles, and the like. During a collaboration session, the platform may receive or determine the type of user interacting with the platform. A user type may be specified by an administrator or a curator of a project or a session. A user type may be associated with an identity or credentials of a user. In some cases, a user may specify their own role or type. In some cases, the sequence of interfaces or available computations may be different for each user type in a session. For example, during a collaboration session configured with a goal of selecting one or more designs, different user types may be shown different parameters of a design under consideration. The parameters and data shown to the user may depend on the expertise of the user. For example, a user designated as a financial expert may be show parameters that are focused on the cost, time, resources, personnel, and the like associated with the design. Another user that is designated as an expert in patient recruitment may be shown parameters of the designs that focus on the patient requirement and/or assumptions associated with each design. In embodiments, each interface customized for each user type may provide options to search for other designs according to the parameters associated with the user type. In some cases, some users may be provided with interfaces that hide certain aspects, such as aspects that are sensitive or that the user is not authorized to view. In some embodiments, interfaces may be configured such that every group member can view the same interface during a collaboration session.

In some embodiments, decisions in a collaboration session may be achieved by consensus, voting, and the like. In embodiments, some users or user types may be designed as owners or curators of one or more parameters of the designs. The owners or curators may be specified according to expertise of the user. In some embodiments, consensus on a design decision may require approval by each curator of one or more parameters of the design. In some cases, design parameters may be divided into subsets and different users may be assigned as experts for each subset of parameters. In one example, during a collaboration session, different users may be shown different parameters of a design based on their expertise. The interfaces for each user may show options for approving a design based on the respective parameters, rejecting the design based on the respective parameters, and the like. In one configuration, consensus on a design or a selection of a design during a collaborative session may require approval from each user responsible for a subset of the design parameters. In another example, interfaces for voting on designs may allow a user to collectively agree or disagree on a design by voting. In some cases, votes of users may be weighted based on their expertise, seniority, and the like. In embodiments, the platform may trac each user vote (a binary value such as yes or no, a range of values or rating such as 1-10, or 1-100). The votes may be associated with the user expertise such that the votes may be filtered according to each expertise or type of user. The votes may be associated with a weight (based on seniority, expertise, assigned weight). A vote score for a design may be determined by summing all the votes and/or vote value for each design. In some embodiments, each vote or each vote value may be multiplied by the weight associated with each vote to determine a vote score.

In another example, a goal of a collaboration session may include selection of one or more trial designs from a set of simulated trial designs. A collaboration session may be configured to divide users into multiple groups of one or more users. Each group may be provided with a sequence of interfaces and computations to evaluate and select one or more designs. Each user or group of users may individually explore and/or be guided to explore and consider different designs. Design selections made by the individuals or subgroups of users may then be evaluated collectively in a joint collaborative session.

In another example, a goal of a collaboration session may include development of simulation parameters for running a design simulation. Based on the specified goal, a platform may load or determine a proposed starting point for the session (such as which interface to show) and what interfaces may be shown and/or computations may be performed as a result of selections or actions in the first interface. As an example, the starting point for the session in this example may be an interface for specifying design goals and design parameters. The sequence of interfaces may step through the design, scenario, and performance parameters that need to be defined before the simulation is executed. In embodiments, different users may be identified as experts or associated with different parameter types. In some cases one type of users may be shown only parameters for scenarios while another may be shown only parameters for designs.

As shown in FIG. 152, a method for determining a collaborative session sequence may include receiving a goal for a collaboration session 15202. Based on the goal, a framework for a sequence of interfaces and/or computations for the collaboration session may be identified 15204. The method may further include determining the next sequence based user input in the initial interface, according to the framework 15208.

As shown in FIG. 153, a method for generating a collaborative interface may include displaying a graphical user interface structured to evaluate designs by a group of users 15302. The method may further include identifying expertise parameters for each user in the group of users 15304 and configuring the graphical user interface for each user based at least in part on the expertise parameters 15306. The method may further include receiving user input from users via the graphical user interface 15308 and scoring designs based on the user input and expertise parameters 15310.

FIG. 1154 shows aspects of an apparatus for generating a collaborative interface. The apparatus may include a collaborative interface circuit 15408. The collaborative interface circuit 15408 may generate interfaces 15416. The collaborative interface circuit 15408 may receive user interaction 15402 from the interfaces 15416. The collaborative interface circuit 15408 may receive user type definitions 15404 that may be used for interface customization with the selection parameter provisioning component 15410. The sequence of the interfaces may be defined by the sequence component 15412 according to the user interactions 15402 with the user interfaces 15416 populated with simulation data 15406.

The space of simulated designs can be explored in a systematic way using convex hulls and convex hull peeling. As described herein, convex hulls separate out P-designs that are reachable by linear weighting criteria (CH-designs or CH-points). In many cases, design analysis and recommendation may start with recommendations of CH-designs or designs that are twins, siblings, or are withing an epsilon distance to the CH-designs. Designs that are on or near the convex hull are often the most desirable designs (designs that are often ultimately selected for a study). Concentrating recommendations and design analysis on designs on or near the convex hull greatly reduces the number of designs that need to be examined. In some cases only one or two percent of the total simulated designs need to be considered when initial design recommendations provided by the platform are on or near the convex hull. Design recommendations based on convex hull designs may have further benefits such as providing fast evaluation for any weights specified and allowing introduction of constraints that can be used to eliminate unlikely or uninteresting designs and scenarios.

In embodiments, simulated designs may be explored based on a hierarchy of convex hulls. A hierarchy of convex hulls may be created by determining a convex hull of designs, removing the designs that are on the convex hull, and determining another convex hull of the remaining designs. The "peeling" of convex hulls and determining new convex hulls can be performed iteratively to identify a series of convex hulls in a simulated design space. The designs associated with each convex hull can create a hierarchy of designs.

FIG. 155 shows a graphical example of a hierarchy of convex hulls. The figure shows four layers (CH_1, CH_2, CH_3, and CH_4) of convex hulls in a two dimensional example. The first convex hull (CH_1) of the designs (represented by points in the graph) may be determined by finding the convex hull of all the designs. The second convex hull (CH_2) may be determined by finding the convex hull of all the design except the designs that are on CH_1. The third convex hull (CH_3) may be determined by finding the convex hull of all the design except the designs that are on CH_1 and CH_2. The fourth convex hull (CH_4) may be determined by finding the convex hull of all the design except the designs that are on CH_1, CH_2, and CH_3, and so on. In the example, the convex hulls are peeled to identify a new convex hull of the remaining design to create a hierarchy of designs according to each convex hull layer. It should be understood that although FIG. 155 shows a convex hull peeling example in two dimensions, a hierarchy of convex hulls may be determined for any number of dimensions for data related to any number of performance parameters.

Designs from each convex hull may be associated with a level. The designs in each convex hull may be stored and associated with the convex hull level on which they can be found. In general, designs on the first convex hull (first level) may have better performance than designs on following convex hulls (higher levels). In some cases, although a design from a higher lever may have worse performance than a design in a first level convex hull, the design from a higher level may be preferrable for a study due to other considerations such as practicality, familiarity with the design type, regulatory approval delays, and the like. The hierarchy of designs may provide for quick identification of designs that are within a given percentage of the optimum designs (designs that are on the first convex hull). In some embodiments, convex hull levels may be used for recommending designs to a user (such as with the recommendation engine described herein). Initial recommendations may include recommendations from the first convex hull or the first couple of convex hulls. In response to a user request or other triggers, additional recommendations from other levels of convex hulls may be provided to the user. The organization and progressive suggestion of designs from higher level convex hulls provides for a systematic organization of designs for recommendations allowing a user to consider designs ordered by their optimality.

In some embodiments convex hull levels may be associated with an epsilon distance. Convex hull peeling may include peeling of designs that are on a convex hull and designs that an epsilon distance from the designs on the convex hull. Designs associated with each convex hull level may include designs that are on a convex hull and designs that are epsilon distance away from the designs on a convex hull. Epsilon distance convex hulls level may be defined by first determining designs on the convex hull and epsilon distance designs from the designs on the convex hull. The designs on the first convex hull and epsilon distance away from the designs on the first convex hull may be associated with the first level. The second level designs may be determined by finding designs a convex hull of all the design except the designs that are in the first level. The second level designs may include designs that are on the second convex hull and all the designs that are epsilon distance away from the second convex hull. Additional levels of designs may be determined in a like manner. In embodiments, epsilon distance may be refined based on the number of designs in each level. In some cases, a different epsilon distance may be defined for each level such that each level has the same number of designs, less than predetermined number of designs, at least minimum number of designs, or other metric.

As shown in FIG. 156, a method for determining a design hierarchy based on convex hull peeling may include obtaining trial design simulation results for a set of trial designs 15602. The method may further include determining designs on a first convex hull of the set of trial designs 15604. In some cases, the method may include identifying designs that are epsilon distance from the designs on the first convex hull 15606 and the designs epsilon distance away from the first convex hull may be identified as first level designs 15608. In embodiments, the epsilon distance may be adjusted such that the number of designs that in the first level is within a range of values or is less than or more than a threshold value. To determine the second level of designs, the designs identified as being in the first level may be removed from the set of designs 15610 and a second convex hull of the remaining designs may be determined 15612. Optionally, designs that are an epsilon distance from the second convex hull may also be identified 15614. Designs on the second convex hull and the designs epsilon distance away from the second convex hull may be identified as second level designs 15616. In embodiments, the epsilon distance may be adjusted such that the number of designs in the second level is within a range of values or is less than or more than a threshold value. In some cases, the epsilon distance may be adjusted such that the number of designs in the second level is the same or within a threshold value to the number of designs in the first level. The process of "peeling" the convex hulls (and optionally designs that are epsilon distance away from the designs on the convex hull) and determining new a convex hull may repeat until a desired number of design levels is obtained. Designs in each level may be presented and/or recommended to a user and ranked or filtered according to their associated level. The platform may use the hierarchy of convex hulls to suggest or identify the best designs (designs that are on the first convex hull) and second-best designs (designs that are on the second convex hull) and so on.

In some embodiments, a hierarchy of convex hulls and convex hull peeling may be used to reduce the number of simulations in a study. In some cases where scenarios are monotone with respect to criteria, results of simulation of one scenario may be leveraged to reduce the number of designs that need to be simulated to find the convex hull for designs for other scenarios. In one embodiment, an algorithm may iteratively determine a convex hull of designs under a first scenario and simulate the designs for a second scenario. The convex hull of the designs in the second scenario may be determined without simulating all of the designs but only designs that are within the first couple of convex hulls under the first scenario until no improvement to the convex hull of the designs under the second scenario is observed. In some examples, a 4×-8× reduction in simulations needed to find the convex hull for a second scenario can be achieved by leveraging convex hull peeling in simulated designs for a first scenario.

FIGS. 157(*a-e*) shows a graphical example of how convex hull peeling may be leveraged to reduce the number of simulations needed to find a convex hull for designs for a scenario. In embodiments, some scenarios may be monotone with respect to criteria and can be ordered. In some cases, some scenarios parameters may be known to have a direct correlation to one or more performance parameters of designs. In cases where the scenarios may be ordered with respect to the performance of the designs, convex hulls of simulations for one scenario may be leveraged to reduce the number of simulations needed to find a convex hull for another (worse) scenario. In embodiments, simulations may be performed for designs under a first scenario. In some cases the simulations for designs under the first scenario may be exhaustive. Levels of convex hulls may be determined for the designs using convex hull peeling as described herein. To determine designs that are on a convex hull for a second scenario, only the designs that are on the convex hulls of the first scenario may be simulated.

FIGS. 157(*a-e*) shows a progression how convex hulls for designs for one scenario (scenario "67") may be used to determine which designs should be simulated for a second scenario (scenario "69") to determine the convex hull designs for the second scenario. It should be noted that the figures, for clarity, do not show all of the simulated designs for the first scenario and only show the designs that are on the convex hull for the first scenario. FIG. 157(*a*) shows the first iteration of the method. In the first iteration a first convex hull for designs for scenario 67 may be determined (CH_67_1). The designs in the first convex hull may then be simulated to determine their performance under the second scenario (CH_67_169) and the convex hull of all the designs simulated for the second scenario may be determined (CH (CH_67_1_69)). After the first iteration, in this example, only designs that are on CH_67_1 are simulated for the second scenario.

FIG. 157(*b*) shows the second iteration of the method. In the second iteration, a second convex hull for designs for scenario 67 is determined (CH_67_2). The second convex hull may be determined by convex hull peeling described herein. The designs in the second convex hull may then be simulated to determine their performance under the second scenario (CH_67_2_69) and the convex hull of all the designs simulated for the second scenario may be determined (CH(CH_67_2_69)). In the second iteration, in this example, only the designs that are on CH_67_2 are simulated for the second scenario. In the second iteration, for this example, the convex hull for the second scenario does not change.

FIG. 157(*c*) shows the third iteration of the method. In the third iteration, a third convex hull for designs for scenario 67 is determined (CH_67_3). The third convex hull may be determined by convex hull peeling described herein. The designs in the third convex hull may then be simulated to determine their performance under the second scenario (CH_67_369) and the convex hull of all the designs simulated for the second scenario may be determined (CH (CH_67_3_69)). In the third iteration, in this example, only the designs that are on CH_67_3 are simulated for the second scenario. In the third iteration, for this example, the convex hull for the second scenario changes compared to the second iterations.

FIG. 157(*d*) shows the fourth iteration of the method. In the fourth iteration, a fourth convex hull for designs for scenario 67 is determined (CH_67_4). The fourth convex hull may be determined by convex hull peeling described herein. The designs in the fourth convex hull may then be simulated to determine their performance under the second scenario (CH_67_4_69) and the convex hull of all the designs simulated for the second scenario may be determined (CH(CH_67_4_69)). In the fourth iteration, in this example, only the designs that are on CH_67_4 are simulated for the second scenario. In the fourth iteration, for this example, the convex hull for the second scenario further changes compared to the second iterations.

The iterations of determining a new convex hull for the first scenario, simulating the designs from the convex hull under the second scenario, and determining the convex hull of all the simulated designs under the second scenario may continue until there is no improvement or change in the convex hull for the second scenario for a threshold number of iterations (such as two or more, or three or more iterations). FIG. 157(*e*) shows the tenth iteration of the method. In the tenth iteration, a tenth convex hull for designs for scenario 67 is determined (CH_67_10). The tenth convex hull may be determined by convex hull peeling described herein. The designs in the tenth convex hull may then be simulated to determine their performance under the second scenario (CH_67_10_69) and the convex hull of all the designs simulated for the second scenario may be determined (CH(CH_67_10_69)). In the tenth iteration, in this example, only the designs that are on CH_67_10 are simulated for the second scenario. In the tenth iteration, for this example, the convex hull for the second scenario has not changed for more than two iterations and method may stop wherein the convex hull designs for the second scenario is defined by the convex hull of the designs simulated up to and including the tenth iterations (CH(CH_67_10_69)). For this example, the number of designs that required simulation for determining the convex hull for the second scenario corresponds to the number of designs on the first ten convex hulls for the first scenario. The number of designs on the first ten convex hulls is a small percentage of the total number of designs for this example. In many embodiments, simulation for scenarios based on convex hull peeling may results in a reduction of simulation of four to eight times compared to an exhaustive simulation for a scenario.

A convex hull peeling for finding convex hull for adjacent monotone scenario without simulating full set of designs may take as input a dataset for a first scenario. The dataset for the first scenario may include simulation results for all design for the first scenario and may include design parameters for the designs and a multicriteria vector that identifies the simulated performance of the designs for the first scenario. Input to the algorithm may further include scenario variables for a second scenario. The algorithm may output the designs on the convex hull for the second scenario. The algorithm may start by initializing stopping parameter k to an initial value of 1. In step two of the algorithm, the kth convex hull for the dataset for scenario 1 may be computed using a convex hull algorithm. In step three of the algorithm, each design in the kth convex hull determined in step two may be simulated under the second scenario to calculate its multi-criteria vectors. In step four, the convex hull of the vectors determined in step three may be determined. In step five, the convex hull for the second scenario is compared to the convex hull computed for the second scenario in the k−1 iteration. In step six, the value of k may be incremented and steps two through five of the algorithms may be repeated until the convex hull for the second scenario does not change for at least two iterations.

As shown in FIG. 158, a method for determining a convex hull for a scenario using convex hull peeling in another scenario may include initializing an iteration counter k to a value such as the value one 15802. The method may include computing the kth convex hull for designs simulated for a first scenario 15804. The designs from the kth convex hull may be simulated for a second scenario 15806 and a convex hull for all the designs simulated for the second scenario may be computed 15808. The value of k may be incremented 15810 and the method repeated starting at 15804 until no improvement to the convex hull is observed for i iterations 15812 wherein i may be a variable set by a user and may have a value of two or more.

FIG. 159 shows aspects of an apparatus for convex hull peeling in accordance with an embodiment of the current disclosure. The apparatus may include a peeling engine component 15904. The peeling engine component may receive simulation data 15902. The simulation set 15906 component may store and manipulate the simulation data. The convex hull engine 15908 of the peeling engine may determine a convex hull of the simulation data. The simulation set component 15906 remove designs that are found in a convex hull from the simulation data and associate them with design levels 15912. The epsilon engine 15910 may optionally determine designs that are epsilon distance away from the designs on the convex hull. These designs may be optionally assigned to levels that are associated with each convex hull.

In embodiments, convex hull peeling may provide for evaluation of a design's robustness. For example, in embodiments, each convex hull level can have its own robustness ranking. In such embodiments, a user may be able to determine the most robust designs in each layer. As will be understood, in embodiments, some layers may have designs with an average robustness higher than an average robustness of other layers. Thus, some embodiments of the current disclosure may focus a user to search for designs within a particular layer having a high robustness. Embodiments of the design recommendation algorithm, as described herein, may evaluate the robustness of each layer and rank one or more of the layers based at least in part on robustness. The recommendation algorithm may be configured to recommend one or more layers, e.g., the top three (3), based on preferences derived from historical data, e.g., past user preferences.

Turning to FIG. 160, embodiments of the current disclosure may provide for adaptive replication in clinical trial design simulations and/or other types of simulations described herein. As will be understood, embodiments of the simulation facility 110 (FIG. 1) may evaluate a clinical trial design by using a fixed number of simulated replications. Adaptive replication, however, may involve dynamically changing the number of simulation replications for a particular design. In embodiments, adaptive rules may terminate replication sampling for designs. As will be explained in greater detail below, such changes may be based on computed standard error or other performance criteria.

Accordingly, an embodiment system 16000 for providing adaptive replication in clinical trial design simulation is shown. The system 16000 may include a server 16010 having at least one processor and a memory device. The system 16000 may further include an electronic device 16012, one or more remote servers 16014, 16016, 16018, and/or a database 16020 which may be in electronic communication with the server 16010 and/or each other via a network 16022. The server 16010 may form part of and/or host one or more of the platforms 104 (FIG. 1), 10404 (FIG. 104) and/or 12504 (FIG. 125), e.g., the simulation facilities 110 (FIG. 1), 10410 (FIG. 104) and/or 12510 (FIG. 125); and/or the computational resources 150 (FIG. 1), 10450 (FIG. 104), and/or 12550 (FIG. 125).

The server 16010 may be structured to execute a replication process forming part of a clinical trial design simulation that comprises a plurality of replications of a clinical trial design. As will be understood, a replication of a clinical trial design is a simulated instance of a clinical trial design under a given scenario and with a given set of parameters. During the replication process, the server 16010 may determine a performance criteria, e.g., a member of criteria space 318 (FIG. 3) that defines a characteristic of the clinical trial, e.g., a number of patients who successfully completed the clinical trial. The server 16010 may then adjust the replication process based at least in part on the performance criteria. The adjustment may increase or decrease the number of replications of the clinical trial in the replication process. For example, if the server 16010 determines that there is little variation in the performance criteria of the most recently executed replication as compared to one or more previously executed replications, the server may reduce the number, e.g., the total number, of replications executed/evaluated in the replication process. As will be appreciated, reducing the number of replications in such a manner may reduce the overall time and resources required to complete simulation of the clinical trial design. Conversely, if the server 16010 determines that there is variation (above a desired amount) in the performance criteria of the most recently executed replication as compared to one or more previously executed replications, the server 16010 may increase the number of replications executed/evaluated in the replication process. As will be appreciated, increasing the number of replications in such a manner may improve the accuracy of the simulation. The server 16010 may also make other types of adjustments to the replication process, as described herein.

The electronic device 16012 may be a user device, e.g., 102 (FIG. 1), such as a desktop, laptop, smart device, etc. In embodiments, the electronic device 16012 may provide for and/or present an interactive interface, e.g., 112 (FIG. 1) that presents a plurality of prompts to a user for configuring the clinical trial design. The electronic device 16012 may also receive and display the results of the clinical trial simulation and/or provide notifications to a user regarding any adjustments made to the replication process by the server.

The database 16020 may form part of a data facility, e.g., 138 (FIG. 1) and store replication results data, e.g., data generated during execution/evaluation of a replication of a clinical trial design. In embodiments, the database 16020 may store the replication results in a quick search data structure, as described herein, e.g., a SimCube. As such, embodiments of the server 16010 may access the database to retrieve and/or store replication results data.

The remote servers 16014, 16016, and/or 16018 may form part of a collection of computation resources, e.g., 150 (FIG. 1) which can be accessed by the server 16010 to distribute processing tasks. For example, the server may generate batches of replications of the same replication process and/or of entire clinical trial design simulations for separate processing/evaluation by the remote servers 16014, 16016, and/or 16018. Such batch processing may be accomplished in parallel, e.g., distributed parallel processing of replications, e.g., 100 replications for up to a maximum number, e.g., ten (10), of batches for several designs simultaneously.

In some embodiments, the number of simulated replications used to evaluate a design may be dynamically determined. The number of simulated replications may be dynamically evaluated according to results of simulations. In some embodiments simulations for a design may be configured for a fixed number of replications. As the simulations progress, data from the simulations may be analyzed to determine if the number of simulations may be decreased or should be increased. For example, some embodiments may stop replications when the standard error of the score estimate is sufficiently small. Embodiments may also adapt the number of replications to the quality of the design. For example, some embodiments may stop replications when the difference from the lower 99% confidence interval of the best design found so far is higher than a 99% upper confidence interval of the design being replicated. Embodiments may invoke parallel processing to compute replications in batches, e.g., one-hundred (100) replications for up to a maximum number, e.g., (10), of batches for several designs simultaneously. Adaptive rules, e.g., rules that change over time or in response to a set of conditions, may terminate replication sampling for designs.

Turning to FIG. 161, an embodiment of an apparatus 16100 for providing adaptive replication in clinical trial design simulation is shown. The apparatus may form part of the 16010 and/or other computing devices described herein. The apparatus 16100 may include a replication circuit 16110, a results interpretation circuit 16112, a performance circuit 16114, an adjustment determining circuit 16116, and an adjustment circuit 16118. The replication circuit 16110 may be structured to execute a replication process 16120 that includes a plurality of replications 16122, as discussed herein. Execution of the replication process 16120 generates corresponding replication results data 16124. In embodiments, the replication circuit 16110 may be structured to batch the plurality of replications 16122 into a plurality of batches for parallel execution on two or more processors, e.g., remote servers 16014, 16016, and/or 16018.

The results interpretation circuit 16112 is structured to interpret the replication results data 16124 of at least one of the replications 16122, and the performance circuit 16114 is structured to determine, based at least in part on the replication results data 16124, a performance criteria value 16126. The adjustment determining circuit 16116 is structured to determine, based at least in part on the performance criteria value 16126, an adjustment value 16128 to the replication process 16120. The adjustment circuit 16118 is structured to adjust the replication process 16120 based at least in part on the adjustment value 16128.

The performance criteria value 16126 may include and/or be based at least in part on a standard error. The adjustment determining circuit 16116 may be further structured to configure the adjustment value 16128 to cease the replication process 16120 when the standard error is below a threshold.

The performance criteria value 16126 may include and/or be based at least in part on an upper confidence interval of the clinical trial design corresponding to the replication 16122 that generated the replication results data 16124. In embodiments, the adjustment determining circuit 16116 may be further structured to configure the adjustment value 16128 to cease the replication process 16120 when a difference from a lower confidence interval of another clinical trial design (other than the one corresponding to the replication 16122 which generated the replication results 16124) is higher than the upper confidence interval.

In embodiments, the apparatus 16100 may include a results retrieval circuit 16130 structured to retrieve at least some of the replication results data 16120 from a quick search data structure 16132, which may be stored in a database, e.g., 16020 (FIG. 160).

Illustrated in FIG. 162 is a method 16200 for providing adaptive replication in clinical trial design simulation. The method 16200 may be performed by the server 16010 and/or apparatus 16100 and/or another computing device(s) described herein. The method 16200 includes interpreting, via at least one processor, e.g., apparatus 16100 (FIG. 161), replication results data 16210. As described herein, the replication results data may form part of a replication process of a clinical trial design simulation, or other type of simulation. The method 16200 further includes determining, via the at least one processor, a performance criteria value based at least in part on the replication results data 16212. The method 16200 further includes determining, via the at least one processor and based at least in part on the performance criteria value, an adjustment value 16214. The method 16200 further includes, in response to determining the adjustment value, adjusting, via the at least one processor, the replication process 16216.

In embodiments, adjusting the replication process 16216 may include ceasing the replication process when the performance criteria value includes and/or is based at least in part on a standard error that is below a threshold 16218. In embodiments, adjusting the replication process 16216 may include ceasing the replication process when the performance criteria value incudes and/or is based at least in part on an upper confidence interval of the clinical trial design and a difference from a lower confidence interval of another clinical trial design is higher than the upper confidence interval 16220. In such embodiments, the lower confidence interval and/or the upper confidence interval may be 99%. In embodiments, adjusting the replication process 16216 may include increasing a number of replications in the replication process 16222. In embodiments, adjusting the replication process 16216 may include decreasing a number of replications in the replication process 16222. In some embodiments the number of simulated replications used to evaluate a design may be dynamically determined as part of the replication process or it may be determined outside of the replication process. In embodiments, the number of replications may be fixed based on data from previously simulated designs.

The method 16200 may further include retrieving at least some of the replication results data from a quick search data structure 16226. The quick search data structure may be a SimCube. In embodiments, the quick search data structure may be stored in a database, e.g., database 16020 (FIG. 160).

As will be appreciated, by providing for dynamic changing/adjusting of the number of replications performed as part of a simulation, some embodiments of the present disclosure may reduce the amount of time required to simulate a clinical trial design by reducing the number of replications in situations where continued evaluations produce diminishing returns and by increasing the number of replications in situations where more accuracy is beneficial. In embodiments, the replication process and/or clinical trial simulation may be based at least in part on, or form part if, a simulated annealing analysis. Further, in embodiments, machine learning may be used to determine an adjustment to a replication process. For example, a neural network may be trained to determine, from design and/or scenario criteria, when the number of replications should be increased, decreased, and/or when a replication process should be stopped.

Referring now to FIG. 163, embodiments of the current disclosure may provide for enhanced simulated annealing (SA) in clinical trial design simulations and/or other types of simulations. As described elsewhere in this disclosure, embodiments of the simulation facility 110 (FIG. 1) may evaluate a clinical trial design by using SA. As will be explained in greater detail below, some embodiments of the current disclosure provide for modifications to the SA process that reduce the amount of time and/or computational resources required to complete the analysis. For example, certain embodiments may reduce the number of designs simulated during SA via machine learning based interpolation and/or sampling of designs based on relationships to a convex hull tunnel derived from simulation of the clinical trial designs.

Accordingly, a system 16300 for providing enhanced SA in clinical trial design simulation is shown. The system 16300 may include a server 16310 having at least one processor and a memory device. The system 16300 may further include an electronic device 16312, one or more remote servers 16314, 16316, 16318, and/or a database 16320 which may be in electronic communication with the server 16310 and/or each other via a network 16322. The server 16310 may form part of and/or host one or more of the platforms 104 (FIG. 1), 10404 (FIG. 104) and/or 12504 (FIG. 125), e.g., the simulation facilities 110 (FIG. 1), 10410 (FIG. 104) and/or 12510 (FIG. 125); and/or the computational resources 150 (FIG. 1), 10450 (FIG. 104), and/or 12550 (FIG. 125).

The server 16310 may be structured to execute a SA process forming part of a clinical trial design simulation. The server 16310 may use machine learning to predict simulation results, as opposed to performing a more traditional simulation, for one or more designs identified during the SA process. For example, the server 16310 may select an initial clinical trial design to serve as the starting point for SA analysis/exploration. The server 16310 may determine the direction in which to move from the initial clinical trial design and then identify a new design in the selected direction. The server 16310 may then use machine learning to predict simulation results and then begin the process over again until termination of the SA path. In certain embodiments, the server 16310 may receive and/or generate data defining a convex hull tunnel for the initially selected clinical trial design. The server may then select designs for inclusion in the SA path based at least in part on relationships between the designs and the convex hull tunnel.

The electronic device 16312 may be a user device, e.g., 102 (FIG. 1), such as a desktop, laptop, smart device, etc. In embodiments, the electronic device 16312 may provide for and/or present an interactive interface, e.g., 112 (FIG. 1) that presents a plurality of prompts to a user for configuring the clinical trial design and/or SA process. The electronic device 16312 may also receive and display the results of the clinical trial simulation, SA process, and/or provide notifications to a user regarding any adjustments made to the SA process by the server 16310. The database 16320 may form part of a data facility, e.g., 138 (FIG. 1) and store simulation results data. The remote servers 16314, 16316, and/or 16318 may form part of a collection of computation resources, e.g., 150 (FIG. 1) which can be accessed by the server 16310 to distribute processing tasks.

Illustrated in FIG. 164 is an embodiment of an apparatus 16400 for providing enhanced simulated annealing. The apparatus 16400 may form part of the server 16310 and/or other computing devices described herein. The apparatus 16400 may include a results interpretation circuit 16410, a first identification circuit 16412, a performance prediction circuit 16414, a second identification circuit 16416, a results prediction circuit 16418, and a third identification circuit 16420. In embodiments, the apparatus 16400 may include a convex hull interpretation circuit 16422, a results determining circuit 16424, and/or a transmission circuit 16426.

As will be appreciated, embodiments of the apparatus 16400 may include various combinations of the circuit shown in FIG. 164 wherein some circuits are included while others are excluded. For example, an embodiment may include the convex hull interpretation circuit 16422, the first identification circuit 16412, the performance prediction circuit 16414, the second identification circuit 16416, the results determining circuit 16424, and the third identification circuit 16420 but not include the results interpretation circuit 16410, the performance prediction circuit 16414, the results prediction circuit 16418, and/or the transmission circuit 16426. Further, in embodiments, the first identification circuit 16412, the second identification circuit 16416 and/or the third identification circuit 16420 may be combined into a single identification circuit as indicated by the dashed box 16428.

The results interpretation circuit 16410 may be structured to interpret initial simulation results data 16430 for a set of clinical trial designs. The first identification circuit 16412 is structured to identify an initial clinical trial design 16432 based at least in part on the initial simulation results data 16430. The performance prediction circuit 16414 is structured to predict performance data 16434 for clinical trial designs related to the initial clinical trial design 16432 based at least in part on varying parameters for the initial clinical trial design 16432. The second identification circuit 16416 is structured to identify a first new clinical trial design 16436 for simulation based on the predicting. The results prediction circuit 16418 is structured to predict, via machine learning, first simulation results data 16438 for the first new clinical trial design 16436. The third identification circuit 16420 is structured to identify, based at least in part on the first simulation results data 16438, a second new clinical trial design 16440 for simulation by varying parameters of the first new clinical trial design 16436.

The convex hull interpretation circuit 16422 is structured to interpret convex hull tunnel data 16442 corresponding to a convex hull tunnel defined, in part, by the set of clinical trial designs. The first identification circuit 16412 may be structured to identify the initial clinical trial design 16432 based at least in part on the convex hull tunnel data 16442. The second identification circuit 16416 may be structured to identify the first new clinical trial design 16436 based on the performance criteria data 16434 and on the convex hull tunnel data 16442. The results determining circuit 16424 may be structured to determine first simulation results data 16444 for the first new clinical trial design 16436. The third identification circuit 16420 may be structured to identify, based at least in part on the first simulation results data 16444, the second new clinical trial design 16440 for simulation by varying parameters of the first new clinical trial design 16436.

In embodiments, the machine learning may be based at least in part on a neural network and/or a regression model, e.g., a regression tree. Embodiments of the machine learning may be trained via supervised learning on training sets. Such training sets may include a series of designs with known performance results. Data from the previously calculated neighboring designs may be leveraged to train a neural network via reinforcement learning to predict the value of a design as opposed to simulating the design. The training set may include a subset of values of scenario parameters and the predicted output may be values for the one or more designs.

Shown in FIG. 165 is a design space 16500 with designs 16510 and 16512, for which simulation results data is known, and design 16514, for which simulation results data is unknown. The machine learning may be used to predict the simulation results data of design 16514 from the simulation results data of neighboring designs, e.g., 16512. As used herein, "neighboring" designs are designs that are close to one another in design space 16500 and/or other spaces, as would be understood by those of skill in the art. For example, designs 16512 are neighboring designs to design 16514, while designs 16510 are not neighboring designs to design 16514. As will be understood, in embodiments, feeding simulation results of neighboring designs 16512 into the machine learning model may provide for interpolation of the design 16514.

Turning to FIG. 166, a convex hull tunnel 16600 generated by convex hull peeling (as disclosed herein), is shown. The convex hull tunnel may have an upper bound 16610, a lower bound 16612, and a center line 16614. Designs 16616 may be selected for inclusion in the SA path based on their relationship to the convex hull tunnel 16600. For example, in embodiments, a penalty function may be used to score and/or rank the designs 16616 based on their distance from the centerline 16614, lower bound 16612, and/or upper bound 16610, for inclusion in a SA path. In embodiments, the penalty function may encourage/promote selection of designs 16616, for inclusion in a SA path, that are closer to the center line 16614 over designs 16616 that are father away from the center line 16614. In other words, some embodiments of the disclosure may discourage use of designs 16616, in a SA path, that are father away from the center line 16614.

Referring now to FIG. 167, a method 16700 for enhanced simulated annealing is shown. The method may be performed by the server 16310 (FIG. 163) and/or the apparatus 16400 (FIG. 164). The method 16700 includes interpreting initial simulation results data for a set of clinical trial designs 16710 and identifying an initial clinical trial design based at least in part on the initial simulation results data 16712. The method 16710 further includes predicting performance data for clinical trial designs related to the initial clinical trial design based at least in part on varying parameters for the initial clinical trial design 16714. The method 16700 further includes identifying a first new clinical trial design for simulation based on the predicting 16716, and predicting, via machine learning, first simulation results data for the first new clinical trial design 16718. The method 16700 further includes identifying, based at least in part on the first simulation results data, a second new clinical trial design for simulation by varying parameters of the first new clinical trial design 16720. In embodiments, the method 16700 may further include interpreting convex hull tunnel data corresponding to a convex hull tunnel defined, in part, by the set of clinical trial designs 16722. In such embodiments, identifying the first new clinical trial design for simulation 16716 may be further based at least in part on the convex hull tunnel data.

Illustrated in FIG. 168 is another method 16800 for enhanced simulated annealing. The method may be performed by the server 16310 (FIG. 163) and/or the apparatus 16400 (FIG. 164). The method 16800 includes interpreting convex hull tunnel data corresponding to a convex hull tunnel defined, in part, by a set of clinical trial designs 16810, and identifying an initial clinical trial design based at least in part on the convex hull tunnel data 16812. The method 16800 further includes predicting performance for clinical trial designs based at least in part on varying parameters for the initial clinical trial design 16814, and identifying a first new clinical trial design for simulation based on the predicting and on the convex hull tunnel data 16816. The method 16800 further includes determining first simulation results for the first new clinical trial design 16818, and identifying, based at least in part on the first simulation results, a second new clinical trial design for simulation by varying parameters of the first new clinical trial design 16820. In embodiments, determining first simulation results for the first new clinical trial design 16818 may include predicting the first simulation results via machine learning 16822. In embodiments, the method 16800 may further include interpreting initial simulation results data 16824.

Illustrated in FIG. 169 is yet another method 16900 for enhanced simulated annealing. The method 16900 includes interpreting initial simulation results data for a set of clinical trial designs 16910, and identifying, based at least in part on the initial simulation results data, a clinical trial design for simulation 16912. The method 16910 further includes predicting, via machine learning and based at least in part on the initial simulation results data, simulation results data for the clinical trial design 16914; and transmitting the simulation results data 16916.

In embodiments, one or more of the method of enhanced simulated annealing described herein may be form part of (or work in conjunction with) the recommendation engine/algorithm. For example, embodiments of the recommendation engine may use enhanced simulated annealing to find candidate designs for recommendation. In embodiments, enhanced simulated annealing may be used to dynamically update one or more parameters of a design, which may be in real-time. For example, one or more parameters of a design corresponding to an ongoing trial may analyzed and/or adjusted based on results from an enhanced simulated annealing analysis. In embodiments, the one or more parameters may be updated while the trial is being conducted, i.e., during the trial. In embodiments, enhanced simulated annealing may be used to determine changes in the outcome of an ongoing trial resulting from potential adjustments to the corresponding design.

Referring now to FIG. 170, a system 17000 for design exploration and search is shown. The design exploration and search may be based at least in part on data structures referred to herein as "quick search data structures", e.g., "design libraries". The quick search data structures may enable efficient mapping and/or comparison within a design space and criteria space. The data structures may be configured to enable comparing designs across multiple variables, (e.g., finding "similar designs" for a plurality of criteria). Embodiments of the quick search data structures may have geometries that localize designs resulting in similar criteria, i.e., different designs that result in the same outputs are located next to (or near) each other. Designs may be populated into the quick search data structures after being simulated. Thus, if a design is selected at a later point to be simulated, the quick search data structure can be checked prior to simulation of the design to see if the data for the design already exists. A design does not need to be simulated if it is already in the quick search data structure. Thus, a first simulated annealing (or other design space exploration approach) may cause a first set of designs to be simulated and populated into a quick search data structure. At a later point in time, a second simulated annealing (or other design space exploration approach) may select a second set of designs to be simulated, wherein the quick search data structure provides for the ability to determine designs that overlap the first and second sets to avoid their re-simulation.

Accordingly, the system 17000 may include a server 17010 having at least one processor and a memory device. The system 17000 may further include an electronic device 17012, one or more remote servers 17014, 17016, 17018, and/or a database 17020 which may be in electronic communication with the server 17010 and/or each other via a network 17022. The server 17010 may form part of and/or host one or more of the platforms 104 (FIG. 1), 10404 (FIG. 104) and/or 12504 (FIG. 125), e.g., the simulation facilities 110 (FIG. 1), 10410 (FIG. 104) and/or 12510 (FIG. 125); and/or the computational resources 150 (FIG. 1), 10450 (FIG. 104), and/or 12550 (FIG. 125).

The server 17010 may be structured to execute a SA process forming part of a clinical trial design simulation. The server 17010 may use a quick search data structure to determine/retrieve/lookup results of simulations (if previously simulated), as opposed to performing a more traditional simulation, for one or more designs identified during an SA process (or other searching procedure). For example, the server 17010 may select an initial clinical trial design to serve as the starting point for SA analysis/exploration. The server 17010 may determine the direction in which to move from the initial clinical trial design and then identify a new design in the selected direction. The server 17010 may then check, via a quick search data structure, to see if results for the design have already been simulated, and then begin the process over again until termination of the SA path.

The electronic device 17012 may a user device, e.g., 102 (FIG. 1), such as a desktop, laptop, smart device, etc. In embodiments, the electronic device 17012 may provide for and/or present an interactive interface, e.g., 112 (FIG. 1) that presents a plurality of prompts to a user for configuring the clinical trial design and/or SA process. The electronic device 17012 may also receive and display the results of the clinical trial simulation, SA process, properties of the quick search data structure, and/or receive and/or provide notifications from the server to a user regarding the SA process and/or quick search data structure. The database 17020 may form part of a data facility, e.g., 138 (FIG. 1) and store the quick search data structure in memory. The remote servers 17014, 17016, and/or 17018 may form part of a collection of computation resources, e.g., 150 (FIG. 1) which can be accessed by the server 17010 to distribute processing tasks.

In embodiments, the quick search data structure may take the form of a SimCube having a structure that is a natural fit for simulated annealing algorithms, e.g., a single step in simulated annealing involves moving from a position/cell (within the SimCube) to an adjacent position/cell (within the SimCube) by changing just one design parameter or one scenario variable. The number of iterations of a simulated annealing path from a design to a locally optimal design may be the Manhattan distance between the two designs in the hypercube. For example, in embodiments, the quick search data structure may be a hypercube having a number of dimensions equal to the sum of the number of design parameters and the number of scenario variables that form a plurality of cells, each of which may contain a vector of simulation results that may include a multi-criteria vector.

Turning now to FIGS. 171(*a-b*), an example of a quick search data structure 17100 in the form of a SimCube is shown, wherein the example data set corresponds to one thousand (1,000) replications for each of 40,824 scenario-design combinations, e.g., fifty-four (54) scenarios by seven-hundred and fifty-six (756) designs with three (3) criteria (power, trial costs, and trial duration). The quick search data structure 17100 may include a results data repository 17110 and an index 17112. As shown in FIGS. 171(*a-b*), the results data repository 17110 may be expressed as a flat file, e.g., a text file, where each row represents the results of simulating a particular design and/or design replication. Each row may include a key determined, in part, by a ranking of distinct values of design parameters 17114 in the index 17112. For example, the key for row "1724" is "4,3,3,4,2,4", wherein the value of '70' for "% Events Observed at Interim" is assigned a rank of 4, the value of '0.5' for "min Promising Zone Point" is assigned a rank of '3', the value of '0.99' for "max Promising Zone Point" is assigned a ran of 3, the value of '1.733333' for "max Events Multiplier" is assigned a rank of '4', the value of '1.5' for "max Subjs Multiplier" is assigned a rank of '2', and the value of '0.7' for "Adaptive Wt1" is assigned a rank of '4'. Thus, the index 17112 can be used to locate a design with a desired set of design parameters 17114 with the following relationship: SimCube Row # for a design=(sum of (rank*corresponding rank multiplier) over all dimensions)−sum (rank multipliers). For example, the row of a design having '70' for "% Events Observed at Interim", '0.5' for "min Promising Zone Point", '0.99' for "max Promising Zone Point", '1.733333' for "max Events Multiplier", '1.777778' for "max Subjs Multiplier", and '0.5' for "Adaptive Wt1" can be calculated as sum((4*432)+(3*144)+(3*48)+(4*12)+(3*4)+(2*1))−(432+144+48+12+4+1)=1725, with a corresponding key of '4,3,3,4,3,2'. In embodiments, the repository 17110 can be stored in a compressed form where empty rows can be removed to save memory space. For example, in the scenario shown in FIGS. 171(*a-b*), the total number of empty cells/rows in the repository 17110 may be 40,068, i.e., there repository 17110 may only contain the results for seven-hundred and fifty-six designs. Thus, where the full design of such a SimCube has dimensions of 4×3×4×4×4 with 1,728 cells, the corresponding density of the SimCube would be 43.75%. In embodiments where the repository 17110 is compressed, the rows may be sorted in order of the full row value of a design so that a binary search may be used. In embodiments, the quick search data structure 17100 may include one or more of heaps and/or hash tables (using the full table row value as a key), e.g., some embodiments may combine aspects of SimCubes with heaps and/or hash tables, which may provide for intermediate time-memory usage trade-offs.

Some embodiments of the current disclosure may also include network implementations of SimCubes, wherein each design may be a node within undirected edges joining each pair of designs that differ in rank in only one parameter for which the ranks differ by one (1). In such embodiments, the network data structure may be useful to efficiently compute neighbors to a design of interest and/or for constructing clusters of similar designs. In embodiments, samples of scenario-design combinations, rather than simulating each design for all scenarios, may be used. For example, embodiments of the quick search data structures described herein may be extended to this setting by increasing the number of parameters (and hence SimCube dimensions) to be the sum of design and scenario parameters. As will be further understood, embodiments of the quick search data structures described herein may also be used for simulations of clinical trials operations such as recruitment forecasting and drug supply.

Illustrated in FIG. 172 is a method 17200 of design exploration and search that utilizes a quick search data structure with simulated annealing (SA). A set of initial combination of design parameters is defined 17210. Exclusion criteria are tested for 17212 and a determination is made as to whether the combination of design parameters should be excluded from the SA path 17214 and written to an exclusion log 17216. Combinations passing the exclusion test 17214 are then searched for (looked up) in a quick search data structure 17218 and 17220. If corresponding simulation results are found in the quick search data structure, they are written to a details log 17222. If corresponding simulation results are not found, then the combination of design parameters is simulated 17224 with the results written to the quick search data structure 17226. After the results have been retrieved and/or generated via simulation, they may be checked against the results of prior replications to determine if they are superior/optional as compared to the results of two or more previous replications 17228, and if so, written to an output log 17230. Results that are not superior, as compared to the two or more previous replications, are then evaluated for inclusion in the SA path 17232 and 17234, the next parameter combination/design replication is retrieved and/or generated 17238, and the process beings again until there are no more replications to evaluate. Design parameter combinations that are written to the output log may also be tested to determine if they are the best results thus far, and if so, written to a best output log 17240 and 17242.

Referring now to FIG. 173, in embodiments, simulated annealing may provide for the identification of similar designs by exploring region of interest, e.g., local neighborhoods, around a particular design. Accordingly, another method 17300 for design exploration and search is shown that finds/evaluates one or more designs within a distance d and/or score difference Ae. The method 17300 may be based at least in part on one or more of the following premises: 1) that the starting point for design search is a "good" design, e.g., can be found using a SA process; 2) that SA can be used to find twin (or close to twin) designs within a small score variation Ae, provided the result is within d Manhattan distance of the starting design; and 3) that multiple designs can be found by parallel instances. As such, the method 17300 may provide for rapid discovery of equally (or close to equally) "good" designs in close proximity to a desired design. The method 17300 may include a user providing a "good"/desirable design for use as a starting point 17310. A use score of the initially provided design may then be calculated as ZO 17312. A proximal design may then be selected 17314. An SA process may then be executed until ZO is accomplished wherein each replication is evaluated to see if it is within a Manhattan distance d, and if yes, the simulation results are written to an output log 17316, 17318, and 17320. Replications not falling within d may be discarded 17322.

Turning to FIG. 174, another method 17400 of design exploration and search may be based on one or more of the following premises: 1) near-optimal designs tend to have many "twins" in terms of same or similar scores; 2) once one near-optimal design is found, the score may be used as a target score for finding other designs with other starting points that are twins or are otherwise very close; and 3) such twins are typically found in a small number of replicates/engine calls. As such, the method 17400 may include defining an initial parameter combination 17400, executing a SA process with a large number of replicates R 17412, and noting the best score found ZO 17414. The method 17400 may then enter a loop where various starting design parameter combinations are tested with a SA process until ZO is accomplished with the results written to an output log 17416, 17418, and 17420.

Referring now to FIG. 175, another method 17500 for design exploration and search may be based on one or more of the following premises: 1) the starting point may be a user-specified design already having a good score and desirable attributes (parameter combination); and 2) SA will find twin (or close to twin) designs within the desired type (e.g., Sample Size Re-estimation (SSR) or Group Sequential). The method 17500 may include a user providing a "good"/desirable design for use as a starting point 17510. The score of the provided design may be used as ZO 17512. The method 17500 may then enter a loop where subsequent proximal designs are selected and evaluated with SA until ZO is accomplished with the results written to an output log 17514, 17516, and 17518.

Shown in FIG. 176 is a graphical user interface 17600 that may be provided on the electronic device 17012 (FIG. 170) for configuring the server 17010 (FIG. 170) or other device executing one or more of the methods for design exploration and search disclosed herein. The interface 17600 may include fields for specifying the Manhattan distance d 17610, Δê 17612, and/or one or more design parameters 17614. A button 17616 (or other user input widget) may provide for execution of one or more of the methods described herein using the values specified in the interface 17600 to populate the property 17614 and performance criteria 17618 of one or more neighboring designs 17622.

Illustrated in FIG. 177 is another method 17700 for design exploration and search. The method 17700 may include allocating memory, in a memory device, that defines a quick search data structure having a plurality of storage cells 17710 and simulating a plurality of clinical trial designs to obtain a plurality of simulation results 17712. In embodiments, each of the plurality of simulation results may correspond to one of the plurality of clinical trial designs. The method 17700 may further include storing each of the plurality of simulation results in a corresponding one of the plurality of storage cells based on one or more relationships between two or more of the plurality of clinical trial designs 17714. In embodiments, the one or more relationships between the two or more of the plurality of clinical trial designs is based at least in part on the value of parameters for each of the two or more of the plurality of clinical trial designs. In embodiments, the method 17700 may further include scoring the two or more of the plurality of clinical trial designs based at least in part on the value of the parameters 17716 and determining whether the two or more of the plurality of clinical trial designs are similar designs 17718. Determining whether the two or more of the plurality of clinical trial designs are similar designs may include determining if the two or more of the plurality of clinical trial designs are within an epsilon of a desired score 17720 and/or determining if the two or more of the plurality of clinical trial designs are within an epsilon of each other 17722. In embodiments, the quick search data structure may be a SimCube as described herein.

Referring to FIG. 178, another method 17800 of design exploration and search includes obtaining initial simulation results for a set of clinical trial designs 17810 and identifying an initial clinical trial design based at least in part on the initial simulation results 17812. The method 17800 further includes predicting performance for clinical trial designs related to the initial clinical trial design based at least in part on varying parameters for the initial clinical trial design 17814 and identifying a first new clinical trial design for simulation based on the predicting 17816. The method 17800 further includes determining if a quick search data structure contains first simulation results for the first new clinical trial design 17818 and if the quick search data structure does not contain the first simulation results, simulating the first new clinical trial design to obtain the first simulation results 17820. The method 17800 further includes identifying, based at least in part on the first simulation results, a second new clinical trial design for simulation by varying parameters of the first new clinical trial design 17822. In embodiments, the method 17800 may include storing the first simulation results in the quick search data structure 17824, which may include determining one or more relationships between the first new clinical trial design and another clinical trial design stored in the quick search data structure 17826. In embodiments the one or more relationships between the new clinical trial design and the other clinical trial design may be based at least in part on the value of the parameters for the first new clinical trial design and parameters of the other clinical trial design.

Shown in FIG. 179 is another method 17900 for design exploration and search. The method 17900 includes interpreting, via at least one processor, simulation results data for a set of clinical trial designs 17910, and populating, via the at least one processor, a quick search data structure, defined within a memory device, with the simulation results data 17912. The method 17900 may further include identifying, via the at least one processor, a region of interest within at least one of a performance criteria space of the set of clinical trial designs or the quick search data structure 17914. Referring briefly to FIG. 180, an example performance criteria space 18000 is shown having a plurality of designs 18010. In embodiments, a region of interest may be a region 18012 in the performance criteria space 18000 that is close to a grouping of designs but itself devoid of a design. A region of interest may also be a region 18014 that is distal from designs and/or encircled by designs, e.g., a void. It is to be understood that regions of interest may take other forms as well, i.e., regions that appear interesting to a user and which may contain designs the user wishes to search and/or evaluate, and that similar regions of interest may be found in a quick search data structure and/or various tornado diagrams, as described herein. Accordingly, returning back to FIG. 179, identifying a region of interest may include determining a void 17916. The method 17900 may further include identifying, via at least one processor, a first clinical trial design based at least in part on the region of interest 17918, and determining, via the at least one processor and based at least in part on the quick search data structure and the first clinical trial design, a second clinical trial design 17920. Data corresponding to the second clinical trial design may then be transmitted, e.g., sent to the electronic device 17012 (FIG. 170) for display to a user 17922. In embodiments determining the second clinical trial design may include determining that the second clinical trial design is within a Manhattan distance within the quick search data structure of the first clinical trial design 17924 and/or determining that the second clinical trial design is within an epsilon of a desired score 17926. In embodiments, the region of interest corresponds to two or more similar designs.

In embodiments, the relationship for storing designs in the quick search data structure may be based at least in part on machine learning. For example, a machine learning module, e.g., a neural network, may be trained, via supervised and/or unsupervised learning, to determine one or more relationships, which may optimize the quick search data structure for a particular evaluation session.

Figure 181C:
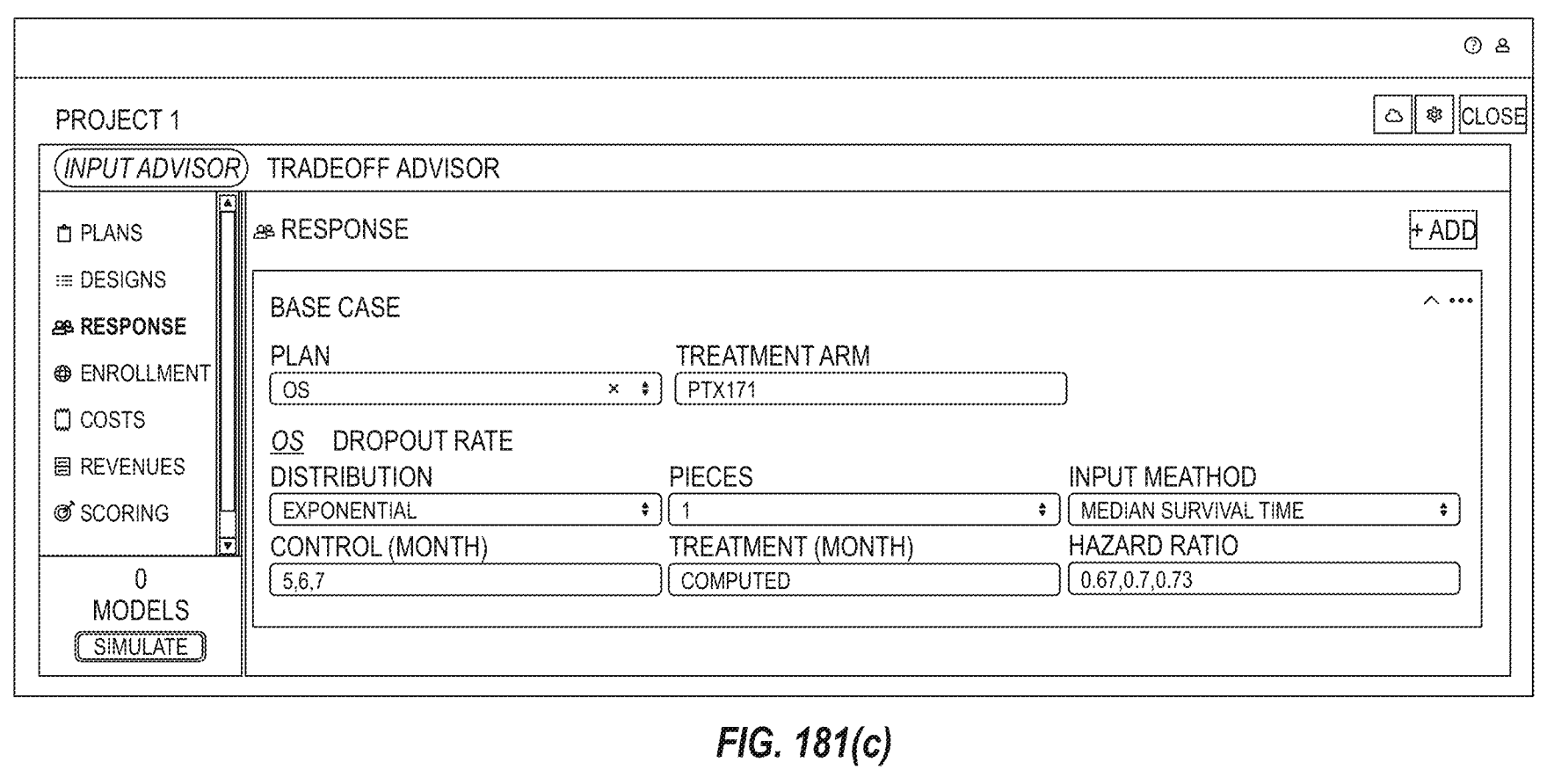

FIGS. 181(*a-k*) show an example use case of the platform described herein. The platform may include various interfaces for inputting and analyzing data. The example use case shows how users may use the platform to specify design parameters, simulate designs, analyze the simulated data, and identify globally optimum or nearly globally optimum designs for a trial. The platform may be used to identify an efficient design that addresses requirements for criteria (such as power, sample size, trial durations, cost, etc.). In the example, the platform may be used to answer questions related to what is the optimal sample size and number of events, what is the optimal number and timing of interim analyses, what is the optimal alpha spending function, and the like.

In embodiments, data entry into the platform may involve data entry into one or more forms. In embodiments, forms may be web based or browser based applications, native applications, or other executable code that proves an interface for data entry. In some embodiment, data entry may be provided with a specification file that that may be read by the platform or via an API connection to another platform or data source.

FIG. 181(*a*) shows one example of an initial data entry interface for specifying design and simulation parameters into the platform. In this example, data may be entered via one or more data entry fields (drop down menus, input boxes, lists and the like). Data entry may include a series of tabs or screens that may guide the user to enter the required data. The first data entry may be related to the "Plan" for the clinical trial. As shown in FIG. 181(*a*), entries related to the "Plan" may include general aspects defining types of designs. Data entry may include specifying a Target Population, Control Arm, Treatment Arm, Endpoints and the like for the study.

FIG. 181(*b*) shows one example of an interface for data entry for specification of design for the study. As shown in the figure, entries related to the "Design" may include specifications of designs and may include data entry for the type of statistical designs, the number of arms for the design and the like. Data entry may further include data related to the design such as hypothesis, follow up sample size, number of events, allocation ratio, the type statistical design, and the like. Data entry may include specifications related to early stopping parameters, sample size re-estimation parameters, and the like.

The next data entry may be related to the "Response" parameters. As shown in FIG. 181(*c*), entries related to the "Response" may include data entry to define the time-to-event distributions that may be used by the platform to simulate the individual subjects' data.

The next data entry may be related to the enrollment parameters. As shown in FIG. 181(*d*), entries related to "Enrollment" may include data entry to target populations, population distributions, geography, enrollment, and the like.

The next data entry may be related to the cost parameters. As shown in FIG. 181(*e*), entries related to the "Costs" may include data entry to define costs per subject or the average investigator grant per patient.

Another portion of the data entry may be related to revenue parameters. As shown in FIG. 181(*f*), entries related to the "Revenues" may include data entry to define when and how the expected revenue will be generated. Data entry may include a regulatory review period in years, annual revenue in a peak year, time to peak annual revenue, and other parameters, including as shown in the figure.

Another data entry may be related to the scoring parameters. As shown in FIG. 181(*g*), entries related to the "Scoring" may include data entry to define weights for computing a score. Data entry may include selections and weights (in % of total score) to minimize study cost, minimize study duration, maximize power, and/or minimize sample size.

Throughout the data entry process, the input advisor may monitor user entries and identify conflicts in data values and/or suggest entries of data values. In some instances, the input advisor may predict, based on historical data and/or data entry what values or types of data are associated with some inputs. The input advisor may highlight or identify ranges of values that are consistent with historical data of data entry values. In the case where some data values are outside of expected or historical data values the entry area may be flagged or highlighted for review.

Once data is entered, the entry data from each input field are assembled and compiled to define the simulation set via the "Collections" tab as shown in FIG. 181(*h*). Once the data is assembled it may be formatted to generate models that may be ready for simulation. In this example, 540 models are generated based on the input data. Assembly of data may include generating design and scenario permutations for simulation. Assembly of data may include removing scenarios or design combinations that are invalid or unlikely.

In some embodiments, generation of models may be a trigger to request and allocate computation resources for simulation. In the case of batch mode computation, the resources may be requested before they are needed to allow time for the allocation.

In the next step, simulations may be started by selecting the "simulate" button. In embodiments, before simulations are queued to run, the user may be informed of the cost of the simulations in units such as dollars or credits. Then the "Simulate" button may be clicked to start the simulations. The models for each simulation may be submitted to one or more engines for simulation. The engines may use one or more cloud computing resources to execute the models to determine the performance of each design model.

In embodiments, simulations may be exhaustive for all of the models. In some cases, only a partial set of the models may be simulated. In some embodiments, the partial set of models may be randomly selected or may be selected based on predictions (based on historical data) as to which designs in the models are likely to have the best performance for the specified criteria. In some embodiments, simulated annealing may be used to simulate a partial set of the models. Simulated annealing may be used to search for local maxima in performance space.

When the simulations end, the user may be prompted to view the results of the simulations via the tradeoff advisor. Clicking the "View Results" button may initiate calculation of scores and robustness scores from the simulation results and may load the simulation results into the tradeoff advisor. In embodiments, simulated data may be analyzed using one or more Pareto, convex hull, or other techniques to identify the optimum or near optimum designs. These Pareto, convex hull, and other recommended designs may be marked or highlighted in various interfaces of the tradeoff advisor.

In embodiments, the tradeoff advisor may include interfaces and tools to explore performance parameters of designs, compare designs, initiate additional simulations, and the like. The tradeoff advisor may include heatmaps as shown in FIG. 181(*i*). The heatmaps may provide a visual view of the relative performance of the simulated designs for one or more performance parameters. The heatmap may be sorted, filtered, rearranged to help identify designs with the desired performance. The heatmap in FIG. 181(*i*) shows designs sorted by robustness score, scenarios sorted by hazard ratio and by control group rate. Users may explore the designs by marking relative cells, viewing details of each design (such as with the tooltip data shown in FIG. 181(*i*)).

In embodiments, the tradeoff advisor may include scatterplots as shown in FIG. 181(*j*). The scatterplot in the upper left is power by duration; note that the 3 clustered rows correspond to the three HR's 0.67, 0.7, and 0.73 from top to bottom.

In embodiments, tradeoff advisor may include boxplots as shown in FIG. 181(*k*) The boxplots may show the distributions of duration, power, cost, and score for simulated designs.

In embodiments, the tradeoff advisor may include additional interfaces for comparing designs (such as card interfaces, tornado diagrams, and the like described herein). Additional interfaces may be shown allowing users to drill down or see related designs that are similar (such as twins, siblings, designs that are within an epsilon-distance of a recommended or selected design, etc.).

The methods and systems described herein may be deployed in part or in whole through a machine having a computer, computing device, processor, circuit, and/or server that executes computer readable instructions, program codes, instructions, and/or includes hardware configured to functionally execute one or more operations of the methods and systems herein. The terms computer, computing device, processor, circuit, and/or server, ("computing device") as utilized herein, should be understood broadly.

An example computing device includes a computer of any type, capable to access instructions stored in communication thereto such as upon a non-transient computer readable medium, whereupon the computer performs operations of the computing device upon executing the instructions. In certain embodiments, such instructions themselves comprise a computing device. Additionally or alternatively, a computing device may be a separate hardware device, one or more computing resources distributed across hardware devices, and/or may include such aspects as logical circuits, embedded circuits, sensors, actuators, input and/or output devices, network and/or communication resources, memory resources of any type, processing resources of any type, and/or hardware devices configured to be responsive to determined conditions to functionally execute one or more operations of systems and methods herein.

Network and/or communication resources include, without limitation, local area network, wide area network, wireless, internet, or any other known communication resources and protocols. Example and non-limiting hardware and/or computing devices include, without limitation, a general purpose computer, a server, an embedded computer, a mobile device, a virtual machine, and/or an emulated computing device. A computing device may be a distributed resource included as an aspect of several devices, included as an interoperable set of resources to perform described functions of the computing device, such that the distributed resources function together to perform the operations of the computing device. In certain embodiments, each computing device may be on separate hardware, and/or one or more hardware devices may include aspects of more than one computing device, for example as separately executable instructions stored on the device, and/or as logically partitioned aspects of a set of executable instructions, with some aspects comprising a part of one of a first computing device, and some aspects comprising a part of another of the computing devices.

A computing device may be part of a server, client, network infrastructure, mobile computing platform, stationary computing platform, or other computing platform. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more threads. The thread may spawn other threads that may have assigned priorities associated with them; the processor may execute these threads based on priority or any other order based on instructions provided in the program code. The processor may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer readable instructions on a server, client, firewall, gateway, hub, router, or other such computer and/or networking hardware. The computer readable instructions may be associated with a server that may include a file server, print server, domain server, internet server, intranet server and other variants such as secondary server, host server, distributed server and the like. The server may include one or more of memories, processors, computer readable transitory and/or non-transitory media, storage media, ports (physical and virtual), communication devices, and interfaces capable of accessing other servers, clients, machines, and devices through a wired or a wireless medium, and the like. The methods, programs, or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers, and the like. Additionally, this coupling and/or connection may facilitate remote execution of instructions across the network. The networking of some or all of these devices may facilitate parallel processing of program code, instructions, and/or programs at one or more locations without deviating from the scope of the disclosure. In addition, all the devices attached to the server through an interface may include at least one storage medium capable of storing methods, program code, instructions, and/or programs. A central repository may provide program instructions to be executed on different devices. In this implementation, the remote repository may act as a storage medium for methods, program code, instructions, and/or programs.

The methods, program code, instructions, and/or programs may be associated with a client that may include a file client, print client, domain client, internet client, intranet client and other variants such as secondary client, host client, distributed client and the like. The client may include one or more of memories, processors, computer readable transitory and/or non-transitory media, storage media, ports (physical and virtual), communication devices, and interfaces capable of accessing other clients, machines, servers, and devices through a wired or a wireless medium, and the like. The methods, program code, instructions, and/or programs as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers, and the like. Additionally, this coupling and/or connection may facilitate remote execution of methods, program code, instructions, and/or programs across the network. The networking of some or all of these devices may facilitate parallel processing of methods, program code, instructions, and/or programs at one or more locations without deviating from the scope of the disclosure. In addition, all the devices attached to the client through an interface may include at least one storage medium capable of storing methods, program code, instructions, and/or programs. A central repository may provide program instructions to be executed on different devices. In this implementation, the remote repository may act as a storage medium for methods, program code, instructions, and/or programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules, and/or components as known in the art. The computing and/or non-computing device(s) associated with the network infrastructure may include, apart from other components, a storage medium such as flash memory, buffer, stack, RAM, ROM and the like. The methods, program code, instructions, and/or programs described herein and elsewhere may be executed by one or more of the network infrastructural elements.

The methods, program code, instructions, and/or programs described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like.

The methods, program code, instructions, and/or programs described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute methods, program code, instructions, and/or programs stored thereon. Alternatively, the mobile devices may be configured to execute instructions in collaboration with other devices. The mobile devices may communicate with base stations interfaced with servers and configured to execute methods, program code, instructions, and/or programs. The mobile devices may communicate on a peer to peer network, mesh network, or other communications network. The methods, program code, instructions, and/or programs may be stored on the storage medium associated with the server and executed by a computing device embedded within the server. The base station may include a computing device and a storage medium. The storage device may store methods, program code, instructions, and/or programs executed by the computing devices associated with the base station.

The methods, program code, instructions, and/or programs may be stored and/or accessed on machine readable transitory and/or non-transitory media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

Certain operations described herein include interpreting, receiving, and/or determining one or more values, parameters, inputs, data, or other information ("receiving data"). Operations to receive data include, without limitation: receiving data via a user input; receiving data over a network of any type; reading a data value from a memory location in communication with the receiving device; utilizing a default value as a received data value; estimating, calculating, or deriving a data value based on other information available to the receiving device; and/or updating any of these in response to a later received data value. In certain embodiments, a data value may be received by a first operation, and later updated by a second operation, as part of the receiving a data value. For example, when communications are down, intermittent, or interrupted, a first receiving operation may be performed, and when communications are restored an updated receiving operation may be performed.

Certain logical groupings of operations herein, for example methods or procedures of the current disclosure, are provided to illustrate aspects of the present disclosure. Operations described herein are schematically described and/or depicted, and operations may be combined, divided, re-ordered, added, or removed in a manner consistent with the disclosure herein. It is understood that the context of an operational description may require an ordering for one or more operations, and/or an order for one or more operations may be explicitly disclosed, but the order of operations should be understood broadly, where any equivalent grouping of operations to provide an equivalent outcome of operations is specifically contemplated herein. For example, if a value is used in one operational step, the determining of the value may be required before that operational step in certain contexts (e.g. where the time delay of data for an operation to achieve a certain effect is important), but may not be required before that operation step in other contexts (e.g. where usage of the value from a previous execution cycle of the operations would be sufficient for those purposes). Accordingly, in certain embodiments an order of operations and grouping of operations as described is explicitly contemplated herein, and in certain embodiments re-ordering, subdivision, and/or different grouping of operations is explicitly contemplated herein.

The methods and systems described herein may transform physical and/or or intangible items from one state to another. The methods and systems described herein may also transform data representing physical and/or intangible items from one state to another.

The methods and/or processes described above, and steps thereof, may be realized in hardware, program code, instructions, and/or programs or any combination of hardware and methods, program code, instructions, and/or programs suitable for a particular application. The hardware may include a dedicated computing device or specific computing device, a particular aspect or component of a specific computing device, and/or an arrangement of hardware components and/or logical circuits to perform one or more of the operations of a method and/or system. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and computer readable instructions, or any other machine capable of executing program instructions.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or computer readable instructions described above. All such permutations and combinations are intended to fall within the scope of the present disclosure.

While the disclosure has been disclosed in connection with certain embodiments shown and described in detail, various modifications and improvements thereon will become readily apparent to those skilled in the art. Accordingly, the spirit and scope of the present disclosure is not to be limited by the foregoing examples, but is to be understood in the broadest sense allowable by law.

What is claimed is:

1. A method comprising:
   presenting on a graphical interface, via at least one processor, a set of cards wherein each card in the set is representative of a different trial design from a set of trial designs;
   monitoring, via the at least one processor, a first set of user interactions with the set of cards;
   determining, via the at least one processor, a user preference for one or more values of one or more parameters of the set of trial designs from the first set of user interactions;
   presenting on the graphical interface, via the at least one processor, a new card that is representative of a trial design consistent with the determined user preference;
   monitoring, via the at least one processor, a second set of user interactions with the new card; and
   refining, via the at least one processor, the determined user preference based at least in part on the second set of user interactions with the new card.

2. The method of claim 1 further comprising:
   emphasizing, via the at least one processor, values shown on each card based on a relative value compared to other displayed cards.

3. The method of claim 1, wherein the interactions include at least one of moving a card, saving a card, or deleting a card.

4. The method of claim 1, wherein the new card is added to the set of cards.

5. The method of claim 1, wherein the new card replaces a card from the set of cards.

6. The method of claim 1, wherein the set of cards is representative of Pareto designs.

7. The method of claim 1, wherein each card represents a different trial type.

8. The method of claim 1, wherein the set of cards is representative of convex hull designs.

9. The method of claim 1 further comprising:
saving, via the at least one processor, at least some of the first and the second sets of user interactions; and
training, via the at least one processor, an artificial intelligence model to identify preferences based on interactions.

10. The method of claim 1 further comprising:
determining the user preference for the one or more values of the one or more parameters of the set of trial designs via an artificial intelligence model trained on historical interactions.

11. The method of claim 1, further comprising:
evaluating historical trial design selections to identify the one or more parameters of the set of trial designs based at least in part on the first set of user interactions;
obtaining trial design simulation results based at least in part on a quick search data structure and the one or more parameters;
generating a substitute for at least some of the trial design simulation results based at least in part on a relationship between the trial design simulation results and supplemental data;
generating a performance surface based at least in part on a set of trial designs corresponding to the trial design simulation results;
evaluating one or more trial designs based at least in part on the performance surface; and
calculating a score based on normalized score component values corresponding to the trial design simulation results.

12. A system comprising:
an electronic device having an electronic display; and
a server in electronic communication with the electronic device and including at least one processor structured to:
present, on the electronic display, a graphical interface having a set of cards, wherein each card in the set is representative of a different trial design from a set of trial designs;
monitor, a first set of user interactions with the set of cards;
determine, a user preference for one or more values of one or more parameters of the set of trial designs from the first set of user interactions;
present, in the graphical interface, a new card that is representative of a trial design consistent with the determined user preference;
monitor a second set of user interactions with the new card; and
refine the determined user preference based at least in part on the second set of user interactions with the new card.

13. The system of claim 12, wherein the at least one processor refines that determined user preference by storing at least some of the first or the second set of user interactions and determines at least one additional user preference based at least in part on the stored user interactions.

14. The system of claim 12, wherein the at least one processor is further structured to:
emphasize values shown on each card based on a relative value compared to other displayed cards.

15. The system of claim 12, wherein the interactions include at least one of moving a card, saving a card, or deleting a card.

16. The system of claim 12, wherein the new card is added to the set of cards.

17. The system of claim 12, wherein the new card replaces a card from the set of cards.

18. The system of claim 12, wherein the set of cards is representative of Pareto designs.

19. The system of claim 12, wherein each card represents a different trial type.

20. The system of claim 12, wherein the set of cards is representative of convex hull designs.

* * * * *

UNITED STATES PATENT AND TRADEMARK OFFICE
CERTIFICATE OF CORRECTION

| | | |
|---|---|---|
| PATENT NO. | : 12,051,488 B2 | |
| APPLICATION NO. | : 17/163438 | |
| DATED | : July 30, 2024 | |
| INVENTOR(S) | : Bhattacharyya et al. | |

It is certified that error appears in the above-identified patent and that said Letters Patent is hereby corrected as shown below:

In the Drawings

On sheet 17 of 160, Fig. 22, delete "22218" and insert --2218-- therefor

On sheet 25 of 160, Fig. 33, reference numeral 3306, Line 1, delete "DAT" and insert --DATA-- therefor On sheet 45 of 160, Fig. 58, reference numeral 5804, Line 1, delete "ON" and insert --ONE-- therefor On sheet 49 of 160, Fig. 64, reference numeral 6408, Line 2, delete "LEASE" and insert --LEAST-- therefor On sheet 49 of 160, Fig. 64, reference numeral 6408, Line 2, delete "PAR" and insert --PART-- therefor On sheet 53 of 160, Fig. 69, reference numeral 6922, Line 2, delete "NOTA" and insert --NOT A-- therefor On sheet 73 of 160, Fig. 94, reference numeral 9416, Line 2, delete "TRIAL 2" and insert --TRIAL C-- therefor On sheet 82 of 160, Fig. 105, reference numeral 1056, Line 1, delete "1056" and insert --10536-- therefor On sheet 94 of 160, Fig. 121, reference numeral 12110, Line 2, after "EXPLORATION OF", delete "SF"

In the Specification

Signed and Sealed this
Twenty-second Day of October, 2024

Katherine Kelly Vidal
*Director of the United States Patent and Trademark Office*

CERTIFICATE OF CORRECTION (continued)
U.S. Pat. No. 12,051,488 B2

In Column 31, Line 2, delete "2114" and insert --2116-- therefor

In Column 60, Line 25, delete "t-filtered" and insert --ε-filtered-- therefor

In Column 60, Line 40, delete "8," and insert --ε,-- therefor

In Column 62, Line 11, delete "5108" and insert --5110-- therefor

In Column 66, Line 30, delete "5708" and insert --5710-- therefor

In Column 67, Line 30, delete "SV57)" and insert --$SV_{57}$-- therefor

In Column 67, Line 58, delete "($Pr_i$..." and insert --($Pr_1$...-- therefor

In Column 67, Line 59, delete "Pr57)." and insert --$Pr_{57}$).-- therefor

In Column 69, Line 42, delete "6208" and insert --6206-- therefor

In Column 69, Line 47, delete "620810" and insert --6208-- therefor

In Column 73, Line 13, delete "6526f" and insert --6526-- therefor

In Column 78, Line 47, delete "7110" and insert --7120-- therefor

In Column 89, Line 3, delete "7118," and insert --9418,-- therefor

In Column 89, Line 48, delete "9410" and insert --9510-- therefor

In Column 91, Line 21, delete "7118," and insert --9418,-- therefor

In Column 101, Line 38, delete "10534" and insert --10536-- therefor

In Column 101, Line 51, delete "10514" and insert --10516-- therefor

In Column 101, Line 55, delete "thereof Δn" and insert --thereof. An-- therefor

In Column 105, Line 26, delete "202" and insert --10702-- therefor

In Column 105, Line 28, delete "202" and insert --10702-- therefor

In Column 106, Line 28, delete "10906." and insert --11006.-- therefor

In Column 122, Line 32, delete "12614" and insert --12616-- therefor

In Column 126, Line 64, delete "13006." and insert --13106.-- therefor

CERTIFICATE OF CORRECTION (continued)
U.S. Pat. No. 12,051,488 B2

In Column 129, Line 23, delete "anon-exhaustive" and insert --a non-exhaustive-- therefor In Column 130, Line 39, delete "13800" and insert --13810-- therefor In Column 135, Line 53, delete "1424." and insert --14424.-- therefor In Column 150, Line 3, delete "FIG. 1154" and insert --FIG. 154-- therefor In Column 152, Line 67, delete "(CH_67_169)" and insert --(CH_67_1_69)-- therefor In Column 153, Line 24, delete "(CH_67_369)" and insert --(CH_67_3_69)-- therefor In Column 157, Line 33, delete "16120" and insert --16124-- therefor In Column 158, Line 1, delete "16222." and insert --16224.-- therefor In Column 164, Line 63, delete "Ae." and insert --$\Delta\hat{e}$.-- therefor In Column 165, Line 1, delete "Ae," and insert --$\Delta\hat{e}$,-- therefor In Column 165, Line 9, delete "ZO" and insert --$Z_0$-- therefor In Column 165, Line 11, delete "ZO" and insert --$Z_0$-- therefor In Column 165, Line 25, delete "17400," and insert --17410,-- therefor In Column 165, Line 27, delete "ZO" and insert --$Z_0$-- therefor In Column 165, Line 29, delete "ZO" and insert --$Z_0$-- therefor In Column 165, Line 41, delete "ZO" and insert --$Z_0$-- therefor In Column 165, Line 44, delete "ZO" and insert --$Z_0$-- therefor In Column 165, Line 52, delete "Ae" and insert --$\Delta\hat{e}$-- therefor